United States Patent
Brennan et al.

(10) Patent No.: US 8,114,600 B2
(45) Date of Patent: Feb. 14, 2012

(54) GENETIC MARKERS OF SCHIZOPHRENIA ENDOPHENOTYPES

(75) Inventors: Mark David Brennan, Jeffersonville, IN (US); Timothy Lynn Ramsey, Shelbyville, KY (US)

(73) Assignee: SureGene, LLC, Louisville, KY (US)

( * ) Notice: Subject to any disclaimer, the term of this patent is extended or adjusted under 35 U.S.C. 154(b) by 0 days.

(21) Appl. No.: 12/612,584

(22) Filed: Nov. 4, 2009

(65) Prior Publication Data

US 2010/0119625 A1 May 13, 2010

Related U.S. Application Data

(63) Continuation of application No. PCT/US2009/058483, filed on Sep. 25, 2009.

(60) Provisional application No. 61/100,176, filed on Sep. 25, 2008.

(51) Int. Cl.
*C12Q 1/68* (2006.01)
*C12P 19/34* (2006.01)

(52) U.S. Cl. .................... 435/6.11; 435/6.16; 435/91.1; 436/63

(58) Field of Classification Search ........................ None
See application file for complete search history.

(56) References Cited

FOREIGN PATENT DOCUMENTS

WO 2006-072075 7/2006

OTHER PUBLICATIONS

O'Donovan et al., "Identification of loci associated with schizophrenia by genome-wide association and follow-up," Nat. Genet., 40(9):1053-1055 (2008).
Nternational Search Report issued in PCT/US2009/058459 on Aug. 24, 2010.
International Search Report issued in PCT/US2009/058487 on Aug. 13, 2010.
International Search Report issued in PCT/US2009/058483 on Aug. 13, 2010.
Braff et al., "Advances in endophenotyping schizophrenia," World Psychiatry, vol. 7(1), pp. 11-18 (2008).
Liu et al., "HTF9C gene of 22q11.21 region associates with schizophrenia having deficit-sustained attention," Psychiatr. Genet., vol. 17(6), pp. 333-338 (2007).
Pinhiero et al., "AKT1 and neurocognition in schizophrenia," Aust. N.Z.J. Psychiatry, vol. 41(2), pp. 169-177 (2007).
Stephens et al., "Association of the 5'-upstream regulatory region of the alpha7 nicotinic acetylcholine receptor subunit gene (CHRNA7) with schizophrenia," Schizophr. Res., vol. 109(1-3), pp. 102-112, Epub. (2009).

*Primary Examiner* — Sarae Bausch
(74) *Attorney, Agent, or Firm* — Fish & Richardson P.C.

(57) ABSTRACT

This document provides methods and materials related to genetic markers of schizophrenia (SZ), schizotypal personality disorder (SPD), and/or schizoaffective disorder (SD), (collectively referred to herein as "schizophrenia spectrum disorders" or SSDs). For example, methods for using such genetic markers to identify an SSD (e.g., SZ) endophenotype are provided.

11 Claims, No Drawings

GENETIC MARKERS OF SCHIZOPHRENIA ENDOPHENOTYPES

CROSS-REFERENCE TO RELATED APPLICATIONS

This application is a continuation of International Patent Application No. PCT/US2009/058483, filed Sep. 25, 2009, which claims priority to U.S. Provisional Application Ser. No. 61/100,176, filed on Sep. 25, 2008, which are incorporated by reference in their entirety herein.

FEDERALLY SPONSORED RESEARCH OR DEVELOPMENT

This invention was made with government support under Grant Nos. R43 MH078437, N01 MH900001, and MH074027, awarded by National Institutes of Health. The government has certain rights in the invention.

TECHNICAL FIELD

This document provides methods and materials related to genetic markers of endophenotypes of schizophrenia (SZ), schizotypal personality disorder (SPD), and/or schizoaffective disorder (SD), (collectively referred to herein as "schizophrenia spectrum disorders" or SSDs). For example, this document provides methods for using such genetic markers to identify an SSD (e.g., SZ) endophenotype in a subject.

BACKGROUND

The schizophrenia spectrum disorders include schizophrenia (SZ), schizotypal personality disorder (SPD), and schizoaffective disorder (SD). Schizophrenia (SZ) is considered a clinical syndrome, and is probably a constellation of several pathologies. Substantial heterogeneity is seen between cases, which is thought to reflect multiple overlapping etiologic factors, including both genetic and environmental contributions. SD is characterized by the presence of affective (depressive or manic) symptoms and schizophrenic symptoms within the same, uninterrupted episode of illness. SPD is characterized by a pervasive pattern of social and interpersonal deficits marked by acute discomfort with, and reduced capacity for, close relationships as well as by cognitive or perceptual distortions and eccentricities of behavior, beginning by early adulthood and present in a variety of contexts.

Endophenotypes are quantitative, continuously distributed traits, symptoms or disease dimensions s typically assessed by laboratory-based methods or clinical observation. The use of endophenotypes allows complex psychiatric illnesses like SZ to be divided into more stable, readily definable categories that are more amendable to identification of clear genetic associations, as they are generally more reflective of specific underlying biological processes. Identifying the genetic basis of specific endophenotypes also facilitates identification and development of new drugs that target the specific physiological deficits underlying disease. See Braff et al., Schiz. Bull. 33(1):21-32 (2007).

SUMMARY

This disclosure provides methods of determining severity of SZ endophenotypes in subjects diagnosed with SZ based on genetic variants in genes involved in a number of pathways including: glutamate signaling and metabolism, cell adhesion, cytoskeletal architecture, vesicle formation, and trafficking, G-protein coupled receptors, carrier proteins and transporters, cell cycle modulators, neuronal development, calcium/calmodulin signaling, neuropeptide signaling, and several additional genes identified by virtue of their interaction with genes in high impact pathways and their expression in the central nervous system. This disclosure provides methods and claims relating to determining the severity of an SSD endophenotype according to a subject's underlying genetic architecture. As described herein, methods for determining severity of an SSD endophenotype include evaluation of SNPs for genes relating to endophenotypes in SSDs including SZ, SPD, and SD.

In one aspect, this document features methods for determining a severity of a schizophrenia (SZ) endophenotype in a human subject. Methods can include determining the identity of an allele of at least one single nucleotide polymorphism (SNP) listed in Tables 1-3 in the subject; comparing the identity of the allele in the subject with a reference allele, wherein the reference allele is associated with a severity of a specific endophenotype; and determining the severity of the endophenotype in the subject, based on the comparison of the allele in the subject to the reference allele; thereby determining the severity of the schizophrenia endophenotype in the subject.

In another aspect, this document features methods for selecting a treatment for schizophrenia in a human subject. Methods can include determining the identity of an allele of at least one polymorphism listed in Tables 1-3 in the subject; comparing the identity of the allele in the subject with a reference allele, wherein the reference allele is associated with a severity of a specific endophenotype; determining the severity of the endophenotype in the subject, based on the comparison of the allele in the subject to the reference allele; and selecting a treatment for the subject based on the determined severity of the specific schizophrenia endophenotype for the subject.

A SZ endophenotype can be a quantitative trait that can be measured using one or more of PANSS Total composite score, PANSS Positive composite score, PANSS Negative composite score, and PANSS General Psychopathology composite score. A SZ endophenotype can be a quantitative trait that can be measured using the PANSS Total composite score and the polymorphism can be at position 31 of a sequence selected from the group consisting of SEQ ID NOs:417, 1471, 704, 419, 1602, 1401, and 1076. A SZ endophenotype can be a quantitative trait that can be measured using the PANSS Positive composite score and the polymorphism can be at position 31 of a sequence selected from the group consisting of SEQ ID NOs:1364, 1562, 534, and 1754. A SZ endophenotype can be a quantitative trait that can be measured using the PANSS Total composite score and the polymorphism can be at position 31 of a sequence selected from the group consisting of SEQ ID NOs:1504, 1401, 275, 165, and 129. A SZ endophenotype can be a quantitative trait that can be measured using the PANSS Total composite score and the polymorphism can be at position 31 of a sequence selected from the group consisting of SEQ ID NOs:688, 1882, 1751, and 1285.

A schizophrenia endophenotype can include one or more of: a Positive Symptom selected from the group consisting of P1—delusions, P2—conceptual disorganization, P3—hallucinatory behavior, P4—excitement, P5—grandiosity, P6—suspiciousness, P7—hostility; a Negative Symptom selected from the group consisting of N1—blunted affect, N2—emotional withdrawal, N3—poor rapport, N4—passive/apathetic social withdrawal, N5—difficulty in abstract thinking, N6—lack of spontaneity and flow of conversation, N7—stereotyped thinking; or a general psychopathology symptom selected from the group consisting of G1—somatic concern, G2—anxiety, G3—guilt feelings, G4—tension, G5—mannerisms and posturing, G6—depression, G7—motor retardation, G8—uncooperativeness, G9—unusual thought content, G10—disorientation, G11—poor attention, G12—lack of judgment and insight, G13—disturbance of volition, G14—poor impulse control, G15—preoccupation, and G16—active social avoidance.

Determining the identity of an allele can include obtaining a sample comprising DNA from the subject, and determining identity of the nucleotide at the polymorphic site. Determining the identity of the nucleotide can include contacting the sample with a probe specific for a selected allele of the polymorphism, and detecting the formation of complexes between the probe and the selected allele of the polymorphism, wherein the formation of complexes between the probe and the test marker indicates the presence of the selected allele in the sample. Determining the identity of an allele can include determining the identity of the nucleotide at position 31 of one of SEQ ID NOs: 1-1894. A reference allele can represent an allele in a subject or subjects who have a known severity of the endophenotype.

A subject can be a patient, i.e., a human patient, having or suspected of having SZ. A subject can have one or more risk factors associated with SZ. Risk factors associated with SZ can include one or more of: a relative afflicted with a schizophrenia spectrum disorder (SSD); and a genetically based phenotypic trait associated with risk for a SSD. Methods can further include selecting or excluding a subject for enrollment in a clinical trial based on the identity of the allele. Methods can further include stratifying a subject population for analysis of a clinical trial based on the identity of the allele in the subjects. Methods can further include confirming a severity of a SZ endophenotype using psychometric instruments. Methods can further include administering the selected treatment to the subject. A selected treatment can be an anti-psychotic drug, an anti-depressant drug, anti-anxiety drug, mood stabilizer, selective serotonin reuptake inhibitor (SSRI), psychotherapy, or a stimulant. A treatment can be a combination of an anti-psychotic drug, plus one or more of an anti-depressant drug, anti-anxiety drug, mood stabilizer, selective serotonin reuptake inhibitor (SSRI), psychotherapy, or a stimulant. A treatment can be psychotherapy. Methods can further include recording the identity of the allele in a tangible medium. A tangible medium can include a computer-readable disk, a solid state memory device, or an optical storage device.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

This document provides methods for determining severity of an endophenotype in a patient diagnosed with SZ based on evaluation of single nucleotide polymorphisms (SNPs) for genes relating to endophenotypes of SSDs including schizophrenia (SZ), schizotypal personality disorder (SPD), and schizoaffective disorder (SD). As described herein, bioinformatic and genetic analyses provided evidence of association of the disclosed SNP alleles with severity of intermediate phenotypes, or "endophenotypes," in patients diagnosed with SZ.

Definitions

As used herein, an "endophenotype" is a quantitative psychiatric trait exhibited by patients diagnosed with SZ. One way that such traits can be measured is by clinical assessment made by administering the Positive and Negative Syndrome Scale (PANSS) (Kay et al., Schizophr. Bull. 13:261-276 (1987); Kay et al., Br. J. Psychiatry Suppl 59-67 (1989); Leucht et al., Schizophr. Res. 79:231-238 (2005)).

As used herein, an "allele" is one of a pair or series of genetic variants of a polymorphism at a specific genomic location. An "endophenotypic allele" is an allele that is statistically associated with severity of a specific endophenotype.

A "haplotype" is one or a set of signature genetic changes (polymorphisms) that are normally grouped closely together on the DNA strand, and are usually inherited as a group; the polymorphisms are also referred to herein as "markers." A "haplotype" as used herein is information regarding the presence or absence of one or more genetic markers in a given chromosomal region in a subject. A haplotype can consist of a variety of genetic markers, including indels (insertions or deletions of the DNA at particular locations on the chromosome); single nucleotide polymorphisms (SNPs) in which a particular nucleotide is changed; microsatellites; and minisatellites.

Microsatellites (sometimes referred to as a variable number of tandem repeats or VNTRs) are short segments of DNA that have a repeated sequence, usually about 2 to 5 nucleotides long (e.g., CACACA), that tend to occur in non-coding DNA. Changes in the microsatellites sometimes occur during the genetic recombination of sexual reproduction, increasing or decreasing the number of repeats found at an allele, changing the length of the allele. Microsatellite markers are stable, polymorphic, easily analyzed and occur regularly throughout the genome, making them especially suitable for genetic analysis.

"Copy number variation" (CNV), as used herein, refers to variation from the normal diploid condition for a gene or polymorphism. Individual segments of human chromosomes can be deleted or duplicated such that the subject's two chromosome carry fewer than two copies of the gene or polymorphism (a deletion or deficiency) or two or more copies (a duplication).

"Linkage disequilibrium" refers to when the observed frequencies of haplotypes in a population does not agree with haplotype frequencies predicted by multiplying together the frequency of individual genetic markers in each haplotype.

The term "chromosome" as used herein refers to a gene carrier of a cell that is derived from chromatin and comprises DNA and protein components (e.g., histones). The conventional internationally recognized individual human genome chromosome numbering identification system is employed herein. The size of an individual chromosome can vary from one type to another with a given multi-chromosomal genome and from one genome to another. In the case of the human genome, the entire DNA mass of a given chromosome is usually greater than about 100,000,000 base pairs. For example, the size of the entire human genome is about $3 \times 10^9$ base pairs.

The term "gene" refers to a DNA sequence in a chromosome that codes for a product (either RNA or its translation product, a polypeptide). A gene contains a coding region and includes regions preceding and following the coding region (termed respectively "leader" and "trailer"). The coding region is comprised of a plurality of coding segments ("exons") and intervening sequences ("introns") between individual coding segments.

The term "probe" refers to an oligonucleotide. A probe can be single stranded at the time of hybridization to a target. As used herein, probes include primers, i.e., oligonucleotides that can be used to prime a reaction, e.g., a PCR reaction.

The term "label" or "label containing moiety" refers in a moiety capable of detection, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). A probe described herein can be bound, e.g., chemically bound to label-containing moieties or can be suitable to be so bound. The probe can be directly or indirectly labeled.

The term "direct label probe" (or "directly labeled probe") refers to a nucleic acid probe whose label after hybrid formation with a target is detectable without further reactive processing of hybrid. The term "indirect label probe" (or "indirectly labeled probe") refers to a nucleic acid probe whose label after hybrid formation with a target is further reacted in subsequent processing with one or more reagents to associate therewith one or more moieties that finally result in a detectable entity.

The terms "target," "DNA target," or "DNA target region" refers to a nucleotide sequence that occurs at a specific chromosomal location. Each such sequence or portion is preferably at least partially, single stranded (e.g., denatured) at the time of hybridization. When the target nucleotide sequences are located only in a single region or fraction of a given chromosome, the term "target region" is sometimes used. Targets for hybridization can be derived from specimens which include, but are not limited to, chromosomes or regions of chromosomes in normal, diseased or malignant human cells, either interphase or at any state of meiosis or mitosis, and either extracted or derived from living or postmortem tissues, organs or fluids; germinal cells including sperm and egg cells, or cells from zygotes, fetuses, or embryos, or chorionic or amniotic cells, or cells from any other germinating body; cells grown in vitro, from either long-term or short-term culture, and either normal, immortalized or transformed; inter- or intraspecific hybrids of different types of cells or differentiation states of these cells; individual chromosomes or portions of chromosomes, or translocated, deleted or other damaged chromosomes, isolated by any of a number of means known to those with skill in the art, including libraries of such chromosomes cloned and propagated in prokaryotic or other cloning vectors, or amplified in vitro by means well known to those with skill; or any forensic material, including but not limited to blood, or other samples.

The term "hybrid" refers to the product of a hybridization procedure between a probe and a target.

The term "hybridizing conditions" has general reference to the combinations of conditions that are employable in a given hybridization procedure to produce hybrids, such conditions typically involving controlled temperature, liquid phase, and contact between a probe (or probe composition) and a target. Conveniently and preferably, at least one denaturation step precedes a step wherein a probe or probe composition is contacted with a target. Guidance for performing hybridization reactions can be found in Ausubel et al., *Current Protocols in Molecular Biology*, John Wiley & Sons, N.Y. (2003), 6.3.1-6.3.6. Aqueous and nonaqueous methods are described in that reference and either can be used. Hybridization conditions referred to herein are a 50% formamide, 2×SSC wash for 10 minutes at 45° C. followed by a 2×SSC wash for 10 minutes at 37° C.

Calculations of "identity" between two sequences can be performed as follows. The sequences are aligned for optimal comparison purposes (e.g., gaps can be introduced in one or both of a first and a second nucleic acid sequence for optimal alignment and non-identical sequences can be disregarded for comparison purposes). The length of a sequence aligned for comparison purposes is at least 30% (e.g., at least 40%, 50%, 60%, 70%, 80%, 90% or 100%) of the length of the reference sequence. The nucleotides at corresponding nucleotide positions are then compared. When a position in the first sequence is occupied by the same nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In some embodiments, the percent identity between two nucleotide sequences is determined using the GAP program in the GCG software package, using a Blossum 62 scoring matrix with a gap penalty of 12, a gap extend penalty of 4, and a frameshift gap penalty of 5.

As used herein, the term "substantially identical" is used to refer to a first nucleotide sequence that contains a sufficient number of identical nucleotides to a second nucleotide sequence such that the first and second nucleotide sequences have similar activities. Nucleotide sequences that are substantially identical are at least 80% (e.g., 85%, 90%, 95%, 97% or more) identical.

The term "nonspecific binding DNA" refers to DNA which is complementary to DNA segments of a probe, which DNA occurs in at least one other position in a genome, outside of a selected chromosomal target region within that genome. An example of nonspecific binding DNA comprises a class of DNA repeated segments whose members commonly occur in more than one chromosome or chromosome region. Such common repetitive segments tend to hybridize to a greater extent than other DNA segments that are present in probe composition.

Methods of Determining the Degree of Specific Endophenotypes

Quantitative traits, by definition, are measured by degree rather than simply presence or absence, like blood glucose or cholesterol. The genetically-based methods described herein can give a biological indication of the degree (or severity) of a phenotype a patient might show, and not be dependent upon the results of a particular psychiatric test done on one particular day. This is similar to testing for LDL receptor variants to understand why a person might have high cholesterol and how it would be best to treat the patient, rather than simply looking at cholesterol levels. In the SZ context, this is particularly important since a subject's presentation of disease may vary from day to day. For example, a subject with SZ may display more mania one day than the next; if a medical professional evaluates them on a day when they are displaying fewer symptoms of mania, an inappropriate treatment plan might be prepared.

Described herein are a variety of methods for identifying, predicting, or determining severity or degree of a subject's SSD (e.g., SZ) endophenotype. "Severity" includes the whole spectrum of expression of the endophenotype, including both positive and negative scores on the PANSS test, e.g., extremely severe expression to mild or substantially no expression of the endophenotype. As used herein, determining severity or degree of an SSD endophenotype is based on the presence or absence of one or more alleles associated with severity of the endophenotypes in patients diagnosed with SZ as described herein. Ascertaining whether the subject has such an allele is included in the concept of determining SSD (e.g., SZ) endophenotypes as used herein. The presence an allele associated with a particular severity indicates a specific genetic (biological) contribution to the particular endophenotype. Such contributions can be positive (tending to increase the degree of the endophenotype) or negative (tending to decrease the degree of the endophenotype) depending on the specific allele of the polymorphism.

As used herein, "determining the identity of an allele" includes obtaining information regarding the identity, presence or absence of one or more specific alleles in a subject. Determining the identity of an allele can, but need not, include obtaining a sample comprising DNA from a subject, and/or assessing the identity, presence or absence of one or more genetic markers in the sample. The individual or organization who determines the identity of the allele need not actually carry out the physical analysis of a sample from a subject; the methods can include using information obtained by analysis of the sample by a third party. Thus the methods can include steps that occur at more than one site. For example, a sample can be obtained from a subject at a first site, such as at a health care provider, or at the subject's home in the case of a self-testing kit. The sample can be analyzed at the same or a second site, e.g., at a laboratory or other testing facility.

Determining the identity of an allele can also include or consist of reviewing a subject's medical history, where the medical history includes information regarding the identity, presence or absence of one or more response alleles in the subject, e.g., results of a genetic test.

In some embodiments, to determine the identity of an allele described herein, a biological sample that includes nucleated cells (such as blood, a cheek swab or mouthwash) is prepared and analyzed for the presence or absence of preselected markers. Such diagnoses may be performed by diagnostic laboratories, or, alternatively, diagnostic kits can be manufactured and sold to health care providers or to private individuals for self-diagnosis. Diagnostic or prognostic tests can be performed as described herein or using well known techniques, such as described in U.S. Pat. No. 5,800,998.

Results of these tests, and optionally interpretive information, can be returned to the subject, the health care provider or to a third party payor. The results can be used in a number of ways. The information can be, e.g., communicated to the tested subject, e.g., with a prognosis and optionally interpretive materials that help the subject understand the test results and prognosis. The information can be used, e.g., by a health care provider, to determine whether to administer a specific drug, or whether a subject should be assigned to a specific category, e.g., a category associated with a specific disease endophenotype, or with drug response or non-response. The information can be used, e.g., by a third party payor such as a healthcare payer (e.g., insurance company or HMO) or other agency, to determine whether or not to reimburse a health care provider for services to the subject, or whether to approve the provision of services to the subject. For example, the health-care payer may decide to reimburse a health care provider for treatments for an SSD if the subject has a particular response allele. As another example, a drug or treatment may be indicated for individuals with a certain allele, and the insurance company would only reimburse the health care provider (or the insured individual) for prescription or purchase of the drug if the insured individual has that response allele. The presence or absence of the response allele in a patient may be ascertained by using any of the methods described herein.

Alleles Associated with Severity of SSD Endophenotypes

This document provides methods for determining the degree of an SSD (e.g., SZ) endophenotype based on evaluation of single nucleotide polymorphisms (SNPs) for genes relating to endophenotypes of SZ-spectrum disorders including schizophrenia (SZ), schizotypal personality disorder (SPD), and schizoaffective disorder (SD). The alleles described herein can be used both to determine patients who are likely to display higher or lower values for specific endophenotypes and to determine the contribution of genetic makeup and specific biological/cellular pathways to specific endophenotypes and severity thereof. Tables 1-3 and Table A list specific SNPs, variation of which is associated with variations in severity of specific endophenotypes. One of skill in the art will appreciate that other variants can be identified via TDT using families with multiple affected individuals or by Case/Control comparisons using the SNP markers presented herein. Using SNP markers that are identical to or in linkage disequilibrium with the exemplary SNPs, one can determine other alleles, including haplotypes and single SNP alleles in these genes relating response to an endophenotype of an SSD (e.g., of SZ). The allelic variants thus identified can be used equivalently to the exemplary SNPs, e.g., to determine a diagnosis of a specific endophenotype in a patient.

Markers in Linkage disequilibrium (LD)

Linkage disequilibrium (LD) is a measure of the degree of association between alleles in a population. One of skill in the art will appreciate that alleles involving markers in LD with the polymorphisms described herein can also be used in a similar manner to those described herein. Methods of calculating LD are known in the art (see, e.g., Morton et al., *Proc. Natl. Acad. Sci. USA* 98(9):5217-21 (2001); Tapper et al., *Proc. Natl. Acad. Sci. USA* 102(33):11835-11839 (2005); Maniatis et al., *Proc. Natl. Acad. Sci. USA* 99:2228-2233 (2002)). Thus, in some cases, the methods can include analysis of polymorphisms that are in LD with a polymorphism described herein. Methods are known in the art for identifying such polymorphisms; for example, the International HapMap Project provides a public database that can be used, see hapmap.org, as well as The International HapMap Consortium, *Nature* 426:789-796 (2003), and The International HapMap Consortium, *Nature* 437:1299-1320 (2005). Generally, it will be desirable to use a HapMap constructed using data from individuals who share ethnicity with the subject. For example, a HapMap for African Americans would ideally be used to identify markers in LD with an exemplary marker described herein for use in genotyping a subject of African American descent.

Alternatively, methods described herein can include analysis of polymorphisms that show a correlation coefficient ($r^2$) of value $\geq 0.5$ with the markers described herein. Results can be obtained from on line public resources such as HapMap.org on the World Wide Web. The correlation coefficient is a measure of LD, and reflects the degree to which alleles at two loci (for example, two SNPs) occur together, such that an allele at one SNP position can predict the correlated allele at a second SNP position, in the case where $r^2$ is >0.5.

Identifying Additional Genetic Markers

In general, genetic markers can be identified using any of a number of methods well known in the art. For example, numerous polymorphisms in the regions described herein are known to exist and are available in public databases, which can be searched using methods and algorithms known in the art. Alternately, polymorphisms can be identified by sequencing either genomic DNA or cDNA in the region in which it is desired to find a polymorphism. According to one approach, primers are designed to amplify such a region, and DNA from a subject is obtained and amplified. The DNA is sequenced, and the sequence (referred to as a "subject sequence" or "test sequence") is compared with a reference sequence, which can represent the "normal" or "wild type" sequence, or the "affected" sequence. In some embodiments, a reference sequence can be from, for example, the human draft genome sequence, publicly available in various databases, or a sequence deposited in a database such as GenBank In some embodiments, the reference sequence is a composite of ethnically diverse individuals.

In general, if sequencing reveals a difference between the sequenced region and the reference sequence, a polymorphism has been identified. The fact that a difference in nucleotide sequence is identified at a particular site that determines that a polymorphism exists at that site. In most instances, particularly in the case of SNPs, only two polymorphic variants will exist at any location. However, in the case of SNPs, up to four variants may exist since there are four naturally occurring nucleotides in DNA. Other polymorphisms, such as insertions and deletions, may have more than four alleles.

The methods described herein can also include determining the presence or absence of other markers known or suspected to be associated with an SSD (e.g., SZ) endophenotype, e.g., markers outside of a region identified herein, see, e.g., Harrison and Owen, Lancet, 361(9355):417-419 (2003). In some embodiments, the methods include determining the presence or absence of one or more other markers that are or may be associated with an SSD (e.g., SZ) endophenotype, e.g., in one or more genes, e.g., e.g., as described in WO 2009/092032, WO 2009/089120, WO 2009/082743, US2006/0177851, and US2009/0012371 incorporated herein in their entirety. See also, e.g., OMIM entry no. 181500 (SCZD).

Methods of Determining the Identity of an Allele

The methods described herein include determining the identity, presence or absence of alleles associated with a severity of specific SSD (e.g., SZ) endophenotype. In some cases, an association with severity of an SSD (e.g., SZ) endophenotype is determined by the presence of the same allele in both the subject and an affected reference individual, e.g., in an unrelated reference subject or a first or second-degree relation of the subject, and the absence of the allele in an unaffected reference individual. Thus the methods can include obtaining and analyzing a sample from a suitable reference individual. Samples that are suitable for use in the methods described herein contain genetic material, e.g., genomic DNA (gDNA). Genomic DNA is typically extracted from biological samples such as blood or mucosal scrapings of the lining of the mouth, but can be extracted from other biological samples including urine or expectorant. The sample itself will typically include nucleated cells (e.g., blood or buccal cells) or tissue removed from the subject. The subject can be an adult, child, fetus, or embryo. In some embodiments, the sample is obtained prenatally, either from a fetus or embryo or from the mother (e.g., from fetal or embryonic cells in the maternal circulation). Methods and reagents are known in the art for obtaining, processing, and analyzing samples. In some embodiments, the sample is obtained with the assistance of a health care provider, e.g., to draw blood. In some embodiments, the sample is obtained without the assistance of a health care provider, e.g., where the sample is obtained non-invasively, such as a sample comprising buccal cells that is obtained using a buccal swab or brush, or a mouthwash sample.

In some cases, a biological sample may be processed for DNA isolation. For example, DNA in a cell or tissue sample can be separated from other components of the sample. Cells can be harvested from a biological sample using standard techniques known in the art. For example, cells can be harvested by centrifuging a cell sample and resuspending the pelleted cells. The cells can be resuspended in a buffered solution such as phosphate-buffered saline (PBS). After centrifuging the cell suspension to obtain a cell pellet, the cells can be lysed to extract DNA, e.g., gDNA. See, e.g., Ausubel et al., 2003, supra. The sample can be concentrated and/or purified to isolate DNA. All samples obtained from a subject, including those subjected to any sort of further processing, are considered to be obtained from the subject. Routine methods can be used to extract genomic DNA from a biological sample, including, for example, phenol extraction. Alternatively, genomic DNA can be extracted with kits such as the QIAamp® Tissue Kit (Qiagen, Chatsworth, Calif.) and the Wizard® Genomic DNA purification kit (Promega). Non-limiting examples of sources of samples include urine, blood, and tissue.

The absence or presence of an allele associated with severity of an SSD (e.g., SZ) endophenotype as described herein can be determined using methods known in the art. For example, gel electrophoresis, capillary electrophoresis, size exclusion chromatography, sequencing, and/or arrays can be used to detect the presence or absence of the allele. Amplification of nucleic acids, where desirable, can be accomplished using methods known in the art, e.g., PCR. In one example, a sample (e.g., a sample comprising genomic DNA), is obtained from a subject. The DNA in the sample is then examined to determine the identity of an allele as described herein. The identity of the allele can be determined by any method described herein, e.g., by sequencing or by hybridization of the gene in the genomic DNA, RNA, or cDNA to a nucleic acid probe, e.g., a DNA probe (which includes cDNA and oligonucleotide probes) or an RNA probe. The nucleic acid probe can be designed to specifically or preferentially hybridize with a particular polymorphic variant.

Other methods of nucleic acid analysis can include direct manual sequencing (Church and Gilbert, *Proc. Natl. Acad. Sci. USA* 81:1991-1995 (1988); Sanger et al., *Proc. Natl. Acad. Sci. USA* 74:5463-5467 (1977); Beavis et al., U.S. Pat. No. 5,288,644); automated fluorescent sequencing; single-stranded conformation polymorphism assays (SSCP) (Schafer et al., *Nat. Biotechnol.* 15:33-39 (1995)); clamped denaturing gel electrophoresis (CDGE); two-dimensional gel electrophoresis (2DGE or TDGE); conformational sensitive gel electrophoresis (CSGE); denaturing gradient gel electrophoresis (DGGE) (Sheffield et al., *Proc. Natl. Acad. Sci. USA* 86:232-236 (1989)); denaturing high performance liquid chromatography (DHPLC, Underhill et al., *Genome Res.* 7:996-1005 (1997)); infrared matrix-assisted laser desorption/ionization (IR-MALDI) mass spectrometry (WO 99/57318); mobility shift analysis (Orita et al., *Proc. Natl. Acad. Sci. USA* 86:2766-2770 (1989)); restriction enzyme analysis (Flavell et al., *Cell* 15:25 (1978); Geever et al., *Proc. Natl. Acad. Sci. USA* 78:5081 (1981)); quantitative real-time PCR (Raca et al., *Genet Test* 8(4):387-94 (2004)); heteroduplex analysis; chemical mismatch cleavage (CMC) (Cotton et al., *Proc. Natl. Acad. Sci. USA* 85:4397-4401 (1985)); RNase protection assays (Myers et al., *Science* 230:1242 (1985)); use of polypeptides that recognize nucleotide mismatches, e.g., *E. coli* mutS protein; allele-specific PCR, and combinations of such methods. See, e.g., Gerber et al., U.S. Patent Publication No. 2004/0014095 which is incorporated herein by reference in its entirety.

Sequence analysis can also be used to detect specific polymorphic variants. For example, polymorphic variants can be detected by sequencing exons, introns, 5' untranslated sequences, or 3' untranslated sequences. A sample comprising DNA or RNA is obtained from the subject. PCR or other appropriate methods can be used to amplify a portion encompassing the polymorphic site, if desired. The sequence is then ascertained, using any standard method, and the presence of a polymorphic variant is determined. Real-time pyrophosphate DNA sequencing is yet another approach to detection of polymorphisms and polymorphic variants (Alderborn et al., *Genome Research* 10(8):1249-1258 (2000)). Additional methods include, for example, PCR amplification in combination with denaturing high performance liquid chromatography (dHPLC) (Underhill et al., *Genome Research* 7(10): 996-1005 (1997)).

In order to detect polymorphisms and/or polymorphic variants, it will frequently be desirable to amplify a portion of genomic DNA (gDNA) encompassing the polymorphic site. Such regions can be amplified and isolated by PCR using oligonucleotide primers designed based on genomic and/or cDNA sequences that flank the site. PCR refers to procedures in which target nucleic acid (e.g., genomic DNA) is amplified in a manner similar to that described in U.S. Pat. No. 4,683,195, and subsequent modifications of the procedure described therein. Generally, sequence information from the ends of the region of interest or beyond are used to design oligonucleotide primers that are identical or similar in sequence to opposite strands of a potential template to be amplified. See e.g., *PCR Primer: A Laboratory Manual*, Dieffenbach and Dveksler, (Eds.); McPherson et al., *PCR Basics: From Background to Bench* (Springer Verlag, 2000); Mattila et al., *Nucleic Acids Res.*, 19:4967 (1991); Eckert et al., *PCR Methods and Applications*, 1:17 (1991); PCR (eds. McPherson et al., IRL Press, Oxford); and U.S. Pat. No. 4,683,202. Other amplification methods that may be employed include the ligase chain reaction (LCR) (Wu and Wallace, *Genomics* 4:560 (1989), Landegren et al., *Science* 241:1077 (1988), transcription amplification (Kwoh et al., *Proc. Natl. Acad. Sci. USA* 86:1173 (1989)), self-sustained sequence replication (Guatelli et al., *Proc. Nat. Acad. Sci. USA* 87:1874 (1990)), and nucleic acid based sequence amplification (NASBA). Guidelines for selecting primers for PCR amplification are well known in the art. See, e.g., McPherson et al., *PCR Basics: From Background to Bench*, Springer-Verlag, 2000. A variety of computer programs for designing primers are available, e.g., 'Oligo' (National Biosciences, Inc, Plymouth Minn.), MacVector (Kodak/IBI), and the GCG suite of sequence analysis programs (Genetics Computer Group, Madison, Wis. 53711).

In some cases, PCR conditions and primers can be developed that amplify a product only when the variant allele is present or only when the wild type allele is present (MSPCR or allele-specific PCR). For example, patient DNA and a control can be amplified separately using either a wild type primer or a primer specific for the variant allele. Each set of reactions is then examined for the presence of amplification products using standard methods to visualize the DNA. For example, the reactions can be electrophoresed through an agarose gel and the DNA visualized by staining with ethidium bromide or other DNA intercalating dye. In DNA samples from heterozygous patients, reaction products would be detected in each reaction.

Real-time quantitative PCR can also be used to determine copy number. Quantitative PCR permits both detection and quantification of specific DNA sequence in a sample as an absolute number of copies or as a relative amount when normalized to DNA input or other normalizing genes. A key feature of quantitative PCR is that the amplified DNA product is quantified in real-time as it accumulates in the reaction after each amplification cycle. Methods of quantification can include the use of fluorescent dyes that intercalate with double-stranded DNA, and modified DNA oligonucleotide probes that fluoresce when hybridized with a complementary DNA.

In some embodiments, a peptide nucleic acid (PNA) probe can be used instead of a nucleic acid probe in the hybridization methods described above. PNA is a DNA mimetic with a peptide-like, inorganic backbone, e.g., N-(2-aminoethyl)glycine units, with an organic base (A, G, C, T or U) attached to the glycine nitrogen via a methylene carbonyl linker (see, e.g., Nielsen et al., *Bioconjugate Chemistry*, The American Chemical Society, 5:1 (1994)). The PNA probe can be designed to specifically hybridize to a nucleic acid comprising a polymorphic variant indicative of an SSD (e.g., SZ) endophenotype.

In some cases, allele-specific oligonucleotides can also be used to detect the presence of a polymorphic variant. For example, polymorphic variants can be detected by performing allele-specific hybridization or allele-specific restriction digests. Allele specific hybridization is an example of a method that can be used to detect sequence variants, including complete haplotypes of a subject (e.g., a mammal such as a human). See Stoneking et al., *Am. J. Hum. Genet.* 48:370-382 (1991); and Prince et al., *Genome Res.* 11:152-162 (2001). An "allele-specific oligonucleotide" (also referred to herein as an "allele-specific oligonucleotide probe") is an oligonucleotide that is specific for particular a polymorphism can be prepared using standard methods (see Ausubel et al., *Current Protocols in Molecular Biology*, supra). Allele-specific oligonucleotide probes typically can be approximately 10-50 base pairs, preferably approximately 15-30 base pairs, that specifically hybridizes to a nucleic acid region that contains a polymorphism. Hybridization conditions are selected such that a nucleic acid probe can specifically bind to the sequence of interest, e.g., the variant nucleic acid sequence. Such hybridizations typically are performed under high stringency as some sequence variants include only a single nucleotide difference. In some cases, dot-blot hybridization of amplified oligonucleotides with allele-specific oligonucleotide (ASO) probes can be performed. See, for example, Saiki et al., *Nature* (London) 324:163-166 (1986).

In some embodiments, allele-specific restriction digest analysis can be used to detect the existence of a polymorphic variant of a polymorphism, if alternate polymorphic variants of the polymorphism result in the creation or elimination of a restriction site. Allele-specific restriction digests can be performed in the following manner. A sample containing genomic DNA is obtained from the individual and genomic DNA is isolated for analysis. For nucleotide sequence variants that introduce a restriction site, restriction digest with the particular restriction enzyme can differentiate the alleles. In some cases, polymerase chain reaction (PCR) can be used to amplify a region comprising the polymorphic site, and restriction fragment length polymorphism analysis is conducted (see Ausubel et al., *Current Protocols in Molecular Biology*, supra). The digestion pattern of the relevant DNA fragment indicates the presence or absence of a particular polymorphic variant of the polymorphism and is therefore indicative of severity of an SSD endophenotype. For sequence variants that do not alter a common restriction site, mutagenic primers can be designed that introduce a restriction site when the variant allele is present or when the wild type allele is present. For example, a portion of a nucleic acid can be amplified using the mutagenic primer and a wild type primer, followed by digest with the appropriate restriction endonuclease.

In some embodiments, fluorescence polarization template-directed dye-terminator incorporation (FP-TDI) is used to determine which of multiple polymorphic variants of a polymorphism is present in a subject (Chen et al., *Genome Research* 9(5):492-498 (1999)). Rather than involving use of allele-specific probes or primers, this method employs primers that terminate adjacent to a polymorphic site, so that extension of the primer by a single nucleotide results in incorporation of a nucleotide complementary to the polymorphic variant at the polymorphic site.

In some cases, DNA containing an amplified portion may be dot-blotted, using standard methods (see Ausubel et al., *Current Protocols in Molecular Biology*, supra), and the blot contacted with the oligonucleotide probe. The presence of specific hybridization of the probe to the DNA is then detected. Specific hybridization of an allele-specific oligonucleotide probe to DNA from the subject can be indicative of the presence of an allele associated with an SSD (e.g., SZ) endophenotype.

The methods can include determining the genotype of a subject with respect to both copies of the polymorphic site present in the genome. For example, the complete genotype may be characterized as −/−, as −/+, or as +/+, where a minus sign indicates the presence of the reference or wild type sequence at the polymorphic site, and the plus sign indicates the presence of a polymorphic variant other than the reference sequence. If multiple polymorphic variants exist at a site, this can be appropriately indicated by specifying which ones are present in the subject. Any of the detection means described herein can be used to determine the genotype of a subject with respect to one or both copies of the polymorphism present in the subject's genome.

Methods of nucleic acid analysis to detect polymorphisms and/or polymorphic variants can include, e.g., microarray analysis. Hybridization methods, such as Southern analysis, Northern analysis, or in situ hybridizations, can also be used (see Ausubel et al., *Current Protocols in Molecular Biology*, eds., John Wiley & Sons (2003)). To detect microdeletions, fluorescence in situ hybridization (FISH) using DNA probes that are directed to a putatively deleted region in a chromosome can be used. For example, probes that detect all or a part of a microsatellite marker can be used to detect microdeletions in the region that contains that marker.

In some embodiments, it is desirable to employ methods that can detect the presence of multiple polymorphisms (e.g., polymorphic variants at a plurality of polymorphic sites) in parallel or substantially simultaneously. Oligonucleotide arrays represent one suitable means for doing so. Other methods, including methods in which reactions (e.g., amplification, hybridization) are performed in individual vessels, e.g., within individual wells of a multi-well plate or other vessel may also be performed so as to detect the presence of multiple polymorphic variants (e.g., polymorphic variants at a plurality of polymorphic sites) in parallel or substantially simultaneously according to the methods provided herein.

Nucleic acid probes can be used to detect and/or quantify the presence of a particular target nucleic acid sequence within a sample of nucleic acid sequences, e.g., as hybridization probes, or to amplify a particular target sequence within a sample, e.g., as a primer. Probes have a complimentary nucleic acid sequence that selectively hybridizes to the target nucleic acid sequence. In order for a probe to hybridize to a target sequence, the hybridization probe must have sufficient identity with the target sequence, i.e., at least 70% (e.g., 80%, 90%, 95%, 98% or more) identity to the target sequence. The probe sequence must also be sufficiently long so that the probe exhibits selectivity for the target sequence over non-target sequences. For example, the probe will be at least 20 (e.g., 25, 30, 35, 50, 100, 200, 300, 400, 500, 600, 700, 800, 900 or more) nucleotides in length. In some embodiments, the probes are not more than 30, 50, 100, 200, 300, 500, 750, or 1000 nucleotides in length. Probes are typically about 20 to about $1 \times 10^6$ nucleotides in length. Probes include primers, which generally refers to a single-stranded oligonucleotide probe that can act as a point of initiation of template-directed DNA synthesis using methods such as PCR (polymerase chain reaction), LCR (ligase chain reaction), etc., for amplification of a target sequence.

The probe can be a test probe such as a probe that can be used to detect polymorphisms in a region described herein (e.g., polymorphisms as described herein). In some embodiments, the probe can bind to another marker sequence associated with SZ, SPD, or SD as described herein.

Control probes can also be used. For example, a probe that binds a less variable sequence, e.g., repetitive DNA associated with a centromere of a chromosome, can be used as a control. Probes that hybridize with various centromeric DNA and locus-specific DNA are available commercially, for example, from Vysis, Inc. (Downers Grove, Ill.), Molecular Probes, Inc. (Eugene, Oreg.), or from Cytocell (Oxfordshire, UK). Probe sets are available commercially such from Applied Biosystems, e.g., the Assays-on-Demand SNP kits Alternatively, probes can be synthesized, e.g., chemically or in vitro, or made from chromosomal or genomic DNA through standard techniques. For example, sources of DNA that can be used include genomic DNA, cloned DNA sequences, somatic cell hybrids that contain one, or a part of one, human chromosome along with the normal chromosome complement of the host, and chromosomes purified by flow cytometry or microdissection. The region of interest can be isolated through cloning, or by site-specific amplification via the polymerase chain reaction (PCR). See, for example, Nath and Johnson, *Biotechnic. Histochem.* 73(1):6-22 (1998); Wheeless et al., *Cytometry* 17:319-326 (1994); and U.S. Pat. No. 5,491,224.

In some embodiments, the probes are labeled, e.g., by direct labeling, with a fluorophore, an organic molecule that fluoresces after absorbing light of lower wavelength/higher energy. A directly labeled fluorophore allows the probe to be visualized without a secondary detection molecule. After covalently attaching a fluorophore to a nucleotide, the nucleotide can be directly incorporated into the probe with standard techniques such as nick translation, random priming, and PCR labeling. Alternatively, deoxycytidine nucleotides within the probe can be transaminated with a linker. The fluorophore then is covalently attached to the transaminated deoxycytidine nucleotides. See, e.g., U.S. Pat. No. 5,491,224.

Fluorophores of different colors can be chosen such that each probe in a set can be distinctly visualized. For example, a combination of the following fluorophores can be used: 7-amino-4-methylcoumarin-3-acetic acid (AMCA), TEXAS RED™ (Molecular Probes, Inc., Eugene, Oreg.), 5-(and -6)-carboxy-X-rhodamine, lissamine rhodamine B, 5-(and -6)-carboxyfluorescein, fluorescein-5-isothiocyanate (FITC), 7-diethylaminocoumarin-3-carboxylic acid, tetramethylrhodamine-5-(and -6)-isothiocyanate, 5-(and -6)-carboxytetramethylrhodamine, 7-hydroxycoumarin-3-carboxylic acid, 6-[fluorescein 5-(and -6)-carboxamido]hexanoic acid, N-(4, 4-difluoro-5,7-dimethyl-4-bora-3a,4a diaza-3-indacenepropionic acid, eosin-5-isothiocyanate, erythrosin-5-isothiocyanate, and CASCADE™ blue acetylazide (Molecular Probes, Inc., Eugene, Oreg.). Fluorescently labeled probes can be viewed with a fluorescence microscope and an appropriate filter for each fluorophore, or by using dual or triple band-pass filter sets to observe multiple fluorophores. See, for example, U.S. Pat. No. 5,776,688. Alternatively, techniques such as flow cytometry can be used to examine the hybridization pattern of the probes. Fluorescence-based arrays are also known in the art.

In other embodiments, the probes can be indirectly labeled with, e.g., biotin or digoxygenin, or labeled with radioactive isotopes such as $^{32}P$ and $^{3}H$. For example, a probe indirectly labeled with biotin can be detected by avidin conjugated to a detectable marker. For example, avidin can be conjugated to an enzymatic marker such as alkaline phosphatase or horseradish peroxidase. Enzymatic markers can be detected in standard colorimetric reactions using a substrate and/or a catalyst for the enzyme. Catalysts for alkaline phosphatase include 5-bromo-4-chloro-3-indolylphosphate and nitro blue tetrazolium. Diaminobenzoate can be used as a catalyst for horseradish peroxidase.

In another aspect, this document features arrays that include a substrate having a plurality of addressable areas, and methods of using them. At least one area of the plurality includes a nucleic acid probe that binds specifically to a sequence comprising a polymorphism listed in any of Tables 1-3, and can be used to detect the absence or presence of said polymorphism, e.g., one or more SNPs, microsatellites, minisatellites, or indels, as described herein, to determine the identity of an allele. For example, the array can include one or more nucleic acid probes that can be used to detect a polymorphism listed in any of Tables 1-3. In some embodiments, the array further includes at least one area that includes a nucleic acid probe that can be used to specifically detect another marker associated with severity of an SSD (e.g., SZ), as described herein. In some embodiments, the probes are nucleic acid capture probes.

Generally, microarray hybridization is performed by hybridizing a nucleic acid of interest (e.g., a nucleic acid encompassing a polymorphic site) with the array and detecting hybridization using nucleic acid probes. In some cases, the nucleic acid of interest is amplified prior to hybridization. Hybridization and detecting are generally carried out according to standard methods. See, e.g., Published PCT Application Nos. WO 92/10092 and WO 95/11995, and U.S. Pat. No. 5,424,186. For example, the array can be scanned to determine the position on the array to which the nucleic acid hybridizes. The hybridization data obtained from the scan is typically in the form of fluorescence intensities as a function of location on the array.

Arrays can be formed on substrates fabricated with materials such as paper, glass, plastic (e.g., polypropylene, nylon, or polystyrene), polyacrylamide, nitrocellulose, silicon, optical fiber, or any other suitable solid or semisolid support, and can be configured in a planar (e.g., glass plates, silicon chips) or three dimensional (e.g., pins, fibers, beads, particles, microtiter wells, capillaries) configuration. Methods for generating arrays are known in the art and include, e.g., photolithographic methods (see, e.g., U.S. Pat. Nos. 5,143,854; 5,510,270; and 5,527,681), mechanical methods (e.g., directed-flow methods as described in U.S. Pat. No. 5,384, 261), pin-based methods (e.g., as described in U.S. Pat. No. 5,288,514), and bead-based techniques (e.g., as described in PCT US/93/04145). The array typically includes oligonucleotide hybridization probes capable of specifically hybridizing to different polymorphic variants. Oligonucleotide probes that exhibit differential or selective binding to polymorphic sites may readily be designed by one of ordinary skill in the art. For example, an oligonucleotide that is perfectly complementary to a sequence that encompasses a polymorphic site (i.e., a sequence that includes the polymorphic site, within it or at one end) will generally hybridize preferentially to a nucleic acid comprising that sequence, as opposed to a nucleic acid comprising an alternate polymorphic variant.

Oligonucleotide probes forming an array may be attached to a substrate by any number of techniques, including, without limitation, (i) in situ synthesis (e.g., high-density oligonucleotide arrays) using photolithographic techniques; (ii) spotting/printing at medium to low density on glass, nylon or nitrocellulose; (iii) by masking, and (iv) by dot-blotting on a nylon or nitrocellulose hybridization membrane. Oligonucleotides can be immobilized via a linker, including by covalent, ionic, or physical linkage. Linkers for immobilizing nucleic acids and polypeptides, including reversible or cleavable linkers, are known in the art. See, for example, U.S. Pat. No. 5,451,683 and WO98/20019. Alternatively, oligonucleotides can be non-covalently immobilized on a substrate by hybridization to anchors, by means of magnetic beads, or in a fluid phase such as in microtiter wells or capillaries. Immobilized oligonucleotide probes are typically about 20 nucleotides in length, but can vary from about 10 nucleotides to about 1000 nucleotides in length.

Arrays can include multiple detection blocks (i.e., multiple groups of probes designed for detection of particular polymorphisms). Such arrays can be used to analyze multiple different polymorphisms. Detection blocks may be grouped within a single array or in multiple, separate arrays so that varying conditions (e.g., conditions optimized for particular polymorphisms) may be used during the hybridization. For example, it may be desirable to provide for the detection of those polymorphisms that fall within G-C rich stretches of a genomic sequence, separately from those falling in A-T rich segments. General descriptions of using oligonucleotide arrays for detection of polymorphisms can be found, for example, in U.S. Pat. Nos. 5,858,659 and 5,837,832. In addition to oligonucleotide arrays, cDNA arrays may be used similarly in certain embodiments.

The methods described herein can include providing an array as described herein; contacting the array with a sample (e.g., all or a portion of genomic DNA that includes at least a portion of a human chromosome comprising a response allele) and/or optionally, a different portion of genomic DNA (e.g., a portion that includes a different portion of one or more human chromosomes), and detecting binding of a nucleic acid from the sample to the array. Optionally, the method includes amplifying nucleic acid from the sample, e.g., genomic DNA that includes a portion of a human chromosome described herein, and, optionally, a region that includes another region associated with a diagnosis of an SSD, severity of an SZ endophenotype, or a predicted response to a method of treating SZ, SD, or SPD, prior to or during contact with the array.

In some aspects, the methods described herein can include using an array that can ascertain differential expression patterns or copy numbers of one or more genes in samples from normal and affected individuals (see, e.g., Redon et al., *Nature* 444(7118):444-54 (2006)). For example, arrays of probes to a marker described herein can be used to measure polymorphisms between DNA from a subject having a known severity of an SSD (e.g., SZ) endophenotype, and control DNA, e.g., DNA obtained from an individual that does not have an SSD (e.g., SZ) endophenotype, or has a different severity of the SSD (e.g., SZ) endophenotype. Since the clones on the array contain sequence tags, their positions on the array are accurately known relative to the genomic sequence. Different hybridization patterns between DNA from an individual afflicted with a severe SSD (e.g., SZ) endophenotype and DNA from a normal individual (or an individual with SZ not displaying the endophenotype, or displaying a more or less severe degree of the endophenotype) at areas in the array corresponding to markers as described herein, indicate the severity of the endophenotype. Methods for array production, hybridization, and analysis are described, e.g., in Snijders et al., *Nat. Genetics* 29:263-264 (2001); Klein et al., *Proc. Natl. Acad. Sci. USA* 96:4494-4499 (1999); Albertson et al., *Breast Cancer Research and Treatment* 78:289-298 (2003); and Snijders et al., "BAC microarray based comparative genomic hybridization," in: Zhao et al. (eds), *Bacterial Artificial Chromosomes: Methods and Protocols*, Methods in Molecular Biology, Humana Press, 2002.

In another aspect, this document provides methods of determining the absence or presence of one or more alleles associated with severity of an SSD (e.g., SZ) endophenotype as described herein, using an array described above. The methods can include providing a two dimensional array having a plurality of addresses, each address of the plurality being positionally distinguishable from each other address of the plurality having a unique nucleic acid capture probe, contacting the array with a first sample from a test subject, and comparing the binding of the first sample with one or more references, e.g., binding of a sample from a subject who has a known severity of an SSD (e.g., SZ) endophenotype, and/or binding of a sample from a subject who has a different known severity of the endophenotype, e.g., is unaffected, e.g., a control sample from a subject who has SZ but displays the endophenotype to a more or less severe degree. In some embodiments, the methods can include contacting the array with a second sample from a subject who has a known severity of an SSD (e.g., SZ) endophenotype; and comparing the binding of the first sample with the binding of the second sample. In some embodiments, the methods can include contacting the array with a third sample from a cell or subject that does not display an SSD (e.g., SZ) endophenotype (e.g., a low score); and comparing the binding of the first sample with the binding of the third sample. In some embodiments, the second and third samples are from first or second-degree relatives of the test subject. In the case of a nucleic acid hybridization, binding with a capture probe at an address of the plurality, can be detected by any method known in the art, e.g., by detection of a signal generated from a label attached to the nucleic acid.

Schizophrenia Spectrum Disorders

The methods described herein can be used to determine severity of an endophenotype of a schizophrenia spectrum disorder (SSD) in an individual diagnosed with the SSD. The SSDs include schizophrenia (SZ), schizotypal personality disorder (SPD), and schizoaffective disorder (SD). Methods for diagnosing SSDs are known in the art, see, e.g., the *Diagnostic and Statistical Manual of Mental Disorders—Fourth Edition* ("DSM-IV"). See, e.g., WO 2009/092032, incorporated herein by reference.

Psychiatric Endophenotypes

A number of endophenotypes, i.e., intermediate phenotypes, that may more closely reflect biological mechanisms behind SZ, have been suggested, such as prepulse inhibition, structural abnormalities evident in MRI scans, specific domains of cognition (e.g., executive function), fine motor performance, and working memory, inter alia.

Endophenotypes also can include clinical manifestations such as hallucinations, paranoia, mania, depression, obsessive-compulsive symptoms, etc., as well as response or lack of response to drugs and comorbidity for substance and alcohol abuse. See, e.g., Kendler et al., *Am J Psychiatry* 152(5): 749-54 (1995); Gottesman and Gould, *Am J Psychiatry* 160 (4):636-45 (2003); Cadenhead, *Psychiatric Clinics of North America* 25(4):837-53 (2002); Heinrichs, *Neuroscience & Biobehavioral Reviews* 28(4):379-94 (2004); and Zobel and Maier, *Nervenarzt.* 75(3):205-14 (2004). There is now evidence that some candidate genes that were identified using DSM-IV type categorical definitions for "affected" individuals may influence specific endophenotypes, see, e.g., Baker et al., *Biol Psychiatry* 58(1):23-31 (2005); Cannon et al., *Arch Gen Psychiatry* 62(11):1205-13 (2005); Gothelf et al., *Nat Neurosci* 8(11):1500-2 (2005); Hallmayer et al., *Am J Hum Genet* 77(3):468-76 (2005); Callicott et al., *Proc Natl Acad Sci USA* 102(24):8627-32 (2005); Gornick et al., *J Autism Dev Disord* 1-8 (2005). Thus, the methods described herein can be used to associate alleles with specific psychiatric endophenotypes.

Positive and Negative Syndrome Scale (PANSS)

The Positive and Negative Syndrome Scale (PANSS) is a comprehensive psychometric scale used to classify psychopathology for severe neuropsychiatric diseases, including SZ. It measures a number of psychiatric endophenotypes or dimensions using quantitative scales based on the scoring of patients by clinicians. It is widely used to classify patients into specific subtypes, and is commonly used for measuring the improvement of symptoms in response to clinical interventions (Kay et al., *Schizophr. Bull.* 13:261-276 (1987); Kay et al., *Br. J. Psychiatry Suppl* 59-67 (1989); Leucht et al., *Schizophr. Res.* 79:231-238 (2005)).

PANSS comprises 30 individual subscales. Seven constitute a Positive Symptom Scale, seven make up a Negative Symptom Scale, and the remaining 16 items make up a General Psychopathology Scale. The scores for these scales are arrived at by summation of ratings across component items. Therefore, the potential ranges are 7 to 49 for the Positive and Negative Scales, and 16 to 112 for the General Psychopathology Scale (Source: The PANSS Institute). Detailed information on PANSS and Scoring Criteria can be found at www-.panss.org or in the book *Positive and Negative Syndromes in Schizophrenia*, Stanley R. Kay, 1991, ISBN: 978-0-87630-608-6, Routledge, which is incorporated herein in its entirety by reference. Based on these sources, the methodology is summarized briefly below.

Each of the 30 items is accompanied by a specific definition as well as detailed anchoring criteria for all seven rating points. These seven points represent increasing levels of psychopathology, as follows:

1—absent
2—minimal
3—mild
4—moderate
5—moderate severe
6—severe
7—extreme

The individual PANSS Individual subscales are described below.

P1. DELUSIONS—Beliefs which are unfounded, unrealistic and idiosyncratic.

P2. CONCEPTUAL DISORGANIZATION—Disorganized process of thinking characterized by disruption of goal-directed sequencing, e.g. circumstantiality, loose associations, tangentiality, gross illogicality or thought block.

P3. HALLUCINATORY BEHAVIOR—Verbal report or behavior indicating perceptions which are not generated by external stimuli. These may occur in the auditory, visual, olfactory or somatic realms.

P4. EXCITEMENT—Hyperactivity as reflected in accelerated motor behavior, heightened responsivity to stimuli, hypervigilance or excessive mood lability.

P5. GRANDIOSITY—Exaggerated self-opinion and unrealistic convictions of superiority, including delusions of extraordinary abilities, wealth, knowledge, fame, power and moral righteousness.

P6. SUSPICIOUSNESS/PERSECUTION—Unrealistic or exaggerated ideas of persecution, as reflected in guardedness, ad distrustful attitude, suspicious hypervigilance or frank delusions that others mean harm.

P7. HOSTILITY—Verbal and nonverbal expressions of anger and resentment, including sarcasm, passive-aggressive behavior, verbal abuse and assualtiveness.

N1. BLUNTED AFFECT—Diminished emotional responsiveness as characterized by a reduction in facial expression, modulation of feelings and communicative gestures.

N2. EMOTIONAL WITHDRAWAL—Lack of interest in, involvement with, and affective commitment to life's events.

N3. POOR RAPPORT—Lack of interpersonal empathy, openness in conversation and sense of closeness, interest or involvement with the interviewer. This is evidenced by interpersonal distancing and reduced verbal and nonverbal communication.

N4. PASSIVE/APATHETIC SOCIAL WITHDRAWAL—Diminished interest and initiative in social interactions due to passivity, apathy, anergy or avolition. This leads to reduced interpersonal involvements and neglect of activities of daily living.

N5. DIFFICULTY IN ABSTRACT THINKING—Impairment in the use of the abstract-symbolic mode of thinking, as evidenced by difficulty in classification, forming generalizations and proceeding beyond concrete or egocentric thinking in problem-solving tasks.

N6. LACK OF SPONTANEITY AND FLOW OF CONVERSATION—Reduction in the normal flow of communication associated with apathy, avolition, defensiveness or cognitive deficit. This is manifested by diminished fluidity and productivity of the verbal interactional process.

N7. STEREOTYPED THINKING—Decreased fluidity, spontaneity and flexibility of thinking, as evidenced in rigid, repetitious or barren thought content.

G1. SOMATIC CONCERN—Physical complaints or beliefs about bodily illness or malfunctions. This may range from a vague sense of ill being to clear-cut delusions of catastrophic physical disease.

G2. ANXIETY—Subjective experience of nervousness, worry, apprehension or restlessness, ranging from excessive concern about the present or future to feelings of panic.

G3. GUILT FEELINGS—Sense of remorse or self-blame for real or imagined misdeeds in the past.

G4. TENSION—Overt physical manifestations of fear, anxiety, and agitation, such as stiffness, tremor, profuse sweating and restlessness.

G5. MANNERISMS AND POSTURING—Unnatural movements or posture as characterized be an awkward, stilted, disorganized, or bizarre appearance.

G6. DEPRESSION—Feelings of sadness, discouragement, helplessness and pessimism.

G7. MOTOR RETARDATION—Reduction in motor activity as reflected in slowing or lessening or movements and speech, diminished responsiveness of stimuli, and reduced body tone.

G8. UNCOOPERATIVENESS—Active refusal to comply with the will of significant others, including the interviewer, hospital staff or family, which may be associated with distrust, defensiveness, stubbornness, negativism, rejection of authority, hostility or belligerence.

G9. UNUSUAL THOUGHT CONTENT—Thinking characterized by strange, fantastic or bizarre ideas, ranging from those which are remote or atypical to those which are distorted, illogical and patently absurd.

G10. DISORIENTATION—Lack of awareness of one's relationship to the milieu, including persons, place and time, which may be due to confusion or withdrawal.

G11. POOR ATTENTION—Failure in focused alertness manifested by poor concentration, distractibility from internal and external stimuli, and difficulty in harnessing, sustaining or shifting focus to new stimuli.

G12. LACK OF JUDGMENT AND INSIGHT—Impaired awareness or understanding of one's own psychiatric condition and life situation. This is evidenced by failure to recognize past or present psychiatric illness or symptoms, denial of need for psychiatric hospitalization or treatment, decisions characterized by poor anticipation or consequences, and unrealistic short-term and long-range planning G13. DISTURBANCE OF VOLITION—Disturbance in the willful initiation, sustenance and control of one's thoughts, behavior, movements and speech.

G14. POOR IMPULSE CONTROL—Disordered regulation and control of action on inner urges, resulting in sudden, unmodulated, arbitrary or misdirected discharge of tension and emotions without concern about consequences.

G15. PREOCCUPATION—Absorption with internally generated thoughts and feelings and with autistic experiences to the detriment of reality orientation and adaptive behavior.

G16. ACTIVE SOCIAL AVOIDANCE—Diminished social involvement associated with unwarranted fear, hostility, or distrust.

Differential Diagnosis and Optimizing Treatment

Each patient's disease manifestation and process is unique. PANSS provides a structured, objective way of describing the various aspects of psychopathology of a given patient. However, proper implementation of the PANSS requires highly trained personnel to conduct the assessment and to interpret the results, and there is potential for site to site variability, especially outside the research setting. Additionally, PANSS does not allow one to determine genetic (or biological) vs. environmental contributions to psychopathology, or which of the many possible genetic contributions are relevant to a particular patient.

Each of the PANSS composite scales and subscales can be considered a clinical endophenotype. The ability to link genetic profiles to these clinical endophenotypes, as described herein, will enable clinicians to refine a patient's diagnosis and develop a personalized therapeutic strategy for each patient. For example, the C allele of rs3096489, located in the COL25A1 gene, is associated with increased in the Negative Symptom of Increased Difficulty with Abstract Thinking as shown in the regression analysis in Table 2. By identifying these genetic contributions to specific endophenotypes, the physician can create a personalized diagnosis and treatment regime for the patient.

Results of the methods described herein (e.g., identifying a specific allele in a subject), and optionally interpretive information, can be returned to the subject, the health care provider or to a third party payor. The results can be provided, e.g., in the form of a report; thus, the methods can include preparing a report comprising the results of a method described herein, and identifying information regarding the subject, and optionally interpretive information (e.g., information regarding the association of the allele in the subject with a particular endophenotype).

The results can be used in a number of ways. The information can be, e.g., communicated to the tested subject, e.g., with a diagnosis/prognosis and optionally interpretive materials that help the subject understand the test results and diagnosis/prognosis. The information can be used, e.g., by a health care provider, to determine whether a subject should be assigned to a specific category (e.g., a category associated with a specific disease endophenotype). The information can be used, e.g., by a third party payor such as a healthcare payer (e.g., insurance company or HMO) or other agency, to determine whether or not to reimburse a health care provider for services to the subject, or whether to approve the provision of services to the subject. For example, the healthcare payer may decide to reimburse a health care provider for treatments for SZ, SD, or SPD if the subject has an allele associated with a particular severity of an SSD endophenotype. In some embodiments, the results are used by a health care provider to select, change, or optimize treatment for the subject.

The addition of a genotype/allele profile which details a patient's individual predicted increased or decreased symptom burden for endophenotypes can provide the treating physician with valuable information required to create an enhanced, personalized treatment regimen for the patient. Thus, the methods described herein can be used to select an antipsychotic medication for the subject, according to treatment and clinical methods known in the art. For example, the methods can include selecting clozapine for positive symptom endophenotypes; quetiapine for subjects with hostility and aggression endophenotypes; olanzapine, clozapine, or amilsupride for negative symptom endophenotypes; and glutamate receptor modulators (several are presently in Phase III clinical trials) for cognitive endophenotypes.

Standard treatment regimens for the majority of patients diagnosed as having SZ typically include polypharmacy. See Pickar et al., PLoS ONE 3(9):e3150 (2008). Physicians often add antidepressants, mood stabilizers, and anti-anxiety medications to the customary treatment with antipsychotics. Additionally, non-medication based therapies such as electroconvulsive shock and cognitive behavioral therapy augment the drug treatment. Thus, in addition, the identification of endophenotypes by a method described herein can be used as an objective criterion to optimize selection of a second drug for administration to the subject. For example, if a patient's allele equates to a reference allele that indicates a likely increased burden for depression, the treating physician might choose to augment antipsychotic therapy with antidepressants. Similarly, an allele that indicates increased symptom burden of mania would suggest that the physician add a mood stabilizer to the patient's drug regimen. An allele associated with disorientation, inattention, lack of judgment or insight, preoccupation, or poor impulse control would indicate administration of a drug for ADHD, e.g., a non-stimulant (such as Atomoxetine (Strattera) or modafinil) or a stimulant, e.g., amphetamine methylphenidate (Ritalin, Metadate, Concerta), dextroamphetamine (Dexedrine), mixed amphetamine salts (Adderall), dextromethamphetamine (Desoxyn) or lisdexamfetamine (Vyvanse). Additional exemplary choices of drugs to be used in addition to an antipsychotic for treating a subject identified as having a specific endophenotype are shown below in Table 4. Changes in a patient's PANSS score and clinical endophenotype can be evaluated following the addition or subtraction of medications or non-medication based therapies with the goal of optimizing treatment for that patient. See, e.g., Chung et al., World J Biol Psychiatry 10(2): 156-62 (2009); Hori et al., World J Biol Psychiatry August 25 E-Pub: 1-5 (2009); Lipkovich et al., BMC Psychiatry 9:44 (2009); Hwang et al., Int Clin Psychopharmacol 24(4):189-98 (2009).

TABLE 4

Example Treatments for Specific Endophenotypes, e.g., in Combination with Anti-Psychotics

| PANSS Item | Treatment/ Drug Class | Example Drug Trade name | Generic name |
|---|---|---|---|
| P1-delusions | Cognitive Behavioral Therapy (CBT) | | |
| P2-conceptual disorganization | CBT | | |
| P3-hallucinatory behavior | CBT | | |
| P4-exitement | Mood stabilizer | | lithium, valproate, lamotrigine |
| P5-grandiosity | Mood stabilizer | | lithium, valproate, lamotrigine |
| P6-suspiciousness | Anti-anxiety | | benzodiazepines |
| P7-hostility | Anti-anxiety | | benzodiazepines |
| N1-blunted affect | SSRI | Prozac | Fluoxetine |
| | NMDA-R agonists | | glycine, d-cycloserine, and d-serine |
| N2-emotional withdrawal | SSRI | Prozac | Fluoxetine |
| | NMDA-R agonists | | glycine, d-cycloserine, and d-serine |
| N3-poor rapport | SSRI | Prozac | Fluoxetine |
| | NMDA-R agonists | | glycine, d-cycloserine, and d-serine |
| N4-passive/appathetic social withdrawal | SSRI | Prozac | Fluoxetine |
| | NMDA-R agonists | | glycine, d-cycloserine, and d-serine |
| N5-difficulty in abstract thinking | NMDA-R agonists | | glycine, d-cycloserine, and d-serine |
| N6-lack of spontaneity and flow of conversation | NMDA-R agonists | | glycine, d-cycloserine, and d-serine |
| N7-stereotyped thinking | NMDA-R agonists | | glycine, d-cycloserine, and d-serine |
| G1-somatic concern | SNRI | Cymbalta | duloxetine |
| G2-anxiety | Anti-anxiety | | benzodiazepines |
| G3-guilt feelings | SSRI | Prozac | fluoxetine |
| G4-tension | Mood stabilizer | | lithium, valproate, lamotrigine |
| G5-mannerisms and posturing | Mood stabilizer | | lithium, valproate, lamotrigine |
| G6-depression | SSRI | Prozac | Fluoxetine |
| G7-motor retardation | Dopaminergics | | |
| G8-uncooperativeness | | | Levomepromazine |
| G9-unusual thought content | CBT | | |
| G10-disorentation | ADHD treatment | Stratera, Ritalin | atomoxetine, methylphenidate |
| G11-poor attention | ADHD treatment; cholinesterase inhibitors | Stratera, Ritalin | atomoxetine, methylphenidate |
| G12-lack of judgment and insight | ADHD treatment; cholinesterase inhibitors | Stratera, Ritalin | atomoxetine, methylphenidate |
| G13-disturbance of volition | cholinesterase inhibitors | | |

TABLE 4-continued

Example Treatments for Specific Endophenotypes, e.g., in Combination with Anti-Psychotics

| | | Example Drug | |
|---|---|---|---|
| PANSS Item | Treatment/ Drug Class | Trade name | Generic name |
| G14-poor impulse control | ADHD treatment; beta-blockers mood stabilizers, | Stratera, Ritalin | atomoxetine, methylphenidate<br><br>lithium, valproate, lamotrigine |
| G15-preoccupation | ADHD treatment; cholinesterase inhibitors | Stratera, Ritalin | atomoxetine, methylphenidate |
| G16-active social avoidance. | CBT; cholinesterase inhibitors | | |

SSRI = selective serotonin reuptake inhibitors
SNRI = serotonin-norepinephrine reuptake inhibitor
ADHD = attention deficit hyperactivity disorder In some cases, a medical or research professional can assess whether a subject has an allele contributing to a clinical endophenotype according to the methods provided herein. Medical professionals can be, for example, doctors, nurses, medical laboratory technologists, and pharmacists. Research professionals can be, for example, principle investigators, research technicians, postdoctoral trainees, and graduate students. A professional can be assisted by (1) determining whether specific polymorphic variants are present in a biological sample from a subject, and (2) communicating information about polymorphic variants to that professional.

Using information about specific polymorphic variants obtained using a method described herein, a medical professional can take one or more actions that can affect patient care. For example, a medical professional can record information in the patient's medical record regarding the presence or absence of an SSD (e.g., SZ) endophenotype. In some cases, a medical professional can record information regarding an SSD (e.g., SZ) endophenotype, or otherwise transform the patient's medical record, to reflect the patient's current medical condition. In some cases, a medical professional can review and evaluate a patient's entire medical record and assess multiple treatment strategies for clinical intervention of a patient's condition.

In some cases, a medical professional can initiate or modify treatment after receiving genetic information regarding endophenotype. In some cases, a medical professional can recommend a change in therapy. In some cases, a medical professional can enroll a patient in a clinical trial for, by way of example, detecting correlations between an allele as described herein and any measurable or quantifiable parameter relating to an endophenotype as described above.

A medical professional can communicate information regarding severity of an SSD (e.g., SZ) endophenotype to a patient or a patient's family. In some cases, a medical professional can provide a patient and/or a patient's family with information regarding SSDs and severity of endophenotype information, including treatment options, prognosis, and referrals to specialists. In some cases, a medical professional can provide a copy of a patient's medical records to a specialist.

A research professional can apply information regarding the presence of alleles associated with a severity of an SSD (e.g., SZ) endophenotype in a subject to advance scientific research. For example, a researcher can compile data on specific polymorphic variants. In some cases, a research professional can obtain information regarding the identity of an allele associated with a specific endophenotype in a subject as described herein to evaluate a subject's enrollment, or continued participation, in a research study or clinical trial. In some cases, a research professional can communicate information regarding a subject's alleles associated with severity of an SSD (e.g., SZ) endophenotype to a medical professional. In some cases, a research professional can refer a subject to a medical professional.

Any appropriate method can be used to communicate information to another person (e.g., a professional). For example, information can be given directly or indirectly to a professional. For example, a laboratory technician can input a patient's polymorphic variant alleles as described herein into a computer-based record. In some cases, information is communicated by making a physical alteration to medical or research records. For example, a medical professional can make a permanent notation or flag a medical record for communicating the risk assessment to other medical professionals reviewing the record. In addition, any type of communication can be used to communicate allelic, genotypic, severity of endophenotype, and/or treatment information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

Articles of Manufacture

Also provided herein are articles of manufacture comprising a probe that hybridizes with a region of human chromosome as described herein and can be used to detect a polymorphism described herein. For example, any of the probes for detecting polymorphisms described herein can be combined with packaging material to generate articles of manufacture or kits. The kit can include one or more other elements including: instructions for use; and other reagents such as a label or an agent useful for attaching a label to the probe. Instructions for use can include instructions for diagnostic applications of the probe for assessing the severity of an SSD (e.g., SZ) endophenotype in a method described herein. Other instructions can include instructions for attaching a label to the probe, instructions for performing in situ analysis with the probe, and/or instructions for obtaining a sample to be analyzed from a subject. In some cases, the kit can include a labeled probe that hybridizes to a region of human chromosome as described herein.

The kit can also include one or more additional reference or control probes that hybridize to the same chromosome or another chromosome or portion thereof that can have an abnormality associated with a particular endophenotype. A kit that includes additional probes can further include labels, e.g., one or more of the same or different labels for the probes. In other embodiments, the additional probe or probes provided with the kit can be a labeled probe or probes. When the kit further includes one or more additional probe or probes, the kit can further provide instructions for the use of the additional probe or probes. Kits for use in self-testing can also be provided. Such test kits can include devices and instructions that a subject can use to obtain a biological sample (e.g., buccal cells, blood) without the aid of a health care provider. For example, buccal cells can be obtained using a buccal swab or brush, or using mouthwash.

Kits as provided herein can also include a mailer (e.g., a postage paid envelope or mailing pack) that can be used to return the sample for analysis, e.g., to a laboratory. The kit can include one or more containers for the sample, or the sample can be in a standard blood collection vial. The kit can also include one or more of an informed consent form, a test requisition form, and instructions on how to use the kit in a method described herein. Methods for using such kits are also included herein. One or more of the forms (e.g., the test requisition form) and the container holding the sample can be coded, for example, with a bar code for identifying the subject who provided the sample.

Databases and Reports

Also provided herein are databases that include a list of polymorphisms as described herein, and wherein the list is largely or entirely limited to polymorphisms identified as useful for determining severity of an SSD (e.g., SZ) endophenotype as described herein. The list is stored, e.g., on a flat file or computer-readable medium. The databases can further include information regarding one or more subjects, e.g., whether a subject is affected or unaffected, clinical information such as endophenotype, age of onset of symptoms, any treatments administered and outcomes (e.g., data relevant to pharmacogenomics, diagnostics or theranostics), and other details, e.g., about the disorder in the subject, or environmental or other genetic factors. The databases can be used to detect correlations between a particular severity of an SSD (e.g., SZ) endophenotype and the information regarding the subject.

The methods described herein can also include the generation of reports, e.g., for use by a patient, care giver, payor, or researcher, that include information regarding a subject's response allele(s), and optionally further information such as treatments administered, treatment history, medical history, predicted response, and actual response. The reports can be recorded in a tangible medium, e.g., a computer-readable disk, a solid state memory device, or an optical storage device.

Engineered Cells and Methods of Screening

Also provided herein are engineered cells that harbor one or more polymorphism described herein, e.g., one or more polymorphisms associated with severity of one or more SSD (e.g., SZ) endophenotypes. Such cells are useful for studying the effect of a polymorphism on physiological function, and for identifying and/or evaluating potential therapeutic agents such as anti-psychotics for the treatment of specific SSD endophenotypes. Methods of using such cells to identify candidate therapeutics for the treatment of SZ are known in the art, e.g., contacting the cells with a test compound and assaying for an effect of the test compound on the cell. The methods can also include detecting an effect of a polymorphism described herein on the activity or levels of a gene or protein associated with that polymorphism, to identify a target for therapeutics.

As one example, included herein are cells in which one of the various alleles of the genes described herein has be recreated that is associated with a particular severity of an SSD (e.g., SZ) endophenotype. Methods are known in the art for generating cells, e.g., by homologous recombination between the endogenous gene and an exogenous DNA molecule introduced into a cell, e.g., a cell of an animal. In some cases, the cells can be used to generate transgenic animals using methods known in the art.

The cells are preferably mammalian cells (e.g., neuronal type cells) in which an endogenous gene has been altered to include a polymorphism as described herein. Techniques such as targeted homologous recombinations, can be used to insert the heterologous DNA as described in, e.g., Chappel, U.S. Pat. No. 5,272,071; WO 91/06667, published in May 16, 1991.

EXAMPLES

The invention is further described in the following examples, which do not limit the scope of the invention described in the claims.

Example 1

Novel Markers Associated with Overall Psychiatric Endophenotypes in SZ

The Clinical Antipsychotic Trials of Intervention Effectiveness (CATIE), a large federally funded clinical trial designed to assess the efficacy of antipsychotics in a real world setting, is a valuable resource for determining the role of genes in drug response (Stroup et al., Schizophr. Bull. 29:15-31 (2003); Lieberman et al., N. Engl. J. Med. 353: 1209-1223 (2005)). As part of the CATIE trial, SNP genotyping was performed for roughly half of the trial participants (Sullivan et al., Mol. Psychiatry. 13:570-584 (2008)). When combined with disease status, PANSS scores, and clinical drug response data, the genotyping data allows the identification of genetic variants (e.g., SNPs) that are statistically associated with specific endophenotypes.

The design of the CATIE study has been described in detail by others (see, e.g., Stroup et al., Schizophr. Bull. 29:15-31 (2003); Lieberman et al., N. Engl. J. Med. 353:1209-1223 (2005)). Briefly, 1460 subjects were randomly assigned one of several antipsychotics and those who did not respond or chose to quit their current medication were re-randomized to another drug. Details regarding SNP genotyping and quality control have been recently published (Sullivan et al., Mol. Psychiatry. 13:570-584 (2008)).

Genotype and phenotype data for the CATIE trial were made available to qualified researchers through the NIMH Center for Collaborative Genetic Studies on Mental Disorders. Data for 417 patients with schizophrenia and 419 unaffected controls self reported as having exclusively European ancestry were evaluated. This same patient population was described in a recent study by Sullivan and coworkers, which confirmed that there is no hidden stratification in the sample (Sullivan et al., Mol. Psychiatry. 13:570-584 (2008)).

For the CATIE study, individual cases were diagnosed as having SZ based on DSM-III/IV criteria.

Confirmation of SNP Effects on Psychiatric Endophenotypes

Genotype and PANSS phenotype data were evaluated for 417 SZ patients enrolled in the CATIE trial. Following a period of drug wash-out, the CATIE study investigators rated each participant at baseline for psychopathology using the PANSS.

Each of the individual and composite scores is a quantitative trait that can be assessed using quantitative statistical genetics methods. Genetic analysis to determine the influence of haplotypes on quantitative PANSS values was performed using the PLINK 1.03 whole genome analysis toolset developed by Purcell and coworkers (Purcell et al., *Am. J. Hum. Genet.* 81:559-575 (2007). For dichotomous values, PLINK calculates P values for the allele-specific chi-squared test and the odds ratio (OR; or relative risk) associated with the minor allele. For quantitative values, PLINK performs a linear regression using an additive model for the minor allele.

Tables 1-3 report results for specific SNP alleles that affect quantitative endophenotypes for SZ, along with Beta values and P values for the particular alleles of SNPs listed therein. The Beta, beta weight from the regression, measures the impact of the SNP allele on the particular scale. A positive Beta means that the allele for the test SNP increases the score for that measure of psychopathology by the stated Beta value, while a negative Beta means that the allele for the test SNP decreases the score that for that measure of psychopathology by the stated Beta value.

Table 1 shows selected examples for PANSS Total score, and Table 2 shows selected examples for Positive Symptoms subscale, Negative Symptoms subscale, and the General Psychopathology subscale, analyzed as quantitative traits in PLINK using linear regression.

Table 3 shows selected examples for the individual PANSS components. The component evaluated in each row is identified by one of the following abbreviations: Positive Symptoms: P1—delusions, P2—conceptual disorganization, P3—hallucinatory behavior, P4—excitement, P5—grandiosity, P6—suspiciousness, P7—hostility; Negative Symptoms: N1—blunted affect, N2—emotional withdrawal, N3—poor rapport, N4—passive/apathetic social withdrawal, N5—difficulty in abstract thinking, N6—lack of spontaneity and flow of conversation, N7—stereotyped thinking; General Psychopathology Symptoms: G1—somatic concern, G2—anxiety, G3—guilt feelings, G4-tension, G5—mannerisms and posturing, G6—depression, G7—motor retardation, G8—uncooperativeness, G9—unusual thought content, G10—disorientation, G11—poor attention, G12—lack of judgment and insight, G13 disturbance of volition, G14—poor impulse control, G15—preoccupation, G16—active social avoidance.

Table A lists the chromosome and position for each SNP, by SEQ ID NO.; the genomic position is relative to NCBI Human Genome Reference Assembly Build 36.3.

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

TABLE 1

Alleles Influencing Total PANSS

| Gene | SEQ ID NO: | NCBI RS # | Allele | Beta | P |
|---|---|---|---|---|---|
| KIF1B | 3 | 1555849 | G | 2.66 | 0.0467 |
| CGN | 16 | 1547832 | A | −3.95 | 0.0421 |
| RALGPS2 | 32 | 12076230 | G | −3.02 | 0.0169 |
| USH2A | 42 | 7548730 | C | 2.92 | 0.0239 |
| RYR2 | 66 | 2779400 | A | −2.62 | 0.0355 |
| CHRM3 | 69 | 16838633 | G | 2.40 | 0.0397 |
| FMN2 | 86 | 10926257 | T | 5.23 | 0.0181 |
| AGBL4-C1ORF165 | 91 | 319965 | A | 2.78 | 0.0262 |
| SCP2 | 98 | 3766762 | C | −6.05 | 0.0383 |
| ELTD1 | 100 | 17102632 | T | 3.37 | 0.0425 |
| HPCAL1 | 105 | 16856020 | T | 4.55 | 0.0102 |
| NTSR2 | 108 | 4669767 | C | −2.99 | 0.0158 |
| RAB3GAP1 | 112 | 16831315 | C | 4.04 | 0.0490 |
| KYNU | 130 | 10176234 | A | 2.57 | 0.0375 |
| ARHGAP15 | 141 | 13031917 | C | 2.65 | 0.0353 |
| FMNL2 | 144 | 2164402 | G | −3.03 | 0.0327 |
| KCNJ3 | 149 | 2961962 | C | −2.71 | 0.0244 |
| PKP4 | 158 | 2528582 | G | −3.43 | 0.0072 |
| PKP4 | 159 | 2711072 | C | 2.73 | 0.0354 |

TABLE 1-continued

Alleles Influencing Total PANSS

| Gene | SEQ ID NO: | NCBI RS # | Allele | Beta | P |
|---|---|---|---|---|---|
| SCN3A | 165 | 11677254 | C | −3.94 | 0.0018 |
| SCN9A | 169 | 7589835 | A | 4.64 | 0.0134 |
| PDE1A | 177 | 13400054 | C | −3.25 | 0.0367 |
| PDE1A | 190 | 9332425 | T | −2.50 | 0.0493 |
| NRP2 | 203 | 955395 | T | −3.37 | 0.0064 |
| NRP2 | 205 | 6435306 | A | −2.70 | 0.0272 |
| PIP5K3 | 207 | 10497899 | T | −9.28 | 0.0055 |
| SAG | 220 | 2304773 | A | 5.04 | 0.0106 |
| SAG | 221 | 894100 | A | 2.74 | 0.0406 |
| KLHL29 | 225 | 6727901 | G | −2.60 | 0.0383 |
| KLHL29 | 227 | 7560892 | A | −2.50 | 0.0392 |
| KCNK3 | 228 | 7584568 | G | −2.55 | 0.0404 |
| DPYSL5 | 231 | 540490 | T | 2.63 | 0.0320 |
| DPYSL5 | 232 | 3769138 | G | 2.47 | 0.0442 |
| SLC8A1 | 246 | 417614 | A | 2.70 | 0.0427 |
| SLC8A1 | 247 | 2072531 | T | −2.48 | 0.0411 |
| SLC8A1 | 248 | 417591 | G | 3.06 | 0.0352 |
| SLC8A1 | 249 | 11885401 | C | 3.92 | 0.0329 |
| PLEKHH2 | 254 | 2288710 | C | 5.00 | 0.0393 |
| C2ORF34 | 261 | 1067378 | A | −3.54 | 0.0120 |
| C2ORF34 | 264 | 1067402 | T | −3.20 | 0.0284 |
| C2ORF34 | 265 | 698792 | A | −3.09 | 0.0330 |
| C2ORF34 | 266 | 698823 | G | −2.93 | 0.0318 |
| C2ORF34 | 267 | 698827 | G | −2.72 | 0.0467 |
| C2ORF34 | 275 | 3738980 | C | −4.91 | 0.0037 |
| PRKCE | 277 | 6748375 | C | 2.89 | 0.0155 |
| FBXO11 | 281 | 12620679 | C | −2.57 | 0.0379 |
| PSME4 | 282 | 805391 | T | −3.54 | 0.0029 |
| ACYP2 | 287 | 918357 | G | 2.62 | 0.0282 |
| ACYP2 | 288 | 12615749 | G | −4.46 | 0.0165 |
| ACYP2 | 290 | 17045754 | C | −4.22 | 0.0195 |
| CTNNA2 | 301 | 2566539 | T | −2.94 | 0.0297 |
| CTNNA2 | 302 | 1971766 | A | −2.75 | 0.0288 |
| CTNNA2 | 307 | 895388 | T | −4.50 | 0.0439 |
| CTNNA2 | 312 | 6547316 | T | 2.52 | 0.0451 |
| DDEF2 | 316 | 10204214 | T | 4.32 | 0.0174 |
| PLCXD2 | 320 | 1513331 | C | 3.64 | 0.0362 |
| PLCXD2 | 323 | 6784753 | C | −2.69 | 0.0308 |
| KALRN | 327 | 16835912 | C | 3.37 | 0.0065 |
| CPNE4 | 330 | 10934970 | C | 6.26 | 0.0438 |
| CPNE4 | 331 | 13319291 | G | 2.57 | 0.0419 |
| CPNE4 | 336 | 9289395 | G | 3.12 | 0.0187 |
| RAB6B | 340 | 6765093 | G | 3.07 | 0.0112 |
| CLSTN2 | 356 | 9836487 | G | 2.76 | 0.0251 |
| CLSTN2 | 358 | 4683499 | G | 2.85 | 0.0256 |
| SLC7A14 | 372 | 6788596 | G | −3.22 | 0.0130 |
| PLD1 | 377 | 7633686 | G | −4.21 | 0.0222 |
| HTR3D | 385 | 939334 | G | 2.63 | 0.0430 |
| HTR3D | 386 | 6779545 | A | 3.28 | 0.0102 |
| IL1RAP | 394 | 6791374 | C | −5.85 | 0.0128 |
| RARB | 400 | 17525900 | C | −4.17 | 0.0416 |
| STAC | 413 | 17186340 | T | 4.22 | 0.0484 |
| ULK4 | 415 | 1495698 | C | 3.37 | 0.0094 |
| ULK4 | 417 | 1691966 | G | 4.37 | 0.0003 |
| ULK4 | 419 | 13069172 | G | 4.24 | 0.0004 |
| ERC2 | 447 | 885211 | A | −2.83 | 0.0249 |
| FHIT | 454 | 639244 | G | 3.50 | 0.0068 |
| FHIT | 455 | 2253211 | C | 2.64 | 0.0283 |
| FHIT | 456 | 2121865 | T | 2.61 | 0.0359 |
| CADPS | 471 | 13313979 | A | −2.74 | 0.0387 |
| CADPS | 474 | 17280557 | A | −3.33 | 0.0236 |
| CADPS | 475 | 17280571 | T | −3.21 | 0.0187 |
| CADPS | 477 | 11925708 | A | −2.91 | 0.0163 |
| MAGI1 | 482 | 2371948 | A | 7.83 | 0.0451 |
| GBE1 | 490 | 7622741 | G | 3.30 | 0.0118 |
| GBE1 | 491 | 6769230 | A | 3.27 | 0.0133 |
| GBE1 | 492 | 2307058 | T | 2.96 | 0.0259 |
| GBE1 | 494 | 7613144 | T | 2.90 | 0.0290 |
| GBE1 | 498 | 2680245 | A | −2.44 | 0.0446 |
| HTR1F | 500 | 1027689 | T | 5.15 | 0.0121 |
| ANK2 | 517 | 29306 | G | 3.14 | 0.0233 |
| ANK2 | 518 | 29311 | A | 4.00 | 0.0040 |
| INPP4B | 528 | 2667101 | G | 2.61 | 0.0376 |
| INPP4B | 529 | 2667108 | C | 8.45 | 0.0314 |
| INPP4B | 532 | 336329 | G | 8.45 | 0.0314 |

TABLE 1-continued

Alleles Influencing Total PANSS

| Gene | SEQ ID NO: | NCBI RS # | Allele | Beta | P |
|---|---|---|---|---|---|
| INPP4B | 534 | 2276942 | A | 4.56 | 0.0322 |
| POU4F2 | 538 | 1979903 | C | −5.99 | 0.0175 |
| FSTL5 | 543 | 6825091 | A | 3.12 | 0.0229 |
| FSTL5 | 544 | 7442468 | C | 2.85 | 0.0358 |
| TLL1 | 557 | 11942650 | G | −6.56 | 0.0244 |
| PALLD | 559 | 17054309 | A | −3.49 | 0.0344 |
| PALLD | 564 | 3109206 | T | −2.74 | 0.0255 |
| PALLD | 565 | 11930576 | C | −2.63 | 0.0380 |
| PALLD | 566 | 4425335 | G | −2.92 | 0.0417 |
| ODZ3 | 572 | 2675532 | C | 3.79 | 0.0030 |
| ENPP6 | 574 | 6830766 | G | −2.79 | 0.0260 |
| ENPP6 | 577 | 4340829 | A | −2.65 | 0.0364 |
| ENPP6 | 578 | 6815145 | A | −2.57 | 0.0486 |
| ENPP6 | 579 | 17584049 | C | −3.47 | 0.0057 |
| KIAA1239 | 592 | 2973226 | C | −2.48 | 0.0387 |
| KIAA1239 | 593 | 1382979 | A | −2.88 | 0.0372 |
| LIMCH1 | 598 | 4343753 | T | 3.30 | 0.0201 |
| NPFFR2 | 614 | 17775309 | G | −2.83 | 0.0283 |
| SCARB2 | 616 | 17001533 | C | −3.95 | 0.0274 |
| SCD5 | 621 | 7684732 | C | −3.76 | 0.0163 |
| SCD5 | 622 | 17006038 | C | −4.16 | 0.0121 |
| PDLIM5 | 632 | 6812098 | C | 3.30 | 0.0380 |
| SLC2A9 | 643 | 7671266 | T | −3.12 | 0.0334 |
| FBXL17 | 646 | 11242664 | G | 3.29 | 0.0410 |
| KCNN2 | 654 | 1457762 | A | 2.56 | 0.0346 |
| HSD17B4 | 662 | 246968 | A | −2.49 | 0.0354 |
| SNX2 | 669 | 12109789 | G | 2.49 | 0.0444 |
| SNX2 | 670 | 10519715 | A | 3.11 | 0.0183 |
| SNX24 | 672 | 6888023 | T | 3.11 | 0.0180 |
| SNX24 | 673 | 246286 | T | −2.76 | 0.0328 |
| SNX24 | 674 | 246266 | C | −2.73 | 0.0345 |
| DNAH5 | 686 | 10513155 | A | 2.82 | 0.0289 |
| DNAH5 | 691 | 13154455 | G | 3.35 | 0.0082 |
| ODZ2 | 704 | 2337017 | C | −6.04 | 0.0004 |
| ODZ2 | 707 | 7714651 | A | −4.53 | 0.0148 |
| ODZ2 | 708 | 1421989 | G | −5.09 | 0.0015 |
| ODZ2 | 711 | 6868169 | G | 2.88 | 0.0246 |
| CDH10 | 722 | 3822429 | T | −3.57 | 0.0032 |
| SLC45A2 | 723 | 35388 | T | −2.72 | 0.0199 |
| CMYA5 | 753 | 11960229 | C | 3.66 | 0.0275 |
| CMYA5 | 754 | 6880680 | C | 5.09 | 0.0115 |
| CMYA5 | 755 | 3828611 | G | 5.34 | 0.0158 |
| SEMA5A | 770 | 11134354 | A | −3.63 | 0.0162 |
| NKAIN2 | 794 | 1832252 | G | 2.47 | 0.0424 |
| NKAIN2 | 796 | 1031881 | C | −4.54 | 0.0044 |
| NKAIN2 | 797 | 687667 | A | −3.12 | 0.0487 |
| UTRN | 817 | 11155367 | A | 3.10 | 0.0467 |
| SYNE1 | 819 | 718527 | A | 2.96 | 0.0146 |
| ATXN1 | 841 | 909786 | G | −2.89 | 0.0172 |
| SLC17A4 | 844 | 9358890 | G | 8.10 | 0.0048 |
| SLC17A1 | 845 | 1324082 | A | −3.20 | 0.0299 |
| BTN3A1 | 851 | 17610161 | A | −4.15 | 0.0202 |
| ELOVL5 | 867 | 9474507 | A | 3.73 | 0.0259 |
| KLHL32 | 882 | 1737646 | A | −4.54 | 0.0199 |
| CUX1 | 885 | 2960266 | A | 2.63 | 0.0354 |
| CUX1 | 886 | 2694158 | T | 3.06 | 0.0170 |
| CADPS2 | 892 | 2428769 | G | −2.82 | 0.0281 |
| EXOC4 | 910 | 6954842 | A | 2.81 | 0.0384 |
| DGKI | 916 | 980796 | A | −2.74 | 0.0389 |
| CNTNAP2 | 928 | 6963627 | T | 2.45 | 0.0457 |
| CNTNAP2 | 931 | 11972784 | C | 3.19 | 0.0238 |
| CNTNAP2 | 934 | 10952682 | G | 3.24 | 0.0202 |
| CNTNAP2 | 935 | 6953679 | A | 3.57 | 0.0107 |
| CNTNAP2 | 936 | 700320 | A | 3.89 | 0.0040 |
| CHN2 | 958 | 7781003 | T | −2.79 | 0.0332 |
| CRHR2 | 965 | 2190242 | C | 3.49 | 0.0166 |
| BMPER | 979 | 7806522 | C | −3.72 | 0.0046 |
| BMPER | 981 | 12672492 | A | −2.99 | 0.0345 |
| CDC2L5 | 989 | 9639817 | T | 2.54 | 0.0432 |
| CACNA2D1 | 1037 | 12531682 | T | −3.63 | 0.0071 |
| CACNA2D1 | 1039 | 2237524 | G | −3.87 | 0.0058 |
| CACNA2D1 | 1040 | 7788848 | A | −3.38 | 0.0128 |
| PCLO | 1054 | 4129230 | T | 3.91 | 0.0028 |
| PCLO | 1055 | 10240976 | T | 3.07 | 0.0119 |
| SEMA3E | 1057 | 17287452 | T | −4.42 | 0.0227 |
| SEMA3E | 1061 | 1972459 | C | −2.71 | 0.0381 |
| SEMA3A | 1063 | 6965990 | A | 3.20 | 0.0092 |
| SEMA3A | 1064 | 11976072 | T | 3.05 | 0.0127 |
| SEMA3A | 1066 | 7806871 | G | −3.06 | 0.0131 |
| SEMA3A | 1067 | 17298417 | C | −2.88 | 0.0190 |
| SEMA3A | 1069 | 3801629 | G | 2.81 | 0.0237 |
| SEMA3A | 1070 | 727651 | G | 2.57 | 0.0378 |
| ADAM22 | 1076 | 1688886 | G | 4.01 | 0.0012 |
| ADAM22 | 1077 | 2282948 | C | 3.51 | 0.0055 |
| ADAM22 | 1078 | 2282949 | C | 3.40 | 0.0066 |
| ADAM22 | 1083 | 4140919 | G | 3.35 | 0.0471 |
| NXPH1 | 1086 | 6962955 | A | −2.97 | 0.0163 |
| DYNC1I1 | 1093 | 6968143 | G | 4.08 | 0.0412 |
| GRHL2 | 1096 | 13275653 | C | −2.71 | 0.0346 |
| GRHL2 | 1097 | 4734037 | C | −3.86 | 0.0120 |
| NCALD | 1098 | 1131862 | G | −3.80 | 0.0101 |
| NCALD | 1101 | 2226401 | C | −3.66 | 0.0125 |
| ZFPM2 | 1104 | 1481026 | T | 3.17 | 0.0283 |
| FER1L6 | 1126 | 4355755 | T | −2.85 | 0.0397 |
| FER1L6 | 1127 | 7838453 | A | −3.59 | 0.0024 |
| FER1L6 | 1133 | 7819868 | G | 3.30 | 0.0069 |
| COL22A1 | 1150 | 4475485 | T | −4.12 | 0.0408 |
| CSMD1 | 1179 | 4487803 | G | 3.28 | 0.0112 |
| CSMD1 | 1180 | 17065933 | A | −2.94 | 0.0425 |
| CSMD1 | 1182 | 7829968 | T | 3.21 | 0.0237 |
| CSMD1 | 1185 | 7014880 | A | −2.75 | 0.0204 |
| SFRP1 | 1188 | 4736959 | C | 2.58 | 0.0407 |
| SFRP1 | 1189 | 11781990 | A | 2.82 | 0.0353 |
| MCPH1 | 1197 | 1530408 | C | 3.54 | 0.0247 |
| MCPH1 | 1209 | 2515435 | G | 2.86 | 0.0247 |
| KCNB2 | 1227 | 13251896 | G | −2.61 | 0.0327 |
| KCNB2 | 1230 | 2196904 | C | −2.70 | 0.0378 |
| KCNB2 | 1232 | 13277104 | G | −2.53 | 0.0397 |
| MMP16 | 1236 | 6994019 | T | −3.07 | 0.0256 |
| MMP16 | 1238 | 3844198 | A | −2.99 | 0.0331 |
| MMP16 | 1241 | 4548227 | A | −3.15 | 0.0177 |
| GABBR2 | 1245 | 1930139 | G | −3.17 | 0.0258 |
| ABL1 | 1273 | 10901294 | T | −4.94 | 0.0394 |
| OLFM1 | 1278 | 665748 | A | 6.28 | 0.0044 |
| OLFM1 | 1279 | 542172 | A | 6.02 | 0.0064 |
| KIAA1797 | 1285 | 12338810 | T | −4.00 | 0.0135 |
| KIAA1797 | 1286 | 12336110 | A | −3.94 | 0.0163 |
| KIAA1797 | 1288 | 16938162 | C | 3.99 | 0.0016 |
| KIAA1797 | 1289 | 10511687 | G | 3.87 | 0.0020 |
| KIAA1797 | 1294 | 10511693 | G | 3.60 | 0.0094 |
| KIAA1797 | 1298 | 7030990 | G | 3.66 | 0.0105 |
| KIAA1797 | 1299 | 4977881 | A | 3.38 | 0.0125 |
| KIAA1797 | 1300 | 4468020 | T | 3.24 | 0.0162 |
| TEK | 1308 | 2273719 | T | −3.63 | 0.0418 |
| PIP5K1B | 1317 | 4745375 | T | 3.21 | 0.0184 |
| PCSK5 | 1329 | 914367 | T | −3.25 | 0.0118 |
| NTRK2 | 1335 | 1187321 | A | 4.47 | 0.0069 |
| NTRK2 | 1336 | 1187328 | G | 3.46 | 0.0409 |
| ATE1 | 1363 | 7086628 | C | −2.76 | 0.0196 |
| ATE1 | 1364 | 1219505 | T | −3.04 | 0.0093 |
| MYO3A | 1380 | 3781117 | C | −3.63 | 0.0401 |
| KCNMA1 | 1401 | 7897566 | C | 4.28 | 0.0006 |
| ELMOD1 | 1419 | 683266 | A | 2.66 | 0.0404 |
| MICAL2 | 1422 | 10765929 | T | −2.82 | 0.0286 |
| ARNTL | 1430 | 7107711 | C | −3.27 | 0.0325 |
| SPON1 | 1440 | 10832170 | T | 2.59 | 0.0336 |
| SPON1 | 1441 | 1406356 | A | 2.70 | 0.0285 |
| SPON1 | 1442 | 7116296 | T | −2.45 | 0.0472 |
| INSC | 1445 | 1792571 | A | 3.42 | 0.0146 |
| C11ORF49 | 1453 | 12796744 | T | −2.44 | 0.0483 |
| DLG2 | 1466 | 6592202 | C | −3.34 | 0.0072 |
| DLG2 | 1467 | 4451754 | A | −3.43 | 0.0068 |
| DLG2 | 1469 | 11234194 | C | −2.80 | 0.0278 |
| DLG2 | 1471 | 11234222 | A | −4.38 | 0.0004 |
| DLG2 | 1474 | 6592211 | A | −3.49 | 0.0044 |
| DLG2 | 1475 | 7101454 | C | −3.35 | 0.0067 |
| KCNC2 | 1503 | 10735985 | G | 2.70 | 0.0349 |
| KCNC2 | 1504 | 2471664 | C | 3.44 | 0.0209 |
| NAV3 | 1510 | 10859620 | G | −2.87 | 0.0220 |
| NAV3 | 1513 | 1012088 | G | 3.39 | 0.0127 |

TABLE 1-continued

Alleles Influencing Total PANSS

| Gene | SEQ ID NO: | NCBI RS # | Allele | Beta | P |
|---|---|---|---|---|---|
| NAV3 | 1515 | 7295890 | C | 3.30 | 0.0152 |
| ITGBL1 | 1532 | 4772403 | T | -2.73 | 0.0378 |
| ITGBL1 | 1535 | 1436261 | C | -3.57 | 0.0159 |
| FGF14 | 1538 | 7334753 | C | 2.84 | 0.0230 |
| FGF14 | 1539 | 9518534 | T | 2.71 | 0.0305 |
| FGF14 | 1540 | 10508075 | A | 2.49 | 0.0455 |
| N4BP2L2 | 1543 | 206337 | A | 3.64 | 0.0169 |
| N4BP2L2 | 1544 | 1081796 | A | 3.26 | 0.0422 |
| N4BP2L2 | 1545 | 169600 | A | 2.86 | 0.0471 |
| TRPC4 | 1562 | 3812837 | C | 3.67 | 0.0069 |
| TRPC4 | 1563 | 1538146 | T | 3.40 | 0.0102 |
| TRPC4 | 1564 | 9594238 | C | -3.51 | 0.0315 |
| FNDC3A | 1567 | 2181539 | G | 3.11 | 0.0179 |
| FNDC3A | 1568 | 1983805 | G | 2.86 | 0.0285 |
| SLAIN1 | 1573 | 1343911 | A | -3.64 | 0.0227 |
| SLAIN1 | 1575 | 9318496 | T | 3.29 | 0.0475 |
| SLAIN1 | 1576 | 1146920 | C | 4.21 | 0.0023 |
| SLAIN1 | 1577 | 8000788 | T | 4.37 | 0.0206 |
| SLAIN1 | 1578 | 10507874 | G | 4.22 | 0.0235 |
| GPC5 | 1585 | 9556229 | G | 5.01 | 0.0107 |
| GPC6 | 1588 | 9516222 | G | 3.28 | 0.0370 |
| GPC6 | 1595 | 9561551 | C | -3.18 | 0.0257 |
| NPAS3 | 1602 | 6571604 | C | -5.66 | 0.0006 |
| NPAS3 | 1603 | 6571605 | A | -4.86 | 0.0024 |
| SAMD4A | 1617 | 8006657 | A | 2.82 | 0.0254 |
| RGS6 | 1624 | 36318 | G | 2.73 | 0.0291 |
| RGS6 | 1625 | 11158926 | T | 2.49 | 0.0392 |
| CCDC88C | 1642 | 4904770 | T | -3.07 | 0.0493 |
| BCL11B | 1650 | 2614463 | T | 2.44 | 0.0429 |
| RYR3 | 1654 | 2572175 | A | -2.54 | 0.0380 |
| RYR3 | 1658 | 11638307 | A | -2.97 | 0.0499 |
| C15ORF41 | 1663 | 8024344 | C | -4.39 | 0.0190 |
| TBC1D2B | 1682 | 2241885 | C | 2.87 | 0.0222 |
| TBC1D2B | 1684 | 11634607 | T | 3.53 | 0.0061 |
| TBC1D2B | 1685 | 2867985 | A | 2.67 | 0.0456 |
| ARNT2 | 1688 | 4628923 | C | -3.39 | 0.0133 |
| ARNT2 | 1689 | 11072931 | T | -3.48 | 0.0356 |
| ARNT2 | 1691 | 4778615 | T | -3.63 | 0.0271 |
| KIFC3 | 1697 | 8058401 | G | -2.74 | 0.0441 |
| KIFC3 | 1698 | 1559404 | T | -4.24 | 0.0213 |
| CDH13 | 1719 | 11150496 | T | 2.79 | 0.0246 |
| CDH13 | 1722 | 2059230 | T | 2.55 | 0.0461 |
| USP10 | 1732 | 8060725 | A | 3.56 | 0.0055 |
| CA10 | 1749 | 11652641 | G | -3.48 | 0.0220 |
| MSI2 | 1751 | 8066677 | G | -3.11 | 0.0158 |
| SDK2 | 1754 | 1846334 | A | -3.32 | 0.0086 |
| OSBPL1A | 1758 | 275857 | C | 7.89 | 0.0075 |
| CDH7 | 1781 | 8092259 | G | 2.55 | 0.0466 |
| PTPRM | 1798 | 8089695 | C | 5.08 | 0.0245 |
| KIAA0802 | 1803 | 12386117 | A | -4.72 | 0.0055 |
| MACROD2 | 1809 | 6079395 | G | 2.65 | 0.0309 |
| PTPRT | 1836 | 6065487 | A | -2.54 | 0.0436 |
| KCNB1 | 1844 | 6095546 | A | -2.82 | 0.0441 |
| CDH4 | 1847 | 4812313 | A | -2.65 | 0.0485 |
| PLCB4 | 1859 | 6077505 | C | -2.74 | 0.0322 |
| SLC37A1 | 1871 | 401396 | C | -2.39 | 0.0418 |
| SLC37A1 | 1872 | 381899 | A | -2.75 | 0.0456 |
| ARFGAP3 | 1876 | 6002963 | G | -3.00 | 0.0178 |
| PACSIN2 | 1882 | 4140554 | C | -3.67 | 0.0027 |
| PACSIN2 | 1883 | 7291153 | C | -3.47 | 0.0048 |
| PACSIN2 | 1887 | 737782 | G | 3.23 | 0.0081 |
| PACSIN2 | 1888 | 2284097 | C | -3.35 | 0.0061 |
| PACSIN2 | 1889 | 738379 | A | -3.24 | 0.0080 |
| TTLL1 | 1891 | 135001 | C | 2.68 | 0.0263 |
| TTLL1 | 1892 | 135002 | C | 2.63 | 0.0298 |
| EFCAB6 | 1893 | 137160 | G | 2.61 | 0.0333 |

TABLE 2

Alleles Influencing PANSS Scales

| Gene Name | SEQ ID NO: | NCBI RS # | Allele | PANSS Scale | Beta | P |
|---|---|---|---|---|---|---|
| NGF | 6 | 6327 | A | General | -1.31 | 0.03698 |
| NGF | 7 | 7513144 | C | Positive | 1.13 | 0.02823 |
| CGN | 16 | 1547832 | A | General | -2.33 | 0.02189 |
| RP1-21O18.1 | 17 | 4661563 | A | Negative | -0.90 | 0.04530 |
| RP1-21O18.1 | 22 | 2235787 | G | General | -1.39 | 0.03026 |
| OLFML2B | 25 | 4657131 | A | Negative | 1.08 | 0.02441 |
| OLFML2B | 26 | 2499836 | T | Negative | 1.04 | 0.03150 |
| SEC16B | 30 | 1934650 | C | Positive | 1.26 | 0.03996 |
| RALGPS2 | 31 | 4652319 | T | General | -1.76 | 0.01175 |
| RALGPS2 | 32 | 12076230 | G | General | -1.66 | 0.01214 |
| USH2A | 42 | 7548730 | C | Positive | 1.08 | 0.01006 |
| USH2A | 43 | 6665313 | A | Positive | 1.37 | 0.01278 |
| USH2A | 44 | 12403674 | T | Positive | 1.36 | 0.01382 |
| USH2A | 45 | 301759 | T | Negative | 0.93 | 0.02905 |
| USH2A | 46 | 301760 | C | Negative | 0.92 | 0.03137 |
| USH2A | 49 | 12030122 | C | Negative | 1.59 | 0.03936 |
| ESRRG | 50 | 6658528 | T | General | -1.49 | 0.02399 |
| ESRRG | 56 | 2820879 | A | General | -1.68 | 0.04989 |
| ESRRG | 56 | 2820879 | A | Negative | -1.32 | 0.02803 |
| RYR2 | 63 | 10802596 | T | General | 1.69 | 0.01523 |
| RYR2 | 64 | 16835155 | G | Negative | -1.50 | 0.02501 |
| RYR2 | 65 | 3924864 | C | General | 2.32 | 0.03225 |
| RYR2 | 66 | 2779400 | A | General | -1.76 | 0.00703 |
| CHRM3 | 69 | 16838637 | G | General | 1.27 | 0.03790 |
| FMN2 | 76 | 12145060 | A | Negative | 0.92 | 0.04972 |
| FMN2 | 76 | 12145060 | A | General | 1.57 | 0.01831 |
| FMN2 | 77 | 12021945 | C | General | 1.41 | 0.03332 |
| FMN2 | 79 | 11801848 | C | General | 1.48 | 0.03579 |
| FMN2 | 83 | 1542400 | G | General | -1.27 | 0.03929 |
| FMN2 | 83 | 1542400 | G | Positive | -0.79 | 0.03629 |
| FMN2 | 85 | 11799544 | T | Positive | 1.43 | 0.04573 |
| FMN2 | 86 | 10926257 | T | General | 2.29 | 0.04767 |
| PLD5 | 88 | 924775 | A | General | -1.84 | 0.02179 |
| AGBL4-C1ORF165 | 91 | 319965 | A | Negative | 1.17 | 0.01131 |
| AGBL4-C1ORF165 | 97 | 3121518 | A | General | -1.34 | 0.03132 |
| SCP2 | 98 | 3766762 | C | General | -3.52 | 0.02101 |
| ELTD1 | 100 | 17102632 | T | Positive | 1.23 | 0.02211 |
| PRKACB | 104 | 2134646 | T | Positive | 0.92 | 0.01931 |
| HPCAL1 | 105 | 16856020 | T | General | 1.87 | 0.04416 |
| HPCAL1 | 105 | 16856020 | T | Negative | 2.04 | 0.00178 |
| KCNF1 | 106 | 4669647 | T | Negative | 1.08 | 0.04260 |
| NTSR2 | 108 | 4669767 | C | General | -1.38 | 0.03301 |
| NAP5 | 109 | 4283469 | A | Positive | -2.24 | 0.01708 |
| RAB3GAP1 | 112 | 16831315 | C | General | 2.96 | 0.00574 |
| RAB3GAP1 | 113 | 935614 | G | General | 2.00 | 0.04759 |
| ZRANB3 | 114 | 16831601 | T | General | 2.57 | 0.01784 |
| ZRANB3 | 115 | 16831751 | G | General | 2.89 | 0.00863 |
| LRP1B | 122 | 9283437 | C | Positive | 0.97 | 0.02021 |
| LRP1B | 125 | 12616665 | G | Positive | -1.06 | 0.02819 |
| LRP1B | 127 | 12990449 | C | Positive | -1.00 | 0.03679 |
| LRP1B | 128 | 352994 | T | Positive | -0.98 | 0.03320 |
| KYNU | 129 | 2043944 | T | Negative | 1.52 | 0.00074 |
| KYNU | 130 | 10176234 | A | Negative | 1.48 | 0.00110 |
| KYNU | 131 | 351673 | T | Negative | 1.27 | 0.00346 |
| ARHGAP15 | 140 | 10928200 | T | Positive | 0.98 | 0.01803 |
| ARHGAP15 | 141 | 13031917 | C | Negative | 0.93 | 0.04590 |
| ARHGAP15 | 141 | 13031917 | C | Positive | 0.94 | 0.02134 |
| KIF5C | 142 | 7355478 | T | Positive | 1.36 | 0.04467 |
| KIF5C | 143 | 4667369 | C | Positive | -0.82 | 0.04565 |
| FMNL2 | 145 | 1370504 | T | Positive | 0.91 | 0.04383 |
| FMNL2 | 146 | 6434113 | C | Positive | 1.03 | 0.02260 |
| FMNL2 | 148 | 3817620 | G | Negative | -1.72 | 0.02497 |
| KCNJ3 | 149 | 2961962 | C | General | -1.77 | 0.00502 |
| KCNJ3 | 150 | 2961925 | C | General | -1.55 | 0.01804 |
| KCNJ3 | 151 | 2937600 | G | Positive | -0.91 | 0.03136 |
| PKP4 | 152 | 6437190 | G | Negative | 1.43 | 0.01279 |
| PKP4 | 153 | 2108217 | C | Negative | 1.39 | 0.01531 |
| PKP4 | 154 | 2051946 | T | Negative | 1.00 | 0.02982 |
| PKP4 | 155 | 1476672 | T | Negative | 1.16 | 0.04007 |
| PKP4 | 157 | 2528635 | G | Negative | 1.02 | 0.02743 |
| PKP4 | 158 | 2528582 | G | General | -1.56 | 0.01977 |
| PKP4 | 158 | 2528582 | G | Negative | -1.12 | 0.01771 |
| PKP4 | 159 | 2711072 | C | Negative | 1.03 | 0.03103 |

TABLE 2-continued

Alleles Influencing PANSS Scales

| Gene Name | SEQ ID NO: | NCBI RS # | Allele | PANSS Scale | Beta | P |
|---|---|---|---|---|---|---|
| PLA2R1 | 161 | 3828324 | C | Negative | −0.92 | 0.03300 |
| PLA2R1 | 162 | 2667012 | C | Negative | 1.23 | 0.00572 |
| KCNH7 | 164 | 12613181 | C | Negative | −1.42 | 0.04160 |
| SCN3A | 165 | 11677254 | C | General | −1.86 | 0.00493 |
| SCN3A | 165 | 11677254 | C | Negative | −1.57 | 0.00074 |
| SCN1A | 166 | 6731591 | C | Negative | −1.30 | 0.02573 |
| SCN1A | 167 | 7607543 | C | Negative | −1.13 | 0.04935 |
| SCN9A | 169 | 7589835 | A | Negative | 1.40 | 0.04401 |
| SCN9A | 169 | 7589835 | A | General | 2.73 | 0.00528 |
| SCN9A | 170 | 6725008 | C | General | 2.05 | 0.02469 |
| SCN9A | 171 | 6746030 | A | General | 2.03 | 0.02833 |
| SCN9A | 172 | 2226711 | C | General | 1.98 | 0.03274 |
| PDE1A | 187 | 16823124 | A | General | −1.77 | 0.00963 |
| PDE1A | 188 | 10497597 | T | General | −1.63 | 0.01735 |
| PDE1A | 190 | 9332425 | T | General | −1.66 | 0.01271 |
| ALS2 | 191 | 3731702 | C | General | −1.13 | 0.03035 |
| PARD3B | 196 | 1540369 | G | Positive | 0.91 | 0.04019 |
| PARD3B | 199 | 10490293 | T | Positive | 0.86 | 0.04547 |
| PARD3B | 202 | 1079943 | G | General | −1.29 | 0.04578 |
| NRP2 | 203 | 955395 | T | General | −1.62 | 0.01216 |
| NRP2 | 203 | 955395 | T | Negative | −1.16 | 0.01021 |
| NRP2 | 205 | 6435306 | A | General | −1.38 | 0.03253 |
| NRP2 | 205 | 6435306 | A | Negative | −0.97 | 0.02904 |
| PIP5K3 | 207 | 10497899 | T | General | −4.21 | 0.01635 |
| PIP5K3 | 207 | 10497899 | T | Positive | −2.73 | 0.01236 |
| ERBB4 | 209 | 12998535 | T | Negative | −1.01 | 0.04673 |
| CUL3 | 211 | 11891006 | G | Negative | −1.31 | 0.03780 |
| IRS1 | 212 | 2396427 | G | Positive | 1.43 | 0.03569 |
| COL4A4 | 213 | 1317770 | C | Positive | −0.95 | 0.01597 |
| COL4A4 | 214 | 4566357 | A | Positive | −0.79 | 0.04094 |
| SAG | 220 | 2304773 | A | Negative | 2.44 | 0.00076 |
| SAG | 221 | 894100 | A | Positive | 1.00 | 0.01983 |
| KLHL29 | 222 | 747345 | A | Positive | −1.03 | 0.01222 |
| KLHL29 | 223 | 737565 | A | Positive | −0.98 | 0.01504 |
| KLHL29 | 224 | 747344 | G | Positive | −0.97 | 0.01602 |
| KLHL29 | 226 | 7570872 | G | Positive | −1.00 | 0.01732 |
| KCNK3 | 228 | 7584568 | G | General | −1.35 | 0.03767 |
| DPYSL5 | 231 | 540490 | T | General | 1.33 | 0.03877 |
| BRE | 234 | 17006590 | C | Negative | −1.18 | 0.02453 |
| CRIM1 | 237 | 6757374 | T | General | 2.27 | 0.04854 |
| CRIM1 | 238 | 3770939 | T | Negative | −1.09 | 0.02472 |
| CRIM1 | 239 | 11885390 | A | Negative | −0.97 | 0.04757 |
| CRIM1 | 241 | 3732073 | G | Negative | −1.09 | 0.01727 |
| SLC8A1 | 246 | 417614 | A | General | 1.56 | 0.02508 |
| SLC8A1 | 247 | 2072531 | T | Positive | −0.87 | 0.02680 |
| SLC8A1 | 248 | 417591 | G | General | 1.54 | 0.04341 |
| SLC8A1 | 249 | 11885401 | C | General | 2.19 | 0.02219 |
| SLC8A1 | 250 | 17026033 | G | General | 1.85 | 0.02261 |
| SLC8A1 | 251 | 17026039 | G | General | 1.76 | 0.03210 |
| HAAO | 252 | 6738169 | G | Negative | −1.06 | 0.02751 |
| C2ORF34 | 257 | 786616 | C | Negative | −1.36 | 0.01079 |
| C2ORF34 | 259 | 1067343 | A | Negative | −1.33 | 0.01141 |
| C2ORF34 | 261 | 1067378 | A | General | −1.49 | 0.04429 |
| C2ORF34 | 261 | 1067378 | A | Positive | −0.96 | 0.03708 |
| C2ORF34 | 264 | 1067402 | T | Negative | −1.31 | 0.01452 |
| C2ORF34 | 265 | 698792 | A | Negative | −1.28 | 0.01651 |
| C2ORF34 | 275 | 3738980 | C | General | −2.20 | 0.01320 |
| C2ORF34 | 275 | 3738980 | C | Negative | −2.13 | 0.00060 |
| PRKCE | 276 | 666334 | T | Negative | 1.13 | 0.02631 |
| PRKCE | 277 | 6748375 | C | Negative | 0.90 | 0.04040 |
| PRKCE | 277 | 6748375 | C | General | 1.51 | 0.01573 |
| PSME4 | 282 | 805391 | T | General | −1.78 | 0.00430 |
| PSME4 | 282 | 805391 | T | Negative | −1.41 | 0.00121 |
| PSME4 | 283 | 805330 | A | Negative | −1.19 | 0.00681 |
| PSME4 | 284 | 805360 | T | Negative | −1.16 | 0.01190 |
| PSME4 | 286 | 10183655 | T | Negative | −1.15 | 0.01001 |
| ACYP2 | 287 | 918357 | G | Negative | 1.17 | 0.00787 |
| ACYP2 | 288 | 12615749 | G | Negative | −1.55 | 0.02400 |
| ACYP2 | 289 | 12615793 | A | Negative | −1.46 | 0.03388 |
| ACYP2 | 290 | 17045754 | C | General | −2.54 | 0.00730 |
| CCDC85A | 291 | 4672096 | G | Positive | −1.56 | 0.02603 |
| CCDC85A | 292 | 1159916 | G | Negative | 1.32 | 0.00552 |
| CCDC85A | 293 | 214047 | C | General | −2.12 | 0.02041 |
| AAK1 | 299 | 12622388 | G | General | −1.40 | 0.04950 |
| CTNNA2 | 300 | 7597912 | T | General | −1.95 | 0.00726 |
| CTNNA2 | 301 | 2566539 | T | General | −1.87 | 0.00808 |
| CTNNA2 | 303 | 2566542 | C | General | −1.64 | 0.03645 |
| CTNNA2 | 304 | 7571658 | C | Positive | −1.05 | 0.00824 |
| CTNNA2 | 306 | 318362 | C | Positive | 0.85 | 0.03781 |
| CTNNA2 | 307 | 895388 | T | Positive | −1.69 | 0.02012 |
| CTNNA2 | 308 | 7589069 | C | Negative | 1.78 | 0.00945 |
| CTNNA2 | 309 | 1444539 | C | Negative | 1.36 | 0.04336 |
| CTNNA2 | 310 | 1434064 | G | Negative | −0.99 | 0.03073 |
| CTNNA2 | 311 | 216616 | G | Negative | −1.03 | 0.03792 |
| CTNNA2 | 312 | 6547316 | T | General | 1.38 | 0.03631 |
| C2ORF46 | 313 | 7577544 | G | Positive | −1.34 | 0.04931 |
| DDEF2 | 316 | 10204214 | T | Positive | 1.46 | 0.01377 |
| DDEF2 | 316 | 10204214 | T | General | 1.91 | 0.04488 |
| PLCXD2 | 320 | 1513331 | C | General | 2.46 | 0.00661 |
| PLCXD2 | 322 | 6796087 | T | Positive | −1.10 | 0.00678 |
| PLCXD2 | 323 | 6784753 | C | Positive | −1.06 | 0.00841 |
| PLCXD2 | 324 | 12490166 | A | Positive | 0.87 | 0.03462 |
| KALRN | 327 | 16835912 | C | Positive | 1.05 | 0.00881 |
| KALRN | 327 | 16835912 | C | General | 1.60 | 0.01344 |
| CNTN6 | 328 | 3772339 | T | Positive | −1.06 | 0.01236 |
| CNTN6 | 329 | 4286413 | T | Positive | −0.87 | 0.03300 |
| CPNE4 | 330 | 10934970 | C | General | 3.49 | 0.03174 |
| CPNE4 | 331 | 13319291 | G | Positive | 0.85 | 0.03827 |
| CPNE4 | 333 | 9289393 | T | Negative | 0.92 | 0.04938 |
| CPNE4 | 334 | 1875619 | T | Positive | 2.47 | 0.02017 |
| CPNE4 | 335 | 1393561 | T | Positive | 2.45 | 0.02112 |
| CPNE4 | 336 | 9289395 | G | Negative | 1.33 | 0.00639 |
| CPNE4 | 337 | 17297521 | C | General | 2.25 | 0.01856 |
| CPNE4 | 338 | 6806898 | T | General | 2.12 | 0.02401 |
| CNTN6 | 339 | 265799 | G | Positive | −0.84 | 0.02808 |
| RAB6B | 340 | 6765093 | G | Positive | 0.79 | 0.04449 |
| RAB6B | 340 | 6765093 | G | Negative | 0.91 | 0.04151 |
| RAB6B | 340 | 6765093 | G | General | 1.37 | 0.03067 |
| CNTN6 | 341 | 265767 | A | Positive | −0.95 | 0.01664 |
| CNTN6 | 342 | 2055738 | C | Positive | −0.96 | 0.01615 |
| CNTN6 | 343 | 3772290 | T | Positive | −0.83 | 0.03513 |
| EPHB1 | 345 | 4955510 | A | Positive | 1.08 | 0.00739 |
| EPHB1 | 347 | 4955522 | A | Positive | 1.08 | 0.00739 |
| EPHB1 | 348 | 185257 | T | Positive | 0.99 | 0.01383 |
| EPHB1 | 349 | 9825380 | T | Positive | 1.09 | 0.00745 |
| EPHB1 | 350 | 4955524 | A | Positive | 1.04 | 0.01026 |
| EPHB1 | 351 | 936323 | T | Positive | 0.97 | 0.01685 |
| CLSTN2 | 356 | 9836487 | G | General | 1.50 | 0.02082 |
| CLSTN2 | 358 | 4683499 | G | Negative | 0.97 | 0.03915 |
| CLSTN2 | 358 | 4683499 | G | General | 1.43 | 0.03220 |
| CLSTN2 | 359 | 6439927 | C | Negative | 1.34 | 0.00714 |
| SPSB4 | 363 | 7651293 | T | Positive | −2.08 | 0.02000 |
| SLC6A6 | 365 | 1156567 | C | Negative | −1.47 | 0.03132 |
| SERPINI1 | 369 | 1492023 | A | Positive | −1.22 | 0.03118 |
| SERPINI1 | 370 | 11928048 | T | Positive | −1.19 | 0.03397 |
| SLC7A14 | 371 | 1861938 | T | General | −1.51 | 0.02914 |
| SLC7A14 | 372 | 6788596 | G | General | −1.46 | 0.03211 |
| SLC7A14 | 372 | 6788596 | G | Positive | −0.89 | 0.03413 |
| PLD1 | 377 | 7633686 | G | General | −1.90 | 0.04844 |
| PLD1 | 378 | 6767600 | T | Positive | −1.32 | 0.02048 |
| PLD1 | 379 | 2178532 | A | Positive | −1.31 | 0.02693 |
| NLGN1 | 380 | 4894645 | T | Positive | 1.58 | 0.00617 |
| NLGN1 | 381 | 12636180 | T | Positive | 0.95 | 0.04199 |
| HTR3D | 385 | 939334 | G | Negative | 1.14 | 0.01755 |
| HTR3D | 386 | 6779545 | A | Negative | 1.29 | 0.00582 |
| HTR3D | 386 | 6779545 | A | General | 1.34 | 0.04623 |
| IL1RAP | 394 | 6791374 | C | Negative | −2.58 | 0.00275 |
| CENTB2 | 396 | 2050810 | A | Negative | 1.13 | 0.04537 |
| CENTB2 | 397 | 9859822 | G | Negative | −1.11 | 0.03605 |
| UBXD7 | 398 | 3973 | T | General | −1.38 | 0.04893 |
| RARB | 400 | 17525900 | C | Negative | −1.88 | 0.01234 |
| CNTN4 | 405 | 1420020 | G | General | 2.22 | 0.04942 |
| CLASP2 | 410 | 9853831 | T | General | −1.28 | 0.04451 |
| CLASP2 | 411 | 7641020 | G | General | −1.44 | 0.02355 |
| STAC | 413 | 17186340 | T | General | 2.69 | 0.01598 |
| ULK4 | 415 | 1495698 | T | General | 1.87 | 0.00579 |
| ULK4 | 416 | 1691964 | T | General | 2.35 | 0.00019 |
| ULK4 | 417 | 1691966 | G | Negative | 1.34 | 0.00244 |
| ULK4 | 418 | 1691998 | G | Negative | 1.22 | 0.00598 |
| ULK4 | 419 | 13069172 | G | Negative | 1.18 | 0.00788 |

TABLE 2-continued

Alleles Influencing PANSS Scales

| Gene Name | SEQ ID NO: | NCBI RS # | Allele | PANSS Scale | Beta | P |
|---|---|---|---|---|---|---|
| ULK4 | 419 | 13069172 | G | General | 2.34 | 0.00019 |
| SEMA3F | 424 | 2518796 | G | Positive | 0.84 | 0.04723 |
| SEMA3F | 425 | 12632110 | A | Negative | -0.95 | 0.04788 |
| CACNA2D2 | 426 | 743757 | C | Positive | -1.10 | 0.04985 |
| CACNA2D3 | 427 | 11130396 | T | Positive | -1.07 | 0.01458 |
| ERC2 | 433 | 1993539 | T | Negative | 1.17 | 0.04242 |
| ERC2 | 435 | 7647972 | C | Negative | -0.98 | 0.04457 |
| ERC2 | 438 | 7619653 | C | Negative | -1.01 | 0.03263 |
| ERC2 | 440 | 17825409 | C | Negative | -1.29 | 0.00721 |
| ERC2 | 442 | 4974200 | G | Negative | -1.26 | 0.00942 |
| ERC2 | 443 | 4974206 | G | Negative | -1.10 | 0.02160 |
| ERC2 | 444 | 13064525 | C | Negative | -1.09 | 0.02620 |
| ERC2 | 445 | 1546060 | C | Negative | -1.51 | 0.00117 |
| ERC2 | 446 | 6805882 | C | Negative | -1.44 | 0.00174 |
| ERC2 | 447 | 885211 | A | Negative | -1.25 | 0.00744 |
| ERC2 | 450 | 9873381 | A | Negative | -1.16 | 0.01153 |
| ERC2 | 453 | 7627759 | C | Negative | -1.06 | 0.02017 |
| FHIT | 454 | 639244 | G | Negative | 1.46 | 0.00222 |
| FHIT | 454 | 639244 | G | General | 1.86 | 0.00613 |
| FHIT | 455 | 2253211 | C | Negative | 1.24 | 0.00506 |
| FHIT | 455 | 2253211 | C | General | 1.31 | 0.03719 |
| FHIT | 456 | 2121865 | T | General | 1.45 | 0.02600 |
| FHIT | 457 | 13320646 | A | Negative | 0.93 | 0.04266 |
| FHIT | 458 | 7631246 | T | Negative | 0.91 | 0.04386 |
| PTPRG | 459 | 624755 | G | Positive | 0.86 | 0.03164 |
| CADPS | 467 | 1355551 | T | Negative | 1.60 | 0.00679 |
| CADPS | 469 | 9311842 | T | Negative | 1.24 | 0.01790 |
| CADPS | 471 | 13313979 | A | General | -1.53 | 0.02767 |
| CADPS | 471 | 13313979 | A | Negative | -1.13 | 0.02112 |
| CADPS | 473 | 186236 | C | Negative | -1.19 | 0.01263 |
| CADPS | 474 | 17280557 | A | General | -1.61 | 0.03648 |
| CADPS | 474 | 17280557 | A | Negative | -1.48 | 0.00616 |
| CADPS | 475 | 17280571 | T | Negative | -1.46 | 0.00361 |
| CADPS | 476 | 17357618 | C | General | -1.60 | 0.02389 |
| CADPS | 476 | 17357618 | C | Negative | -1.30 | 0.00899 |
| CADPS | 477 | 11925708 | A | General | -1.65 | 0.00918 |
| PRICKLE2 | 479 | 161661 | A | Negative | 1.10 | 0.01731 |
| MAGI1 | 482 | 2371948 | A | General | 4.96 | 0.01513 |
| MAGI1 | 483 | 9845819 | C | General | -1.65 | 0.01521 |
| MAGI1 | 484 | 7612636 | C | Positive | 0.80 | 0.04761 |
| FAM19A1 | 485 | 11707519 | G | Negative | -1.62 | 0.01054 |
| FOXP1 | 487 | 2196356 | C | Positive | 0.94 | 0.02442 |
| GBE1 | 490 | 7622741 | G | Negative | 1.06 | 0.02757 |
| GBE1 | 490 | 7622741 | G | General | 1.75 | 0.01095 |
| GBE1 | 491 | 6769230 | A | Negative | 1.00 | 0.03881 |
| GBE1 | 491 | 6769230 | A | General | 1.75 | 0.01152 |
| GBE1 | 492 | 2307058 | T | General | 1.63 | 0.01934 |
| GBE1 | 494 | 7613144 | T | General | 1.59 | 0.02238 |
| GBE1 | 495 | 17019088 | T | Positive | -0.99 | 0.04502 |
| GBE1 | 498 | 2680245 | A | General | -1.43 | 0.02444 |
| GBE1 | 498 | 2680245 | A | Negative | -0.98 | 0.02995 |
| GBE1 | 499 | 3860595 | C | Negative | 0.96 | 0.03451 |
| HTR1F | 500 | 1027689 | T | Positive | 1.46 | 0.02814 |
| HTR1F | 500 | 1027689 | T | General | 2.38 | 0.02649 |
| DKK2 | 505 | 379333 | T | Positive | -1.49 | 0.03572 |
| COL25A1 | 508 | 794149 | G | Negative | 0.97 | 0.03330 |
| COL25A1 | 509 | 3096483 | C | Negative | 0.94 | 0.04193 |
| COL25A1 | 510 | 3096489 | C | Negative | 0.91 | 0.04566 |
| ANK2 | 512 | 13134375 | C | Negative | -1.38 | 0.00232 |
| ANK2 | 513 | 13107082 | G | Negative | 1.37 | 0.00252 |
| ANK2 | 514 | 413019 | C | Negative | 1.34 | 0.00306 |
| ANK2 | 517 | 29306 | G | Negative | 1.14 | 0.02465 |
| ANK2 | 518 | 29311 | A | Negative | 1.37 | 0.00716 |
| ANK2 | 518 | 29311 | A | General | 1.80 | 0.01303 |
| NDST3 | 521 | 2389501 | A | Positive | -1.24 | 0.04798 |
| MAML3 | 525 | 6819304 | A | General | -1.91 | 0.04975 |
| IL15 | 527 | 17007695 | C | Positive | 1.51 | 0.03432 |
| INPP4B | 528 | 2667101 | G | Negative | 0.96 | 0.03672 |
| INPP4B | 529 | 2667108 | C | General | 4.31 | 0.03599 |
| INPP4B | 531 | 1353603 | A | Negative | 3.06 | 0.00875 |
| INPP4B | 532 | 336329 | G | Negative | 2.97 | 0.03997 |
| INPP4B | 532 | 336329 | G | General | 4.31 | 0.03599 |
| INPP4B | 533 | 17015544 | T | Positive | 1.63 | 0.00671 |
| INPP4B | 534 | 2276942 | A | Positive | 2.11 | 0.00222 |
| INPP4B | 535 | 3775655 | C | Positive | 1.84 | 0.00689 |
| INPP4B | 536 | 2627828 | G | Positive | 1.91 | 0.03133 |
| POU4F2 | 538 | 1979903 | C | Negative | -2.17 | 0.01897 |
| FSTL5 | 543 | 6825091 | A | General | 1.85 | 0.01004 |
| FSTL5 | 544 | 7442468 | C | General | 1.79 | 0.01173 |
| FSTL5 | 545 | 1431490 | G | General | 2.68 | 0.01648 |
| FSTL5 | 546 | 12499128 | A | General | 2.60 | 0.01918 |
| FSTL5 | 547 | 17459658 | C | General | 2.01 | 0.03261 |
| LDB2 | 552 | 157631 | G | General | 3.03 | 0.01049 |
| LDB2 | 553 | 284210 | T | General | 2.50 | 0.04007 |
| LDB2 | 556 | 13110882 | G | Negative | -1.30 | 0.00288 |
| TLL1 | 557 | 11942650 | G | Positive | -1.88 | 0.04937 |
| PALLD | 559 | 17054309 | A | Negative | -1.21 | 0.04563 |
| PALLD | 564 | 3109206 | T | Negative | -1.20 | 0.00755 |
| PALLD | 565 | 11930576 | C | Negative | -1.15 | 0.01329 |
| PALLD | 566 | 4425335 | G | Negative | -1.45 | 0.00572 |
| PALLD | 567 | 4280700 | T | Negative | -1.46 | 0.02035 |
| PALLD | 568 | 12511925 | T | Negative | -1.31 | 0.04313 |
| ODZ3 | 570 | 2726792 | G | Positive | 1.01 | 0.01596 |
| ODZ3 | 571 | 2675534 | T | Negative | 1.77 | 0.00084 |
| ODZ3 | 572 | 2675532 | C | Positive | 0.90 | 0.03094 |
| ODZ3 | 572 | 2675532 | C | Negative | 1.38 | 0.00338 |
| ODZ3 | 572 | 2675532 | C | General | 1.51 | 0.02450 |
| ENPP6 | 574 | 6830766 | G | General | -1.36 | 0.03770 |
| ENPP6 | 575 | 4431268 | A | General | -1.55 | 0.02259 |
| ENPP6 | 576 | 4241786 | C | General | -1.53 | 0.02423 |
| ENPP6 | 577 | 4340829 | A | General | -1.46 | 0.02730 |
| ENPP6 | 578 | 6815145 | A | General | -1.47 | 0.03043 |
| ENPP6 | 579 | 17584049 | C | General | -1.85 | 0.00475 |
| ENPP6 | 579 | 17584049 | C | Positive | -1.02 | 0.01215 |
| KIAA1239 | 589 | 4585313 | C | General | 3.06 | 0.01647 |
| KIAA1239 | 590 | 17575883 | A | Positive | -1.10 | 0.04116 |
| KIAA1239 | 592 | 2973226 | C | Positive | -0.95 | 0.01429 |
| KIAA1239 | 593 | 1382979 | A | Positive | -1.04 | 0.02140 |
| UBE2K | 595 | 2054718 | T | Positive | 1.27 | 0.01985 |
| UBE2K | 596 | 192779 | A | Positive | 1.28 | 0.01435 |
| LIMCH1 | 598 | 4343753 | T | General | 2.02 | 0.00656 |
| NPFFR2 | 611 | 7654531 | T | Negative | 1.04 | 0.03353 |
| NPFFR2 | 612 | 6824703 | C | Negative | 1.04 | 0.03375 |
| NPFFR2 | 614 | 17775309 | G | General | -1.64 | 0.01530 |
| SCD5 | 620 | 7679857 | A | Positive | -1.24 | 0.02071 |
| SCD5 | 621 | 7684732 | C | General | -1.83 | 0.02561 |
| SCD5 | 622 | 17006038 | C | Positive | -1.24 | 0.02202 |
| SCD5 | 622 | 17006038 | C | Negative | -1.20 | 0.04882 |
| SCD5 | 623 | 6848340 | T | General | -2.27 | 0.03066 |
| FAM13A1 | 626 | 4544678 | C | General | 1.49 | 0.01797 |
| FAM13A1 | 627 | 7691186 | G | General | 1.48 | 0.01929 |
| PDLIM5 | 632 | 6812098 | C | General | 1.68 | 0.04393 |
| SLC2A9 | 637 | 13111638 | T | Negative | -1.40 | 0.01145 |
| SLC2A9 | 641 | 12509955 | T | Negative | -1.34 | 0.01153 |
| SLC2A9 | 643 | 7671266 | T | Negative | -1.45 | 0.00682 |
| FBXL17 | 646 | 11242664 | G | Negative | 1.33 | 0.02514 |
| FBXL17 | 646 | 11242664 | G | General | 1.86 | 0.02767 |
| PJA2 | 653 | 11957188 | T | Positive | -2.79 | 0.00495 |
| KCNN2 | 654 | 1457762 | A | General | 1.34 | 0.03426 |
| HSD17B4 | 662 | 246968 | A | General | -1.60 | 0.00943 |
| SNX2 | 669 | 12109789 | G | Positive | 0.79 | 0.04779 |
| SNX2 | 670 | 10519715 | A | Negative | 0.97 | 0.04493 |
| SNX2 | 670 | 10519715 | A | General | 1.42 | 0.03964 |
| SNX2 | 671 | 2407403 | G | Negative | -1.14 | 0.01761 |
| SNX24 | 672 | 6888023 | T | General | 1.42 | 0.03843 |
| SNX24 | 673 | 246286 | T | Negative | -0.97 | 0.03999 |
| SNX24 | 674 | 246266 | C | Negative | -0.96 | 0.04460 |
| SNX24 | 674 | 246266 | C | Positive | -0.86 | 0.04092 |
| SNX24 | 675 | 6866400 | A | Negative | 0.96 | 0.04515 |
| VDAC1 | 677 | 4958172 | A | General | -1.98 | 0.03716 |
| TRPC7 | 680 | 3777150 | A | Negative | 1.13 | 0.01239 |
| TRPC7 | 682 | 963590 | C | Positive | -0.91 | 0.03266 |
| DNAH5 | 686 | 10513155 | A | General | 1.39 | 0.03933 |
| DNAH5 | 688 | 4701997 | T | General | 2.38 | 0.00027 |
| DNAH5 | 691 | 13154455 | G | General | 2.22 | 0.00079 |
| GRIA1 | 694 | 7735696 | C | Negative | 0.98 | 0.02728 |
| GRIA1 | 695 | 17518831 | C | Negative | 0.90 | 0.04258 |
| GRIA1 | 696 | 778822 | C | Positive | -1.18 | 0.00987 |
| GRIA1 | 701 | 7708391 | A | General | -1.47 | 0.03123 |
| ODZ2 | 704 | 2337017 | C | General | -3.31 | 0.00022 |

TABLE 2-continued

Alleles Influencing PANSS Scales

| Gene Name | SEQ ID NO: | NCBI RS # | Allele | PANSS Scale | Beta | P |
|---|---|---|---|---|---|---|
| ODZ2 | 704 | 2337017 | C | Negative | −1.45 | 0.02177 |
| MYO10 | 705 | 428263 | A | Positive | 0.92 | 0.02306 |
| MYO10 | 706 | 388887 | T | Positive | 0.87 | 0.03024 |
| ODZ2 | 707 | 7714651 | A | General | −2.07 | 0.03300 |
| ODZ2 | 707 | 7714651 | A | Positive | −1.38 | 0.02204 |
| ODZ2 | 708 | 1421989 | G | General | −2.67 | 0.00145 |
| ODZ2 | 708 | 1421989 | G | Positive | −1.53 | 0.00320 |
| ODZ2 | 711 | 6868169 | G | Positive | 1.19 | 0.00429 |
| ODZ2 | 711 | 6868169 | G | General | 1.55 | 0.02104 |
| ODZ2 | 712 | 11748886 | G | Positive | 1.72 | 0.04326 |
| MYO10 | 713 | 11750538 | G | Positive | −0.88 | 0.03391 |
| MYO10 | 714 | 11133860 | G | Positive | −1.16 | 0.01532 |
| PLEKHG4B | 716 | 9312845 | T | Negative | 1.69 | 0.00876 |
| PLEKHG4B | 717 | 9312850 | G | Negative | 1.56 | 0.01509 |
| PLEKHG4B | 718 | 6888246 | T | Negative | 1.55 | 0.01701 |
| PLEKHG4B | 719 | 3853521 | A | Negative | 1.57 | 0.01763 |
| PLEKHG4B | 720 | 6885136 | C | General | 1.37 | 0.02941 |
| CDH10 | 722 | 3822429 | T | General | −1.48 | 0.02017 |
| CDH10 | 722 | 3822429 | T | Negative | −1.07 | 0.01629 |
| CDH10 | 722 | 3822429 | T | Positive | −1.02 | 0.00950 |
| SLC45A2 | 723 | 35388 | T | Negative | −1.00 | 0.02024 |
| SLC45A2 | 724 | 2278008 | C | Negative | −0.98 | 0.04719 |
| C1QTNF3 | 725 | 17583316 | C | Negative | −1.27 | 0.00913 |
| C1QTNF3 | 728 | 9292523 | C | Negative | −1.11 | 0.01589 |
| EGFLAM | 730 | 4869580 | T | Negative | 1.66 | 0.01214 |
| AHRR | 734 | 4956936 | C | Negative | 1.01 | 0.03880 |
| AHRR | 735 | 2672734 | C | Negative | −1.12 | 0.01572 |
| EXOC3 | 736 | 2561667 | T | Negative | −1.05 | 0.02605 |
| ITGA1 | 739 | 1047481 | G | General | −1.35 | 0.04787 |
| ITGA2 | 740 | 3212576 | G | Negative | 1.17 | 0.04568 |
| CMYA5 | 753 | 11960229 | C | General | 2.02 | 0.01984 |
| CMYA5 | 754 | 6880680 | C | General | 2.80 | 0.00792 |
| CMYA5 | 755 | 3828611 | G | Negative | 1.86 | 0.02235 |
| CMYA5 | 755 | 3828611 | G | General | 2.70 | 0.01945 |
| SEMA5A | 768 | 985723 | A | Negative | 1.48 | 0.02151 |
| SEMA5A | 769 | 257094 | C | Negative | 1.30 | 0.04861 |
| SEMA5A | 770 | 11134354 | A | General | −2.05 | 0.00944 |
| SEMA5A | 771 | 4702625 | G | General | −1.88 | 0.01741 |
| SEMA5A | 772 | 268481 | C | General | −2.13 | 0.02437 |
| SEMA5A | 773 | 268529 | G | General | −1.34 | 0.04990 |
| SLC22A16 | 775 | 9398237 | T | Negative | −1.24 | 0.01156 |
| TRDN | 778 | 2873479 | A | Negative | 1.59 | 0.03459 |
| TRDN | 779 | 17737379 | T | Negative | −1.54 | 0.01951 |
| TRDN | 780 | 1367674 | T | Negative | 1.33 | 0.03747 |
| NKAIN2 | 793 | 6910988 | T | Negative | −0.95 | 0.02895 |
| NKAIN2 | 794 | 1832252 | G | Negative | 1.01 | 0.02390 |
| NKAIN2 | 795 | 1871329 | C | General | −2.30 | 0.00182 |
| NKAIN2 | 796 | 1031881 | C | General | −2.58 | 0.00200 |
| NKAIN2 | 796 | 1031881 | C | Positive | −1.11 | 0.03233 |
| NKAIN2 | 797 | 687667 | A | General | −2.04 | 0.01379 |
| NKAIN2 | 798 | 497817 | G | General | −1.77 | 0.02935 |
| NKAIN2 | 799 | 609783 | T | General | −1.76 | 0.03029 |
| NKAIN2 | 800 | 781487 | C | Positive | 1.85 | 0.00482 |
| PDE7B | 810 | 6570049 | T | Positive | −2.10 | 0.02725 |
| UTRN | 817 | 11155367 | A | General | 1.73 | 0.03241 |
| SYNE1 | 818 | 2813484 | G | Negative | −0.94 | 0.04334 |
| SYNE1 | 819 | 718527 | A | General | 1.40 | 0.02741 |
| PARK2 | 824 | 9365311 | G | General | −1.45 | 0.02482 |
| PARK2 | 826 | 7750426 | G | Negative | −0.99 | 0.02186 |
| PARK2 | 827 | 9295173 | G | Negative | 0.92 | 0.03672 |
| PARK2 | 828 | 10945823 | A | Negative | 1.08 | 0.03564 |
| PARK2 | 829 | 2846470 | A | Negative | −1.00 | 0.03486 |
| PDE10A | 837 | 566759 | G | Negative | −1.47 | 0.02131 |
| ATXN1 | 839 | 235147 | A | Negative | −1.11 | 0.01191 |
| ATXN1 | 841 | 909786 | G | General | −1.42 | 0.02549 |
| SLC17A4 | 844 | 9358890 | G | Positive | 2.64 | 0.00453 |
| SLC17A4 | 844 | 9358890 | G | General | 4.20 | 0.00520 |
| SLC17A1 | 845 | 1324082 | A | Negative | −1.16 | 0.03294 |
| SLC17A3 | 848 | 1165158 | T | Positive | −1.03 | 0.03652 |
| SLC17A2 | 849 | 442601 | T | General | −1.56 | 0.02006 |
| BTN3A1 | 851 | 17610161 | A | General | −2.16 | 0.02111 |
| LRFN2 | 861 | 9369205 | A | Negative | 1.30 | 0.00591 |
| LRFN2 | 863 | 403319 | A | Negative | −0.93 | 0.04704 |
| PPP2R5D | 864 | 3823423 | A | Positive | 1.57 | 0.03282 |
| KLC4 | 865 | 4714658 | A | Positive | 2.32 | 0.01682 |
| ELOVL5 | 867 | 9474507 | A | General | 1.85 | 0.03489 |
| RIMS1 | 869 | 530028 | G | Positive | −1.11 | 0.00434 |
| RIMS1 | 870 | 511211 | C | Positive | −1.10 | 0.00527 |
| RIMS1 | 875 | 2463749 | C | Positive | −0.85 | 0.03747 |
| RIMS1 | 877 | 1015945 | G | Positive | −0.92 | 0.02887 |
| KLHL32 | 882 | 1737646 | A | General | −2.34 | 0.02228 |
| CUX1 | 884 | 940482 | T | Negative | −1.52 | 0.01147 |
| CUX1 | 885 | 2960266 | A | Positive | 0.94 | 0.02025 |
| CUX1 | 886 | 2694158 | T | Positive | 1.04 | 0.01248 |
| CUX1 | 886 | 2694158 | T | General | 1.46 | 0.02952 |
| CADPS2 | 887 | 2471212 | G | Positive | 1.20 | 0.01064 |
| CADPS2 | 888 | 1476898 | T | Positive | 0.99 | 0.04874 |
| CADPS2 | 889 | 2471194 | A | Positive | 0.99 | 0.04663 |
| CADPS2 | 892 | 2428769 | G | General | −1.41 | 0.03591 |
| CADPS2 | 892 | 2428769 | G | Negative | −0.95 | 0.04415 |
| EXOC4 | 910 | 6954842 | A | Negative | 1.08 | 0.03039 |
| DGKI | 915 | 16874961 | C | Positive | −1.14 | 0.00805 |
| DGKI | 916 | 980796 | A | Positive | −1.07 | 0.01273 |
| CREB3L2 | 917 | 273981 | C | Positive | 1.07 | 0.00707 |
| CREB3L2 | 918 | 273988 | A | Positive | 1.06 | 0.00696 |
| CREB3L2 | 919 | 273992 | C | Positive | −0.95 | 0.02157 |
| TBXAS1 | 923 | 41723 | G | Negative | 1.51 | 0.01523 |
| ETV1 | 924 | 9639168 | C | General | 1.52 | 0.02832 |
| CNTNAP2 | 926 | 1639481 | G | Positive | 0.86 | 0.02913 |
| CNTNAP2 | 929 | 1639484 | T | Positive | 0.82 | 0.03752 |
| CNTNAP2 | 931 | 11972784 | C | General | 1.61 | 0.02929 |
| CNTNAP2 | 932 | 4726861 | A | Positive | 0.98 | 0.03148 |
| CNTNAP2 | 933 | 2022226 | C | Positive | 1.00 | 0.01451 |
| CNTNAP2 | 934 | 10952682 | G | Positive | 1.08 | 0.01747 |
| CNTNAP2 | 934 | 10952682 | G | General | 1.64 | 0.02495 |
| CNTNAP2 | 935 | 6953679 | A | Positive | 1.27 | 0.00514 |
| CNTNAP2 | 935 | 6953679 | A | General | 1.76 | 0.01632 |
| CNTNAP2 | 936 | 700320 | A | Positive | 1.25 | 0.00455 |
| CNTNAP2 | 936 | 700320 | A | General | 1.77 | 0.01287 |
| CNTNAP2 | 937 | 1404731 | C | General | −2.25 | 0.04818 |
| PTPRN2 | 943 | 10265417 | T | Positive | −0.80 | 0.04787 |
| STK31 | 944 | 12532929 | T | General | 1.71 | 0.03979 |
| CHN2 | 958 | 7781003 | T | General | −1.41 | 0.03974 |
| CHN2 | 958 | 7781003 | T | Positive | −0.88 | 0.03774 |
| CHN2 | 959 | 3750103 | C | General | 2.93 | 0.02045 |
| CHN2 | 960 | 10951234 | C | Positive | −1.04 | 0.04125 |
| ZNRF2 | 964 | 42603 | G | Negative | 2.11 | 0.04303 |
| CRHR2 | 965 | 2190242 | C | Positive | 0.97 | 0.03961 |
| CRHR2 | 965 | 2190242 | C | Negative | 1.14 | 0.03332 |
| CRHR2 | 966 | 4723003 | T | General | 2.30 | 0.03182 |
| FLJ22374 | 968 | 7781249 | A | General | 1.31 | 0.03675 |
| FLJ22374 | 971 | 10258097 | A | General | −1.43 | 0.02758 |
| BMPER | 976 | 6975236 | T | Negative | 1.09 | 0.02086 |
| BMPER | 979 | 7806522 | C | General | −1.86 | 0.00672 |
| BMPER | 979 | 7806522 | C | Negative | −1.02 | 0.03492 |
| BMPER | 979 | 7806522 | C | Positive | −0.84 | 0.04938 |
| VPS41 | 983 | 17768153 | A | Negative | 1.25 | 0.04993 |
| CDC2L5 | 987 | 10272641 | G | Negative | 0.89 | 0.04734 |
| CDC2L5 | 989 | 9639817 | T | Negative | 1.11 | 0.01672 |
| CDC2L5 | 990 | 17171658 | T | Negative | 0.97 | 0.03259 |
| SDK1 | 991 | 11766511 | G | Positive | 0.77 | 0.04561 |
| ABCA13 | 1001 | 3923511 | G | Positive | −0.92 | 0.04200 |
| GRB10 | 1003 | 2244347 | C | Negative | 1.11 | 0.02401 |
| GRB10 | 1004 | 6976501 | G | General | −1.65 | 0.04393 |
| WBSCR17 | 1006 | 757841 | C | General | 1.31 | 0.03691 |
| WBSCR17 | 1008 | 2190223 | C | General | 1.32 | 0.03726 |
| LIMK1 | 1011 | 2855726 | A | Negative | 1.01 | 0.03860 |
| LIMK1 | 1012 | 444606 | G | General | 0.99 | 0.04151 |
| LIMK1 | 1013 | 398608 | T | Negative | 1.01 | 0.04762 |
| GTF2IRD1 | 1014 | 2267834 | G | Positive | 1.07 | 0.01631 |
| MAGI2 | 1020 | 10238177 | A | Positive | −0.94 | 0.03100 |
| MAGI2 | 1026 | 6954793 | C | Negative | 1.65 | 0.01244 |
| MAGI2 | 1027 | 10280554 | T | Negative | 1.59 | 0.01300 |
| MAGI2 | 1028 | 7778707 | G | Negative | 1.55 | 0.02511 |
| MAGI2 | 1031 | 4730226 | A | General | 1.31 | 0.01825 |
| CACNA2D1 | 1033 | 258728 | A | Negative | −1.26 | 0.01477 |
| CACNA2D1 | 1034 | 2059037 | C | Negative | −1.70 | 0.00734 |
| CACNA2D1 | 1036 | 7781562 | A | Positive | −1.07 | 0.01486 |
| CACNA2D1 | 1037 | 12531682 | T | General | −1.54 | 0.02929 |
| CACNA2D1 | 1037 | 12531682 | T | Negative | −1.06 | 0.03247 |

TABLE 2-continued

Alleles Influencing PANSS Scales

| Gene Name | SEQ ID NO: | NCBI RS # | Allele | PANSS Scale | Beta | P |
|---|---|---|---|---|---|---|
| CACNA2D1 | 1038 | 978326 | C | General | −1.58 | 0.02696 |
| CACNA2D1 | 1038 | 978326 | C | Negative | −1.11 | 0.02788 |
| CACNA2D1 | 1039 | 2237524 | G | General | −1.60 | 0.02896 |
| CACNA2D1 | 1039 | 2237524 | G | Positive | −1.16 | 0.01094 |
| CACNA2D1 | 1039 | 2237524 | G | Negative | −1.12 | 0.03117 |
| CACNA2D1 | 1040 | 7788848 | A | General | −1.44 | 0.04357 |
| CACNA2D1 | 1040 | 7788848 | A | Negative | −1.01 | 0.04418 |
| CACNA2D1 | 1040 | 7788848 | A | Positive | −0.93 | 0.03516 |
| PCLO | 1046 | 2888019 | T | Positive | 0.77 | 0.04641 |
| PCLO | 1049 | 12539066 | T | Positive | −1.33 | 0.00307 |
| PCLO | 1052 | 17157177 | T | General | −1.45 | 0.02225 |
| PCLO | 1053 | 16887406 | G | General | −1.25 | 0.04624 |
| PCLO | 1054 | 4129230 | T | Positive | 0.90 | 0.03415 |
| PCLO | 1054 | 4129230 | T | General | 1.88 | 0.00620 |
| PCLO | 1055 | 10240976 | T | Negative | 1.24 | 0.00568 |
| PCLO | 1055 | 10240976 | T | General | 1.36 | 0.03362 |
| SEMA3E | 1056 | 2722963 | G | General | 1.34 | 0.04670 |
| SEMA3E | 1057 | 17287452 | T | Negative | −1.62 | 0.02340 |
| SEMA3E | 1060 | 3801562 | C | General | 1.41 | 0.02882 |
| SEMA3E | 1061 | 1972459 | C | General | −1.50 | 0.02815 |
| SEMA3A | 1062 | 2535786 | A | Negative | −1.15 | 0.03083 |
| SEMA3A | 1063 | 6965990 | A | Positive | 0.86 | 0.03141 |
| SEMA3A | 1063 | 6965990 | A | Negative | 1.10 | 0.01479 |
| SEMA3A | 1064 | 11976072 | T | Negative | 1.08 | 0.01598 |
| SEMA3A | 1065 | 13228082 | G | Negative | 1.06 | 0.01895 |
| SEMA3A | 1066 | 7806871 | G | Negative | −1.03 | 0.02271 |
| SEMA3A | 1066 | 7806871 | G | Positive | −0.86 | 0.03166 |
| SEMA3A | 1067 | 17298417 | C | Negative | −1.00 | 0.02690 |
| SEMA3A | 1067 | 17298417 | C | Positive | −0.79 | 0.04662 |
| SEMA3A | 1068 | 10488268 | T | Negative | 0.96 | 0.03467 |
| SEMA3A | 1069 | 3801629 | G | Negative | 0.95 | 0.03703 |
| ABCB4 | 1072 | 2097937 | G | Negative | −1.18 | 0.04542 |
| ABCB4 | 1073 | 31662 | A | General | −2.27 | 0.02439 |
| ABCB4 | 1074 | 31671 | G | Positive | 0.98 | 0.04998 |
| ADAM22 | 1076 | 1688886 | G | Positive | 1.41 | 0.00059 |
| ADAM22 | 1076 | 1688886 | G | General | 1.73 | 0.00790 |
| ADAM22 | 1077 | 2282948 | C | General | 1.50 | 0.02362 |
| ADAM22 | 1078 | 2282949 | C | Positive | 1.38 | 0.00067 |
| ADAM22 | 1078 | 2282949 | C | General | 1.42 | 0.02975 |
| ADAM22 | 1079 | 6951172 | T | Positive | 1.06 | 0.01095 |
| ADAM22 | 1080 | 9632709 | C | Positive | 1.09 | 0.00887 |
| ADAM22 | 1081 | 2299199 | G | Positive | 1.03 | 0.01243 |
| ADAM22 | 1083 | 4140919 | G | Positive | 1.09 | 0.04647 |
| ADAM22 | 1083 | 4140919 | G | General | 1.85 | 0.03572 |
| ADAM22 | 1084 | 2299205 | T | Positive | 1.38 | 0.04647 |
| NXPH1 | 1086 | 6962955 | A | General | −1.65 | 0.01131 |
| PON1 | 1090 | 2057681 | G | General | −1.36 | 0.04956 |
| PON1 | 1091 | 705378 | T | General | 1.38 | 0.03793 |
| DYNC1I1 | 1093 | 6968143 | G | General | 2.57 | 0.01413 |
| GRHL2 | 1096 | 13275653 | C | General | −1.56 | 0.02002 |
| GRHL2 | 1096 | 13275653 | C | Negative | −1.02 | 0.03158 |
| GRHL2 | 1097 | 4734037 | C | General | −2.00 | 0.01321 |
| NCALD | 1098 | 1131862 | G | General | −2.12 | 0.00599 |
| NCALD | 1098 | 1131862 | G | Negative | −1.15 | 0.03461 |
| NCALD | 1099 | 16868201 | A | General | −2.08 | 0.01430 |
| NCALD | 1099 | 16868201 | A | Negative | −1.17 | 0.04984 |
| NCALD | 1101 | 2226401 | C | General | −1.87 | 0.01488 |
| ZFPM2 | 1102 | 16873003 | C | General | 2.06 | 0.00671 |
| ZFPM2 | 1103 | 6992053 | A | General | 2.01 | 0.00736 |
| ZFPM2 | 1104 | 1481026 | T | General | 1.95 | 0.00957 |
| ZFPM2 | 1105 | 302957 | C | General | 1.29 | 0.04556 |
| ZFPM2 | 1107 | 7003141 | C | Positive | 1.04 | 0.01769 |
| ZFPM2 | 1108 | 1025856 | C | Positive | 0.83 | 0.03562 |
| ZFPM2 | 1110 | 2958710 | G | Positive | 0.81 | 0.04240 |
| CSMD3 | 1111 | 6981814 | A | Positive | −1.16 | 0.01347 |
| CSMD3 | 1112 | 10505174 | A | Positive | −1.01 | 0.03301 |
| CSMD3 | 1113 | 10216803 | T | Positive | −0.99 | 0.03494 |
| CSMD3 | 1114 | 16883753 | T | Positive | −0.97 | 0.03940 |
| CSMD3 | 1118 | 4354335 | G | Negative | 1.04 | 0.03539 |
| SAMD12 | 1119 | 4629902 | A | Positive | 0.86 | 0.03641 |
| SAMD12 | 1123 | 1607924 | G | Negative | 0.95 | 0.04672 |
| FBXO32 | 1125 | 6990407 | G | Positive | −1.07 | 0.04614 |
| FER1L6 | 1127 | 7838453 | A | General | −1.65 | 0.00776 |
| FER1L6 | 1127 | 7838453 | A | Positive | −1.09 | 0.00467 |
| FER1L6 | 1127 | 7838453 | A | Negative | −0.86 | 0.04907 |
| FER1L6 | 1133 | 7819868 | G | Positive | 1.05 | 0.00814 |
| FER1L6 | 1133 | 7819868 | G | General | 1.49 | 0.02014 |
| FER1L6 | 1134 | 4521739 | G | Positive | 0.99 | 0.01293 |
| FER1L6 | 1135 | 11784115 | A | Positive | 0.94 | 0.01813 |
| FER1L6 | 1136 | 10103694 | T | Negative | −1.18 | 0.02336 |
| DLC1 | 1139 | 2203838 | C | Negative | −1.51 | 0.01065 |
| ADCY8 | 1142 | 7464362 | G | General | 1.35 | 0.03729 |
| ADCY8 | 1143 | 11781997 | A | General | 1.58 | 0.01106 |
| ADCY8 | 1144 | 7459573 | G | General | 1.43 | 0.02701 |
| KCNQ3 | 1146 | 6471066 | G | General | 1.71 | 0.04615 |
| COL22A1 | 1150 | 4475485 | T | General | −2.77 | 0.00847 |
| COL22A1 | 1151 | 7838450 | C | Positive | −0.80 | 0.04576 |
| COL22A1 | 1152 | 13279213 | A | Negative | 1.12 | 0.02925 |
| SGCZ | 1154 | 11990657 | T | General | 1.52 | 0.03744 |
| SGCZ | 1156 | 4427170 | T | General | 1.51 | 0.01977 |
| SLC7A2 | 1159 | 2720574 | C | General | −1.89 | 0.04017 |
| ENTPD4 | 1173 | 17089263 | G | Positive | 1.47 | 0.04339 |
| CSMD1 | 1179 | 4487803 | G | General | 1.72 | 0.01061 |
| CSMD1 | 1182 | 7829968 | T | General | 1.67 | 0.02433 |
| CSMD1 | 1185 | 7014880 | A | General | −1.60 | 0.00997 |
| UNC5D | 1186 | 2589344 | T | Negative | −1.56 | 0.00589 |
| SFRP1 | 1188 | 4736959 | C | Positive | 1.07 | 0.00917 |
| SFRP1 | 1190 | 11779707 | C | Positive | 0.99 | 0.01758 |
| SFRP1 | 1191 | 7833518 | T | Positive | 0.82 | 0.04424 |
| SFRP1 | 1192 | 968427 | G | Negative | −0.88 | 0.04825 |
| MCPH1 | 1197 | 1530408 | C | General | 2.01 | 0.01503 |
| MCPH1 | 1202 | 2920660 | A | General | 1.83 | 0.03201 |
| MCPH1 | 1203 | 2916741 | G | General | 1.74 | 0.04297 |
| NKAIN3 | 1207 | 17245081 | A | General | 1.39 | 0.03183 |
| MCPH1 | 1208 | 3020213 | T | Positive | 0.90 | 0.03313 |
| MCPH1 | 1209 | 2515435 | G | General | 1.33 | 0.04676 |
| DEPDC2 | 1216 | 7006061 | T | Positive | 1.30 | 0.03870 |
| DEPDC2 | 1219 | 6990381 | T | Negative | 0.94 | 0.03520 |
| KCNB2 | 1227 | 13251896 | G | Negative | −1.10 | 0.01395 |
| KCNB2 | 1227 | 13251896 | G | Positive | −0.82 | 0.03948 |
| KCNB2 | 1230 | 2196904 | C | Negative | −1.11 | 0.01975 |
| KCNB2 | 1231 | 1866740 | A | Negative | −0.93 | 0.04845 |
| KCNB2 | 1232 | 13277104 | G | Negative | −1.02 | 0.02351 |
| KCNB2 | 1232 | 13277104 | G | Positive | −0.89 | 0.02549 |
| MMP16 | 1236 | 6994019 | T | General | −1.78 | 0.01335 |
| MMP16 | 1236 | 6994019 | T | Negative | −1.07 | 0.03595 |
| MMP16 | 1237 | 1879203 | C | Negative | −1.10 | 0.03726 |
| MMP16 | 1238 | 3844198 | A | General | −1.70 | 0.02028 |
| MMP16 | 1241 | 4548227 | A | Negative | −1.40 | 0.00384 |
| GABBR2 | 1242 | 1435293 | T | General | −1.91 | 0.01335 |
| GABBR2 | 1243 | 10985765 | C | General | −1.86 | 0.01922 |
| GABBR2 | 1244 | 2778913 | T | General | −2.14 | 0.03218 |
| GABBR2 | 1245 | 1930139 | G | Negative | −1.24 | 0.01820 |
| STOM | 1260 | 17086 | G | Positive | −0.79 | 0.04711 |
| FREQ | 1269 | 12003792 | A | Positive | 0.88 | 0.04157 |
| ABL1 | 1273 | 10901294 | T | General | −3.10 | 0.01311 |
| TSC1 | 1275 | 11243940 | G | Positive | −1.03 | 0.02027 |
| TSC1 | 1276 | 7035870 | A | Positive | −0.90 | 0.04546 |
| OLFM1 | 1278 | 665748 | A | Positive | 1.49 | 0.03800 |
| OLFM1 | 1278 | 665748 | A | General | 3.50 | 0.00246 |
| OLFM1 | 1279 | 542172 | A | General | 3.19 | 0.00573 |
| INPP5E | 1280 | 3812591 | C | Negative | 1.28 | 0.01173 |
| KIAA1797 | 1285 | 12338810 | T | General | −2.65 | 0.00175 |
| KIAA1797 | 1285 | 12338810 | T | Positive | −1.17 | 0.02646 |
| KIAA1797 | 1286 | 12336110 | A | General | −2.65 | 0.00204 |
| KIAA1797 | 1286 | 12336110 | A | Positive | −1.12 | 0.03654 |
| KIAA1797 | 1289 | 10511687 | G | Negative | 1.52 | 0.00099 |
| KIAA1797 | 1289 | 10511687 | G | General | 2.10 | 0.00138 |
| KIAA1797 | 1291 | 2383162 | G | General | −1.37 | 0.04082 |
| KIAA1797 | 1292 | 4977823 | T | General | −1.54 | 0.02497 |
| KIAA1797 | 1294 | 10511693 | G | Negative | 1.24 | 0.01526 |
| KIAA1797 | 1295 | 4579612 | C | General | 2.05 | 0.00322 |
| KIAA1797 | 1296 | 4977848 | A | General | −1.44 | 0.03549 |
| KIAA1797 | 1298 | 7030990 | G | Negative | 1.22 | 0.02058 |
| KIAA1797 | 1299 | 4977881 | A | Negative | 1.10 | 0.02813 |
| KIAA1797 | 1299 | 4977881 | A | General | 1.93 | 0.00666 |
| KIAA1797 | 1300 | 4468020 | T | Negative | 1.03 | 0.03784 |
| KIAA1797 | 1300 | 4468020 | T | General | 1.89 | 0.00718 |
| TEK | 1306 | 10967731 | A | Positive | −1.11 | 0.00607 |
| TEK | 1307 | 1322051 | A | Positive | −1.89 | 0.04390 |

TABLE 2-continued

Alleles Influencing PANSS Scales

| Gene Name | SEQ ID NO: | NCBI RS # | Allele | PANSS Scale | Beta | P |
|---|---|---|---|---|---|---|
| TEK | 1308 | 2273719 | T | General | −2.13 | 0.02223 |
| TEK | 1309 | 12339867 | C | General | −2.01 | 0.02410 |
| PIP5K1B | 1312 | 7023009 | T | Positive | 0.81 | 0.03533 |
| PIP5K1B | 1313 | 12686355 | A | Positive | −0.96 | 0.01543 |
| PIP5K1B | 1316 | 11144133 | T | Negative | 1.07 | 0.01861 |
| PIP5K1B | 1317 | 4745375 | T | Negative | 1.24 | 0.01342 |
| APBA1 | 1318 | 10481751 | T | Negative | 1.24 | 0.01613 |
| APBA1 | 1318 | 10481751 | T | General | 1.52 | 0.03800 |
| TRPM3 | 1319 | 1932701 | C | Negative | −1.89 | 0.00415 |
| TRPM3 | 1322 | 1337028 | T | Negative | −0.93 | 0.04526 |
| TRPM3 | 1323 | 2993010 | A | Negative | −1.07 | 0.02022 |
| PCSK5 | 1327 | 7862766 | T | General | 2.16 | 0.02270 |
| PCSK5 | 1329 | 914367 | T | General | −1.37 | 0.04347 |
| PCSK5 | 1329 | 914367 | T | Negative | −1.26 | 0.00808 |
| NTRK2 | 1335 | 1187321 | A | Negative | 1.39 | 0.02333 |
| NTRK2 | 1335 | 1187321 | A | General | 2.22 | 0.01051 |
| NTRK2 | 1336 | 1187328 | G | Negative | 1.31 | 0.03538 |
| NTRK2 | 1337 | 1899641 | G | General | 1.60 | 0.02849 |
| DAPK1 | 1338 | 1927976 | G | Negative | −1.00 | 0.02631 |
| SORCS3 | 1341 | 10884026 | G | Positive | −1.01 | 0.04628 |
| SORCS3 | 1345 | 2496022 | A | General | −1.28 | 0.04790 |
| CUGBP2 | 1353 | 3243 | C | General | 1.45 | 0.04284 |
| VTI1A | 1355 | 10885352 | T | Positive | −0.91 | 0.03509 |
| VTI1A | 1357 | 7907012 | G | Negative | 1.07 | 0.02739 |
| VTI1A | 1360 | 4145776 | G | Negative | 0.99 | 0.04223 |
| ATE1 | 1363 | 7086628 | C | Positive | −1.09 | 0.00447 |
| ATE1 | 1364 | 1219505 | T | Positive | −1.29 | 0.00067 |
| ATE1 | 1364 | 1219505 | T | General | −1.21 | 0.04798 |
| ATE1 | 1365 | 1693682 | A | General | −1.29 | 0.04510 |
| ATE1 | 1366 | 10732824 | A | General | −2.18 | 0.04567 |
| ATE1 | 1367 | 2420970 | T | Positive | 1.23 | 0.00122 |
| ATE1 | 1368 | 11200251 | T | Positive | 0.89 | 0.03135 |
| ATE1 | 1369 | 11200260 | T | General | 1.82 | 0.04378 |
| CTBP2 | 1370 | 4962718 | C | Positive | −0.96 | 0.02804 |
| ARMC3 | 1371 | 17440393 | A | Positive | 1.18 | 0.01570 |
| ARMC3 | 1372 | 11013210 | T | Positive | 1.11 | 0.02029 |
| PITRM1 | 1383 | 3740607 | A | Positive | −0.82 | 0.03317 |
| PITRM1 | 1384 | 4242746 | T | Positive | −0.85 | 0.04967 |
| SLC16A9 | 1386 | 6481469 | A | General | 2.59 | 0.03613 |
| SLC16A9 | 1387 | 3763747 | C | Negative | −1.48 | 0.00519 |
| SLC16A9 | 1388 | 2242206 | T | Negative | −1.30 | 0.00719 |
| SLC16A9 | 1389 | 1171648 | A | Negative | −1.34 | 0.00846 |
| SLC16A9 | 1390 | 1171643 | G | Negative | −1.33 | 0.01007 |
| PRKCQ | 1392 | 9423765 | A | Negative | 0.96 | 0.03963 |
| KCNMA1 | 1401 | 7897566 | C | Positive | 1.04 | 0.01086 |
| KCNMA1 | 1401 | 7897566 | C | General | 1.60 | 0.01494 |
| KCNMA1 | 1401 | 7897566 | C | Negative | 1.64 | 0.00034 |
| NRG3 | 1408 | 11193681 | T | Positive | −1.24 | 0.02809 |
| NRG3 | 1410 | 474496 | G | General | 1.42 | 0.03465 |
| NRG3 | 1411 | 512064 | A | General | 1.25 | 0.04994 |
| GALNTL4 | 1421 | 7122801 | T | General | −1.49 | 0.03276 |
| MICAL2 | 1422 | 10765929 | T | Positive | −1.21 | 0.00386 |
| MICAL2 | 1423 | 2010463 | A | Positive | −0.80 | 0.04857 |
| MICAL2 | 1424 | 11822285 | T | Positive | −0.84 | 0.03138 |
| OPCML | 1428 | 10894536 | A | Negative | 1.68 | 0.03902 |
| ARNTL | 1430 | 7107711 | C | General | −1.86 | 0.01999 |
| ARNTL | 1431 | 7112233 | T | General | −1.70 | 0.03204 |
| OPCML | 1432 | 7107122 | C | General | −1.89 | 0.04851 |
| SPON1 | 1435 | 1507527 | C | General | 1.48 | 0.03603 |
| SPON1 | 1436 | 2049723 | C | General | 1.59 | 0.02683 |
| SPON1 | 1437 | 1528668 | C | Negative | 1.03 | 0.02759 |
| SPON1 | 1440 | 10832170 | T | Negative | 1.20 | 0.00721 |
| SPON1 | 1440 | 10832170 | T | General | 1.31 | 0.04048 |
| SPON1 | 1441 | 1406356 | A | Negative | 1.20 | 0.00803 |
| SPON1 | 1441 | 1406356 | A | General | 1.40 | 0.03069 |
| SPON1 | 1442 | 7116296 | T | General | −1.33 | 0.04002 |
| SPON1 | 1442 | 7116296 | T | Negative | −1.03 | 0.02319 |
| SPON1 | 1443 | 11023088 | T | Negative | −0.98 | 0.03476 |
| INSC | 1445 | 1792571 | A | Negative | 1.62 | 0.00168 |
| INSC | 1445 | 1792571 | A | General | 1.63 | 0.02657 |
| KCNA4 | 1446 | 11030913 | C | Positive | 1.25 | 0.01607 |
| KCNA4 | 1447 | 10835607 | A | Positive | 1.08 | 0.03341 |
| STIM1 | 1448 | 7952083 | C | Positive | −0.85 | 0.02340 |
| STIM1 | 1449 | 10835249 | G | Positive | −0.80 | 0.04205 |
| STIM1 | 1451 | 2959068 | T | Positive | −0.84 | 0.04313 |
| TRIM21 | 1452 | 1426378 | A | Positive | −1.17 | 0.02572 |
| DLG2 | 1455 | 11233564 | A | Positive | −2.74 | 0.00227 |
| DLG2 | 1456 | 11233565 | C | Positive | −2.49 | 0.00550 |
| DLG2 | 1457 | 6592113 | A | Negative | −0.99 | 0.03066 |
| DLG2 | 1458 | 2507850 | A | Negative | −0.97 | 0.04316 |
| DLG2 | 1459 | 7108874 | T | Negative | −1.22 | 0.02033 |
| DLG2 | 1462 | 2514147 | G | Negative | 1.58 | 0.03268 |
| DLG2 | 1463 | 10898192 | G | Negative | 1.66 | 0.02050 |
| DLG2 | 1465 | 1945832 | T | Positive | −1.58 | 0.02446 |
| DLG2 | 1466 | 6592202 | C | General | −1.35 | 0.03773 |
| DLG2 | 1466 | 6592202 | C | Positive | −1.04 | 0.00980 |
| DLG2 | 1466 | 6592202 | C | Negative | −0.94 | 0.03982 |
| DLG2 | 1467 | 4451754 | A | General | −1.40 | 0.03522 |
| DLG2 | 1467 | 4451754 | A | Positive | −1.07 | 0.00927 |
| DLG2 | 1468 | 1943708 | C | Positive | −0.89 | 0.02995 |
| DLG2 | 1469 | 11234194 | C | Positive | −0.88 | 0.03398 |
| DLG2 | 1470 | 11234221 | A | Positive | −1.13 | 0.00457 |
| DLG2 | 1471 | 11234222 | A | General | −1.86 | 0.00385 |
| DLG2 | 1471 | 11234222 | A | Negative | −1.45 | 0.00134 |
| DLG2 | 1472 | 4943900 | C | Negative | 1.00 | 0.02898 |
| DLG2 | 1474 | 6592211 | A | General | −1.49 | 0.02007 |
| DLG2 | 1474 | 6592211 | A | Positive | −1.14 | 0.00424 |
| DLG2 | 1475 | 7101454 | C | General | −1.42 | 0.02852 |
| DLG2 | 1475 | 7101454 | C | Positive | −1.08 | 0.00720 |
| DLG2 | 1476 | 582652 | A | Negative | −1.34 | 0.04170 |
| ATXN2 | 1480 | 1544396 | G | Negative | 1.09 | 0.04327 |
| ITPR2 | 1490 | 1049376 | G | General | −1.44 | 0.04725 |
| TMEM16B | 1491 | 9645764 | C | General | −1.14 | 0.02799 |
| TMEM16B | 1499 | 11612136 | A | Positive | 1.25 | 0.01255 |
| KCNC2 | 1502 | 10879888 | G | Negative | 1.74 | 0.00069 |
| KCNC2 | 1503 | 10735985 | G | Negative | 1.53 | 0.00116 |
| KCNC2 | 1504 | 2471664 | C | Negative | 2.13 | 0.00009 |
| NAV3 | 1508 | 1677923 | G | Negative | 1.57 | 0.04286 |
| NAV3 | 1510 | 10859620 | G | General | −1.72 | 0.00858 |
| NAV3 | 1512 | 11107419 | T | General | −1.46 | 0.03758 |
| NAV3 | 1514 | 1677893 | A | Positive | 0.79 | 0.04382 |
| NAV3 | 1515 | 7295890 | C | General | 1.80 | 0.01110 |
| NAV3 | 1516 | 998070 | T | General | −1.24 | 0.04974 |
| NALCN | 1524 | 7337100 | G | General | 1.38 | 0.04041 |
| NALCN | 1529 | 9557622 | G | General | −1.43 | 0.02253 |
| ITGBL1 | 1530 | 1335594 | A | General | −1.55 | 0.02549 |
| ITGBL1 | 1532 | 4772403 | T | General | −1.58 | 0.02099 |
| ITGBL1 | 1532 | 4772403 | T | Positive | −0.93 | 0.02766 |
| ITGBL1 | 1533 | 7338172 | G | General | −1.53 | 0.04581 |
| ITGBL1 | 1535 | 1436261 | A | General | −2.13 | 0.00591 |
| ITGBL1 | 1536 | 9518494 | T | General | −1.28 | 0.04145 |
| FGF14 | 1537 | 7319796 | A | Negative | −1.02 | 0.02862 |
| FGF14 | 1538 | 7334753 | C | Positive | 0.90 | 0.02586 |
| FGF14 | 1539 | 9518534 | T | Positive | 0.88 | 0.02965 |
| MTIF3 | 1542 | 7334690 | A | Negative | 1.11 | 0.03028 |
| N4BP2L2 | 1543 | 206337 | A | General | 1.98 | 0.01322 |
| N4BP2L2 | 1545 | 169600 | A | General | 1.67 | 0.02673 |
| N4BP2L2 | 1546 | 208431 | G | General | 1.52 | 0.04552 |
| TRPC4 | 1553 | 9576332 | G | General | 1.79 | 0.00793 |
| TRPC4 | 1554 | 7336008 | A | General | 1.56 | 0.01718 |
| TRPC4 | 1555 | 7338239 | G | General | 1.45 | 0.02776 |
| TRPC4 | 1557 | 4943529 | C | General | 1.39 | 0.03093 |
| TRPC4 | 1558 | 1577007 | C | Positive | −0.89 | 0.02610 |
| TRPC4 | 1559 | 1556541 | C | Positive | −0.89 | 0.03077 |
| TRPC4 | 1560 | 1924378 | A | General | −1.28 | 0.04723 |
| TRPC4 | 1562 | 3812837 | C | Positive | 1.40 | 0.00147 |
| TRPC4 | 1562 | 3812837 | C | General | 1.62 | 0.02264 |
| TRPC4 | 1563 | 1538146 | T | Positive | 1.34 | 0.00176 |
| TRPC4 | 1564 | 9594238 | C | General | −1.83 | 0.03205 |
| TRPC4 | 1564 | 9594238 | C | Positive | −1.23 | 0.02001 |
| FNDC3A | 1567 | 2181539 | G | General | 1.87 | 0.00633 |
| FNDC3A | 1568 | 1983805 | G | General | 1.57 | 0.02200 |
| SLAIN1 | 1573 | 1343911 | A | General | −2.17 | 0.00964 |
| SLAIN1 | 1574 | 1279445 | G | Positive | 1.50 | 0.02077 |
| SLAIN1 | 1575 | 9318496 | T | General | 1.71 | 0.04936 |
| SLAIN1 | 1576 | 1146920 | C | Positive | 1.09 | 0.01523 |
| SLAIN1 | 1576 | 1146920 | C | Negative | 1.16 | 0.02302 |
| SLAIN1 | 1576 | 1146920 | C | General | 1.97 | 0.00651 |
| SLAIN1 | 1577 | 8000788 | T | General | 2.62 | 0.00773 |
| SLAIN1 | 1578 | 10507874 | G | General | 2.52 | 0.00977 |

TABLE 2-continued

Alleles Influencing PANSS Scales

| Gene Name | SEQ ID NO: | NCBI RS # | Allele | PANSS Scale | Beta | P |
|---|---|---|---|---|---|---|
| GPC5 | 1579 | 7992120 | T | General | 1.86 | 0.03400 |
| GPC5 | 1584 | 913005 | T | General | -1.58 | 0.01369 |
| GPC5 | 1585 | 9556229 | G | Negative | 1.77 | 0.01409 |
| GPC5 | 1585 | 9556229 | G | General | 2.24 | 0.02954 |
| GPC5 | 1586 | 6492630 | A | Negative | -0.92 | 0.04368 |
| GPC5 | 1587 | 2148226 | G | Negative | 1.04 | 0.02066 |
| GPC6 | 1588 | 9516222 | G | Positive | 1.04 | 0.04055 |
| GPC6 | 1593 | 9524193 | T | Negative | 1.08 | 0.03752 |
| GPC6 | 1594 | 10492635 | C | General | -1.74 | 0.03755 |
| GPC6 | 1595 | 9561551 | C | Positive | -0.99 | 0.03328 |
| NPAS3 | 1597 | 8022434 | T | Negative | 1.56 | 0.04940 |
| NPAS3 | 1599 | 243291 | G | Negative | -0.88 | 0.04978 |
| NPAS3 | 1601 | 10133530 | A | General | 1.84 | 0.02280 |
| NPAS3 | 1602 | 6571604 | C | General | -3.41 | 0.00007 |
| NPAS3 | 1602 | 6571604 | C | Positive | -1.59 | 0.00300 |
| NPAS3 | 1603 | 6571605 | A | General | -2.95 | 0.00042 |
| NPAS3 | 1603 | 6571605 | A | Positive | -1.35 | 0.00913 |
| GNG2 | 1615 | 10873056 | G | Negative | -2.70 | 0.01947 |
| SAMD4A | 1617 | 8006657 | A | General | 1.94 | 0.00326 |
| SAMD4A | 1619 | 8021151 | G | General | 1.77 | 0.00588 |
| PPP2R5E | 1620 | 10137202 | C | General | 2.11 | 0.02322 |
| PPP2R5E | 1621 | 972984 | C | Negative | -1.55 | 0.00440 |
| PPP2R5E | 1622 | 1255741 | A | Negative | -1.18 | 0.01323 |
| RGS6 | 1624 | 36318 | G | General | 1.69 | 0.00984 |
| RGS6 | 1625 | 11158926 | T | Positive | 0.79 | 0.04420 |
| RGS6 | 1625 | 11158926 | T | General | 1.45 | 0.02171 |
| RGS6 | 1629 | 847241 | A | Negative | -1.19 | 0.00792 |
| RGS6 | 1631 | 2283380 | T | General | 1.34 | 0.04679 |
| KCNK10 | 1632 | 12587003 | C | General | 1.82 | 0.00754 |
| KCNK10 | 1633 | 12185033 | T | Positive | -0.83 | 0.04727 |
| RPS6KA5 | 1634 | 1152423 | C | Negative | 1.00 | 0.03427 |
| RPS6KA5 | 1635 | 941847 | T | Positive | 0.90 | 0.04654 |
| RPS6KA5 | 1636 | 1286148 | C | Negative | 1.38 | 0.01088 |
| RPS6KA5 | 1637 | 7156252 | T | Positive | 1.07 | 0.01018 |
| RPS6KA5 | 1639 | 1075014 | C | Positive | 1.07 | 0.01208 |
| RPS6KA5 | 1641 | 7492628 | G | Positive | 1.20 | 0.00460 |
| CCDC88C | 1642 | 4904770 | T | Positive | -1.48 | 0.00338 |
| CCDC88C | 1644 | 10131741 | G | Positive | -1.20 | 0.00746 |
| CCDC88C | 1646 | 8007791 | A | Positive | -1.20 | 0.00785 |
| CCDC88C | 1647 | 11160004 | C | General | 1.67 | 0.03585 |
| BCL11B | 1648 | 807450 | G | Negative | 0.98 | 0.04426 |
| BCL11B | 1650 | 2614463 | T | Positive | 0.83 | 0.03335 |
| ATP10A | 1651 | 12442216 | T | Negative | -0.91 | 0.04698 |
| RYR3 | 1654 | 2572175 | A | General | -1.40 | 0.02906 |
| RYR3 | 1654 | 2572175 | A | Positive | -0.95 | 0.01583 |
| RYR3 | 1656 | 1390159 | T | General | 3.29 | 0.03110 |
| RYR3 | 1657 | 1495284 | C | General | 3.08 | 0.03459 |
| RYR3 | 1658 | 11638307 | A | Negative | -1.26 | 0.02375 |
| C15ORF41 | 1661 | 12443190 | G | Negative | 1.11 | 0.01131 |
| C15ORF41 | 1663 | 8024344 | C | General | -2.87 | 0.00336 |
| C15ORF41 | 1663 | 8024344 | C | Negative | -1.79 | 0.00919 |
| C15ORF41 | 1664 | 4923723 | C | General | -2.06 | 0.01990 |
| GLDN | 1670 | 2445781 | G | General | 1.53 | 0.03501 |
| GLDN | 1671 | 17648128 | A | Positive | 1.14 | 0.00603 |
| GLDN | 1672 | 17648140 | G | Positive | 1.08 | 0.00897 |
| RORA | 1679 | 12914584 | G | General | -1.51 | 0.03438 |
| TBC1D2B | 1682 | 2241885 | C | Negative | 0.98 | 0.03548 |
| TBC1D2B | 1682 | 2241885 | C | General | 1.35 | 0.04053 |
| TBC1D2B | 1683 | 8030999 | G | Positive | 1.38 | 0.01666 |
| TBC1D2B | 1684 | 11634607 | T | Negative | 1.18 | 0.01249 |
| TBC1D2B | 1684 | 11634607 | T | General | 1.63 | 0.01540 |
| ARNT2 | 1688 | 4628923 | C | Negative | -1.17 | 0.01854 |
| ARNT2 | 1688 | 4628923 | C | Positive | -1.06 | 0.01677 |
| ARNT2 | 1689 | 11072931 | T | Positive | -1.10 | 0.04031 |
| ARNT2 | 1691 | 4778615 | T | Negative | -1.19 | 0.04811 |
| ARNT2 | 1691 | 4778615 | T | Positive | -1.13 | 0.03351 |
| SH3GL3 | 1692 | 10520577 | T | Positive | 1.28 | 0.00472 |
| TMC5 | 1694 | 1985395 | C | Negative | 0.96 | 0.04800 |
| TMC5 | 1694 | 1985395 | C | General | 1.66 | 0.01583 |
| EEF2K | 1696 | 10521118 | A | Positive | 1.95 | 0.01256 |
| KIFC3 | 1698 | 1559404 | T | Negative | -1.53 | 0.02447 |
| A2BP1 | 1701 | 1155959 | C | General | 1.47 | 0.02311 |
| WWOX | 1708 | 8061908 | C | Positive | -0.84 | 0.03862 |
| WWOX | 1711 | 11641213 | G | Positive | 0.80 | 0.04062 |
| MPHOSPH6 | 1714 | 7405231 | C | Positive | 0.89 | 0.01797 |
| CDH13 | 1719 | 11150496 | T | General | 1.43 | 0.02777 |
| CDH13 | 1722 | 2059230 | T | Positive | 0.82 | 0.04825 |
| CDH13 | 1730 | 889491 | G | Positive | 0.85 | 0.04749 |
| USP10 | 1732 | 8060725 | A | Positive | 0.82 | 0.04831 |
| USP10 | 1732 | 8060725 | A | Negative | 1.32 | 0.00519 |
| USP10 | 1732 | 8060725 | A | General | 1.42 | 0.03482 |
| CRISPLD2 | 1733 | 2641697 | C | Positive | 1.21 | 0.00331 |
| CRISPLD2 | 1734 | 2641698 | T | Positive | 1.14 | 0.00651 |
| CRISPLD2 | 1735 | 16974822 | G | Positive | -1.40 | 0.00247 |
| CRISPLD2 | 1736 | 774205 | G | Positive | 0.84 | 0.04168 |
| CRISPLD2 | 1738 | 982994 | T | Positive | 0.85 | 0.04298 |
| CRISPLD2 | 1739 | 2646107 | C | Positive | -1.07 | 0.01544 |
| DNAH9 | 1741 | 16945383 | G | Positive | 0.80 | 0.03533 |
| DNAH9 | 1742 | 1468501 | C | Positive | -1.04 | 0.02836 |
| CA10 | 1749 | 11652641 | G | General | -1.95 | 0.01410 |
| CA10 | 1749 | 11652641 | G | Positive | -1.08 | 0.02873 |
| MSI2 | 1751 | 8066677 | G | General | -2.14 | 0.00148 |
| MSI2 | 1752 | 8067335 | A | Positive | -0.83 | 0.04425 |
| SDK2 | 1754 | 1846334 | A | Positive | -1.22 | 0.00294 |
| OSBPL1A | 1758 | 275857 | C | Positive | 2.65 | 0.00557 |
| OSBPL1A | 1758 | 275857 | C | General | 3.17 | 0.04077 |
| OSBPL1A | 1759 | 641885 | T | General | -2.46 | 0.03775 |
| CHST9 | 1760 | 17703962 | G | Positive | 1.38 | 0.01471 |
| CHST9 | 1762 | 9965371 | C | Positive | 1.21 | 0.02735 |
| DLGAP1 | 1763 | 9635857 | G | Positive | 0.94 | 0.04321 |
| NEDD4L | 1766 | 7243662 | G | Positive | 1.24 | 0.01038 |
| NEDD4L | 1767 | 1008899 | A | Positive | 1.18 | 0.01254 |
| NEDD4L | 1768 | 4941364 | G | Positive | 1.14 | 0.01420 |
| NEDD4L | 1769 | 292444 | C | Positive | 0.93 | 0.02791 |
| NEDD4L | 1770 | 525839 | A | Positive | 0.90 | 0.03453 |
| NEDD4L | 1771 | 11663936 | T | Negative | -1.18 | 0.03859 |
| NEDD4L | 1772 | 17064977 | C | Negative | 1.10 | 0.03738 |
| NEDD4L | 1773 | 11152073 | A | Negative | 1.07 | 0.04122 |
| CDH7 | 1781 | 8092259 | G | Negative | 1.38 | 0.00316 |
| CDH7 | 1781 | 8092259 | G | General | 1.41 | 0.03486 |
| CDH7 | 1782 | 7228669 | T | General | 1.34 | 0.04448 |
| CDH7 | 1783 | 1942832 | A | Negative | 1.26 | 0.00745 |
| CDH7 | 1784 | 1942831 | G | General | 1.34 | 0.04464 |
| CDH7 | 1786 | 1484725 | T | Negative | 1.24 | 0.00820 |
| CDH7 | 1790 | 1564815 | C | Negative | 2.42 | 0.02279 |
| DOK6 | 1791 | 12961718 | C | General | 1.58 | 0.02195 |
| DOK6 | 1792 | 8097743 | G | Positive | -0.85 | 0.02753 |
| DOK6 | 1793 | 4426448 | G | Positive | 0.94 | 0.01905 |
| DOK6 | 1794 | 12605879 | G | Positive | 0.90 | 0.02201 |
| MBP | 1796 | 11660462 | A | Negative | 1.07 | 0.02397 |
| PTPRM | 1797 | 495288 | G | Negative | 2.51 | 0.02561 |
| PTPRM | 1798 | 8089695 | C | Negative | 2.27 | 0.00638 |
| KIAA0802 | 1803 | 12386117 | A | General | -2.31 | 0.00964 |
| KIAA0802 | 1803 | 12386117 | A | Positive | -1.32 | 0.01762 |
| KIAA0802 | 1804 | 7235093 | A | Negative | 2.20 | 0.00394 |
| LDLR | 1805 | 8110695 | A | General | 1.72 | 0.02348 |
| LDLR | 1807 | 1433099 | A | Positive | -0.88 | 0.04421 |
| MACROD2 | 1809 | 6079395 | G | Positive | 0.84 | 0.03441 |
| MACROD2 | 1809 | 6079395 | G | Negative | 0.99 | 0.02883 |
| MACROD2 | 1810 | 6079910 | C | General | -2.02 | 0.04025 |
| KIF16B | 1813 | 6043875 | C | General | -1.62 | 0.01173 |
| KIF16B | 1818 | 6135739 | G | General | -1.34 | 0.04077 |
| KIF16B | 1821 | 6034464 | A | General | -1.40 | 0.02717 |
| KIF16B | 1823 | 12624938 | A | General | 1.83 | 0.03290 |
| KIF16B | 1826 | 6075069 | T | General | 2.46 | 0.00261 |
| KIF16B | 1827 | 6080359 | C | Negative | -1.16 | 0.02720 |
| PTPRT | 1832 | 6065432 | T | Negative | -1.35 | 0.00638 |
| PTPRT | 1833 | 746413 | C | Negative | -1.04 | 0.02087 |
| PTPRT | 1833 | 746413 | C | Positive | 1.15 | 0.00399 |
| PTPRT | 1834 | 6065434 | T | Negative | -1.27 | 0.00885 |
| PTPRT | 1835 | 6016688 | T | Positive | 0.98 | 0.03708 |
| PTPRT | 1836 | 6065487 | A | Positive | -1.00 | 0.01421 |
| PTPRT | 1838 | 2017914 | G | General | 1.40 | 0.04442 |
| PTPRT | 1839 | 6072869 | G | Negative | 1.24 | 0.01854 |
| KCNB1 | 1841 | 1961192 | T | Negative | -0.95 | 0.03860 |
| KCNB1 | 1844 | 6095546 | A | General | -1.48 | 0.04378 |
| KCNB1 | 1844 | 6095546 | A | Positive | -0.93 | 0.04204 |
| KCNB1 | 1845 | 4647 | T | Positive | -0.95 | 0.03795 |
| CDH4 | 1846 | 6028127 | G | General | -1.41 | 0.04280 |
| CDH4 | 1847 | 4812313 | G | General | -1.42 | 0.04339 |

TABLE 2-continued

Alleles Influencing PANSS Scales

| Gene Name | SEQ ID NO: | NCBI RS # | Allele | PANSS Scale | Beta | P |
|---|---|---|---|---|---|---|
| FERMT1 | 1855 | 8121939 | G | General | -1.34 | 0.04231 |
| PLCB1 | 1856 | 6055577 | A | Positive | 1.06 | 0.04019 |
| PLCB1 | 1857 | 2235212 | A | Positive | 0.95 | 0.04340 |
| PLCB4 | 1859 | 6077505 | C | Negative | -1.17 | 0.01308 |
| PLCB4 | 1860 | 6039424 | G | Negative | -0.92 | 0.04737 |
| C21ORF37 | 1861 | 12483129 | C | Negative | 0.97 | 0.02832 |
| SLC37A1 | 1872 | 381899 | A | Negative | -1.39 | 0.00591 |
| SGSM1 | 1874 | 5760752 | C | Negative | 0.97 | 0.04133 |
| ARFGAP3 | 1876 | 6002963 | G | General | -1.76 | 0.00781 |
| ARFGAP3 | 1877 | 738536 | A | General | 1.37 | 0.02863 |
| PACSIN2 | 1882 | 4140554 | C | General | -2.05 | 0.00135 |
| PACSIN2 | 1883 | 7291153 | C | General | -1.95 | 0.00238 |
| PACSIN2 | 1887 | 737782 | G | Negative | 1.16 | 0.01019 |
| PACSIN2 | 1887 | 737782 | G | General | 1.70 | 0.00803 |
| PACSIN2 | 1888 | 2284097 | C | General | -1.87 | 0.00345 |
| PACSIN2 | 1889 | 738379 | A | General | -1.71 | 0.00737 |
| PACSIN2 | 1889 | 738379 | A | Negative | -0.96 | 0.03380 |
| TTLL1 | 1891 | 135001 | C | Negative | 0.99 | 0.02599 |
| TTLL1 | 1891 | 135001 | C | General | 1.26 | 0.04582 |
| TTLL1 | 1892 | 135002 | C | Negative | 0.96 | 0.03155 |
| TTLL1 | 1892 | 135002 | C | General | 1.25 | 0.04902 |
| EFCAB6 | 1893 | 137160 | G | Positive | 0.97 | 0.01465 |
| EFCAB6 | 1893 | 137160 | G | General | 1.35 | 0.03556 |

TABLE 3

Alleles Influencing Individual PANSS Items

| Gene | SEQ ID NO: | NCBI RS # | Allele | PANSS Item | Beta | P |
|---|---|---|---|---|---|---|
| KIF1B | 1 | 3748577 | G | G15 | 0.24 | 0.0074930 |
| KIF1B | 2 | 2297881 | C | N4 | 0.90 | 0.0098590 |
| KIF1B | 3 | 1555849 | G | N1 | 0.33 | 0.0023450 |
| KIF1B | 3 | 1555849 | G | G15 | 0.24 | 0.0082990 |
| KIF1B | 4 | 3748578 | A | N1 | 0.35 | 0.0016060 |
| SYT6 | 5 | 611514 | A | G2 | 0.23 | 0.0088800 |
| SYT6 | 5 | 611514 | A | P4 | 0.20 | 0.0070350 |
| NGF | 6 | 6327 | A | N1 | -0.30 | 0.0021770 |
| SLC22A15 | 8 | 2488433 | T | P7 | -0.40 | 0.0060930 |
| SLC22A15 | 9 | 7547928 | T | G8 | -0.17 | 0.0031870 |
| SLC22A15 | 10 | 2051060 | C | G8 | -0.16 | 0.0047370 |
| SLC22A15 | 11 | 17035177 | T | N1 | 0.56 | 0.0084980 |
| PTGFRN | 12 | 943371 | C | G4 | -0.77 | 0.0029300 |
| PTGFRN | 13 | 12078461 | A | G7 | 0.65 | 0.0051320 |
| PTGFRN | 14 | 4641299 | G | P5 | -0.27 | 0.0057720 |
| PTGFRN | 15 | 3829681 | A | G1 | -0.28 | 0.0025710 |
| RP1-21O18.1 | 18 | 10803343 | G | G14 | 0.95 | 0.0002941 |
| RP1-21O18.1 | 19 | 1000313 | G | G14 | 0.27 | 0.0003008 |
| RP1-21O18.1 | 20 | 4501834 | C | G14 | 0.22 | 0.0031970 |
| RP1-21O18.1 | 21 | 2221926 | T | G14 | 0.28 | 0.0034020 |
| RP1-21O18.1 | 21 | 2221926 | T | G13 | 0.32 | 0.0056050 |
| ATF6 | 23 | 10918029 | A | G11 | 0.41 | 0.0033720 |
| ATF6 | 24 | 7552420 | C | N1 | 0.51 | 0.0021620 |
| OLFML2B | 26 | 2499836 | T | N4 | 0.30 | 0.0026610 |
| OLFML2B | 27 | 12025136 | C | G16 | 0.32 | 0.0020010 |
| OLFML2B | 27 | 12025136 | C | N6 | 0.29 | 0.0071570 |
| FAM78B | 28 | 6662013 | T | G5 | 0.21 | 0.0039550 |
| FAM78B | 29 | 10800181 | G | G11 | -0.22 | 0.0086260 |
| RALGPS2 | 31 | 4652319 | T | N7 | -0.25 | 0.0043700 |
| RALGPS2 | 31 | 4652319 | T | G15 | -0.25 | 0.0065890 |
| RALGPS2 | 32 | 12076230 | G | G12 | -0.26 | 0.0085520 |
| KCNK2 | 33 | 10864143 | A | N5 | 0.29 | 0.0068860 |
| KCNK2 | 34 | 2363557 | A | G10 | -0.18 | 0.0078510 |
| KCNK2 | 35 | 2363567 | T | G10 | -0.18 | 0.0085910 |
| KCNK2 | 36 | 6684084 | G | N5 | 0.27 | 0.0087360 |
| KCNK2 | 37 | 10779651 | C | N6 | 0.36 | 0.0001705 |
| KCNK2 | 37 | 10779651 | C | N5 | 0.27 | 0.0089470 |
| KCNK2 | 38 | 1112101 | G | N6 | 0.36 | 0.0005514 |
| KCNK2 | 39 | 11120527 | T | G5 | 0.22 | 0.0049310 |
| USH2A | 40 | 2211125 | T | N6 | 0.32 | 0.0023270 |
| USH2A | 41 | 1339411 | T | N6 | 0.29 | 0.0077170 |

TABLE 3-continued

Alleles Influencing Individual PANSS Items

| Gene | SEQ ID NO: | NCBI RS # | Allele | PANSS Item | Beta | P |
|---|---|---|---|---|---|---|
| USH2A | 42 | 7548730 | C | N7 | 0.22 | 0.0094820 |
| USH2A | 43 | 6665313 | A | P3 | 0.46 | 0.0025330 |
| USH2A | 44 | 12403674 | T | P3 | 0.44 | 0.0041770 |
| USH2A | 47 | 386654 | T | G11 | 0.26 | 0.0035990 |
| USH2A | 48 | 680410 | G | G11 | 0.25 | 0.0051510 |
| USH2A | 49 | 12030122 | C | N5 | 0.47 | 0.0072360 |
| ESRRG | 50 | 6658528 | T | G5 | -0.23 | 0.0010100 |
| ESRRG | 51 | 6604635 | A | G5 | -0.21 | 0.0022990 |
| ESRRG | 51 | 6604635 | A | G10 | -0.16 | 0.0089390 |
| ESRRG | 52 | 10218694 | A | P7 | 0.17 | 0.0069140 |
| ESRRG | 53 | 12088947 | A | P7 | 0.18 | 0.0074210 |
| ESRRG | 54 | 1498276 | A | G14 | 0.21 | 0.0016130 |
| ESRRG | 55 | 17670802 | G | G7 | 0.24 | 0.0022500 |
| EPHB2 | 57 | 10799762 | C | G14 | 0.32 | 0.0029190 |
| EPHB2 | 58 | 309473 | T | N4 | -0.28 | 0.0030420 |
| SLC35F3 | 59 | 10495346 | T | P7 | 0.28 | 0.0061170 |
| RYR2 | 60 | 1806641 | C | N3 | 0.25 | 0.0028740 |
| RYR2 | 61 | 637520 | T | G11 | -0.22 | 0.0048860 |
| RYR2 | 62 | 2275287 | A | G14 | 0.19 | 0.0067060 |
| RYR2 | 63 | 10802596 | T | G13 | 0.22 | 0.0100000 |
| RYR2 | 63 | 10802596 | T | G14 | 0.20 | 0.0034720 |
| RYR2 | 65 | 3924864 | C | G13 | 0.37 | 0.0057310 |
| RYR2 | 65 | 3924864 | C | G14 | 0.29 | 0.0071300 |
| RYR2 | 66 | 2779400 | A | G3 | -0.29 | 0.0043720 |
| RYR2 | 66 | 2779400 | A | G13 | -0.21 | 0.0086230 |
| RYR2 | 67 | 12141182 | T | G5 | -0.20 | 0.0091040 |
| RYR2 | 68 | 2819743 | T | G5 | -0.23 | 0.0042810 |
| CHRM3 | 69 | 16838637 | G | G5 | 0.20 | 0.0017450 |
| CHRM3 | 70 | 1867264 | T | G5 | 0.21 | 0.0019340 |
| CHRM3 | 70 | 1867264 | T | G7 | 0.25 | 0.0010800 |
| CHRM3 | 71 | 10802795 | C | G7 | 0.25 | 0.0013130 |
| CHRM3 | 72 | 6663632 | A | G7 | 0.22 | 0.0030570 |
| CHRM3 | 73 | 6657343 | A | G7 | -0.20 | 0.0082860 |
| CHRM3 | 74 | 10802801 | A | G7 | 0.22 | 0.0042560 |
| CHRM3 | 75 | 479933 | A | G3 | -0.34 | 0.0058350 |
| FMN2 | 76 | 12145060 | A | G4 | 0.22 | 0.0084360 |
| FMN2 | 76 | 12145060 | A | G2 | 0.27 | 0.0039240 |
| FMN2 | 77 | 12021945 | C | G2 | 0.25 | 0.0070300 |
| FMN2 | 78 | 9970045 | A | G6 | 0.30 | 0.0096920 |
| FMN2 | 80 | 7520065 | G | P4 | 0.21 | 0.0060730 |
| FMN2 | 81 | 897662 | T | P4 | 0.21 | 0.0045960 |
| FMN2 | 82 | 10926188 | G | P4 | 0.21 | 0.0051100 |
| FMN2 | 84 | 16832176 | C | G16 | -0.27 | 0.0094940 |
| FMN2 | 85 | 11799544 | T | G13 | 0.38 | 0.0072610 |
| FMN2 | 86 | 10926257 | T | G13 | 0.37 | 0.0087780 |
| RGS7 | 87 | 12038803 | A | G11 | -0.25 | 0.0055160 |
| RGS7 | 87 | 12038803 | A | N1 | -0.33 | 0.0025720 |
| CLIC4 | 89 | 6604978 | C | G2 | -0.30 | 0.0016950 |
| CLIC4 | 90 | 9332415 | T | G2 | -0.29 | 0.0022220 |
| AGBL4-C1ORF165 | 91 | 319965 | A | N3 | 0.24 | 0.0061090 |
| AGBL4-C1ORF165 | 91 | 319965 | A | N7 | 0.22 | 0.0068310 |
| AGBL4-C1ORF165 | 92 | 1934395 | G | G3 | -0.28 | 0.0094430 |
| AGBL4-C1ORF165 | 93 | 4285747 | C | G6 | -0.28 | 0.0038460 |
| AGBL4-C1ORF165 | 94 | 12023014 | C | G6 | -0.27 | 0.0053990 |
| AGBL4-C1ORF165 | 95 | 12043418 | T | G6 | -0.27 | 0.0062110 |
| AGBL4-C1ORF165 | 96 | 3121273 | G | G7 | -0.20 | 0.0088860 |
| SCP2 | 98 | 3766762 | C | G15 | -0.53 | 0.0080520 |
| SCP2 | 98 | 3766762 | C | G11 | -0.55 | 0.0046630 |
| LRP8 | 99 | 1288523 | A | P6 | 0.28 | 0.0061260 |
| ELTD1 | 101 | 4650634 | A | G9 | -0.32 | 0.0088300 |
| PRKACB | 102 | 3915908 | T | P2 | -0.28 | 0.0031410 |
| PRKACB | 103 | 3903924 | G | P2 | 0.27 | 0.0056920 |
| HPCAL1 | 105 | 16856020 | T | N3 | 0.40 | 0.0013070 |
| HPCAL1 | 105 | 16856020 | T | N5 | 0.42 | 0.0044340 |
| KCNF1 | 107 | 4669651 | T | G6 | 0.40 | 0.0006391 |
| NAP5 | 109 | 4283469 | A | P7 | -0.41 | 0.0062590 |
| NAP5 | 109 | 4283469 | A | P4 | -0.49 | 0.0066410 |
| NAP5 | 110 | 1434231 | C | G14 | 0.19 | 0.0081370 |

TABLE 3-continued

Alleles Influencing Individual PANSS Items

| Gene | SEQ ID NO: | NCBI RS # | Allele | PANSS Item | Beta | P |
|---|---|---|---|---|---|---|
| RAB3GAP1 | 111 | 10174944 | T | G6 | 0.38 | 0.0067730 |
| NXPH2 | 116 | 17651262 | A | G6 | 0.30 | 0.0020160 |
| LRP1B | 117 | 1486963 | C | G6 | −0.40 | 0.0001314 |
| LRP1B | 118 | 13021003 | C | G6 | −0.33 | 0.0008647 |
| LRP1B | 119 | 10469593 | C | G6 | −0.32 | 0.0011370 |
| LRP1B | 120 | 12479163 | A | G6 | −0.45 | 0.0000142 |
| LRP1B | 120 | 12479163 | A | P6 | −0.31 | 0.0031180 |
| LRP1B | 121 | 2171107 | A | G13 | 0.22 | 0.0075710 |
| LRP1B | 122 | 9283437 | C | P1 | 0.31 | 0.0061220 |
| LRP1B | 123 | 4954907 | T | G6 | 0.28 | 0.0082880 |
| LRP1B | 124 | 11681928 | A | N4 | −0.26 | 0.0089250 |
| LRP1B | 125 | 12616665 | G | P6 | −0.40 | 0.0007633 |
| LRP1B | 126 | 10496897 | A | N7 | 0.24 | 0.0063040 |
| LRP1B | 127 | 12990449 | C | P6 | −0.38 | 0.0012510 |
| KYNU | 129 | 2043944 | T | N2 | 0.31 | 0.0003813 |
| KYNU | 129 | 2043944 | T | N4 | 0.37 | 0.0001105 |
| KYNU | 129 | 2043944 | T | G12 | 0.27 | 0.0038560 |
| KYNU | 129 | 2043944 | T | N3 | 0.27 | 0.0012600 |
| KYNU | 130 | 10176234 | A | G13 | 0.22 | 0.0045350 |
| KYNU | 130 | 10176234 | A | G12 | 0.26 | 0.0062530 |
| KYNU | 130 | 10176234 | A | N2 | 0.29 | 0.0008502 |
| KYNU | 130 | 10176234 | A | N3 | 0.26 | 0.0022680 |
| KYNU | 131 | 351673 | T | N2 | 0.21 | 0.0095860 |
| KYNU | 131 | 351673 | T | N4 | 0.34 | 0.0002347 |
| KYNU | 132 | 6429997 | C | N4 | 0.28 | 0.0035140 |
| KYNU | 133 | 6732786 | G | G6 | −0.38 | 0.0018490 |
| ARHGAP15 | 134 | 1869009 | A | N6 | 0.27 | 0.0069890 |
| ARHGAP15 | 135 | 11895997 | A | N1 | −0.29 | 0.0031330 |
| ARHGAP15 | 136 | 17814502 | A | P2 | 0.40 | 0.0003225 |
| ARHGAP15 | 137 | 10048784 | T | G3 | −0.29 | 0.0084780 |
| ARHGAP15 | 138 | 13011344 | G | G16 | −0.29 | 0.0082560 |
| ARHGAP15 | 139 | 3795872 | T | G16 | −0.29 | 0.0082980 |
| ARHGAP15 | 141 | 13031917 | C | P3 | 0.30 | 0.0079410 |
| FMNL2 | 147 | 1561267 | C | P7 | −0.27 | 0.0097290 |
| PKP4 | 156 | 2007493 | G | G5 | −0.20 | 0.0056870 |
| PKP4 | 158 | 2528582 | G | N7 | −0.24 | 0.0036000 |
| PKP4 | 158 | 2528582 | G | G5 | −0.20 | 0.0057130 |
| PKP4 | 158 | 2528582 | G | P2 | −0.25 | 0.0081930 |
| PLA2R1 | 160 | 949753 | G | P2 | −0.31 | 0.0071790 |
| PLA2R1 | 161 | 3828324 | C | N1 | −0.25 | 0.0083020 |
| PLA2R1 | 161 | 3828324 | C | N6 | −0.27 | 0.0023180 |
| PLA2R1 | 162 | 2667012 | C | N6 | 0.26 | 0.0054070 |
| PLA2R1 | 162 | 2667012 | C | N1 | 0.27 | 0.0049360 |
| PLA2R1 | 163 | 4665145 | T | G11 | 0.25 | 0.0095000 |
| PLA2R1 | 163 | 4665145 | T | G3 | 0.34 | 0.0030190 |
| SCN3A | 165 | 11677254 | C | G7 | −0.24 | 0.0025100 |
| SCN3A | 165 | 11677254 | C | N4 | −0.28 | 0.0041850 |
| SCN3A | 165 | 11677254 | C | N1 | −0.28 | 0.0070540 |
| SCN3A | 165 | 11677254 | C | N2 | −0.29 | 0.0009855 |
| SCN1A | 166 | 6731591 | C | G7 | −0.28 | 0.0056940 |
| SCN1A | 168 | 497594 | G | G7 | 0.25 | 0.0045790 |
| SCN9A | 169 | 7589835 | A | G5 | 0.28 | 0.0082980 |
| SCN9A | 169 | 7589835 | A | N1 | 0.41 | 0.0084640 |
| SCN9A | 169 | 7589835 | A | G7 | 0.35 | 0.0039360 |
| SCN9A | 173 | 4447616 | C | P2 | 0.26 | 0.0067540 |
| SCN9A | 174 | 6732627 | A | G4 | −0.25 | 0.0025060 |
| SCN7A | 175 | 5024296 | T | G13 | 0.22 | 0.0078780 |
| SCN7A | 175 | 5024296 | T | G4 | −0.24 | 0.0055560 |
| CERKL | 176 | 4018756 | A | N5 | 0.27 | 0.0088890 |
| PDE1A | 177 | 13400054 | C | N4 | −0.41 | 0.0005951 |
| PDE1A | 178 | 3769794 | C | N3 | 0.32 | 0.0022070 |
| PDE1A | 179 | 3769789 | G | N3 | 0.29 | 0.0088030 |
| PDE1A | 180 | 2623438 | G | N4 | −0.40 | 0.0009703 |
| PDE1A | 180 | 2623438 | G | N2 | −0.32 | 0.0032780 |
| PDE1A | 181 | 4666828 | A | N4 | −0.38 | 0.0016920 |
| PDE1A | 181 | 4666828 | A | N2 | −0.29 | 0.0082390 |
| PDE1A | 182 | 6726543 | G | G1 | 0.26 | 0.0067830 |
| PDE1A | 183 | 833142 | A | G1 | −0.26 | 0.0043210 |
| PDE1A | 183 | 833142 | A | G8 | −0.15 | 0.0089830 |
| PDE1A | 183 | 833142 | A | P1 | −0.31 | 0.0047960 |
| PDE1A | 184 | 833119 | C | G4 | 0.29 | 0.0009323 |
| PDE1A | 185 | 12988258 | A | G4 | 0.26 | 0.0040120 |
| PDE1A | 186 | 6736414 | T | G1 | 0.27 | 0.0083740 |
| PDE1A | 187 | 16823124 | A | G6 | −0.29 | 0.0047680 |
| PDE1A | 188 | 10497597 | T | G6 | −0.28 | 0.0059250 |
| PDE1A | 189 | 2887202 | A | G1 | −0.25 | 0.0072430 |
| PDE1A | 189 | 2887202 | A | P1 | −0.33 | 0.0039330 |
| PDE1A | 190 | 9332425 | T | G3 | −0.32 | 0.0016990 |
| PDE1A | 190 | 9332425 | T | P6 | −0.27 | 0.0085150 |
| PDE1A | 190 | 9332425 | T | G6 | −0.28 | 0.0047890 |
| ALS2 | 192 | 2302610 | G | G10 | −0.26 | 0.0023280 |
| PARD3B | 193 | 1477179 | T | G14 | 0.21 | 0.0092930 |
| PARD3B | 194 | 2098462 | G | G14 | 0.20 | 0.0074160 |
| PARD3B | 195 | 2878473 | C | G4 | −0.34 | 0.0010800 |
| PARD3B | 196 | 1540369 | G | G5 | 0.23 | 0.0027160 |
| PARD3B | 196 | 1540369 | G | G12 | 0.28 | 0.0077080 |
| PARD3B | 197 | 2704638 | G | G5 | 0.30 | 0.0017260 |
| PARD3B | 198 | 3845806 | A | G5 | 0.20 | 0.0065550 |
| PARD3B | 198 | 3845806 | A | P5 | 0.30 | 0.0017910 |
| PARD3B | 199 | 10490293 | T | G12 | 0.26 | 0.0095200 |
| PARD3B | 200 | 1606237 | T | P5 | 0.28 | 0.0026520 |
| PARD3B | 201 | 698906 | T | P5 | 0.37 | 0.0033850 |
| NRP2 | 203 | 955395 | T | G13 | −0.25 | 0.0012450 |
| NRP2 | 203 | 955395 | T | N1 | −0.29 | 0.0036830 |
| NRP2 | 203 | 955395 | T | N2 | −0.27 | 0.0018830 |
| NRP2 | 204 | 13396083 | C | G13 | −0.21 | 0.0066730 |
| NRP2 | 205 | 6435306 | A | N1 | −0.27 | 0.0057680 |
| PIP5K3 | 206 | 7586020 | C | G5 | −0.20 | 0.0049350 |
| PIP5K3 | 207 | 10497899 | T | P1 | −0.88 | 0.0035790 |
| PIP5K3 | 207 | 10497899 | T | P6 | −0.76 | 0.0059020 |
| ERBB4 | 208 | 11901831 | C | G10 | 0.27 | 0.0075730 |
| ERBB4 | 210 | 1992029 | G | G11 | −0.26 | 0.0065430 |
| COL4A3 | 215 | 2178631 | C | G12 | −0.31 | 0.0010500 |
| COL4A3 | 215 | 2178631 | C | P5 | −0.24 | 0.0061530 |
| DNER | 216 | 6733289 | G | G10 | −0.16 | 0.0063000 |
| DNER | 217 | 12611671 | C | G14 | 0.20 | 0.0040080 |
| ECEL1 | 218 | 12616972 | C | P5 | 0.29 | 0.0016390 |
| CHRNG | 219 | 1201451 | T | G15 | −0.25 | 0.0060940 |
| SAG | 220 | 2304773 | A | P7 | 0.28 | 0.0070970 |
| SAG | 220 | 2304773 | A | N4 | 0.45 | 0.0030830 |
| SAG | 220 | 2304773 | A | N6 | 0.47 | 0.0020440 |
| KLHL29 | 222 | 747345 | A | N4 | −0.29 | 0.0025940 |
| KLHL29 | 222 | 747345 | A | G16 | −0.27 | 0.0048360 |
| KLHL29 | 222 | 747345 | A | P5 | −0.25 | 0.0062440 |
| KLHL29 | 225 | 6727901 | G | N4 | −0.30 | 0.0017570 |
| KLHL29 | 225 | 6727901 | G | G16 | −0.25 | 0.0086370 |
| KCNK3 | 228 | 7584568 | G | G13 | −0.21 | 0.0081610 |
| KCNK3 | 229 | 1627854 | G | G13 | −0.21 | 0.0090110 |
| DPYSL5 | 230 | 486582 | C | G10 | 0.17 | 0.0048990 |
| DPYSL5 | 232 | 3769138 | G | G10 | 0.17 | 0.0050320 |
| BRE | 233 | 10189434 | T | G6 | 0.31 | 0.0046780 |
| BRE | 235 | 10189899 | A | G1 | −0.27 | 0.0030600 |
| BRE | 236 | 1546029 | C | G10 | 0.18 | 0.0068080 |
| CRIM1 | 237 | 6757374 | T | P7 | −0.33 | 0.0043140 |
| CRIM1 | 237 | 6757374 | T | G10 | 0.29 | 0.0061260 |
| CRIM1 | 240 | 888074 | G | N6 | −0.25 | 0.0071850 |
| CRIM1 | 242 | 2160367 | C | N6 | −0.26 | 0.0061580 |
| CRIM1 | 243 | 848556 | T | P1 | −0.31 | 0.0039740 |
| CRIM1 | 244 | 848532 | C | G1 | −0.31 | 0.0013040 |
| CRIM1 | 245 | 848531 | A | G1 | −0.28 | 0.0038690 |
| SLC8A1 | 247 | 2072531 | T | P6 | −0.29 | 0.0028790 |
| SLC8A1 | 247 | 2072531 | T | P1 | −0.29 | 0.0079460 |
| SLC8A1 | 248 | 417591 | A | N5 | 0.31 | 0.0096150 |
| HAAO | 252 | 6738169 | G | N1 | −0.29 | 0.0060670 |
| PLEKHH2 | 253 | 17414362 | A | G10 | −0.24 | 0.0007199 |
| PLEKHH2 | 253 | 17414362 | A | G11 | −0.25 | 0.0074160 |
| PLEKHH2 | 254 | 2288710 | C | G14 | 0.35 | 0.0070470 |
| PLEKHH2 | 254 | 2288710 | C | G11 | 0.53 | 0.0010930 |
| PLEKHH2 | 254 | 2288710 | C | N5 | 0.52 | 0.0099950 |
| PLEKHH2 | 254 | 2288710 | C | N7 | 0.52 | 0.0012830 |
| PLEKHH2 | 255 | 7570252 | A | G10 | −0.18 | 0.0043850 |
| PLEKHH2 | 256 | 10165660 | C | G10 | −0.17 | 0.0061410 |
| C2ORF34 | 257 | 786616 | C | N7 | −0.31 | 0.0011430 |
| C2ORF34 | 257 | 786616 | C | P2 | −0.31 | 0.0047180 |
| C2ORF34 | 257 | 786616 | C | G15 | −0.28 | 0.0038400 |
| C2ORF34 | 258 | 786626 | G | G9 | −0.28 | 0.0042620 |
| C2ORF34 | 259 | 1067343 | A | P2 | −0.29 | 0.0062780 |
| C2ORF34 | 260 | 1584885 | C | G9 | −0.26 | 0.0023430 |
| C2ORF34 | 262 | 1067367 | A | G9 | −0.27 | 0.0059360 |
| C2ORF34 | 263 | 1065786 | T | G9 | −0.28 | 0.0048720 |

TABLE 3-continued

Alleles Influencing Individual PANSS Items

| Gene | SEQ ID NO: | NCBI RS # | Allele | PANSS Item | Beta | P |
|---|---|---|---|---|---|---|
| C2ORF34 | 265 | 698792 | A | G15 | −0.28 | 0.0049980 |
| C2ORF34 | 265 | 698792 | A | N7 | −0.27 | 0.0038670 |
| C2ORF34 | 268 | 2341457 | A | G9 | −0.24 | 0.0058060 |
| C2ORF34 | 269 | 1377906 | G | G15 | −0.22 | 0.0083300 |
| C2ORF34 | 270 | 7567272 | A | P2 | −0.25 | 0.0057880 |
| C2ORF34 | 271 | 4953105 | G | G9 | −0.23 | 0.0077590 |
| C2ORF34 | 272 | 10445928 | C | G9 | −0.23 | 0.0090270 |
| C2ORF34 | 273 | 4953122 | G | P2 | −0.24 | 0.0091370 |
| C2ORF34 | 274 | 7603180 | C | N7 | 0.29 | 0.0047560 |
| C2ORF34 | 275 | 3738980 | C | N2 | −0.37 | 0.0020550 |
| C2ORF34 | 275 | 3738980 | C | G7 | −0.40 | 0.0002342 |
| C2ORF34 | 275 | 3738980 | C | N4 | −0.37 | 0.0046210 |
| C2ORF34 | 275 | 3738980 | C | N7 | −0.30 | 0.0063550 |
| C2ORF34 | 275 | 3738980 | C | G16 | −0.40 | 0.0017670 |
| C2ORF34 | 275 | 3738980 | C | N5 | −0.47 | 0.0008419 |
| PRKCE | 276 | 666334 | T | G10 | 0.18 | 0.0080830 |
| PRKCE | 277 | 6748375 | C | N3 | 0.27 | 0.0010920 |
| PRKCE | 278 | 1020445 | C | G1 | −0.27 | 0.0042010 |
| EPAS1 | 279 | 4953340 | C | N4 | −0.28 | 0.0027890 |
| FBXO11 | 280 | 12463595 | T | G10 | 0.19 | 0.0030790 |
| FBXO11 | 281 | 12620679 | C | G13 | −0.21 | 0.0075070 |
| PSME4 | 282 | 805391 | T | G7 | −0.24 | 0.0015200 |
| PSME4 | 282 | 805391 | T | N6 | −0.25 | 0.0054780 |
| PSME4 | 282 | 805391 | T | N1 | −0.26 | 0.0068310 |
| PSME4 | 282 | 805391 | T | G13 | −0.23 | 0.0020840 |
| PSME4 | 282 | 805391 | T | G15 | −0.27 | 0.0008523 |
| PSME4 | 282 | 805391 | T | N7 | −0.25 | 0.0012910 |
| PSME4 | 283 | 805330 | A | N7 | −0.22 | 0.0047520 |
| PSME4 | 284 | 805360 | T | G10 | −0.17 | 0.0059760 |
| PSME4 | 284 | 805360 | T | N7 | −0.21 | 0.0092440 |
| PSME4 | 285 | 3731967 | A | G7 | −0.20 | 0.0099430 |
| PSME4 | 286 | 10183655 | T | N6 | −0.25 | 0.0074630 |
| ACYP2 | 290 | 17045754 | C | G1 | −0.37 | 0.0050170 |
| CCDC85A | 291 | 4672096 | G | P2 | −0.42 | 0.0097740 |
| CCDC85A | 292 | 1159916 | G | N5 | 0.28 | 0.0090120 |
| CCDC85A | 294 | 2111470 | C | G4 | 0.25 | 0.0045680 |
| CCDC85A | 295 | 1030091 | C | G14 | 0.40 | 0.0099130 |
| OTX1 | 296 | 11125946 | A | N7 | 0.23 | 0.0074160 |
| AAK1 | 297 | 9789387 | A | G9 | −0.25 | 0.0048970 |
| AAK1 | 298 | 12471316 | G | N5 | 0.25 | 0.0095590 |
| AAK1 | 299 | 12622388 | G | G9 | −0.27 | 0.0064650 |
| CTNNA2 | 300 | 7597912 | T | N7 | −0.24 | 0.0090330 |
| CTNNA2 | 301 | 2566539 | T | G15 | −0.24 | 0.0077290 |
| CTNNA2 | 305 | 1319241 | A | P3 | −0.48 | 0.0040350 |
| CTNNA2 | 307 | 895388 | T | P3 | −0.60 | 0.0030370 |
| CTNNA2 | 308 | 7589069 | C | N1 | 0.47 | 0.0019290 |
| CTNNA2 | 308 | 7589069 | C | N5 | 0.45 | 0.0037440 |
| CTNNA2 | 308 | 7589069 | C | G7 | 0.38 | 0.0016780 |
| CTNNA2 | 309 | 1444539 | C | G7 | 0.31 | 0.0074740 |
| CTNNA2 | 310 | 1434064 | G | G7 | −0.22 | 0.0058730 |
| C2ORF46 | 313 | 7577544 | G | P4 | −0.46 | 0.0003160 |
| C2ORF46 | 314 | 3111414 | C | G8 | 0.19 | 0.0091600 |
| C2ORF46 | 314 | 3111414 | C | G15 | 0.33 | 0.0013790 |
| C2ORF46 | 315 | 2914424 | T | G15 | 0.36 | 0.0041090 |
| DDEF2 | 316 | 10204214 | T | G15 | 0.38 | 0.0022250 |
| INPP4A | 317 | 17031905 | G | G14 | 0.20 | 0.0076740 |
| INPP4A | 318 | 2278214 | A | P7 | 0.20 | 0.0057790 |
| ATP2B2 | 319 | 241508 | A | P1 | 0.30 | 0.0068740 |
| PLCXD2 | 320 | 1513331 | C | G15 | 0.32 | 0.0063110 |
| PLCXD2 | 321 | 6788543 | C | P1 | −0.30 | 0.0074850 |
| PLCXD2 | 322 | 6796087 | T | P1 | −0.30 | 0.0075950 |
| PLCXD2 | 323 | 6784753 | C | G15 | −0.23 | 0.0056890 |
| PLCXD2 | 323 | 6784753 | C | P1 | −0.29 | 0.0085480 |
| PLCXD2 | 323 | 6784753 | C | P2 | −0.27 | 0.0032880 |
| PLCXD2 | 324 | 12490166 | A | P3 | 0.34 | 0.0033240 |
| CDGAP | 325 | 6438623 | A | P6 | 0.27 | 0.0091290 |
| STXBP5L | 326 | 17249426 | A | G6 | −0.34 | 0.0064750 |
| KALRN | 327 | 16835912 | C | G11 | 0.23 | 0.0050790 |
| CNTN6 | 328 | 3772339 | T | P1 | −0.32 | 0.0053750 |
| CNTN6 | 329 | 4286413 | T | N1 | 0.31 | 0.0018330 |
| CPNE4 | 332 | 9812534 | C | N5 | −0.29 | 0.0051580 |
| CPNE4 | 336 | 9289395 | G | G13 | 0.22 | 0.0086320 |
| CPNE4 | 336 | 9289395 | G | N4 | 0.27 | 0.0089350 |
| CPNE4 | 336 | 9289395 | G | N2 | 0.27 | 0.0032240 |
| CPNE4 | 336 | 9289395 | G | N5 | 0.29 | 0.0089530 |
| CPNE4 | 337 | 17297521 | C | G13 | 0.37 | 0.0016770 |
| CPNE4 | 337 | 17297521 | C | N6 | 0.40 | 0.0047080 |
| CPNE4 | 338 | 6806898 | T | N6 | 0.37 | 0.0070530 |
| CPNE4 | 338 | 6806898 | T | G13 | 0.35 | 0.0021460 |
| RAB6B | 340 | 6765093 | G | N2 | 0.23 | 0.0064270 |
| RAB6B | 340 | 6765093 | G | P6 | 0.27 | 0.0053900 |
| EPHB1 | 344 | 36172 | C | P2 | 0.25 | 0.0056950 |
| EPHB1 | 346 | 7644369 | T | P2 | 0.28 | 0.0028780 |
| EPHB1 | 347 | 4955522 | A | P2 | 0.26 | 0.0054500 |
| EPHB1 | 348 | 185257 | T | P5 | 0.26 | 0.0033630 |
| EPHB1 | 349 | 9825380 | T | P5 | 0.28 | 0.0022360 |
| EPHB1 | 350 | 4955524 | A | P2 | 0.26 | 0.0057940 |
| EPHB1 | 351 | 936323 | G | P2 | 0.25 | 0.0073630 |
| EPHB1 | 351 | 936323 | T | P5 | 0.27 | 0.0025230 |
| EPHB1 | 352 | 1870196 | T | G8 | 0.18 | 0.0049260 |
| CNTN6 | 353 | 1479530 | G | G11 | −0.23 | 0.0059820 |
| CNTN6 | 354 | 2291100 | C | N3 | −0.23 | 0.0074750 |
| CLSTN2 | 355 | 13086670 | G | G15 | 0.24 | 0.0047240 |
| CLSTN2 | 356 | 9836487 | G | G15 | 0.23 | 0.0061830 |
| CLSTN2 | 356 | 9836487 | G | N5 | 0.27 | 0.0085550 |
| CLSTN2 | 357 | 7632885 | G | N3 | 0.24 | 0.0069350 |
| CLSTN2 | 358 | 4683499 | G | G15 | 0.23 | 0.0066830 |
| CLSTN2 | 359 | 6439927 | C | G7 | 0.23 | 0.0085600 |
| CLSTN2 | 359 | 6439927 | C | N3 | 0.25 | 0.0072760 |
| CLSTN2 | 360 | 4683509 | G | G2 | −0.32 | 0.0018500 |
| CLSTN2 | 361 | 347975 | G | P6 | −0.31 | 0.0030380 |
| CLSTN2 | 361 | 347975 | G | G2 | −0.27 | 0.0042070 |
| CLSTN2 | 362 | 347973 | A | G2 | −0.25 | 0.0091370 |
| CLSTN2 | 362 | 347973 | A | P6 | −0.28 | 0.0077160 |
| SPSB4 | 364 | 7620622 | A | G7 | 0.30 | 0.0014580 |
| SLC6A6 | 365 | 1156567 | C | P5 | 0.37 | 0.0055120 |
| SLC6A6 | 365 | 1156567 | C | N1 | −0.41 | 0.0063420 |
| DAZL | 366 | 4685357 | A | G8 | 0.20 | 0.0015550 |
| DAZL | 367 | 6787063 | G | P3 | −0.30 | 0.0078670 |
| DAZL | 368 | 13064112 | G | P3 | 0.32 | 0.0098920 |
| PLD1 | 373 | 181715 | T | G8 | −0.15 | 0.0078600 |
| PLD1 | 374 | 2290480 | A | P6 | 0.31 | 0.0098860 |
| PLD1 | 374 | 2290480 | A | G6 | 0.31 | 0.0080730 |
| PLD1 | 375 | 16856569 | G | G6 | 0.31 | 0.0092840 |
| PLD1 | 375 | 16856569 | G | P6 | 0.31 | 0.0099570 |
| PLD1 | 376 | 4446237 | T | P6 | 0.29 | 0.0040360 |
| NLGN1 | 381 | 12636180 | T | P1 | 0.33 | 0.0097910 |
| NLGN1 | 382 | 10936780 | G | G13 | −0.41 | 0.0042770 |
| NLGN1 | 383 | 12634066 | A | G13 | −0.39 | 0.0061200 |
| NLGN1 | 384 | 7614469 | A | P7 | −0.21 | 0.0091360 |
| HTR3D | 385 | 939334 | G | N3 | 0.27 | 0.0025300 |
| HTR3D | 385 | 939334 | G | G13 | 0.25 | 0.0024460 |
| HTR3D | 386 | 6779545 | A | N6 | 0.28 | 0.0041680 |
| HTR3D | 386 | 6779545 | A | G13 | 0.27 | 0.0009273 |
| HTR3D | 386 | 6779545 | A | N3 | 0.29 | 0.0010920 |
| HTR3D | 386 | 6779545 | A | G15 | 0.23 | 0.0083220 |
| HTR3E | 387 | 11718245 | A | P5 | −0.32 | 0.0044630 |
| LEPREL1 | 388 | 1719615 | T | G6 | 0.32 | 0.0083790 |
| LEPREL1 | 389 | 1666486 | A | G6 | 0.32 | 0.0083790 |
| LEPREL1 | 390 | 1526031 | C | P4 | −0.33 | 0.0004817 |
| LEPREL1 | 391 | 1522930 | G | P4 | −0.28 | 0.0039020 |
| LEPREL1 | 392 | 2667709 | G | P4 | −0.22 | 0.0098150 |
| IL1RAP | 393 | 2885545 | G | N2 | −0.50 | 0.0025450 |
| IL1RAP | 394 | 6791374 | C | N7 | −0.46 | 0.0032290 |
| IL1RAP | 394 | 6791374 | C | N2 | −0.44 | 0.0081860 |
| IL1RAP | 394 | 6791374 | C | N4 | −0.58 | 0.0013920 |
| LRRC15 | 395 | 6799698 | A | G8 | −0.21 | 0.0075670 |
| UBXD7 | 398 | 3973 | T | G15 | −0.25 | 0.0060970 |
| CNTN4 | 399 | 6785626 | A | P4 | 0.20 | 0.0097310 |
| RARB | 400 | 17525900 | C | G13 | −0.38 | 0.0041060 |
| RARB | 400 | 17525900 | C | N3 | −0.40 | 0.0049540 |
| RARB | 401 | 1286738 | T | P7 | 0.26 | 0.0012390 |
| RARB | 402 | 17526942 | T | G5 | −0.29 | 0.0098670 |
| RARB | 403 | 1656463 | A | P7 | 0.28 | 0.0012580 |
| CNTN4 | 404 | 12494838 | G | N2 | 0.26 | 0.0060730 |
| CNTN4 | 405 | 1420020 | G | N7 | 0.39 | 0.0062210 |
| CNTN4 | 406 | 163352 | G | G12 | −0.34 | 0.0057050 |
| CLASP2 | 407 | 4679039 | C | P4 | −0.22 | 0.0035350 |
| CLASP2 | 408 | 6772776 | T | P4 | −0.21 | 0.0064810 |
| CLASP2 | 409 | 9862261 | G | P4 | −0.19 | 0.0096500 |

TABLE 3-continued

Alleles Influencing Individual PANSS Items

| Gene | SEQ ID NO: | NCBI RS # | Allele | PANSS Item | Beta | P |
|---|---|---|---|---|---|---|
| CLASP2 | 411 | 7641020 | G | P4 | −0.20 | 0.0084190 |
| ARPP-21 | 412 | 2305234 | A | G11 | 0.38 | 0.0045210 |
| STAC | 413 | 17186340 | T | G13 | 0.35 | 0.0100000 |
| STAC | 413 | 17186340 | T | P7 | 0.34 | 0.0024810 |
| STAC | 413 | 17186340 | T | P4 | 0.45 | 0.0005653 |
| ULK4 | 414 | 7618902 | G | P5 | 0.26 | 0.0064860 |
| ULK4 | 415 | 1495698 | C | G15 | 0.25 | 0.0039090 |
| ULK4 | 415 | 1495698 | C | G13 | 0.24 | 0.0032920 |
| ULK4 | 416 | 1691964 | T | N7 | 0.25 | 0.0015390 |
| ULK4 | 417 | 1691966 | G | N7 | 0.24 | 0.0023360 |
| ULK4 | 418 | 1691998 | G | N7 | 0.23 | 0.0032560 |
| ULK4 | 418 | 1691998 | G | G10 | 0.16 | 0.0069320 |
| ULK4 | 418 | 1691998 | G | G8 | 0.15 | 0.0081990 |
| ULK4 | 419 | 13069172 | G | N7 | 0.22 | 0.0053180 |
| ULK4 | 419 | 13069172 | G | G15 | 0.23 | 0.0039650 |
| ULK4 | 419 | 13069172 | G | G13 | 0.22 | 0.0039610 |
| ULK4 | 420 | 2272007 | A | G11 | 0.31 | 0.0064130 |
| ITPR1 | 421 | 9880562 | T | N6 | 0.26 | 0.0064910 |
| ITPR1 | 422 | 7432768 | G | G12 | −0.24 | 0.0092850 |
| ITPR1 | 422 | 7432768 | G | G6 | 0.32 | 0.0007960 |
| SEMA3F | 423 | 2624837 | T | P3 | −0.51 | 0.0045480 |
| SEMA3F | 425 | 12632110 | A | N5 | −0.32 | 0.0031660 |
| CACNA2D3 | 427 | 11130396 | T | P7 | −0.19 | 0.0075930 |
| CACNA2D3 | 428 | 4928040 | A | N5 | −0.30 | 0.0094690 |
| ERC2 | 429 | 815453 | G | G15 | −0.26 | 0.0063400 |
| ERC2 | 430 | 2132237 | C | N4 | 0.29 | 0.0028920 |
| ERC2 | 431 | 11130482 | C | G15 | −0.31 | 0.0029250 |
| ERC2 | 432 | 2168818 | T | G14 | 0.23 | 0.0076590 |
| ERC2 | 434 | 9810436 | A | N5 | 0.39 | 0.0013900 |
| ERC2 | 434 | 9810436 | A | P1 | −0.35 | 0.0075910 |
| ERC2 | 436 | 4974168 | C | N5 | 0.38 | 0.0025340 |
| ERC2 | 437 | 1485672 | T | N5 | −0.34 | 0.0015390 |
| ERC2 | 439 | 1869156 | G | N5 | −0.29 | 0.0046120 |
| ERC2 | 441 | 4974134 | A | N5 | −0.30 | 0.0061560 |
| ERC2 | 442 | 4974200 | G | N5 | −0.29 | 0.0073480 |
| ERC2 | 445 | 1546060 | C | N1 | −0.30 | 0.0031360 |
| ERC2 | 445 | 1546060 | C | N6 | −0.30 | 0.0015960 |
| ERC2 | 446 | 6805882 | C | N6 | −0.30 | 0.0020990 |
| ERC2 | 446 | 6805882 | C | N2 | −0.27 | 0.0020750 |
| ERC2 | 447 | 885211 | A | G5 | −0.19 | 0.0064520 |
| ERC2 | 448 | 9814545 | A | N1 | −0.31 | 0.0052050 |
| ERC2 | 449 | 1878270 | C | G7 | −0.22 | 0.0046770 |
| ERC2 | 450 | 9873381 | A | N1 | −0.29 | 0.0046080 |
| ERC2 | 450 | 9873381 | A | G7 | −0.26 | 0.0014620 |
| ERC2 | 450 | 9873381 | A | N2 | −0.23 | 0.0089980 |
| ERC2 | 451 | 9881216 | T | G7 | −0.21 | 0.0068840 |
| ERC2 | 451 | 9881216 | T | N1 | −0.30 | 0.0027270 |
| ERC2 | 452 | 7633140 | A | G7 | −0.21 | 0.0072940 |
| ERC2 | 453 | 7627759 | C | N1 | −0.30 | 0.0032360 |
| ERC2 | 453 | 7627759 | C | G7 | −0.21 | 0.0075200 |
| FHIT | 454 | 639244 | G | G5 | 0.20 | 0.0050940 |
| FHIT | 454 | 639244 | G | N4 | 0.29 | 0.0039900 |
| FHIT | 454 | 639244 | G | G7 | 0.24 | 0.0035580 |
| FHIT | 454 | 639244 | G | G16 | 0.26 | 0.0072680 |
| FHIT | 454 | 639244 | G | N2 | 0.23 | 0.0098560 |
| FHIT | 454 | 639244 | G | N6 | 0.32 | 0.0014180 |
| FHIT | 455 | 2253211 | C | N3 | 0.22 | 0.0081450 |
| PTPRG | 459 | 624755 | G | P1 | 0.29 | 0.0074050 |
| PTPRG | 459 | 624755 | G | G9 | 0.24 | 0.0084740 |
| PTPRG | 460 | 3821880 | A | N5 | −0.27 | 0.0086610 |
| PTPRG | 460 | 3821880 | A | G1 | −0.24 | 0.0070780 |
| PTPRG | 461 | 1713531 | C | G15 | −0.25 | 0.0043390 |
| PTPRG | 462 | 9683044 | C | N5 | −0.35 | 0.0032220 |
| PTPRG | 463 | 7651505 | G | G1 | 0.28 | 0.0023500 |
| PTPRG | 464 | 1388612 | A | G3 | −0.33 | 0.0081380 |
| PTPRG | 465 | 1388613 | C | N5 | 0.38 | 0.0008341 |
| PTPRG | 465 | 1388613 | C | G3 | −0.38 | 0.0006554 |
| PTPRG | 466 | 2242352 | G | N5 | 0.34 | 0.0012430 |
| CADPS | 467 | 1355551 | T | N5 | 0.43 | 0.0012130 |
| CADPS | 467 | 1355551 | T | N3 | 0.34 | 0.0022110 |
| CADPS | 468 | 9843019 | T | G3 | −0.38 | 0.0018590 |
| CADPS | 469 | 9311842 | T | N6 | 0.32 | 0.0034610 |
| CADPS | 469 | 9311842 | T | N3 | 0.29 | 0.0029930 |
| CADPS | 469 | 9311842 | T | N5 | 0.37 | 0.0015880 |
| CADPS | 470 | 704356 | T | G9 | −0.45 | 0.0033380 |
| CADPS | 471 | 13313979 | A | N2 | −0.24 | 0.0095670 |
| CADPS | 471 | 13313979 | A | G9 | −0.26 | 0.0065630 |
| CADPS | 472 | 12636581 | A | N6 | −0.26 | 0.0081180 |
| CADPS | 472 | 12636581 | A | N2 | −0.24 | 0.0072280 |
| CADPS | 474 | 17280557 | A | N6 | −0.30 | 0.0075210 |
| CADPS | 475 | 17280571 | T | N6 | −0.31 | 0.0033290 |
| CADPS | 475 | 17280571 | T | N2 | −0.27 | 0.0050670 |
| CADPS | 476 | 17357618 | C | G8 | −0.17 | 0.0075370 |
| CADPS | 476 | 17357618 | C | N6 | −0.29 | 0.0058430 |
| SYNPR | 478 | 11130939 | T | G7 | 0.26 | 0.0068900 |
| PRICKLE2 | 479 | 161661 | A | G7 | 0.21 | 0.0085940 |
| PRICKLE2 | 479 | 161661 | A | N1 | 0.30 | 0.0034810 |
| PRICKLE2 | 480 | 4994608 | A | P3 | −0.30 | 0.0097530 |
| MAGI1 | 481 | 9883580 | G | G12 | 1.01 | 0.0021390 |
| MAGI1 | 482 | 2371948 | A | G8 | 0.50 | 0.0076160 |
| MAGI1 | 482 | 2371948 | A | G12 | 0.93 | 0.0022050 |
| MAGI1 | 482 | 2371948 | A | N7 | 0.67 | 0.0094890 |
| MAGI1 | 483 | 9845819 | C | G8 | −0.16 | 0.0094880 |
| FAM19A1 | 486 | 1491748 | A | N7 | 0.23 | 0.0083170 |
| FOXP1 | 487 | 2196356 | C | G14 | 0.17 | 0.0094540 |
| FOXP1 | 488 | 2597312 | C | P7 | 0.17 | 0.0079850 |
| FOXP1 | 489 | 2166780 | T | G8 | −0.17 | 0.0052460 |
| GBE1 | 490 | 7622741 | G | G15 | 0.27 | 0.0020670 |
| GBE1 | 491 | 6769230 | A | G15 | 0.26 | 0.0031950 |
| GBE1 | 492 | 2307058 | T | G15 | 0.26 | 0.0044090 |
| GBE1 | 493 | 11922101 | T | N5 | −0.77 | 0.0083960 |
| GBE1 | 494 | 7613144 | T | G15 | 0.25 | 0.0064530 |
| GBE1 | 496 | 3772899 | G | G8 | −0.15 | 0.0097220 |
| GBE1 | 497 | 3772891 | A | G8 | 0.20 | 0.0039690 |
| GBE1 | 498 | 2680245 | A | N3 | −0.24 | 0.0035420 |
| HTR1F | 500 | 1027689 | T | N3 | 0.37 | 0.0095000 |
| EPHA6 | 501 | 12107680 | T | G4 | −0.60 | 0.0086820 |
| EPHA6 | 502 | 16838196 | A | G1 | 0.65 | 0.0014370 |
| EPHA6 | 503 | 9848688 | A | G1 | 0.55 | 0.0074920 |
| DKK2 | 504 | 447372 | A | G5 | 0.23 | 0.0018330 |
| DKK2 | 505 | 379333 | T | N4 | −0.44 | 0.0094420 |
| PAPSS1 | 506 | 2189158 | T | G2 | 0.26 | 0.0026850 |
| COL25A1 | 507 | 2305438 | A | G11 | −0.23 | 0.0050050 |
| COL25A1 | 510 | 3096489 | C | N5 | 0.50 | 0.0000011 |
| COL25A1 | 511 | 3096490 | A | N5 | 0.50 | 0.0000011 |
| ANK2 | 512 | 13134375 | C | N2 | −0.23 | 0.0082630 |
| ANK2 | 512 | 13134375 | C | N4 | −0.26 | 0.0066540 |
| ANK2 | 513 | 13107082 | G | N1 | 0.28 | 0.0047720 |
| ANK2 | 513 | 13107082 | G | N6 | 0.25 | 0.0081860 |
| ANK2 | 513 | 13107082 | G | G10 | −0.17 | 0.0043110 |
| ANK2 | 514 | 413019 | C | N1 | 0.28 | 0.0058060 |
| ANK2 | 514 | 413019 | C | G10 | −0.17 | 0.0054180 |
| ANK2 | 514 | 413019 | C | N6 | 0.25 | 0.0085470 |
| ANK2 | 515 | 29336 | T | P2 | 0.23 | 0.0092650 |
| ANK2 | 515 | 29336 | T | G1 | −0.30 | 0.0006090 |
| ANK2 | 516 | 29329 | T | G1 | −0.23 | 0.0066080 |
| ANK2 | 518 | 29311 | A | G8 | 0.18 | 0.0070150 |
| ANK2 | 518 | 29311 | A | P2 | 0.32 | 0.0024950 |
| ANK2 | 518 | 29311 | A | G7 | 0.25 | 0.0050810 |
| CAMK2D | 519 | 11946664 | G | G14 | −0.21 | 0.0025330 |
| CAMK2D | 520 | 10488894 | C | G14 | −0.19 | 0.0052980 |
| NDST3 | 522 | 6820367 | A | G14 | −0.18 | 0.0064980 |
| PRSS12 | 523 | 883686 | C | P1 | −0.31 | 0.0038050 |
| PRSS12 | 523 | 883686 | C | G2 | −0.28 | 0.0010810 |
| GPR103 | 524 | 11732033 | A | G7 | 0.23 | 0.0085620 |
| MAML3 | 526 | 2246759 | G | G4 | −0.23 | 0.0056290 |
| IL15 | 527 | 17007695 | C | G2 | 0.43 | 0.0078580 |
| INPP4B | 528 | 2667101 | G | N5 | 0.30 | 0.0042020 |
| INPP4B | 529 | 2667108 | C | G8 | 0.66 | 0.0004086 |
| INPP4B | 529 | 2667108 | C | G13 | 0.67 | 0.0081900 |
| INPP4B | 530 | 336378 | T | N3 | 0.84 | 0.0010640 |
| INPP4B | 530 | 336378 | T | G11 | 0.97 | 0.0000950 |
| INPP4B | 530 | 336378 | T | N7 | 0.64 | 0.0082390 |
| INPP4B | 531 | 1353603 | A | G10 | 0.42 | 0.0079750 |
| INPP4B | 531 | 1353603 | A | N3 | 0.67 | 0.0021800 |
| INPP4B | 532 | 336329 | G | G13 | 0.67 | 0.0081900 |
| INPP4B | 532 | 336329 | G | N3 | 0.82 | 0.0025920 |
| INPP4B | 532 | 336329 | G | G11 | 0.88 | 0.0008613 |
| INPP4B | 532 | 336329 | G | G8 | 0.66 | 0.0004086 |
| INPP4B | 534 | 2276942 | A | P5 | 0.42 | 0.0059510 |

TABLE 3-continued

Alleles Influencing Individual PANSS Items

| Gene | SEQ ID NO: | NCBI RS # | Allele | PANSS Item | Beta | P |
|---|---|---|---|---|---|---|
| INPP4B | 537 | 2627802 | T | P5 | −0.24 | 0.0055920 |
| POU4F2 | 538 | 1979903 | C | G7 | −0.47 | 0.0040450 |
| LDB2 | 539 | 2135442 | A | N5 | 0.31 | 0.0041740 |
| LDB2 | 540 | 12500134 | A | N5 | 0.33 | 0.0076190 |
| FSTL5 | 541 | 4501178 | C | G2 | 0.32 | 0.0064200 |
| FSTL5 | 541 | 4501178 | C | G4 | 0.33 | 0.0019340 |
| FSTL5 | 542 | 17041222 | G | G7 | 0.25 | 0.0093290 |
| FSTL5 | 548 | 7699959 | A | G12 | 0.26 | 0.0066450 |
| FSTL5 | 548 | 7699959 | A | N3 | 0.25 | 0.0038910 |
| FSTL5 | 548 | 7699959 | A | G7 | 0.21 | 0.0079750 |
| FSTL5 | 549 | 10031537 | T | N3 | 0.25 | 0.0022850 |
| FSTL5 | 549 | 10031537 | T | G7 | 0.20 | 0.0084240 |
| FSTL5 | 550 | 1994770 | G | N3 | −0.24 | 0.0037350 |
| FSTL5 | 551 | 13101933 | T | G3 | −0.36 | 0.0099150 |
| LDB2 | 552 | 157631 | G | G8 | 0.29 | 0.0070260 |
| LDB2 | 554 | 1990280 | G | N3 | −0.22 | 0.0062200 |
| LDB2 | 554 | 1990280 | G | G13 | −0.20 | 0.0070020 |
| LDB2 | 555 | 992704 | T | N3 | −0.26 | 0.0038550 |
| LDB2 | 556 | 13110882 | G | P5 | 0.23 | 0.0062780 |
| LDB2 | 556 | 13110882 | G | N3 | −0.22 | 0.0062690 |
| LDB2 | 556 | 13110882 | G | N6 | −0.33 | 0.0003358 |
| PALLD | 558 | 10009393 | G | G10 | −0.19 | 0.0031440 |
| PALLD | 559 | 17054309 | A | G16 | −0.34 | 0.0063510 |
| PALLD | 560 | 10009813 | G | G10 | −0.17 | 0.0073640 |
| PALLD | 561 | 2319901 | G | N1 | −0.27 | 0.0080660 |
| PALLD | 562 | 2712118 | C | G10 | 0.17 | 0.0063330 |
| PALLD | 563 | 2319900 | T | G10 | 0.16 | 0.0079250 |
| PALLD | 566 | 4425335 | G | N4 | −0.30 | 0.0059900 |
| PALLD | 569 | 10033898 | C | G8 | 0.16 | 0.0065860 |
| ODZ3 | 571 | 2675534 | T | P7 | 0.25 | 0.0007318 |
| ODZ3 | 571 | 2675534 | T | P2 | 0.29 | 0.0065920 |
| ODZ3 | 571 | 2675534 | T | N1 | 0.40 | 0.0007424 |
| ODZ3 | 572 | 2675532 | C | P7 | 0.17 | 0.0086620 |
| ODZ3 | 572 | 2675532 | C | N1 | 0.28 | 0.0082390 |
| ODZ3 | 572 | 2675532 | C | G12 | 0.29 | 0.0030980 |
| ODZ3 | 572 | 2675532 | C | N4 | 0.29 | 0.0030560 |
| ODZ3 | 573 | 9312304 | A | G4 | −0.24 | 0.0062270 |
| ENPP6 | 574 | 6830766 | G | G7 | −0.22 | 0.0058610 |
| ENPP6 | 579 | 17584049 | C | G9 | −0.26 | 0.0040030 |
| CASP3 | 580 | 9685847 | G | G9 | −0.28 | 0.0017520 |
| CASP3 | 581 | 2720376 | C | G9 | −0.27 | 0.0019420 |
| SLIT2 | 582 | 1323068 | A | G16 | −0.25 | 0.0092420 |
| SLIT2 | 583 | 621806 | C | G4 | −0.28 | 0.0008018 |
| SLIT2 | 584 | 10516357 | A | G2 | 0.28 | 0.0044990 |
| SLIT2 | 585 | 609535 | A | G4 | −0.27 | 0.0008318 |
| SLIT2 | 586 | 2168802 | T | G2 | 0.36 | 0.0006412 |
| SLIT2 | 587 | 9992591 | C | G4 | −0.28 | 0.0008484 |
| PCDH7 | 588 | 12331633 | C | N6 | 0.23 | 0.0099580 |
| KIAA1239 | 589 | 4585313 | C | G9 | 0.48 | 0.0068600 |
| KIAA1239 | 591 | 2928297 | A | P1 | −0.28 | 0.0082720 |
| TBC1D1 | 594 | 13110318 | A | G5 | −0.31 | 0.0076540 |
| UBE2K | 596 | 192779 | A | P3 | 0.48 | 0.0010760 |
| UBE2K | 597 | 1003212 | T | P7 | 0.25 | 0.0062240 |
| LIMCH1 | 598 | 4343753 | T | P7 | 0.22 | 0.0029980 |
| LIMCH1 | 598 | 4343753 | T | G8 | 0.18 | 0.0076530 |
| LIMCH1 | 599 | 6447080 | G | G1 | 0.30 | 0.0012160 |
| LIMCH1 | 600 | 6447081 | G | G1 | 0.28 | 0.0020740 |
| LIMCH1 | 601 | 7671360 | T | G1 | 0.27 | 0.0034520 |
| LIMCH1 | 602 | 4610372 | G | G1 | 0.26 | 0.0045040 |
| LIMCH1 | 603 | 7683275 | G | G3 | 0.38 | 0.0007506 |
| LIMCH1 | 604 | 4861118 | A | G1 | 0.24 | 0.0077590 |
| LIMCH1 | 605 | 10026359 | T | N2 | −0.31 | 0.0053650 |
| LIMCH1 | 606 | 6811377 | A | G14 | −0.17 | 0.0075290 |
| LIMCH1 | 607 | 6821712 | C | N7 | −0.25 | 0.0038440 |
| LIMCH1 | 608 | 17444879 | T | P6 | 0.43 | 0.0081320 |
| LOC389207 | 609 | 1597565 | A | G7 | 0.24 | 0.0099900 |
| NPFFR2 | 610 | 6856651 | T | G8 | 0.19 | 0.0022320 |
| NPFFR2 | 611 | 7654531 | T | G8 | 0.19 | 0.0025550 |
| NPFFR2 | 612 | 6824703 | C | G8 | 0.18 | 0.0038090 |
| NPFFR2 | 613 | 4694192 | A | N2 | −0.89 | 0.0027340 |
| NPFFR2 | 614 | 17775309 | G | P1 | −0.33 | 0.0038050 |
| NPFFR2 | 615 | 2365797 | T | N7 | −0.28 | 0.0011530 |
| NPFFR2 | 615 | 2365797 | T | G1 | 0.28 | 0.0036590 |
| NPFFR2 | 615 | 2365797 | T | P3 | 0.34 | 0.0041650 |
| SCARB2 | 616 | 17001533 | C | G12 | −0.37 | 0.0078630 |
| SHROOM3 | 617 | 10013334 | T | G2 | −0.34 | 0.0057150 |
| SHROOM3 | 618 | 344141 | C | G15 | −0.24 | 0.0050660 |
| SCD5 | 619 | 10014168 | G | P5 | −0.28 | 0.0087720 |
| SCD5 | 620 | 7679857 | A | N7 | −0.34 | 0.0015940 |
| SCD5 | 622 | 17006038 | C | N7 | −0.34 | 0.0018380 |
| HERC3 | 624 | 3796660 | A | P4 | 0.34 | 0.0090780 |
| FAM13A1 | 625 | 12507401 | C | N4 | 0.35 | 0.0025900 |
| SLC2A9 | 628 | 1401438 | T | P3 | −0.39 | 0.0058430 |
| PDLIM5 | 629 | 13435066 | A | G15 | 0.25 | 0.0023570 |
| PDLIM5 | 629 | 13435066 | A | G10 | 0.15 | 0.0077160 |
| SLC2A9 | 630 | 4481233 | T | N5 | −0.39 | 0.0029370 |
| PDLIM5 | 631 | 2433325 | A | G1 | −0.32 | 0.0015350 |
| PDLIM5 | 632 | 6812098 | C | G16 | 0.46 | 0.0001203 |
| PDLIM5 | 632 | 6812098 | C | N4 | 0.36 | 0.0035100 |
| PDLIM5 | 632 | 6812098 | C | N2 | 0.34 | 0.0021210 |
| PDLIM5 | 633 | 3805274 | A | N2 | 0.26 | 0.0086370 |
| PDLIM5 | 634 | 2452593 | G | G16 | 0.37 | 0.0003595 |
| PDLIM5 | 635 | 11735212 | A | G16 | 0.31 | 0.0009057 |
| PDLIM5 | 635 | 11735212 | A | P6 | 0.29 | 0.0036940 |
| PDLIM5 | 636 | 7689746 | A | G1 | −0.35 | 0.0044800 |
| SLC2A9 | 637 | 13111638 | T | N5 | −0.36 | 0.0035700 |
| SLC2A9 | 638 | 3733588 | C | G10 | −0.18 | 0.0069930 |
| SLC2A9 | 638 | 3733588 | C | G6 | −0.29 | 0.0099750 |
| SLC2A9 | 639 | 7669607 | T | N5 | −0.34 | 0.0046140 |
| SLC2A9 | 640 | 9291642 | C | N5 | −0.38 | 0.0056060 |
| SLC2A9 | 642 | 6820230 | T | G5 | 0.20 | 0.0090260 |
| SLC2A9 | 643 | 7671266 | T | N5 | −0.33 | 0.0072290 |
| FBXL17 | 644 | 6871209 | T | G16 | −0.26 | 0.0084320 |
| FBXL17 | 645 | 286769 | T | P3 | −0.36 | 0.0098200 |
| FBXL17 | 646 | 11242664 | G | P3 | 0.38 | 0.0089410 |
| FBXL17 | 647 | 4957551 | T | G3 | −0.28 | 0.0095000 |
| FBXL17 | 648 | 2416188 | G | P3 | 0.30 | 0.0067080 |
| FBXL17 | 649 | 4957554 | T | P3 | −0.32 | 0.0062560 |
| FBXL17 | 650 | 2024528 | A | P1 | 0.29 | 0.0081400 |
| FBXL17 | 651 | 1421972 | G | G3 | 0.35 | 0.0009893 |
| PJA2 | 652 | 2963034 | A | G4 | −0.22 | 0.0063020 |
| PJA2 | 653 | 11957188 | T | P5 | −0.64 | 0.0042340 |
| PJA2 | 653 | 11957188 | T | G9 | −0.65 | 0.0036440 |
| KCNN2 | 655 | 337689 | G | G15 | 0.21 | 0.0084230 |
| KCNN2 | 656 | 1072922 | A | N1 | 0.27 | 0.0096620 |
| KCNN2 | 657 | 13163662 | A | N1 | 0.29 | 0.0070520 |
| KCNN2 | 658 | 338625 | T | N1 | 0.26 | 0.0093140 |
| KCNN2 | 659 | 4435855 | A | G5 | −0.33 | 0.0009679 |
| SEMA6A | 660 | 254231 | G | G11 | 0.23 | 0.0033470 |
| HSD17B4 | 661 | 6897978 | A | N3 | −0.28 | 0.0075120 |
| HSD17B4 | 662 | 246968 | A | G4 | −0.25 | 0.0016710 |
| SNCAIP | 663 | 10052918 | A | G15 | 0.33 | 0.0012040 |
| SNCAIP | 664 | 7444144 | G | G15 | 0.32 | 0.0018020 |
| SNCAIP | 665 | 17149128 | A | G15 | 0.41 | 0.0009740 |
| SNCAIP | 666 | 17149141 | A | G15 | 0.40 | 0.0015110 |
| SNCAIP | 667 | 304379 | C | N2 | −0.23 | 0.0056100 |
| SNX2 | 668 | 4343835 | C | P6 | 0.26 | 0.0091950 |
| SNX2 | 669 | 12109789 | G | P3 | 0.32 | 0.0041350 |
| SNX2 | 671 | 2407403 | G | G12 | −0.26 | 0.0098520 |
| SNX24 | 673 | 246286 | T | P6 | −0.32 | 0.0023260 |
| SNX24 | 674 | 246266 | C | P6 | −0.32 | 0.0023640 |
| SNX24 | 675 | 6866400 | A | P7 | 0.18 | 0.0085110 |
| ADAMTS19 | 676 | 17163231 | G | G8 | 0.20 | 0.0066970 |
| VDAC1 | 677 | 4958172 | A | G8 | −0.23 | 0.0065340 |
| TRPC7 | 678 | 7701815 | C | N1 | 0.27 | 0.0049180 |
| TRPC7 | 678 | 7701815 | C | G8 | 0.16 | 0.0031180 |
| TRPC7 | 679 | 6596300 | N | N1 | −0.30 | 0.0019470 |
| TRPC7 | 680 | 3777150 | A | N2 | 0.24 | 0.0049440 |
| TRPC7 | 680 | 3777150 | A | N1 | 0.28 | 0.0055900 |
| TRPC7 | 681 | 953096 | C | N1 | −0.30 | 0.0036380 |
| DNAH5 | 683 | 6554811 | G | G8 | −0.16 | 0.0071830 |
| DNAH5 | 684 | 7715811 | T | G15 | −0.31 | 0.0015590 |
| DNAH5 | 685 | 1502050 | G | G15 | −0.31 | 0.0019200 |
| DNAH5 | 686 | 10513155 | A | G12 | 0.26 | 0.0082530 |
| DNAH5 | 686 | 10513155 | A | N3 | 0.24 | 0.0061840 |
| DNAH5 | 686 | 10513155 | A | G11 | 0.23 | 0.0075800 |
| DNAH5 | 686 | 10513155 | A | G15 | 0.28 | 0.0011570 |
| DNAH5 | 687 | 7709692 | C | G15 | −0.33 | 0.0022890 |
| DNAH5 | 689 | 1445823 | C | P3 | 0.30 | 0.0060050 |
| DNAH5 | 689 | 1445823 | C | G1 | 0.27 | 0.0031900 |

TABLE 3-continued

Alleles Influencing Individual PANSS Items

| Gene | SEQ ID NO: | NCBI RS # | Allele | PANSS Item | Beta | P |
|---|---|---|---|---|---|---|
| DNAH5 | 690 | 1530498 | G | G1 | 0.25 | 0.0054000 |
| DNAH5 | 690 | 1530498 | G | G14 | 0.16 | 0.0094470 |
| DNAH5 | 691 | 13154455 | G | G1 | 0.25 | 0.0072620 |
| DNAH5 | 691 | 13154455 | G | G2 | 0.26 | 0.0043680 |
| DNAH5 | 692 | 339424 | T | G1 | 0.28 | 0.0077300 |
| GRIA1 | 693 | 1463748 | A | N1 | −0.31 | 0.0016600 |
| GRIA1 | 694 | 7735696 | C | N1 | 0.26 | 0.0083580 |
| GRIA1 | 695 | 17518831 | C | N1 | 0.31 | 0.0018810 |
| GRIA1 | 696 | 778822 | C | G4 | −0.26 | 0.0048090 |
| GRIA1 | 697 | 778825 | A | P4 | −0.24 | 0.0019700 |
| GRIA1 | 697 | 778825 | A | P5 | −0.28 | 0.0025320 |
| GRIA1 | 698 | 11953799 | T | G13 | −0.23 | 0.0077120 |
| GRIA1 | 699 | 4424038 | G | G15 | −0.31 | 0.0019480 |
| GRIA1 | 699 | 4424038 | G | G13 | −0.36 | 0.0001153 |
| GRIA1 | 700 | 11167640 | C | G15 | −0.30 | 0.0025210 |
| GRIA1 | 700 | 11167640 | C | G13 | −0.36 | 0.0001515 |
| GRIA1 | 701 | 7708391 | A | G15 | −0.23 | 0.0085600 |
| GRIA1 | 701 | 7708391 | A | G13 | −0.27 | 0.0010290 |
| GRIA1 | 702 | 4958351 | A | P2 | 0.26 | 0.0069350 |
| GRIA1 | 703 | 10070447 | T | G9 | −0.25 | 0.0077290 |
| ODZ2 | 704 | 2337017 | C | P6 | −0.37 | 0.0077140 |
| ODZ2 | 704 | 2337017 | C | G13 | −0.34 | 0.0019890 |
| ODZ2 | 704 | 2337017 | C | G11 | −0.32 | 0.0046270 |
| ODZ2 | 704 | 2337017 | C | G14 | −0.24 | 0.0073700 |
| MYO10 | 705 | 428263 | A | P3 | 0.35 | 0.0019020 |
| MYO10 | 706 | 388887 | T | P3 | 0.33 | 0.0032930 |
| ODZ2 | 708 | 1421989 | G | G11 | −0.28 | 0.0080900 |
| ODZ2 | 708 | 1421989 | G | P2 | −0.31 | 0.0091440 |
| ODZ2 | 709 | 13158058 | T | P4 | 0.20 | 0.0081150 |
| ODZ2 | 710 | 17069979 | G | P3 | −0.52 | 0.0078660 |
| ODZ2 | 711 | 6868169 | G | G9 | 0.24 | 0.0097920 |
| ODZ2 | 711 | 6868169 | G | G15 | 0.23 | 0.0072560 |
| MYO10 | 714 | 11133860 | G | P2 | −0.31 | 0.0050130 |
| BASP1 | 715 | 2956564 | C | G11 | −0.22 | 0.0086320 |
| PLEKHG4B | 716 | 9312845 | T | N5 | 0.51 | 0.0004538 |
| PLEKHG4B | 718 | 6888246 | T | N5 | 0.48 | 0.0010580 |
| PLEKHG4B | 719 | 3853521 | A | N5 | 0.48 | 0.0012290 |
| CDH10 | 721 | 7731953 | T | N1 | −0.43 | 0.0041710 |
| CDH10 | 722 | 3822429 | T | P7 | −0.19 | 0.0027610 |
| CDH10 | 722 | 3822429 | T | N2 | −0.24 | 0.0054650 |
| CDH10 | 722 | 3822429 | T | P6 | −0.30 | 0.0025310 |
| SLC45A2 | 723 | 35388 | T | N2 | −0.22 | 0.0086070 |
| C1QTNF3 | 725 | 17583316 | C | G13 | −0.25 | 0.0031540 |
| C1QTNF3 | 725 | 17583316 | C | N5 | −0.31 | 0.0041570 |
| C1QTNF3 | 726 | 301506 | G | P5 | −0.23 | 0.0094750 |
| C1QTNF3 | 727 | 6898170 | G | G5 | −0.19 | 0.0051580 |
| C1QTNF3 | 727 | 6898170 | G | G13 | −0.22 | 0.0049640 |
| C1QTNF3 | 728 | 9292523 | C | N1 | −0.32 | 0.0017980 |
| C1QTNF3 | 728 | 9292523 | C | G5 | −0.18 | 0.0083330 |
| SLC1A3 | 729 | 2113099 | C | P3 | 0.32 | 0.0072760 |
| EGFLAM | 730 | 4869580 | T | N6 | 0.41 | 0.0032350 |
| EGFLAM | 730 | 4869580 | T | N3 | 0.35 | 0.0045490 |
| EGFLAM | 730 | 4869580 | T | N5 | 0.40 | 0.0080270 |
| EGFLAM | 731 | 2589787 | A | N5 | 0.48 | 0.0094900 |
| EGFLAM | 732 | 2886890 | C | N5 | 0.31 | 0.0021350 |
| AHRR | 733 | 2721012 | G | N2 | 0.31 | 0.0013310 |
| AHRR | 735 | 2672734 | C | N1 | −0.27 | 0.0092760 |
| EXOC3 | 736 | 2561667 | T | N1 | −0.27 | 0.0099230 |
| ITGA1 | 737 | 1820167 | A | N5 | −0.29 | 0.0044460 |
| ITGA1 | 738 | 12520591 | G | P3 | 0.57 | 0.0094040 |
| ITGA2 | 740 | 3212576 | G | N4 | 0.32 | 0.0093410 |
| ITGA2 | 741 | 7719848 | A | N4 | 0.26 | 0.0095610 |
| PDE4D | 742 | 2910641 | A | N7 | −0.29 | 0.0064530 |
| PDE4D | 743 | 258125 | T | G6 | 0.25 | 0.0072690 |
| ELOVL7 | 744 | 4541610 | T | N7 | 0.42 | 0.0082400 |
| ELOVL7 | 745 | 4482855 | G | G10 | −0.16 | 0.0060400 |
| ELOVL7 | 746 | 6449505 | C | P3 | −0.42 | 0.0015620 |
| ELOVL7 | 747 | 4700397 | A | G10 | 0.17 | 0.0040410 |
| ELOVL7 | 748 | 17332824 | C | G10 | 0.19 | 0.0013010 |
| TNPO1 | 749 | 153320 | T | G8 | 0.22 | 0.0024000 |
| TNPO1 | 749 | 153320 | T | P3 | −0.43 | 0.0021820 |
| TNPO1 | 750 | 34653 | T | P3 | −0.41 | 0.0031040 |
| TNPO1 | 751 | 266444 | C | P3 | −0.40 | 0.0047670 |
| TNPO1 | 751 | 266444 | C | G8 | 0.20 | 0.0066290 |
| FCHO2 | 752 | 185435 | G | P3 | −0.42 | 0.0033610 |
| CMYA5 | 754 | 6880680 | C | N1 | 0.44 | 0.0078380 |
| CMYA5 | 755 | 3828611 | G | G4 | 0.51 | 0.0004989 |
| THBS4 | 756 | 256447 | C | N1 | −0.33 | 0.0088410 |
| THBS4 | 757 | 256444 | C | N1 | −0.32 | 0.0097460 |
| THBS4 | 758 | 1866389 | C | P4 | −0.26 | 0.0037190 |
| VCAN | 759 | 11749904 | C | G1 | −0.24 | 0.0069440 |
| VCAN | 760 | 188703 | T | G2 | −0.25 | 0.0095740 |
| MEF2C | 761 | 304151 | C | G16 | 0.27 | 0.0051420 |
| MEF2C | 762 | 17560451 | C | G8 | 0.19 | 0.0096180 |
| GPR98 | 763 | 16868901 | C | G9 | 0.35 | 0.0056920 |
| GPR98 | 764 | 16869032 | A | G9 | 0.38 | 0.0094120 |
| GPR98 | 765 | 12519770 | A | P7 | −0.20 | 0.0011720 |
| GPR98 | 766 | 2247870 | C | P7 | −0.19 | 0.0028700 |
| GPR98 | 767 | 3098356 | C | P7 | −0.18 | 0.0080740 |
| SEMA5A | 768 | 985723 | A | N4 | 0.36 | 0.0078940 |
| SEMA5A | 770 | 11134354 | A | G4 | −0.28 | 0.0051780 |
| SEMA5A | 770 | 11134354 | A | P6 | −0.31 | 0.0097070 |
| SEMA5A | 771 | 4702625 | G | G3 | −0.39 | 0.0015410 |
| SEMA5A | 772 | 268481 | C | G10 | −0.26 | 0.0039070 |
| CAST | 774 | 11135479 | C | G4 | 0.24 | 0.0053220 |
| SLC22A16 | 776 | 2428175 | A | G11 | 0.27 | 0.0070460 |
| HS3ST5 | 777 | 12211751 | A | G9 | 0.37 | 0.0049540 |
| TRDN | 781 | 1431284 | G | P2 | 0.30 | 0.0017680 |
| TRDN | 782 | 17686735 | G | P2 | 0.29 | 0.0024370 |
| TRDN | 783 | 873460 | T | P2 | 0.26 | 0.0054160 |
| TRDN | 784 | 17085362 | T | G15 | 0.23 | 0.0092100 |
| TRDN | 785 | 7452290 | C | P6 | −0.39 | 0.0024190 |
| TRDN | 786 | 9490794 | T | P6 | −0.36 | 0.0076160 |
| TRDN | 787 | 10499125 | T | G2 | −0.33 | 0.0002309 |
| TRDN | 788 | 2317707 | T | G2 | −0.30 | 0.0013080 |
| TRDN | 789 | 7453704 | C | G11 | −0.23 | 0.0094070 |
| TRDN | 790 | 2169092 | T | G2 | −0.22 | 0.0097970 |
| NKAIN2 | 791 | 12195023 | T | G16 | −0.27 | 0.0090830 |
| NKAIN2 | 792 | 6939050 | A | G14 | −0.20 | 0.0021930 |
| NKAIN2 | 793 | 6910988 | T | N3 | −0.22 | 0.0066830 |
| NKAIN2 | 794 | 1832252 | G | N4 | 0.25 | 0.0075970 |
| NKAIN2 | 795 | 1871329 | G | G4 | −0.30 | 0.0011400 |
| NKAIN2 | 796 | 1031881 | C | G15 | −0.31 | 0.0041450 |
| NKAIN2 | 796 | 1031881 | C | P2 | −0.34 | 0.0046210 |
| NKAIN2 | 800 | 781487 | C | P5 | 0.53 | 0.0003526 |
| NKAIN2 | 800 | 781487 | C | P3 | 0.52 | 0.0051620 |
| NKAIN2 | 800 | 781487 | C | G8 | 0.28 | 0.0031870 |
| PHACTR1 | 801 | 6458439 | C | N7 | 0.23 | 0.0046730 |
| PHACTR1 | 802 | 9395497 | G | G16 | −0.34 | 0.0007332 |
| PHACTR1 | 803 | 12527257 | C | G16 | −0.33 | 0.0011440 |
| PHACTR1 | 804 | 9367368 | C | G16 | −0.31 | 0.0018350 |
| EYA4 | 805 | 2327321 | G | N5 | −0.53 | 0.0000173 |
| EYA4 | 806 | 9321396 | G | N5 | −0.49 | 0.0000361 |
| EYA4 | 807 | 9375573 | A | N5 | −0.40 | 0.0014570 |
| EYA4 | 808 | 2027210 | A | N3 | −0.24 | 0.0049670 |
| PDE7B | 809 | 6906788 | T | N5 | −0.54 | 0.0057170 |
| PDE7B | 810 | 6570049 | T | G9 | −0.67 | 0.0019710 |
| PDE7B | 811 | 6931583 | C | G10 | 0.38 | 0.0055780 |
| PLAGL1 | 812 | 9321951 | T | P5 | −0.30 | 0.0023360 |
| PLAGL1 | 813 | 6916498 | A | P5 | −0.38 | 0.0003815 |
| PLAGL1 | 814 | 9484836 | A | P5 | −0.38 | 0.0003871 |
| UTRN | 815 | 601873 | A | N4 | −0.26 | 0.0066050 |
| UTRN | 816 | 656471 | C | G10 | 0.19 | 0.0032640 |
| SYNE1 | 819 | 718527 | A | G3 | 0.34 | 0.0005636 |
| SYNE1 | 819 | 718527 | A | N7 | 0.21 | 0.0091670 |
| JARID2 | 820 | 13192234 | A | P4 | 0.24 | 0.0055470 |
| SLC22A3 | 821 | 376520 | T | P2 | −0.26 | 0.0033320 |
| PARK2 | 822 | 2003713 | A | G10 | 0.15 | 0.0090390 |
| PARK2 | 823 | 6455738 | A | G10 | 0.16 | 0.0052030 |
| PARK2 | 824 | 9365311 | C | G15 | −0.23 | 0.0048690 |
| PARK2 | 825 | 9355924 | A | N6 | −0.26 | 0.0075820 |
| PARK2 | 825 | 9355924 | A | G7 | −0.22 | 0.0060100 |
| PARK2 | 826 | 7750426 | G | N5 | −0.28 | 0.0044080 |
| PARK2 | 827 | 9295173 | G | N5 | 0.29 | 0.0036830 |
| PARK2 | 828 | 10945823 | G | G5 | 0.20 | 0.0093000 |
| PARK2 | 828 | 10945823 | A | N2 | 0.28 | 0.0049730 |
| PARK2 | 830 | 7750033 | T | N2 | −0.26 | 0.0029560 |
| PARK2 | 831 | 4636000 | C | N2 | 0.23 | 0.0073420 |
| PARK2 | 832 | 2155510 | G | N2 | 0.22 | 0.0091110 |
| PARK2 | 833 | 2846528 | G | N4 | 0.27 | 0.0042590 |

TABLE 3-continued

Alleles Influencing Individual PANSS Items

| Gene | SEQ ID NO: | NCBI RS # | Allele | PANSS Item | Beta | P |
|---|---|---|---|---|---|---|
| PACRG | 834 | 7740626 | G | G13 | 0.23 | 0.0042910 |
| PACRG | 835 | 761625 | A | G9 | −0.30 | 0.0007418 |
| PDE10A | 836 | 525643 | A | G5 | 0.25 | 0.0086370 |
| PDE10A | 837 | 566759 | G | G11 | −0.31 | 0.0078720 |
| PDE10A | 837 | 566759 | G | N6 | −0.35 | 0.0077690 |
| PDE10A | 838 | 484594 | C | P1 | 0.38 | 0.0089850 |
| ATXN1 | 839 | 235147 | A | N4 | −0.25 | 0.0076850 |
| ATXN1 | 840 | 2237165 | A | N1 | −0.26 | 0.0091670 |
| ATXN1 | 842 | 11754887 | C | G10 | −0.16 | 0.0096370 |
| SLC17A4 | 843 | 1937131 | A | G1 | 0.26 | 0.0091520 |
| SLC17A4 | 844 | 9358890 | G | P7 | 0.69 | 0.0000048 |
| SLC17A4 | 844 | 9358890 | G | G14 | 0.48 | 0.0016380 |
| SLC17A4 | 844 | 9358890 | G | G9 | 0.70 | 0.0009106 |
| SLC17A4 | 846 | 1575535 | T | G1 | 0.28 | 0.0085140 |
| SLC17A1 | 847 | 4712976 | T | P5 | 0.28 | 0.0088790 |
| SLC17A2 | 849 | 442601 | C | G5 | −0.19 | 0.0070930 |
| BTN3A1 | 850 | 12208788 | T | P4 | −0.31 | 0.0037000 |
| BTN3A1 | 852 | 10946826 | G | P4 | −0.28 | 0.0045120 |
| BTN3A1 | 853 | 10447390 | G | P4 | −0.27 | 0.0062400 |
| BTN2A3 | 854 | 10946829 | A | P4 | −0.27 | 0.0062400 |
| BTN3A3 | 855 | 3846847 | T | P4 | −0.28 | 0.0051800 |
| BTNL2 | 856 | 4424066 | G | P2 | 0.27 | 0.0020450 |
| BTNL2 | 857 | 2076533 | A | P2 | 0.27 | 0.0024150 |
| BTNL2 | 858 | 2076530 | G | P2 | 0.23 | 0.0074490 |
| SLC22A23 | 859 | 17136575 | G | G7 | 0.31 | 0.0025780 |
| LRFN2 | 860 | 4714349 | C | G3 | −0.27 | 0.0089060 |
| LRFN2 | 860 | 4714349 | C | N3 | 0.24 | 0.0050500 |
| LRFN2 | 861 | 9369205 | A | N3 | 0.24 | 0.0072610 |
| LRFN2 | 861 | 9369205 | A | G12 | 0.28 | 0.0044510 |
| LRFN2 | 862 | 1036288 | A | G8 | −0.17 | 0.0038250 |
| LRFN2 | 862 | 1036288 | A | G5 | −0.20 | 0.0046120 |
| LRFN2 | 863 | 403319 | A | G8 | −0.16 | 0.0052610 |
| PPP2R5D | 864 | 3823423 | A | P1 | 0.56 | 0.0054740 |
| KLC4 | 865 | 4714658 | A | P2 | 0.61 | 0.0064770 |
| ELOVL5 | 866 | 9370196 | C | N5 | 0.34 | 0.0019440 |
| ELOVL5 | 868 | 1429143 | G | N5 | 0.30 | 0.0087170 |
| RIMS1 | 870 | 511211 | C | P3 | −0.32 | 0.0032160 |
| RIMS1 | 871 | 9446563 | G | N5 | −0.27 | 0.0087340 |
| RIMS1 | 871 | 9446563 | G | G3 | 0.28 | 0.0058150 |
| RIMS1 | 871 | 9446563 | G | P3 | 0.30 | 0.0077580 |
| RIMS1 | 872 | 9293862 | G | P3 | −0.29 | 0.0092360 |
| RIMS1 | 872 | 9293862 | G | G1 | −0.27 | 0.0024820 |
| RIMS1 | 873 | 2496495 | G | P5 | −0.24 | 0.0100000 |
| RIMS1 | 874 | 2496517 | C | P5 | −0.25 | 0.0086970 |
| RIMS1 | 875 | 2463749 | C | G2 | −0.24 | 0.0082510 |
| RIMS1 | 875 | 2463749 | C | P3 | −0.30 | 0.0075470 |
| RIMS1 | 876 | 2254147 | G | G1 | −0.27 | 0.0031340 |
| RIMS1 | 877 | 1015945 | G | G6 | −0.32 | 0.0020480 |
| RIMS1 | 877 | 1015945 | G | P3 | −0.36 | 0.0019480 |
| RIMS1 | 878 | 11754022 | T | N5 | −0.29 | 0.0093480 |
| HTR1B | 879 | 6296 | C | G7 | −0.26 | 0.0027960 |
| KLHL32 | 880 | 1206084 | A | G8 | −0.18 | 0.0074420 |
| KLHL32 | 881 | 1629523 | T | G8 | −0.28 | 0.0024920 |
| KLHL32 | 882 | 1737646 | A | G8 | −0.26 | 0.0040920 |
| KLHL32 | 883 | 1206149 | A | G13 | −0.25 | 0.0009723 |
| CUX1 | 886 | 2694158 | T | G14 | 0.22 | 0.0011170 |
| CADPS2 | 887 | 2471212 | G | P7 | 0.27 | 0.0004120 |
| CADPS2 | 890 | 2251761 | G | P7 | 0.24 | 0.0007916 |
| CADPS2 | 891 | 2159827 | A | P7 | 0.23 | 0.0010370 |
| CADPS2 | 892 | 2428769 | G | G9 | −0.25 | 0.0074430 |
| CADPS2 | 892 | 2428769 | G | N7 | −0.26 | 0.0016860 |
| GRM8 | 893 | 1989850 | C | G15 | −0.24 | 0.0037200 |
| GRM8 | 894 | 954661 | T | G15 | −0.24 | 0.0050950 |
| GRM8 | 895 | 2283079 | G | G15 | −0.23 | 0.0065480 |
| GRM8 | 896 | 2283062 | G | P2 | 0.34 | 0.0004788 |
| GRM8 | 897 | 2283064 | C | G15 | 0.23 | 0.0056490 |
| GRM8 | 898 | 6950264 | C | G15 | 0.24 | 0.0061690 |
| GRM8 | 898 | 6950264 | G | G4 | −0.25 | 0.0034660 |
| GRM8 | 898 | 6950264 | G | G7 | 0.24 | 0.0045350 |
| GRM8 | 899 | 13240418 | C | G15 | −0.24 | 0.0037280 |
| GRM8 | 900 | 4731330 | C | G15 | −0.24 | 0.0039610 |
| GRM8 | 901 | 6975541 | T | G15 | −0.21 | 0.0097330 |
| GRM8 | 902 | 1419442 | T | G2 | 0.23 | 0.0089740 |
| GRM8 | 903 | 2106183 | T | G7 | 0.28 | 0.0010190 |
| GRM8 | 904 | 916597 | C | G4 | 0.25 | 0.0074300 |
| EXOC4 | 905 | 7786489 | A | G6 | 0.40 | 0.0008424 |
| EXOC4 | 905 | 7786489 | A | N4 | 0.33 | 0.0047400 |
| EXOC4 | 906 | 7778778 | G | G6 | 0.41 | 0.0006110 |
| EXOC4 | 906 | 7778778 | G | N4 | 0.35 | 0.0032260 |
| EXOC4 | 907 | 1946303 | T | N4 | 0.31 | 0.0085270 |
| EXOC4 | 907 | 1946303 | T | G6 | 0.40 | 0.0009938 |
| EXOC4 | 908 | 11980047 | A | N4 | 0.31 | 0.0091850 |
| EXOC4 | 908 | 11980047 | A | G6 | 0.37 | 0.0017280 |
| EXOC4 | 909 | 6975109 | T | G6 | 0.36 | 0.0021400 |
| EXOC4 | 910 | 6954842 | A | G11 | 0.24 | 0.0072040 |
| EXOC4 | 910 | 6954842 | A | N4 | 0.39 | 0.0002372 |
| EXOC4 | 910 | 6954842 | A | N2 | 0.26 | 0.0055730 |
| EXOC4 | 911 | 12707127 | A | G13 | −0.22 | 0.0050630 |
| EXOC4 | 912 | 6970436 | A | G13 | −0.20 | 0.0084370 |
| EXOC4 | 913 | 4731992 | A | G6 | 0.30 | 0.0076580 |
| EXOC4 | 914 | 6950383 | C | N4 | −0.23 | 0.0099900 |
| DGKI | 915 | 16874961 | C | G12 | −0.28 | 0.0063030 |
| DGKI | 915 | 16874961 | C | G9 | −0.32 | 0.0009730 |
| DGKI | 916 | 980796 | A | G9 | −0.29 | 0.0029290 |
| CREB3L2 | 917 | 273981 | C | P6 | 0.27 | 0.0055160 |
| CREB3L2 | 918 | 273988 | A | P6 | 0.27 | 0.0058800 |
| TBXAS1 | 920 | 2270163 | G | G16 | −0.28 | 0.0013640 |
| TBXAS1 | 921 | 4590360 | G | N4 | −0.27 | 0.0033670 |
| TBXAS1 | 922 | 12534299 | G | N4 | −0.26 | 0.0042550 |
| TBXAS1 | 923 | 41723 | G | N2 | 0.34 | 0.0044530 |
| TBXAS1 | 923 | 41723 | G | G7 | 0.29 | 0.0087490 |
| TBXAS1 | 923 | 41723 | G | N6 | 0.39 | 0.0025320 |
| CNTNAP2 | 925 | 1639480 | T | G12 | 0.26 | 0.0060870 |
| CNTNAP2 | 925 | 1639480 | T | P2 | 0.27 | 0.0041550 |
| CNTNAP2 | 926 | 1639481 | G | P2 | 0.31 | 0.0006389 |
| CNTNAP2 | 927 | 986264 | A | P2 | 0.30 | 0.0009067 |
| CNTNAP2 | 928 | 6963627 | T | P2 | 0.32 | 0.0005588 |
| CNTNAP2 | 929 | 1639484 | T | P2 | 0.29 | 0.0012660 |
| CNTNAP2 | 930 | 12535047 | T | G8 | −0.17 | 0.0056230 |
| CNTNAP2 | 931 | 11972784 | C | P1 | 0.32 | 0.0098660 |
| CNTNAP2 | 933 | 2022226 | C | G16 | 0.25 | 0.0078870 |
| CNTNAP2 | 934 | 10952682 | G | P1 | 0.35 | 0.0051770 |
| CNTNAP2 | 935 | 6953679 | A | G5 | 0.20 | 0.0099500 |
| CNTNAP2 | 936 | 700320 | A | G13 | 0.25 | 0.0046060 |
| CNTNAP2 | 938 | 6958824 | A | N7 | 0.33 | 0.0026150 |
| CNTNAP2 | 939 | 1637840 | T | G3 | −0.49 | 0.0003246 |
| PTPRN2 | 940 | 1049325 | T | N4 | −0.54 | 0.0015840 |
| PTPRN2 | 940 | 1049325 | T | G16 | −0.44 | 0.0085630 |
| PTPRN2 | 941 | 4909289 | A | G7 | −0.25 | 0.0042670 |
| PTPRN2 | 942 | 2335836 | G | G6 | −0.29 | 0.0042990 |
| PTPRN2 | 943 | 10265417 | T | P2 | −0.24 | 0.0084970 |
| STK31 | 944 | 12532929 | T | N7 | 0.38 | 0.0002619 |
| STK31 | 945 | 7791283 | C | P2 | 0.28 | 0.0084170 |
| SKAP2 | 946 | 3801846 | A | G1 | −0.32 | 0.0022280 |
| SKAP2 | 947 | 13438513 | C | G1 | −0.29 | 0.0049670 |
| SKAP2 | 948 | 13438514 | A | G1 | −0.29 | 0.0055540 |
| SKAP2 | 949 | 17315929 | T | G1 | −0.27 | 0.0089990 |
| SKAP2 | 950 | 10486483 | A | G1 | −0.27 | 0.0095690 |
| CREB5 | 951 | 177486 | A | G6 | 0.26 | 0.0062190 |
| CREB5 | 952 | 2237361 | C | G2 | −0.28 | 0.0018250 |
| CREB5 | 953 | 1544469 | G | P7 | −0.20 | 0.0048410 |
| CREB5 | 954 | 17669844 | C | G7 | 0.21 | 0.0091950 |
| CREB5 | 954 | 17669844 | C | G2 | −0.30 | 0.0011890 |
| CREB5 | 955 | 4722864 | A | P5 | 0.35 | 0.0034100 |
| CREB5 | 956 | 886750 | A | P7 | −0.19 | 0.0086880 |
| CREB5 | 956 | 886750 | A | P1 | 0.33 | 0.0077470 |
| CARD11 | 957 | 3735131 | C | G14 | 0.53 | 0.0047800 |
| CHN2 | 958 | 7781003 | T | G6 | −0.35 | 0.0006594 |
| CHN2 | 959 | 3750103 | C | G5 | 0.43 | 0.0017980 |
| SCRN1 | 961 | 13834 | T | N1 | −0.29 | 0.0056070 |
| SCRN1 | 962 | 6976789 | T | N1 | −0.28 | 0.0070480 |
| SCRN1 | 963 | 1465327 | T | N1 | −0.33 | 0.0038670 |
| CRHR2 | 965 | 2190242 | C | N3 | 0.34 | 0.0008023 |
| CRHR2 | 965 | 2190242 | C | G15 | 0.32 | 0.0013330 |
| CRHR2 | 966 | 4723003 | T | G1 | 0.46 | 0.0025620 |
| FLJ22374 | 967 | 6956143 | G | P4 | −0.26 | 0.0009240 |
| FLJ22374 | 967 | 6956143 | G | P7 | −0.18 | 0.0067100 |
| FLJ22374 | 969 | 12690795 | C | G10 | 0.17 | 0.0035590 |
| FLJ22374 | 970 | 10243139 | C | G4 | 0.40 | 0.0081700 |
| FLJ22374 | 972 | 10229281 | A | G4 | 0.43 | 0.0051690 |

TABLE 3-continued

Alleles Influencing Individual PANSS Items

| Gene | SEQ ID NO: | NCBI RS # | Allele | PANSS Item | Beta | P |
|---|---|---|---|---|---|---|
| PDE1C | 973 | 12701142 | G | G14 | 0.19 | 0.0067130 |
| PDE1C | 974 | 30589 | G | P4 | -0.33 | 0.0032030 |
| PDE1C | 975 | 30586 | A | P4 | -0.38 | 0.0017520 |
| BMPER | 976 | 6975236 | T | N2 | 0.27 | 0.0023920 |
| BMPER | 977 | 7802225 | G | P2 | 0.24 | 0.0071620 |
| BMPER | 978 | 12539069 | G | N7 | -0.24 | 0.0034980 |
| BMPER | 979 | 7806522 | C | G8 | -0.18 | 0.0027810 |
| BMPER | 979 | 7806522 | C | P2 | -0.26 | 0.0077620 |
| BMPER | 979 | 7806522 | C | N2 | -0.25 | 0.0060680 |
| BMPER | 979 | 7806522 | C | P7 | -0.18 | 0.0068380 |
| BMPER | 980 | 4140982 | A | G8 | -0.21 | 0.0007372 |
| BMPER | 980 | 4140982 | A | G10 | -0.17 | 0.0070920 |
| BMPER | 980 | 4140982 | A | N2 | -0.26 | 0.0051770 |
| BMPER | 981 | 12672492 | A | G8 | -0.18 | 0.0051760 |
| BMPER | 982 | 969363 | C | N6 | -0.27 | 0.0059830 |
| VPS41 | 984 | 3801127 | T | G14 | -0.19 | 0.0031280 |
| VPS41 | 985 | 10951578 | G | G14 | 0.18 | 0.0053030 |
| VPS41 | 986 | 859522 | G | N6 | 0.41 | 0.0065930 |
| CDC2L5 | 987 | 10272641 | G | P6 | 0.28 | 0.0041930 |
| CDC2L5 | 987 | 10272641 | G | N4 | 0.29 | 0.0024270 |
| CDC2L5 | 988 | 10277422 | C | N4 | 0.33 | 0.0028310 |
| CDC2L5 | 989 | 9639817 | T | G2 | 0.23 | 0.0095010 |
| CDC2L5 | 989 | 9639817 | T | N4 | 0.34 | 0.0003946 |
| CDC2L5 | 990 | 17171658 | T | P6 | 0.27 | 0.0076810 |
| CDC2L5 | 990 | 17171658 | T | N4 | 0.31 | 0.0012590 |
| SDK1 | 992 | 4723505 | T | P6 | -0.25 | 0.0097690 |
| SDK1 | 993 | 1044701 | A | G14 | -0.17 | 0.0090940 |
| IGFBP3 | 994 | 10282088 | A | P5 | 0.38 | 0.0022290 |
| IGFBP3 | 995 | 13223993 | A | P5 | 0.33 | 0.0033910 |
| IGFBP3 | 996 | 10499637 | A | G7 | 0.28 | 0.0050940 |
| ABCA13 | 997 | 6943725 | A | G15 | 0.25 | 0.0019980 |
| ABCA13 | 998 | 17132289 | T | P2 | -0.47 | 0.0086710 |
| ABCA13 | 999 | 17729627 | A | P2 | -0.28 | 0.0093140 |
| ABCA13 | 1000 | 17662118 | A | P2 | -0.31 | 0.0088530 |
| ABCA13 | 1002 | 9642323 | T | G8 | -0.22 | 0.0090370 |
| WBSCR17 | 1005 | 10950221 | A | G9 | 0.28 | 0.0017610 |
| WBSCR17 | 1007 | 10950251 | A | G1 | 0.29 | 0.0012950 |
| WBSCR17 | 1009 | 12666361 | A | G1 | 0.24 | 0.0055900 |
| WBSCR17 | 1010 | 1012127 | T | G11 | -0.27 | 0.0053600 |
| LIMK1 | 1011 | 2855726 | A | N6 | 0.30 | 0.0031480 |
| GTF2IRD1 | 1014 | 2267834 | G | P4 | 0.23 | 0.0069550 |
| HIP1 | 1015 | 2260429 | A | G6 | -0.26 | 0.0064490 |
| HIP1 | 1016 | 2696213 | T | G6 | -0.28 | 0.0051910 |
| HIP1 | 1017 | 2253020 | G | G6 | -0.26 | 0.0081350 |
| HIP1 | 1018 | 2285875 | G | G7 | -0.31 | 0.0006662 |
| MAGI2 | 1019 | 3807797 | T | G4 | -0.28 | 0.0090180 |
| MAGI2 | 1020 | 10238177 | A | P4 | -0.21 | 0.0097590 |
| MAGI2 | 1021 | 38103 | A | P5 | 0.26 | 0.0065150 |
| MAGI2 | 1022 | 38111 | G | G3 | 0.28 | 0.0078920 |
| MAGI2 | 1023 | 12531031 | T | G14 | 0.22 | 0.0082170 |
| MAGI2 | 1024 | 848913 | C | G13 | 0.31 | 0.0045930 |
| MAGI2 | 1025 | 6971099 | T | G13 | 0.28 | 0.0026290 |
| MAGI2 | 1026 | 6954793 | C | N2 | 0.34 | 0.0073860 |
| MAGI2 | 1029 | 10953851 | T | G4 | -0.32 | 0.0067460 |
| MAGI2 | 1030 | 9969364 | C | G4 | -0.23 | 0.0041770 |
| CACNA2D1 | 1032 | 12535840 | G | N6 | -0.27 | 0.0047260 |
| CACNA2D1 | 1033 | 258728 | A | G7 | -0.27 | 0.0025660 |
| CACNA2D1 | 1033 | 258728 | A | N6 | -0.29 | 0.0069820 |
| CACNA2D1 | 1034 | 2059037 | C | G2 | 0.35 | 0.0049850 |
| CACNA2D1 | 1034 | 2059037 | C | G7 | -0.41 | 0.0002072 |
| CACNA2D1 | 1034 | 2059037 | C | N3 | -0.34 | 0.0044630 |
| CACNA2D1 | 1034 | 2059037 | C | N6 | -0.40 | 0.0028950 |
| CACNA2D1 | 1034 | 2059037 | C | G10 | -0.22 | 0.0082140 |
| PCLO | 1035 | 10954689 | T | G7 | 0.22 | 0.0039160 |
| PCLO | 1041 | 9656532 | A | N5 | -0.29 | 0.0072800 |
| PCLO | 1042 | 2715148 | A | G13 | 0.21 | 0.0059090 |
| PCLO | 1042 | 2715148 | A | G7 | 0.21 | 0.0067400 |
| PCLO | 1043 | 2522833 | C | G13 | 0.22 | 0.0050570 |
| PCLO | 1043 | 2522833 | C | G7 | 0.22 | 0.0041040 |
| PCLO | 1044 | 2371214 | C | G13 | 0.23 | 0.0029330 |
| PCLO | 1045 | 2522843 | A | G13 | 0.22 | 0.0054520 |
| PCLO | 1045 | 2522843 | A | G7 | 0.21 | 0.0059480 |
| PCLO | 1047 | 1986742 | G | G13 | -0.20 | 0.0072170 |
| PCLO | 1048 | 17282763 | C | N5 | -0.27 | 0.0079140 |
| PCLO | 1049 | 12539066 | T | P3 | -0.32 | 0.0097250 |
| PCLO | 1050 | 12531615 | C | G6 | -0.29 | 0.0016810 |
| PCLO | 1051 | 17157155 | T | G6 | -0.28 | 0.0027380 |
| PCLO | 1053 | 16887406 | G | G6 | -0.28 | 0.0028090 |
| PCLO | 1054 | 4129230 | T | P1 | 0.36 | 0.0018800 |
| PCLO | 1054 | 4129230 | T | N7 | 0.28 | 0.0009215 |
| PCLO | 1054 | 4129230 | T | P6 | 0.32 | 0.0026010 |
| PCLO | 1054 | 4129230 | T | G5 | 0.20 | 0.0077110 |
| PCLO | 1054 | 4129230 | T | G9 | 0.30 | 0.0018250 |
| SEMA3A | 1058 | 11978893 | G | N5 | -0.35 | 0.0029920 |
| SEMA3E | 1059 | 169992 | C | N4 | -0.27 | 0.0063570 |
| SEMA3E | 1060 | 3801562 | C | G1 | 0.24 | 0.0080620 |
| SEMA3E | 1061 | 1972459 | C | G13 | -0.23 | 0.0066110 |
| SEMA3A | 1063 | 6965990 | A | P3 | 0.30 | 0.0071050 |
| SEMA3A | 1063 | 6965990 | A | N4 | 0.27 | 0.0045080 |
| SEMA3A | 1063 | 6965990 | A | N2 | 0.23 | 0.0062760 |
| SEMA3A | 1064 | 11976072 | T | P3 | 0.29 | 0.0099500 |
| SEMA3A | 1064 | 11976072 | T | N4 | 0.26 | 0.0054950 |
| SEMA3A | 1065 | 13228082 | G | N2 | 0.22 | 0.0090980 |
| SEMA3A | 1065 | 13228082 | G | N4 | 0.25 | 0.0076380 |
| NXPH1 | 1071 | 970526 | G | G11 | 0.24 | 0.0085230 |
| ABCB4 | 1072 | 2097937 | G | N3 | -0.29 | 0.0079540 |
| ABCB4 | 1073 | 31662 | A | G4 | -0.39 | 0.0022740 |
| ADAM22 | 1075 | 17255978 | A | G1 | 0.69 | 0.0015120 |
| ADAM22 | 1076 | 1688886 | G | G16 | 0.25 | 0.0094840 |
| ADAM22 | 1076 | 1688886 | G | P6 | 0.46 | 0.0000073 |
| ADAM22 | 1078 | 2282949 | C | P6 | 0.42 | 0.0000409 |
| ADAM22 | 1078 | 2282949 | C | P1 | 0.41 | 0.0002684 |
| ADAM22 | 1079 | 6951172 | T | P5 | 0.30 | 0.0013760 |
| ADAM22 | 1079 | 6951172 | T | G9 | 0.27 | 0.0041660 |
| ADAM22 | 1079 | 6951172 | T | P1 | 0.33 | 0.0039290 |
| ADAM22 | 1080 | 9632709 | C | P5 | 0.28 | 0.0021550 |
| ADAM22 | 1080 | 9632709 | C | G9 | 0.26 | 0.0048850 |
| ADAM22 | 1080 | 9632709 | C | P1 | 0.33 | 0.0042990 |
| ADAM22 | 1081 | 2299199 | G | P1 | 0.32 | 0.0045500 |
| ADAM22 | 1081 | 2299199 | G | G9 | 0.24 | 0.0091970 |
| ADAM22 | 1081 | 2299199 | G | P5 | 0.26 | 0.0045860 |
| ADAM22 | 1082 | 10268574 | T | G10 | 0.20 | 0.0099450 |
| ADAM22 | 1083 | 4140919 | G | N7 | 0.32 | 0.0035660 |
| ADAM22 | 1085 | 17150307 | C | G4 | 0.38 | 0.0024420 |
| NXPH1 | 1086 | 6962955 | A | G1 | -0.24 | 0.0085140 |
| NXPH1 | 1086 | 6962955 | A | G13 | -0.25 | 0.0018330 |
| PPP1R9A | 1087 | 854535 | C | G5 | 0.23 | 0.0009944 |
| PPP1R9A | 1088 | 3917551 | T | G8 | -0.31 | 0.0075500 |
| PON1 | 1089 | 2158155 | A | G8 | -0.30 | 0.0093400 |
| PON1 | 1091 | 705378 | T | G1 | 0.24 | 0.0083890 |
| DYNC1I1 | 1092 | 319329 | G | N5 | 0.30 | 0.0022040 |
| GRHL2 | 1094 | 536022 | G | G11 | 0.40 | 0.0044060 |
| GRHL2 | 1095 | 608337 | C | G11 | 0.39 | 0.0086210 |
| GRHL2 | 1096 | 13275653 | C | G11 | -0.24 | 0.0048940 |
| GRHL2 | 1096 | 13275653 | C | N3 | -0.27 | 0.0026210 |
| GRHL2 | 1097 | 4734037 | C | G11 | -0.27 | 0.0090110 |
| NCALD | 1098 | 1131862 | G | G12 | -0.32 | 0.0048430 |
| NCALD | 1098 | 1131862 | G | N3 | -0.30 | 0.0032540 |
| NCALD | 1098 | 1131862 | G | G11 | -0.33 | 0.0006944 |
| NCALD | 1099 | 16868201 | A | G11 | -0.30 | 0.0053330 |
| NCALD | 1100 | 2387620 | G | G5 | -0.20 | 0.0075570 |
| NCALD | 1101 | 2226401 | C | G13 | -0.27 | 0.0038330 |
| NCALD | 1101 | 2226401 | C | G5 | -0.23 | 0.0049780 |
| ZFPM2 | 1102 | 16873003 | C | G16 | 0.29 | 0.0070860 |
| ZFPM2 | 1104 | 1481026 | T | G16 | 0.29 | 0.0074670 |
| ZFPM2 | 1106 | 13280496 | C | P5 | 0.29 | 0.0024180 |
| ZFPM2 | 1107 | 7003141 | C | P6 | 0.36 | 0.0010060 |
| ZFPM2 | 1107 | 7003141 | C | P1 | 0.36 | 0.0028050 |
| ZFPM2 | 1107 | 7003141 | C | G9 | 0.28 | 0.0040850 |
| ZFPM2 | 1109 | 12546300 | G | G10 | 0.16 | 0.0073250 |
| CSMD3 | 1115 | 7012235 | C | G8 | 0.53 | 0.0004453 |
| CSMD3 | 1116 | 1382469 | C | P7 | 0.19 | 0.0095280 |
| CSMD3 | 1117 | 720406 | C | P7 | 0.19 | 0.0098290 |
| SAMD12 | 1120 | 7825963 | A | P5 | 0.30 | 0.0010170 |
| SAMD12 | 1120 | 7825963 | A | P1 | 0.35 | 0.0025560 |
| SAMD12 | 1121 | 4876840 | A | P5 | 0.29 | 0.0017730 |
| SAMD12 | 1121 | 4876840 | A | P1 | 0.33 | 0.0039540 |
| SAMD12 | 1122 | 7830423 | C | P5 | 0.23 | 0.0084430 |
| FBXO32 | 1124 | 12548263 | T | P5 | -0.32 | 0.0020230 |
| FER1L6 | 1127 | 7838453 | A | G15 | -0.24 | 0.0024640 |

TABLE 3-continued

Alleles Influencing Individual PANSS Items

| Gene | SEQ ID NO: | NCBI RS # | Allele | PANSS Item | Beta | P |
|---|---|---|---|---|---|---|
| FER1L6 | 1127 | 7838453 | A | N2 | −0.22 | 0.0081370 |
| FER1L6 | 1127 | 7838453 | A | G16 | −0.29 | 0.0011000 |
| FER1L6 | 1127 | 7838453 | A | G9 | −0.22 | 0.0096400 |
| FER1L6 | 1128 | 4537289 | T | G14 | −0.26 | 0.0016260 |
| FER1L6 | 1129 | 4478556 | T | G14 | −0.24 | 0.0023000 |
| FER1L6 | 1130 | 13279726 | G | G14 | −0.21 | 0.0046370 |
| FER1L6 | 1131 | 4242352 | C | G14 | −0.19 | 0.0089120 |
| FER1L6 | 1132 | 6981430 | G | G12 | 0.30 | 0.0023030 |
| FER1L6 | 1133 | 7819868 | G | P1 | 0.31 | 0.0043000 |
| FER1L6 | 1133 | 7819868 | G | P6 | 0.27 | 0.0052110 |
| MTSS1 | 1137 | 6470252 | C | P6 | −0.31 | 0.0027990 |
| MTSS1 | 1137 | 6470252 | C | G1 | −0.24 | 0.0097950 |
| MTSS1 | 1138 | 4871503 | C | P6 | 0.38 | 0.0054270 |
| DLC1 | 1139 | 2203838 | C | N3 | −0.31 | 0.0056340 |
| DLC1 | 1139 | 2203838 | C | N4 | −0.36 | 0.0038230 |
| DDEF1 | 1140 | 2670882 | C | N5 | −0.40 | 0.0084760 |
| ADCY8 | 1141 | 7016933 | A | G5 | 0.22 | 0.0014840 |
| ADCY8 | 1142 | 7464362 | G | G1 | 0.24 | 0.0073450 |
| ADCY8 | 1143 | 11781997 | A | G5 | 0.23 | 0.0004697 |
| ADCY8 | 1143 | 11781997 | A | G2 | 0.24 | 0.0043980 |
| ADCY8 | 1143 | 11781997 | A | N7 | 0.22 | 0.0043180 |
| KCNQ3 | 1145 | 977939 | A | P3 | 0.31 | 0.0041890 |
| ST3GAL1 | 1147 | 2978015 | T | G7 | −0.24 | 0.0026210 |
| ST3GAL1 | 1148 | 2945779 | A | G7 | −0.21 | 0.0070080 |
| ST3GAL1 | 1149 | 17722401 | A | G1 | −0.25 | 0.0097290 |
| COL22A1 | 1150 | 4475485 | T | G2 | −0.40 | 0.0061060 |
| COL22A1 | 1152 | 13279213 | A | P2 | 0.28 | 0.0068430 |
| SGCZ | 1153 | 1382147 | A | G2 | −0.41 | 0.0013960 |
| SGCZ | 1154 | 11990657 | T | G5 | 0.22 | 0.0048200 |
| SGCZ | 1154 | 11990657 | T | G4 | 0.27 | 0.0029710 |
| SGCZ | 1155 | 13261120 | C | P3 | 0.38 | 0.0009172 |
| SGCZ | 1156 | 4427170 | T | P3 | 0.29 | 0.0093140 |
| SGCZ | 1156 | 4427170 | T | G6 | 0.29 | 0.0029130 |
| SLC7A2 | 1157 | 2588222 | A | N4 | 0.27 | 0.0034900 |
| SLC7A2 | 1158 | 2588223 | T | P6 | 0.29 | 0.0050040 |
| PSD3 | 1160 | 1386688 | G | G4 | −0.31 | 0.0038880 |
| PSD3 | 1161 | 7837572 | T | G4 | −0.32 | 0.0043610 |
| PSD3 | 1162 | 13272436 | G | G14 | −0.19 | 0.0070860 |
| PSD3 | 1163 | 11782622 | C | G4 | 0.26 | 0.0038310 |
| PSD3 | 1164 | 7007413 | T | G4 | 0.26 | 0.0012340 |
| PSD3 | 1165 | 1492289 | C | G14 | −0.17 | 0.0057410 |
| PSD3 | 1166 | 4921968 | A | P7 | −0.17 | 0.0077580 |
| PSD3 | 1166 | 4921968 | A | G14 | −0.20 | 0.0019750 |
| PSD3 | 1167 | 6998537 | G | G9 | 0.42 | 0.0061480 |
| PSD3 | 1168 | 11778310 | G | P7 | −0.22 | 0.0019470 |
| PSD3 | 1169 | 1506894 | C | G6 | −0.47 | 0.0071880 |
| ATP6V1B2 | 1170 | 952148 | T | G15 | −0.40 | 0.0023880 |
| GFRA2 | 1171 | 4077793 | C | P3 | −0.38 | 0.0018170 |
| PEBP4 | 1172 | 4872594 | C | G9 | 0.25 | 0.0090260 |
| SLC25A37 | 1174 | 10503726 | C | G12 | −0.36 | 0.0014890 |
| SLC25A37 | 1175 | 11778179 | T | G12 | −0.46 | 0.0004472 |
| CSMD1 | 1176 | 622765 | A | G4 | 0.29 | 0.0064730 |
| CSMD1 | 1177 | 7845140 | G | P7 | 0.37 | 0.0081810 |
| CSMD1 | 1178 | 4875250 | G | G1 | −0.32 | 0.0061320 |
| CSMD1 | 1179 | 4487803 | G | G3 | 0.30 | 0.0036250 |
| CSMD1 | 1181 | 17065959 | C | N3 | −0.30 | 0.0088110 |
| CSMD1 | 1183 | 12543159 | T | G3 | 0.27 | 0.0075310 |
| CSMD1 | 1184 | 2938236 | T | P6 | 0.58 | 0.0047560 |
| CSMD1 | 1184 | 2938236 | T | G16 | 0.53 | 0.0053610 |
| UNC5D | 1186 | 2589344 | T | N1 | −0.34 | 0.0073910 |
| UNC5D | 1186 | 2589344 | T | N2 | −0.29 | 0.0080970 |
| UNC5D | 1186 | 2589344 | T | N4 | −0.35 | 0.0030110 |
| UNC5D | 1187 | 7826624 | T | N3 | −0.26 | 0.0049960 |
| SFRP1 | 1188 | 4736959 | C | P2 | 0.25 | 0.0089270 |
| SNTG1 | 1193 | 318851 | T | G7 | −0.49 | 0.0038520 |
| SNTG1 | 1194 | 10504093 | G | G7 | −0.47 | 0.0052210 |
| SNTG1 | 1195 | 10957739 | G | G7 | −0.27 | 0.0052140 |
| SNTG1 | 1196 | 2106156 | A | G11 | −0.27 | 0.0043320 |
| MCPH1 | 1197 | 1530408 | C | G15 | 0.43 | 0.0000761 |
| MCPH1 | 1197 | 1530408 | C | P4 | 0.33 | 0.0007420 |
| MCPH1 | 1198 | 2916750 | T | P4 | 0.30 | 0.0023730 |
| MCPH1 | 1199 | 1054073 | T | G15 | 0.32 | 0.0021200 |
| MCPH1 | 1200 | 1868551 | T | P4 | 0.29 | 0.0036450 |
| MCPH1 | 1201 | 2922818 | T | P4 | 0.29 | 0.0040630 |
| MCPH1 | 1202 | 2920660 | A | G15 | 0.34 | 0.0024740 |
| MCPH1 | 1203 | 2916741 | G | P4 | 0.29 | 0.0044610 |
| MCPH1 | 1203 | 2916741 | G | G15 | 0.33 | 0.0029680 |
| MCPH1 | 1204 | 2440399 | C | P4 | 0.26 | 0.0056170 |
| MCPH1 | 1205 | 2442492 | T | G15 | 0.28 | 0.0070860 |
| MCPH1 | 1205 | 2442492 | T | P4 | 0.26 | 0.0057890 |
| NKAIN3 | 1206 | 4257998 | A | G8 | 0.22 | 0.0082730 |
| MCPH1 | 1208 | 3020213 | T | G15 | 0.26 | 0.0026600 |
| MCPH1 | 1208 | 3020213 | T | P2 | 0.29 | 0.0028620 |
| MCPH1 | 1209 | 2515435 | G | G15 | 0.25 | 0.0042120 |
| MCPH1 | 1209 | 2515435 | G | P2 | 0.27 | 0.0041080 |
| NKAIN3 | 1210 | 1480194 | C | G12 | 0.36 | 0.0034440 |
| NKAIN3 | 1211 | 1383154 | A | G7 | −0.26 | 0.0084630 |
| NKAIN3 | 1212 | 16929903 | G | N1 | −0.32 | 0.0036450 |
| NKAIN3 | 1213 | 11989852 | A | N3 | 0.46 | 0.0043540 |
| NKAIN3 | 1214 | 17279355 | G | N3 | 0.39 | 0.0086890 |
| NKAIN3 | 1214 | 17279355 | G | P7 | 0.31 | 0.0058980 |
| MCPH1 | 1215 | 11998083 | T | G3 | −0.26 | 0.0082850 |
| DEPDC2 | 1217 | 6988386 | C | P3 | 0.47 | 0.0090370 |
| DEPDC2 | 1218 | 2053140 | A | G8 | −0.16 | 0.0065190 |
| DEPDC2 | 1219 | 6990381 | T | P3 | 0.29 | 0.0092950 |
| DEPDC2 | 1219 | 6990381 | T | N5 | 0.31 | 0.0020080 |
| DEPDC2 | 1219 | 6990381 | T | N1 | 0.27 | 0.0055850 |
| DEPDC2 | 1220 | 2380437 | T | N5 | 0.31 | 0.0025060 |
| DEPDC2 | 1221 | 16934215 | A | G6 | 0.44 | 0.0024850 |
| DEPDC2 | 1222 | 3793381 | A | G6 | 0.41 | 0.0041560 |
| DEPDC2 | 1223 | 7821308 | A | P7 | −0.19 | 0.0057980 |
| DEPDC2 | 1224 | 10808759 | C | P7 | −0.18 | 0.0057040 |
| KCNB2 | 1225 | 349355 | G | N5 | −0.37 | 0.0061060 |
| KCNB2 | 1226 | 349355 | C | N5 | −0.37 | 0.0066520 |
| KCNB2 | 1228 | 2256431 | A | G7 | −0.23 | 0.0049940 |
| KCNB2 | 1229 | 1972888 | C | G7 | −0.25 | 0.0022710 |
| KCNB2 | 1230 | 2196904 | C | G7 | −0.22 | 0.0073420 |
| MMP16 | 1233 | 278887 | C | P7 | −0.19 | 0.0068410 |
| MMP16 | 1234 | 2664370 | C | P7 | −0.18 | 0.0071640 |
| MMP16 | 1235 | 2616493 | C | G5 | 0.23 | 0.0038820 |
| MMP16 | 1235 | 2616493 | C | N1 | 0.31 | 0.0063300 |
| MMP16 | 1236 | 6994019 | T | N7 | −0.24 | 0.0089210 |
| MMP16 | 1239 | 4961087 | C | N3 | −0.29 | 0.0015200 |
| MMP16 | 1240 | 10504845 | T | N3 | −0.28 | 0.0062940 |
| MMP16 | 1241 | 4548227 | A | N3 | −0.28 | 0.0019820 |
| GABBR2 | 1244 | 2778913 | T | G4 | −0.36 | 0.0043020 |
| GABBR2 | 1244 | 2778913 | T | G15 | −0.37 | 0.0040610 |
| GABBR2 | 1245 | 1930139 | G | G12 | −0.29 | 0.0092010 |
| RP11-35N6.1 | 1246 | 10989207 | T | G15 | 0.22 | 0.0085370 |
| GRIN3A | 1247 | 7023041 | A | G12 | 0.41 | 0.0004123 |
| GRIN3A | 1248 | 10989589 | A | N5 | −0.28 | 0.0069490 |
| GRIN3A | 1249 | 4615635 | T | N5 | −0.32 | 0.0018750 |
| FKTN | 1250 | 2768294 | C | P5 | −0.28 | 0.0025840 |
| FKTN | 1251 | 885954 | C | G14 | −0.18 | 0.0064680 |
| FKTN | 1252 | 635712 | C | G2 | 0.30 | 0.0009908 |
| SVEP1 | 1253 | 963143 | A | G13 | −0.21 | 0.0069400 |
| SVEP1 | 1254 | 10759422 | C | P4 | −0.27 | 0.0026430 |
| SVEP1 | 1255 | 7875389 | C | P4 | −0.23 | 0.0019450 |
| CDK5RAP2 | 1256 | 2282168 | C | G11 | −0.27 | 0.0083170 |
| CDK5RAP2 | 1257 | 12238807 | C | P5 | −0.42 | 0.0089250 |
| CDK5RAP2 | 1258 | 10818467 | C | P5 | −0.50 | 0.0082280 |
| CDK5RAP2 | 1259 | 4837782 | T | P5 | −0.51 | 0.0083630 |
| DAB2IP | 1261 | 10985431 | T | G14 | 0.27 | 0.0045700 |
| RALGPS1 | 1262 | 561041 | C | G14 | −0.20 | 0.0016520 |
| RALGPS1 | 1263 | 665249 | G | G14 | −0.19 | 0.0022890 |
| RALGPS1 | 1264 | 1123684 | T | G14 | 0.22 | 0.0013510 |
| RALGPS1 | 1265 | 10760473 | G | G14 | −0.19 | 0.0024290 |
| RALGPS1 | 1266 | 13298677 | G | G14 | −0.21 | 0.0046150 |
| SLC25A25 | 1267 | 4837235 | A | G12 | 0.37 | 0.0082150 |
| SLC25A25 | 1267 | 4837235 | A | G2 | −0.36 | 0.0060960 |
| SLC25A25 | 1268 | 9695803 | C | N3 | 0.34 | 0.0042130 |
| SLC25A25 | 1268 | 9695803 | C | G12 | 0.35 | 0.0087230 |
| FREQ | 1269 | 12003792 | A | G6 | 0.28 | 0.0086910 |
| EXOSC2 | 1270 | 10901275 | C | P2 | 0.27 | 0.0074950 |
| ABL1 | 1271 | 6597642 | A | P2 | −0.42 | 0.0018260 |
| ABL1 | 1272 | 1800609 | C | P2 | −0.38 | 0.0044690 |
| ABL1 | 1274 | 3824400 | A | P2 | −0.37 | 0.0056390 |
| VAV2 | 1277 | 2519102 | G | G2 | −0.27 | 0.0079990 |
| OLFM1 | 1279 | 542172 | A | G15 | 0.39 | 0.0096740 |
| OLFM1 | 1279 | 542172 | A | G11 | 0.61 | 0.0000435 |

TABLE 3-continued

Alleles Influencing Individual PANSS Items

| Gene | SEQ ID NO: | NCBI RS # | Allele | PANSS Item | Beta | P |
|---|---|---|---|---|---|---|
| OLFM1 | 1279 | 542172 | A | G13 | 0.39 | 0.0062000 |
| INPP5E | 1280 | 3812591 | C | N6 | 0.32 | 0.0021870 |
| NOTCH1 | 1281 | 3013304 | C | G2 | -0.26 | 0.0052680 |
| CACNA1B | 1282 | 2278975 | C | G10 | 1.19 | 0.0023780 |
| CACNA1B | 1283 | 7860423 | A | G10 | 0.20 | 0.0097920 |
| ASAH3L | 1284 | 12335928 | A | G10 | -0.17 | 0.0082630 |
| KIAA1797 | 1285 | 12338810 | T | G6 | -0.34 | 0.0076580 |
| KIAA1797 | 1285 | 12338810 | T | G3 | -0.37 | 0.0047610 |
| KIAA1797 | 1286 | 12336110 | A | G3 | -0.37 | 0.0060610 |
| KIAA1797 | 1286 | 12336110 | A | G6 | -0.34 | 0.0085570 |
| KIAA1797 | 1287 | 7021708 | G | G1 | 0.26 | 0.0049190 |
| KIAA1797 | 1288 | 16938162 | C | G7 | 0.23 | 0.0041240 |
| KIAA1797 | 1288 | 16938162 | C | N1 | 0.37 | 0.0003204 |
| KIAA1797 | 1289 | 10511687 | G | N1 | 0.35 | 0.0005773 |
| KIAA1797 | 1289 | 10511687 | G | G13 | 0.26 | 0.0013150 |
| KIAA1797 | 1289 | 10511687 | G | N3 | 0.28 | 0.0010380 |
| KIAA1797 | 1289 | 10511687 | G | G11 | 0.22 | 0.0082980 |
| KIAA1797 | 1289 | 10511687 | G | N6 | 0.31 | 0.0013040 |
| KIAA1797 | 1289 | 10511687 | G | G7 | 0.23 | 0.0044350 |
| KIAA1797 | 1290 | 10964719 | T | G2 | -0.29 | 0.0014030 |
| KIAA1797 | 1293 | 6475491 | G | G2 | -0.29 | 0.0020350 |
| KIAA1797 | 1294 | 10511693 | G | N5 | 0.30 | 0.0088380 |
| KIAA1797 | 1294 | 10511693 | G | G15 | 0.29 | 0.0020850 |
| KIAA1797 | 1295 | 4579612 | C | G2 | 0.29 | 0.0023610 |
| KIAA1797 | 1297 | 7025851 | G | G2 | -0.25 | 0.0060460 |
| KIAA1797 | 1298 | 7030990 | G | P4 | 0.24 | 0.0062690 |
| KIAA1797 | 1299 | 4977881 | A | G15 | 0.28 | 0.0021590 |
| KIAA1797 | 1300 | 4468020 | T | G15 | 0.26 | 0.0051060 |
| SMARCA2 | 1301 | 6475520 | G | G6 | 0.41 | 0.0067800 |
| SMARCA2 | 1302 | 6475522 | A | G6 | 0.41 | 0.0089820 |
| SMARCA2 | 1303 | 3793499 | G | G6 | 0.55 | 0.0001478 |
| SMARCA2 | 1304 | 10116703 | A | N5 | 0.27 | 0.0066510 |
| IFT74 | 1305 | 17694549 | C | G13 | 0.44 | 0.0068240 |
| IFT74 | 1305 | 17694549 | C | G14 | 0.42 | 0.0018630 |
| TEK | 1309 | 12339867 | C | G11 | -0.31 | 0.0058700 |
| SLC1A1 | 1310 | 9886720 | T | N5 | 0.33 | 0.0043410 |
| SLC1A1 | 1311 | 4742008 | A | N5 | 0.30 | 0.0065550 |
| PIP5K1B | 1314 | 2152647 | T | N3 | 0.23 | 0.0075090 |
| PIP5K1B | 1314 | 2152647 | T | N6 | 0.28 | 0.0026870 |
| PIP5K1B | 1315 | 1414949 | T | N3 | -0.22 | 0.0082530 |
| PIP5K1B | 1315 | 1414949 | T | N6 | -0.27 | 0.0046400 |
| PIP5K1B | 1316 | 11144133 | T | N6 | 0.27 | 0.0048250 |
| APBA1 | 1318 | 10481751 | T | G13 | 0.23 | 0.0094210 |
| TRPM3 | 1319 | 1932701 | C | N1 | -0.42 | 0.0045100 |
| TRPM3 | 1320 | 2275242 | G | P1 | 0.29 | 0.0085320 |
| TRPM3 | 1320 | 2275242 | G | P5 | 0.25 | 0.0067130 |
| TRPM3 | 1321 | 6560161 | G | N5 | -0.30 | 0.0046320 |
| TRPM3 | 1323 | 2993010 | A | N5 | -0.34 | 0.0011450 |
| TRPM3 | 1323 | 2993010 | A | N2 | -0.23 | 0.0090390 |
| TMC1 | 1324 | 6560297 | T | N5 | -0.29 | 0.0061080 |
| TMC1 | 1325 | 12347235 | A | N5 | -0.36 | 0.0028060 |
| TMC1 | 1326 | 2501914 | T | N5 | 0.30 | 0.0031990 |
| PCSK5 | 1328 | 1029035 | C | N6 | -0.28 | 0.0014380 |
| PCSK5 | 1328 | 1029035 | C | N3 | -0.21 | 0.0068430 |
| PCSK5 | 1329 | 914367 | T | N7 | -0.24 | 0.0049840 |
| GNAQ | 1330 | 1030828 | A | G13 | -0.23 | 0.0056920 |
| GNAQ | 1331 | 2378100 | C | G7 | -0.24 | 0.0016740 |
| GNAQ | 1332 | 10870048 | T | N3 | -0.27 | 0.0093900 |
| PTPRD | 1333 | 1500326 | T | P5 | -0.25 | 0.0072700 |
| PTPRD | 1334 | 7036240 | A | P5 | -0.26 | 0.0044690 |
| PTPRD | 1334 | 7036240 | A | N3 | 0.24 | 0.0057980 |
| NTRK2 | 1335 | 1187321 | A | N5 | 0.38 | 0.0065870 |
| NTRK2 | 1335 | 1187321 | A | G8 | 0.24 | 0.0023610 |
| DAPK1 | 1338 | 1927976 | G | G8 | -0.19 | 0.0010070 |
| DAPK1 | 1339 | 1927975 | G | G8 | 0.14 | 0.0098350 |
| DAPK1 | 1340 | 1056719 | G | G13 | 0.22 | 0.0055050 |
| SORCS3 | 1341 | 10884026 | G | P5 | -0.31 | 0.0061140 |
| SORCS3 | 1342 | 10884052 | C | P6 | 0.31 | 0.0020190 |
| SOPCS3 | 1343 | 2491377 | T | P6 | -0.30 | 0.0098710 |
| SORCS3 | 1344 | 2451498 | C | P6 | -0.29 | 0.0098930 |
| SORCS3 | 1346 | 1961640 | C | P6 | 0.27 | 0.0056240 |
| SORCS3 | 1347 | 790663 | T | G12 | -0.26 | 0.0060990 |
| SORCS3 | 1348 | 2696864 | A | G12 | -0.34 | 0.0008217 |
| SORCS3 | 1349 | 10160134 | A | G12 | 0.30 | 0.0020400 |
| SORCS3 | 1350 | 697189 | C | G12 | 0.29 | 0.0022860 |
| SORCS3 | 1351 | 697190 | C | G12 | 0.27 | 0.0069240 |
| SORCS3 | 1352 | 7072425 | T | G11 | 0.38 | 0.0061330 |
| SORCS3 | 1352 | 7072425 | T | G13 | 0.37 | 0.0055370 |
| CUGBP2 | 1353 | 3243 | C | G7 | 0.23 | 0.0084640 |
| VTI1A | 1354 | 10509963 | A | P3 | -0.31 | 0.0093380 |
| VTI1A | 1355 | 10885352 | T | P3 | -0.31 | 0.0099750 |
| VTI1A | 1355 | 10885352 | T | G16 | -0.26 | 0.0098450 |
| VTI1A | 1356 | 11196051 | G | G3 | 0.29 | 0.0097550 |
| VTI1A | 1357 | 7907012 | G | N5 | 0.33 | 0.0023160 |
| VTI1A | 1358 | 7907540 | A | N5 | 0.30 | 0.0052170 |
| VTI1A | 1359 | 7068695 | C | N1 | 0.26 | 0.0082790 |
| VTI1A | 1360 | 4145776 | G | N1 | 0.29 | 0.0067390 |
| HSPA12A | 1361 | 3010460 | C | G8 | 0.17 | 0.0038730 |
| HSPA12A | 1362 | 735412 | G | G8 | 0.25 | 0.0097560 |
| ATE1 | 1363 | 7086628 | C | P6 | -0.31 | 0.0010380 |
| ATE1 | 1363 | 7086628 | C | N3 | -0.21 | 0.0087970 |
| ATE1 | 1364 | 1219505 | T | P1 | -0.28 | 0.0060540 |
| ATE1 | 1364 | 1219505 | T | N3 | -0.21 | 0.0080360 |
| ATE1 | 1365 | 1693682 | A | P6 | -0.32 | 0.0015320 |
| ATE1 | 1365 | 1693682 | A | N3 | -0.25 | 0.0029740 |
| ATE1 | 1366 | 10732824 | A | G13 | -0.38 | 0.0047450 |
| ATE1 | 1366 | 10732824 | A | N7 | -0.40 | 0.0036090 |
| ATE1 | 1367 | 2420970 | T | P1 | 0.37 | 0.0004130 |
| CTBP2 | 1370 | 4962718 | C | N5 | 0.29 | 0.0089980 |
| ARMC3 | 1371 | 17440393 | A | G1 | 0.33 | 0.0020190 |
| ARMC3 | 1371 | 17440393 | A | P1 | 0.47 | 0.0004260 |
| ARMC3 | 1372 | 11013210 | T | G1 | 0.29 | 0.0074760 |
| ARMC3 | 1373 | 7084413 | C | G6 | 0.30 | 0.0044130 |
| ARMC3 | 1374 | 10828389 | T | G1 | 0.28 | 0.0055940 |
| ARMC3 | 1374 | 10828389 | T | G6 | 0.30 | 0.0053160 |
| ARMC3 | 1375 | 10828395 | A | G1 | 0.35 | 0.0015950 |
| ARMC3 | 1376 | 7898656 | A | G1 | 0.34 | 0.0039890 |
| ARMC3 | 1377 | 1382579 | G | P2 | 0.67 | 0.0014970 |
| ARHGAP21 | 1378 | 7897303 | A | G1 | -0.30 | 0.0055920 |
| MYO3A | 1379 | 7084614 | T | G4 | -0.23 | 0.0096120 |
| PITRM1 | 1381 | 2306310 | C | P7 | -0.23 | 0.0089410 |
| PITRM1 | 1382 | 9129 | T | P7 | -0.23 | 0.0089410 |
| PITRM1 | 1383 | 3740607 | A | G13 | 0.23 | 0.0027190 |
| PITRM1 | 1385 | 7092621 | A | G13 | 0.26 | 0.0029930 |
| SLC16A9 | 1386 | 6481469 | A | G4 | 0.56 | 0.0003589 |
| SLC16A9 | 1387 | 3763747 | G | N6 | -0.30 | 0.0062020 |
| SLC16A9 | 1387 | 3763747 | C | N1 | -0.31 | 0.0078040 |
| PRKCQ | 1391 | 661891 | T | N6 | 0.35 | 0.0001849 |
| PRKCQ | 1392 | 9423765 | A | N6 | 0.27 | 0.0051980 |
| CDH23 | 1393 | 17635709 | T | G3 | 0.33 | 0.0067420 |
| CDH23 | 1394 | 10999947 | A | G10 | -0.20 | 0.0042540 |
| CDH23 | 1395 | 7094357 | A | N3 | 0.24 | 0.0096950 |
| KCNMA1 | 1396 | 2288840 | G | P7 | 0.19 | 0.0041030 |
| KCNMA1 | 1397 | 10740460 | A | G6 | -0.28 | 0.0095040 |
| KCNMA1 | 1398 | 4639876 | T | G6 | -0.27 | 0.0061470 |
| KCNMA1 | 1399 | 7067873 | C | P4 | 0.22 | 0.0052870 |
| KCNMA1 | 1399 | 7067873 | C | P7 | 0.18 | 0.0096960 |
| KCNMA1 | 1400 | 1907729 | T | G6 | -0.40 | 0.0046610 |
| KCNMA1 | 1401 | 7897566 | C | N4 | 0.39 | 0.0000659 |
| KCNMA1 | 1401 | 7897566 | C | N6 | 0.29 | 0.0025480 |
| KCNMA1 | 1401 | 7897566 | C | N7 | 0.21 | 0.0083090 |
| KCNMA1 | 1401 | 7897566 | C | G14 | 0.18 | 0.0049070 |
| KCNMA1 | 1401 | 7897566 | C | G15 | 0.23 | 0.0059900 |
| KCNMA1 | 1401 | 7897566 | C | G7 | 0.24 | 0.0024660 |
| KCNMA1 | 1401 | 7897566 | C | G13 | 0.24 | 0.0024780 |
| KCNMA1 | 1401 | 7897566 | C | G16 | 0.25 | 0.0068400 |
| KCNMA1 | 1401 | 7897566 | C | G11 | 0.30 | 0.0003752 |
| KCNMA1 | 1401 | 7897566 | C | P2 | 0.34 | 0.0002477 |
| KCNMA1 | 1402 | 10824520 | T | G12 | -0.29 | 0.0019630 |
| KCNMA1 | 1403 | 11002121 | A | G12 | -0.29 | 0.0025370 |
| KCNMA1 | 1404 | 11002139 | A | G12 | -0.30 | 0.0025480 |
| KCNMA1 | 1405 | 1371457 | A | G12 | -0.28 | 0.0033410 |
| KCNMA1 | 1406 | 10824547 | T | G12 | 0.53 | 0.0005635 |
| KCNMA1 | 1406 | 10824547 | T | N3 | 0.43 | 0.0015520 |
| KCNMA1 | 1407 | 2719986 | T | P6 | -0.30 | 0.0020550 |
| NRG3 | 1409 | 10884538 | T | G5 | -0.22 | 0.0071700 |
| NRG3 | 1412 | 495978 | A | G15 | 0.26 | 0.0036690 |
| SORBS1 | 1413 | 3814150 | G | N3 | -0.27 | 0.0021460 |
| SORBS1 | 1414 | 11188298 | C | G13 | 0.25 | 0.0020830 |
| SORBS1 | 1415 | 11188299 | C | G6 | -0.64 | 0.0065380 |

TABLE 3-continued

Alleles Influencing Individual PANSS Items

| Gene | SEQ ID NO: | NCBI RS # | Allele | PANSS Item | Beta | P |
|---|---|---|---|---|---|---|
| SORBS1 | 1416 | 4918921 | G | N3 | −0.24 | 0.0053900 |
| SORBS1 | 1416 | 4918921 | G | G13 | −0.23 | 0.0051310 |
| SORBS1 | 1417 | 1536556 | A | G13 | −0.23 | 0.0034250 |
| SORBS1 | 1418 | 540746 | T | G16 | −0.25 | 0.0045690 |
| ELMOD1 | 1419 | 683266 | A | P3 | 0.32 | 0.0073560 |
| GALNTL4 | 1420 | 10831565 | A | G10 | 0.18 | 0.0018020 |
| GALNTL4 | 1420 | 10831565 | A | G16 | −0.23 | 0.0098840 |
| GALNTL4 | 1421 | 7122801 | T | G16 | −0.27 | 0.0065250 |
| MICAL2 | 1422 | 10765929 | T | P1 | −0.51 | 0.0000098 |
| MICAL2 | 1423 | 2010463 | A | P1 | −0.43 | 0.0000911 |
| MICAL2 | 1424 | 11822285 | T | P1 | −0.39 | 0.0002196 |
| MICAL2 | 1425 | 7117024 | G | P1 | −0.44 | 0.0002173 |
| MICAL2 | 1426 | 17477949 | T | G13 | −0.23 | 0.0034800 |
| MICAL2 | 1427 | 2270511 | G | P1 | 0.41 | 0.0082260 |
| OPCML | 1429 | 3016384 | A | G8 | 0.15 | 0.0076470 |
| ARNTL | 1430 | 7107711 | C | N7 | −0.26 | 0.0094590 |
| OPCML | 1433 | 7936263 | G | G15 | 0.27 | 0.0051090 |
| OPCML | 1433 | 7936263 | G | P2 | 0.28 | 0.0070530 |
| OPCML | 1434 | 7108751 | T | P2 | 0.29 | 0.0080810 |
| SPON1 | 1435 | 1507527 | C | G6 | 0.29 | 0.0061720 |
| SPON1 | 1436 | 2049723 | C | G6 | 0.34 | 0.0017820 |
| SPON1 | 1437 | 1528668 | C | N3 | 0.25 | 0.0048540 |
| SPON1 | 1438 | 7112850 | A | N3 | 0.24 | 0.0060470 |
| SPON1 | 1439 | 10766134 | G | N3 | 0.23 | 0.0061030 |
| SPON1 | 1440 | 10832170 | T | N3 | 0.22 | 0.0087010 |
| SPON1 | 1440 | 10832170 | T | N2 | 0.25 | 0.0033110 |
| SPON1 | 1440 | 10832170 | T | N4 | 0.25 | 0.0081060 |
| SPON1 | 1441 | 1406356 | A | N2 | 0.27 | 0.0018150 |
| SPON1 | 1441 | 1406356 | A | N4 | 0.26 | 0.0065680 |
| SPON1 | 1442 | 7116296 | T | N2 | −0.25 | 0.0045770 |
| SPON1 | 1443 | 11023088 | T | N2 | −0.24 | 0.0054460 |
| SPON1 | 1444 | 4757244 | A | N5 | −0.35 | 0.0021520 |
| INSC | 1445 | 1792571 | A | N1 | 0.33 | 0.0041810 |
| INSC | 1445 | 1792571 | A | N4 | 0.30 | 0.0058370 |
| INSC | 1445 | 1792571 | A | G7 | 0.24 | 0.0063900 |
| INSC | 1445 | 1792571 | A | N2 | 0.37 | 0.0001496 |
| KCNA4 | 1446 | 11030913 | C | G9 | 0.36 | 0.0020210 |
| KCNA4 | 1447 | 10835607 | A | G9 | 0.34 | 0.0027960 |
| STIM1 | 1449 | 10835249 | G | P3 | −0.36 | 0.0009898 |
| STIM1 | 1450 | 2923944 | G | G15 | 0.22 | 0.0098320 |
| 81.99 mb | 1454 | 2186693 | T | G5 | −0.20 | 0.0074750 |
| DLG2 | 1455 | 11233564 | A | P4 | −0.49 | 0.0044530 |
| DLG2 | 1456 | 11233565 | C | P2 | −0.67 | 0.0013580 |
| DLG2 | 1456 | 11233565 | C | N7 | −0.52 | 0.0047130 |
| DLG2 | 1456 | 11233565 | C | P4 | −0.44 | 0.0097570 |
| DLG2 | 1457 | 6592113 | A | N7 | −0.26 | 0.0013040 |
| DLG2 | 1457 | 6592113 | A | G11 | −0.23 | 0.0046300 |
| DLG2 | 1460 | 558211 | G | G6 | 0.26 | 0.0080380 |
| DLG2 | 1461 | 635823 | G | G2 | 0.26 | 0.0048390 |
| DLG2 | 1462 | 2514147 | G | G16 | 0.41 | 0.0067680 |
| DLG2 | 1462 | 2514147 | G | G7 | 0.36 | 0.0051240 |
| DLG2 | 1463 | 10898192 | G | N3 | 0.38 | 0.0049450 |
| DLG2 | 1463 | 10898192 | G | G7 | 0.33 | 0.0076490 |
| DLG2 | 1464 | 7928752 | C | N3 | 0.38 | 0.0089480 |
| DLG2 | 1465 | 1945832 | T | P4 | −0.37 | 0.0057640 |
| DLG2 | 1466 | 6592202 | C | G9 | −0.25 | 0.0055200 |
| DLG2 | 1466 | 6592202 | C | N7 | −0.21 | 0.0085500 |
| DLG2 | 1467 | 4451754 | A | G9 | −0.24 | 0.0093620 |
| DLG2 | 1470 | 11234221 | A | G9 | −0.23 | 0.0095600 |
| DLG2 | 1470 | 11234221 | A | G11 | −0.21 | 0.0093050 |
| DLG2 | 1470 | 11234221 | A | N7 | −0.22 | 0.0065310 |
| DLG2 | 1470 | 11234221 | A | P6 | −0.29 | 0.0034420 |
| DLG2 | 1471 | 11234222 | A | N7 | −0.21 | 0.0081670 |
| DLG2 | 1471 | 11234222 | A | P6 | −0.29 | 0.0038850 |
| DLG2 | 1471 | 11234222 | A | N2 | −0.25 | 0.0036900 |
| DLG2 | 1473 | 11234225 | T | P3 | −0.43 | 0.0001278 |
| DLG2 | 1473 | 11234225 | T | G11 | −0.21 | 0.0090030 |
| DLG2 | 1474 | 6592211 | A | P3 | −0.44 | 0.0000786 |
| DLG2 | 1475 | 7101454 | C | P3 | −0.41 | 0.0002288 |
| DLG2 | 1476 | 582652 | A | N2 | −0.34 | 0.0074060 |
| CHST11 | 1477 | 1795849 | G | P4 | −0.25 | 0.0037010 |
| CHST11 | 1478 | 2055861 | C | P6 | −0.25 | 0.0091200 |
| CHST11 | 1479 | 1097245 | G | G9 | 0.24 | 0.0099240 |
| PLA2G1B | 1481 | 2701632 | G | P6 | −0.38 | 0.0001323 |
| LOC729025 | 1482 | 1913253 | T | G1 | 0.24 | 0.0054970 |
| LOC729025 | 1483 | 1799491 | T | G1 | −0.24 | 0.0067540 |
| PIK3C2G | 1484 | 10770343 | C | P6 | 0.28 | 0.0072800 |
| PIK3C2G | 1485 | 9300118 | G | P6 | 0.28 | 0.0034110 |
| PIK3C2G | 1486 | 11044057 | A | G6 | 0.45 | 0.0059650 |
| PIK3C2G | 1487 | 11044165 | C | G4 | 0.30 | 0.0003435 |
| PIK3C2G | 1487 | 11044165 | C | G7 | −0.21 | 0.0090200 |
| PIK3C2G | 1488 | 10841059 | A | G10 | −0.17 | 0.0058320 |
| ITPR2 | 1489 | 10842708 | G | G2 | −0.27 | 0.0093630 |
| TMEM16B | 1491 | 9645764 | C | N1 | −0.31 | 0.0077220 |
| LRP1 | 1492 | 1799986 | T | N5 | −0.40 | 0.0047260 |
| TMEM16B | 1493 | 10774369 | T | G12 | 0.28 | 0.0036530 |
| TMEM16B | 1494 | 2277401 | C | G8 | 0.15 | 0.0088880 |
| TMEM16B | 1494 | 2277401 | C | G10 | 0.17 | 0.0041830 |
| TMEM16B | 1495 | 2159952 | A | G6 | 0.34 | 0.0005129 |
| TMEM16B | 1496 | 10849338 | G | G6 | 0.36 | 0.0012240 |
| TMEM16B | 1497 | 3782659 | T | G6 | 0.25 | 0.0093090 |
| TMEM16B | 1498 | 11063875 | T | G1 | 0.26 | 0.0063660 |
| CNOT2 | 1500 | 1595410 | C | G1 | 0.26 | 0.0040450 |
| CNOT2 | 1501 | 3817487 | A | N2 | 0.23 | 0.0070250 |
| KCNC2 | 1502 | 10879888 | G | N1 | 0.35 | 0.0019890 |
| KCNC2 | 1503 | 10735985 | G | N5 | 0.35 | 0.0008785 |
| KCNC2 | 1503 | 10735985 | G | N6 | 0.28 | 0.0047040 |
| KCNC2 | 1504 | 2471664 | C | N5 | 0.34 | 0.0063280 |
| KCNC2 | 1504 | 2471664 | C | N7 | 0.26 | 0.0068700 |
| KCNC2 | 1504 | 2471664 | C | G15 | 0.32 | 0.0017050 |
| KCNC2 | 1504 | 2471664 | C | N3 | 0.29 | 0.0045910 |
| KCNC2 | 1504 | 2471664 | C | G11 | 0.28 | 0.0042050 |
| KCNC2 | 1504 | 2471664 | C | N6 | 0.37 | 0.0012390 |
| KCNC2 | 1504 | 2471664 | C | N1 | 0.36 | 0.0028950 |
| KCNC2 | 1505 | 4290307 | T | G11 | 0.29 | 0.0067140 |
| NAV3 | 1506 | 11106732 | G | N4 | 0.29 | 0.0042190 |
| NAV3 | 1507 | 939458 | G | N4 | 0.27 | 0.0059560 |
| NAV3 | 1508 | 1677923 | G | N3 | 0.46 | 0.0015940 |
| NAV3 | 1509 | 1677914 | G | N3 | 0.40 | 0.0057700 |
| NAV3 | 1510 | 10859620 | G | G5 | −0.19 | 0.0062940 |
| NAV3 | 1511 | 1479027 | G | N3 | 0.36 | 0.0090810 |
| NAV3 | 1511 | 1479027 | G | G4 | 0.34 | 0.0087190 |
| NAV3 | 1512 | 11107419 | T | G2 | −0.28 | 0.0040500 |
| NAV3 | 1513 | 1012088 | G | N2 | 0.27 | 0.0039940 |
| NAV3 | 1513 | 1012088 | G | G4 | 0.25 | 0.0060590 |
| NAV3 | 1515 | 7295890 | G | G4 | 0.23 | 0.0087880 |
| NAV3 | 1517 | 7139116 | C | N3 | 0.38 | 0.0017840 |
| NAV3 | 1518 | 10777655 | A | N3 | 0.36 | 0.0027780 |
| NAV3 | 1519 | 438209 | A | G13 | −0.26 | 0.0054940 |
| NALCN | 1520 | 12863308 | T | G4 | 0.25 | 0.0033430 |
| NALCN | 1521 | 9300653 | G | G4 | 0.28 | 0.0015320 |
| NALCN | 1522 | 9582457 | A | G4 | 0.25 | 0.0033390 |
| NALCN | 1523 | 896560 | T | G2 | 0.27 | 0.0031740 |
| NALCN | 1525 | 479648 | G | G7 | −0.20 | 0.0065120 |
| NALCN | 1526 | 9513866 | G | G2 | 0.26 | 0.0030020 |
| NALCN | 1526 | 9513866 | G | G4 | 0.25 | 0.0016280 |
| NALCN | 1527 | 9513873 | C | G4 | 0.21 | 0.0070890 |
| NALCN | 1528 | 9513875 | G | G4 | 0.20 | 0.0093640 |
| NALCN | 1529 | 9557622 | G | G3 | −0.29 | 0.0022740 |
| NALCN | 1529 | 9557622 | G | G2 | −0.22 | 0.0097580 |
| ITGBL1 | 1531 | 1140605 | T | G14 | −0.39 | 0.0023940 |
| ITGBL1 | 1532 | 4772403 | T | G10 | −0.17 | 0.0061000 |
| ITGBL1 | 1534 | 9300686 | G | P1 | −0.66 | 0.0075520 |
| ITGBL1 | 1534 | 9300686 | G | G14 | −0.38 | 0.0083450 |
| FGF14 | 1537 | 7319796 | A | N4 | −0.27 | 0.0063930 |
| FGF14 | 1541 | 3916921 | T | G14 | −0.17 | 0.0079030 |
| MTIF3 | 1542 | 7334690 | A | N2 | 0.30 | 0.0019510 |
| N4BP2L2 | 1543 | 206337 | A | G6 | 0.37 | 0.0019540 |
| N4BP2L2 | 1544 | 1081796 | A | G4 | 0.29 | 0.0066550 |
| N4BP2L2 | 1544 | 1081796 | A | P4 | 0.26 | 0.0078880 |
| N4BP2L2 | 1545 | 169600 | A | G6 | 0.31 | 0.0056210 |
| N4BP2L2 | 1546 | 208431 | G | G6 | 0.30 | 0.0075390 |
| NBEA | 1547 | 2247674 | T | G6 | 0.59 | 0.0028400 |
| NBEA | 1548 | 1197852 | A | G13 | 0.30 | 0.0056870 |
| NBEA | 1549 | 3794388 | G | G2 | −0.34 | 0.0076090 |
| NBEA | 1549 | 3794388 | C | G12 | 0.40 | 0.0030910 |
| NBEA | 1550 | 275960 | T | N7 | −0.27 | 0.0089030 |
| NBEA | 1551 | 9545075 | C | N7 | −0.27 | 0.0093760 |
| TRPC4 | 1552 | 9566247 | C | G7 | 0.23 | 0.0047640 |
| TRPC4 | 1552 | 9566247 | C | G14 | 0.20 | 0.0028790 |

TABLE 3-continued

Alleles Influencing Individual PANSS Items

| Gene | SEQ ID NO: | NCBI RS # | Allele | PANSS Item | Beta | P |
|---|---|---|---|---|---|---|
| TRPC4 | 1553 | 9576332 | G | G15 | 0.23 | 0.0095400 |
| TRPC4 | 1553 | 9576332 | G | G5 | 0.24 | 0.0010710 |
| TRPC4 | 1553 | 9576332 | G | G14 | 0.20 | 0.0025250 |
| TRPC4 | 1554 | 7336008 | A | N7 | 0.27 | 0.0012410 |
| TRPC4 | 1554 | 7336008 | A | G7 | 0.22 | 0.0053720 |
| TRPC4 | 1555 | 7338239 | G | G5 | 0.22 | 0.0017960 |
| TRPC4 | 1555 | 7338239 | G | N7 | 0.24 | 0.0037660 |
| TRPC4 | 1555 | 7338239 | G | G14 | 0.19 | 0.0039390 |
| TRPC4 | 1555 | 7338239 | G | G7 | 0.21 | 0.0095930 |
| TRPC4 | 1556 | 2181747 | G | G14 | −0.23 | 0.0002923 |
| TRPC4 | 1557 | 4943529 | C | G14 | 0.18 | 0.0045480 |
| TRPC4 | 1557 | 4943529 | C | G5 | 0.18 | 0.0079780 |
| TRPC4 | 1557 | 4943529 | C | N7 | 0.21 | 0.0094170 |
| TRPC4 | 1559 | 1556541 | C | G14 | −0.22 | 0.0010430 |
| TRPC4 | 1559 | 1556541 | C | P7 | −0.24 | 0.0003256 |
| TRPC4 | 1560 | 1924378 | A | G5 | −0.19 | 0.0069170 |
| TRPC4 | 1561 | 9548076 | A | P4 | 0.26 | 0.0073400 |
| TRPC4 | 1563 | 1538146 | T | P5 | 0.26 | 0.0060540 |
| TRPC4 | 1563 | 1538146 | T | P2 | 0.45 | 0.0000059 |
| TRPC4 | 1564 | 9594238 | C | P2 | −0.37 | 0.0028640 |
| TRPC4 | 1564 | 9594238 | C | G11 | −0.31 | 0.0046340 |
| TRPC4 | 1564 | 9594238 | C | P4 | −0.27 | 0.0073630 |
| FNDC3A | 1565 | 4942796 | T | G11 | 0.22 | 0.0098170 |
| FNDC3A | 1565 | 4942796 | T | G15 | 0.23 | 0.0084670 |
| FNDC3A | 1566 | 2994379 | G | G12 | 0.37 | 0.0002755 |
| FNDC3A | 1567 | 2181539 | G | G15 | 0.23 | 0.0087220 |
| FNDC3A | 1568 | 1983805 | G | G12 | 0.36 | 0.0004063 |
| KPNA3 | 1569 | 3903768 | A | G15 | −0.22 | 0.0070320 |
| PCDH17 | 1570 | 9527676 | G | N7 | −0.24 | 0.0026590 |
| PCDH17 | 1570 | 9527676 | G | N5 | 0.29 | 0.0032020 |
| PCDH17 | 1571 | 9591821 | A | N5 | −0.29 | 0.0042650 |
| SLAIN1 | 1572 | 9530678 | A | G2 | −0.31 | 0.0060950 |
| GPC5 | 1580 | 9560813 | T | G7 | 0.21 | 0.0093730 |
| GPC5 | 1581 | 634099 | C | G3 | −0.29 | 0.0069480 |
| GPC5 | 1581 | 634099 | C | G2 | −0.27 | 0.0039700 |
| GPC5 | 1582 | 10507992 | T | P4 | 0.27 | 0.0013220 |
| GPC5 | 1583 | 17188557 | G | P4 | 0.24 | 0.0035120 |
| GPC5 | 1584 | 913005 | T | G13 | −0.23 | 0.0029440 |
| GPC5 | 1584 | 913005 | T | N1 | −0.26 | 0.0080970 |
| GPC5 | 1585 | 9556229 | G | N6 | 0.44 | 0.0031230 |
| GPC5 | 1586 | 6492630 | A | N3 | −0.22 | 0.0092900 |
| GPC5 | 1587 | 2148226 | G | G7 | 0.20 | 0.0088650 |
| GPC5 | 1587 | 2148226 | G | N1 | 0.31 | 0.0020230 |
| GPC5 | 1587 | 2148226 | G | N6 | 0.25 | 0.0085330 |
| GPC6 | 1588 | 9516222 | G | G16 | 0.32 | 0.0060390 |
| GPC6 | 1588 | 9516222 | G | G9 | 0.40 | 0.0004041 |
| GPC6 | 1589 | 1323974 | C | G9 | 0.36 | 0.0013320 |
| GPC6 | 1589 | 1323974 | C | G2 | −0.32 | 0.0046990 |
| GPC6 | 1590 | 4394948 | C | G6 | −0.33 | 0.0010280 |
| GPC6 | 1591 | 7987964 | T | G6 | −0.31 | 0.0021180 |
| GPC6 | 1592 | 7993501 | C | G6 | −0.29 | 0.0041020 |
| GPC6 | 1595 | 9561551 | C | P3 | −0.41 | 0.0013940 |
| GPC6 | 1595 | 9561551 | C | G12 | −0.34 | 0.0017870 |
| GPC6 | 1595 | 9561551 | C | G9 | −0.29 | 0.0054850 |
| GPC6 | 1596 | 9561558 | G | G14 | 0.29 | 0.0061680 |
| NPAS3 | 1598 | 1290203 | T | G16 | −0.27 | 0.0028010 |
| NPAS3 | 1598 | 1290203 | T | G6 | −0.25 | 0.0085470 |
| NPAS3 | 1599 | 243291 | G | P2 | −0.25 | 0.0051370 |
| NPAS3 | 1600 | 243284 | G | P2 | −0.25 | 0.0060460 |
| NPAS3 | 1601 | 10133530 | A | G8 | 0.25 | 0.0005158 |
| NPAS3 | 1601 | 10133530 | A | P7 | 0.22 | 0.0071150 |
| NPAS3 | 1601 | 10133530 | A | G1 | 0.31 | 0.0066340 |
| NPAS3 | 1602 | 6571604 | C | G4 | −0.34 | 0.0019570 |
| NPAS3 | 1602 | 6571604 | C | G2 | −0.32 | 0.0080670 |
| NPAS3 | 1602 | 6571604 | C | P3 | −0.42 | 0.0046270 |
| NPAS3 | 1603 | 6571605 | A | G4 | −0.29 | 0.0061820 |
| NPAS3 | 1604 | 7144144 | C | G11 | −0.22 | 0.0050680 |
| NPAS3 | 1605 | 2383521 | C | G5 | 0.18 | 0.0069980 |
| NPAS3 | 1605 | 2383521 | C | G11 | 0.21 | 0.0096830 |
| NPAS3 | 1606 | 11156807 | T | G15 | 0.22 | 0.0054810 |
| NPAS3 | 1607 | 7152838 | A | G15 | 0.23 | 0.0099530 |
| SLC25A21 | 1608 | 12185044 | G | G3 | −0.51 | 0.0076230 |
| SLC25A21 | 1609 | 1367029 | A | G10 | −0.16 | 0.0056360 |
| LRFN5 | 1610 | 8020273 | G | G4 | 0.23 | 0.0055820 |
| LRFN5 | 1611 | 12884688 | T | G3 | −0.33 | 0.0015010 |
| GNG2 | 1612 | 4901168 | A | G12 | −0.28 | 0.0086310 |
| GNG2 | 1613 | 10138800 | A | G14 | −0.18 | 0.0049000 |
| GNG2 | 1614 | 12882906 | G | G13 | 0.22 | 0.0066200 |
| GNG2 | 1615 | 10873056 | G | G16 | −0.79 | 0.0008798 |
| GNG2 | 1615 | 10873056 | G | G14 | 0.52 | 0.0015880 |
| SAMD4A | 1616 | 1307289 | G | G1 | 0.31 | 0.0092750 |
| SAMD4A | 1617 | 8006657 | A | G15 | 0.25 | 0.0040450 |
| SAMD4A | 1617 | 8006657 | A | P6 | 0.33 | 0.0010530 |
| SAMD4A | 1618 | 709939 | C | G4 | 0.28 | 0.0004590 |
| SAMD4A | 1618 | 709939 | C | P6 | 0.28 | 0.0039730 |
| SAMD4A | 1619 | 8021151 | G | G4 | 0.31 | 0.0001717 |
| PPP2R5E | 1620 | 10137202 | C | G7 | 0.32 | 0.0046730 |
| PPP2R5E | 1620 | 10137202 | C | G3 | 0.43 | 0.0027250 |
| PPP2R5E | 1621 | 972984 | C | P5 | 0.28 | 0.0092860 |
| PPP2R5E | 1621 | 972984 | C | N6 | −0.43 | 0.0001646 |
| PPP2R5E | 1622 | 1255741 | A | N1 | −0.28 | 0.0071480 |
| PPP2R5E | 1622 | 1255741 | A | N4 | −0.29 | 0.0040290 |
| PPP2R5E | 1623 | 7154718 | G | P6 | 0.93 | 0.0045130 |
| RGS6 | 1624 | 36318 | G | P6 | 0.28 | 0.0050200 |
| RGS6 | 1624 | 36318 | G | G6 | 0.26 | 0.0074530 |
| RGS6 | 1625 | 11158926 | T | P6 | 0.29 | 0.0028720 |
| RGS6 | 1625 | 11158926 | T | G6 | 0.29 | 0.0018240 |
| RGS6 | 1626 | 11623588 | C | G6 | −0.26 | 0.0063130 |
| RGS6 | 1627 | 12586968 | G | G8 | 0.19 | 0.0045030 |
| RGS6 | 1628 | 10151019 | A | P5 | 0.32 | 0.0054910 |
| RGS6 | 1629 | 847241 | A | N7 | −0.22 | 0.0057730 |
| RGS6 | 1630 | 765221 | A | G4 | 0.26 | 0.0030130 |
| RGS6 | 1631 | 2283389 | T | G5 | 0.20 | 0.0057700 |
| KCNK10 | 1632 | 12587003 | C | G6 | 0.29 | 0.0049450 |
| KCNK10 | 1633 | 12185033 | T | P5 | −0.24 | 0.0074730 |
| RPS6KA5 | 1634 | 1152423 | C | N1 | 0.27 | 0.0093070 |
| RPS6KA5 | 1636 | 1286148 | C | N1 | 0.33 | 0.0051490 |
| RPS6KA5 | 1636 | 1286148 | C | N6 | 0.35 | 0.0017090 |
| RPS6KA5 | 1636 | 1286148 | C | N3 | 0.27 | 0.0068710 |
| RPS6KA5 | 1637 | 7156252 | T | P6 | 0.41 | 0.0000700 |
| RPS6KA5 | 1638 | 1285989 | G | P6 | 0.31 | 0.0020140 |
| RPS6KA5 | 1639 | 1075014 | A | P6 | 0.38 | 0.0003627 |
| RPS6KA5 | 1640 | 11159988 | C | P6 | 0.36 | 0.0005594 |
| RPS6KA5 | 1641 | 7492628 | G | P6 | 0.32 | 0.0022000 |
| CCDC88C | 1642 | 4904770 | T | P1 | −0.41 | 0.0031170 |
| CCDC88C | 1642 | 4904770 | T | P3 | −0.40 | 0.0040540 |
| CCDC88C | 1642 | 4904770 | T | G3 | −0.36 | 0.0042010 |
| CCDC88C | 1643 | 8015982 | C | P1 | −0.34 | 0.0055030 |
| CCDC88C | 1644 | 10131741 | G | P5 | −0.27 | 0.0077650 |
| CCDC88C | 1644 | 10131741 | G | P1 | −0.34 | 0.0060010 |
| CCDC88C | 1645 | 8008996 | T | P5 | −0.26 | 0.0084630 |
| CCDC88C | 1646 | 8007791 | A | P1 | −0.34 | 0.0061070 |
| CCDC88C | 1646 | 8007791 | A | P5 | −0.26 | 0.0084630 |
| CCDC88C | 1647 | 11160004 | C | G6 | 0.33 | 0.0059360 |
| BCL11B | 1649 | 807567 | C | P4 | 0.28 | 0.0051440 |
| BCL11B | 1650 | 2614463 | T | P1 | 0.28 | 0.0097100 |
| ATP10A | 1652 | 10873606 | A | G3 | 0.26 | 0.0085920 |
| RYR3 | 1653 | 2572189 | T | P4 | −0.20 | 0.0080530 |
| RYR3 | 1654 | 2572175 | A | G8 | −0.16 | 0.0038570 |
| RYR3 | 1654 | 2572175 | A | P4 | −0.19 | 0.0088300 |
| RYR3 | 1655 | 10519839 | G | G5 | 0.23 | 0.0007472 |
| RYR3 | 1656 | 1390159 | T | G10 | 0.48 | 0.0009035 |
| RYR3 | 1657 | 1495284 | G | G10 | 0.45 | 0.0010110 |
| RYR3 | 1658 | 11638307 | A | G7 | −0.27 | 0.0059210 |
| RYR3 | 1659 | 8036377 | A | G7 | −0.23 | 0.0069290 |
| RYR3 | 1660 | 2043054 | G | N1 | −0.39 | 0.0002070 |
| C15ORF41 | 1662 | 11073189 | G | N7 | −0.26 | 0.0058370 |
| C15ORF41 | 1663 | 8024344 | C | G4 | −0.33 | 0.0077180 |
| C15ORF41 | 1665 | 2381888 | T | N7 | −0.28 | 0.0023710 |
| C15ORF41 | 1666 | 9302317 | T | N7 | −0.25 | 0.0059890 |
| C15ORF41 | 1667 | 1990659 | A | N7 | −0.22 | 0.0076630 |
| RASGRP1 | 1668 | 11855910 | G | G12 | 0.26 | 0.0097590 |
| PLA2G4D | 1669 | 776699 | A | N4 | 0.52 | 0.0035160 |
| GLDN | 1671 | 17648128 | A | P5 | 0.25 | 0.0069100 |
| GLDN | 1672 | 17648140 | A | P4 | 0.20 | 0.0090160 |
| CGNL1 | 1673 | 12595188 | G | G8 | 0.21 | 0.0036450 |
| CGNL1 | 1674 | 7182648 | T | N4 | −0.37 | 0.0013360 |
| CGNL1 | 1675 | 8034215 | G | N4 | −0.30 | 0.0034690 |
| CGNL1 | 1676 | 16977561 | A | N5 | −0.42 | 0.0058780 |
| CGNL1 | 1677 | 1620402 | G | G10 | −0.20 | 0.0053030 |

TABLE 3-continued

Alleles Influencing Individual PANSS Items

| Gene | SEQ ID NO: | NCBI RS # | Allele | PANSS Item | Beta | P |
|---|---|---|---|---|---|---|
| CGNL1 | 1678 | 1623697 | G | G10 | −0.19 | 0.0078490 |
| RORA | 1679 | 12914584 | G | G4 | −0.24 | 0.0075730 |
| RORA | 1680 | 4774370 | C | N1 | 0.33 | 0.0092280 |
| CLK3 | 1681 | 12441932 | G | N1 | 0.40 | 0.0069560 |
| TBC1D2B | 1683 | 8030999 | G | P3 | 0.52 | 0.0012850 |
| TBC1D2B | 1683 | 8030999 | G | G10 | 0.25 | 0.0041290 |
| TBC1D2B | 1683 | 8030999 | G | G14 | 0.27 | 0.0036100 |
| TBC1D2B | 1684 | 11634607 | T | N4 | 0.30 | 0.0024460 |
| TBC1D2B | 1684 | 11634607 | T | G11 | 0.29 | 0.0008413 |
| ARNT2 | 1686 | 8041887 | A | G6 | 0.24 | 0.0090900 |
| ARNT2 | 1687 | 4778835 | G | N4 | −0.28 | 0.0088630 |
| ARNT2 | 1688 | 4628923 | C | P1 | −0.41 | 0.0007190 |
| ARNT2 | 1688 | 4628923 | C | N4 | −0.27 | 0.0099790 |
| ARNT2 | 1689 | 11072931 | T | P1 | −0.43 | 0.0034780 |
| ARNT2 | 1690 | 7180510 | G | P1 | −0.36 | 0.0040010 |
| ARNT2 | 1691 | 4778615 | T | P3 | −0.39 | 0.0086420 |
| ARNT2 | 1691 | 4778615 | T | P1 | −0.38 | 0.0098670 |
| SH3GL3 | 1692 | 10520577 | T | P2 | 0.32 | 0.0021760 |
| PCSK6 | 1693 | 11247300 | A | G15 | 0.32 | 0.0051620 |
| GDE1 | 1695 | 12447418 | G | P5 | 0.30 | 0.0064830 |
| A2BP1 | 1699 | 1476979 | T | G1 | 0.24 | 0.0059520 |
| A2BP1 | 1700 | 11077043 | G | G1 | 0.24 | 0.0062720 |
| A2BP1 | 1702 | 4289011 | C | G7 | −0.27 | 0.0007420 |
| HYDIN | 1703 | 1424137 | G | N4 | −0.31 | 0.0015820 |
| A2BP1 | 1704 | 8055711 | T | G7 | −0.26 | 0.0026420 |
| HYDIN | 1705 | 9939194 | T | N4 | −0.30 | 0.0019340 |
| A2BP1 | 1706 | 11860241 | G | G12 | 0.27 | 0.0049040 |
| A2BP1 | 1707 | 1507031 | A | G10 | 0.16 | 0.0071550 |
| WWOX | 1708 | 8061908 | C | N7 | −0.25 | 0.0027750 |
| WWOX | 1709 | 1922620 | C | N7 | −0.23 | 0.0043490 |
| WWOX | 1710 | 2344926 | G | N7 | −0.22 | 0.0088960 |
| WWOX | 1711 | 11641213 | G | P6 | 0.27 | 0.0060550 |
| WWOX | 1712 | 7184271 | G | P6 | 0.26 | 0.0079320 |
| WWOX | 1713 | 7201683 | G | G3 | −1.14 | 0.0068500 |
| MPHOSPH6 | 1714 | 7405231 | C | P5 | 0.24 | 0.0033010 |
| MPHOSPH6 | 1715 | 8052512 | T | G6 | −0.40 | 0.0021070 |
| MPHOSPH6 | 1716 | 8047857 | C | G6 | −0.37 | 0.0060150 |
| MPHOSPH6 | 1717 | 4530129 | C | G6 | −0.38 | 0.0088290 |
| CDH13 | 1718 | 4598906 | T | G8 | −0.17 | 0.0037190 |
| CDH13 | 1719 | 11150496 | T | N7 | 0.24 | 0.0026140 |
| CDH13 | 1720 | 4782734 | T | N7 | 0.22 | 0.0072300 |
| CDH13 | 1721 | 9933935 | T | G3 | 0.27 | 0.0087900 |
| CDH13 | 1723 | 4783293 | C | G3 | 0.27 | 0.0093560 |
| CDH13 | 1724 | 7201829 | T | N7 | 0.27 | 0.0041410 |
| CDH13 | 1725 | 11150517 | T | N1 | 0.36 | 0.0031150 |
| CDH13 | 1726 | 1035569 | G | G14 | −0.20 | 0.0040860 |
| CDH13 | 1727 | 10514579 | C | G14 | −0.20 | 0.0045860 |
| CDH13 | 1728 | 11864731 | A | G14 | −0.19 | 0.0026430 |
| CDH13 | 1729 | 1833965 | A | N5 | 0.27 | 0.0098150 |
| USP10 | 1731 | 744839 | T | N1 | −0.30 | 0.0024100 |
| USP10 | 1732 | 8060725 | A | N2 | 0.27 | 0.0031360 |
| CRISPLD2 | 1733 | 2641697 | C | P7 | 0.19 | 0.0042800 |
| CRISPLD2 | 1735 | 16974822 | G | G9 | −0.31 | 0.0030320 |
| CRISPLD2 | 1735 | 16974822 | G | P2 | −0.28 | 0.0079670 |
| CRISPLD2 | 1736 | 774205 | G | P4 | 0.22 | 0.0040940 |
| CRISPLD2 | 1737 | 11149692 | C | P3 | −0.34 | 0.0076950 |
| CRISPLD2 | 1737 | 11149692 | C | P5 | −0.34 | 0.0007284 |
| CRISPLD2 | 1738 | 982994 | T | P4 | 0.21 | 0.0083490 |
| CRISPLD2 | 1738 | 982994 | T | P5 | 0.24 | 0.0092360 |
| CRISPLD2 | 1739 | 2646107 | C | P5 | −0.27 | 0.0071640 |
| DNAH9 | 1740 | 3744581 | G | P4 | −0.23 | 0.0046180 |
| DNAH9 | 1741 | 16945383 | G | G9 | 0.28 | 0.0012220 |
| RAB11FIP4 | 1743 | 315431 | T | G1 | −0.33 | 0.0007109 |
| CA10 | 1744 | 11869209 | C | P4 | 0.22 | 0.0054890 |
| CA10 | 1745 | 4794315 | G | P4 | −0.23 | 0.0012360 |
| CA10 | 1746 | 1393735 | G | P4 | −0.22 | 0.0019830 |
| CA10 | 1747 | 1875675 | T | P4 | 0.25 | 0.0006519 |
| CA10 | 1748 | 9893317 | A | P4 | 0.26 | 0.0005388 |
| CA10 | 1749 | 11652641 | G | G4 | −0.29 | 0.0041050 |
| CA10 | 1749 | 11652641 | G | G12 | −0.33 | 0.0048860 |
| CA10 | 1749 | 11652641 | G | P4 | −0.31 | 0.0008907 |
| CA10 | 1750 | 12942636 | T | P6 | −0.32 | 0.0022370 |
| MSI2 | 1751 | 8066677 | G | G6 | −0.28 | 0.0059210 |
| MSI2 | 1751 | 8066677 | G | G7 | −0.23 | 0.0054900 |
| MSI2 | 1753 | 8077599 | A | N1 | −0.30 | 0.0030850 |
| SDK2 | 1754 | 1846334 | A | P3 | −0.32 | 0.0055460 |
| HRNBP3 | 1755 | 907898 | C | P6 | 0.44 | 0.0064750 |
| HRNBP3 | 1756 | 4313839 | C | G3 | 0.29 | 0.0035960 |
| OSBPL1A | 1757 | 6508259 | A | G6 | −0.35 | 0.0016990 |
| OSBPL1A | 1758 | 275857 | C | G16 | 0.61 | 0.0059070 |
| OSBPL1A | 1758 | 275857 | C | P4 | 0.48 | 0.0092890 |
| OSBPL1A | 1758 | 275857 | C | N4 | 0.71 | 0.0021820 |
| OSBPL1A | 1758 | 275857 | C | N7 | 0.56 | 0.0042880 |
| CHST9 | 1760 | 17703962 | G | G3 | 0.37 | 0.0091660 |
| CHST9 | 1761 | 9949654 | C | G9 | 0.40 | 0.0003672 |
| DLGAP1 | 1763 | 9635857 | G | P1 | 0.40 | 0.0014780 |
| DLGAP1 | 1763 | 9635857 | G | P3 | 0.45 | 0.0004842 |
| DLGAP1 | 1764 | 7245298 | G | P3 | 0.43 | 0.0016550 |
| ZFP161 | 1765 | 9965501 | T | G4 | −0.76 | 0.0026240 |
| NEDD4L | 1773 | 11152073 | A | P3 | 0.36 | 0.0047540 |
| CCBE1 | 1774 | 12969965 | A | P2 | 0.28 | 0.0099730 |
| CCBE1 | 1775 | 4488565 | C | P5 | −0.25 | 0.0064570 |
| CDH7 | 1776 | 2658046 | C | G14 | 0.17 | 0.0052290 |
| CDH7 | 1777 | 7241038 | T | G14 | 0.17 | 0.0060130 |
| CDH7 | 1778 | 4455070 | A | G14 | 0.16 | 0.0081910 |
| CDH7 | 1779 | 976882 | A | G14 | 0.16 | 0.0090970 |
| CDH7 | 1780 | 7237421 | T | N3 | 0.27 | 0.0016680 |
| CDH7 | 1780 | 7237421 | T | N5 | 0.27 | 0.0098740 |
| CDH7 | 1781 | 8092259 | G | N3 | 0.27 | 0.0024310 |
| CDH7 | 1783 | 1942832 | A | N3 | 0.26 | 0.0033240 |
| CDH7 | 1784 | 1942831 | G | N3 | 0.26 | 0.0035760 |
| CDH7 | 1785 | 8093720 | A | N3 | 0.25 | 0.0046980 |
| CDH7 | 1786 | 1484725 | T | N3 | 0.25 | 0.0050040 |
| CDH7 | 1786 | 1484725 | T | N2 | 0.28 | 0.0017760 |
| CDH7 | 1787 | 1994230 | T | P6 | 0.53 | 0.0075190 |
| CDH7 | 1788 | 8089669 | A | G4 | 0.23 | 0.0052220 |
| CDH7 | 1789 | 12606480 | C | G4 | 0.21 | 0.0082640 |
| CDH7 | 1790 | 1564815 | C | N3 | 0.54 | 0.0067680 |
| DOK6 | 1791 | 12961718 | C | G7 | 0.23 | 0.0063950 |
| DOK6 | 1793 | 4426448 | G | G9 | 0.30 | 0.0008687 |
| DOK6 | 1793 | 4426448 | G | P2 | 0.29 | 0.0016190 |
| DOK6 | 1793 | 4426448 | G | P5 | 0.23 | 0.0097090 |
| DOK6 | 1794 | 12605879 | G | P1 | 0.30 | 0.0057610 |
| DOK6 | 1794 | 12605879 | G | G9 | 0.28 | 0.0013060 |
| DOK6 | 1794 | 12605879 | G | P2 | 0.27 | 0.0025790 |
| MBP | 1795 | 470181 | A | G12 | 0.30 | 0.0026850 |
| MBP | 1796 | 11660442 | A | G13 | 0.22 | 0.0072860 |
| PTPRM | 1798 | 8089695 | C | N1 | 0.62 | 0.0008150 |
| PTPRM | 1799 | 6506570 | A | G1 | −0.27 | 0.0031230 |
| PTPRM | 1800 | 6506572 | T | G2 | −0.25 | 0.0091560 |
| PTPRM | 1801 | 9949149 | C | G2 | −0.24 | 0.0094030 |
| KIAA0802 | 1802 | 4798677 | A | G1 | 0.25 | 0.0042410 |
| KIAA0802 | 1803 | 12386117 | A | G6 | −0.35 | 0.0094890 |
| KIAA0802 | 1803 | 12386117 | A | G5 | −0.25 | 0.0099120 |
| KIAA0802 | 1804 | 7235093 | A | N3 | 0.54 | 0.0001818 |
| KIAA0802 | 1804 | 7235093 | A | N1 | 0.64 | 0.0001433 |
| LDLR | 1806 | 2116897 | T | P6 | 0.31 | 0.0091270 |
| LDLR | 1807 | 1433099 | A | G14 | −0.19 | 0.0080220 |
| ZNF667 | 1808 | 7251105 | G | G14 | −0.19 | 0.0042940 |
| MACROD2 | 1809 | 6079395 | G | N5 | 0.27 | 0.0075940 |
| MACROD2 | 1811 | 11697488 | T | P1 | 0.35 | 0.0027420 |
| MACROD2 | 1812 | 809587 | G | N7 | 0.25 | 0.0079290 |
| KIF16B | 1813 | 6043875 | C | P6 | −0.28 | 0.0061930 |
| KIF16B | 1813 | 6043875 | C | G2 | −0.24 | 0.0076280 |
| KIF16B | 1813 | 6043875 | C | G1 | −0.24 | 0.0066360 |
| KIF16B | 1813 | 6043875 | C | G16 | −0.27 | 0.0041690 |
| KIF16B | 1813 | 6043875 | C | G3 | −0.26 | 0.0086990 |
| KIF16B | 1813 | 6043875 | C | G6 | −0.32 | 0.0009477 |
| KIF16B | 1814 | 6111022 | T | G16 | 0.28 | 0.0049120 |
| KIF16B | 1815 | 4814474 | A | G1 | 0.25 | 0.0064230 |
| KIF16B | 1815 | 4814474 | A | G16 | 0.24 | 0.0080570 |
| KIF16B | 1816 | 6034462 | T | P6 | −0.29 | 0.0040210 |
| KIF16B | 1817 | 2328019 | C | G6 | −0.25 | 0.0089580 |
| KIF16B | 1817 | 2328019 | C | P6 | −0.26 | 0.0094690 |
| KIF16B | 1818 | 6135739 | G | P6 | −0.29 | 0.0042470 |
| KIF16B | 1819 | 6111075 | T | G6 | −0.26 | 0.0081000 |
| KIF16B | 1820 | 6111076 | C | P6 | −0.27 | 0.0063350 |
| KIF16B | 1821 | 6034464 | A | G1 | −0.24 | 0.0073690 |
| KIF16B | 1822 | 2876428 | C | G6 | −0.25 | 0.0086240 |
| KIF16B | 1823 | 12624938 | A | G7 | 0.30 | 0.0046690 |

TABLE 3-continued

Alleles Influencing Individual PANSS Items

| Gene | SEQ ID NO: | NCBI RS # | Allele | PANSS Item | Beta | P |
|---|---|---|---|---|---|---|
| KIF16B | 1824 | 2143988 | A | G7 | 0.23 | 0.0026840 |
| KIF16B | 1825 | 7352372 | G | G1 | 0.28 | 0.0090750 |
| KIF16B | 1826 | 6075069 | T | G1 | 0.42 | 0.0003007 |
| KIF16B | 1826 | 6075069 | T | G2 | 0.30 | 0.0079190 |
| KIF16B | 1826 | 6075069 | T | P2 | -0.32 | 0.0072410 |
| KIF16B | 1826 | 6075069 | T | G3 | 0.41 | 0.0012840 |
| KIF16B | 1827 | 6080359 | C | N1 | -0.36 | 0.0018350 |
| MAPRE1 | 1828 | 410488 | A | G16 | 0.27 | 0.0029080 |
| MAPRE1 | 1829 | 2070090 | T | G8 | 0.24 | 0.0020120 |
| MAPRE1 | 1829 | 2070090 | T | G14 | 0.29 | 0.0007217 |
| PTPRT | 1830 | 4810349 | T | P5 | 0.24 | 0.0055900 |
| PTPRT | 1831 | 2013923 | G | P5 | 0.25 | 0.0060750 |
| PTPRT | 1833 | 746413 | C | P1 | 0.35 | 0.0013050 |
| PTPRT | 1833 | 746413 | C | N6 | -0.28 | 0.0029880 |
| PTPRT | 1834 | 6065434 | T | N6 | -0.27 | 0.0068540 |
| PTPRT | 1836 | 6065487 | A | P2 | -0.27 | 0.0048940 |
| PTPRT | 1837 | 4810366 | C | G10 | 0.19 | 0.0043630 |
| PTPRT | 1838 | 2017914 | G | G7 | 0.22 | 0.0080940 |
| PTPRT | 1838 | 2017914 | G | G10 | 0.19 | 0.0041790 |
| PTPRT | 1839 | 6072869 | G | N5 | 0.33 | 0.0050000 |
| PRNT | 1840 | 6052824 | A | G1 | 0.27 | 0.0075650 |
| KCNB1 | 1842 | 9636516 | A | P3 | 0.36 | 0.0025780 |
| KCNB1 | 1843 | 496511 | C | G6 | -0.28 | 0.0040330 |
| KCNB1 | 1844 | 6095546 | A | G2 | -0.29 | 0.0039110 |
| KCNB1 | 1845 | 4647 | T | G2 | -0.28 | 0.0058190 |
| KCNB1 | 1845 | 4647 | T | P3 | -0.33 | 0.0096390 |
| CDH4 | 1848 | 6089265 | T | G2 | -0.32 | 0.0021190 |
| CDH4 | 1849 | 1891572 | T | N5 | -0.28 | 0.0055020 |
| CDH4 | 1850 | 17811544 | G | N5 | -0.27 | 0.0059340 |
| CDH4 | 1850 | 17811544 | G | P4 | -0.19 | 0.0083060 |
| CDH4 | 1851 | 6142884 | A | G15 | -0.22 | 0.0061750 |
| FERMT1 | 1852 | 6117072 | C | G12 | -0.29 | 0.0021930 |
| FERMT1 | 1853 | 6085406 | A | G4 | -0.25 | 0.0019890 |
| FERMT1 | 1854 | 10373 | T | G4 | -0.24 | 0.0033280 |
| PLCB1 | 1857 | 2235212 | A | P1 | 0.35 | 0.0057060 |
| PLCB1 | 1858 | 6055678 | T | G16 | 0.33 | 0.0040720 |
| C21ORF37 | 1861 | 12483129 | C | N2 | 0.26 | 0.0025100 |
| C21ORF37 | 1861 | 12483129 | C | N6 | 0.27 | 0.0033900 |
| NCAM2 | 1862 | 2826830 | G | G11 | 0.27 | 0.0059510 |
| NCAM2 | 1862 | 2826830 | G | G4 | 0.28 | 0.0041390 |
| NCAM2 | 1863 | 3787603 | G | G11 | 0.26 | 0.0079430 |
| NCAM2 | 1864 | 1599228 | C | N3 | 0.30 | 0.0015950 |
| ERG | 1865 | 461592 | C | G9 | -0.30 | 0.0030480 |
| ERG | 1865 | 461592 | C | N7 | -0.27 | 0.0033130 |
| ERG | 1866 | 461488 | G | N7 | -0.26 | 0.0036820 |
| ERG | 1867 | 2070527 | A | G9 | -0.27 | 0.0062580 |
| PCP4 | 1868 | 2837257 | C | G3 | 0.30 | 0.0064480 |
| PCP4 | 1868 | 2837257 | C | G6 | 0.34 | 0.0016930 |
| PCP4 | 1869 | 398802 | G | G15 | 0.24 | 0.0076060 |
| SLC37A1 | 1870 | 412212 | C | N5 | -0.34 | 0.0048170 |
| SLC37A1 | 1872 | 381899 | A | N5 | -0.32 | 0.0049270 |
| SLC37A1 | 1872 | 381899 | A | N4 | -0.28 | 0.0093920 |
| ARVCF | 1873 | 2239395 | G | P5 | 0.66 | 0.0098270 |
| HPS4 | 1875 | 739289 | C | G9 | 0.40 | 0.0049610 |
| ARFGAP3 | 1876 | 6002963 | G | G10 | -0.18 | 0.0037870 |
| ARFGAP3 | 1877 | 738536 | A | G6 | 0.33 | 0.0005261 |
| ARFGAP3 | 1878 | 4822208 | T | G6 | 0.31 | 0.0007756 |
| PACSIN2 | 1879 | 1076118 | T | G10 | -0.18 | 0.0020710 |
| PACSIN2 | 1880 | 738383 | C | G6 | 0.31 | 0.0010780 |
| PACSIN2 | 1881 | 1071960 | C | N6 | 0.26 | 0.0072050 |
| PACSIN2 | 1882 | 4140554 | C | G10 | -0.17 | 0.0033560 |
| PACSIN2 | 1883 | 7291153 | C | G10 | -0.17 | 0.0052570 |
| PACSIN2 | 1883 | 7291153 | C | G6 | -0.28 | 0.0033790 |
| PACSIN2 | 1884 | 1569507 | G | G10 | -0.17 | 0.0056840 |
| PACSIN2 | 1885 | 5751410 | A | G10 | -0.16 | 0.0083500 |
| PACSIN2 | 1886 | 713717 | T | G6 | 0.28 | 0.0033910 |
| PACSIN2 | 1887 | 737782 | G | G6 | 0.27 | 0.0048780 |
| PACSIN2 | 1889 | 738379 | A | G10 | -0.16 | 0.0084240 |
| TTLL1 | 1890 | 2076156 | G | G8 | 0.33 | 0.0041600 |
| TTLL1 | 1891 | 135001 | C | P7 | 0.17 | 0.0063380 |
| TTLL1 | 1892 | 135002 | C | P7 | 0.17 | 0.0072570 |
| EFCAB6 | 1894 | 12628583 | C | G2 | -0.37 | 0.0082480 |

TABLE A

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 1 | KIF1B | 1 | 10,279,993 | 2 | KIF1B | 1 | 10,320,154 |
| 3 | KIF1B | 1 | 10,323,189 | 4 | KIF1B | 1 | 10,343,505 |
| 5 | SYT6 | 1 | 114,452,599 | 6 | NGF | 1 | 115,631,509 |
| 7 | NGF | 1 | 115,664,140 | 8 | SLC22A15 | 1 | 116,328,295 |
| 9 | SLC22A15 | 1 | 116,329,613 | 10 | SLC22A15 | 1 | 116,353,502 |
| 11 | SLC22A15 | 1 | 116,381,302 | 12 | PTGFRN | 1 | 117,269,213 |
| 13 | PTGFRN | 1 | 117,273,572 | 14 | PTGFRN | 1 | 117,284,884 |
| 15 | PTGFRN | 1 | 117,333,336 | 16 | CGN | 1 | 149,743,817 |
| 17 | RP1-21O18.1 | 1 | 15,214,000 | 18 | RP1-21O18.1 | 1 | 15,265,882 |
| 19 | RP1-21O18.1 | 1 | 15,278,076 | 20 | RP1-21O18.1 | 1 | 15,281,743 |
| 21 | RP1-21O18.1 | 1 | 15,285,942 | 22 | RP1-21O18.1 | 1 | 15,316,063 |
| 23 | ATF6 | 1 | 160,062,520 | 24 | ATF6 | 1 | 160,107,168 |
| 25 | OLFML2B | 1 | 160,230,414 | 26 | OLFML2B | 1 | 160,234,305 |
| 27 | OLFML2B | 1 | 160,247,126 | 28 | FAM78B | 1 | 164,309,282 |
| 29 | FAM78B | 1 | 164,314,302 | 30 | SEC16B | 1 | 176,215,337 |
| 31 | RALGPS2 | 1 | 176,976,589 | 32 | RALGPS2 | 1 | 177,051,615 |
| 33 | KCNK2 | 1 | 213,266,926 | 34 | KCNK2 | 1 | 213,387,083 |
| 35 | KCNK2 | 1 | 213,405,370 | 36 | KCNK2 | 1 | 213,405,685 |
| 37 | KCNK2 | 1 | 213,412,561 | 38 | KCNK2 | 1 | 213,426,881 |
| 39 | KCNK2 | 1 | 213,474,680 | 40 | USH2A | 1 | 213,526,280 |
| 41 | USH2A | 1 | 213,537,370 | 42 | USH2A | 1 | 213,911,770 |
| 43 | USH2A | 1 | 213,954,742 | 44 | USH2A | 1 | 213,955,280 |
| 45 | USH2A | 1 | 214,404,070 | 46 | USH2A | 1 | 214,404,156 |
| 47 | USH2A | 1 | 214,498,585 | 48 | USH2A | 1 | 214,506,786 |
| 49 | USH2A | 1 | 214,572,091 | 50 | ESRRG | 1 | 214,788,713 |
| 51 | ESRRG | 1 | 214,789,473 | 52 | ESRRG | 1 | 214,827,730 |
| 53 | ESRRG | 1 | 214,836,783 | 54 | ESRRG | 1 | 214,855,550 |
| 55 | ESRRG | 1 | 214,861,049 | 56 | ESRRG | 1 | 214,950,266 |
| 57 | EPHB2 | 1 | 22,984,956 | 58 | EPHB2 | 1 | 23,091,301 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 59 | SLC35F3 | 1 | 232,525,097 | 60 | RYR2 | 1 | 235,413,480 |
| 61 | RYR2 | 1 | 235,435,907 | 62 | RYR2 | 1 | 235,500,248 |
| 63 | RYR2 | 1 | 235,513,475 | 64 | RYR2 | 1 | 235,569,612 |
| 65 | RYR2 | 1 | 235,661,657 | 66 | RYR2 | 1 | 235,795,490 |
| 67 | RYR2 | 1 | 235,805,642 | 68 | RYR2 | 1 | 236,056,960 |
| 69 | CHRM3 | 1 | 237,894,973 | 70 | CHRM3 | 1 | 237,911,900 |
| 71 | CHRM3 | 1 | 237,937,398 | 72 | CHRM3 | 1 | 237,944,344 |
| 73 | CHRIVI3 | 1 | 237,958,134 | 74 | CHRM3 | 1 | 237,969,464 |
| 75 | CHRM3 | 1 | 237,996,528 | 76 | FMN2 | 1 | 238,349,704 |
| 77 | FMN2 | 1 | 238,353,478 | 78 | FMN2 | 1 | 238,416,539 |
| 79 | FMN2 | 1 | 238,426,833 | 80 | FMN2 | 1 | 238,455,099 |
| 81 | FMN2 | 1 | 238,486,712 | 82 | FMN2 | 1 | 238,494,888 |
| 83 | FMN2 | 1 | 238,512,719 | 84 | FMN2 | 1 | 238,525,003 |
| 85 | FMN2 | 1 | 238,669,725 | 86 | FMN2 | 1 | 238,670,023 |
| 87 | RGS7 | 1 | 239,588,948 | 88 | PLD5 | 1 | 240,632,975 |
| 89 | CLIC4 | 1 | 24,963,033 | 90 | CLIC4 | 1 | 24,970,832 |
| 91 | AGBL4-C1ORF165 | 1 | 48,833,568 | 92 | AGBL4-C1ORF165 | 1 | 49,006,963 |
| 93 | AGBL4-C1ORF165 | 1 | 49,124,764 | 94 | AGBL4-C1ORF165 | 1 | 49,125,312 |
| 95 | AGBL4-C1ORF165 | 1 | 49,133,207 | 96 | AGBL4-C1ORF165 | 1 | 49,239,649 |
| 97 | AGBL4-C1ORF165 | 1 | 49,243,353 | 98 | SCP2 | 1 | 53,287,104 |
| 99 | LRP8 | 1 | 53,561,462 | 100 | ELTD1 | 1 | 79,259,313 |
| 101 | ELTD1 | 1 | 79,260,672 | 102 | PRKACB | 1 | 84,299,506 |
| 103 | PRKACB | 1 | 84,301,022 | 104 | PRKACB | 1 | 84,450,848 |
| 105 | HPCAL1 | 2 | 10,301,740 | 106 | KCNF1 | 2 | 10,981,799 |
| 107 | KCNF1 | 2 | 10,999,213 | 108 | NTSR2 | 2 | 11,726,315 |
| 109 | NAPS | 2 | 133,607,512 | 110 | NAPS | 2 | 133,642,409 |
| 111 | RAB3GAP1 | 2 | 135,514,217 | 112 | RAB3GAP1 | 2 | 135,541,544 |
| 113 | RAB3GAP1 | 2 | 135,649,190 | 114 | ZRANB3 | 2 | 135,868,244 |
| 115 | ZRANB3 | 2 | 135,981,101 | 116 | NXPH2 | 2 | 139,154,184 |
| 117 | LRP1B | 2 | 140,708,533 | 118 | LRP1B | 2 | 140,730,389 |
| 119 | LRP1B | 2 | 140,740,113 | 120 | LRP1B | 2 | 140,749,675 |
| 121 | LRP1B | 2 | 140,986,740 | 122 | LRP1B | 2 | 141,715,030 |
| 123 | LRP1B | 2 | 141,896,198 | 124 | LRP1B | 2 | 142,066,600 |
| 125 | LRP1B | 2 | 142,278,834 | 126 | LRP1B | 2 | 142,283,237 |
| 127 | LRP1B | 2 | 142,284,380 | 128 | LRP1B | 2 | 142,293,931 |
| 129 | KYNU | 2 | 143,368,826 | 130 | KYNU | 2 | 143,405,309 |
| 131 | KYNU | 2 | 143,430,832 | 132 | KYNU | 2 | 143,455,211 |
| 133 | KYNU | 2 | 143,598,044 | 134 | ARHGAP15 | 2 | 143,651,019 |
| 135 | ARHGAP15 | 2 | 143,685,981 | 136 | ARHGAP15 | 2 | 143,769,771 |
| 137 | ARHGAP15 | 2 | 143,884,507 | 138 | ARHGAP15 | 2 | 143,903,015 |
| 139 | ARHGAP15 | 2 | 143,961,757 | 140 | ARHGAP15 | 2 | 144,294,622 |
| 141 | ARHGAP15 | 2 | 144,295,364 | 142 | KIF5C | 2 | 149,333,649 |
| 143 | KIF5C | 2 | 149,600,091 | 144 | FMNL2 | 2 | 152,981,465 |
| 145 | FMNL2 | 2 | 153,122,655 | 146 | FMNL2 | 2 | 153,166,996 |
| 147 | FMNL2 | 2 | 153,201,156 | 148 | FMNL2 | 2 | 153,207,856 |
| 149 | KCNJ3 | 2 | 155,324,938 | 150 | KCNJ3 | 2 | 155,326,572 |
| 151 | KCNJ3 | 2 | 155,411,014 | 152 | PKP4 | 2 | 159,148,211 |
| 153 | PKP4 | 2 | 159,155,564 | 154 | PKP4 | 2 | 159,163,035 |
| 155 | PKP4 | 2 | 159,168,396 | 156 | PKP4 | 2 | 159,172,437 |
| 157 | PKP4 | 2 | 159,204,636 | 158 | PKP4 | 2 | 159,219,409 |
| 159 | PKP4 | 2 | 159,232,049 | 160 | PLA2R1 | 2 | 160,519,430 |
| 161 | PLA2R1 | 2 | 160,543,237 | 162 | PLA2R1 | 2 | 160,575,799 |
| 163 | PLA2R1 | 2 | 160,616,115 | 164 | KCNH7 | 2 | 163,221,260 |
| 165 | SCN3A | 2 | 165,732,374 | 166 | SCN1A | 2 | 166,606,495 |
| 167 | SCN1A | 2 | 166,629,033 | 168 | SCN1A | 2 | 166,650,019 |
| 169 | SCN9A | 2 | 166,781,097 | 170 | SCN9A | 2 | 166,784,624 |
| 171 | SCN9A | 2 | 166,807,404 | 172 | SCN9A | 2 | 166,817,960 |
| 173 | SCN9A | 2 | 166,871,909 | 174 | SCN9A | 2 | 166,874,107 |
| 175 | SCN7A | 2 | 166,989,998 | 176 | CERKL | 2 | 182,239,099 |
| 177 | PDE1A | 2 | 182,752,922 | 178 | PDE1A | 2 | 182,763,240 |
| 179 | PDE1A | 2 | 182,767,445 | 180 | PDE1A | 2 | 182,804,991 |
| 181 | PDE1A | 2 | 182,821,396 | 182 | PDE1A | 2 | 182,833,270 |
| 183 | PDE1A | 2 | 182,871,393 | 184 | PDE1A | 2 | 182,886,451 |
| 185 | PDE1A | 2 | 182,910,657 | 186 | PDE1A | 2 | 182,918,516 |
| 187 | PDE1A | 2 | 182,932,372 | 188 | PDE1A | 2 | 182,971,998 |
| 189 | PDE1A | 2 | 183,029,113 | 190 | PDE1A | 2 | 183,067,065 |
| 191 | ALS2 | 2 | 202,315,109 | 192 | ALS2 | 2 | 202,354,735 |
| 193 | PARD3B | 2 | 205,291,115 | 194 | PARD3B | 2 | 205,326,956 |
| 195 | PARD3B | 2 | 205,347,353 | 196 | PARD3B | 2 | 205,858,397 |
| 197 | PARD3B | 2 | 205,866,562 | 198 | PARD3B | 2 | 205,906,564 |
| 199 | PARD3B | 2 | 205,932,117 | 200 | PARD3B | 2 | 205,955,695 |
| 201 | PARD3B | 2 | 205,967,382 | 202 | PARD3B | 2 | 206,172,710 |
| 203 | NRP2 | 2 | 206,426,955 | 204 | NRP2 | 2 | 206,441,948 |
| 205 | NRP2 | 2 | 206,443,765 | 206 | PIP5K3 | 2 | 208,948,035 |
| 207 | PIP5K3 | 2 | 208,956,492 | 208 | ERBB4 | 2 | 211,933,765 |
| 209 | ERBB4 | 2 | 211,975,964 | 210 | ERBB4 | 2 | 212,022,377 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 211 | CUL3 | 2 | 225,109,321 | 212 | IRS1 | 2 | 227,388,355 |
| 213 | COL4A4 | 2 | 227,619,969 | 214 | COL4A4 | 2 | 227,630,259 |
| 215 | COL4A3 | 2 | 227,795,722 | 216 | DNER | 2 | 229,972,935 |
| 217 | DNER | 2 | 230,024,102 | 218 | ECEL1 | 2 | 233,048,959 |
| 219 | CHRNG | 2 | 233,127,640 | 220 | SAG | 2 | 233,900,559 |
| 221 | SAG | 2 | 233,902,504 | 222 | KLHL29 | 2 | 23,504,556 |
| 223 | KLHL29 | 2 | 23,504,709 | 224 | KLHL29 | 2 | 23,504,805 |
| 225 | KLHL29 | 2 | 23,507,416 | 226 | KLHL29 | 2 | 23,519,201 |
| 227 | KLHL29 | 2 | 23,782,141 | 228 | KCNK3 | 2 | 26,798,797 |
| 229 | KCNK3 | 2 | 26,807,044 | 230 | DPYSL5 | 2 | 26,957,635 |
| 231 | DPYSL5 | 2 | 26,986,326 | 232 | DPYSL5 | 2 | 27,023,044 |
| 233 | BRE | 2 | 28,212,255 | 234 | BRE | 2 | 28,243,350 |
| 235 | BRE | 2 | 28,373,587 | 236 | BRE | 2 | 28,396,438 |
| 237 | CRIM1 | 2 | 36,443,527 | 238 | CRIM1 | 2 | 36,471,032 |
| 239 | CRIM1 | 2 | 36,477,691 | 240 | CRIM1 | 2 | 36,510,809 |
| 241 | CRIM1 | 2 | 36,523,515 | 242 | CRIM1 | 2 | 36,535,123 |
| 243 | CRIM1 | 2 | 36,549,124 | 244 | CRIM1 | 2 | 36,581,523 |
| 245 | CRIM1 | 2 | 36,581,946 | 246 | SLC8A1 | 2 | 40,230,588 |
| 247 | SLC8A1 | 2 | 40,241,861 | 248 | SLC8A1 | 2 | 40,253,816 |
| 249 | SLC8A1 | 2 | 40,267,644 | 250 | SLC8A1 | 2 | 40,524,155 |
| 251 | SLC8A1 | 2 | 40,524,198 | 252 | HAAO | 2 | 42,918,059 |
| 253 | PLEKHH2 | 2 | 43,822,986 | 254 | PLEKHH2 | 2 | 43,823,791 |
| 255 | PLEKHH2 | 2 | 43,839,444 | 256 | PLEKHH2 | 2 | 43,846,952 |
| 257 | C2ORF34 | 2 | 44,446,479 | 258 | C2ORF34 | 2 | 44,457,570 |
| 259 | C2ORF34 | 2 | 44,474,546 | 260 | C2ORF34 | 2 | 44,500,542 |
| 261 | C2ORF34 | 2 | 44,501,551 | 262 | C2ORF34 | 2 | 44,508,409 |
| 263 | C2ORF34 | 2 | 44,514,120 | 264 | C2ORF34 | 2 | 44,529,730 |
| 265 | C2ORF34 | 2 | 44,536,723 | 266 | C2ORF34 | 2 | 44,574,451 |
| 267 | C2ORF34 | 2 | 44,584,000 | 268 | C2ORF34 | 2 | 44,621,606 |
| 269 | C2ORF34 | 2 | 44,631,967 | 270 | C2ORF34 | 2 | 44,641,482 |
| 271 | C2ORF34 | 2 | 44,645,163 | 272 | C2ORF34 | 2 | 44,686,360 |
| 273 | C2ORF34 | 2 | 44,715,296 | 274 | C2ORF34 | 2 | 44,834,212 |
| 275 | C2ORF34 | 2 | 44,834,623 | 276 | PRKCE | 2 | 45,737,717 |
| 277 | PRKCE | 2 | 46,130,026 | 278 | PRKCE | 2 | 46,226,779 |
| 279 | EPAS1 | 2 | 46,401,568 | 280 | FBXO11 | 2 | 47,952,212 |
| 281 | FBXO11 | 2 | 47,978,008 | 282 | PSME4 | 2 | 53,957,822 |
| 283 | PSME4 | 2 | 54,001,835 | 284 | PSME4 | 2 | 54,018,352 |
| 285 | PSME4 | 2 | 54,055,952 | 286 | PSME4 | 2 | 54,064,285 |
| 287 | ACYP2 | 2 | 54,189,467 | 288 | ACYP2 | 2 | 54,329,389 |
| 289 | ACYP2 | 2 | 54,329,418 | 290 | ACYP2 | 2 | 54,350,261 |
| 291 | CCDC85A | 2 | 56,266,849 | 292 | CCDC85A | 2 | 56,312,732 |
| 293 | CCDC85A | 2 | 56,344,184 | 294 | CCDC85A | 2 | 56,416,774 |
| 295 | CCDC85A | 2 | 56,493,023 | 296 | OTX1 | 2 | 63,151,654 |
| 297 | AAK1 | 2 | 69,639,692 | 298 | AAK1 | 2 | 69,768,980 |
| 299 | AAK1 | 2 | 69,834,530 | 300 | CTNNA2 | 2 | 79,631,620 |
| 301 | CTNNA2 | 2 | 79,635,253 | 302 | CTNNA2 | 2 | 79,644,485 |
| 303 | CTNNA2 | 2 | 79,648,869 | 304 | CTNNA2 | 2 | 79,728,810 |
| 305 | CTNNA2 | 2 | 80,246,403 | 306 | CTNNA2 | 2 | 80,346,411 |
| 307 | CTNNA2 | 2 | 80,348,223 | 308 | CTNNA2 | 2 | 80,493,928 |
| 309 | CTNNA2 | 2 | 80,498,999 | 310 | CTNNA2 | 2 | 80,652,425 |
| 311 | CTNNA2 | 2 | 80,657,667 | 312 | CTNNA2 | 2 | 80,663,934 |
| 313 | C2ORF46 | 2 | 8,262,682 | 314 | C2ORF46 | 2 | 8,361,310 |
| 315 | C2ORF46 | 2 | 8,384,366 | 316 | DDEF2 | 2 | 9,458,300 |
| 317 | INPP4A | 2 | 98,437,334 | 318 | INPP4A | 2 | 98,502,170 |
| 319 | ATP2B2 | 3 | 10,358,996 | 320 | PLCXD2 | 3 | 112,883,336 |
| 321 | PLCXD2 | 3 | 112,941,527 | 322 | PLCXD2 | 3 | 112,944,650 |
| 323 | PLCXD2 | 3 | 112,961,319 | 324 | PLCXD2 | 3 | 112,964,847 |
| 325 | CDGAP | 3 | 120,527,813 | 326 | STXBP5L | 3 | 122,476,483 |
| 327 | KALRN | 3 | 125,928,594 | 328 | CNTN6 | 3 | 1,268,504 |
| 329 | CNTN6 | 3 | 1,292,727 | 330 | CPNE4 | 3 | 132,865,247 |
| 331 | CPNE4 | 3 | 132,865,495 | 332 | CPNE4 | 3 | 132,885,425 |
| 333 | CPNE4 | 3 | 132,886,287 | 334 | CPNE4 | 3 | 132,889,696 |
| 335 | CPNE4 | 3 | 132,890,801 | 336 | CPNE4 | 3 | 132,907,690 |
| 337 | CPNE4 | 3 | 133,142,633 | 338 | CPNE4 | 3 | 133,145,979 |
| 339 | CNTN6 | 3 | 1,336,323 | 340 | RAB6B | 3 | 135,041,388 |
| 341 | CNTN6 | 3 | 1,350,581 | 342 | CNTN6 | 3 | 1,357,151 |
| 343 | CNTN6 | 3 | 1,357,358 | 344 | EPHBI | 3 | 136,133,973 |
| 345 | EPHB1 | 3 | 136,152,557 | 346 | EPHB1 | 3 | 136,153,214 |
| 347 | EPHB1 | 3 | 136,154,213 | 348 | EPHB1 | 3 | 136,154,975 |
| 349 | EPHB1 | 3 | 136,156,084 | 350 | EPHB1 | 3 | 136,158,491 |
| 351 | EPHB1 | 3 | 136,165,323 | 352 | EPHB1 | 3 | 136,172,644 |
| 353 | CNTN6 | 3 | 1,375,419 | 354 | CNTN6 | 3 | 1,399,850 |
| 355 | CLSTN2 | 3 | 141,648,210 | 356 | CLSTN2 | 3 | 141,660,969 |
| 357 | CLSTN2 | 3 | 141,661,175 | 358 | CLSTN2 | 3 | 141,662,920 |
| 359 | CLSTN2 | 3 | 141,663,200 | 360 | CLSTN2 | 3 | 141,764,774 |
| 361 | CLSTN2 | 3 | 141,774,103 | 362 | CLSTN2 | 3 | 141,775,226 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 363 | SPSB4 | 3 | 142,258,988 | 364 | SPSB4 | 3 | 142,287,637 |
| 365 | SLC6A6 | 3 | 14,421,894 | 366 | DAZL | 3 | 16,611,406 |
| 367 | DAZL | 3 | 16,611,469 | 368 | DAZL | 3 | 16,627,901 |
| 369 | SERPINI1 | 3 | 169,041,318 | 370 | SERPINI1 | 3 | 169,077,645 |
| 371 | SLC7A14 | 3 | 171,678,031 | 372 | SLC7A14 | 3 | 171,682,206 |
| 373 | PLD1 | 3 | 172,791,538 | 374 | PLD1 | 3 | 172,887,172 |
| 375 | PLD1 | 3 | 172,897,589 | 376 | PLD1 | 3 | 172,954,990 |
| 377 | PLD1 | 3 | 172,963,579 | 378 | PLD1 | 3 | 172,989,645 |
| 379 | PLD1 | 3 | 172,991,671 | 380 | NLGN1 | 3 | 175,384,416 |
| 381 | NLGN1 | 3 | 175,458,980 | 382 | NLGN1 | 3 | 175,493,649 |
| 383 | NLGN1 | 3 | 175,515,979 | 384 | NLGN1 | 3 | 175,541,245 |
| 385 | HTR3D | 3 | 185,232,425 | 386 | HTR3D | 3 | 185,236,739 |
| 387 | HTR3E | 3 | 185,313,087 | 388 | LEPREL1 | 3 | 191,236,401 |
| 389 | LEPREL1 | 3 | 191,237,107 | 390 | LEPREL1 | 3 | 191,261,577 |
| 391 | LEPREL1 | 3 | 191,280,803 | 392 | LEPREL1 | 3 | 191,356,831 |
| 393 | IL1RAP | 3 | 191,892,719 | 394 | IL1RAP | 3 | 191,914,687 |
| 395 | LRRC15 | 3 | 195,586,726 | 396 | CENTB2 | 3 | 196,483,019 |
| 397 | CENTB2 | 3 | 196,647,738 | 398 | UBXD7 | 3 | 197,608,675 |
| 399 | CNTN4 | 3 | 2,375,967 | 400 | RARB | 3 | 25,544,885 |
| 401 | RARB | 3 | 25,589,536 | 402 | RARB | 3 | 25,592,407 |
| 403 | RARB | 3 | 25,593,163 | 404 | CNTN4 | 3 | 2,734,283 |
| 405 | CNTN4 | 3 | 3,035,913 | 406 | CNTN4 | 3 | 3,073,041 |
| 407 | CLASP2 | 3 | 33,516,308 | 408 | CLASP2 | 3 | 33,516,362 |
| 409 | CLASP2 | 3 | 33,537,118 | 410 | CLASP2 | 3 | 33,668,798 |
| 411 | CLASP2 | 3 | 33,726,022 | 412 | ARPP-21 | 3 | 35,760,612 |
| 413 | STAC | 3 | 36,407,617 | 414 | ULK4 | 3 | 41,482,456 |
| 415 | ULK4 | 3 | 41,507,554 | 416 | ULK4 | 3 | 41,563,607 |
| 417 | ULK4 | 3 | 41,564,968 | 418 | ULK4 | 3 | 41,574,775 |
| 419 | ULK4 | 3 | 41,575,331 | 420 | ULK4 | 3 | 41,971,140 |
| 421 | ITPR1 | 3 | 4,729,125 | 422 | ITPR1 | 3 | 4,846,598 |
| 423 | SEMA3F | 3 | 50,180,966 | 424 | SEMA3F | 3 | 50,182,079 |
| 425 | SEMA3F | 3 | 50,199,229 | 426 | CACNA2D2 | 3 | 50,451,382 |
| 427 | CACNA2D3 | 3 | 54,127,859 | 428 | CACNA2D3 | 3 | 54,331,793 |
| 429 | ERC2 | 3 | 55,743,028 | 430 | ERC2 | 3 | 55,757,809 |
| 431 | ERC2 | 3 | 55,760,546 | 432 | ERC2 | 3 | 55,828,309 |
| 433 | ERC2 | 3 | 55,877,492 | 434 | ERC2 | 3 | 55,902,605 |
| 435 | ERC2 | 3 | 56,116,883 | 436 | ERC2 | 3 | 56,119,301 |
| 437 | ERC2 | 3 | 56,164,173 | 438 | ERC2 | 3 | 56,298,486 |
| 439 | ERC2 | 3 | 56,318,391 | 440 | ERC2 | 3 | 56,347,766 |
| 441 | ERC2 | 3 | 56,348,984 | 442 | ERC2 | 3 | 56,360,378 |
| 443 | ERC2 | 3 | 56,368,109 | 444 | ERC2 | 3 | 56,393,831 |
| 445 | ERC2 | 3 | 56,410,435 | 446 | ERC2 | 3 | 56,414,093 |
| 447 | ERC2 | 3 | 56,422,909 | 448 | ERC2 | 3 | 56,433,200 |
| 449 | ERC2 | 3 | 56,462,620 | 450 | ERC2 | 3 | 56,464,816 |
| 451 | ERC2 | 3 | 56,491,685 | 452 | ERC2 | 3 | 56,496,204 |
| 453 | BRC2 | 3 | 56,496,259 | 454 | FHIT | 3 | 59,814,275 |
| 455 | FHIT | 3 | 59,824,587 | 456 | FHIT | 3 | 60,462,353 |
| 457 | FHIT | 3 | 61,135,266 | 458 | FHIT | 3 | 61,137,444 |
| 459 | PTPRG | 3 | 61,709,002 | 460 | PTPRG | 3 | 61,709,579 |
| 461 | PTPRG | 3 | 61,723,402 | 462 | PTPRG | 3 | 61,753,808 |
| 463 | PTPRG | 3 | 62,036,852 | 464 | PTPRG | 3 | 62,219,484 |
| 465 | PTPRC | 3 | 62,219,610 | 466 | PTPRG | 3 | 62,256,476 |
| 467 | CADPS | 3 | 62,480,839 | 468 | CADPS | 3 | 62,487,886 |
| 469 | CADPS | 3 | 62,498,262 | 470 | CADPS | 3 | 62,503,301 |
| 471 | CADPS | 3 | 62,716,081 | 472 | CADPS | 3 | 62,748,900 |
| 473 | CADPS | 3 | 62,748,989 | 474 | CADPS | 3 | 62,777,879 |
| 475 | CADI'S | 3 | 62,786,626 | 476 | CADPS | 3 | 62,789,812 |
| 477 | CADPS | 3 | 62,801,974 | 478 | SVKPR | 3 | 63,493,103 |
| 479 | PRICKLE2 | 3 | 64,091,416 | 480 | PRICKLE2 | 3 | 64,176,516 |
| 481 | MAGI1 | 3 | 65,330,646 | 482 | MAGI1 | 3 | 65,337,837 |
| 483 | MAGI1 | 3 | 65,476,046 | 484 | MAGI1 | 3 | 65,576,717 |
| 485 | FAM19A1 | 3 | 68,409,920 | 486 | FAM19A1 | 3 | 68,470,682 |
| 487 | FOXP1 | 3 | 70,972,978 | 488 | FOXP1 | 3 | 71,021,299 |
| 489 | FOXP1 | 3 | 71,295,488 | 490 | GBE1 | 3 | 81,633,005 |
| 491 | GBE1 | 3 | 81,643,783 | 492 | GBE1 | 3 | 81,669,129 |
| 493 | GBE1 | 3 | 81,687,469 | 494 | GBE1 | 3 | 81,687,869 |
| 495 | GBE1 | 3 | 81,694,225 | 496 | GBE1 | 3 | 81,816,787 |
| 497 | GBE1 | 3 | 81,859,450 | 498 | GBE1 | 3 | 81,888,207 |
| 499 | GBE1 | 3 | 81,894,474 | 500 | HTR1F | 3 | 88,105,976 |
| 501 | EPHA6 | 3 | 97,967,793 | 502 | EPHA6 | 3 | 98,268,377 |
| 503 | EPHA6 | 3 | 98,270,901 | 504 | DKJC2 | 4 | 108,073,445 |
| SOS | DKK2 | 4 | 108,257,617 | 506 | PAPSS1 | 4 | 108,875,283 |
| 507 | COL25A1 | 4 | 109,954,162 | 508 | COL25A1 | 4 | 110,179,691 |
| 509 | COL25A1 | 4 | 110,189,985 | 510 | COL2SA1 | 4 | 110,198,274 |
| 511 | COL25A1 | 4 | 110,198,580 | 512 | ANK2 | 4 | 114,298,380 |
| 513 | ANK2 | 4 | 114,298,464 | 514 | ANK2 | 4 | 114,298,576 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 515 | ANK2 | 4 | 114,399,491 | 516 | ANK2 | 4 | 114,424,380 |
| 517 | ANK2 | 4 | 114,436,352 | 518 | ANK2 | 4 | 114,445,280 |
| 519 | CAMK2D | 4 | 114,723,041 | 520 | CAMK2D | 4 | 114,723,767 |
| 521 | NDST3 | 4 | 119,197,389 | 522 | NDST3 | 4 | 119,312,058 |
| 523 | PRSS12 | 4 | 119,462,492 | 524 | GPR103 | 4 | 122,518,528 |
| 525 | MAML3 | 4 | 140,868,325 | 526 | MAML3 | 4 | 140,870,180 |
| 527 | IL15 | 4 | 142,929,173 | 528 | INPP4B | 4 | 143,195,583 |
| 529 | INPP4B | 4 | 143,201,848 | 530 | INPP4B | 4 | 143,221,023 |
| 531 | INPP4B | 4 | 143,222,465 | 532 | INPP4B | 4 | 143,223,756 |
| 533 | INPP4B | 4 | 143,262,085 | 534 | INPP4B | 4 | 143,264,932 |
| 535 | INPP4B | 4 | 143,269,935 | 536 | INPP4B | 4 | 143,405,941 |
| 537 | INPP4B | 4 | 143,476,047 | 538 | POU4F2 | 4 | 147,768,753 |
| 539 | LDB2 | 4 | 16,200,696 | 540 | LDB2 | 4 | 16,208,501 |
| 541 | FSTL5 | 4 | 162,696,532 | 542 | FSTL5 | 4 | 162,744,370 |
| 543 | FSTL5 | 4 | 162,828,621 | 544 | FSTL5 | 4 | 162,852,707 |
| 545 | FSTL5 | 4 | 163,022,990 | 546 | FSTL5 | 4 | 163,038,911 |
| 547 | FSTL5 | 4 | 163,171,406 | 548 | FSTL5 | 4 | 163,275,058 |
| 549 | FSTL5 | 4 | 163,281,294 | 550 | FSTL5 | 4 | 163,316,581 |
| 551 | FSTL5 | 4 | 163,369,235 | 552 | LDB2 | 4 | 16,363,986 |
| 553 | LDB2 | 4 | 16,365,914 | 554 | LDB2 | 4 | 16,513,031 |
| 555 | LDB2 | 4 | 16,515,486 | 556 | LDB2 | 4 | 16,525,999 |
| 557 | TLL1 | 4 | 167,073,589 | 558 | PALLD | 4 | 169,684,483 |
| 559 | PALLD | 4 | 169,690,892 | 560 | PALLD | 4 | 169,693,682 |
| 561 | PALLD | 4 | 169,702,565 | 562 | PALLD | 4 | 169,713,776 |
| 563 | PALLD | 4 | 169,721,943 | 564 | PALLD | 4 | 169,831,259 |
| 565 | PALLD | 4 | 169,831,979 | 566 | PALLD | 4 | 169,854,703 |
| 567 | PALLD | 4 | 169,855,143 | 568 | PALLD | 4 | 169,866,028 |
| 569 | PALLD | 4 | 169,971,032 | 570 | ODZ3 | 4 | 183,473,721 |
| 571 | ODZ3 | 4 | 183,476,755 | 572 | ODZ3 | 4 | 183,478,510 |
| 573 | ODZ3 | 4 | 183,917,862 | 574 | ENPP6 | 4 | 185,269,255 |
| 575 | ENPP6 | 4 | 185,283,835 | 576 | ENPP6 | 4 | 185,287,394 |
| 577 | ENPP6 | 4 | 185,287,415 | 578 | ENPP6 | 4 | 185,300,448 |
| 579 | ENPP6 | 4 | 185,314,095 | 580 | CASP3 | 4 | 185,783,023 |
| 581 | CASP3 | 4 | 185,791,294 | 582 | SLIT2 | 4 | 19,872,156 |
| 583 | SLIT2 | 4 | 20,162,402 | 584 | SLIT2 | 4 | 20,172,206 |
| 585 | SLIT2 | 4 | 20,177,664 | 586 | SLIT2 | 4 | 20,194,981 |
| 587 | SLIT2 | 4 | 20,202,844 | 588 | PCDH7 | 4 | 30,441,417 |
| 589 | KIAA1239 | 4 | 36,916,631 | 590 | KIAA1239 | 4 | 37,005,415 |
| 591 | KIAA1239 | 4 | 37,133,996 | 592 | KIAA1239 | 4 | 37,134,494 |
| 593 | KIAA1239 | 4 | 37,157,082 | 594 | TBC1D1 | 4 | 37,815,251 |
| 595 | UBE2K | 4 | 39,386,342 | 596 | UBE2K | 4 | 39,464,805 |
| 597 | UBE2K | 4 | 39,494,511 | 598 | LIMCH1 | 4 | 41,194,791 |
| 599 | LIMCH1 | 4 | 41,213,350 | 600 | LIMCH1 | 4 | 41,213,408 |
| 601 | LIMCH1 | 4 | 41,215,951 | 602 | LIMCH1 | 4 | 41,221,506 |
| 603 | LIMCH1 | 4 | 41,221,779 | 604 | LIMCH1 | 4 | 41,223,320 |
| 605 | LIMCH1 | 4 | 41,308,688 | 606 | LIMCH1 | 4 | 41,351,387 |
| 607 | LIMCH1 | 4 | 41,354,243 | 608 | LIMCH1 | 4 | 41,429,386 |
| 609 | LOC389207 | 4 | 42,634,794 | 610 | NPFFR2 | 4 | 73,115,321 |
| 611 | NPFFR2 | 4 | 73,119,485 | 612 | NPFFR2 | 4 | 73,122,182 |
| 613 | NPFFR2 | 4 | 73,163,818 | 614 | NPFFR2 | 4 | 73,236,822 |
| 615 | NPFFR2 | 4 | 73,291,379 | 616 | SCARB2 | 4 | 77,296,499 |
| 617 | SHROOM3 | 4 | 77,855,667 | 618 | SHROOM3 | 4 | 77,879,755 |
| 619 | SCD5 | 4 | 83,785,141 | 620 | SCD5 | 4 | 83,788,761 |
| 621 | SCD5 | 4 | 83,794,856 | 622 | SCD5 | 4 | 83,794,931 |
| 623 | SCD5 | 4 | 83,845,049 | 624 | HERC3 | 4 | 89,741,644 |
| 625 | FAM13A1 | 4 | 89,915,913 | 626 | FAM13A1 | 4 | 89,950,302 |
| 627 | FAM13A1 | 4 | 89,950,932 | 628 | SLC2A9 | 4 | 9,423,554 |
| 629 | PDLIM5 | 4 | 95,558,356 | 630 | SLC2A9 | 4 | 9,565,177 |
| 631 | PDLIM5 | 4 | 95,660,615 | 632 | PDLIM5 | 4 | 95,701,398 |
| 633 | PDLIM5 | 4 | 95,701,843 | 634 | PDLIM5 | 4 | 95,706,737 |
| 635 | PDLIM5 | 4 | 95,747,196 | 636 | PDLIM5 | 4 | 95,793,146 |
| 637 | SLC2A9 | 4 | 9,605,988 | 638 | SLC2A9 | 4 | 9,606,401 |
| 639 | SLC2A9 | 4 | 9,606,899 | 640 | SLC2A9 | 4 | 9,616,373 |
| 641 | SLC2A9 | 4 | 9,633,401 | 642 | SLC2A9 | 4 | 9,636,640 |
| 643 | SLC2A9 | 4 | 9,665,474 | 644 | FBXL17 | 5 | 107,441,485 |
| 645 | FBXL17 | 5 | 107,546,460 | 646 | FBXL17 | 5 | 107,612,678 |
| 647 | FBXL17 | 5 | 107,624,474 | 648 | FBXL17 | 5 | 107,704,154 |
| 649 | FBXL17 | 5 | 107,773,275 | 650 | FBXL17 | 5 | 107,810,930 |
| 651 | FBXL17 | 5 | 107,812,906 | 652 | PJA2 | 5 | 108,787,364 |
| 653 | PJA2 | 5 | 108,817,419 | 654 | KCNN2 | 5 | 113,739,288 |
| 655 | KCNN2 | 5 | 113,751,518 | 656 | KCNN2 | 5 | 113,763,996 |
| 657 | KCNN2 | 5 | 113,784,704 | 658 | KCNN2 | 5 | 113,790,709 |
| 659 | KCNN2 | 5 | 113,858,701 | 660 | SEMA6A | 5 | 115,914,844 |
| 661 | HSD17B4 | 5 | 118,817,237 | 662 | HSD17B4 | 5 | 118,927,674 |
| 663 | SNCAIP | 5 | 121,678,639 | 664 | SNCAIP | 5 | 121,699,768 |
| 665 | SNCAIP | 5 | 121,757,816 | 666 | SNCAIP | 5 | 121,768,808 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 667 | SNCAIP | 5 | 121,796,570 | 668 | SNX2 | 5 | 122,116,630 |
| 669 | SNX2 | 5 | 122,174,518 | 670 | SNX2 | 5 | 122,194,062 |
| 671 | SNX2 | 5 | 122,201,930 | 672 | SNX24 | 5 | 122,255,495 |
| 673 | SNX24 | 5 | 122,273,273 | 674 | SNX24 | 5 | 122,283,900 |
| 675 | SNX24 | 5 | 122,363,934 | 676 | ADAMTS19 | 5 | 129,005,631 |
| 677 | VDAC1 | 5 | 133,405,061 | 678 | TRPC7 | 5 | 135,649,997 |
| 679 | TRPC7 | 5 | 135,695,682 | 680 | TRPC7 | 5 | 135,705,746 |
| 681 | TRPC7 | 5 | 135,712,132 | 682 | TRPC7 | 5 | 135,724,949 |
| 683 | DNAH5 | 5 | 13,795,858 | 684 | DNAH5 | 5 | 13,822,974 |
| 685 | DNAH5 | 5 | 13,832,743 | 686 | DNAH5 | 5 | 13,841,886 |
| 687 | DNAH5 | 5 | 13,842,420 | 688 | DNAH5 | 5 | 13,947,894 |
| 689 | DNAH5 | 5 | 13,953,345 | 690 | DNAH5 | 5 | 13,955,220 |
| 691 | DNAH5 | 5 | 13,957,400 | 692 | DNAH5 | 5 | 14,034,968 |
| 693 | GRIA1 | 5 | 152,893,595 | 694 | GRIA1 | 5 | 152,916,373 |
| 695 | GRIA1 | 5 | 152,931,785 | 696 | GRIAI | 5 | 152,952,893 |
| 697 | GRIA1 | 5 | 152,956,518 | 698 | GRIAI | 5 | 153,075,197 |
| 699 | GRIA1 | 5 | 153,100,457 | 700 | GRIA1 | 5 | 153,112,499 |
| 701 | GRIA1 | 5 | 153,127,393 | 702 | GRIAI | 5 | 153,150,567 |
| 703 | GRIA1 | 5 | 153,159,007 | 704 | ODZ2 | 5 | 167,085,900 |
| 705 | MYO10 | 5 | 16,711,495 | 706 | MYO10 | 5 | 16,711,524 |
| 707 | ODZ2 | 5 | 167,162,881 | 708 | ODZ2 | 5 | 167,191,250 |
| 709 | ODZ2 | 5 | 167,391,524 | 710 | ODZ2 | 5 | 167,556,686 |
| 711 | ODZ2 | 5 | 167,610,277 | 712 | ODZ2 | 5 | 167,634,619 |
| 713 | MYO10 | 5 | 16,822,273 | 714 | MYO10 | 5 | 16,838,077 |
| 715 | BASP1 | 5 | 17,266,319 | 716 | PLEKHG4B | 5 | 208,367 |
| 717 | PLEKHG4B | 5 | 208,629 | 718 | PLEKHG4B | 5 | 208,831 |
| 719 | PLEKHG4B | 5 | 210,750 | 720 | PLEKHG4B | 5 | 226,200 |
| 721 | CDH10 | 5 | 24,500,153 | 722 | CDH10 | 5 | 24,533,855 |
| 723 | SLC45A2 | 5 | 34,019,127 | 724 | SLC45A2 | 5 | 34,025,275 |
| 725 | C1QTNF3 | 5 | 34,071,366 | 726 | C1QTNF3 | 5 | 34,074,611 |
| 727 | C1QTNF3 | 5 | 34,083,721 | 728 | C1QTNF3 | 5 | 34,087,314 |
| 729 | SLC1A3 | 5 | 36,738,812 | 730 | EGFLAM | 5 | 38,269,319 |
| 731 | EGFLAM | 5 | 38,296,060 | 732 | EGFLAM | 5 | 38,320,906 |
| 733 | AHRR | 5 | 431,413 | 734 | AHRR | 5 | 465,694 |
| 735 | AHRR | 5 | 508,696 | 736 | EXOC3 | 5 | 517,153 |
| 737 | ITGA1 | 5 | 52,155,113 | 738 | ITGA1 | 5 | 52,265,502 |
| 739 | ITGA1 | 5 | 52,285,233 | 740 | ITGA2 | 5 | 52,402,662 |
| 741 | ITGA2 | 5 | 52,425,212 | 742 | PDE4D | 5 | 58,432,005 |
| 743 | PDE4D | 5 | 58,744,184 | 744 | ELOVL7 | 5 | 60,101,698 |
| 745 | ELOVL7 | 5 | 60,132,254 | 746 | ELOVL7 | 5 | 60,152,637 |
| 747 | ELOVL7 | 5 | 60,171,719 | 748 | ELOVL7 | 5 | 60,201,944 |
| 749 | TNPOI | 5 | 72,174,208 | 750 | TNPOI | 5 | 72,182,236 |
| 751 | TNPO1 | 5 | 72,217,160 | 752 | FCHO2 | 5 | 72,384,028 |
| 753 | CMYA5 | 5 | 79,029,508 | 754 | CMYA5 | 5 | 79,058,467 |
| 755 | CMYA5 | 5 | 79,070,418 | 756 | THBS4 | 5 | 79,375,707 |
| 757 | THBS4 | 5 | 79,376,918 | 758 | THBS4 | 5 | 79,397,021 |
| 759 | VCAN | 5 | 82,818,286 | 760 | VCAN | 5 | 82,870,055 |
| 761 | MEF2C | 5 | 88,161,609 | 762 | MEF2C | 5 | 88,219,759 |
| 763 | GPR98 | 5 | 89,976,245 | 764 | GPR98 | 5 | 90,052,627 |
| 765 | GPR98 | 5 | 90,109,033 | 766 | GPR98 | 5 | 90,187,345 |
| 767 | GPR98 | 5 | 90,203,767 | 768 | SEMA5A | 5 | 9,066,544 |
| 769 | SEMA5A | 5 | 9,107,741 | 770 | SEMA5A | 5 | 9,474,794 |
| 771 | SEMA5A | 5 | 9,477,130 | 772 | SEMA5A | 5 | 9,487,606 |
| 773 | SEMA5A | 5 | 9,495,994 | 774 | CAST | 5 | 96,088,713 |
| 775 | SLC22A16 | 6 | 110,857,358 | 776 | SLC22A16 | 6 | 110,914,475 |
| 777 | HS3ST5 | 6 | 114,509,285 | 778 | TRDN | 6 | 123,728,987 |
| 779 | TRDN | 6 | 123,738,465 | 780 | TRDN | 6 | 123,743,637 |
| 781 | TRDN | 6 | 123,749,431 | 782 | TRDN | 6 | 123,753,816 |
| 783 | TRDN | 6 | 123,766,181 | 784 | TRDN | 6 | 123,791,627 |
| 785 | TRDN | 6 | 123,871,263 | 786 | TRDN | 6 | 123,877,575 |
| 787 | TRDN | 6 | 123,903,977 | 788 | TRDN | 6 | 123,931,045 |
| 789 | TRDN | 6 | 124,006,657 | 790 | TRDN | 6 | 124,017,012 |
| 791 | NKAIN2 | 6 | 124,481,807 | 792 | NKAIN2 | 6 | 124,747,202 |
| 793 | NKAIN2 | 6 | 124,828,559 | 794 | NKAIN2 | 6 | 124,867,074 |
| 795 | NKAIN2 | 6 | 124,953,233 | 796 | NKAIN2 | 6 | 124,962,839 |
| 797 | NKAIN2 | 6 | 124,982,795 | 798 | NKAIN2 | 6 | 124,986,819 |
| 799 | NKAIN2 | 6 | 124,987,301 | 800 | NKAIN2 | 6 | 125,020,491 |
| 801 | PHACTR1 | 6 | 12,858,919 | 802 | PHACTR1 | 6 | 13,276,521 |
| 803 | PHACTR1 | 6 | 13,286,048 | 804 | PHACTR1 | 6 | 13,297,254 |
| 805 | EYA4 | 6 | 133,636,045 | 806 | EYA4 | 6 | 133,643,088 |
| 807 | EYA4 | 6 | 133,651,991 | 808 | EYA4 | 6 | 133,668,941 |
| 809 | PDE7B | 6 | 136,218,421 | 810 | PDE7B | 6 | 136,244,527 |
| 811 | PDE7B | 6 | 136,375,641 | 812 | PLAGL1 | 6 | 144,319,261 |
| 813 | PLAGL1 | 6 | 144,354,821 | 814 | PLAGL1 | 6 | 144,355,380 |
| 815 | UTRN | 6 | 144,651,202 | 816 | UTRN | 6 | 144,657,997 |
| 817 | UTRN | 6 | 145,021,020 | 818 | SYNE1 | 6 | 152,505,595 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 819 | SYNE1 | 6 | 152,511,829 | 820 | JARID2 | 6 | 15,608,978 |
| 821 | SLC22A3 | 6 | 160,771,756 | 822 | PARK2 | 6 | 161,938,126 |
| 823 | PARK2 | 6 | 161,960,395 | 824 | PARK2 | 6 | 162,001,753 |
| 825 | PARK2 | 6 | 162,026,087 | 826 | PARK2 | 6 | 162,201,362 |
| 827 | PARK2 | 6 | 162,204,134 | 828 | PARK2 | 6 | 162,725,125 |
| 829 | PARK2 | 6 | 162,877,565 | 830 | PARK2 | 6 | 162,891,538 |
| 831 | PARK2 | 6 | 162,899,137 | 832 | PARK2 | 6 | 162,914,629 |
| 833 | PARK2 | 6 | 162,959,624 | 834 | PACRG | 6 | 163,515,155 |
| 835 | PACRG | 6 | 163,523,252 | 836 | PDE10A | 6 | 165,674,966 |
| 837 | PDE10A | 6 | 165,835,911 | 838 | PDE10A | 6 | 165,868,541 |
| 839 | ATXN1 | 6 | 16,595,385 | 840 | ATXN1 | 6 | 16,762,002 |
| 841 | ATXN1 | 6 | 16,767,074 | 842 | ATXN1 | 6 | 16,799,821 |
| 843 | SLC17A4 | 6 | 25,852,810 | 844 | SLC17A4 | 6 | 25,887,371 |
| 845 | SLC17A1 | 6 | 25,909,950 | 846 | SLC17A4 | 6 | 25,917,888 |
| 847 | SLC17A1 | 6 | 25,950,182 | 848 | SLC17A3 | 6 | 25,972,877 |
| 849 | SLC17A2 | 6 | 26,042,503 | 850 | BTN3A1 | 6 | 26,506,534 |
| 851 | BTN3A1 | 6 | 26,513,969 | 852 | BTN3A1 | 6 | 26,525,105 |
| 853 | BTN3A1 | 6 | 26,528,031 | 854 | BTN2A3 | 6 | 26,534,466 |
| 855 | BTN3A3 | 6 | 26,553,839 | 856 | BTNL2 | 6 | 32,462,406 |
| 857 | BTNL2 | 6 | 32,463,841 | 858 | BTNL2 | 6 | 32,471,794 |
| 859 | SLC22A23 | 6 | 3,395,265 | 860 | LRFN2 | 6 | 40,526,934 |
| 861 | LRFN2 | 6 | 40,535,717 | 862 | LRFN2 | 6 | 40,585,166 |
| 863 | LRFN2 | 6 | 40,598,884 | 864 | PPP2R5D | 6 | 43,095,976 |
| 865 | KLC4 | 6 | 43,139,233 | 866 | ELOVL5 | 6 | 53,298,209 |
| 867 | ELOVL5 | 6 | 53,350,763 | 868 | ELOVL5 | 6 | 53,372,444 |
| 869 | RIMS1 | 6 | 72,772,376 | 870 | RIMS1 | 6 | 72,784,876 |
| 871 | RIMS1 | 6 | 72,860,627 | 872 | RIMS1 | 6 | 72,866,707 |
| 873 | RIMS1 | 6 | 72,939,135 | 874 | RIMS1 | 6 | 72,963,198 |
| 875 | RIMS1 | 6 | 72,974,869 | 876 | RIMS1 | 6 | 72,977,664 |
| 877 | RIMS1 | 6 | 72,982,413 | 878 | RIMS1 | 6 | 73,031,069 |
| 879 | HTR1B | 6 | 78,228,979 | 880 | KLHL32 | 6 | 97,480,306 |
| 881 | KLHL32 | 6 | 97,589,639 | 882 | KLHL32 | 6 | 97,595,870 |
| 883 | KLHL32 | 6 | 97,673,659 | 884 | CUX1 | 7 | 100,785,884 |
| 885 | CUX1 | 7 | 101,306,594 | 886 | CUX1 | 7 | 101,694,544 |
| 887 | CADPS2 | 7 | 122,055,480 | 888 | CADPS2 | 7 | 122,066,038 |
| 889 | CADPS2 | 7 | 122,074,175 | 890 | CADPS2 | 7 | 122,090,557 |
| 891 | CADPS2 | 7 | 122,093,518 | 892 | CADPS2 | 7 | 122,329,881 |
| 893 | GRM8 | 7 | 125,808,541 | 894 | GRM8 | 7 | 125,837,771 |
| 895 | GRM8 | 7 | 125,879,584 | 896 | GRM8 | 7 | 125,888,427 |
| 897 | GAMS | 7 | 125,912,289 | 898 | GRM8 | 7 | 126,156,034 |
| 899 | GRM8 | 7 | 126,225,935 | 900 | GRM8 | 7 | 126,234,800 |
| 901 | GRM8 | 7 | 126,299,256 | 902 | GRM8 | 7 | 126,521,407 |
| 903 | GRM8 | 7 | 126,552,824 | 904 | GRM8 | 7 | 126,699,931 |
| 905 | EXOC4 | 7 | 132,456,559 | 906 | EXOC4 | 7 | 132,754,129 |
| 907 | EXOC4 | 7 | 132,789,020 | 908 | EXOC4 | 7 | 132,895,544 |
| 909 | EXOC4 | 7 | 132,917,865 | 910 | EXOC4 | 7 | 132,938,673 |
| 911 | EXOC4 | 7 | 133,236,629 | 912 | EXOC4 | 7 | 133,265,250 |
| 913 | EXOC4 | 7 | 133,352,637 | 914 | EXOC4 | 7 | 133,378,037 |
| 915 | DGKI | 7 | 136,730,489 | 916 | DGKI | 7 | 136,735,790 |
| 917 | CREB3L2 | 7 | 137,269,815 | 918 | CREB3L2 | 7 | 137,275,099 |
| 919 | CREB3L2 | 7 | 137,278,186 | 920 | TBXAS1 | 7 | 139,135,304 |
| 921 | TBXAS1 | 7 | 139,175,131 | 922 | TBXAS1 | 7 | 139,184,991 |
| 923 | TBXAS1 | 7 | 139,311,144 | 924 | ETV1 | 7 | 13,945,334 |
| 925 | CNTNAP2 | 7 | 145,430,948 | 926 | CNTNAP2 | 7 | 145,431,076 |
| 927 | CNTNAP2 | 7 | 145,688,576 | 928 | CNTNAP2 | 7 | 145,710,838 |
| 929 | CNTNAP2 | 7 | 145,724,542 | 930 | CNTNAP2 | 7 | 145,906,353 |
| 931 | CNTNAP2 | 7 | 146,782,515 | 932 | CNTNAP2 | 7 | 146,786,412 |
| 933 | CNTNAP2 | 7 | 146,788,354 | 934 | CNTNAP2 | 7 | 146,800,067 |
| 935 | CNTNAP2 | 7 | 147,069,599 | 936 | CNTNAP2 | 7 | 147,102,055 |
| 937 | CNTNAP2 | 7 | 147,136,686 | 938 | CNTNAP2 | 7 | 147,669,284 |
| 939 | CNTNAP2 | 7 | 147,712,266 | 940 | PTPRN2 | 7 | 157,024,663 |
| 941 | PTPRN2 | 7 | 157,175,770 | 942 | PTPRN2 | 7 | 157,662,662 |
| 943 | PTPRN2 | 7 | 157,973,350 | 944 | STK31 | 7 | 23,760,407 |
| 945 | STK31 | 7 | 23,799,768 | 946 | SKAP2 | 7 | 26,795,178 |
| 947 | SKAP2 | 7 | 26,827,158 | 948 | SKAP2 | 7 | 26,827,213 |
| 949 | SKAP2 | 7 | 26,830,698 | 950 | SKAP2 | 7 | 26,858,965 |
| 951 | CREB5 | 7 | 28,286,559 | 952 | CREB5 | 7 | 28,798,822 |
| 953 | CREB5 | 7 | 28,812,569 | 954 | CREB5 | 7 | 28,818,987 |
| 955 | CREB5 | 7 | 28,870,041 | 956 | CREB5 | 7 | 28,906,935 |
| 957 | CARD11 | 7 | 2,928,819 | 958 | CHN2 | 7 | 29,483,175 |
| 959 | CHN2 | 7 | 29,486,454 | 960 | CHN2 | 7 | 29,560,895 |
| 961 | SCRN1 | 7 | 29,926,987 | 962 | SCRNI | 7 | 29,929,459 |
| 963 | SCRN1 | 7 | 30,052,432 | 964 | ZNRF2 | 7 | 30,379,551 |
| 965 | CRI R2 | 7 | 30,676,000 | 966 | CRHR2 | 7 | 30,775,386 |
| 967 | FLJ22374 | 7 | 30,787,631 | 968 | FLJ22374 | 7 | 30,803,801 |
| 969 | FLJ22374 | 7 | 30,813,272 | 970 | FLJ22374 | 7 | 30,832,290 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 971 | FLJ22374 | 7 | 30,842,957 | 972 | FLJ22374 | 7 | 30,843,167 |
| 973 | PDE1C | 7 | 31,841,400 | 974 | PDE1C | 7 | 32,064,508 |
| 975 | PDE1C | 7 | 32,141,959 | 976 | BMPER | 7 | 33,942,093 |
| 977 | BMPER | 7 | 33,994,557 | 978 | BMPER | 7 | 34,050,872 |
| 979 | BMPER | 7 | 34,056,348 | 980 | BMPER | 7 | 34,077,080 |
| 981 | BMPER | 7 | 34,077,746 | 982 | BMPER | 7 | 34,107,862 |
| 983 | VPS41 | 7 | 38,759,185 | 984 | VPS41 | 7 | 38,859,847 |
| 985 | VPS41 | 7 | 38,882,602 | 986 | VPS41 | 7 | 38,936,691 |
| 987 | CDC2L5 | 7 | 40,056,457 | 988 | CDC2L5 | 7 | 40,083,623 |
| 989 | CDC2L5 | 7 | 40,124,213 | 990 | CDC2L5 | 7 | 40,125,052 |
| 991 | SDK1 | 7 | 4,140,139 | 992 | SDK1 | 7 | 4,230,185 |
| 993 | SDKI | 7 | 4,272,360 | 994 | IGFBP3 | 7 | 45,916,971 |
| 995 | IGFBP3 | 7 | 45,990,559 | 996 | IGFBP3 | 7 | 46,061,993 |
| 997 | ABCA13 | 7 | 48,380,796 | 998 | ABCA13 | 7 | 48,399,261 |
| 999 | ABCA13 | 7 | 48,425,013 | 1000 | ABCA13 | 7 | 48,425,630 |
| 1001 | ABCA13 | 7 | 48,656,578 | 1002 | ABCA13 | 7 | 48,681,043 |
| 1003 | GRB10 | 7 | 50,707,082 | 1004 | GRB10 | 7 | 50,727,714 |
| 1005 | WBSCR17 | 7 | 69,982,663 | 1006 | WBSCR17 | 7 | 70,020,032 |
| 1007 | WBSCRI7 | 7 | 70,024,662 | 1008 | WBSCR17 | 7 | 70,327,601 |
| 1009 | WBSCRI7 | 7 | 70,328,803 | 1010 | WBSCR17 | 7 | 70,508,901 |
| 1011 | LIMK1 | 7 | 73,155,050 | 1012 | LIMK1 | 7 | 73,189,576 |
| 1013 | LIMK1 | 7 | 73,201,992 | 1014 | GTF2IRD1 | 7 | 73,552,324 |
| 1015 | HIP1 | 7 | 74,641,558 | 1016 | HIP1 | 7 | 75,137,795 |
| 1017 | HIP1 | 7 | 75,149,973 | 1018 | HIP1 | 7 | 75,189,895 |
| 1019 | MAGI2 | 7 | 77,497,177 | 1020 | MAGI2 | 7 | 77,707,944 |
| 1021 | MA012 | 7 | 78,081,016 | 1022 | MAGI2 | 7 | 78,087,129 |
| 1023 | MAGI2 | 7 | 78,091,049 | 1024 | MAGI2 | 7 | 78,331,358 |
| 1025 | MAGI2 | 7 | 78,639,527 | 1026 | MAGI2 | 7 | 78,753,565 |
| 1027 | MAGI2 | 7 | 78,779,395 | 1028 | MAGI2 | 7 | 78,817,962 |
| 1029 | MAGI2 | 7 | 78,865,894 | 1030 | MAGI2 | 7 | 78,873,419 |
| 1031 | MAGI2 | 7 | 78,902,124 | 1032 | CACNA2D1 | 7 | 81,000,419 |
| 1033 | CACNA2D1 | 7 | 81,501,211 | 1034 | CACNA2D1 | 7 | 81,551,628 |
| 1035 | PCLO | 7 | 81,734,489 | 1036 | CACNA2D1 | 7 | 81,827,271 |
| 1037 | CACNA2D1 | 7 | 81,829,947 | 1038 | CACNA2D1 | 7 | 81,841,829 |
| 1039 | CACNA2D1 | 7 | 81,844,366 | 1040 | CACNA2D1 | 7 | 81,846,503 |
| 1041 | PCLO | 7 | 82,252,869 | 1042 | PCLO | 7 | 82,287,971 |
| 1043 | PCLO | 7 | 82,291,644 | 1044 | PCLO | 7 | 82,292,608 |
| 1045 | PCLO | 7 | 82,317,658 | 1046 | PCLO | 7 | 82,341,345 |
| 1047 | PCLO | 7 | 82,341,378 | 1048 | PCLO | 7 | 82,358,102 |
| 1049 | PCLO | 7 | 82,391,885 | 1050 | PCLO | 7 | 82,562,475 |
| 1051 | PCLO | 7 | 82,567,345 | 1052 | PCLO | 7 | 82,573,554 |
| 1053 | PCLO | 7 | 82,573,594 | 1054 | PCLO | 7 | 82,636,908 |
| 1055 | PCLO | 7 | 82,659,120 | 1056 | SEMA3E | 7 | 82,895,964 |
| 1057 | SEMA3E | 7 | 82,901,024 | 1058 | SEMA3A | 7 | 82,965,762 |
| 1059 | SEMA3E | 7 | 83,047,248 | 1060 | SEMA3E | 7 | 83,061,152 |
| 1061 | SEMA3E | 7 | 83,125,543 | 1062 | SEMA3A | 7 | 83,451,819 |
| 1063 | SEMA3A | 7 | 83,559,228 | 1064 | SEMA3A | 7 | 83,559,858 |
| 1065 | SEMA3A | 7 | 83,564,904 | 1066 | SEMA3A | 7 | 83,565,919 |
| 1067 | SEMA3A | 7 | 83,568,098 | 1068 | SEMA3A | 7 | 83,571,382 |
| 1069 | SEMA3A | 7 | 83,572,529 | 1070 | SEMA3A | 7 | 83,573,829 |
| 1071 | NXPH1 | 7 | 8,662,332 | 1072 | ABCB4 | 7 | 86,868,839 |
| 1073 | ABCB4 | 7 | 86,883,520 | 1074 | ABCB4 | 7 | 86,897,339 |
| 1075 | ADAM22 | 7 | 87,086,253 | 1076 | ADAM22 | 7 | 87,441,679 |
| 1077 | ADAM22 | 7 | 87,471,187 | 1078 | ADAM22 | 7 | 87,471,440 |
| 1079 | ADAM22 | 7 | 87,554,236 | 1080 | ADAM22 | 7 | 87,557,024 |
| 1081 | ADAM22 | 7 | 87,579,450 | 1082 | ADAM22 | 7 | 87,606,110 |
| 1083 | ADAM22 | 7 | 87,613,210 | 1084 | ADAM22 | 7 | 87,632,643 |
| 1085 | ADAM22 | 7 | 87,634,202 | 1086 | NXPH1 | 7 | 8,780,133 |
| 1087 | PPP1R9A | 7 | 94,747,598 | 1088 | PPP1R9A | 7 | 94,772,391 |
| 1089 | PON1 | 7 | 94,776,112 | 1090 | PON1 | 7 | 94,776,193 |
| 1091 | PON1 | 7 | 94,784,507 | 1092 | DYNC1I1 | 7 | 95,385,967 |
| 1093 | DYNC1I1 | 7 | 95,451,958 | 1094 | GRHL2 | 8 | 102,577,101 |
| 1095 | GRHL2 | 8 | 102,580,894 | 1096 | GRHL2 | 8 | 102,718,857 |
| 1097 | GRHL2 | 8 | 102,740,588 | 1098 | NCALD | 8 | 102,769,504 |
| 1099 | NCALD | 8 | 102,769,812 | 1100 | NCALD | 8 | 102,777,547 |
| 1101 | NCALD | 8 | 102,812,988 | 1102 | ZFPM2 | 8 | 106,505,157 |
| 1103 | ZFPM2 | 8 | 106,521,287 | 1104 | ZFPM2 | 8 | 106,530,047 |
| 1105 | ZFPM2 | 8 | 106,567,598 | 1106 | ZFPM2 | 8 | 106,614,970 |
| 1107 | ZFPM2 | 8 | 106,794,185 | 1108 | ZFPM2 | 8 | 106,803,045 |
| 1109 | ZFPM2 | 8 | 106,828,892 | 1110 | ZFPM2 | 8 | 106,841,629 |
| 1111 | CSMD3 | 8 | 113,479,682 | 1112 | CSMD3 | 8 | 113,554,821 |
| 1113 | CSMD3 | 8 | 113,568,517 | 1114 | CSMD3 | 8 | 113,570,484 |
| 1115 | CSMD3 | 8 | 114,319,937 | 1116 | CSMD3 | 8 | 114,432,523 |
| 1117 | CSMD3 | 8 | 114,441,419 | 1118 | CSMD3 | 8 | 114,475,512 |
| 1119 | SAMD12 | 8 | 119,514,024 | 1120 | SAMD12 | 8 | 119,530,374 |
| 1121 | SAMD12 | 8 | 119,532,252 | 1122 | SAMD12 | 8 | 119,536,976 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 1123 | SAMD12 | 8 | 119,671,788 | 1124 | FBXO32 | 8 | 124,567,915 |
| 1125 | FBXO32 | 8 | 124,583,159 | 1126 | FER1L6 | 8 | 124,996,892 |
| 1127 | FER1L6 | 8 | 125,011,048 | 1128 | FER1L6 | 8 | 125,014,271 |
| 1129 | FER1L6 | 8 | 125,014,506 | 1130 | FER1L6 | 8 | 125,020,334 |
| 1131 | FER1L6 | 8 | 125,032,627 | 1132 | FER1L6 | 8 | 125,053,616 |
| 1133 | FER1L6 | 8 | 125,102,576 | 1134 | FER1L6 | 8 | 125,104,714 |
| 1135 | FER1L6 | 8 | 125,108,933 | 1136 | FER1L6 | 8 | 125,218,759 |
| 1137 | MTSS1 | 8 | 125,649,171 | 1138 | MTSS1 | 8 | 125,651,280 |
| 1139 | DLC1 | 8 | 13,014,125 | 1140 | DDEF1 | 8 | 131,407,018 |
| 1141 | ADCY8 | 8 | 131,972,316 | 1142 | ADCY8 | 8 | 131,983,404 |
| 1143 | ADCY8 | 8 | 131,985,500 | 1144 | ADCY8 | 8 | 131,997,583 |
| 1145 | KCNQ3 | 8 | 133,208,937 | 1146 | KCNQ3 | 8 | 133,473,613 |
| 1147 | ST3GAL1 | 8 | 134,609,061 | 1148 | ST3GAL1 | 8 | 134,610,724 |
| 1149 | ST3GAL1 | 8 | 134,664,388 | 1150 | COL22A1 | 8 | 139,668,834 |
| 1151 | COL22A1 | 8 | 139,892,385 | 1152 | COL22A1 | 8 | 139,901,545 |
| 1153 | SGCZ | 8 | 14,059,709 | 1154 | SGCZ | 8 | 14,594,583 |
| 1155 | SGCZ | 8 | 14,876,643 | 1156 | SGCZ | 8 | 14,898,152 |
| 1157 | SLC7A2 | 8 | 17,431,231 | 1158 | SLC7A2 | 8 | 17,431,383 |
| 1159 | SLC7A2 | 8 | 17,480,455 | 1160 | PSD3 | 8 | 18,708,574 |
| 1161 | PSD3 | 8 | 18,709,420 | 1162 | PSD3 | 8 | 18,732,409 |
| 1163 | PSD3 | 8 | 18,737,733 | 1164 | PSD3 | 8 | 18,749,712 |
| 1165 | PSD3 | 8 | 18,757,428 | 1166 | PSD3 | 8 | 18,765,584 |
| 1167 | PSD3 | 8 | 18,773,018 | 1168 | PSD3 | 8 | 18,819,182 |
| 1169 | PSD3 | 8 | 18,953,685 | 1170 | ATP6V1B2 | 8 | 20,135,799 |
| 1171 | GFRA2 | 8 | 21,616,512 | 1172 | PEBP4 | 8 | 22,632,507 |
| 1173 | ENTPD4 | 8 | 23,353,499 | 1174 | SLC25A37 | 8 | 23,453,211 |
| 1175 | SLC25A37 | 8 | 23,471,600 | 1176 | CSMD1 | 8 | 2,849,233 |
| 1177 | CSMD1 | 8 | 2,864,416 | 1178 | CSMD1 | 8 | 2,958,438 |
| 1179 | CSMD1 | 8 | 3,206,762 | 1180 | CSMD1 | 8 | 3,209,023 |
| 1181 | CSMD1 | 8 | 3,211,642 | 1182 | CSMD1 | 8 | 3,216,613 |
| 1183 | CSMD1 | 8 | 3,245,103 | 1184 | CSMD1 | 8 | 3,275,090 |
| 1185 | CSMD1 | 8 | 3,292,328 | 1186 | UNC5D | 8 | 35,516,694 |
| 1187 | UNC5D | 8 | 35,586,829 | 1188 | SFRP1 | 8 | 41,244,318 |
| 1189 | SFRP1 | 8 | 41,247,567 | 1190 | SFRP1 | 8 | 41,247,867 |
| 1191 | SFRP1 | 8 | 41,262,183 | 1192 | SFRP1 | 8 | 41,284,951 |
| 1193 | SNTG1 | 8 | 50,981,354 | 1194 | SNTG1 | 8 | 51,028,383 |
| 1195 | SNTG1 | 8 | 51,082,766 | 1196 | SNTG1 | 8 | 51,127,991 |
| 1197 | MCPH1 | 8 | 6,266,787 | 1198 | MCPH1 | 8 | 6,290,817 |
| 1199 | MCPH1 | 8 | 6,290,919 | 1200 | MCPH1 | 8 | 6,297,826 |
| 1201 | MCPH1 | 8 | 6,306,930 | 1202 | MCPH1 | 8 | 6,307,055 |
| 1203 | MCPH1 | 8 | 6,307,171 | 1204 | MCPH1 | 8 | 6,313,383 |
| 1205 | MCPH1 | 8 | 6,316,969 | 1206 | NKAIN3 | 8 | 63,450,524 |
| 1207 | NKAIN3 | 8 | 63,573,341 | 1208 | MCPH1 | 8 | 6,357,338 |
| 1209 | MCPH1 | 8 | 6,362,452 | 1210 | NKAIN3 | 8 | 63,670,367 |
| 1211 | NKAIN3 | 8 | 63,897,057 | 1212 | NKAIN3 | 8 | 64,008,938 |
| 1213 | NKAIN3 | 8 | 64,056,708 | 1214 | NKAIN3 | 8 | 64,084,956 |
| 1215 | MCPH1 | 8 | 6,460,526 | 1216 | DEPDC2 | 8 | 69,098,456 |
| 1217 | DEPDC2 | 8 | 69,098,725 | 1218 | DEPDC2 | 8 | 69,121,712 |
| 1219 | DEPDC2 | 8 | 69,144,533 | 1220 | DEPDC2 | 8 | 69,156,370 |
| 1221 | DEPDC2 | 8 | 69,207,400 | 1222 | DEPDC2 | 8 | 69,209,296 |
| 1223 | DEPDC2 | 8 | 69,301,731 | 1224 | DEPDC2 | 8 | 69,314,054 |
| 1225 | KCNB2 | 8 | 73,614,029 | 1226 | KCNB2 | 8 | 73,618,324 |
| 1227 | KCNB2 | 8 | 73,754,111 | 1228 | KCNB2 | 8 | 73,756,664 |
| 1229 | KCNB2 | 8 | 73,762,984 | 1230 | KCNB2 | 8 | 73,776,211 |
| 1231 | KCNB2 | 8 | 73,783,806 | 1232 | KCNB2 | 8 | 73,813,319 |
| 1233 | MMP16 | 8 | 89,061,627 | 1234 | MMP16 | 8 | 89,120,413 |
| 1235 | MMP16 | 8 | 89,148,139 | 1236 | MMP16 | 8 | 89,337,659 |
| 1237 | MMP16 | 8 | 89,367,315 | 1238 | MMP16 | 8 | 89,392,120 |
| 1239 | MMP16 | 8 | 89,413,738 | 1240 | MMP16 | 8 | 89,414,303 |
| 1241 | MMP16 | 8 | 89,421,430 | 1242 | GABBR2 | 9 | 100,094,975 |
| 1243 | GABBR2 | 9 | 100,095,943 | 1244 | GABBR2 | 9 | 100,419,601 |
| 1245 | GABBR2 | 9 | 100,469,409 | 1246 | RP11-35N6.1 | 9 | 102,472,272 |
| 1247 | FER1L6 | 9 | 103,382,443 | 1248 | GRIN3A | 9 | 103,473,056 |
| 1249 | GRIN3A | 9 | 103,521,201 | 1250 | FKTN | 9 | 107,409,195 |
| 1251 | FKTN | 9 | 107,449,221 | 1252 | FKTN | 9 | 107,455,377 |
| 1253 | SVEP1 | 9 | 112,152,393 | 1254 | SVEP1 | 9 | 112,166,117 |
| 1255 | SVEP1 | 9 | 112,167,878 | 1256 | CDK5RAP2 | 9 | 122,209,539 |
| 1257 | CDK5RAP2 | 9 | 122,337,266 | 1258 | CDK5RAP2 | 9 | 122,362,134 |
| 1259 | CDK5RAP2 | 9 | 122,370,634 | 1260 | STOM | 9 | 123,165,341 |
| 1261 | DAB2IP | 9 | 123,691,611 | 1262 | RALGPS1 | 9 | 128,698,499 |
| 1263 | RALGPS1 | 9 | 128,769,224 | 1264 | RALGPS1 | 9 | 128,789,061 |
| 1265 | RALGPS1 | 9 | 128,809,594 | 1266 | RALGPS1 | 9 | 128,902,817 |
| 1267 | SLC25A25 | 9 | 129,886,889 | 1268 | SLC25A25 | 9 | 129,899,153 |
| 1269 | FREQ | 9 | 131,997,035 | 1270 | EXOSC2 | 9 | 132,588,852 |
| 1271 | ABL1 | 9 | 132,715,588 | 1272 | ABL1 | 9 | 132,721,005 |
| 1273 | ABL1 | 9 | 132,722,573 | 1274 | ABL1 | 9 | 132,723,896 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 1275 | TSC1 | 9 | 134,811,193 | 1276 | TSC1 | 9 | 134,812,111 |
| 1277 | VAV2 | 9 | 135,795,115 | 1278 | OLFM1 | 9 | 137,113,249 |
| 1279 | OLFM1 | 9 | 137,127,054 | 1280 | INPP5E | 9 | 138,461,433 |
| 1281 | NOTCH1 | 9 | 138,555,218 | 1282 | CACNA1B | 9 | 140,072,737 |
| 1283 | CACNA1B | 9 | 140,075,368 | 1284 | ASAH3L | 9 | 19,460,804 |
| 1285 | KIAA1797 | 9 | 20,673,404 | 1286 | KIAA1797 | 9 | 20,678,117 |
| 1287 | KIAA1797 | 9 | 20,732,210 | 1288 | KIAA1797 | 9 | 20,753,840 |
| 1289 | KIAA1797 | 9 | 20,754,870 | 1290 | KIAA1797 | 9 | 20,804,142 |
| 1291 | KIAA1797 | 9 | 20,898,513 | 1292 | KIAA1797 | 9 | 20,921,349 |
| 1293 | KIAA1797 | 9 | 20,935,372 | 1294 | KIAA1797 | 9 | 20,943,233 |
| 1295 | KIAA1797 | 9 | 20,943,335 | 1296 | KIAA1797 | 9 | 20,943,750 |
| 1297 | KIAA1797 | 9 | 20,951,906 | 1298 | KIAA1797 | 9 | 20,977,703 |
| 1299 | KIAA1797 | 9 | 20,978,426 | 1300 | KIAA1797 | 9 | 20,986,709 |
| 1301 | SMARCA2 | 9 | 2,120,828 | 1302 | SMARCA2 | 9 | 2,120,917 |
| 1303 | SMARCA2 | 9 | 2,121,990 | 1304 | SMARCA2 | 9 | 2,178,383 |
| 1305 | IFT74 | 9 | 26,999,100 | 1306 | TEK | 9 | 27,129,817 |
| 1307 | TEK | 9 | 27,175,101 | 1308 | TEK | 9 | 27,210,066 |
| 1309 | TEK | 9 | 27,224,049 | 1310 | SLC1A1 | 9 | 4,550,348 |
| 1311 | SLC1A1 | 9 | 4,552,472 | 1312 | PIP5K1B | 9 | 70,507,948 |
| 1313 | PIP5K1B | 9 | 70,552,216 | 1314 | PIP5K1B | 9 | 70,672,108 |
| 1315 | PIP5K1B | 9 | 70,687,329 | 1316 | PIP5K1B | 9 | 70,691,508 |
| 1317 | PIP5K1B | 9 | 70,703,782 | 1318 | APBA1 | 9 | 71,324,196 |
| 1319 | TRPM3 | 9 | 72,346,211 | 1320 | TRPM3 | 9 | 72,637,875 |
| 1321 | TRPM3 | 9 | 72,648,924 | 1322 | TRPM3 | 9 | 72,649,911 |
| 1323 | TRPM3 | 9 | 72,673,741 | 1324 | TMC1 | 9 | 74,397,486 |
| 1325 | TMC1 | 9 | 74,443,712 | 1326 | TMC1 | 9 | 74,579,921 |
| 1327 | PCSK5 | 9 | 77,687,086 | 1328 | PCSK5 | 9 | 77,896,771 |
| 1329 | PCSK5 | 9 | 77,912,756 | 1330 | GNAQ | 9 | 79,595,252 |
| 1331 | GNAQ | 9 | 79,703,143 | 1332 | GNAQ | 9 | 79,908,612 |
| 1333 | PTPRD | 9 | 8,372,966 | 1334 | PTPRD | 9 | 8,390,681 |
| 1335 | NTRK2 | 9 | 86,472,851 | 1336 | NTRK2 | 9 | 86,479,077 |
| 1337 | NTRK2 | 9 | 86,599,187 | 1338 | DAPK1 | 9 | 89,448,453 |
| 1339 | DAPK1 | 9 | 89,452,483 | 1340 | DAPK1 | 9 | 89,511,843 |
| 1341 | SORCS3 | 10 | 106,371,034 | 1342 | SORCS3 | 10 | 106,592,352 |
| 1343 | SORCS3 | 10 | 106,614,338 | 1344 | SORCS3 | 10 | 106,622,111 |
| 1345 | SORCS3 | 10 | 106,622,468 | 1346 | SORCS3 | 10 | 106,625,786 |
| 1347 | SORCS3 | 10 | 106,777,753 | 1348 | SORCS3 | 10 | 106,782,237 |
| 1349 | SORCS3 | 10 | 106,897,228 | 1350 | SORCS3 | 10 | 106,906,037 |
| 1351 | SORCS3 | 10 | 106,906,641 | 1352 | SORCS3 | 10 | 107,025,958 |
| 1353 | CUGBP2 | 10 | 11,277,934 | 1354 | VTI1A | 10 | 114,226,855 |
| 1355 | VTI1A | 10 | 114,228,361 | 1356 | VTI1A | 10 | 114,424,611 |
| 1357 | VTI1A | 10 | 114,458,106 | 1358 | VTI1A | 10 | 114,458,428 |
| 1359 | VTI1A | 10 | 114,506,363 | 1360 | VTI1A | 10 | 114,508,308 |
| 1361 | HSPA12A | 10 | 118,432,901 | 1362 | HSPA12A | 10 | 118,469,221 |
| 1363 | ATE1 | 10 | 123,432,831 | 1364 | ATE1 | 10 | 123,450,896 |
| 1365 | ATE1 | 10 | 123,453,723 | 1366 | ATE1 | 10 | 123,644,015 |
| 1367 | ATE1 | 10 | 123,651,712 | 1368 | ATE1 | 10 | 123,663,196 |
| 1369 | ATE1 | 10 | 123,669,674 | 1370 | CTBP2 | 10 | 126,677,518 |
| 1371 | ARMC3 | 10 | 23,277,574 | 1372 | ARMC3 | 10 | 23,289,115 |
| 1373 | ARMC3 | 10 | 23,314,154 | 1374 | ARMC3 | 10 | 23,318,053 |
| 1375 | ARMC3 | 10 | 23,337,258 | 1376 | ARMC3 | 10 | 23,364,367 |
| 1377 | ARMC3 | 10 | 23,372,952 | 1378 | ARHGAP21 | 10 | 25,046,553 |
| 1379 | MYO3A | 10 | 26,398,660 | 1380 | MYO3A | 10 | 26,552,050 |
| 1381 | PITRM1 | 10 | 3,166,363 | 1382 | PITRM1 | 10 | 3,169,968 |
| 1383 | PITRM1 | 10 | 3,179,380 | 1384 | PITRM1 | 10 | 3,192,065 |
| 1385 | PITRM1 | 10 | 3,213,179 | 1386 | SLC16A9 | 10 | 61,024,452 |
| 1387 | SLC16A9 | 10 | 61,082,341 | 1388 | SLC16A9 | 10 | 61,084,017 |
| 1389 | SLC16A9 | 10 | 61,120,938 | 1390 | SLC16A9 | 10 | 61,122,758 |
| 1391 | PRKCQ | 10 | 6,567,350 | 1392 | PRKCQ | 10 | 7,152,082 |
| 1393 | CDH23 | 10 | 72,997,429 | 1394 | CDH23 | 10 | 73,104,912 |
| 1395 | CDH23 | 10 | 73,126,384 | 1396 | KCNMA1 | 10 | 78,319,405 |
| 1397 | KCNMA1 | 10 | 78,319,936 | 1398 | KCNMA1 | 10 | 78,320,267 |
| 1399 | KCNMA1 | 10 | 78,324,802 | 1400 | KCNMA1 | 10 | 78,348,173 |
| 1401 | KCNMA1 | 10 | 78,626,486 | 1402 | KCNMA1 | 10 | 78,738,970 |
| 1403 | KCNMA1 | 10 | 78,757,625 | 1404 | KCNMA1 | 10 | 78,799,763 |
| 1405 | KCNMA1 | 10 | 78,817,839 | 1406 | KCNMA1 | 10 | 78,872,456 |
| 1407 | KCNMA1 | 10 | 79,094,637 | 1408 | NRG3 | 10 | 84,068,972 |
| 1409 | NRG3 | 10 | 84,070,208 | 1410 | NRG3 | 10 | 84,604,364 |
| 1411 | NRG3 | 10 | 84,613,706 | 1412 | NRG3 | 10 | 84,616,939 |
| 1413 | SORBS1 | 10 | 97,061,507 | 1414 | SORBS1 | 10 | 97,122,546 |
| 1415 | SORBS1 | 10 | 97,122,783 | 1416 | SORBS1 | 10 | 97,126,192 |
| 1417 | SORBS1 | 10 | 97,127,095 | 1418 | SORBS1 | 10 | 97,216,419 |
| 1419 | ELMOD1 | 11 | 107,077,060 | 1420 | GALNTL4 | 11 | 11,246,740 |
| 1421 | GALNTL4 | 11 | 11,497,136 | 1422 | MICAL2 | 11 | 12,139,036 |
| 1423 | MICAL2 | 11 | 12,142,872 | 1424 | MICAL2 | 11 | 12,149,199 |
| 1425 | MICAL2 | 11 | 12,155,884 | 1426 | MICAL2 | 11 | 12,175,779 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 1427 | MICAL2 | 11 | 12,222,118 | 1428 | OPCML | 11 | 131,718,194 |
| 1429 | OPCML | 11 | 132,078,600 | 1430 | ARNTL | 11 | 13,212,114 |
| 1431 | ARNTL | 11 | 13,212,547 | 1432 | OPCML | 11 | 132,803,817 |
| 1433 | OPCML | 11 | 132,884,694 | 1434 | OPCML | 11 | 132,895,944 |
| 1435 | SPON1 | 11 | 13,882,655 | 1436 | SPON1 | 11 | 13,922,920 |
| 1437 | SPON1 | 11 | 13,994,054 | 1438 | SPON1 | 11 | 14,008,775 |
| 1439 | SPON1 | 11 | 14,014,762 | 1440 | SPON1 | 11 | 14,023,125 |
| 1441 | SPON1 | 11 | 14,034,087 | 1442 | SPON1 | 11 | 14,070,335 |
| 1443 | SPON1 | 11 | 14,075,677 | 1444 | SPON1 | 11 | 14,215,231 |
| 1445 | INSC | 11 | 15,138,272 | 1446 | KCNA4 | 11 | 29,964,590 |
| 1447 | KCNA4 | 11 | 29,984,859 | 1448 | STIM1 | 11 | 3,847,536 |
| 1449 | STIM1 | 11 | 3,867,621 | 1450 | STIM1 | 11 | 3,927,655 |
| 1451 | STIM1 | 11 | 4,033,624 | 1452 | TRIM21 | 11 | 4,371,449 |
| 1453 | C11ORF49 | 11 | 47,089,300 | 1454 | 81.99 mb | 11 | 81,921,684 |
| 1455 | DLG2 | 11 | 82,719,582 | 1456 | DLG2 | 11 | 82,720,706 |
| 1457 | DLG2 | 11 | 82,743,548 | 1458 | DLG2 | 11 | 82,843,293 |
| 1459 | DLG2 | 11 | 82,856,041 | 1460 | DLG2 | 11 | 82,974,099 |
| 1461 | DLG2 | 11 | 82,982,760 | 1462 | DLG2 | 11 | 83,366,230 |
| 1463 | DLG2 | 11 | 83,418,483 | 1464 | DLG2 | 11 | 83,444,686 |
| 1465 | DLG2 | 11 | 83,457,074 | 1466 | DLG2 | 11 | 84,138,503 |
| 1467 | DLG2 | 11 | 84,147,518 | 1468 | DLG2 | 11 | 84,153,124 |
| 1469 | DLG2 | 11 | 84,214,566 | 1470 | DLG2 | 11 | 84,251,688 |
| 1471 | DLG2 | 11 | 84,251,805 | 1472 | DLG2 | 11 | 84,261,681 |
| 1473 | DLG2 | 11 | 84,273,766 | 1474 | DLG2 | 11 | 84,283,321 |
| 1475 | DLG2 | 11 | 84,283,477 | 1476 | DLG2 | 11 | 84,425,370 |
| 1477 | CHST11 | 12 | 103,435,376 | 1478 | CHST11 | 12 | 103,448,913 |
| 1479 | CHST11 | 12 | 103,599,400 | 1480 | ATXN2 | 12 | 110,547,258 |
| 1481 | PLA2G1B | 12 | 119,254,040 | 1482 | LOC729025 | 12 | 16,298,403 |
| 1483 | LOC729025 | 12 | 16,302,981 | 1484 | PIK3C2G | 12 | 18,305,520 |
| 1485 | PIK3C2G | 12 | 18,356,504 | 1486 | PIK3C2G | 12 | 18,426,133 |
| 1487 | PIK3C2G | 12 | 18,576,788 | 1488 | PIK3C2G | 12 | 18,701,315 |
| 1489 | ITPR2 | 12 | 26,366,134 | 1490 | ITPR2 | 12 | 26,382,742 |
| 1491 | TMEM16B | 12 | 5,505,585 | 1492 | LRP1 | 12 | 55,821,533 |
| 1493 | TMEM16B | 12 | 5,690,939 | 1494 | TMEM16B | 12 | 5,712,102 |
| 1495 | TMEM16B | 12 | 5,755,581 | 1496 | TMEM16B | 12 | 5,760,697 |
| 1497 | TMEM16B | 12 | 5,786,169 | 1498 | TMEM16B | 12 | 5,794,409 |
| 1499 | TMEM16B | 12 | 5,901,003 | 1500 | CNOT2 | 12 | 68,831,198 |
| 1501 | CNOT2 | 12 | 69,026,461 | 1502 | KCNC2 | 12 | 73,877,027 |
| 1503 | KCNC2 | 12 | 73,886,479 | 1504 | KCNC2 | 12 | 73,898,155 |
| 1505 | KCNC2 | 12 | 73,944,836 | 1506 | NAV3 | 12 | 76,718,256 |
| 1507 | NAV3 | 12 | 76,748,290 | 1508 | NAV3 | 12 | 76,793,282 |
| 1509 | NAV3 | 12 | 76,798,556 | 1510 | NAV3 | 12 | 76,824,819 |
| 1511 | NAV3 | 12 | 76,839,838 | 1512 | NAV3 | 12 | 76,845,308 |
| 1513 | NAV3 | 12 | 76,854,382 | 1514 | NAV3 | 12 | 76,862,517 |
| 1515 | NAV3 | 12 | 76,862,929 | 1516 | NAV3 | 12 | 76,893,657 |
| 1517 | NAV3 | 12 | 76,913,545 | 1518 | NAV3 | 12 | 76,922,312 |
| 1519 | NAV3 | 12 | 77,013,958 | 1520 | NALCN | 13 | 100,607,424 |
| 1521 | NALCN | 13 | 100,611,279 | 1522 | NALCN | 13 | 100,618,459 |
| 1523 | NALCN | 13 | 100,631,451 | 1524 | NALCN | 13 | 100,633,744 |
| 1525 | NALCN | 13 | 100,638,349 | 1526 | NALCN | 13 | 100,645,729 |
| 1527 | NALCN | 13 | 100,686,017 | 1528 | NALCN | 13 | 100,689,460 |
| 1529 | NALCN | 13 | 100,803,215 | 1530 | ITGBL1 | 13 | 100,951,158 |
| 1531 | ITGBL1 | 13 | 101,018,194 | 1532 | ITGBL1 | 13 | 101,066,640 |
| 1533 | ITGBL1 | 13 | 101,070,551 | 1534 | ITGBL1 | 13 | 101,071,354 |
| 1535 | ITGBL1 | 13 | 101,088,453 | 1536 | ITGBL1 | 13 | 101,144,171 |
| 1537 | FGF14 | 13 | 101,180,363 | 1538 | FGF14 | 13 | 101,217,477 |
| 1539 | FGF14 | 13 | 101,224,288 | 1540 | FGF14 | 13 | 101,237,184 |
| 1541 | FGF14 | 13 | 101,904,537 | 1542 | MTIF3 | 13 | 26,979,535 |
| 1543 | N4BP2L2 | 13 | 31,899,297 | 1544 | N4BP2L2 | 13 | 31,934,759 |
| 1545 | N4BP2L2 | 13 | 31,953,620 | 1546 | N4BP2L2 | 13 | 32,021,516 |
| 1547 | NBEA | 13 | 34,773,125 | 1548 | NBEA | 13 | 34,848,999 |
| 1549 | NBEA | 13 | 35,142,667 | 1550 | NBEA | 13 | 35,170,524 |
| 1551 | NBEA | 13 | 35,171,922 | 1552 | TRPC4 | 13 | 37,131,370 |
| 1553 | TRPC4 | 13 | 37,131,795 | 1554 | TRPC4 | 13 | 37,134,885 |
| 1555 | TRPC4 | 13 | 37,134,956 | 1556 | TRPC4 | 13 | 37,135,147 |
| 1557 | TRPC4 | 13 | 37,148,211 | 1558 | TRPC4 | 13 | 37,201,686 |
| 1559 | TRPC4 | 13 | 37,203,414 | 1560 | TRPC4 | 13 | 37,259,744 |
| 1561 | TRPC4 | 13 | 37,316,370 | 1562 | TRPC4 | 13 | 37,343,196 |
| 1563 | TRPC4 | 13 | 37,343,288 | 1564 | TRPC4 | 13 | 37,354,793 |
| 1565 | FNDC3A | 13 | 48,484,019 | 1566 | FNDC3A | 13 | 48,526,907 |
| 1567 | FNDC3A | 13 | 48,569,216 | 1568 | FNDC3A | 13 | 48,609,971 |
| 1569 | KPNA3 | 13 | 49,294,756 | 1570 | PCDH17 | 13 | 57,113,277 |
| 1571 | PCDH17 | 13 | 57,133,204 | 1572 | SLAIN1 | 13 | 77,130,842 |
| 1573 | SLAIN1 | 13 | 77,151,328 | 1574 | SLAIN1 | 13 | 77,192,452 |
| 1575 | SLAIN1 | 13 | 77,211,551 | 1576 | SLAIN1 | 13 | 77,232,218 |
| 1577 | SLAIN1 | 13 | 77,273,814 | 1578 | SLAIN1 | 13 | 77,290,759 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 1579 | GPC5 | 13 | 90,547,957 | 1580 | GPC5 | 13 | 90,931,610 |
| 1581 | GPC5 | 13 | 91,966,983 | 1582 | GPC5 | 13 | 92,117,714 |
| 1583 | GPC5 | 13 | 92,121,270 | 1584 | GPC5 | 13 | 92,275,844 |
| 1585 | GPC5 | 13 | 92,302,532 | 1586 | GPC5 | 13 | 92,332,949 |
| 1587 | GPC5 | 13 | 92,347,342 | 1588 | GPC6 | 13 | 92,775,697 |
| 1589 | GPC6 | 13 | 92,807,479 | 1590 | GPC6 | 13 | 93,185,878 |
| 1591 | GPC6 | 13 | 93,196,895 | 1592 | GPC6 | 13 | 93,196,981 |
| 1593 | GPC6 | 13 | 93,204,846 | 1594 | GPC6 | 13 | 93,497,436 |
| 1595 | GPC6 | 13 | 93,851,561 | 1596 | GPC6 | 13 | 93,863,575 |
| 1597 | NPAS3 | 14 | 32,590,670 | 1598 | NPAS3 | 14 | 32,661,665 |
| 1599 | NPAS3 | 14 | 32,777,738 | 1600 | NPAS3 | 14 | 32,782,805 |
| 1601 | NPAS3 | 14 | 32,983,731 | 1602 | NPAS3 | 14 | 33,099,951 |
| 1603 | NPAS3 | 14 | 33,099,995 | 1604 | NPAS3 | 14 | 33,192,848 |
| 1605 | NPAS3 | 14 | 33,194,275 | 1606 | NPAS3 | 14 | 33,206,451 |
| 1607 | NPAS3 | 14 | 33,207,004 | 1608 | SLC25A21 | 14 | 36,242,267 |
| 1609 | SLC25A21 | 14 | 36,419,536 | 1610 | LRFN5 | 14 | 41,384,489 |
| 1611 | LRFN5 | 14 | 41,391,684 | 1612 | GNG2 | 14 | 51,400,583 |
| 1613 | GNG2 | 14 | 51,409,101 | 1614 | GNG2 | 14 | 51,428,644 |
| 1615 | GNG2 | 14 | 51,520,930 | 1616 | SAMD4A | 14 | 54,112,365 |
| 1617 | SAMD4A | 14 | 54,314,899 | 1618 | SAMD4A | 14 | 54,319,095 |
| 1619 | SAMD4A | 14 | 54,335,321 | 1620 | PPP2R5E | 14 | 62,858,991 |
| 1621 | PPP2R5E | 14 | 63,091,961 | 1622 | PPP2R5E | 14 | 63,099,534 |
| 1623 | PPP2R5E | 14 | 63,213,578 | 1624 | RGS6 | 14 | 71,479,105 |
| 1625 | RGS6 | 14 | 71,524,688 | 1626 | RGS6 | 14 | 71,532,447 |
| 1627 | RGS6 | 14 | 71,538,158 | 1628 | RGS6 | 14 | 71,730,259 |
| 1629 | RGS6 | 14 | 71,789,160 | 1630 | RGS6 | 14 | 71,870,813 |
| 1631 | RGS6 | 14 | 71,979,491 | 1632 | KCNK10 | 14 | 87,843,799 |
| 1633 | KCNK10 | 14 | 87,887,777 | 1634 | RPS6KA5 | 14 | 90,431,677 |
| 1635 | RPS6KA5 | 14 | 90,501,524 | 1636 | RPS6KA5 | 14 | 90,536,260 |
| 1637 | RPS6KA5 | 14 | 90,572,871 | 1638 | RPS6KA5 | 14 | 90,592,117 |
| 1639 | RPS6KA5 | 14 | 90,600,783 | 1640 | RPS6KA5 | 14 | 90,600,927 |
| 1641 | RPS6KA5 | 14 | 90,616,889 | 1642 | CCDC88C | 14 | 90,910,934 |
| 1643 | CCDC88C | 14 | 90,916,433 | 1644 | CCDC88C | 14 | 90,918,598 |
| 1645 | CCDC88C | 14 | 90,919,949 | 1646 | CCDC88C | 14 | 90,920,049 |
| 1647 | CCDC88C | 14 | 90,926,910 | 1648 | BCL11B | 14 | 98,713,688 |
| 1649 | BCL11B | 14 | 98,742,719 | 1650 | BCL11B | 14 | 98,816,027 |
| 1651 | ATP10A | 15 | 23,478,440 | 1652 | ATP10A | 15 | 23,496,935 |
| 1653 | RYR3 | 15 | 31,550,764 | 1654 | RYR3 | 15 | 31,564,997 |
| 1655 | RYR3 | 15 | 31,695,608 | 1656 | RYR3 | 15 | 31,744,674 |
| 1657 | RYR3 | 15 | 31,745,083 | 1658 | RYR3 | 15 | 31,814,492 |
| 1659 | RYR3 | 15 | 31,815,285 | 1660 | RYR3 | 15 | 31,899,901 |
| 1661 | C15ORF41 | 15 | 34,691,218 | 1662 | C15ORF41 | 15 | 34,707,884 |
| 1663 | C15ORF41 | 15 | 34,751,160 | 1664 | C15ORF41 | 15 | 34,755,325 |
| 1665 | C15ORF41 | 15 | 34,780,489 | 1666 | C15ORF41 | 15 | 34,793,623 |
| 1667 | C15ORF41 | 15 | 34,833,829 | 1668 | RASGRPI | 15 | 36,607,181 |
| 1669 | PLA2G4D | 15 | 40,137,329 | 1670 | GLDN | 15 | 49,440,552 |
| 1671 | GLDN | 15 | 49,477,064 | 1672 | GLDN | 15 | 49,481,784 |
| 1673 | CGNL1 | 15 | 55,403,598 | 1674 | CGNL1 | 15 | 55,518,865 |
| 1675 | CGNL1 | 15 | 55,521,306 | 1676 | CGNL1 | 15 | 55,595,257 |
| 1677 | CGNL1 | 15 | 55,623,195 | 1678 | CGNL1 | 15 | 55,623,569 |
| 1679 | RORA | 15 | 58,605,378 | 1680 | RORA | 15 | 58,680,723 |
| 1681 | CLK3 | 15 | 72,697,052 | 1682 | TBC1D2B | 15 | 76,096,608 |
| 1683 | TBCID2B | 15 | 76,098,398 | 1684 | TBC1D2B | 15 | 76,121,710 |
| 1685 | TBCID2B | 15 | 76,150,830 | 1686 | ARNT2 | 15 | 78,539,124 |
| 1687 | ARNT2 | 15 | 78,700,178 | 1688 | ARNT2 | 15 | 78,703,747 |
| 1689 | ARNT2 | 15 | 78,704,322 | 1690 | ARNT2 | 15 | 78,718,605 |
| 1691 | ARNT2 | 15 | 78,719,745 | 1692 | SH3GL3 | 15 | 81,818,542 |
| 1693 | PCSK6 | 15 | 99,842,741 | 1694 | TMC5 | 16 | 19,254,444 |
| 1695 | GDE1 | 16 | 19,447,359 | 1696 | EEF2K | 16 | 22,114,775 |
| 1697 | KIFC3 | 16 | 56,376,436 | 1698 | KIFC3 | 16 | 56,379,768 |
| 1699 | A2BP1 | 16 | 6,527,248 | 1700 | A2BP1 | 16 | 6,528,853 |
| 1701 | A2BP1 | 16 | 6,691,358 | 1702 | A2BP1 | 16 | 6,974,269 |
| 1703 | HYDIN | 16 | 69,783,066 | 1704 | A2BP1 | 16 | 6,980,934 |
| 1705 | HYDIN | 16 | 69,818,152 | 1706 | A2BP1 | 16 | 7,234,640 |
| 1707 | A2BP1 | 16 | 7,551,379 | 1708 | WWOX | 16 | 76,643,771 |
| 1709 | WWOX | 16 | 76,655,506 | 1710 | WWOX | 16 | 76,669,786 |
| 1711 | WWOX | 16 | 76,672,696 | 1712 | WWOX | 16 | 76,674,781 |
| 1713 | WWOX | 16 | 77,016,308 | 1714 | MPHOSPH6 | 16 | 80,705,905 |
| 1715 | MPHOSPH6 | 16 | 80,722,907 | 1716 | MPHOSPH6 | 16 | 80,723,078 |
| 1717 | MPHOSPH6 | 16 | 80,728,084 | 1718 | CDH13 | 16 | 81,390,450 |
| 1719 | CMH3 | 16 | 81,426,803 | 1720 | CDH13 | 16 | 81,436,845 |
| 1721 | CDH13 | 16 | 81,470,072 | 1722 | CDH13 | 16 | 81,474,183 |
| 1723 | CDH13 | 16 | 81,477,191 | 1724 | CDH13 | 16 | 81,481,182 |
| 1725 | CDH13 | 16 | 81,487,112 | 1726 | CDH13 | 16 | 81,906,325 |
| 1727 | CDH13 | 16 | 81,917,154 | 1728 | CDH13 | 16 | 81,919,816 |
| 1729 | CDH13 | 16 | 82,194,302 | 1730 | CDH13 | 16 | 82,357,323 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 1731 | USP10 | 16 | 83,331,937 | 1732 | USP10 | 16 | 83,371,654 |
| 1733 | CRISPLD2 | 16 | 83,443,278 | 1734 | CRISPLD2 | 16 | 83,443,531 |
| 1735 | CRISPLD2 | 16 | 83,475,493 | 1736 | CRISPLD2 | 16 | 83,476,363 |
| 1737 | CRISPLD2 | 16 | 83,484,480 | 1738 | CRISPLD2 | 16 | 83,484,845 |
| 1739 | CRISPLD2 | 16 | 83,497,517 | 1740 | DNAH9 | 17 | 11,591,782 |
| 1741 | DNAH9 | 17 | 11,672,736 | 1742 | DNAH9 | 17 | 11,862,669 |
| 1743 | RAB11FIP4 | 17 | 27,005,299 | 1744 | CA10 | 17 | 47,163,241 |
| 1745 | CA10 | 17 | 47,434,848 | 1746 | CA10 | 17 | 47,528,183 |
| 1747 | CA10 | 17 | 47,534,336 | 1748 | CA10 | 17 | 47,547,164 |
| 1749 | CA10 | 17 | 47,599,744 | 1750 | CA10 | 17 | 48,292,853 |
| 1751 | MSI2 | 17 | 52,817,244 | 1752 | MSI2 | 17 | 52,993,137 |
| 1753 | MSI2 | 17 | 53,122,443 | 1754 | SDK2 | 17 | 68,829,410 |
| 1755 | HRNBP3 | 17 | 74,857,410 | 1756 | HRNBP3 | 17 | 75,313,214 |
| 1757 | OSBPL1A | 18 | 20,042,294 | 1758 | OSBPL1A | 18 | 20,093,929 |
| 1759 | OSBPL1A | 18 | 20,243,361 | 1760 | CHST9 | 18 | 22,886,548 |
| 1761 | CHST9 | 18 | 22,965,754 | 1762 | CH5T9 | 18 | 23,000,286 |
| 1763 | DLGAP1 | 18 | 3,829,680 | 1764 | DLGAP1 | 18 | 3,840,002 |
| 1765 | ZFP161 | 18 | 5,398,814 | 1766 | NEDD4L | 18 | 54,010,852 |
| 1767 | NEDD4L | 18 | 54,013,845 | 1768 | NEDD4L | 18 | 54,014,157 |
| 1769 | NEDD4L | 18 | 54,016,611 | 1770 | NEDD4L | 18 | 54,028,916 |
| 1771 | NEDD4L | 18 | 54,100,941 | 1772 | NEDD4L | 18 | 54,258,677 |
| 1773 | NEDD4L | 18 | 54,259,246 | 1774 | CCBE1 | 18 | 55,241,702 |
| 1775 | CCBE1 | 18 | 55,487,763 | 1776 | CDH7 | 18 | 61,273,210 |
| 1777 | CDH7 | 18 | 61,289,294 | 1778 | CDH7 | 18 | 61,305,341 |
| 1779 | CDH7 | 18 | 61,305,944 | 1780 | CDH7 | 18 | 61,586,240 |
| 1781 | CDH7 | 18 | 61,590,121 | 1782 | CDH7 | 18 | 61,594,009 |
| 1783 | CDH7 | 18 | 61,594,926 | 1784 | CDH7 | 18 | 61,594,980 |
| 1785 | CDH7 | 18 | 61,595,280 | 1786 | CDH7 | 18 | 61,595,696 |
| 1787 | CDH7 | 18 | 61,627,079 | 1788 | CDH7 | 18 | 61,668,497 |
| 1789 | CDH7 | 18 | 61,688,917 | 1790 | CDH7 | 18 | 61,715,545 |
| 1791 | DOK6 | 18 | 65,238,984 | 1792 | DOK6 | 18 | 65,437,835 |
| 1793 | DOK6 | 18 | 65,516,648 | 1794 | DOK6 | 18 | 65,516,906 |
| 1795 | MBP | 18 | 72,823,708 | 1796 | MBP | 18 | 73,018,369 |
| 1797 | PTPRM | 18 | 7,522,635 | 1798 | PTPRM | 18 | 7,585,927 |
| 1799 | PTPRM | 18 | 8,277,805 | 1800 | PTPRM | 18 | 8,288,088 |
| 1801 | PTPRM | 18 | 8,288,633 | 1802 | KIAA0802 | 18 | 8,689,988 |
| 1803 | KIAA0802 | 18 | 8,788,185 | 1804 | KIAA0802 | 18 | 8,820,180 |
| 1805 | LDLR | 19 | 11,067,530 | 1806 | LDLR | 19 | 11,102,877 |
| 1807 | LDLR | 19 | 11,103,658 | 1808 | ZNF667 | 19 | 61,678,984 |
| 1809 | MACROD2 | 20 | 14,275,899 | 1810 | MACROD2 | 20 | 15,551,153 |
| 1811 | MACROD2 | 20 | 15,890,876 | 1812 | MACROD2 | 20 | 15,992,978 |
| 1813 | KIF16B | 20 | 16,221,665 | 1814 | KIF16B | 20 | 16,221,933 |
| 1815 | KIF16B | 20 | 16,270,199 | 1816 | KIF16B | 20 | 16,275,325 |
| 1817 | KIFI6B | 20 | 16,275,825 | 1818 | KIF16B | 20 | 16,284,694 |
| 1819 | KIF16B | 20 | 16,294,439 | 1820 | KIF16B | 20 | 16,294,523 |
| 1821 | KIF16B | 20 | 16,307,567 | 1822 | KIF16B | 20 | 16,314,615 |
| 1823 | KIF16B | 20 | 16,371,330 | 1824 | KIF16B | 20 | 16,420,825 |
| 1825 | KIF16B | 20 | 16,459,991 | 1826 | KIF16B | 20 | 16,476,914 |
| 1827 | KIF16B | 20 | 16,591,934 | 1828 | MAPRE1 | 20 | 30,888,730 |
| 1829 | MAPRE1 | 20 | 30,891,296 | 1830 | PTPRT | 20 | 40,079,104 |
| 1831 | PTPRT | 20 | 40,112,645 | 1832 | PTPRT | 20 | 40,141,648 |
| 1833 | PTPRT | 20 | 40,143,404 | 1834 | PTPRT | 20 | 40,153,367 |
| 1835 | PTPRT | 20 | 40,176,580 | 1836 | PTPRT | 20 | 40,534,688 |
| 1837 | PTPRT | 20 | 40,759,651 | 1838 | PTPRT | 20 | 40,766,955 |
| 1839 | PTPRT | 20 | 40,832,585 | 1840 | PRNT | 20 | 4,676,075 |
| 1841 | KCNB1 | 20 | 47,439,714 | 1842 | KCNB1 | 20 | 47,440,607 |
| 1843 | KCNB1 | 20 | 47,543,084 | 1844 | KCNB1 | 20 | 47,550,362 |
| 1845 | KCNB1 | 20 | 47,554,184 | 1846 | CDH4 | 20 | 59,349,681 |
| 1847 | CDH4 | 20 | 59,359,672 | 1848 | CDH4 | 20 | 59,708,754 |
| 1849 | CDH4 | 20 | 59,852,651 | 1850 | CDH4 | 20 | 59,854,564 |
| 1851 | CDH4 | 20 | 59,936,745 | 1852 | FERMT1 | 20 | 6,011,187 |
| 1853 | FERMT1 | 20 | 6,037,797 | 1854 | FERMT1 | 20 | 6,048,088 |
| 1855 | FERMT1 | 20 | 6,162,234 | 1856 | PLCB1 | 20 | 8,082,140 |
| 1857 | PLCB1 | 20 | 8,092,135 | 1858 | PLCB1 | 20 | 8,159,200 |
| 1859 | PLCB4 | 20 | 9,133,981 | 1860 | PLCB4 | 20 | 9,173,164 |
| 1861 | C21ORF37 | 21 | 17,711,037 | 1862 | NCAM2 | 21 | 21,717,043 |
| 1863 | NCAM2 | 21 | 21,722,038 | 1864 | NCAM2 | 21 | 21,849,510 |
| 1865 | ERG | 21 | 38,941,206 | 1866 | ERG | 21 | 38,947,119 |
| 1867 | ERG | 21 | 38,989,365 | 1868 | PCP4 | 21 | 40,145,066 |
| 1869 | PCP4 | 21 | 40,147,412 | 1870 | SLC37A1 | 21 | 42,866,712 |
| 1871 | SLC37A1 | 21 | 42,871,651 | 1872 | SLC37A1 | 21 | 42,877,191 |
| 1873 | ARVCF | 22 | 18,342,203 | 1874 | SGSM1 | 22 | 23,675,537 |
| 1875 | HPS4 | 22 | 25,192,153 | 1876 | ARFGAP3 | 22 | 41,576,090 |
| 1877 | ARFGAP3 | 22 | 41,590,371 | 1878 | ARFGAP3 | 22 | 41,591,167 |
| 1879 | PACSIN2 | 22 | 41,629,654 | 1880 | PACSIN2 | 22 | 41,645,337 |
| 1881 | PACSIN2 | 22 | 41,679,576 | 1882 | PACSIN2 | 22 | 41,685,200 |

TABLE A-continued

Summary of SNPs (NCBI Human Genome Reference Assembly Build 36.3)

| Seq ID | Gene | Chr | Position (BP) | Seq ID | Gene | Chr | Position (BP) |
|---|---|---|---|---|---|---|---|
| 1883 | PACSIN2 | 22 | 41,686,443 | 1884 | PACSIN2 | 22 | 41,686,643 |
| 1885 | PACSIN2 | 22 | 41,723,929 | 1886 | PACSIN2 | 22 | 41,726,053 |
| 1887 | PACSIN2 | 22 | 41,727,507 | 1888 | PACSIN2 | 22 | 41,729,950 |
| 1889 | PACSIN2 | 22 | 41,730,708 | 1890 | TTLL1 | 22 | 41,796,161 |
| 1891 | TTLL1 | 22 | 41,822,583 | 1892 | TTLL1 | 22 | 41,822,906 |
| 1893 | EFCAB6 | 22 | 42,278,436 | 1894 | EFCAB6 | 22 | 42,320,777 |

What is claimed is:

1. A method of determining likelihood of having a schizophrenia (SZ) endophenotype in a human subject, the method comprising:
   obtaining a sample comprising genomic DNA of the subject;
   determining the presence of an A allele at rs2779400 in the sample;
   wherein the presence of an A allele at rs2779400 indicates that the subject is more likely to have a schizophrenia endophenotype of a lower PANSS Total composite score, a lower PANSS General Psychopathology composite score, a lower G3 score, and a lower G13 score, as compared to a subject who does not have an A allele at rs2779400.

2. The method of claim 1, wherein determining the identity of the nucleotide comprises contacting the sample with a probe specific for a selected allele of the polymorphism, and detecting the formation of complexes between the probe and the selected allele of the polymorphism, wherein the formation of complexes between the probe and the test marker indicates the presence of the selected allele in the sample.

3. The method of the claim 1, wherein determining the identity of an allele comprises determining the identity of the nucleotide at position 31 of SEQ ID NO:66.

4. The method of claim 1, wherein the subject is a patient having or suspected of having SZ.

5. The method of claim 1, wherein the subject has one or more risk factors associated with SZ.

6. The method of claim 5, wherein the risk factors associated with SZ include one or more of: a relative afflicted with a schizophrenia spectrum disorder (SSD); and a genetically based phenotypic trait associated with risk for a SSD.

7. The method of claim 1, further comprising selecting or excluding a subject for enrollment in a clinical trial based on the identity of the allele.

8. The method of claim 1 further comprising stratifying a subject population for analysis of a clinical trial based on the identity of the allele in the subjects.

9. The method of claim 1, further comprising confirming a severity of a SZ endophenotype using psychometric instruments.

10. The method of claim 1, further comprising recording the identity of the allele in a tangible medium.

11. The method of claim 10, wherein the tangible medium comprises a computer-readable disk, a solid state memory device, or an optical storage device.

* * * * *

SEQUENCE LISTING

<160> NUMBER OF SEQ ID NOS: 1894

<210> SEQ ID NO 1
<211> LENGTH: 61
<212> TYPE: DNA
<213> ORGANISM: Homo Sapiens

<400> SEQUENCE: 1
gcagtactca cccaaattgc ttctgtctca rtgataccaa gcactattct ttaatttcct    60
t                                                                    61

<210> SEQ ID NO 2
<211> LENGTH: 61
<212> TYPE: DNA
<213> ORGANISM: Homo Sapiens

<400> SEQUENCE: 2
gcttacttga actgacagaa gatatctgca yactctggga ggattccact ggcctgcaac    60
a                                                                    61

<210> SEQ ID NO 3
<211> LENGTH: 61
<212> TYPE: DNA
<213> ORGANISM: Homo Sapiens

<400> SEQUENCE: 3
gcgcccagcc tgatgagtga ctttaattgc kctatgcttc agtcatctca gctaacacag    60
g                                                                    61

<210> SEQ ID NO 4
<211> LENGTH: 61
<212> TYPE: DNA
<213> ORGANISM: Homo Sapiens

<400> SEQUENCE: 4
ttggcgtatg gttctttagg atgattgaca rtggcagtac ctggactaac gtgactttag    60
c                                                                    61

<210> SEQ ID NO 5
<211> LENGTH: 61
<212> TYPE: DNA
<213> ORGANISM: Homo Sapiens

<400> SEQUENCE: 5
gagacctgga ctttagaccc tctaccccca rttagctgtg agaccttgag caaatcattt    60
c                                                                    61

```
<210> SEQ ID NO 6
<211> LENGTH: 61
<212> TYPE: DNA
<213> ORGANISM: Homo Sapiens
<220> FEATURE:
<221> NAME/KEY: misc_feature
<222> LOCATION: (31)..(31)
<223> OTHER INFORMATION: n is a, c, g, or t

<400> SEQUENCE: 6
gacgctttgt gaattcataa caagggctcc nagtcaccag atcttagagc tgacccagtg      60
c                                                                    61

<210> SEQ ID NO 7
<211> LENGTH: 61
<212> TYPE: DNA
<213> ORGANISM: Homo Sapiens

<400> SEQUENCE: 7
tctttcttag ctgcctggta ttaactcatg sggacgttct ggatcctggg agaatccaga      60
t                                                                    61

<210> SEQ ID NO 8
<211> LENGTH: 61
<212> TYPE: DNA
<213> ORGANISM: Homo Sapiens

<400> SEQUENCE: 8
ttttccctaa cttcagtcat ctgagtaccc yttgctagtt ttcacatgcc cattttctgt      60
c                                                                    61

<210> SEQ ID NO 9
<211> LENGTH: 61
<212> TYPE: DNA
<213> ORGANISM: Homo Sapiens

<400> SEQUENCE: 9
ttgttgagtg atgcatgaca tatgactgtt ygttgtcctc atttgaatgc atgtgccttg      60
a                                                                    61

<210> SEQ ID NO 10
<211> LENGTH: 61
<212> TYPE: DNA
<213> ORGANISM: Homo Sapiens

<400> SEQUENCE: 10
ttggaacagc acccagacag gcctctaaag yacaaagcag aagtacagtg cgtgaactaa      60
c                                                                    61

<210> SEQ ID NO 11
<211> LENGTH: 61
<212> TYPE: DNA
<213> ORGANISM: Homo Sapiens

<400> SEQUENCE: 11
tggttattta ttttgagtcc tagtcagttt yctatcagtc acatttgcca cttagcctta      60
a                                                                    61

<210> SEQ ID NO 12
<211> LENGTH: 61
<212> TYPE: DNA
<213> ORGANISM: Homo Sapiens
```

<400> SEQUENCE: 12
actcatttga actcattaag tcttgatgat sagtaggttt tgtctggca gagaagggt    60
g                                                                  61

<210> SEQ ID NO 13
<211> LENGTH: 61
<212> TYPE: DNA
<213> ORGANISM: Homo Sapiens

<400> SEQUENCE: 13
gaaatttcta caaagaaagt aggctctatc rtttctcgt tgatgtgctt cccatttcaa    60
c                                                                  61

<210> SEQ ID NO 14
<211> LENGTH: 61
<212> TYPE: DNA
<213> ORGANISM: Homo Sapiens

<400> SEQUENCE: 14
aagtcaaagg taagagaggt ctctcagatt rcaacttagg tctccttgat ttcagacatg    60
c                                                                  61

<210> SEQ ID NO 15
<211> LENGTH: 61
<212> TYPE: DNA
<213> ORGANISM: Homo Sapiens

<400> SEQUENCE: 15
gaaaggaaaa ggtacagtgt gtaagcaccc rtcacattta ccaccatcga gtgtctgctg    60
t                                                                  61

<210> SEQ ID NO 16
<211> LENGTH: 61
<212> TYPE: DNA
<213> ORGANISM: Homo Sapiens

<400> SEQUENCE: 16
tgactaggga ggcagagcta cagagatttc rtgaatggac atcactgagg tagcgtacca    60
a                                                                  61

<210> SEQ ID NO 17
<211> LENGTH: 61
<212> TYPE: DNA
<213> ORGANISM: Homo Sapiens

<400> SEQUENCE: 17
gggtcatgag aaataagcct ctggaggctg rcgcttctct actgtgggac cttggctgca    60
t                                                                  61

<210> SEQ ID NO 18
<211> LENGTH: 61
<212> TYPE: DNA
<213> ORGANISM: Homo Sapiens

<400> SEQUENCE: 18
cattggattt caaagcttgc tttttctgtt sgttcttctc tctccttctc tctctgtctc    60
t                                                                  61

<210> SEQ ID NO 19

-continued

```
<211> LENGTH: 61
<212> TYPE: DNA
<213> ORGANISM: Homo Sapiens

<400> SEQUENCE: 19
gcatagtgaa agccgctcac cactggctta rgaaactccc gggaggcagt tgcaaagctt      60
t                                                                     61

<210> SEQ ID NO 20
<211> LENGTH: 61
<212> TYPE: DNA
<213> ORGANISM: Homo Sapiens

<400> SEQUENCE: 20
atgcagggtg ggcataggag aatttacaag sccttttacct ctaagcctct gcagtttgtt     60
```

```
atgcagggtg ggcataggag aatttacaag sccttttacct ctaagcctct gcagtttgtt     60
t                                                                     61

<210> SEQ ID NO 21
<211> LENGTH: 61
<212> TYPE: DNA
<213> ORGANISM: Homo Sapiens

<400> SEQUENCE: 21
ctgaggtatt ctcaagttct agaaccacgg ycttaatgat taccccttgaa aagtcactat     60 a                                                                     61

<210> SEQ ID NO 22
<211> LENGTH: 61
<212> TYPE: DNA
<213> ORGANISM: Homo Sapiens

<400> SEQUENCE: 22
cacctggctg tcagggatgg ggagcctcat sggtgaaaga gggttgtgat ggcataattt      60
a                                                                     61

<210> SEQ ID NO 23
<211> LENGTH: 61
<212> TYPE: DNA
<213> ORGANISM: Homo Sapiens

<400> SEQUENCE: 23
aattcacagg catattcttg agggaacata raagtaacca gtaacgctgc tagtggcaat      60
c                                                                     61

<210> SEQ ID NO 24
<211> LENGTH: 61
<212> TYPE: DNA
<213> ORGANISM: Homo Sapiens

<400> SEQUENCE: 24
tctaaaataa cttgctttat gtttgagaaa mgattgttca gtagtctgta agtagacttg      60
t                                                                     61

<210> SEQ ID NO 25
<211> LENGTH: 61
<212> TYPE: DNA
<213> ORGANISM: Homo Sapiens

<400> SEQUENCE: 25
taatactaga tgactcttta tcctcatcaa raggcttaga cttcagtcct ttaccacctg      60
``` c                                                              61

<210> SEQ ID NO 26
<211> LENGTH: 61
<212> TYPE: DNA
<213> ORGANISM: Homo Sapiens

<400> SEQUENCE: 26
gactcgctgg ggaaagatgc tcctgctggg yggggaacaa ccctgccag ccccacgctg    60 a                                                              61

<210> SEQ ID NO 27
<211> LENGTH: 61
<212> TYPE: DNA
<213> ORGANISM: Homo Sapiens

<400> SEQUENCE: 27
gggcagaatt ctggcagttc tctgtggtct ygtttttaca aatagaacca gggacagggg    60
t                                                              61

<210> SEQ ID NO 28
<211> LENGTH: 61
<212> TYPE: DNA
<213> ORGANISM: Homo Sapiens

<400> SEQUENCE: 28
atttaagtct agtgaatagg gagttgctat ytgaaaaata tcaaatttt cctttatgaa    60 a                                                              61

<210> SEQ ID NO 29
<211> LENGTH: 61
<212> TYPE: DNA
<213> ORGANISM: Homo Sapiens

<400> SEQUENCE: 29
caatcagcta ttgacccaaa gctcacagct ratggacttg ccaatgggcc taataatgaa    60
a                                                              61

<210> SEQ ID NO 30
<211> LENGTH: 61
<212> TYPE: DNA
<213> ORGANISM: Homo Sapiens

<400> SEQUENCE: 30
caatgtcctc cagaacctga aatttgaatt yggttttttg gcatcataag tggcttctat    60
g                                                              61

<210> SEQ ID NO 31
<211> LENGTH: 61
<212> TYPE: DNA
<213> ORGANISM: Homo Sapiens

<400> SEQUENCE: 31
agattgtagg cttggtgtc agacatttga yattagaatt ctggctttt taccagcccc    60 t                                                              61

<210> SEQ ID NO 32
<211> LENGTH: 61
<212> TYPE: DNA
<213> ORGANISM: Homo Sapiens -continued

```
<400> SEQUENCE: 32
tatgtaagtg ggatcctaca gaaagctatt rcttgtggtt gactactctt gctcaccatg    60
t                                                                   61

<210> SEQ ID NO 33
<211> LENGTH: 61
<212> TYPE: DNA
<213> ORGANISM: Homo Sapiens

<400> SEQUENCE: 33 gatcatttttt cattcttaca acaggattta wagctttcat gggctctatc ccttgcttat   60
t                                                                   61

<210> SEQ ID NO 34
<211> LENGTH: 61
<212> TYPE: DNA
<213> ORGANISM: Homo Sapiens

<400> SEQUENCE: 34
gacagaggca ggtttacctc gagactgaaa rttaagactc ctcatttgta tgggtcttct    60
t                                                                   61

<210> SEQ ID NO 35
<211> LENGTH: 61
<212> TYPE: DNA
<213> ORGANISM: Homo Sapiens

<400> SEQUENCE: 35
ttgccattgt cccttataaa gaatggcatc yataatttga caaaacattc agaacatagt    60
g                                                                   61

<210> SEQ ID NO 36
<211> LENGTH: 61
<212> TYPE: DNA
<213> ORGANISM: Homo Sapiens

<400> SEQUENCE: 36
gaggaaataa tttgcccagg taactaagga rtgatggttc caggaatggc tataatatac    60
t                                                                   61

<210> SEQ ID NO 37
<211> LENGTH: 61
<212> TYPE: DNA
<213> ORGANISM: Homo Sapiens

<400> SEQUENCE: 37
ccagtcaaat tatattatag gcccatccta ygcaagtata acataaccac atcttaacta    60
a                                                                   61

<210> SEQ ID NO 38
<211> LENGTH: 61
<212> TYPE: DNA
<213> ORGANISM: Homo Sapiens

<400> SEQUENCE: 38
agtggcaagt gcagagtaat tcttcctaaa rggtgagaag agagaaagga aattattttg    60
c                                                                   61

<210> SEQ ID NO 39
```

```
<211> LENGTH: 61
<212> TYPE: DNA
<213> ORGANISM: Homo Sapiens

<400> SEQUENCE: 39
atcaattctc agaccaccag tgctgtaaaa kactactcca ctcttctttt taaaatccca      60
a                                                                     61

<210> SEQ ID NO 40
<211> LENGTH: 61
<212> TYPE: DNA
<213> ORGANISM: Homo Sapiens

<400> SEQUENCE: 40
agttttctgt tgttatcatc gctgctcaac kctaacagaa gctcctgtgt tggtgtttgt      60
t                                                                     61

<210> SEQ ID NO 41
<211> LENGTH: 61
<212> TYPE: DNA
<213> ORGANISM: Homo Sapiens

<400> SEQUENCE: 41
accagagact gaagaacact tttggaagca yaaaatctgt gattattatc tagctttcca      60
g                                                                     61

<210> SEQ ID NO 42
<211> LENGTH: 61
<212> TYPE: DNA
<213> ORGANISM: Homo Sapiens

<400> SEQUENCE: 42
ctacctttgc agctagagct aaatgatccc ycaggaatgt ttccaggtca tgaaggaaca      60
t                                                                     61

<210> SEQ ID NO 43
<211> LENGTH: 61
<212> TYPE: DNA
<213> ORGANISM: Homo Sapiens

<400> SEQUENCE: 43
agaagaccaa aaagcttgga ggattgtgca rttttagaga ataaaacatc aatatgacct      60
a                                                                     61

<210> SEQ ID NO 44
<211> LENGTH: 61
<212> TYPE: DNA
<213> ORGANISM: Homo Sapiens

<400> SEQUENCE: 44
cttttaattg ttgatgtcat catcaaggaa katagtggag tcttaactgt tttccccaaa      60
a                                                                     61

<210> SEQ ID NO 45
<211> LENGTH: 61
<212> TYPE: DNA
<213> ORGANISM: Homo Sapiens

<400> SEQUENCE: 45
tcgtaaaaag gatactgagc aacacaagaa ygattcctaa ccttagggag cttaaagtct      60
``` t                                                              61

<210> SEQ ID NO 46
<211> LENGTH: 61
<212> TYPE: DNA
<213> ORGANISM: Homo Sapiens

<400> SEQUENCE: 46
cctttaaatg gaagagttca atcactcatt yggttcgtat gcagttttc cttatttcac    60 t                                                              61

<210> SEQ ID NO 47
<211> LENGTH: 61
<212> TYPE: DNA
<213> ORGANISM: Homo Sapiens

<400> SEQUENCE: 47
tactgcttac agagtatttc tagaccacga yttagggaga gaaatcccag atggagctca    60
g                                                              61

<210> SEQ ID NO 48
<211> LENGTH: 61
<212> TYPE: DNA
<213> ORGANISM: Homo Sapiens

<400> SEQUENCE: 48
atccatagtc tttcattctt cctagattca rtaattcctt tgcttgtcta tttagttttc    60
t                                                              61

<210> SEQ ID NO 49
<211> LENGTH: 61
<212> TYPE: DNA
<213> ORGANISM: Homo Sapiens

<400> SEQUENCE: 49
aatcagggtg aaaaccagca gcctagttac ygctagagga tcagaatggg agtggagctg    60
t                                                              61

<210> SEQ ID NO 50
<211> LENGTH: 61
<212> TYPE: DNA
<213> ORGANISM: Homo Sapiens

<400> SEQUENCE: 50
atagagcact gttataaatg cctccttgct ygtccgtatt ccccaataga ctctaagctt    60
t                                                              61

<210> SEQ ID NO 51
<211> LENGTH: 61
<212> TYPE: DNA
<213> ORGANISM: Homo Sapiens

<400> SEQUENCE: 51
caggtcatca gcagatattg agttgccagg mgagcataat tagagaaaag acattcagat    60
c                                                              61

<210> SEQ ID NO 52
<211> LENGTH: 61
<212> TYPE: DNA
<213> ORGANISM: Homo Sapiens -continued

```
<400> SEQUENCE: 52
aaggagtaag aagcatgtat agttcacctc mttagtaata aaccttctta aaacagggag    60
a                                                                   61

<210> SEQ ID NO 53
<211> LENGTH: 61
<212> TYPE: DNA
<213> ORGANISM: Homo Sapiens

<400> SEQUENCE: 53
tatgtttgca tctgtctaca atatgacttg rgccaaatct gatctggcca tggcatcctg    60
a                                                                   61

<210> SEQ ID NO 54
<211> LENGTH: 61
<212> TYPE: DNA
<213> ORGANISM: Homo Sapiens

<400> SEQUENCE: 54 ggggagatt aatgtttctc acaatgccat rtaccaaaca cagagttgac ttttcagtac     60
c                                                                   61

<210> SEQ ID NO 55
<211> LENGTH: 61
<212> TYPE: DNA
<213> ORGANISM: Homo Sapiens

<400> SEQUENCE: 55
gaatatggat aagatcctag aagcagcccc rgatatgtat ccacagtaga agcttaatgt    60
a                                                                   61

<210> SEQ ID NO 56
<211> LENGTH: 61
<212> TYPE: DNA
<213> ORGANISM: Homo Sapiens

<400> SEQUENCE: 56
tctgtacagt agcttttgtc cagcttcttc rttagttta gtgggatttc tctgagcagc    60
g                                                                   61

<210> SEQ ID NO 57
<211> LENGTH: 61
<212> TYPE: DNA
<213> ORGANISM: Homo Sapiens

<400> SEQUENCE: 57
catttaatcc tcacaaggac cctgtgacag maagtactgt tgtatatgaa gaagctgagg    60
c                                                                   61

<210> SEQ ID NO 58
<211> LENGTH: 61
<212> TYPE: DNA
<213> ORGANISM: Homo Sapiens

<400> SEQUENCE: 58
ctgtatcccc ttccctgccc tatgccttga wgagttaagc gtaagagccc ttgttcagcc    60
t                                                                   61

<210> SEQ ID NO 59
```

```
<211> LENGTH: 61
<212> TYPE: DNA
<213> ORGANISM: Homo Sapiens

<400> SEQUENCE: 59
ctcatctcct caactgccct tcattcactt kttttaatca cataaatcaa tgtttgaact    60
a                                                                    61

<210> SEQ ID NO 60
<211> LENGTH: 61
<212> TYPE: DNA
<213> ORGANISM: Homo Sapiens

<400> SEQUENCE: 60
tctttctcct aacctgaata cgtcatatta mcatttcaat actctttcct tcattaggtg    60
c                                                                    61

<210> SEQ ID NO 61
<211> LENGTH: 61
<212> TYPE: DNA
<213> ORGANISM: Homo Sapiens

<400> SEQUENCE: 61
gacctggtct agaaattgga gaagttccag ygggagatcc tcttccacga ggaaatggct    60
c                                                                    61

<210> SEQ ID NO 62
<211> LENGTH: 61
<212> TYPE: DNA
<213> ORGANISM: Homo Sapiens

<400> SEQUENCE: 62
aaagaaaccc ctacggaatc aatccctcac rtacttttta tttgcaaaaa ggcaactgag    60
t                                                                    61

<210> SEQ ID NO 63
<211> LENGTH: 61
<212> TYPE: DNA
<213> ORGANISM: Homo Sapiens

<400> SEQUENCE: 63
ctcaataaat gtgcattgat ttttgactgg wtttccttat ttaggctaat aatattgatg    60
t                                                                    61

<210> SEQ ID NO 64
<211> LENGTH: 61
<212> TYPE: DNA
<213> ORGANISM: Homo Sapiens

<400> SEQUENCE: 64
attcagattt agttgatcca agctctaggt sagatttctg tagttctctt tgccctgttc    60
t                                                                    61

<210> SEQ ID NO 65
<211> LENGTH: 61
<212> TYPE: DNA
<213> ORGANISM: Homo Sapiens

<400> SEQUENCE: 65
aagatttcaa gtgtttggta ctggaggctc ycagagggca gaacagtatc tgttttgttc    60
```

-continued a 61

<210> SEQ ID NO 66
<211> LENGTH: 61
<212> TYPE: DNA
<213> ORGANISM: Homo Sapiens

<400> SEQUENCE: 66
acctggctga aaactagcat ttaaccagta wctagtaact ctgtgcgagc tattggaggc 60
a 61

<210> SEQ ID NO 67
<211> LENGTH: 61
<212> TYPE: DNA
<213> ORGANISM: Homo Sapiens

<400> SEQUENCE: 67
gagaaatgta attacagagc acttataaaa yctttcagta ctttagcaac cacaacttat 60
t 61

<210> SEQ ID NO 68
<211> LENGTH: 61
<212> TYPE: DNA
<213> ORGANISM: Homo Sapiens

<400> SEQUENCE: 68
aagtcatgtt atcttttccg cttaacacat ktatcctggc ttgaattaaa tgtctgtaaa 60
t 61

<210> SEQ ID NO 69
<211> LENGTH: 61
<212> TYPE: DNA
<213> ORGANISM: Homo Sapiens

<400> SEQUENCE: 69
ctcattctcc catcacacca tcggtctctg raaaaaaatg gtcccttcca cgactatatt 60
c 61

<210> SEQ ID NO 70
<211> LENGTH: 61
<212> TYPE: DNA
<213> ORGANISM: Homo Sapiens

<400> SEQUENCE: 70
ataaattaga tctgcaaaca cactttagct wtgctgatga aaataattta gaataaagaa 60
g 61

<210> SEQ ID NO 71
<211> LENGTH: 61
<212> TYPE: DNA
<213> ORGANISM: Homo Sapiens

<400> SEQUENCE: 71
ccttcagtca ttttgcaaac ctcaatgttc ygaattatga gctaactgtt ttggaagtga 60
a 61

<210> SEQ ID NO 72
<211> LENGTH: 61
<212> TYPE: DNA
<213> ORGANISM: Homo Sapiens

<400> SEQUENCE: 72

```
gatgtgagct catcaagaat gctcagggga mgtttcttct tggaaggtcc agttaagctg    60
a                                                                    61
```

<210> SEQ ID NO 73
<211> LENGTH: 61
<212> TYPE: DNA
<213> ORGANISM: Homo Sapiens

<400> SEQUENCE: 73

```
gagcaaatat gcttcactct taacaaacac wtacttcaca acattcccac tgacagaagc    60
t                                                                    61
```

<210> SEQ ID NO 74
<211> LENGTH: 61
<212> TYPE: DNA
<213> ORGANISM: Homo Sapiens

<400> SEQUENCE: 74

```
agtccacact gaatgaagat ggtgaatact raggtttccc acccactctt ggaactggct    60
a                                                                    61
```

<210> SEQ ID NO 75
<211> LENGTH: 61
<212> TYPE: DNA
<213> ORGANISM: Homo Sapiens

<400> SEQUENCE: 75

```
ttatgtctat ctatagacag atatcctgtg racttcgttt gtattttgta tccacaaaag    60
c                                                                    61
```

<210> SEQ ID NO 76
<211> LENGTH: 61
<212> TYPE: DNA
<213> ORGANISM: Homo Sapiens

<400> SEQUENCE: 76

```
tggaactcct ttgataattt ttggctggat rtgcacgtac acatttacct tcagtcacac    60
a                                                                    61
```

<210> SEQ ID NO 77
<211> LENGTH: 61
<212> TYPE: DNA
<213> ORGANISM: Homo Sapiens

<400> SEQUENCE: 77

```
aagaaaaaaa actagcgtat taagtacatt ygccaaacct ccttttcttg acagatggtc    60
a                                                                    61
```

<210> SEQ ID NO 78
<211> LENGTH: 61
<212> TYPE: DNA
<213> ORGANISM: Homo Sapiens

<400> SEQUENCE: 78

```
cagccacaga gtggggcttg cagattttgg raagaagagt gagtgcagtg ctctgggcag    60
a                                                                    61
```

<210> SEQ ID NO 79
<211> LENGTH: 61

```
<212> TYPE: DNA
<213> ORGANISM: Homo Sapiens

<400> SEQUENCE: 79
ctacaggaca ggcaaaggag tattttgttg saggataaga tgcttgatat tatgaaacat    60
a                                                                   61

<210> SEQ ID NO 80
<211> LENGTH: 61
<212> TYPE: DNA
<213> ORGANISM: Homo Sapiens

<400> SEQUENCE: 80
acgaggctta aaataatat tgcagtcatc kctggcagtc tgaaagctgt gtacataccc    60
a                                                                   61

<210> SEQ ID NO 81
<211> LENGTH: 61
<212> TYPE: DNA
<213> ORGANISM: Homo Sapiens

<400> SEQUENCE: 81
actttcagaa ggaccaacca cgaaaaccac yctgatcttt tttgttgtcg ttgtttgttt    60
g                                                                   61

<210> SEQ ID NO 82
<211> LENGTH: 61
<212> TYPE: DNA
<213> ORGANISM: Homo Sapiens

<400> SEQUENCE: 82
tatagtaggg ggaattcagg tttatagatg ragtctgcct agttctttat ctccataggg    60
c                                                                   61

<210> SEQ ID NO 83
<211> LENGTH: 61
<212> TYPE: DNA
<213> ORGANISM: Homo Sapiens

<400> SEQUENCE: 83
atgaatatgg tagcaagtgt cttccttcct ktgaaatatg agttttcatc agctgttgga    60
t                                                                   61

<210> SEQ ID NO 84
<211> LENGTH: 61
<212> TYPE: DNA
<213> ORGANISM: Homo Sapiens

<400> SEQUENCE: 84
aacaaatgtg tggtctcatg gtttgaaaaa ytgtgaatca atcatattg catatgaggt     60
c                                                                   61

<210> SEQ ID NO 85
<211> LENGTH: 61
<212> TYPE: DNA
<213> ORGANISM: Homo Sapiens

<400> SEQUENCE: 85
taagtgatat ttaccaaaaa caggcttgct yagtttggaa gattgtaaag aggaaactct    60
t                                                                   61
```

<210> SEQ ID NO 86
<211> LENGTH: 61
<212> TYPE: DNA
<213> ORGANISM: Homo Sapiens

<400> SEQUENCE: 86
gactgatgac gttgtcactt tggagtagct kgtccgatgc acatcaggta agcaagtgca    60
t                                                                   61

<210> SEQ ID NO 87
<211> LENGTH: 61
<212> TYPE: DNA
<213> ORGANISM: Homo Sapiens

<400> SEQUENCE: 87
atataatatc tcttgacacc cttccactt rttgccaccc tattttcctt cttccttta     60
t                                                                   61

<210> SEQ ID NO 88
<211> LENGTH: 61
<212> TYPE: DNA
<213> ORGANISM: Homo Sapiens

<400> SEQUENCE: 88
catcctacct actcaatcaa acctttagc rccagcctga gaaacagaaa acatgtggag    60
g                                                                   61

<210> SEQ ID NO 89
<211> LENGTH: 61
<212> TYPE: DNA
<213> ORGANISM: Homo Sapiens

<400> SEQUENCE: 89
tattcatctt tgcgtccacc acgatattta stagattgtc tgcctcataa taggcattca    60
g                                                                   61

<210> SEQ ID NO 90
<211> LENGTH: 61
<212> TYPE: DNA
<213> ORGANISM: Homo Sapiens

<400> SEQUENCE: 90
tattgaactt gagacatgta attggggttt ygtaactagc tactcactat atagctattg    60
g                                                                   61

<210> SEQ ID NO 91
<211> LENGTH: 61
<212> TYPE: DNA
<213> ORGANISM: Homo Sapiens

<400> SEQUENCE: 91
tgattttttt caatccacag gaccagaaca mggcctggta tatagtaggt catcattaaa    60
g                                                                   61

<210> SEQ ID NO 92
<211> LENGTH: 61
<212> TYPE: DNA
<213> ORGANISM: Homo Sapiens

<400> SEQUENCE: 92

```
cagaatttca tcctggctaa caaactcata scaaattagg ctctctgaca ttggattatt    60
t                                                                    61

<210> SEQ ID NO 93
<211> LENGTH: 61
<212> TYPE: DNA
<213> ORGANISM: Homo Sapiens

<400> SEQUENCE: 93
ctaaaacctg ctgtgggcgt cacacttctc ygggagcatc attgggcagc tcagccggcc    60
a                                                                    61

<210> SEQ ID NO 94
<211> LENGTH: 61
<212> TYPE: DNA
<213> ORGANISM: Homo Sapiens

<400> SEQUENCE: 94
atcttgacaa atttcctaaa gagaaggact yaggactgtt tcttataggg tggctggatt    60
t                                                                    61

<210> SEQ ID NO 95
<211> LENGTH: 61
<212> TYPE: DNA
<213> ORGANISM: Homo Sapiens

<400> SEQUENCE: 95
tatgcttcat catattagcc tttacctctc yagacaaagt tcatccacct atttggtaag    60
t                                                                    61

<210> SEQ ID NO 96
<211> LENGTH: 61
<212> TYPE: DNA
<213> ORGANISM: Homo Sapiens

<400> SEQUENCE: 96
cttgcattcg aatgttccca ttttataggc ragaatacca acaaacagaa gttaagaact    60
t                                                                    61

<210> SEQ ID NO 97
<211> LENGTH: 61
<212> TYPE: DNA
<213> ORGANISM: Homo Sapiens

<400> SEQUENCE: 97
ttgaaccctg cattttccac tataactagc rtctaataaa aaccaaccaa gaatatttag    60
t                                                                    61

<210> SEQ ID NO 98
<211> LENGTH: 61
<212> TYPE: DNA
<213> ORGANISM: Homo Sapiens

<400> SEQUENCE: 98
ctttctgtca acttgatata tactgagctt yccattaata aaaagaaac taagacgttt     60
c                                                                    61

<210> SEQ ID NO 99
<211> LENGTH: 61
```

```
<212> TYPE: DNA
<213> ORGANISM: Homo Sapiens

<400> SEQUENCE: 99
agacagtaca agttccatag ctggtcaccc rcattcacac cccagcagtt ctacaccctt    60
g                                                                   61

<210> SEQ ID NO 100
<211> LENGTH: 61
<212> TYPE: DNA
<213> ORGANISM: Homo Sapiens

<400> SEQUENCE: 100
catacaagtg gaaagaata  acatttgat  wtttaaagtc aacttttgat agactttatt    60
a                                                                   61

<210> SEQ ID NO 101
<211> LENGTH: 61
<212> TYPE: DNA
<213> ORGANISM: Homo Sapiens

<400> SEQUENCE: 101
ggaatattgg ttttttgac  caatttcaaa rtgccgtatc aatgctgttc ttttctttta    60
a                                                                   61

<210> SEQ ID NO 102
<211> LENGTH: 61
<212> TYPE: DNA
<213> ORGANISM: Homo Sapiens

<400> SEQUENCE: 102
caggaaatgt agctaaatga atgaatgagg ycaactctat cacatgatgc ttctagtaac    60
a                                                                   61

<210> SEQ ID NO 103
<211> LENGTH: 61
<212> TYPE: DNA
<213> ORGANISM: Homo Sapiens

<400> SEQUENCE: 103
gtttaggtag atgtcataca tttggatgaa kaagttccct tctattccta gatgaaagtt    60
g                                                                   61

<210> SEQ ID NO 104
<211> LENGTH: 61
<212> TYPE: DNA
<213> ORGANISM: Homo Sapiens

<400> SEQUENCE: 104
attcatgaag ctacaaatca tgactagatt wctggtccca actctgccac tttatggcct    60
g                                                                   61

<210> SEQ ID NO 105
<211> LENGTH: 61
<212> TYPE: DNA
<213> ORGANISM: Homo Sapiens

<400> SEQUENCE: 105 tggttttttcc tgtggctcgg gcctcagctt ygtatcacct ctgcagagag gctctccgtg    60
g                                                                    61
```

<210> SEQ ID NO 106
<211> LENGTH: 61
<212> TYPE: DNA
<213> ORGANISM: Homo Sapiens

<400> SEQUENCE: 106
gccaggagca ggtctggggc ccaccttctg ygttgcgtag accaggcttt ggtcggctgt    60
g                                                                   61

<210> SEQ ID NO 107
<211> LENGTH: 61
<212> TYPE: DNA
<213> ORGANISM: Homo Sapiens

<400> SEQUENCE: 107
acccaaaagt gactgggctg actgccaaga katggctttta aaccagaaga aatggagatg    60
t                                                                   61

<210> SEQ ID NO 108
<211> LENGTH: 61
<212> TYPE: DNA
<213> ORGANISM: Homo Sapiens

<400> SEQUENCE: 108
gaccagagga cactggcttg tagaacgatg yggaaatgga gacagacact tcgaaggtg    60
a                                                                   61

<210> SEQ ID NO 109
<211> LENGTH: 61
<212> TYPE: DNA
<213> ORGANISM: Homo Sapiens

<400> SEQUENCE: 109
tctcttagca aagatctcaa atcgctgcac magaacacaa gcaacagctc aaaggctgag    60
t                                                                   61

<210> SEQ ID NO 110
<211> LENGTH: 61
<212> TYPE: DNA
<213> ORGANISM: Homo Sapiens

<400> SEQUENCE: 110
cagggaatag tccattaggg aaagtgttgg ytgggggctt tatatatggt catatgctac    60
t                                                                   61

<210> SEQ ID NO 111
<211> LENGTH: 61
<212> TYPE: DNA
<213> ORGANISM: Homo Sapiens

<400> SEQUENCE: 111
accttggata tagcaggaat atttgtggac ygagtgagga aatgaataga gatggttcct    60
a                                                                   61

<210> SEQ ID NO 112
<211> LENGTH: 61
<212> TYPE: DNA
<213> ORGANISM: Homo Sapiens

<400> SEQUENCE: 112

```
gttatatctc tgattcattc aaattggaag ytttgggaat cttgctgtta ttgttgtcaa    60
c                                                                    61

<210> SEQ ID NO 113
<211> LENGTH: 61
<212> TYPE: DNA
<213> ORGANISM: Homo Sapiens

<400> SEQUENCE: 113
ttagtccagg tgagcaaatt accctgaata rgtgtgtagg ctccctccct gccaccgagg    60
g                                                                    61

<210> SEQ ID NO 114
<211> LENGTH: 61
<212> TYPE: DNA
<213> ORGANISM: Homo Sapiens

<400> SEQUENCE: 114
atactcagcc gagataccccc cgatttgtta ygggatggca aaaagatatt taaggctatt   60
c                                                                    61

<210> SEQ ID NO 115
<211> LENGTH: 61
<212> TYPE: DNA
<213> ORGANISM: Homo Sapiens

<400> SEQUENCE: 115
aactgttttc aggttgcaac agacaaggca raaaacccttt agcagtgaaa ctgaaaagat   60
t                                                                    61

<210> SEQ ID NO 116
<211> LENGTH: 61
<212> TYPE: DNA
<213> ORGANISM: Homo Sapiens

<400> SEQUENCE: 116
ttgatttatt agaaggattt ggcatcagga rcataaaaat ggttaatggg tgctgtaact    60
t                                                                    61

<210> SEQ ID NO 117
<211> LENGTH: 61
<212> TYPE: DNA
<213> ORGANISM: Homo Sapiens

<400> SEQUENCE: 117
aaaagtttat tcagttttaa tttctggcta sagcttcttt gctaagaata acaaatactc    60
a                                                                    61

<210> SEQ ID NO 118
<211> LENGTH: 61
<212> TYPE: DNA
<213> ORGANISM: Homo Sapiens

<400> SEQUENCE: 118
tcacacattg cactcagatc tagcctctta ygttttaacc ttagtctccc ccttaaatct    60
c                                                                    61

<210> SEQ ID NO 119
<211> LENGTH: 61
```

```
<212> TYPE: DNA
<213> ORGANISM: Homo Sapiens

<400> SEQUENCE: 119
ccctaatagc aggccttgaa tagtgcaaaa yagtcttctt aaatacatta gtctttcttg    60
t                                                                  61

<210> SEQ ID NO 120
<211> LENGTH: 61
<212> TYPE: DNA
<213> ORGANISM: Homo Sapiens

<400> SEQUENCE: 120
aaacaacgag ttatgcctct catggaactc rgagaggaaa gcaaactggg agactaactg    60
a                                                                  61

<210> SEQ ID NO 121
<211> LENGTH: 61
<212> TYPE: DNA
<213> ORGANISM: Homo Sapiens

<400> SEQUENCE: 121
tgtaaacaca ttctttattg atatgcacat mgtgattctg atttggaata ttaagggtcc    60
c                                                                  61

<210> SEQ ID NO 122
<211> LENGTH: 61
<212> TYPE: DNA
<213> ORGANISM: Homo Sapiens

<400> SEQUENCE: 122
ttctggaaag aagattaaaa atgtcaaaaa mggtgctaga ctgtgaagat gatatcccct    60
a                                                                  61

<210> SEQ ID NO 123
<211> LENGTH: 61
<212> TYPE: DNA
<213> ORGANISM: Homo Sapiens

<400> SEQUENCE: 123
tacaaaataa agataacaag agtacctgtc wgatacagtt ataacaaaag gcaaatgagt    60
t                                                                  61

<210> SEQ ID NO 124
<211> LENGTH: 61
<212> TYPE: DNA
<213> ORGANISM: Homo Sapiens

<400> SEQUENCE: 124
atatatgaag ttgggggaca cagacattcc raaaatagcc agactctcat ttatctaaaa    60
t                                                                  61

<210> SEQ ID NO 125
<211> LENGTH: 61
<212> TYPE: DNA
<213> ORGANISM: Homo Sapiens

<400> SEQUENCE: 125
tgagcacttt actgtgaggc aggtactacc rtttccattg tacagatggg ataatgaagg    60
c                                                                  61
```

<210> SEQ ID NO 126
<211> LENGTH: 61
<212> TYPE: DNA
<213> ORGANISM: Homo Sapiens

<400> SEQUENCE: 126
ataaagcgaa gcaattcctg caaatattca rgtattcacc ttttgagaaa ccttaaaagg    60
a                                                                   61

<210> SEQ ID NO 127
<211> LENGTH: 61
<212> TYPE: DNA
<213> ORGANISM: Homo Sapiens

<400> SEQUENCE: 127
cagtcagggt ccccatcaca cagccagctc ygggagacac aagtcacgtg atcgtggcaa    60
a                                                                   61

<210> SEQ ID NO 128
<211> LENGTH: 61
<212> TYPE: DNA
<213> ORGANISM: Homo Sapiens

<400> SEQUENCE: 128
gaaaatttgg tgttttcac tgaagccttt kttatatttt tgacatataa taattgcata    60
t                                                                   61

<210> SEQ ID NO 129
<211> LENGTH: 61
<212> TYPE: DNA
<213> ORGANISM: Homo Sapiens

<400> SEQUENCE: 129
tattttcttt tttaaactaa tgccatagtt yaattattta agccagacag ctaaaactgc    60
t                                                                   61

<210> SEQ ID NO 130
<211> LENGTH: 61
<212> TYPE: DNA
<213> ORGANISM: Homo Sapiens

<400> SEQUENCE: 130
cattcccgtc tatttggttg tagataaaag rgataagggg cctctttctc ataactact    60 t                                                                   61

<210> SEQ ID NO 131
<211> LENGTH: 61
<212> TYPE: DNA
<213> ORGANISM: Homo Sapiens

<400> SEQUENCE: 131
attacatttc ttatcaagta agaataaaca wctcatcatc aagtaaagta atgtgactt    60 t                                                                   61

<210> SEQ ID NO 132
<211> LENGTH: 61
<212> TYPE: DNA
<213> ORGANISM: Homo Sapiens

<400> SEQUENCE: 132

```
tttttcaacg tggtaccaca aatgtggcca saaggatttt cataatggga tattgtacat    60
a                                                                    61
```

<210> SEQ ID NO 133
<211> LENGTH: 61
<212> TYPE: DNA
<213> ORGANISM: Homo Sapiens

<400> SEQUENCE: 133

```
aattacctct gccatggata cttgcaatag stagcaaact ggtctccctg gttcaactcc    60
t                                                                    61
```

<210> SEQ ID NO 134
<211> LENGTH: 61
<212> TYPE: DNA
<213> ORGANISM: Homo Sapiens

<400> SEQUENCE: 134

```
tggcataggg actacgttcc aggagccagt rttccaagag gaccagaaag aagttgtata    60
a                                                                    61
```

<210> SEQ ID NO 135
<211> LENGTH: 61
<212> TYPE: DNA
<213> ORGANISM: Homo Sapiens

<400> SEQUENCE: 135

```
caataactta aatacatcag cagagaaaac rttatgaggc ataaggacca tgtggttctg    60
g                                                                    61
```

<210> SEQ ID NO 136
<211> LENGTH: 61
<212> TYPE: DNA
<213> ORGANISM: Homo Sapiens

<400> SEQUENCE: 136

```
aattttagga attagtgaga gttacatctt watccatttt tactttagaa cttattttt     60
t                                                                    61
```

<210> SEQ ID NO 137
<211> LENGTH: 61
<212> TYPE: DNA
<213> ORGANISM: Homo Sapiens

<400> SEQUENCE: 137

```
tctcatattt gagatagaat acctatagtc yatcctggag gggaagaaag catgcaaaaa    60
t                                                                    61
```

<210> SEQ ID NO 138
<211> LENGTH: 61
<212> TYPE: DNA
<213> ORGANISM: Homo Sapiens

<400> SEQUENCE: 138

```
ttatctacag acaagtacac cccccccagtt kaaaaattaa gagcaataaa agtctaagtt   60
g                                                                    61
```

<210> SEQ ID NO 139
<211> LENGTH: 61

```
<212> TYPE: DNA
<213> ORGANISM: Homo Sapiens

<400> SEQUENCE: 139
tcctagtgca gaacacagat cctctgtggg yaaaactagg tatattgttc aatggcccca      60
t                                                                      61

<210> SEQ ID NO 140
<211> LENGTH: 61
<212> TYPE: DNA
<213> ORGANISM: Homo Sapiens

<400> SEQUENCE: 140
acaggtgtct ctgtaattgt gatacgttgg kaaaattcac actgttaaat gagcctcaaa      60
t                                                                      61

<210> SEQ ID NO 141
<211> LENGTH: 61
<212> TYPE: DNA
<213> ORGANISM: Homo Sapiens

<400> SEQUENCE: 141
tctccataat atttgtttaa attgaccaca yggttagaaa tgagaaatct aagattttg       60 t                                                                      61

<210> SEQ ID NO 142
<211> LENGTH: 61
<212> TYPE: DNA
<213> ORGANISM: Homo Sapiens

<400> SEQUENCE: 142
aaatatgttt atgtgtatgt gtaccttttt yctacatttc ttctgttaga gtttaaggac      60
t                                                                      61

<210> SEQ ID NO 143
<211> LENGTH: 61
<212> TYPE: DNA
<213> ORGANISM: Homo Sapiens

<400> SEQUENCE: 143
gtggtggcct cataccatag tagctgctta sttaattatg actaatataa ggaggtatag      60
g                                                                      61

<210> SEQ ID NO 144
<211> LENGTH: 61
<212> TYPE: DNA
<213> ORGANISM: Homo Sapiens

<400> SEQUENCE: 144
aaatatagca gctacaatct aatttcattg raagtctcct ccaaatcaca gaagtgccac      60
t                                                                      61

<210> SEQ ID NO 145
<211> LENGTH: 61
<212> TYPE: DNA
<213> ORGANISM: Homo Sapiens

<400> SEQUENCE: 145
aacttattat ttgttggagt ttgaaactta stgaaggttt aatcaggtac catatgttgt      60
t                                                                      61
```

<210> SEQ ID NO 146
<211> LENGTH: 61
<212> TYPE: DNA
<213> ORGANISM: Homo Sapiens

<400> SEQUENCE: 146
ataggtggct gtgttagcag actgaagtct stggtccagg attggagcct gatcattttt    60
a    61

<210> SEQ ID NO 147
<211> LENGTH: 61
<212> TYPE: DNA
<213> ORGANISM: Homo Sapiens

<400> SEQUENCE: 147
ctaaagcaga gaaagaacat cccagtgaaa mtcaatgggg aagtcacaac cacagcgaat    60
c    61

<210> SEQ ID NO 148
<211> LENGTH: 61
<212> TYPE: DNA
<213> ORGANISM: Homo Sapiens

<400> SEQUENCE: 148
agtatgtcct ccatcccaat tacacctggc kttataaaat gaatgtacat tttctatttg    60
c    61

<210> SEQ ID NO 149
<211> LENGTH: 61
<212> TYPE: DNA
<213> ORGANISM: Homo Sapiens

<400> SEQUENCE: 149
aacaatggca gtgtaacatt tcacagtaat mcagctggcc caaaatttta aagatttaat    60
a    61

<210> SEQ ID NO 150
<211> LENGTH: 61
<212> TYPE: DNA
<213> ORGANISM: Homo Sapiens

<400> SEQUENCE: 150
gacatcttta aggagtcatt tttctgctta ytacaaaagg taaattttaa aaagcaagta    60
c    61

<210> SEQ ID NO 151
<211> LENGTH: 61
<212> TYPE: DNA
<213> ORGANISM: Homo Sapiens

<400> SEQUENCE: 151
tatagacaac atagtctgta tcaaattgcc rgaaattaac atggtgaaaa ttattctatg    60
c    61

<210> SEQ ID NO 152
<211> LENGTH: 61
<212> TYPE: DNA
<213> ORGANISM: Homo Sapiens

<400> SEQUENCE: 152

```
aatggcattc cttttagaca agttgtaaag ktcaggaaag tataaagaga aaaattcctg    60
a                                                                   61

<210> SEQ ID NO 153
<211> LENGTH: 61
<212> TYPE: DNA
<213> ORGANISM: Homo Sapiens

<400> SEQUENCE: 153
aatagtgaca aaccaatgat caccaatggc yactaaaatc atcagctgga aaggtagtga    60
g                                                                   61

<210> SEQ ID NO 154
<211> LENGTH: 61
<212> TYPE: DNA
<213> ORGANISM: Homo Sapiens

<400> SEQUENCE: 154
aagagactag taacagtagc ttgtgtatac ktgtgataaa atgagcccta cctgaaagaa    60
g                                                                   61

<210> SEQ ID NO 155
<211> LENGTH: 61
<212> TYPE: DNA
<213> ORGANISM: Homo Sapiens

<400> SEQUENCE: 155
ttacattaag gagactgtct gtcacttaca yaaatcgttg atgtcttcat actcagcctt    60
c                                                                   61

<210> SEQ ID NO 156
<211> LENGTH: 61
<212> TYPE: DNA
<213> ORGANISM: Homo Sapiens

<400> SEQUENCE: 156
actggtgagg gttaggagaa aaattgcatg sggaaatcag ggtatttctc tggctctatt    60
t                                                                   61

<210> SEQ ID NO 157
<211> LENGTH: 61
<212> TYPE: DNA
<213> ORGANISM: Homo Sapiens

<400> SEQUENCE: 157
caggcgcatg gcctttctgc ctcaacttcc rtttctctaa ggttgccgta agaataaatt    60
a                                                                   61

<210> SEQ ID NO 158
<211> LENGTH: 61
<212> TYPE: DNA
<213> ORGANISM: Homo Sapiens

<400> SEQUENCE: 158
tggtttcagc aaccatctgt tttggtctca rtgtgaaagg caggcaaaac tatgctgaca    60
a                                                                   61

<210> SEQ ID NO 159
<211> LENGTH: 61
```

```
<212> TYPE: DNA
<213> ORGANISM: Homo Sapiens

<400> SEQUENCE: 159
acctgagctt cgttcccagg atgtgctgct sactggccat gcaacctggg gtatcctata    60
t                                                                    61

<210> SEQ ID NO 160
<211> LENGTH: 61
<212> TYPE: DNA
<213> ORGANISM: Homo Sapiens

<400> SEQUENCE: 160 tgttttatt tatagtactc aaggtcagtt rtagtgcatt cacactattc attgaccctg     60
t                                                                    61

<210> SEQ ID NO 161
<211> LENGTH: 61
<212> TYPE: DNA
<213> ORGANISM: Homo Sapiens

<400> SEQUENCE: 161
gtgatttgaa ttcattttgt ccagcagata ytagtgagaa gctcggccac tgcttcatgg    60
c                                                                    61

<210> SEQ ID NO 162
<211> LENGTH: 61
<212> TYPE: DNA
<213> ORGANISM: Homo Sapiens

<400> SEQUENCE: 162
aaaaacaaac ttctctatgc catagttctg mtttacagat ggaccaggca tgagcgcttg    60
c                                                                    61

<210> SEQ ID NO 163
<211> LENGTH: 61
<212> TYPE: DNA
<213> ORGANISM: Homo Sapiens

<400> SEQUENCE: 163
ccccagtcca taggtttgaa attgcttcta ytccatctac ccacagagct agtgctgggc    60
t                                                                    61

<210> SEQ ID NO 164
<211> LENGTH: 61
<212> TYPE: DNA
<213> ORGANISM: Homo Sapiens

<400> SEQUENCE: 164
ataaatcata aatcgaaagc atatagagaa yatgaggaag catgaaaagt cattacgctg    60
a                                                                    61

<210> SEQ ID NO 165
<211> LENGTH: 61
<212> TYPE: DNA
<213> ORGANISM: Homo Sapiens

<400> SEQUENCE: 165
atataagtag cctatataac cactttgttt sactaaaaac tatgtttctt tgatgcaaat    60
a                                                                    61
```

<210> SEQ ID NO 166
<211> LENGTH: 61
<212> TYPE: DNA
<213> ORGANISM: Homo Sapiens

<400> SEQUENCE: 166
ggctcagcac ttggcctcaa gttaaatgag yggtctttca tgtgacgtct caatgggaac    60
a                                                                   61

<210> SEQ ID NO 167
<211> LENGTH: 61
<212> TYPE: DNA
<213> ORGANISM: Homo Sapiens

<400> SEQUENCE: 167
cttgaaaaca gaataaatgt acttagctca yagaggtaat gtgattccaa tttagctggt    60
c                                                                   61

<210> SEQ ID NO 168
<211> LENGTH: 61
<212> TYPE: DNA
<213> ORGANISM: Homo Sapiens

<400> SEQUENCE: 168
atgtggaatg tttagtcatt agtgttatta rgaaatcata gttatttaat ttatgtttta    60
a                                                                   61

<210> SEQ ID NO 169
<211> LENGTH: 61
<212> TYPE: DNA
<213> ORGANISM: Homo Sapiens

<400> SEQUENCE: 169
aagatcagga acaagacaag gatatcgact rttaccactt cttttttgaca tagtactaga    60
a                                                                   61

<210> SEQ ID NO 170
<211> LENGTH: 61
<212> TYPE: DNA
<213> ORGANISM: Homo Sapiens

<400> SEQUENCE: 170
gtgaagtgat ggttatgtta attagcgtga ytgaaaattt ctacaatgtt tatgtagatc    60
a                                                                   61

<210> SEQ ID NO 171
<211> LENGTH: 61
<212> TYPE: DNA
<213> ORGANISM: Homo Sapiens

<400> SEQUENCE: 171
ctatgttaac ttggcagcat gagaacctcc rtacacaacc tgacaagaaa gacatgcatg    60
t                                                                   61

<210> SEQ ID NO 172
<211> LENGTH: 61
<212> TYPE: DNA
<213> ORGANISM: Homo Sapiens

<400> SEQUENCE: 172

-continued

```
tacatcattc cttatgtaca atactttatc matgccattt ttatgatgtt gtatactagg    60
t                                                                   61

<210> SEQ ID NO 173
<211> LENGTH: 61
<212> TYPE: DNA
<213> ORGANISM: Homo Sapiens

<400> SEQUENCE: 173
ttttcacatc aatatcagca gtttaccttt ytacatggca gtgttatatt gaagaaacac    60
t                                                                   61

<210> SEQ ID NO 174
<211> LENGTH: 61
<212> TYPE: DNA
<213> ORGANISM: Homo Sapiens

<400> SEQUENCE: 174
taaaaacttt taagtgattt ttgggtctgc rtacacatga gagttaatta ttagcaggaa    60
a                                                                   61

<210> SEQ ID NO 175
<211> LENGTH: 61
<212> TYPE: DNA
<213> ORGANISM: Homo Sapiens

<400> SEQUENCE: 175
tctctttaag gtctacctct acctcctctc ytggccacct gatgcataaa tagagacaac    60
t                                                                   61

<210> SEQ ID NO 176
<211> LENGTH: 61
<212> TYPE: DNA
<213> ORGANISM: Homo Sapiens

<400> SEQUENCE: 176
ggaacctagg aactaaaaac acatgttatc rtcccacaca aatccaacat acaataatga    60
g                                                                   61

<210> SEQ ID NO 177
<211> LENGTH: 61
<212> TYPE: DNA
<213> ORGANISM: Homo Sapiens

<400> SEQUENCE: 177
tatctgtgaa atagagctta agggttaata ygatgatgag caaacatctg gaattctctt    60
c                                                                   61

<210> SEQ ID NO 178
<211> LENGTH: 61
<212> TYPE: DNA
<213> ORGANISM: Homo Sapiens

<400> SEQUENCE: 178
aggtcacaga aattcttatt ccttgttttc yctgagttat gacatagtga aatgttcctg    60
t                                                                   61

<210> SEQ ID NO 179
<211> LENGTH: 61
```

```
<212> TYPE: DNA
<213> ORGANISM: Homo Sapiens

<400> SEQUENCE: 179
ttaatacaat taatgtctcc tcgagttttc rtgcagatca acacacctac tgacagtaat    60
g                                                                    61

<210> SEQ ID NO 180
<211> LENGTH: 61
<212> TYPE: DNA
<213> ORGANISM: Homo Sapiens

<400> SEQUENCE: 180
aaatcagcca agatagagc aaataataat rgttgaaaag tagtgtaaaa ataccttttt    60
a                                                                    61

<210> SEQ ID NO 181
<211> LENGTH: 61
<212> TYPE: DNA
<213> ORGANISM: Homo Sapiens

<400> SEQUENCE: 181
ccagtggagt caataaagca taaagtcaag rgtttctaaa cacgacctgg gtgcagatgg    60
c                                                                    61

<210> SEQ ID NO 182
<211> LENGTH: 61
<212> TYPE: DNA
<213> ORGANISM: Homo Sapiens
<220> FEATURE:
<221> NAME/KEY: misc_feature
<222> LOCATION: (31)..(31)
<223> OTHER INFORMATION: n is a, c, g, or t

<400> SEQUENCE: 182
tactcacggc atcgaatttt ctatcaaaaa ncatttcaga agtcaaaagg ttttttaaagt   60
t                                                                    61

<210> SEQ ID NO 183
<211> LENGTH: 61
<212> TYPE: DNA
<213> ORGANISM: Homo Sapiens

<400> SEQUENCE: 183
atgttgcctt attgtgagaa aggctaaaac mgaaccagta agtcctatat ggtgaagtaa    60
g                                                                    61

<210> SEQ ID NO 184
<211> LENGTH: 61
<212> TYPE: DNA
<213> ORGANISM: Homo Sapiens

<400> SEQUENCE: 184
aggcaatcag atgttcagca aataacagtt ytaatccttt ctaatccaga tttttctttc    60
t                                                                    61

<210> SEQ ID NO 185
<211> LENGTH: 61
<212> TYPE: DNA
<213> ORGANISM: Homo Sapiens

<400> SEQUENCE: 185
```

```
tcctttcccc atccatggtc aataaccttc racagctgat ctaaaaaggt cgcctattct    60
a                                                                   61

<210> SEQ ID NO 186
<211> LENGTH: 61
<212> TYPE: DNA
<213> ORGANISM: Homo Sapiens

<400> SEQUENCE: 186
gcttgctaat acgacttaag agactctaca yagccttatc ccagttatta cagacctcct    60
c                                                                   61

<210> SEQ ID NO 187
<211> LENGTH: 61
<212> TYPE: DNA
<213> ORGANISM: Homo Sapiens

<400> SEQUENCE: 187
ccatccgatt cttgataggt tttattgagc ractttataa cgtaaaactg cttttagaga    60
g                                                                   61

<210> SEQ ID NO 188
<211> LENGTH: 61
<212> TYPE: DNA
<213> ORGANISM: Homo Sapiens

<400> SEQUENCE: 188
taatacctat tgaactatcc tactaaatga yattttgatg accgtcaagg atgaagtggg    60
c                                                                   61

<210> SEQ ID NO 189
<211> LENGTH: 61
<212> TYPE: DNA
<213> ORGANISM: Homo Sapiens

<400> SEQUENCE: 189
gaactagtat aatatgttag agaacccgat wagagctagg taaccctgat gactagttgg    60
g                                                                   61

<210> SEQ ID NO 190
<211> LENGTH: 61
<212> TYPE: DNA
<213> ORGANISM: Homo Sapiens

<400> SEQUENCE: 190
tcagaaatgt acattcaaaa caatcgaggt wggctttaaa ggagcattca aaatcattaa    60
c                                                                   61

<210> SEQ ID NO 191
<211> LENGTH: 61
<212> TYPE: DNA
<213> ORGANISM: Homo Sapiens

<400> SEQUENCE: 191
atgaccagag agttgcatta gctcagtggt yctcaaattt ggctcatctt taaaatcacc    60
t                                                                   61

<210> SEQ ID NO 192
<211> LENGTH: 61
```

```
<212> TYPE: DNA
<213> ORGANISM: Homo Sapiens

<400> SEQUENCE: 192
ataggagttt cagaacccga ctacacatct stcgttgatg gtctaaatat ttgcatgttt    60
g                                                                   61

<210> SEQ ID NO 193
<211> LENGTH: 61
<212> TYPE: DNA
<213> ORGANISM: Homo Sapiens

<400> SEQUENCE: 193
aaagaaatag aaaaaaaaag ataacacaaa wgctgagaca ttaatttctt caggtcctga    60
c                                                                   61

<210> SEQ ID NO 194
<211> LENGTH: 61
<212> TYPE: DNA
<213> ORGANISM: Homo Sapiens

<400> SEQUENCE: 194
cctggctgca gctatgcaga ctatacagaa ytgtgaactt ctttcctgac ctttggatat    60
a                                                                   61

<210> SEQ ID NO 195
<211> LENGTH: 61
<212> TYPE: DNA
<213> ORGANISM: Homo Sapiens

<400> SEQUENCE: 195
tccatgtaat tgtttaaaaa atgaaaattc maagaactaa ggctgaacag gcgtagaaat    60
c                                                                   61

<210> SEQ ID NO 196
<211> LENGTH: 61
<212> TYPE: DNA
<213> ORGANISM: Homo Sapiens

<400> SEQUENCE: 196
gatccaaaca tagtcactct aatgcacatg sacaataggc aaggcaggga cttatatcta    60
t                                                                   61

<210> SEQ ID NO 197
<211> LENGTH: 61
<212> TYPE: DNA
<213> ORGANISM: Homo Sapiens

<400> SEQUENCE: 197
caaagataag ttaagcaaaa ggaacaacta rtatgcaaag aaaggcaaaa tacagagatg    60
a                                                                   61

<210> SEQ ID NO 198
<211> LENGTH: 61
<212> TYPE: DNA
<213> ORGANISM: Homo Sapiens

<400> SEQUENCE: 198
tatatcagaa acctgatttg ataaacaaac raagaggaa tttctctgat ggaattggct    60
g                                                                   61
```

<210> SEQ ID NO 199
<211> LENGTH: 61
<212> TYPE: DNA
<213> ORGANISM: Homo Sapiens

<400> SEQUENCE: 199
aataaagcaa agttaaagcg atggaaacct ygagagaatt gcttggtgtt tgtaagagtc    60
a                                                                   61

<210> SEQ ID NO 200
<211> LENGTH: 61
<212> TYPE: DNA
<213> ORGANISM: Homo Sapiens

<400> SEQUENCE: 200
ctttctccca ccactaatgt ctctattcgc ytagttatgt cattatgaga ttcatggata    60
t                                                                   61

<210> SEQ ID NO 201
<211> LENGTH: 61
<212> TYPE: DNA
<213> ORGANISM: Homo Sapiens

<400> SEQUENCE: 201
gcagcctagg agaggaaaat agcttgttta yggagctggt aaagagaaag tagaggaatt    60
c                                                                   61

<210> SEQ ID NO 202
<211> LENGTH: 61
<212> TYPE: DNA
<213> ORGANISM: Homo Sapiens

<400> SEQUENCE: 202
tcctccctac agaaccaaga agattcatac rtgactggaa cctgaatgca gaaactcttt    60
c                                                                   61

<210> SEQ ID NO 203
<211> LENGTH: 61
<212> TYPE: DNA
<213> ORGANISM: Homo Sapiens

<400> SEQUENCE: 203
aggatggttt gtccatctag gaaatgaagc ycctagtcca acagtcttcc aaaaactgaa    60
t                                                                   61

<210> SEQ ID NO 204
<211> LENGTH: 61
<212> TYPE: DNA
<213> ORGANISM: Homo Sapiens

<400> SEQUENCE: 204
cacctcccat gtgacctgat gctggagaaa stgtggttta gcgggaggct gatggggaag    60
t                                                                   61

<210> SEQ ID NO 205
<211> LENGTH: 61
<212> TYPE: DNA
<213> ORGANISM: Homo Sapiens

<400> SEQUENCE: 205

-continued

```
attgcaaatg aggagaagca ttctagtgat rggcttggat tctcatgacc aacgatggta    60
c                                                                   61

<210> SEQ ID NO 206
<211> LENGTH: 61
<212> TYPE: DNA
<213> ORGANISM: Homo Sapiens

<400> SEQUENCE: 206
tctcagagaa tatttaatta gcaacatgac maaaattagt tgatttattt gaaggatatt    60
t                                                                   61

<210> SEQ ID NO 207
<211> LENGTH: 61
<212> TYPE: DNA
<213> ORGANISM: Homo Sapiens

<400> SEQUENCE: 207
tgcttaaatg tttaaataag cttcttgaaa wctcatggaa cattcaatca caactccaac    60
a                                                                   61

<210> SEQ ID NO 208
<211> LENGTH: 61
<212> TYPE: DNA
<213> ORGANISM: Homo Sapiens

<400> SEQUENCE: 208 acctttttcct gtcctcctgt ctctcgggcc yattccccac tgaggctagc catagaagct   60
a                                                                   61

<210> SEQ ID NO 209
<211> LENGTH: 61
<212> TYPE: DNA
<213> ORGANISM: Homo Sapiens

<400> SEQUENCE: 209
gtttaagctt tagactcttc agttataggc ytgatgaaga acccaagtca tagattcaca    60
t                                                                   61

<210> SEQ ID NO 210
<211> LENGTH: 61
<212> TYPE: DNA
<213> ORGANISM: Homo Sapiens

<400> SEQUENCE: 210
ttataatgaa taaccatttc ctaatttaat raaaccctat gccttaactg caaatgttaa    60
t                                                                   61

<210> SEQ ID NO 211
<211> LENGTH: 61
<212> TYPE: DNA
<213> ORGANISM: Homo Sapiens

<400> SEQUENCE: 211
tttattttgc tcaaatttca tctctggaga rgtctttccc aaccaattac ttcaaagaaa    60
g                                                                   61

<210> SEQ ID NO 212
<211> LENGTH: 61
```

```
<212> TYPE: DNA
<213> ORGANISM: Homo Sapiens

<400> SEQUENCE: 212
atgaatgctt tcctagaatc ttccttctgg ratcctactt tttatgtagt ttggagattc     60
t                                                                     61

<210> SEQ ID NO 213
<211> LENGTH: 61
<212> TYPE: DNA
<213> ORGANISM: Homo Sapiens

<400> SEQUENCE: 213
gccagtgtaa gtggtgcgcc attgttgagc yatcattgaa tctattttaa tttactaaaa     60
a                                                                     61

<210> SEQ ID NO 214
<211> LENGTH: 61
<212> TYPE: DNA
<213> ORGANISM: Homo Sapiens

<400> SEQUENCE: 214
ggtgacatgg gggaagtgat gcaaaccaac rtgaaactca tgagtaacga agtcctttgt     60
c                                                                     61

<210> SEQ ID NO 215
<211> LENGTH: 61
<212> TYPE: DNA
<213> ORGANISM: Homo Sapiens

<400> SEQUENCE: 215
gtgagaagtg ggcatgtcag gccaaaaaac yatgtggaaa agcacaggaa tatgaaagca     60
a                                                                     61

<210> SEQ ID NO 216
<211> LENGTH: 61
<212> TYPE: DNA
<213> ORGANISM: Homo Sapiens

<400> SEQUENCE: 216
gctgacctaa gtgactttgg aaatgggtag sattgataag actaaatgca aaataagtgg     60
t                                                                     61

<210> SEQ ID NO 217
<211> LENGTH: 61
<212> TYPE: DNA
<213> ORGANISM: Homo Sapiens

<400> SEQUENCE: 217
agtacggttc ccagtccaag gctggaagaa ygaatgaatt aaaaatgcta ataataacag     60
c                                                                     61

<210> SEQ ID NO 218
<211> LENGTH: 61
<212> TYPE: DNA
<213> ORGANISM: Homo Sapiens

<400> SEQUENCE: 218
ctgcttctta atggatggta gacagtgaaa ytcatatcta taaaaataac cctctgcagt     60
c                                                                     61
```

<210> SEQ ID NO 219
<211> LENGTH: 61
<212> TYPE: DNA
<213> ORGANISM: Homo Sapiens

<400> SEQUENCE: 219
ccagggaggc tgaataaaac cagagagatg ktagcattag caacaaaatg aaactcccct    60
c                                                                   61

<210> SEQ ID NO 220
<211> LENGTH: 61
<212> TYPE: DNA
<213> ORGANISM: Homo Sapiens

<400> SEQUENCE: 220
ctcttacttc ttggggattt tgtcctcttc rgcatcggtg ctgtctgtgg cgaatgcttt    60
g                                                                   61

<210> SEQ ID NO 221
<211> LENGTH: 61
<212> TYPE: DNA
<213> ORGANISM: Homo Sapiens

<400> SEQUENCE: 221
acccacacac gtgtatacac acagtgcaca matggctgac tgctgaccag aggaaccaga    60
g                                                                   61

<210> SEQ ID NO 222
<211> LENGTH: 61
<212> TYPE: DNA
<213> ORGANISM: Homo Sapiens

<400> SEQUENCE: 222
ctgccatcca gagagaacag agtttggacc rtgtccgcag aaggccttgg agtgttgacg    60
t                                                                   61

<210> SEQ ID NO 223
<211> LENGTH: 61
<212> TYPE: DNA
<213> ORGANISM: Homo Sapiens

<400> SEQUENCE: 223
gaggcttggg acctgaaggc ccattttccc mcagtgatgt tgcgaggtag gtgtttaggg    60
t                                                                   61

<210> SEQ ID NO 224
<211> LENGTH: 61
<212> TYPE: DNA
<213> ORGANISM: Homo Sapiens

<400> SEQUENCE: 224
acttctatcc ctccttcctg gcactccata rtcactttac tatgctttgt cttttgctgt    60
g                                                                   61

<210> SEQ ID NO 225
<211> LENGTH: 61
<212> TYPE: DNA
<213> ORGANISM: Homo Sapiens

<400> SEQUENCE: 225

```
tagacggaca caacagatac tcctttctcc stgctgtgca gcctggagag tgtccccaga    60
g                                                                   61

<210> SEQ ID NO 226
<211> LENGTH: 61
<212> TYPE: DNA
<213> ORGANISM: Homo Sapiens

<400> SEQUENCE: 226
atgtttggtt ggggtgtca ccaaagtaac rgtccattat tcaaactggc agacatttga    60
c                                                                   61

<210> SEQ ID NO 227
<211> LENGTH: 61
<212> TYPE: DNA
<213> ORGANISM: Homo Sapiens

<400> SEQUENCE: 227
ccaggaagaa atggccatta gctgaaatga ragagtgtca gggctagaaa caaggatgtg    60
g                                                                   61

<210> SEQ ID NO 228
<211> LENGTH: 61
<212> TYPE: DNA
<213> ORGANISM: Homo Sapiens

<400> SEQUENCE: 228
ttattgatct caatgtccta agcatgttaa rtctatgaac tcaatcaagt ccccacacca    60
a                                                                   61

<210> SEQ ID NO 229
<211> LENGTH: 61
<212> TYPE: DNA
<213> ORGANISM: Homo Sapiens

<400> SEQUENCE: 229
ctctagtctc tggggacccc tgggggaag ragtctaccc tgcttgtgag tcccgtctca    60
g                                                                   61

<210> SEQ ID NO 230
<211> LENGTH: 61
<212> TYPE: DNA
<213> ORGANISM: Homo Sapiens

<400> SEQUENCE: 230
tccctctaaa acagggccct gaaatccaga ygcgatcagc ctagtggtat cactgcccca    60
g                                                                   61

<210> SEQ ID NO 231
<211> LENGTH: 61
<212> TYPE: DNA
<213> ORGANISM: Homo Sapiens

<400> SEQUENCE: 231
tggatatgtt tattatattg tgatggcttc wtgatgtatg tatatgtcaa aatgtatcaa    60
a                                                                   61

<210> SEQ ID NO 232
<211> LENGTH: 61
```

```
<212> TYPE: DNA
<213> ORGANISM: Homo Sapiens

<400> SEQUENCE: 232
agtgaagttg gcacagtggg cagttaataa kgtcggctct gaatcaggaa aacctgggtc    60
c                                                                   61

<210> SEQ ID NO 233
<211> LENGTH: 61
<212> TYPE: DNA
<213> ORGANISM: Homo Sapiens

<400> SEQUENCE: 233
gggtcctgag gggctcttaa cttctagttc yttcctattt cagtttatcc atgtggaact    60
g                                                                   61

<210> SEQ ID NO 234
<211> LENGTH: 61
<212> TYPE: DNA
<213> ORGANISM: Homo Sapiens

<400> SEQUENCE: 234
atttaggatt agggacttgg aaatagattg mgactggata tagctttagt gttaacatgc    60
t                                                                   61

<210> SEQ ID NO 235
<211> LENGTH: 61
<212> TYPE: DNA
<213> ORGANISM: Homo Sapiens

<400> SEQUENCE: 235
actagatttg agtcttgccc ctgcctgact rtgacatgag caagttaata tacctcttag    60
a                                                                   61

<210> SEQ ID NO 236
<211> LENGTH: 61
<212> TYPE: DNA
<213> ORGANISM: Homo Sapiens

<400> SEQUENCE: 236
gctcaaatac aatttccagc atgaattgag yggtggaaat cggatctgac cacaacactg    60
c                                                                   61

<210> SEQ ID NO 237
<211> LENGTH: 61
<212> TYPE: DNA
<213> ORGANISM: Homo Sapiens

<400> SEQUENCE: 237
cccagttaat tccccacatg aaaataccta yatgttggtg gaaaagtgta atgttcaaga    60
a                                                                   61

<210> SEQ ID NO 238
<211> LENGTH: 61
<212> TYPE: DNA
<213> ORGANISM: Homo Sapiens

<400> SEQUENCE: 238
tccaggtgca aataaatgcc agggacagct yacctgggcc agtattttta tttgagttct    60
t                                                                   61
```

<210> SEQ ID NO 239
<211> LENGTH: 61
<212> TYPE: DNA
<213> ORGANISM: Homo Sapiens

<400> SEQUENCE: 239
gccagccctc ctaggccacc tctgcataat rgatgatttc acaagcggtg tgcttgagat    60
c                                                                   61

<210> SEQ ID NO 240
<211> LENGTH: 61
<212> TYPE: DNA
<213> ORGANISM: Homo Sapiens

<400> SEQUENCE: 240
tccctgttca tcacagtcag tatgggttta kaagcacctt tttctatttc aaaataccag    60
c                                                                   61

<210> SEQ ID NO 241
<211> LENGTH: 61
<212> TYPE: DNA
<213> ORGANISM: Homo Sapiens

<400> SEQUENCE: 241
agatacatat aaataccaag taatgcaaac rgttcagtga tttcttccag agaaacagga    60
a                                                                   61

<210> SEQ ID NO 242
<211> LENGTH: 61
<212> TYPE: DNA
<213> ORGANISM: Homo Sapiens

<400> SEQUENCE: 242
ttctaccctg aagcccccca tcatgcctca sagacctcgg ttcattcctg acgatcactt    60
c                                                                   61

<210> SEQ ID NO 243
<211> LENGTH: 61
<212> TYPE: DNA
<213> ORGANISM: Homo Sapiens

<400> SEQUENCE: 243
gatcttgttc agccaaagcc tcataagttc ycctttcggc gcttgtcaga gaatgcagtt    60
a                                                                   61

<210> SEQ ID NO 244
<211> LENGTH: 61
<212> TYPE: DNA
<213> ORGANISM: Homo Sapiens

<400> SEQUENCE: 244
tccagcaaag gaatgctctg atgtattttg yaatatattt tgacttcaga caagatacgg    60
g                                                                   61

<210> SEQ ID NO 245
<211> LENGTH: 61
<212> TYPE: DNA
<213> ORGANISM: Homo Sapiens

<400> SEQUENCE: 245

```
ttcaaaaata tttttaaaat agtgacaaat rattaaggtt aagtggtatg ttaaagcctg    60
a                                                                   61
```

<210> SEQ ID NO 246
<211> LENGTH: 61
<212> TYPE: DNA
<213> ORGANISM: Homo Sapiens

<400> SEQUENCE: 246

```
ggttaaggcg ttggttctac aactccagaa raaaaatgag caatgcttta tggtgcagca    60
g                                                                   61
```

<210> SEQ ID NO 247
<211> LENGTH: 61
<212> TYPE: DNA
<213> ORGANISM: Homo Sapiens

<400> SEQUENCE: 247

```
atgtagtgct gaatagggca tatgttaatt yacttgcaga cgaaacacta cagatgaaac    60
c                                                                   61
```

<210> SEQ ID NO 248
<211> LENGTH: 61
<212> TYPE: DNA
<213> ORGANISM: Homo Sapiens

<400> SEQUENCE: 248

```
ttcagtcatg aagactggct tgccaaattt rtaccttctt caaatctccc agggataact    60
c                                                                   61
```

<210> SEQ ID NO 249
<211> LENGTH: 61
<212> TYPE: DNA
<213> ORGANISM: Homo Sapiens

<400> SEQUENCE: 249

```
ctattattct tattagttga aaaggagtgg yttgttttgc agttcttgcc tgcctgttta    60
c                                                                   61
```

<210> SEQ ID NO 250
<211> LENGTH: 61
<212> TYPE: DNA
<213> ORGANISM: Homo Sapiens

<400> SEQUENCE: 250

```
cccttctctg taacaggatt attcacagac staccttctt agatatgctg gggtatgaga    60
t                                                                   61
```

<210> SEQ ID NO 251
<211> LENGTH: 61
<212> TYPE: DNA
<213> ORGANISM: Homo Sapiens

<400> SEQUENCE: 251

```
tatgctgggg tatgagatca tgtttggaag sgacaaaaag tagcttctat aatttataca    60
a                                                                   61
```

<210> SEQ ID NO 252
<211> LENGTH: 61

```
<212> TYPE: DNA
<213> ORGANISM: Homo Sapiens

<400> SEQUENCE: 252
ctaggggaga atgggggta tggctattgt sttaagtagt aaattatcat ttgatattta    60
a                                                                   61

<210> SEQ ID NO 253
<211> LENGTH: 61
<212> TYPE: DNA
<213> ORGANISM: Homo Sapiens

<400> SEQUENCE: 253
tttttttttt accttgttta gtggtcaagc rttaaccacc atgttcttca gaagagaatt    60
c                                                                   61

<210> SEQ ID NO 254
<211> LENGTH: 61
<212> TYPE: DNA
<213> ORGANISM: Homo Sapiens

<400> SEQUENCE: 254 tgtttttat ttttctgtcc atcagaatca yaatggcagt gaagcccatc ccttatttgg     60
t                                                                   61

<210> SEQ ID NO 255
<211> LENGTH: 61
<212> TYPE: DNA
<213> ORGANISM: Homo Sapiens

<400> SEQUENCE: 255
cctgggttat gcctagggat cacagttatg mttaggattg gctcaaggag agttttatct    60
t                                                                   61

<210> SEQ ID NO 256
<211> LENGTH: 61
<212> TYPE: DNA
<213> ORGANISM: Homo Sapiens

<400> SEQUENCE: 256
ttccttggct gtcagtgctg cccagattca saagaatatt gcccacattt cactgtattt    60
g                                                                   61

<210> SEQ ID NO 257
<211> LENGTH: 61
<212> TYPE: DNA
<213> ORGANISM: Homo Sapiens

<400> SEQUENCE: 257
tatttacaaa ccacctaccg aatgaaaaat sttgcctaga ggtatgaata cttggctgaa    60
g                                                                   61

<210> SEQ ID NO 258
<211> LENGTH: 61
<212> TYPE: DNA
<213> ORGANISM: Homo Sapiens

<400> SEQUENCE: 258
taccctggat tttcatttca taactctcaa sacgtaattt gaaacaaaga gtcaccatcc    60
a                                                                   61
```

<210> SEQ ID NO 259
<211> LENGTH: 61
<212> TYPE: DNA
<213> ORGANISM: Homo Sapiens

<400> SEQUENCE: 259
taaaaattcc tttcagtagt ggaacgaaat ractttggag aaaaggaaaa tgattttgga    60
a                                                                   61

<210> SEQ ID NO 260
<211> LENGTH: 61
<212> TYPE: DNA
<213> ORGANISM: Homo Sapiens

<400> SEQUENCE: 260
cgactctttg cactttaaaa aagatattag maaccacaga agaaaaaaaa aatttttta    60
a                                                                   61

<210> SEQ ID NO 261
<211> LENGTH: 61
<212> TYPE: DNA
<213> ORGANISM: Homo Sapiens

<400> SEQUENCE: 261
tactgtgatg aacaatagcg aaaagctctg raagtgatta acaaagataa tgaggtgaca    60
g                                                                   61

<210> SEQ ID NO 262
<211> LENGTH: 61
<212> TYPE: DNA
<213> ORGANISM: Homo Sapiens

<400> SEQUENCE: 262
aatatatggt ctggtttggg ccacaaattc ratataatac aaatctagta tattttgtag    60
c                                                                   61

<210> SEQ ID NO 263
<211> LENGTH: 61
<212> TYPE: DNA
<213> ORGANISM: Homo Sapiens

<400> SEQUENCE: 263
tcttataaga aacattctgg ctacaaaaca kcttttcgta tacaaactta tgaaaccct    60
a                                                                   61

<210> SEQ ID NO 264
<211> LENGTH: 61
<212> TYPE: DNA
<213> ORGANISM: Homo Sapiens

<400> SEQUENCE: 264
acaaagttca cccagttaaa tggtacaact yaatagtttt ttgtgtattt acacaggtgt    60
g                                                                   61

<210> SEQ ID NO 265
<211> LENGTH: 61
<212> TYPE: DNA
<213> ORGANISM: Homo Sapiens

<400> SEQUENCE: 265

-continued

```
caaatatttg aattacacaa ggcaccattt mggttacaag actggtagca tacagcatgt    60
t                                                                    61

<210> SEQ ID NO 266
<211> LENGTH: 61
<212> TYPE: DNA
<213> ORGANISM: Homo Sapiens

<400> SEQUENCE: 266
aaagtaaaac ccttcaaaaa tatgcactta rtcattacaa tttcgtaatt ttctttaaca    60
c                                                                    61

<210> SEQ ID NO 267
<211> LENGTH: 61
<212> TYPE: DNA
<213> ORGANISM: Homo Sapiens

<400> SEQUENCE: 267
ttcccaatag accatcaata tcttaggaca ragcaatctc ttatattcta tcctctttac    60
t                                                                    61

<210> SEQ ID NO 268
<211> LENGTH: 61
<212> TYPE: DNA
<213> ORGANISM: Homo Sapiens

<400> SEQUENCE: 268
ggctcagcaa ttatcctagc atcatttacc raaaagttca tctttgtctc aatgatttga    60
c                                                                    61

<210> SEQ ID NO 269
<211> LENGTH: 61
<212> TYPE: DNA
<213> ORGANISM: Homo Sapiens
<220> FEATURE:
<221> NAME/KEY: misc_feature
<222> LOCATION: (31)..(31)
<223> OTHER INFORMATION: n is a, c, g, or t

<400> SEQUENCE: 269
ataagccatc tgcttagagt cacctgaaca ntgagaattt agagtcttca tgctcaggtt    60
t                                                                    61

<210> SEQ ID NO 270
<211> LENGTH: 61
<212> TYPE: DNA
<213> ORGANISM: Homo Sapiens

<400> SEQUENCE: 270
ttttgcacac ttgccctcaa gttgtttcag waccctggag tgtaatttgt ctaagcttga    60
a                                                                    61

<210> SEQ ID NO 271
<211> LENGTH: 61
<212> TYPE: DNA
<213> ORGANISM: Homo Sapiens

<400> SEQUENCE: 271
agtgaataaa ggcctgcatt gctattattt rccaagctga taacacattt tgtttgtttg    60
t                                                                    61
```

<210> SEQ ID NO 272
<211> LENGTH: 61
<212> TYPE: DNA
<213> ORGANISM: Homo Sapiens

<400> SEQUENCE: 272
gacttgtcaa agtctcatgg gcagtgattg mgaactcctt agatttcagt ttctttgttg    60
a                                                                   61

<210> SEQ ID NO 273
<211> LENGTH: 61
<212> TYPE: DNA
<213> ORGANISM: Homo Sapiens

<400> SEQUENCE: 273
tctttctatc ttcaaggaag ctcacagtct rttagagagg acaaacatgt aatataaata    60
g                                                                   61

<210> SEQ ID NO 274
<211> LENGTH: 61
<212> TYPE: DNA
<213> ORGANISM: Homo Sapiens

<400> SEQUENCE: 274
agctgttcac tcctaagtca gacgttgaat staacctcag tgctgtttct agtcactaaa    60
c                                                                   61

<210> SEQ ID NO 275
<211> LENGTH: 61
<212> TYPE: DNA
<213> ORGANISM: Homo Sapiens

<400> SEQUENCE: 275
aagtctaatg atactaatgg agataagtac maggctaatt acacatgttt acccaacgct    60
a                                                                   61

<210> SEQ ID NO 276
<211> LENGTH: 61
<212> TYPE: DNA
<213> ORGANISM: Homo Sapiens

<400> SEQUENCE: 276
gcaatgatag agaaaaatcc aaaatgtgaa ygagccagct agctgtcacc tgcatgcagc    60
c                                                                   61

<210> SEQ ID NO 277
<211> LENGTH: 61
<212> TYPE: DNA
<213> ORGANISM: Homo Sapiens

<400> SEQUENCE: 277
gcacatagcc cagctctctc tcatgcccac mgatacttta agcttctatt gacttaaagt    60
g                                                                   61

<210> SEQ ID NO 278
<211> LENGTH: 61
<212> TYPE: DNA
<213> ORGANISM: Homo Sapiens

<400> SEQUENCE: 278

```
gcaggaataa ggcaaacaaa cacttcatgc ygagcaaaac atcccaaaca actttcagga    60
a                                                                    61

<210> SEQ ID NO 279
<211> LENGTH: 61
<212> TYPE: DNA
<213> ORGANISM: Homo Sapiens

<400> SEQUENCE: 279
aaatgtttac cattttaact attttaagc stgcaattca atggcattaa gtacgttcat    60
a                                                                    61

<210> SEQ ID NO 280
<211> LENGTH: 61
<212> TYPE: DNA
<213> ORGANISM: Homo Sapiens

<400> SEQUENCE: 280
agatctcatt ttaatttaca tttttctga ygactaatta tttgaacatg tcttcatagg    60
t                                                                    61

<210> SEQ ID NO 281
<211> LENGTH: 61
<212> TYPE: DNA
<213> ORGANISM: Homo Sapiens

<400> SEQUENCE: 281
cactacagta acacagacac caatatcaaa sgttaaaccc acacagtggc cagttaattt    60
c                                                                    61

<210> SEQ ID NO 282
<211> LENGTH: 61
<212> TYPE: DNA
<213> ORGANISM: Homo Sapiens

<400> SEQUENCE: 282
aaagctttaa taaagtttgc taagggactc yggggtgcta agttggaggg attctcatga    60
g                                                                    61

<210> SEQ ID NO 283
<211> LENGTH: 61
<212> TYPE: DNA
<213> ORGANISM: Homo Sapiens

<400> SEQUENCE: 283
taatgcaaag ttcaatgttt ggccactaac mtagtgtttc tctaaatgac tttaattaat    60
t                                                                    61

<210> SEQ ID NO 284
<211> LENGTH: 61
<212> TYPE: DNA
<213> ORGANISM: Homo Sapiens

<400> SEQUENCE: 284
aacacacatt ttcacaatac taaaataaat kccccagttg ggtgcagtag ttcatgcctg    60
t                                                                    61

<210> SEQ ID NO 285
<211> LENGTH: 61
```

```
<212> TYPE: DNA
<213> ORGANISM: Homo Sapiens

<400> SEQUENCE: 285
gaagagacct tattttgctt gctcccgtaa wttcttcaac ttttccagtt cagatgtttg    60
t                                                                    61

<210> SEQ ID NO 286
<211> LENGTH: 61
<212> TYPE: DNA
<213> ORGANISM: Homo Sapiens

<400> SEQUENCE: 286
agtatatacg gctgaagcag agttagatca ygtagtacct tgtaaattgg gttaagaatt    60
t                                                                    61

<210> SEQ ID NO 287
<211> LENGTH: 61
<212> TYPE: DNA
<213> ORGANISM: Homo Sapiens

<400> SEQUENCE: 287
agcattgagt cctttagaaa acaggaagta kgcatctgaa ggtattgagt gagaaaagg     60
t                                                                    61

<210> SEQ ID NO 288
<211> LENGTH: 61
<212> TYPE: DNA
<213> ORGANISM: Homo Sapiens

<400> SEQUENCE: 288
gactaaaaca tcatcttggc ccttgaagaa sttaaaattg agtgacaaat ataaactacg    60
a                                                                    61

<210> SEQ ID NO 289
<211> LENGTH: 61
<212> TYPE: DNA
<213> ORGANISM: Homo Sapiens

<400> SEQUENCE: 289
acttaaaatt gagtgacaaa tataaactac raacatctgt aaacaactaa gctcaaaata    60
c                                                                    61

<210> SEQ ID NO 290
<211> LENGTH: 61
<212> TYPE: DNA
<213> ORGANISM: Homo Sapiens

<400> SEQUENCE: 290
tctgtaaaag ttctggcatg gtgaaagatc staactctag gaagctgaat aacttaccat    60
t                                                                    61

<210> SEQ ID NO 291
<211> LENGTH: 61
<212> TYPE: DNA
<213> ORGANISM: Homo Sapiens

<400> SEQUENCE: 291
tcagaaaaat gccaaggctt actctctcct ktggttgaat tcattactaa cagagtgttt    60
a                                                                    61
```

<210> SEQ ID NO 292
<211> LENGTH: 61
<212> TYPE: DNA
<213> ORGANISM: Homo Sapiens

<400> SEQUENCE: 292
gaatttaaag ccatgggacc agaagaaatt rtgtaaaatg caggaagaaa agaaagatgc    60
a                                                                   61

<210> SEQ ID NO 293
<211> LENGTH: 61
<212> TYPE: DNA
<213> ORGANISM: Homo Sapiens

<400> SEQUENCE: 293
agcttgcaca tccacaagac cagcccaata yacagctaga gtgcaaactg aggaggccat    60
t                                                                   61

<210> SEQ ID NO 294
<211> LENGTH: 61
<212> TYPE: DNA
<213> ORGANISM: Homo Sapiens

<400> SEQUENCE: 294
ataaataaat aaataaataa agagtgtata ygaggaaaat tatctggaag actatagtgg    60
c                                                                   61

<210> SEQ ID NO 295
<211> LENGTH: 61
<212> TYPE: DNA
<213> ORGANISM: Homo Sapiens

<400> SEQUENCE: 295
attatgaaat gagttgtatt ggaactttcc ytgacagaaa tcctactcct ctagcttggg    60
a                                                                   61

<210> SEQ ID NO 296
<211> LENGTH: 61
<212> TYPE: DNA
<213> ORGANISM: Homo Sapiens

<400> SEQUENCE: 296
catttgatac tagtaatcat tttatcttct rtgaaacacc ttttcccccc aggttttggg    60
a                                                                   61

<210> SEQ ID NO 297
<211> LENGTH: 61
<212> TYPE: DNA
<213> ORGANISM: Homo Sapiens

<400> SEQUENCE: 297 taaaagaaa ttttaatggg cttcagttcc raatgtggac tgtgataatg atttaccaga    60
g                                                                   61

<210> SEQ ID NO 298
<211> LENGTH: 61
<212> TYPE: DNA
<213> ORGANISM: Homo Sapiens

<400> SEQUENCE: 298

```
gtcctgtatt tctcactagg agaatagtgg rattttgatt ttgttttata gggattgctt    60
t                                                                   61

<210> SEQ ID NO 299
<211> LENGTH: 61
<212> TYPE: DNA
<213> ORGANISM: Homo Sapiens

<400> SEQUENCE: 299
aaaagtctgt gcattgcaat aactgctact rtcccaattt tatgccaaaa taaaccagct    60
c                                                                   61

<210> SEQ ID NO 300
<211> LENGTH: 61
<212> TYPE: DNA
<213> ORGANISM: Homo Sapiens

<400> SEQUENCE: 300
ggaatagagg aataatggaa tctgtgataa yttgataagt caataaaaaa catttcaata    60
a                                                                   61

<210> SEQ ID NO 301
<211> LENGTH: 61
<212> TYPE: DNA
<213> ORGANISM: Homo Sapiens

<400> SEQUENCE: 301
aatgattctg gatccaatgt ctgttagatt ktcaaggttc ctacaggaat acctctagaa    60
a                                                                   61

<210> SEQ ID NO 302
<211> LENGTH: 61
<212> TYPE: DNA
<213> ORGANISM: Homo Sapiens

<400> SEQUENCE: 302
tgctacattg tacatttgtc attcaaagtc rttataacaa atgccattaa aggctagatt    60
g                                                                   61

<210> SEQ ID NO 303
<211> LENGTH: 61
<212> TYPE: DNA
<213> ORGANISM: Homo Sapiens

<400> SEQUENCE: 303
ttcttattat gtaaatttat agctaactct yattctgaac tgtactttcc tgtacatgcc    60
c                                                                   61

<210> SEQ ID NO 304
<211> LENGTH: 61
<212> TYPE: DNA
<213> ORGANISM: Homo Sapiens

<400> SEQUENCE: 304
ttcctaattc ataaatattg aatgtacagg ygggatgaca ttctcagtta ggagtcacct    60
t                                                                   61

<210> SEQ ID NO 305
<211> LENGTH: 61
```

```
<212> TYPE: DNA
<213> ORGANISM: Homo Sapiens

<400> SEQUENCE: 305
acttgccagg ggtcttagtg gagactatgt raggagcttg aaataccatc atcctactct    60
g                                                                    61

<210> SEQ ID NO 306
<211> LENGTH: 61
<212> TYPE: DNA
<213> ORGANISM: Homo Sapiens

<400> SEQUENCE: 306
agacacttct cttctcttct cagttgttat ytgtgtccac agaggatgca aaaggaaggt    60
a                                                                    61

<210> SEQ ID NO 307
<211> LENGTH: 61
<212> TYPE: DNA
<213> ORGANISM: Homo Sapiens

<400> SEQUENCE: 307
cagatggaat gaaattgcca cctggatggg waactacaaa tgacaataca agctgggaag    60
g                                                                    61

<210> SEQ ID NO 308
<211> LENGTH: 61
<212> TYPE: DNA
<213> ORGANISM: Homo Sapiens

<400> SEQUENCE: 308
gggtagggaa aagcacaggg cctgatagag staattggtt ccattaaaaa gagatgctag    60
t                                                                    61

<210> SEQ ID NO 309
<211> LENGTH: 61
<212> TYPE: DNA
<213> ORGANISM: Homo Sapiens

<400> SEQUENCE: 309
cagtaaatga cacattatac atgagctcac yaataaccaa cattatccca ggcagtaatt    60
t                                                                    61

<210> SEQ ID NO 310
<211> LENGTH: 61
<212> TYPE: DNA
<213> ORGANISM: Homo Sapiens

<400> SEQUENCE: 310
ctgtggatct gcagttagca tatcaaagtg sttcctgagt tggaggattc agaatagggc    60
t                                                                    61

<210> SEQ ID NO 311
<211> LENGTH: 61
<212> TYPE: DNA
<213> ORGANISM: Homo Sapiens

<400> SEQUENCE: 311
gaattctgta tgaaatatgt taatcaacgt rgcctcttaa ggtgtctagt tttattaatt    60
a                                                                    61
```

<210> SEQ ID NO 312
<211> LENGTH: 61
<212> TYPE: DNA
<213> ORGANISM: Homo Sapiens

<400> SEQUENCE: 312
attatcatcc tttctaagag aaatcctttc ygatcacatg atggtgggac aacagaaaag    60
t                                                                    61

<210> SEQ ID NO 313
<211> LENGTH: 61
<212> TYPE: DNA
<213> ORGANISM: Homo Sapiens

<400> SEQUENCE: 313
catttcgagt ttggttcaca aaggcataca rcaagtttat tgtgtgtgtg tttattgata    60
c                                                                    61

<210> SEQ ID NO 314
<211> LENGTH: 61
<212> TYPE: DNA
<213> ORGANISM: Homo Sapiens

<400> SEQUENCE: 314
gggacaggaa accaagagga cacaggggggc sgtgtcgagg ttaacaggga gggctgcaag    60
c                                                                    61

<210> SEQ ID NO 315
<211> LENGTH: 61
<212> TYPE: DNA
<213> ORGANISM: Homo Sapiens

<400> SEQUENCE: 315
tttactctta tttcatttac tctgctcaac watcctatga cacaaacatt gtcaatgtct    60
g                                                                    61

<210> SEQ ID NO 316
<211> LENGTH: 61
<212> TYPE: DNA
<213> ORGANISM: Homo Sapiens

<400> SEQUENCE: 316
tcatggctgt gattgatggg atgtcttaag ytgcttcatt tttgccctac agtggatctc    60
t                                                                    61

<210> SEQ ID NO 317
<211> LENGTH: 61
<212> TYPE: DNA
<213> ORGANISM: Homo Sapiens

<400> SEQUENCE: 317
aagttggatt gtagtgctgg atgtgaaccc ragtcagctt tctcatctgt aaaatgggga    60
a                                                                    61

<210> SEQ ID NO 318
<211> LENGTH: 61
<212> TYPE: DNA
<213> ORGANISM: Homo Sapiens

<400> SEQUENCE: 318

```
cagagctcca gagctcacac tctgctctca raactagatt aagcagcgag aaggtgtttc    60
a                                                                    61

<210> SEQ ID NO 319
<211> LENGTH: 61
<212> TYPE: DNA
<213> ORGANISM: Homo Sapiens

<400> SEQUENCE: 319
ccaggcagcc caagtggaag cattgtgaga rtcggtggtg gtgtgagcgt gtatgccctg    60
c                                                                    61

<210> SEQ ID NO 320
<211> LENGTH: 61
<212> TYPE: DNA
<213> ORGANISM: Homo Sapiens

<400> SEQUENCE: 320
acatgtttct gaagctgagg agttggtttc yaacacgtga tctgacctga cctccactag    60
a                                                                    61

<210> SEQ ID NO 321
<211> LENGTH: 61
<212> TYPE: DNA
<213> ORGANISM: Homo Sapiens

<400> SEQUENCE: 321 tttttttttta cctgaggtta ttttacttct stttgctctc cttctccaca taaaaggaa    60
a                                                                    61

<210> SEQ ID NO 322
<211> LENGTH: 61
<212> TYPE: DNA
<213> ORGANISM: Homo Sapiens

<400> SEQUENCE: 322
gaaaagaaaa tttggattca cagtcttcct ytctaaaaat ccaggctatg aagaaaaagc    60
t                                                                    61

<210> SEQ ID NO 323
<211> LENGTH: 61
<212> TYPE: DNA
<213> ORGANISM: Homo Sapiens

<400> SEQUENCE: 323
gattaagtaa tttgtctaag ggcacacagc ytacaagaga tgacgtcaga ttttggattt    60
g                                                                    61

<210> SEQ ID NO 324
<211> LENGTH: 61
<212> TYPE: DNA
<213> ORGANISM: Homo Sapiens

<400> SEQUENCE: 324
tgacaagtta ctctaacata atagcgaact rcaaactgca cagggctttg agcccaact     60
g                                                                    61

<210> SEQ ID NO 325
<211> LENGTH: 61
```

```
<212> TYPE: DNA
<213> ORGANISM: Homo Sapiens

<400> SEQUENCE: 325
aggcacattt gaagacaagt ggcctacagc ratgctcaga tttttgtgtg cattttcaat    60
c                                                                   61

<210> SEQ ID NO 326
<211> LENGTH: 61
<212> TYPE: DNA
<213> ORGANISM: Homo Sapiens

<400> SEQUENCE: 326
tgaaagtagg taaaagccct gacttataac mcaaggtaag agagcagtca gttatttact    60
t                                                                   61

<210> SEQ ID NO 327
<211> LENGTH: 61
<212> TYPE: DNA
<213> ORGANISM: Homo Sapiens

<400> SEQUENCE: 327
caggctttga aagtttaaat gtgccaccca mgtgcaaatg aggctgattc atggtatact    60
g                                                                   61

<210> SEQ ID NO 328
<211> LENGTH: 61
<212> TYPE: DNA
<213> ORGANISM: Homo Sapiens

<400> SEQUENCE: 328
acataaatta tattaaaggg tcaggaaaat kttgtttgag gtatgtgagg atgatttagt    60
t                                                                   61

<210> SEQ ID NO 329
<211> LENGTH: 61
<212> TYPE: DNA
<213> ORGANISM: Homo Sapiens

<400> SEQUENCE: 329
caataccaat aatttgttcc aattagacca yagtaaggtt gttaaaaaat aagcaaaact    60
a                                                                   61

<210> SEQ ID NO 330
<211> LENGTH: 61
<212> TYPE: DNA
<213> ORGANISM: Homo Sapiens

<400> SEQUENCE: 330
aaggcaactc aagaacatgg ctgttttaaa ycaaccaggc atggcagcct aagatagacg    60
g                                                                   61

<210> SEQ ID NO 331
<211> LENGTH: 61
<212> TYPE: DNA
<213> ORGANISM: Homo Sapiens

<400> SEQUENCE: 331
ctgggcctct ctcctacata aggcatgggg rcgaattgat ccagaacaac tggtgctatc    60
a                                                                   61
```

<210> SEQ ID NO 332
<211> LENGTH: 61
<212> TYPE: DNA
<213> ORGANISM: Homo Sapiens

<400> SEQUENCE: 332
taggactggt ttaaattctt cctccatggg ygcaggatga gttatgccca gtattgcttt    60
c                                                                    61

<210> SEQ ID NO 333
<211> LENGTH: 61
<212> TYPE: DNA
<213> ORGANISM: Homo Sapiens

<400> SEQUENCE: 333
ttctctcagc tccaagtaat tcagcacaag watatcactt ccttcttatc aatgtacctc    60
a                                                                    61

<210> SEQ ID NO 334
<211> LENGTH: 61
<212> TYPE: DNA
<213> ORGANISM: Homo Sapiens

<400> SEQUENCE: 334
aagatagtta ttcccacctc tcatctcctc yttctaacat atactacaaa gtttctagac    60
t                                                                    61

<210> SEQ ID NO 335
<211> LENGTH: 61
<212> TYPE: DNA
<213> ORGANISM: Homo Sapiens

<400> SEQUENCE: 335
gtaccaggca atggactcaa cacttcccat kcaccaggtc ctctaattct tctttgtcac    60
t                                                                    61

<210> SEQ ID NO 336
<211> LENGTH: 61
<212> TYPE: DNA
<213> ORGANISM: Homo Sapiens

<400> SEQUENCE: 336
ttcagtgaga cttgacacct gaatgttagc rgttcatagg tcagaagatg cttgaaggaa    60
t                                                                    61

<210> SEQ ID NO 337
<211> LENGTH: 61
<212> TYPE: DNA
<213> ORGANISM: Homo Sapiens

<400> SEQUENCE: 337
attaattatt tcttttaat cttcataaca sttagtgagt ggaatgctgg agctggcttg     60
c                                                                    61

<210> SEQ ID NO 338
<211> LENGTH: 61
<212> TYPE: DNA
<213> ORGANISM: Homo Sapiens

<400> SEQUENCE: 338

```
tgctgcgtga ctgtaaggtc ttcctgccca yaggttgctc ctggctatta gtactactaa    60
t                                                                    61
```

<210> SEQ ID NO 339
<211> LENGTH: 61
<212> TYPE: DNA
<213> ORGANISM: Homo Sapiens

<400> SEQUENCE: 339

```
tctgaatgtt ttagattaaa agccttttca rttggatact ttgcatgtat ttgttataaa    60
t                                                                    61
```

<210> SEQ ID NO 340
<211> LENGTH: 61
<212> TYPE: DNA
<213> ORGANISM: Homo Sapiens

<400> SEQUENCE: 340

```
ttgcactgtt cagccaccct ttgtgggaga rgaatcaccc catctggaag atcacagtgt    60
c                                                                    61
```

<210> SEQ ID NO 341
<211> LENGTH: 61
<212> TYPE: DNA
<213> ORGANISM: Homo Sapiens

<400> SEQUENCE: 341

```
cacgtctttt cctctctatg gataatggag wacacgctca gctcttcagt ttttgaaagg    60
c                                                                    61
```

<210> SEQ ID NO 342
<211> LENGTH: 61
<212> TYPE: DNA
<213> ORGANISM: Homo Sapiens

<400> SEQUENCE: 342

```
tatgttacgt taaaaatcca atcagtcttc ygaacattgt gtattcacga tgctgtgcca    60
c                                                                    61
```

<210> SEQ ID NO 343
<211> LENGTH: 61
<212> TYPE: DNA
<213> ORGANISM: Homo Sapiens

<400> SEQUENCE: 343

```
tcagagtcta caaaattagg tttacaaaag kggctgagaa taggggacca acctgggtgt    60
g                                                                    61
```

<210> SEQ ID NO 344
<211> LENGTH: 61
<212> TYPE: DNA
<213> ORGANISM: Homo Sapiens

<400> SEQUENCE: 344

```
atcagaccag ataaatcgta attgattttg ytcggctttg gaatggatga ggtgttatta    60
g                                                                    61
```

<210> SEQ ID NO 345
<211> LENGTH: 61

```
<212> TYPE: DNA
<213> ORGANISM: Homo Sapiens

<400> SEQUENCE: 345
agattggctt ttagagcagg tactgtggaa rtgaggaaga aagtccctgc catcacatgg    60
g                                                                   61

<210> SEQ ID NO 346
<211> LENGTH: 61
<212> TYPE: DNA
<213> ORGANISM: Homo Sapiens

<400> SEQUENCE: 346
caaagtagac accattgctg cagatgagag yttctcccag gtggactttg ggggaaggct    60
g                                                                   61

<210> SEQ ID NO 347
<211> LENGTH: 61
<212> TYPE: DNA
<213> ORGANISM: Homo Sapiens

<400> SEQUENCE: 347
tattggaatg ggagtgggac tgtatcatgt rttgtattaa cttttgcttc taaatgacac    60
a                                                                   61

<210> SEQ ID NO 348
<211> LENGTH: 61
<212> TYPE: DNA
<213> ORGANISM: Homo Sapiens

<400> SEQUENCE: 348
tgggatggtt ttaaaactgt tgacgttgat kcatcagtgg atctaagatc tggcactctc    60
t                                                                   61

<210> SEQ ID NO 349
<211> LENGTH: 61
<212> TYPE: DNA
<213> ORGANISM: Homo Sapiens

<400> SEQUENCE: 349
gcaggtgaga cacagtgagc cttcaacaac kaactctctc ccaacacagc cctgagaatt    60
g                                                                   61

<210> SEQ ID NO 350
<211> LENGTH: 61
<212> TYPE: DNA
<213> ORGANISM: Homo Sapiens

<400> SEQUENCE: 350
accaccaagc agtgacaagt gaaaacagca ragaggaata agccactgtt cctcaactga    60
t                                                                   61

<210> SEQ ID NO 351
<211> LENGTH: 61
<212> TYPE: DNA
<213> ORGANISM: Homo Sapiens

<400> SEQUENCE: 351
tgttagtgaa ggcttacatc ttagtccaaa yggaatgctg atgccaactc ccatcaaaaa    60
t                                                                   61
```

<210> SEQ ID NO 352
<211> LENGTH: 61
<212> TYPE: DNA
<213> ORGANISM: Homo Sapiens

<400> SEQUENCE: 352
ttgaagcact gttagccagt tgaaagcttc yattctagcc gactttgcct cctaaacagc    60
t                                                                   61

<210> SEQ ID NO 353
<211> LENGTH: 61
<212> TYPE: DNA
<213> ORGANISM: Homo Sapiens

<400> SEQUENCE: 353
acgttcagaa gaaatatca tttgtattaa sacctattga caggcacaat aaaaatttct    60
a                                                                   61

<210> SEQ ID NO 354
<211> LENGTH: 61
<212> TYPE: DNA
<213> ORGANISM: Homo Sapiens

<400> SEQUENCE: 354
cagagttgag gacaacttac catcttcccc mgagtagaca atggtcacag tactcaggga    60
t                                                                   61

<210> SEQ ID NO 355
<211> LENGTH: 61
<212> TYPE: DNA
<213> ORGANISM: Homo Sapiens

<400> SEQUENCE: 355
tgcctgaggc ttggagacct tcaataacct sctcaagaac ttcctgacct tacaaagcca    60
a                                                                   61

<210> SEQ ID NO 356
<211> LENGTH: 61
<212> TYPE: DNA
<213> ORGANISM: Homo Sapiens

<400> SEQUENCE: 356
ggcacagacg tctctgagta agtacactga rtagttcacc ttgacccagg agcagaaaac    60
a                                                                   61

<210> SEQ ID NO 357
<211> LENGTH: 61
<212> TYPE: DNA
<213> ORGANISM: Homo Sapiens

<400> SEQUENCE: 357
ttcaagtttg acggcaggca gggtgccaaa rtccccgatg ggattgtgcc caagaacctg    60
a                                                                   61

<210> SEQ ID NO 358
<211> LENGTH: 61
<212> TYPE: DNA
<213> ORGANISM: Homo Sapiens

<400> SEQUENCE: 358

```
catcccaatg agacaacagc ctaagaatgt rcagacaaat acaaagcagt gtgagctggg    60
g                                                                   61
```

<210> SEQ ID NO 359
<211> LENGTH: 61
<212> TYPE: DNA
<213> ORGANISM: Homo Sapiens

<400> SEQUENCE: 359

```
cattagaata tattagtgca cttgtaaaaa ygtgtagatg ctagagcccc acccagctca    60
a                                                                   61
```

<210> SEQ ID NO 360
<211> LENGTH: 61
<212> TYPE: DNA
<213> ORGANISM: Homo Sapiens

<400> SEQUENCE: 360

```
cccaagagga gggaccctca ggacacaggt sgtcattgtg actcaagatt atctactcaa    60
c                                                                   61
```

<210> SEQ ID NO 361
<211> LENGTH: 61
<212> TYPE: DNA
<213> ORGANISM: Homo Sapiens

<400> SEQUENCE: 361

```
gagctgaaga tctaaggagg gcccacctcc rcgagacctg ctgagggctt acatttggtg    60
c                                                                   61
```

<210> SEQ ID NO 362
<211> LENGTH: 61
<212> TYPE: DNA
<213> ORGANISM: Homo Sapiens

<400> SEQUENCE: 362

```
tgggctttgg ggtggaagga cagaagagta rcagtctagg aaagggacta gacatgtagc    60
c                                                                   61
```

<210> SEQ ID NO 363
<211> LENGTH: 61
<212> TYPE: DNA
<213> ORGANISM: Homo Sapiens

<400> SEQUENCE: 363

```
agtgctctgc attcccagtt cattcttaag ygttggttct ttctaaggca gtgtattgct    60
t                                                                   61
```

<210> SEQ ID NO 364
<211> LENGTH: 61
<212> TYPE: DNA
<213> ORGANISM: Homo Sapiens

<400> SEQUENCE: 364

```
atcccctggt gagaggtttt ccaaaatgca rtaatacaga aagaatttaa gggaagttct    60
g                                                                   61
```

<210> SEQ ID NO 365
<211> LENGTH: 61

```
<212> TYPE: DNA
<213> ORGANISM: Homo Sapiens

<400> SEQUENCE: 365
gacttttgga aagactttca gagaagtaca sctcccaaat cctttgacaa actgacaggc    60
g                                                                   61

<210> SEQ ID NO 366
<211> LENGTH: 61
<212> TYPE: DNA
<213> ORGANISM: Homo Sapiens

<400> SEQUENCE: 366
tcacagatac agtcatatct atgtaaagag wctcaaagaa ctactatcat gaagcagtca    60
g                                                                   61

<210> SEQ ID NO 367
<211> LENGTH: 61
<212> TYPE: DNA
<213> ORGANISM: Homo Sapiens

<400> SEQUENCE: 367
aaaataaaaa tacaatttga attctgtgct staagaattg gataatttta tttcactcta    60
t                                                                   61

<210> SEQ ID NO 368
<211> LENGTH: 61
<212> TYPE: DNA
<213> ORGANISM: Homo Sapiens

<400> SEQUENCE: 368
tagctaaaca aagaagcaaa accccaaata rcactatggt ctgaatgttt gccctcctca    60
c                                                                   61

<210> SEQ ID NO 369
<211> LENGTH: 61
<212> TYPE: DNA
<213> ORGANISM: Homo Sapiens

<400> SEQUENCE: 369
attactgatt ggagaccaca ttgctatctt rggaaagtat attacatagt atactatttg    60
g                                                                   61

<210> SEQ ID NO 370
<211> LENGTH: 61
<212> TYPE: DNA
<213> ORGANISM: Homo Sapiens

<400> SEQUENCE: 370
ctgaaagaag atttgtatag gaaatgctga ygtctctttg gcaactgcat aaaaattatt    60
g                                                                   61

<210> SEQ ID NO 371
<211> LENGTH: 61
<212> TYPE: DNA
<213> ORGANISM: Homo Sapiens

<400> SEQUENCE: 371
gaagccctca gaataatggc tgatatgtga yaagcacggt acaagtgctc attattacta    60
t                                                                   61
```

<210> SEQ ID NO 372
<211> LENGTH: 61
<212> TYPE: DNA
<213> ORGANISM: Homo Sapiens

<400> SEQUENCE: 372
cctagactag ttctttgatt ttaaggcaaa sttctttagt aaagttccta atcattatgt     60
a                                                                    61

<210> SEQ ID NO 373
<211> LENGTH: 61
<212> TYPE: DNA
<213> ORGANISM: Homo Sapiens

<400> SEQUENCE: 373
aggaaggtac atctcctggg aagtagagct wtcacacaat aatcaattca tgcaaaaagc     60
a                                                                    61

<210> SEQ ID NO 374
<211> LENGTH: 61
<212> TYPE: DNA
<213> ORGANISM: Homo Sapiens

<400> SEQUENCE: 374
agttctgcca cttcacaaat tacttaccag matgaggtct agtgagtcct tgctcagact     60
c                                                                    61

<210> SEQ ID NO 375
<211> LENGTH: 61
<212> TYPE: DNA
<213> ORGANISM: Homo Sapiens

<400> SEQUENCE: 375
ggcctgcagg atcttcctcc tgagccctac sgaggcattt actagctttc tcaagttaac     60
t                                                                    61

<210> SEQ ID NO 376
<211> LENGTH: 61
<212> TYPE: DNA
<213> ORGANISM: Homo Sapiens

<400> SEQUENCE: 376
cctcaacttc atgttccctg ctttttccat ytcctgtaag ttactgcctt catattcaga     60
t                                                                    61

<210> SEQ ID NO 377
<211> LENGTH: 61
<212> TYPE: DNA
<213> ORGANISM: Homo Sapiens

<400> SEQUENCE: 377
tcacactctg agttccagca ccataccaca scaaattgtc ttctatggca aagtctcatg     60
c                                                                    61

<210> SEQ ID NO 378
<211> LENGTH: 61
<212> TYPE: DNA
<213> ORGANISM: Homo Sapiens

<400> SEQUENCE: 378

```
ggtcagggcc aactcaccaa tgcacaggat ktttctatct acaggcagac aagggaggaa    60
g                                                                    61

<210> SEQ ID NO 379
<211> LENGTH: 61
<212> TYPE: DNA
<213> ORGANISM: Homo Sapiens

<400> SEQUENCE: 379
tgttgaataa gtggatttgg atgtaaccac rggcttgcca tatgaaattc tattccatgg    60
g                                                                    61

<210> SEQ ID NO 380
<211> LENGTH: 61
<212> TYPE: DNA
<213> ORGANISM: Homo Sapiens

<400> SEQUENCE: 380
tcctatttac agatggcatg gctgtgctta yggacaatgt atgtgaatta ttatttttca    60
g                                                                    61

<210> SEQ ID NO 381
<211> LENGTH: 61
<212> TYPE: DNA
<213> ORGANISM: Homo Sapiens

<400> SEQUENCE: 381
gtttcaatgt atctatatac tttatactta ycccatgcaa agggaaaata gtaactttct    60
a                                                                    61

<210> SEQ ID NO 382
<211> LENGTH: 61
<212> TYPE: DNA
<213> ORGANISM: Homo Sapiens

<400> SEQUENCE: 382
aaggacagca agatggggta acctaaaata stgttgatag atcacagagg aaataagctg    60
t                                                                    61

<210> SEQ ID NO 383
<211> LENGTH: 61
<212> TYPE: DNA
<213> ORGANISM: Homo Sapiens

<400> SEQUENCE: 383
actatgcaca gacacatttt tccacattat rttgctgctt cagtaaagat gttgtacttg    60
a                                                                    61

<210> SEQ ID NO 384
<211> LENGTH: 61
<212> TYPE: DNA
<213> ORGANISM: Homo Sapiens

<400> SEQUENCE: 384
gtgcgtgctc tgcctgttga tggcaatgtc yctgtttcca atgtccttcc tcatcaactg    60
c                                                                    61

<210> SEQ ID NO 385
<211> LENGTH: 61
```

```
<212> TYPE: DNA
<213> ORGANISM: Homo Sapiens

<400> SEQUENCE: 385
tattaggatc ctaggaagag gtacaaagcc rtcagtgtca cgagcatcat ttttaccata      60
a                                                                     61

<210> SEQ ID NO 386
<211> LENGTH: 61
<212> TYPE: DNA
<213> ORGANISM: Homo Sapiens

<400> SEQUENCE: 386
ccccagaata tgattatagg tagaagagag magtcatctg agtggggctg gagctcgaga      60
a                                                                     61

<210> SEQ ID NO 387
<211> LENGTH: 61
<212> TYPE: DNA
<213> ORGANISM: Homo Sapiens

<400> SEQUENCE: 387
gcctggcccc gttgttttcg ttgcctgctc rtaattttgt gtcctctcag tacctgtata      60
g                                                                     61

<210> SEQ ID NO 388
<211> LENGTH: 61
<212> TYPE: DNA
<213> ORGANISM: Homo Sapiens

<400> SEQUENCE: 388
agaatttaaa ctaagtaact taacaattga kaacataacc tgtatgtacc ctttgtcccc      60
t                                                                     61

<210> SEQ ID NO 389
<211> LENGTH: 61
<212> TYPE: DNA
<213> ORGANISM: Homo Sapiens

<400> SEQUENCE: 389
atgatggcaa gacagaaatt aaaactcata mtctaatgtc aaatcacatt catttccact      60
t                                                                     61

<210> SEQ ID NO 390
<211> LENGTH: 61
<212> TYPE: DNA
<213> ORGANISM: Homo Sapiens

<400> SEQUENCE: 390
ctttgtatat tcctctatag tcagaaacaa yggaatgtcc tagagccctt tagtgaagaa      60
t                                                                     61

<210> SEQ ID NO 391
<211> LENGTH: 61
<212> TYPE: DNA
<213> ORGANISM: Homo Sapiens

<400> SEQUENCE: 391
ctttagtgta tgaaggacct tgagtgccat rgtaagagtt ttggccacac aacatctgat      60
c                                                                     61
```

<210> SEQ ID NO 392
<211> LENGTH: 61
<212> TYPE: DNA
<213> ORGANISM: Homo Sapiens

<400> SEQUENCE: 392
tagcctgaga ccaaagcacg accaacagct rtacctggac tggatccttt tcttctctgc    60
t                                                                    61

<210> SEQ ID NO 393
<211> LENGTH: 61
<212> TYPE: DNA
<213> ORGANISM: Homo Sapiens

<400> SEQUENCE: 393
tatcttctga aattctatgc ttcttctaca rtctcaaatc tcatatctcc tacaatctcc    60
t                                                                    61

<210> SEQ ID NO 394
<211> LENGTH: 61
<212> TYPE: DNA
<213> ORGANISM: Homo Sapiens

<400> SEQUENCE: 394
aaaataaaac aataataaag tttgttccat ygattgactc aagaacattc ttgtcacaaa    60
a                                                                    61

<210> SEQ ID NO 395
<211> LENGTH: 61
<212> TYPE: DNA
<213> ORGANISM: Homo Sapiens

<400> SEQUENCE: 395
cagggcatta agcacccaag ccaactcaac rcctgcagat ggctcttcct cccagtgcag    60
c                                                                    61

<210> SEQ ID NO 396
<211> LENGTH: 61
<212> TYPE: DNA
<213> ORGANISM: Homo Sapiens

<400> SEQUENCE: 396
ttgtcagttt ttaaaaagtg agatttttga rgcaagagat gtcataccaa aagctagaga    60
a                                                                    61

<210> SEQ ID NO 397
<211> LENGTH: 61
<212> TYPE: DNA
<213> ORGANISM: Homo Sapiens

<400> SEQUENCE: 397
aaccaaggtc ccaacatatg aaaataaatt rccaggtgac tcaggccaaa cacaggctgc    60
c                                                                    61

<210> SEQ ID NO 398
<211> LENGTH: 61
<212> TYPE: DNA
<213> ORGANISM: Homo Sapiens

<400> SEQUENCE: 398

```
tatacttgaa ctaaaagaat agcagcagat ytaaaggaat gcagaagcag atctgaagat    60
c                                                                    61

<210> SEQ ID NO 399
<211> LENGTH: 61
<212> TYPE: DNA
<213> ORGANISM: Homo Sapiens

<400> SEQUENCE: 399
tgggcttatt ttctgattgg agagaaccgc rtacagctat gtaattatta caacgtataa    60
t                                                                    61

<210> SEQ ID NO 400
<211> LENGTH: 61
<212> TYPE: DNA
<213> ORGANISM: Homo Sapiens

<400> SEQUENCE: 400
attgtcctgt gaaaccctgt tataacattt yagtggcacc aaaaaagggt gctgggacag    60
g                                                                    61

<210> SEQ ID NO 401
<211> LENGTH: 61
<212> TYPE: DNA
<213> ORGANISM: Homo Sapiens

<400> SEQUENCE: 401
tcctgcgagc ggtccctcac cactgatgag yagaacgtgg agagataaac cccccagct    60
t                                                                    61

<210> SEQ ID NO 402
<211> LENGTH: 61
<212> TYPE: DNA
<213> ORGANISM: Homo Sapiens

<400> SEQUENCE: 402
gagtgcatgg atgttacctt tccatgcttg ycgctctctg caaagtctag ctggagatca    60
a                                                                    61

<210> SEQ ID NO 403
<211> LENGTH: 61
<212> TYPE: DNA
<213> ORGANISM: Homo Sapiens

<400> SEQUENCE: 403 gcttttagc caggctgcta ggaaatactc raaagattct agagaccctc cctacctgcc    60
c                                                                    61

<210> SEQ ID NO 404
<211> LENGTH: 61
<212> TYPE: DNA
<213> ORGANISM: Homo Sapiens

<400> SEQUENCE: 404
aagtcataac tgtgagtatg aatatatgcc ragtcctgtg aatcctccta gtaaacatc    60
a                                                                    61

<210> SEQ ID NO 405
<211> LENGTH: 61
```

-continued

```
<212> TYPE: DNA
<213> ORGANISM: Homo Sapiens

<400> SEQUENCE: 405
gattacacca gtacctgatg gtcatcaaac ktgtacccac cagccttaga atccattaaa    60
g                                                                    61

<210> SEQ ID NO 406
<211> LENGTH: 61
<212> TYPE: DNA
<213> ORGANISM: Homo Sapiens

<400> SEQUENCE: 406
actggaataa aaatgttttt tgcttcttta sgaatggcat tatacagtac ttcctcaaag    60
c                                                                    61

<210> SEQ ID NO 407
<211> LENGTH: 61
<212> TYPE: DNA
<213> ORGANISM: Homo Sapiens

<400> SEQUENCE: 407
tttatcttta tattttatag atgaggaaat macaatatag aatggttaag ttactgcctg    60
a                                                                    61

<210> SEQ ID NO 408
<211> LENGTH: 61
<212> TYPE: DNA
<213> ORGANISM: Homo Sapiens

<400> SEQUENCE: 408
tgcctgaggt cacaggggtg ggtaagaagt kggcaaaaat aggaattcag gtatttgggt    60
t                                                                    61

<210> SEQ ID NO 409
<211> LENGTH: 61
<212> TYPE: DNA
<213> ORGANISM: Homo Sapiens

<400> SEQUENCE: 409
gaggagtaga tctgtgcaag taaggaggta rtagcagaga tagcagaaaa actggtagca    60
t                                                                    61

<210> SEQ ID NO 410
<211> LENGTH: 61
<212> TYPE: DNA
<213> ORGANISM: Homo Sapiens

<400> SEQUENCE: 410
gacttgggat ttctgagctg ttttacactt ytgcatatcc agcagtgact atggttatat    60
c                                                                    61

<210> SEQ ID NO 411
<211> LENGTH: 61
<212> TYPE: DNA
<213> ORGANISM: Homo Sapiens

<400> SEQUENCE: 411
gaggccaaaa gccacagtca gaggagattt katgacagaa caggtcagat gaagagatgt    60
g                                                                    61
```

<210> SEQ ID NO 412
<211> LENGTH: 61
<212> TYPE: DNA
<213> ORGANISM: Homo Sapiens

<400> SEQUENCE: 412
gaagataaca aagcatttga ttgactctgt rtggaaaagt agtaggtaca agaaggtgaa    60
g                                                                   61

<210> SEQ ID NO 413
<211> LENGTH: 61
<212> TYPE: DNA
<213> ORGANISM: Homo Sapiens

<400> SEQUENCE: 413
atacttctct atttctgtgt aacactgatt ycttagatct ggatttgaaa tcagaagcat    60
t                                                                   61

<210> SEQ ID NO 414
<211> LENGTH: 61
<212> TYPE: DNA
<213> ORGANISM: Homo Sapiens

<400> SEQUENCE: 414
ataaccaagg tgtgaagtgg gaagggtaga sgaagataga aactaccaaa agttactaat    60
g                                                                   61

<210> SEQ ID NO 415
<211> LENGTH: 61
<212> TYPE: DNA
<213> ORGANISM: Homo Sapiens

<400> SEQUENCE: 415
aagatcccat taacaatagc aacgaaaaga ygagatcact gagaacacat ttaacaagaa    60
c                                                                   61

<210> SEQ ID NO 416
<211> LENGTH: 61
<212> TYPE: DNA
<213> ORGANISM: Homo Sapiens

<400> SEQUENCE: 416
gtcataagag aaagccaata tgcatacctt ytcaggagca cattataaat catgaaaatt    60
g                                                                   61

<210> SEQ ID NO 417
<211> LENGTH: 61
<212> TYPE: DNA
<213> ORGANISM: Homo Sapiens

<400> SEQUENCE: 417
ctacctgcca ccagcaccca agcacactgt stcaggacct ggtgattatc ctgccctatc    60
c                                                                   61

<210> SEQ ID NO 418
<211> LENGTH: 61
<212> TYPE: DNA
<213> ORGANISM: Homo Sapiens

<400> SEQUENCE: 418

```
catccataaa acagaatagg atgttgctgt staaagaat aaagatctct atgtaccaaa    60
g                                                                  61

<210> SEQ ID NO 419
<211> LENGTH: 61
<212> TYPE: DNA
<213> ORGANISM: Homo Sapiens

<400> SEQUENCE: 419
gtgacagatt ttatcccaag tcatatttct stgaagaact ccacttgata gcttctattt    60
t                                                                    61

<210> SEQ ID NO 420
<211> LENGTH: 61
<212> TYPE: DNA
<213> ORGANISM: Homo Sapiens

<400> SEQUENCE: 420
ttgtagccat tctttgtact gataagtgca raaggcctga ataaccaac tgggtaagtc    60
a                                                                   61

<210> SEQ ID NO 421
<211> LENGTH: 61
<212> TYPE: DNA
<213> ORGANISM: Homo Sapiens

<400> SEQUENCE: 421
agatccattc cttacacctc tgatgttggg yagagcagga cagaaacaat gtcattccct    60
t                                                                   61

<210> SEQ ID NO 422
<211> LENGTH: 61
<212> TYPE: DNA
<213> ORGANISM: Homo Sapiens

<400> SEQUENCE: 422
ctgtctctga tcttactgtg tccaaagatg kgatccattt tttagggttt tttttaaaac    60
a                                                                   61

<210> SEQ ID NO 423
<211> LENGTH: 61
<212> TYPE: DNA
<213> ORGANISM: Homo Sapiens

<400> SEQUENCE: 423 cggggggca gggaggccca gatgcctttg yacgtacctt cctcctgctt ggcacaccca    60
c                                                                   61

<210> SEQ ID NO 424
<211> LENGTH: 61
<212> TYPE: DNA
<213> ORGANISM: Homo Sapiens

<400> SEQUENCE: 424
gcaatgttga gggagggct gggcacaatc ragggttctg tggggatcag gactccagcc    60
c                                                                   61

<210> SEQ ID NO 425
<211> LENGTH: 61
```

```
<212> TYPE: DNA
<213> ORGANISM: Homo Sapiens

<400> SEQUENCE: 425
cggtgctgca ccgtggatgt gagtccttgc rcagtggtga aatgtagtag aggagtgatc    60
t                                                                   61

<210> SEQ ID NO 426
<211> LENGTH: 61
<212> TYPE: DNA
<213> ORGANISM: Homo Sapiens

<400> SEQUENCE: 426 tcagggttg taggagatca gtgatgtcat statgtaaac cacctgcccc agagcagcca     60
g                                                                   61

<210> SEQ ID NO 427
<211> LENGTH: 61
<212> TYPE: DNA
<213> ORGANISM: Homo Sapiens

<400> SEQUENCE: 427
tatattgtaa ttgcattcct ggaaaatatg ktgtttatta aagccatgca aaaactcctc    60
t                                                                   61

<210> SEQ ID NO 428
<211> LENGTH: 61
<212> TYPE: DNA
<213> ORGANISM: Homo Sapiens

<400> SEQUENCE: 428
tgataggagg tagtcttgca gctttaggaa rcacctggat gatgacagga gggaacgtga    60
a                                                                   61

<210> SEQ ID NO 429
<211> LENGTH: 61
<212> TYPE: DNA
<213> ORGANISM: Homo Sapiens

<400> SEQUENCE: 429
attacttggt gactcttgta agcaatgatt raagatattc actaagattc gagttcatta    60
t                                                                   61

<210> SEQ ID NO 430
<211> LENGTH: 61
<212> TYPE: DNA
<213> ORGANISM: Homo Sapiens

<400> SEQUENCE: 430
tctgattgca actggattat actaggcatt ygggatgaag aggatgggct gggagggagc    60
t                                                                   61

<210> SEQ ID NO 431
<211> LENGTH: 61
<212> TYPE: DNA
<213> ORGANISM: Homo Sapiens

<400> SEQUENCE: 431
gtaaaatatg acatactctg cctctctttc stttgttcat tttgttggat tttagcacaa    60
t                                                                   61
```

<210> SEQ ID NO 432
<211> LENGTH: 61
<212> TYPE: DNA
<213> ORGANISM: Homo Sapiens

<400> SEQUENCE: 432
tgtttgttca gtccaatatg ggtcaccgct wtgagtgaaa gatcccttga catggcaaaa    60
c                                                                   61

<210> SEQ ID NO 433
<211> LENGTH: 61
<212> TYPE: DNA
<213> ORGANISM: Homo Sapiens

<400> SEQUENCE: 433
tgaaactctc ttggcaccat tcacttcggc ytcaatggca ccagaacaga aatgataact    60
a                                                                   61

<210> SEQ ID NO 434
<211> LENGTH: 61
<212> TYPE: DNA
<213> ORGANISM: Homo Sapiens

<400> SEQUENCE: 434
tgaggatgac caaaagccaa ctcttgaccc rtgtacacct gcctaaacca aactcctatc    60
a                                                                   61

<210> SEQ ID NO 435
<211> LENGTH: 61
<212> TYPE: DNA
<213> ORGANISM: Homo Sapiens

<400> SEQUENCE: 435
aaagtagaaa gcctaaatag taactgattc stactgtaat agcaactagg tgaatttttt    60
c                                                                   61

<210> SEQ ID NO 436
<211> LENGTH: 61
<212> TYPE: DNA
<213> ORGANISM: Homo Sapiens

<400> SEQUENCE: 436
aatttggtat cagtcttttg ctgaggtatt mtaataggta cacgagcacc ttttaaaaag    60
c                                                                   61

<210> SEQ ID NO 437
<211> LENGTH: 61
<212> TYPE: DNA
<213> ORGANISM: Homo Sapiens

<400> SEQUENCE: 437
atgttagcgt ccctcttgtt tccagctatc kcacatatct attactttt tggtctgccc     60
a                                                                   61

<210> SEQ ID NO 438
<211> LENGTH: 61
<212> TYPE: DNA
<213> ORGANISM: Homo Sapiens

<400> SEQUENCE: 438

```
tctcttccca tccaatccac tgtcaactga ycatcttctc tggtcatgcc attctccagg    60
t                                                                    61

<210> SEQ ID NO 439
<211> LENGTH: 61
<212> TYPE: DNA
<213> ORGANISM: Homo Sapiens

<400> SEQUENCE: 439
cataactcac tttggttgat aatatgtgac rttttgccaa gattcatagc actaagaaca    60
g                                                                    61

<210> SEQ ID NO 440
<211> LENGTH: 61
<212> TYPE: DNA
<213> ORGANISM: Homo Sapiens

<400> SEQUENCE: 440
tgccacatta accactcatt caacatatac maagtgccag gatacagtga ctgttctgag    60
g                                                                    61

<210> SEQ ID NO 441
<211> LENGTH: 61
<212> TYPE: DNA
<213> ORGANISM: Homo Sapiens

<400> SEQUENCE: 441
agccaccaca gcctccgggc tcatctgcac rgacaaaacg aggataacaa gattagtcta    60
c                                                                    61

<210> SEQ ID NO 442
<211> LENGTH: 61
<212> TYPE: DNA
<213> ORGANISM: Homo Sapiens

<400> SEQUENCE: 442
cactgcgaag gaaaattaag cagaactact rgatgacata aaataactga ccatttgtac    60
g                                                                    61

<210> SEQ ID NO 443
<211> LENGTH: 61
<212> TYPE: DNA
<213> ORGANISM: Homo Sapiens

<400> SEQUENCE: 443
cctaaggtga cacttaaggg gctaactcag ktgacagaaa tgtattttaa catgtgtgta    60
c                                                                    61

<210> SEQ ID NO 444
<211> LENGTH: 61
<212> TYPE: DNA
<213> ORGANISM: Homo Sapiens

<400> SEQUENCE: 444
tcacctgtgc ttttggtgtc ctacctaaga yatcacttcc aaatctaatg tcataaattt    60
t                                                                    61

<210> SEQ ID NO 445
<211> LENGTH: 61
```

```
<212> TYPE: DNA
<213> ORGANISM: Homo Sapiens

<400> SEQUENCE: 445
ccaaattccc taaaaactag tcccaatatt matccatctc cccacatgta aacatatggt    60
c                                                                   61

<210> SEQ ID NO 446
<211> LENGTH: 61
<212> TYPE: DNA
<213> ORGANISM: Homo Sapiens

<400> SEQUENCE: 446
ggagaatagt cctggcagac caagcgaacg yacaagcaag ggagatgcaa atacaaatag    60
g                                                                   61

<210> SEQ ID NO 447
<211> LENGTH: 61
<212> TYPE: DNA
<213> ORGANISM: Homo Sapiens

<400> SEQUENCE: 447
ttaaagcgga gtaacaacaa caacagattg rtggttattt ggtttggggg agaaatttcc    60
c                                                                   61

<210> SEQ ID NO 448
<211> LENGTH: 61
<212> TYPE: DNA
<213> ORGANISM: Homo Sapiens

<400> SEQUENCE: 448
tgactcttaa aattctctga ggatgctgtc ratagcgaac aacagtgaat attttggggg    60
t                                                                   61

<210> SEQ ID NO 449
<211> LENGTH: 61
<212> TYPE: DNA
<213> ORGANISM: Homo Sapiens

<400> SEQUENCE: 449
aggacagtgc tttctcactg atttatctct satttctctc ttcctctgca gattaccaaa    60
c                                                                   61

<210> SEQ ID NO 450
<211> LENGTH: 61
<212> TYPE: DNA
<213> ORGANISM: Homo Sapiens

<400> SEQUENCE: 450
tatccacctt ttttatagaa gataaactac rtctctcagt ttcaggaaga gactaaaaaa    60
a                                                                   61

<210> SEQ ID NO 451
<211> LENGTH: 61
<212> TYPE: DNA
<213> ORGANISM: Homo Sapiens

<400> SEQUENCE: 451
tacgctcaat tgacaaatgt tttctgaatg ytttctatac actaagcact gagctaggca    60
a                                                                   61
```

<210> SEQ ID NO 452
<211> LENGTH: 61
<212> TYPE: DNA
<213> ORGANISM: Homo Sapiens

<400> SEQUENCE: 452
ccccacccta tcacctgctt caagactgag rcactcgatc ccctggcttc tgctagcact    60
g                                                                    61

<210> SEQ ID NO 453
<211> LENGTH: 61
<212> TYPE: DNA
<213> ORGANISM: Homo Sapiens

<400> SEQUENCE: 453
gcactggcga ctgactgctc agctgatcct ygtctgggaa ttcactttgg ctgaagagag    60
c                                                                    61

<210> SEQ ID NO 454
<211> LENGTH: 61
<212> TYPE: DNA
<213> ORGANISM: Homo Sapiens

<400> SEQUENCE: 454
ttttgaagta tttagtggat attttattga stgaagatta cacttagttt tcatgttggt    60
a                                                                    61

<210> SEQ ID NO 455
<211> LENGTH: 61
<212> TYPE: DNA
<213> ORGANISM: Homo Sapiens

<400> SEQUENCE: 455
ccttgccaat gggtgagcag gagctgaatt ygagctgcaa tgctttggtt aagcaatgag    60
c                                                                    61

<210> SEQ ID NO 456
<211> LENGTH: 61
<212> TYPE: DNA
<213> ORGANISM: Homo Sapiens

<400> SEQUENCE: 456
ggagtggctg gcttttgtt ttgagttcca yttcctggct cctacgctca acttttgaat    60
t                                                                    61

<210> SEQ ID NO 457
<211> LENGTH: 61
<212> TYPE: DNA
<213> ORGANISM: Homo Sapiens

<400> SEQUENCE: 457 gcgggggga cctcatgatt ccatctttat rgcccaactg ttgattaact tccaaatgaa    60
a                                                                    61

<210> SEQ ID NO 458
<211> LENGTH: 61
<212> TYPE: DNA
<213> ORGANISM: Homo Sapiens

<400> SEQUENCE: 458

```
attcagcagc atattcaaag agacagagaa kaactgacat gatgctgatg aagcttaaac      60
t                                                                    61

<210> SEQ ID NO 459
<211> LENGTH: 61
<212> TYPE: DNA
<213> ORGANISM: Homo Sapiens

<400> SEQUENCE: 459
tgtttgggtg gctggctttg atgcagggat kcttaagtct ggttttctca tctactgcat      60
a                                                                    61

<210> SEQ ID NO 460
<211> LENGTH: 61
<212> TYPE: DNA
<213> ORGANISM: Homo Sapiens

<400> SEQUENCE: 460
cgtagccttc tgtcaacgct ggaagagagg raaacccaca atgagacaaa ggcagcaccc      60
c                                                                    61

<210> SEQ ID NO 461
<211> LENGTH: 61
<212> TYPE: DNA
<213> ORGANISM: Homo Sapiens

<400> SEQUENCE: 461
aaaacaaatc cttatactca ttcatactcc yggaaatgac ttccgtggga atttaggaga      60
a                                                                    61

<210> SEQ ID NO 462
<211> LENGTH: 61
<212> TYPE: DNA
<213> ORGANISM: Homo Sapiens

<400> SEQUENCE: 462
ataaacaagt ggaggaaagg tctccaaggt ycagtgaatg attgtgaata ttggatgcat      60
g                                                                    61

<210> SEQ ID NO 463
<211> LENGTH: 61
<212> TYPE: DNA
<213> ORGANISM: Homo Sapiens

<400> SEQUENCE: 463
tctaaaaatg tatatatata tgtataaaaa stagcccgat atggtggtgt atacccgtag      60
t                                                                    61

<210> SEQ ID NO 464
<211> LENGTH: 61
<212> TYPE: DNA
<213> ORGANISM: Homo Sapiens

<400> SEQUENCE: 464
agaaataaca tcagtccttt tcttgtgata rcgttggatg acaccattac cttggctacc      60
t                                                                    61

<210> SEQ ID NO 465
<211> LENGTH: 61
```

```
<212> TYPE: DNA
<213> ORGANISM: Homo Sapiens

<400> SEQUENCE: 465
cagcctcttc cttggccccc acaaacataa ygcagaaggc ttccaaaaga ccagtgctag    60
c                                                                   61

<210> SEQ ID NO 466
<211> LENGTH: 61
<212> TYPE: DNA
<213> ORGANISM: Homo Sapiens

<400> SEQUENCE: 466
ttgcccatct tgccaaagta gtccaaacac rcttcaatga ggacagttat atttagcagg    60
t                                                                   61

<210> SEQ ID NO 467
<211> LENGTH: 61
<212> TYPE: DNA
<213> ORGANISM: Homo Sapiens

<400> SEQUENCE: 467 atataattt acagttcaga aaggtttac wgatcacagc aaaaagtatg gagactattt     60
a                                                                   61

<210> SEQ ID NO 468
<211> LENGTH: 61
<212> TYPE: DNA
<213> ORGANISM: Homo Sapiens

<400> SEQUENCE: 468
gtacaaactg aaaatcagtg gtggtacctg ytaggctttt agacataggg taagtcttgt    60
g                                                                   61

<210> SEQ ID NO 469
<211> LENGTH: 61
<212> TYPE: DNA
<213> ORGANISM: Homo Sapiens

<400> SEQUENCE: 469
atctttactg actctcctga tacgcagact wtggagaaaa agaatcttct atcaaatcta    60
g                                                                   61

<210> SEQ ID NO 470
<211> LENGTH: 61
<212> TYPE: DNA
<213> ORGANISM: Homo Sapiens

<400> SEQUENCE: 470
actggtcctc acatgcctgc tgcccagagg yacaaatgga ccacttaatt gagaaacaac    60
t                                                                   61

<210> SEQ ID NO 471
<211> LENGTH: 61
<212> TYPE: DNA
<213> ORGANISM: Homo Sapiens

<400> SEQUENCE: 471
tcggaagctt acatgagcta catggttctg rggtgtaata caaggcagtg aagccgccgc    60
t                                                                   61
```

<210> SEQ ID NO 472
<211> LENGTH: 61
<212> TYPE: DNA
<213> ORGANISM: Homo Sapiens

<400> SEQUENCE: 472 ataactgaa ggacaggcag tgaatgcaat rccttttctc attagatacc tcccttaatt    60
a                                                                   61

<210> SEQ ID NO 473
<211> LENGTH: 61
<212> TYPE: DNA
<213> ORGANISM: Homo Sapiens

<400> SEQUENCE: 473
agggtcttgg aagaaatcgg gcaggacata sgccaagtac ttataaccat acgtattgtt   60
a                                                                   61

<210> SEQ ID NO 474
<211> LENGTH: 61
<212> TYPE: DNA
<213> ORGANISM: Homo Sapiens

<400> SEQUENCE: 474
tacatgaaga atcaaaagtt gactgaagag mctttgtaaa catcacgata acagaatatt   60
t                                                                   61

<210> SEQ ID NO 475
<211> LENGTH: 61
<212> TYPE: DNA
<213> ORGANISM: Homo Sapiens

<400> SEQUENCE: 475
cggaatcaca cacttgagct gggagatttt ygcagcactt aaggcatcag gggagaagcg   60
a                                                                   61

<210> SEQ ID NO 476
<211> LENGTH: 61
<212> TYPE: DNA
<213> ORGANISM: Homo Sapiens

<400> SEQUENCE: 476
ggcatatcaa catcttaggg acctgatgac yaatggttta aaagcatgcc agcttttcac   60
c                                                                   61

<210> SEQ ID NO 477
<211> LENGTH: 61
<212> TYPE: DNA
<213> ORGANISM: Homo Sapiens

<400> SEQUENCE: 477
gaagaaaact ctttagtcta aaacaaacaa magaagtcca ctaggtcaga ttctcactgt   60
a                                                                   61

<210> SEQ ID NO 478
<211> LENGTH: 61
<212> TYPE: DNA
<213> ORGANISM: Homo Sapiens

<400> SEQUENCE: 478

```
ccctgcaagt attgccatga gcaataataa kttttttaag ctcactctgt cagactgatt      60
a                                                                     61

<210> SEQ ID NO 479
<211> LENGTH: 61
<212> TYPE: DNA
<213> ORGANISM: Homo Sapiens

<400> SEQUENCE: 479
taccagtcag acaatattga gaaccatagt rttaagacca aactaaattc ttcatcaggt      60
g                                                                     61

<210> SEQ ID NO 480
<211> LENGTH: 61
<212> TYPE: DNA
<213> ORGANISM: Homo Sapiens

<400> SEQUENCE: 480
aaaatatatt acagctgaca atgtaccata wctatagtgt agtaatttaa ttctgttact      60
g                                                                     61

<210> SEQ ID NO 481
<211> LENGTH: 61
<212> TYPE: DNA
<213> ORGANISM: Homo Sapiens

<400> SEQUENCE: 481
ccacttgatg aagtaaatat tcgagtaaaa ratctgaaag agacctgagg cataggcacc      60
t                                                                     61

<210> SEQ ID NO 482
<211> LENGTH: 61
<212> TYPE: DNA
<213> ORGANISM: Homo Sapiens

<400> SEQUENCE: 482
tacaactaac tgagtaggct cttctgtcat ratttggacc ttaagggtaa agtgtgtggg      60
a                                                                     61

<210> SEQ ID NO 483
<211> LENGTH: 61
<212> TYPE: DNA
<213> ORGANISM: Homo Sapiens

<400> SEQUENCE: 483
aagtataaaa aaaaagtta catttgaaga sagcaatttt ttaaattaac cactttataa       60
a                                                                     61

<210> SEQ ID NO 484
<211> LENGTH: 61
<212> TYPE: DNA
<213> ORGANISM: Homo Sapiens

<400> SEQUENCE: 484
ttatgaggag tacaaaaaca aatcaaaagc staagaattc gttgctagcc atgaaagtcc      60
t                                                                     61

<210> SEQ ID NO 485
<211> LENGTH: 61
```

```
<212> TYPE: DNA
<213> ORGANISM: Homo Sapiens

<400> SEQUENCE: 485
agataggcta gaaatagaat tgccaggtca rtatgtgtga agcatgttta aacattctaa      60
t                                                                     61

<210> SEQ ID NO 486
<211> LENGTH: 61
<212> TYPE: DNA
<213> ORGANISM: Homo Sapiens

<400> SEQUENCE: 486
actgccttga gacatttgtt gtttgcttat rggttggtga gttgtctgga gcttgatcta      60
a                                                                     61

<210> SEQ ID NO 487
<211> LENGTH: 61
<212> TYPE: DNA
<213> ORGANISM: Homo Sapiens

<400> SEQUENCE: 487
ataggtttct tcctgttctg agattcctct saaccctacc tctgttgttt gtttagatac      60
a                                                                     61

<210> SEQ ID NO 488
<211> LENGTH: 61
<212> TYPE: DNA
<213> ORGANISM: Homo Sapiens

<400> SEQUENCE: 488
tcctttgctg tgggtccctg tcctgggcac ygtagaattc ttagcagctt tcctggtccc      60
t                                                                     61

<210> SEQ ID NO 489
<211> LENGTH: 61
<212> TYPE: DNA
<213> ORGANISM: Homo Sapiens

<400> SEQUENCE: 489
tgaaacttgt caactcgata ttttctcaca wttcagaaca agcagggaaa caacaacaac      60
a                                                                     61

<210> SEQ ID NO 490
<211> LENGTH: 61
<212> TYPE: DNA
<213> ORGANISM: Homo Sapiens

<400> SEQUENCE: 490
ttagacccaa acatttaatg tgccttttac rcaacgaatg atcaattatg ggaatgtgac      60
a                                                                     61

<210> SEQ ID NO 491
<211> LENGTH: 61
<212> TYPE: DNA
<213> ORGANISM: Homo Sapiens

<400> SEQUENCE: 491
cgatttacaa taggaaaggc agggaatcaa mgtaggtgcc catgaatggt ggattggata      60
a                                                                     61
```

<210> SEQ ID NO 492
<211> LENGTH: 61
<212> TYPE: DNA
<213> ORGANISM: Homo Sapiens

<400> SEQUENCE: 492
aactgaagct ggaccctggg cttctgagtc yaaaggtggt acttcctgtg ctagaccgtg    60
c                                                                   61

<210> SEQ ID NO 493
<211> LENGTH: 61
<212> TYPE: DNA
<213> ORGANISM: Homo Sapiens

<400> SEQUENCE: 493
ttttgtactt catctcccaa tatgcagacc ytgcttcaaa gagccagatg acatgtaata    60
a                                                                   61

<210> SEQ ID NO 494
<211> LENGTH: 61
<212> TYPE: DNA
<213> ORGANISM: Homo Sapiens

<400> SEQUENCE: 494
gagctttgat ctggactatg taggaaggac wtttcagttg tgtgccttac tttgtacagt    60
g                                                                   61

<210> SEQ ID NO 495
<211> LENGTH: 61
<212> TYPE: DNA
<213> ORGANISM: Homo Sapiens

<400> SEQUENCE: 495
tgtagttaga gctgcaccaa caccactacc wacattagca ttcatttttg ggcaaaataa    60
t                                                                   61

<210> SEQ ID NO 496
<211> LENGTH: 61
<212> TYPE: DNA
<213> ORGANISM: Homo Sapiens

<400> SEQUENCE: 496
acactttgtt gtcatttaag gttgaatatc sagagagtag cctgagtcat gctctgtcac    60
t                                                                   61

<210> SEQ ID NO 497
<211> LENGTH: 61
<212> TYPE: DNA
<213> ORGANISM: Homo Sapiens

<400> SEQUENCE: 497
tttacattat gcaatgaatg ctaattgaca rctgattcat aattagttaa ttgtaaacac    60
t                                                                   61

<210> SEQ ID NO 498
<211> LENGTH: 61
<212> TYPE: DNA
<213> ORGANISM: Homo Sapiens

<400> SEQUENCE: 498

```
cagacatttt tagctccagg tgaattgacc rtagactcac tggtatggca caaaggaaaa    60
a                                                                   61

<210> SEQ ID NO 499
<211> LENGTH: 61
<212> TYPE: DNA
<213> ORGANISM: Homo Sapiens

<400> SEQUENCE: 499
gaaactagag aggattgagg atattttct ygttaaaacc cagaactgga ggatcctagg     60
g                                                                   61

<210> SEQ ID NO 500
<211> LENGTH: 61
<212> TYPE: DNA
<213> ORGANISM: Homo Sapiens

<400> SEQUENCE: 500
aggtgggtaa taggatctgg gcatggcttc ygcatggaaa ttagtttccc tggttgcctg    60
c                                                                   61

<210> SEQ ID NO 501
<211> LENGTH: 61
<212> TYPE: DNA
<213> ORGANISM: Homo Sapiens

<400> SEQUENCE: 501
attctaagaa aagaatcacc gatgtgcaaa wagattcgtt accagagaca gcaggtgtcc    60
c                                                                   61

<210> SEQ ID NO 502
<211> LENGTH: 61
<212> TYPE: DNA
<213> ORGANISM: Homo Sapiens

<400> SEQUENCE: 502
tgagcactaa atgttccttg agtatgctca ratgactgta atagcagaca ggacatatcc    60
a                                                                   61

<210> SEQ ID NO 503
<211> LENGTH: 61
<212> TYPE: DNA
<213> ORGANISM: Homo Sapiens

<400> SEQUENCE: 503
tgataggctg agaaggaaga agaagaggaa rggttggttt ttctgtctca gaggtaacag    60
a                                                                   61

<210> SEQ ID NO 504
<211> LENGTH: 61
<212> TYPE: DNA
<213> ORGANISM: Homo Sapiens

<400> SEQUENCE: 504
tttcattgtt gccttataaa tttttcctgat rtcatgacct aattttactt cagagaagta   60
a                                                                   61

<210> SEQ ID NO 505
<211> LENGTH: 61
```

```
<212> TYPE: DNA
<213> ORGANISM: Homo Sapiens

<400> SEQUENCE: 505
accaaagaga ccagagtaat aaacttctca ycagtaacta ggaggatcct cccacaactc    60
c                                                                    61

<210> SEQ ID NO 506
<211> LENGTH: 61
<212> TYPE: DNA
<213> ORGANISM: Homo Sapiens

<400> SEQUENCE: 506
ccatcgcctt acatgggctg atgtgcaagc yctcctaaac atcatgctca cggcagatga    60
g                                                                    61

<210> SEQ ID NO 507
<211> LENGTH: 61
<212> TYPE: DNA
<213> ORGANISM: Homo Sapiens

<400> SEQUENCE: 507
gaaatagttt acatgaaatg gtgaccaaat rtggactcaa agctatgaaa atgtactata    60
c                                                                    61

<210> SEQ ID NO 508
<211> LENGTH: 61
<212> TYPE: DNA
<213> ORGANISM: Homo Sapiens

<400> SEQUENCE: 508
attcctaact cattaatgcc acctaaatcc rccccagtct ctacatctcc cctgctacca    60
t                                                                    61

<210> SEQ ID NO 509
<211> LENGTH: 61
<212> TYPE: DNA
<213> ORGANISM: Homo Sapiens

<400> SEQUENCE: 509
aacagtaagt gaactcattt atacagatca yctcagtttc aaaagaaatt ttacttgact    60
t                                                                    61

<210> SEQ ID NO 510
<211> LENGTH: 61
<212> TYPE: DNA
<213> ORGANISM: Homo Sapiens

<400> SEQUENCE: 510
acaaattaat tacatcagaa ctgtggtaaa yctaattctc aacattatgt gatcattaga    60
g                                                                    61

<210> SEQ ID NO 511
<211> LENGTH: 61
<212> TYPE: DNA
<213> ORGANISM: Homo Sapiens

<400> SEQUENCE: 511
gcacttgaac aataaaagaa atggatttcc raactgagtg caacgttttc tgggctttat    60
a                                                                    61
```

```
<210> SEQ ID NO 512
<211> LENGTH: 61
<212> TYPE: DNA
<213> ORGANISM: Homo Sapiens

<400> SEQUENCE: 512 tagcacctttt gggggaacttt ggggaagtag yaatgaatgg tggtctctat ggtaagactt      60
a                                                                       61

<210> SEQ ID NO 513
<211> LENGTH: 61
<212> TYPE: DNA
<213> ORGANISM: Homo Sapiens

<400> SEQUENCE: 513
cacttcttac cccaaaatat acagatgaat satttaacct tatgagacct tggttttctc      60
a                                                                       61

<210> SEQ ID NO 514
<211> LENGTH: 61
<212> TYPE: DNA
<213> ORGANISM: Homo Sapiens

<400> SEQUENCE: 514
ccttgcacct tacatatttt gttctcacac yttttaccac aatattaata gctaacttta      60
c                                                                       61

<210> SEQ ID NO 515
<211> LENGTH: 61
<212> TYPE: DNA
<213> ORGANISM: Homo Sapiens

<400> SEQUENCE: 515
ccatgtaatt gaagaaggaa gagtttgaca ygaagtaaaa gtctctgata ttgatctatc      60
t                                                                       61

<210> SEQ ID NO 516
<211> LENGTH: 61
<212> TYPE: DNA
<213> ORGANISM: Homo Sapiens

<400> SEQUENCE: 516
cgtaattttc actaagctca tataatgtat yacaaaaagc atcaagacat caaatgacag      60
a                                                                       61

<210> SEQ ID NO 517
<211> LENGTH: 61
<212> TYPE: DNA
<213> ORGANISM: Homo Sapiens

<400> SEQUENCE: 517
taggacacta agaaatcatt gtccacatga rctaaacaag tatctctgtt atctaaatgg      60
a                                                                       61

<210> SEQ ID NO 518
<211> LENGTH: 61
<212> TYPE: DNA
<213> ORGANISM: Homo Sapiens

<400> SEQUENCE: 518
```

```
atcaaccaag ggagtgatat aaactgcatt matttcaagt ggtctaactt agttattgtc    60
a                                                                    61

<210> SEQ ID NO 519
<211> LENGTH: 61
<212> TYPE: DNA
<213> ORGANISM: Homo Sapiens

<400> SEQUENCE: 519
cactcttttt ggtgtatagt tctgagtttc racaaacaca tatcgtcgtg taaccatcat    60
g                                                                    61

<210> SEQ ID NO 520
<211> LENGTH: 61
<212> TYPE: DNA
<213> ORGANISM: Homo Sapiens

<400> SEQUENCE: 520
gccctcagtc tccacccagt ttgctgagat staccactgg ttttaaacaa gaattttcca    60
g                                                                    61

<210> SEQ ID NO 521
<211> LENGTH: 61
<212> TYPE: DNA
<213> ORGANISM: Homo Sapiens

<400> SEQUENCE: 521
agttcttgat atggctatat cccattccag rcatagaggc aggctttagg gatacaatga    60
t                                                                    61

<210> SEQ ID NO 522
<211> LENGTH: 61
<212> TYPE: DNA
<213> ORGANISM: Homo Sapiens

<400> SEQUENCE: 522
gagatttaga ttgctgaggc atttcctatc mtaactcagt aggttcttaa gattttactt    60
t                                                                    61

<210> SEQ ID NO 523
<211> LENGTH: 61
<212> TYPE: DNA
<213> ORGANISM: Homo Sapiens

<400> SEQUENCE: 523
aataacacat acatgcattt gttcagtctc ytataggcca taaattactt ccataaatat    60
t                                                                    61

<210> SEQ ID NO 524
<211> LENGTH: 61
<212> TYPE: DNA
<213> ORGANISM: Homo Sapiens

<400> SEQUENCE: 524
actttggtta atttatcaag gaaattttgc matgattatc ctgtcctata atgcgcaagt    60
t                                                                    61

<210> SEQ ID NO 525
<211> LENGTH: 61
```

```
<212> TYPE: DNA
<213> ORGANISM: Homo Sapiens

<400> SEQUENCE: 525
taaatgtgaa ttcatgccta ctttcaacct rcactgctct gattgccaag tctactgaga    60
a                                                                   61

<210> SEQ ID NO 526
<211> LENGTH: 61
<212> TYPE: DNA
<213> ORGANISM: Homo Sapiens

<400> SEQUENCE: 526
tttatatgac aacctcacac ctcctataag raagagcctg ctgtgcaaga ttctctgtgc    60
a                                                                   61

<210> SEQ ID NO 527
<211> LENGTH: 61
<212> TYPE: DNA
<213> ORGANISM: Homo Sapiens

<400> SEQUENCE: 527
ataatgcttt catgtgtacc attggctttc yttgaaaatc acacatttgt aaattttgaa    60
a                                                                   61

<210> SEQ ID NO 528
<211> LENGTH: 61
<212> TYPE: DNA
<213> ORGANISM: Homo Sapiens

<400> SEQUENCE: 528
tataatcatt cactaaagat tgcctactaa ragataagag tggccaggta tgtacatgtg    60
t                                                                   61

<210> SEQ ID NO 529
<211> LENGTH: 61
<212> TYPE: DNA
<213> ORGANISM: Homo Sapiens

<400> SEQUENCE: 529
attgtcagct aaccttact tgcacatgta yggtagcagg gagtttgcta ctttgggtat     60
c                                                                   61

<210> SEQ ID NO 530
<211> LENGTH: 61
<212> TYPE: DNA
<213> ORGANISM: Homo Sapiens

<400> SEQUENCE: 530
tggtgatctt cttcttcttt tggttttgtc ygtatatgag gaccgtgcca gagtgtgagt    60
g                                                                   61

<210> SEQ ID NO 531
<211> LENGTH: 61
<212> TYPE: DNA
<213> ORGANISM: Homo Sapiens

<400> SEQUENCE: 531
catcagagat agataatttt ctccacctgt rtaatgattt catctctatc tatatttccc    60
c                                                                   61
```

<210> SEQ ID NO 532
<211> LENGTH: 61
<212> TYPE: DNA
<213> ORGANISM: Homo Sapiens

<400> SEQUENCE: 532
aaacaattat accttcctct agagttctgc raagtttatt tatttacttt tattgttaat     60
t                                                                    61

<210> SEQ ID NO 533
<211> LENGTH: 61
<212> TYPE: DNA
<213> ORGANISM: Homo Sapiens

<400> SEQUENCE: 533
tcctcatgca gcaattaaaa gcactaacac yggaatagtt tggacctctg attgagacaa     60
c                                                                    61

<210> SEQ ID NO 534
<211> LENGTH: 61
<212> TYPE: DNA
<213> ORGANISM: Homo Sapiens

<400> SEQUENCE: 534
taatacaaag atgatgacca cttccttcac rgacttcatg ccctgtgaag cagaatttac     60
a                                                                    61

<210> SEQ ID NO 535
<211> LENGTH: 61
<212> TYPE: DNA
<213> ORGANISM: Homo Sapiens

<400> SEQUENCE: 535
gttatttcct gcttataaaa tttttgttga ytttgaaggg cctatgcctt acatcaaccc     60
a                                                                    61

<210> SEQ ID NO 536
<211> LENGTH: 61
<212> TYPE: DNA
<213> ORGANISM: Homo Sapiens

<400> SEQUENCE: 536
cattcctttg tccctagctc atgcaaacca rtgaaagcaa tgttatttta ggataacttt     60
c                                                                    61

<210> SEQ ID NO 537
<211> LENGTH: 61
<212> TYPE: DNA
<213> ORGANISM: Homo Sapiens

<400> SEQUENCE: 537
atttggggtt atgaggagta aaataaatgc yggtattaat ggctaaattc taaaagataa     60
g                                                                    61

<210> SEQ ID NO 538
<211> LENGTH: 61
<212> TYPE: DNA
<213> ORGANISM: Homo Sapiens

<400> SEQUENCE: 538

```
tgggcttatg taatatttgt taattaactc maagatccat tcagggaaga aggggggttaa    60
a                                                                    61

<210> SEQ ID NO 539
<211> LENGTH: 61
<212> TYPE: DNA
<213> ORGANISM: Homo Sapiens

<400> SEQUENCE: 539
gccaggcaca attccaggta gcctacgtac rtaactttat ttaatgaatt ttcctaacat    60
t                                                                    61

<210> SEQ ID NO 540
<211> LENGTH: 61
<212> TYPE: DNA
<213> ORGANISM: Homo Sapiens

<400> SEQUENCE: 540
ttagagcact gtttgctatg tatcaccatc rttttcattc ataatataag aaaagttgaa    60
t                                                                    61

<210> SEQ ID NO 541
<211> LENGTH: 61
<212> TYPE: DNA
<213> ORGANISM: Homo Sapiens

<400> SEQUENCE: 541
tgattagtag aaatgaactt agatgggaat ygaacctgtc taagcccatg aactgtttca    60
a                                                                    61

<210> SEQ ID NO 542
<211> LENGTH: 61
<212> TYPE: DNA
<213> ORGANISM: Homo Sapiens

<400> SEQUENCE: 542
atgttcgaga gacagaacgt ctccgagaca rtaaccaaag taaaggtgtc aacgtacctg    60
a                                                                    61

<210> SEQ ID NO 543
<211> LENGTH: 61
<212> TYPE: DNA
<213> ORGANISM: Homo Sapiens

<400> SEQUENCE: 543
ggagaggctg gcaccttgat cttttgcagc rtcctaaact gtgagaaata aatttctgtt    60
c                                                                    61

<210> SEQ ID NO 544
<211> LENGTH: 61
<212> TYPE: DNA
<213> ORGANISM: Homo Sapiens

<400> SEQUENCE: 544
tgtgtttgtt actacctctc ttccatatta yaccaaactt tgagttggat ggggagtgac    60
t                                                                    61

<210> SEQ ID NO 545
<211> LENGTH: 61
```

```
<212> TYPE: DNA
<213> ORGANISM: Homo Sapiens

<400> SEQUENCE: 545
ttgctttggt acaacagatg aagtttccca rtaatctgct gtgtcgggaa ttagttgagg    60
a                                                                    61

<210> SEQ ID NO 546
<211> LENGTH: 61
<212> TYPE: DNA
<213> ORGANISM: Homo Sapiens

<400> SEQUENCE: 546
tttacccatt cacctatgga aaaaatcttc rtcgcattca atttaggata attttgaata    60
a                                                                    61

<210> SEQ ID NO 547
<211> LENGTH: 61
<212> TYPE: DNA
<213> ORGANISM: Homo Sapiens

<400> SEQUENCE: 547
aataattact gaaatctcaa actctactac ygttttctct gagaactcta gagagatgct    60
c                                                                    61

<210> SEQ ID NO 548
<211> LENGTH: 61
<212> TYPE: DNA
<213> ORGANISM: Homo Sapiens

<400> SEQUENCE: 548
gcaattacac actattttct gttaaatgac rtggtagacc acctgagaat atttcaaaaa    60
t                                                                    61

<210> SEQ ID NO 549
<211> LENGTH: 61
<212> TYPE: DNA
<213> ORGANISM: Homo Sapiens

<400> SEQUENCE: 549
attaaggata gagataaaaa agcaaggaga ycagtcttaa gagtaacata atcgatgtag    60
a                                                                    61

<210> SEQ ID NO 550
<211> LENGTH: 61
<212> TYPE: DNA
<213> ORGANISM: Homo Sapiens

<400> SEQUENCE: 550
taggaagggg caaaactggg attcacatcc rcctaccaca atctaacaac cttgatttt    60
c                                                                    61

<210> SEQ ID NO 551
<211> LENGTH: 61
<212> TYPE: DNA
<213> ORGANISM: Homo Sapiens

<400> SEQUENCE: 551
aacgtgaagt gactgactta ggacggtaat kaggatggta acatttaatg ctatgttcta    60
t                                                                    61
```

<210> SEQ ID NO 552
<211> LENGTH: 61
<212> TYPE: DNA
<213> ORGANISM: Homo Sapiens

<400> SEQUENCE: 552
ttattggttc gaactcaccc agctatattt ktactgtgct tgctatatac atgatttaaa    60
a                                                                   61

<210> SEQ ID NO 553
<211> LENGTH: 61
<212> TYPE: DNA
<213> ORGANISM: Homo Sapiens

<400> SEQUENCE: 553
agaatagtgt ggggaacggt tctgctacat kcctaaaagg agcaaaggga aattaatatt    60
g                                                                   61

<210> SEQ ID NO 554
<211> LENGTH: 61
<212> TYPE: DNA
<213> ORGANISM: Homo Sapiens

<400> SEQUENCE: 554
gtagctggga ttacaggcat ctgccactac rcgtggttaa tattttgtat ttttagtaga    60
g                                                                   61

<210> SEQ ID NO 555
<211> LENGTH: 61
<212> TYPE: DNA
<213> ORGANISM: Homo Sapiens

<400> SEQUENCE: 555
tggagtaagg gattagttct gtgtttcctt yggtttggtt gttggagcaa tattaccagc    60
a                                                                   61

<210> SEQ ID NO 556
<211> LENGTH: 61
<212> TYPE: DNA
<213> ORGANISM: Homo Sapiens

<400> SEQUENCE: 556
atcataattt ataagtcata aaatatcaag sagaagagtt aacatcactc aaggacttta    60
t                                                                   61

<210> SEQ ID NO 557
<211> LENGTH: 61
<212> TYPE: DNA
<213> ORGANISM: Homo Sapiens

<400> SEQUENCE: 557
taccggggta catttacagc ttccgattag raagttaaaa catctttaag tatatgaact    60
t                                                                   61

<210> SEQ ID NO 558
<211> LENGTH: 61
<212> TYPE: DNA
<213> ORGANISM: Homo Sapiens

<400> SEQUENCE: 558

```
tctcacagcc tcacctgtat ggataatttt rtcagccaaa tagagtaagt ggatcttagt    60
t                                                                   61
```

<210> SEQ ID NO 559
<211> LENGTH: 61
<212> TYPE: DNA
<213> ORGANISM: Homo Sapiens

<400> SEQUENCE: 559

```
tgggagttga gggagaagac tggcttttta mtttctacct tgctgttgtt ttaatttta    60
a                                                                   61
```

<210> SEQ ID NO 560
<211> LENGTH: 61
<212> TYPE: DNA
<213> ORGANISM: Homo Sapiens

<400> SEQUENCE: 560

```
ataagcaacg tggtgtgtaa tttacaagaa sacttaaaga actctcagta ccttggtgcc    60
g                                                                   61
```

<210> SEQ ID NO 561
<211> LENGTH: 61
<212> TYPE: DNA
<213> ORGANISM: Homo Sapiens

<400> SEQUENCE: 561

```
ggatgacttg gacaaccctc cagaaacaag kttagctggg agaaacattg tcctggtgta    60
a                                                                   61
```

<210> SEQ ID NO 562
<211> LENGTH: 61
<212> TYPE: DNA
<213> ORGANISM: Homo Sapiens

<400> SEQUENCE: 562

```
agagaaaagg tttaagacct cttagcacag yttctaacac atagtatagt cagtgttcgt    60
a                                                                   61
```

<210> SEQ ID NO 563
<211> LENGTH: 61
<212> TYPE: DNA
<213> ORGANISM: Homo Sapiens

<400> SEQUENCE: 563

```
tgagatacct gaattaacat ttctaggtct yttgttcaaa tgttaataaa gccagtgctt    60
c                                                                   61
```

<210> SEQ ID NO 564
<211> LENGTH: 61
<212> TYPE: DNA
<213> ORGANISM: Homo Sapiens

<400> SEQUENCE: 564

```
gggtatgccg gacacagggc ctatagtcac ygttagtttg gctaaataaa attgaaaatc    60
a                                                                   61
```

<210> SEQ ID NO 565
<211> LENGTH: 61

```
<212> TYPE: DNA
<213> ORGANISM: Homo Sapiens

<400> SEQUENCE: 565
ctgtgtttga aatctctatt tagctagcca ygtggatgtg tcaggccggt agttgcaaat    60
a                                                                  61

<210> SEQ ID NO 566
<211> LENGTH: 61
<212> TYPE: DNA
<213> ORGANISM: Homo Sapiens

<400> SEQUENCE: 566
ccagatggaa aaatccactg attgcacaac rtatggaata aacccagacc caggcacgtc    60
a                                                                  61

<210> SEQ ID NO 567
<211> LENGTH: 61
<212> TYPE: DNA
<213> ORGANISM: Homo Sapiens

<400> SEQUENCE: 567
ccaggagggt gacagctgtg catcaggaat kaagggcaag ttcagattga agcctcgtgt    60
c                                                                  61

<210> SEQ ID NO 568
<211> LENGTH: 61
<212> TYPE: DNA
<213> ORGANISM: Homo Sapiens

<400> SEQUENCE: 568
catcatcatc atcatcatcc ccctcacaat waccgtgtgg tggttaattt tgtgtgtcat    60
g                                                                  61

<210> SEQ ID NO 569
<211> LENGTH: 61
<212> TYPE: DNA
<213> ORGANISM: Homo Sapiens

<400> SEQUENCE: 569
taacatatct tctttacttc caagttagtg yttttcactc tacatcatgc ccaacacttt    60
c                                                                  61

<210> SEQ ID NO 570
<211> LENGTH: 61
<212> TYPE: DNA
<213> ORGANISM: Homo Sapiens

<400> SEQUENCE: 570
caacaagccc caaacacaag aaatgtgaac raaactacac cagggcattt ggttatgttt    60
a                                                                  61

<210> SEQ ID NO 571
<211> LENGTH: 61
<212> TYPE: DNA
<213> ORGANISM: Homo Sapiens

<400> SEQUENCE: 571
ttaaagcaag ttggattact tggttatttg yttcttccca acactctgca aagtatttga    60
c                                                                  61
```

<210> SEQ ID NO 572
<211> LENGTH: 61
<212> TYPE: DNA
<213> ORGANISM: Homo Sapiens

<400> SEQUENCE: 572
cagaagtcag aagagaggcg cgaagcagat ycttctctgg accgcagagg tgtggccctt    60
g                                                                   61

<210> SEQ ID NO 573
<211> LENGTH: 61
<212> TYPE: DNA
<213> ORGANISM: Homo Sapiens

<400> SEQUENCE: 573
ttattgtatc tggtatcagg aagaattcta rgagaagaaa gcctgattcc caataaggtt    60
t                                                                   61

<210> SEQ ID NO 574
<211> LENGTH: 61
<212> TYPE: DNA
<213> ORGANISM: Homo Sapiens

<400> SEQUENCE: 574
atagtgacct ctggccctgc actcccctac staagcctgt tttccaccaa gatgcccgat    60
c                                                                   61

<210> SEQ ID NO 575
<211> LENGTH: 61
<212> TYPE: DNA
<213> ORGANISM: Homo Sapiens

<400> SEQUENCE: 575
gaccctattg ctttctgctt gatatgttgg rttcagggag agcaagggct cctacaatca    60
c                                                                   61

<210> SEQ ID NO 576
<211> LENGTH: 61
<212> TYPE: DNA
<213> ORGANISM: Homo Sapiens

<400> SEQUENCE: 576
gaaagttttg aaaactttt gtctgtaatc ygtggaaaaa tgcactgacg tagtacacaa    60
a                                                                   61

<210> SEQ ID NO 577
<211> LENGTH: 61
<212> TYPE: DNA
<213> ORGANISM: Homo Sapiens

<400> SEQUENCE: 577
tctgtaatcc gtggaaaaat gcactgacgt mgtacacaaa cacccccca acatacacac    60
a                                                                   61

<210> SEQ ID NO 578
<211> LENGTH: 61
<212> TYPE: DNA
<213> ORGANISM: Homo Sapiens

<400> SEQUENCE: 578

```
caataacccc tgtgcgctgc attttatgtg wtgcgagaca ggtgtgcaac tgttgaatgc      60
a                                                                     61

<210> SEQ ID NO 579
<211> LENGTH: 61
<212> TYPE: DNA
<213> ORGANISM: Homo Sapiens

<400> SEQUENCE: 579
ctgctctctg agtagaaaat tataaggagc ytcttgtgga ttgcagagct gttgtatggc      60
t                                                                     61

<210> SEQ ID NO 580
<211> LENGTH: 61
<212> TYPE: DNA
<213> ORGANISM: Homo Sapiens

<400> SEQUENCE: 580
attccctatt agtcccttct tttcatttct stgtctatcc agcttggagt ccatggttca      60
t                                                                     61

<210> SEQ ID NO 581
<211> LENGTH: 61
<212> TYPE: DNA
<213> ORGANISM: Homo Sapiens

<400> SEQUENCE: 581
ttaacgtaca gattgactgc atgatgcact yagatttcaa aatgctaaat cttggtggga      60
a                                                                     61

<210> SEQ ID NO 582
<211> LENGTH: 61
<212> TYPE: DNA
<213> ORGANISM: Homo Sapiens

<400> SEQUENCE: 582
caaaattatt aatttgagtt ttttttggat rctgcataat gtcctagagg gttaaaaaaa      60
t                                                                     61

<210> SEQ ID NO 583
<211> LENGTH: 61
<212> TYPE: DNA
<213> ORGANISM: Homo Sapiens

<400> SEQUENCE: 583
gtggcaacta tctatttaac tatgcctaaa yagcaatgtc agttgtgccc cagtttccta      60
g                                                                     61

<210> SEQ ID NO 584
<211> LENGTH: 61
<212> TYPE: DNA
<213> ORGANISM: Homo Sapiens

<400> SEQUENCE: 584
gttctgtgtc ttaaaattat tgatattgtc rttagtcgtt gaattaagca tgaaggtgat      60
t                                                                     61

<210> SEQ ID NO 585
<211> LENGTH: 61
```

```
<212> TYPE: DNA
<213> ORGANISM: Homo Sapiens

<400> SEQUENCE: 585
aagcaggagg aggttaaagt acagacaatg rccaagaaac acatccacat aaactagtca    60
g                                                                   61

<210> SEQ ID NO 586
<211> LENGTH: 61
<212> TYPE: DNA
<213> ORGANISM: Homo Sapiens

<400> SEQUENCE: 586
accagtcaac tctcgtatat tgcatacaac ygtagaaggc catcctagac aataatacaa    60
c                                                                   61

<210> SEQ ID NO 587
<211> LENGTH: 61
<212> TYPE: DNA
<213> ORGANISM: Homo Sapiens

<400> SEQUENCE: 587
tggaaagaaa atagacgtaa aaatcaaatt mtgtgaagct gctaaagaaa atctctactg    60
a                                                                   61

<210> SEQ ID NO 588
<211> LENGTH: 61
<212> TYPE: DNA
<213> ORGANISM: Homo Sapiens

<400> SEQUENCE: 588
gggatttggg aggtcattgt ggttacttct ytgcttttag ttagcttgct agccatttca    60
g                                                                   61

<210> SEQ ID NO 589
<211> LENGTH: 61
<212> TYPE: DNA
<213> ORGANISM: Homo Sapiens

<400> SEQUENCE: 589
ttgttctaaa tctttcaaat gatagcggaa ygatcttccc atacttatca agaagtgaca    60
g                                                                   61

<210> SEQ ID NO 590
<211> LENGTH: 61
<212> TYPE: DNA
<213> ORGANISM: Homo Sapiens

<400> SEQUENCE: 590
ggatacaggc aaaggaaaac tgtactaggc raggcccata gaataaattg acaggattat    60
t                                                                   61

<210> SEQ ID NO 591
<211> LENGTH: 61
<212> TYPE: DNA
<213> ORGANISM: Homo Sapiens

<400> SEQUENCE: 591
tcacattccc ctagttacac aattttttctg rtaaccctga atcttgggat cttttacagt   60
c                                                                   61
```

<210> SEQ ID NO 592
<211> LENGTH: 61
<212> TYPE: DNA
<213> ORGANISM: Homo Sapiens

<400> SEQUENCE: 592
gtcctgaaac agaaaattaa aactctgact sagtgttgtc aggcattgta gaaaagatgt    60
t                                                                   61

<210> SEQ ID NO 593
<211> LENGTH: 61
<212> TYPE: DNA
<213> ORGANISM: Homo Sapiens

<400> SEQUENCE: 593
gctctgaaaa tgctgctctg tagatatgac mttttctgct ttgctgtaga cagtgtaatt    60
c                                                                   61

<210> SEQ ID NO 594
<211> LENGTH: 61
<212> TYPE: DNA
<213> ORGANISM: Homo Sapiens

<400> SEQUENCE: 594
agcaggccat gcttacctta gaactggagc rgtcggccct gctgcagacg gtggaggagc    60
t                                                                   61

<210> SEQ ID NO 595
<211> LENGTH: 61
<212> TYPE: DNA
<213> ORGANISM: Homo Sapiens

<400> SEQUENCE: 595
atttagaaca gaaaggttgc acagctctta yatactcaaa catagttttta gagttagatc    60
a                                                                   61

<210> SEQ ID NO 596
<211> LENGTH: 61
<212> TYPE: DNA
<213> ORGANISM: Homo Sapiens

<400> SEQUENCE: 596
gagcctgaag agagttttac tgcactgaat rggggacaga aagcagtact ggcaacattt    60
t                                                                   61

<210> SEQ ID NO 597
<211> LENGTH: 61
<212> TYPE: DNA
<213> ORGANISM: Homo Sapiens

<400> SEQUENCE: 597
cctcctgagt aacagggtag gtgggagggc ytcctaagaa ctcctttgtc caggagcccc    60
a                                                                   61

<210> SEQ ID NO 598
<211> LENGTH: 61
<212> TYPE: DNA
<213> ORGANISM: Homo Sapiens

<400> SEQUENCE: 598

```
ccactgagtc tcagctgggc agaggacaaa kaaggactgc atgtggttgg tggtcttaga    60
a                                                                   61

<210> SEQ ID NO 599
<211> LENGTH: 61
<212> TYPE: DNA
<213> ORGANISM: Homo Sapiens

<400> SEQUENCE: 599
cttttctagt ttccaaagtc cataatttcc rgacagcagg aatagttatg caaagaacag    60
a                                                                   61

<210> SEQ ID NO 600
<211> LENGTH: 61
<212> TYPE: DNA
<213> ORGANISM: Homo Sapiens

<400> SEQUENCE: 600
agactgtaaa agatattgga aatggatcaa rgcactctga acatattcaa ataattgctg    60
t                                                                   61

<210> SEQ ID NO 601
<211> LENGTH: 61
<212> TYPE: DNA
<213> ORGANISM: Homo Sapiens

<400> SEQUENCE: 601
aagatggccg tgaattagga tgtatgacag ygagacacgt atgtgcacca ttctggtctt    60
c                                                                   61

<210> SEQ ID NO 602
<211> LENGTH: 61
<212> TYPE: DNA
<213> ORGANISM: Homo Sapiens

<400> SEQUENCE: 602
ttcattctca aagagctaaa tttgttttgg kgtgagaggc tgataattag gttgacccTT    60
g                                                                   61

<210> SEQ ID NO 603
<211> LENGTH: 61
<212> TYPE: DNA
<213> ORGANISM: Homo Sapiens

<400> SEQUENCE: 603
gtctaacgtc atctggagaa ctgtttaagc rgaatccttg cccttctgaa cctatccaca    60
t                                                                   61

<210> SEQ ID NO 604
<211> LENGTH: 61
<212> TYPE: DNA
<213> ORGANISM: Homo Sapiens

<400> SEQUENCE: 604
cgccatcccg caaccccctg ttatgttcat rtacttccac ggttctcgcg tcatgcctgt    60
g                                                                   61

<210> SEQ ID NO 605
<211> LENGTH: 61
```

```
<212> TYPE: DNA
<213> ORGANISM: Homo Sapiens

<400> SEQUENCE: 605
tcagtgagtc atgagttctt ccttttttcag ytagtcaggc ctggcttttg ttcaagtcct    60
g                                                                    61

<210> SEQ ID NO 606
<211> LENGTH: 61
<212> TYPE: DNA
<213> ORGANISM: Homo Sapiens

<400> SEQUENCE: 606
caaagaacag gcaagatctt cataggctga rtttagtctg ggaaggtttt gtgtgggatg    60
t                                                                    61

<210> SEQ ID NO 607
<211> LENGTH: 61
<212> TYPE: DNA
<213> ORGANISM: Homo Sapiens

<400> SEQUENCE: 607
cctggctttg gggatttccc ttgattacag mtagcctata tacattgcag aatacagaaa    60
a                                                                    61

<210> SEQ ID NO 608
<211> LENGTH: 61
<212> TYPE: DNA
<213> ORGANISM: Homo Sapiens

<400> SEQUENCE: 608
tacttaccaa acgggatggt aacttggaca ytgtgtcagg gaagaggcac ttggtcctct    60
g                                                                    61

<210> SEQ ID NO 609
<211> LENGTH: 61
<212> TYPE: DNA
<213> ORGANISM: Homo Sapiens

<400> SEQUENCE: 609
tgttgtgcta tcaaaaatta gatctgattc rttgcatcta actatatttt tgtactcact    60
g                                                                    61

<210> SEQ ID NO 610
<211> LENGTH: 61
<212> TYPE: DNA
<213> ORGANISM: Homo Sapiens

<400> SEQUENCE: 610
agtggtatga ggtactgtgt agagcaatga wtcacaatta tttttgcact ttgatttgag    60
a                                                                    61

<210> SEQ ID NO 611
<211> LENGTH: 61
<212> TYPE: DNA
<213> ORGANISM: Homo Sapiens

<400> SEQUENCE: 611
gtttagaatg ggtcttgtgt ccttgctttg yggagttttc aaatacaaga cttctaaaag    60
t                                                                    61
```

<210> SEQ ID NO 612
<211> LENGTH: 61
<212> TYPE: DNA
<213> ORGANISM: Homo Sapiens

<400> SEQUENCE: 612
aactctctca gcagagttcg tagtcttgtg yttcccttc tacttactca tgatctcctc    60
t                                                                   61

<210> SEQ ID NO 613
<211> LENGTH: 61
<212> TYPE: DNA
<213> ORGANISM: Homo Sapiens

<400> SEQUENCE: 613
gtatgatttc ttcaactat gtgtgagtct rtagttatct caaataaaa tgttaaaaaa     60 a                                                                   61

<210> SEQ ID NO 614
<211> LENGTH: 61
<212> TYPE: DNA
<213> ORGANISM: Homo Sapiens

<400> SEQUENCE: 614
actaatttat atttcttcct cttcctattc kttggccatt ttccctgtgt attttttgtt    60
t                                                                   61

<210> SEQ ID NO 615
<211> LENGTH: 61
<212> TYPE: DNA
<213> ORGANISM: Homo Sapiens

<400> SEQUENCE: 615
tattttagtc actattcctg cactctttcg yttattctag agaaaagtgg gctaaactat    60
t                                                                   61

<210> SEQ ID NO 616
<211> LENGTH: 61
<212> TYPE: DNA
<213> ORGANISM: Homo Sapiens

<400> SEQUENCE: 616
tgccctatta aaggggagac tagtaggatg ygctcttctg aaaccaaaca gcgttgtggg    60
c                                                                   61

<210> SEQ ID NO 617
<211> LENGTH: 61
<212> TYPE: DNA
<213> ORGANISM: Homo Sapiens

<400> SEQUENCE: 617
tctctctaaa atctatcaag ccttgggcta kggtaatgag tcggtaaagg agacaaaatg    60
t                                                                   61

<210> SEQ ID NO 618
<211> LENGTH: 61
<212> TYPE: DNA
<213> ORGANISM: Homo Sapiens

<400> SEQUENCE: 618

```
ggccaacctc tgctgccgac cagcatctac scggtacctt ccctggagcc acactttgcc    60
c                                                                    61

<210> SEQ ID NO 619
<211> LENGTH: 61
<212> TYPE: DNA
<213> ORGANISM: Homo Sapiens

<400> SEQUENCE: 619
ggtttggaat gtgagtgact tcctctctgc statctatga acactcagac tctgggatag    60
g                                                                    61

<210> SEQ ID NO 620
<211> LENGTH: 61
<212> TYPE: DNA
<213> ORGANISM: Homo Sapiens

<400> SEQUENCE: 620
cgattgaggt aggagtctcg gtcttgtctg wgtcattata tatgagtcag ttactgtaag    60
a                                                                    61

<210> SEQ ID NO 621
<211> LENGTH: 61
<212> TYPE: DNA
<213> ORGANISM: Homo Sapiens

<400> SEQUENCE: 621
cagcatgccc gtgggcaaca acatagataa mgtcctctcc aggtaggtgg ctcccagtgg    60
c                                                                    61

<210> SEQ ID NO 622
<211> LENGTH: 61
<212> TYPE: DNA
<213> ORGANISM: Homo Sapiens

<400> SEQUENCE: 622
ctggtcaatg tgatacttcc cgctgttagc staggatacc taggagggaa ggctggatgt    60
c                                                                    61

<210> SEQ ID NO 623
<211> LENGTH: 61
<212> TYPE: DNA
<213> ORGANISM: Homo Sapiens

<400> SEQUENCE: 623
atttgggcag gttctttaac ctcactgaac ytcattctcc tcatctgtaa aatgggacac    60
a                                                                    61

<210> SEQ ID NO 624
<211> LENGTH: 61
<212> TYPE: DNA
<213> ORGANISM: Homo Sapiens

<400> SEQUENCE: 624
tcaacatatg aaggagacag ctaattggct mttctatgca aagtcagctt ttaaaatgac    60
a                                                                    61

<210> SEQ ID NO 625
<211> LENGTH: 61
```

```
<212> TYPE: DNA
<213> ORGANISM: Homo Sapiens

<400> SEQUENCE: 625
aaaaaaaaat agaactgaaa ctaacaagta sagactgttc aacatgtgtg atggtaaaat      60
g                                                                    61

<210> SEQ ID NO 626
<211> LENGTH: 61
<212> TYPE: DNA
<213> ORGANISM: Homo Sapiens

<400> SEQUENCE: 626
gttaaatgca aagagctgaa gttgttagta ytcacagaac agaaattttt agctaacagt      60
a                                                                    61

<210> SEQ ID NO 627
<211> LENGTH: 61
<212> TYPE: DNA
<213> ORGANISM: Homo Sapiens

<400> SEQUENCE: 627
aacctctcat tcaagtgaac tatcctcata rgcagtcgag atacaatatt tttttaaagt      60
t                                                                    61

<210> SEQ ID NO 628
<211> LENGTH: 61
<212> TYPE: DNA
<213> ORGANISM: Homo Sapiens

<400> SEQUENCE: 628
aaatcacagc atttggggac tgcagtttgt ytcagccaag aactagagct tggaagtaat      60
a                                                                    61

<210> SEQ ID NO 629
<211> LENGTH: 61
<212> TYPE: DNA
<213> ORGANISM: Homo Sapiens

<400> SEQUENCE: 629
aagtctcaag tatttctcac atactttgcc rttttttattt ctacatttga ttaccatata    60
a                                                                    61

<210> SEQ ID NO 630
<211> LENGTH: 61
<212> TYPE: DNA
<213> ORGANISM: Homo Sapiens

<400> SEQUENCE: 630
tctttgccta cacactactg acctcctgct ytgccctaac ttcacgatgg agttacttat      60
g                                                                    61

<210> SEQ ID NO 631
<211> LENGTH: 61
<212> TYPE: DNA
<213> ORGANISM: Homo Sapiens

<400> SEQUENCE: 631
tttttgattt gtttgtttca ctgttttttca rgtctgaata gcttgcattt gtttaaagca    60
g                                                                    61
```

```
<210> SEQ ID NO 632
<211> LENGTH: 61
<212> TYPE: DNA
<213> ORGANISM: Homo Sapiens

<400> SEQUENCE: 632
gaggaagaac actgcatgat acaggctgtg ygatagtggt attattcaag ttcccttgag    60
c                                                                    61

<210> SEQ ID NO 633
<211> LENGTH: 61
<212> TYPE: DNA
<213> ORGANISM: Homo Sapiens

<400> SEQUENCE: 633
taatctgagt cttccttact ttggctccaa rgatcccta aaagactgcc agagaatgag     60
a                                                                    61

<210> SEQ ID NO 634
<211> LENGTH: 61
<212> TYPE: DNA
<213> ORGANISM: Homo Sapiens

<400> SEQUENCE: 634
ccagatatgt tacatacatt acctcattgc rtcctcaaaa cagttctgca agggaggtat    60
t                                                                    61

<210> SEQ ID NO 635
<211> LENGTH: 61
<212> TYPE: DNA
<213> ORGANISM: Homo Sapiens

<400> SEQUENCE: 635
caggcagggc ctgaatttgg ccagcatgcc rtggtttgct gacccatgtt atggttctta    60
t                                                                    61

<210> SEQ ID NO 636
<211> LENGTH: 61
<212> TYPE: DNA
<213> ORGANISM: Homo Sapiens

<400> SEQUENCE: 636
acatcaatat ggtgacaaag aatttacagt rggagatagt tattgaatag caaggtttat    60
g                                                                    61

<210> SEQ ID NO 637
<211> LENGTH: 61
<212> TYPE: DNA
<213> ORGANISM: Homo Sapiens

<400> SEQUENCE: 637
catctctcac tacatcatgc agtagttgta yttccaggcc ctgaattccc attaattact    60
g                                                                    61

<210> SEQ ID NO 638
<211> LENGTH: 61
<212> TYPE: DNA
<213> ORGANISM: Homo Sapiens

<400> SEQUENCE: 638
```

```
agttgtagct gaataaataa aaattcttgt yattgaccac attatttggc atttccctca    60
t                                                                    61

<210> SEQ ID NO 639
<211> LENGTH: 61
<212> TYPE: DNA
<213> ORGANISM: Homo Sapiens

<400> SEQUENCE: 639
ttctcactgc ttccttattt gtaatgtaaa ygatctgaaa tgacctaaat gtctctcagt    60
c                                                                    61

<210> SEQ ID NO 640
<211> LENGTH: 61
<212> TYPE: DNA
<213> ORGANISM: Homo Sapiens

<400> SEQUENCE: 640
aagcattgat gttacggcta gtactaacta yagcctaaac tgcaaacaac tgaataaaag    60
g                                                                    61

<210> SEQ ID NO 641
<211> LENGTH: 61
<212> TYPE: DNA
<213> ORGANISM: Homo Sapiens

<400> SEQUENCE: 641
caaggtaggg ctcagtccac aaaagagaga ycgaaaagtt agcaaagtac gtttagtaaa    60
a                                                                    61

<210> SEQ ID NO 642
<211> LENGTH: 61
<212> TYPE: DNA
<213> ORGANISM: Homo Sapiens

<400> SEQUENCE: 642
aaaaaaaagg actgaccaat ttcttttttcg ytgaatcact ttcttcatct tctcctcggt    60
c                                                                    61

<210> SEQ ID NO 643
<211> LENGTH: 61
<212> TYPE: DNA
<213> ORGANISM: Homo Sapiens

<400> SEQUENCE: 643
ggcatcctag ttctctgtac tgggctcctc yagaaagttt atcagattgc tcctgatatt    60
t                                                                    61

<210> SEQ ID NO 644
<211> LENGTH: 61
<212> TYPE: DNA
<213> ORGANISM: Homo Sapiens

<400> SEQUENCE: 644
agaaattaaa actgtgcttt tcttaaagcc ytgaaaatgg aagctaaaca acttaaatga    60
a                                                                    61

<210> SEQ ID NO 645
<211> LENGTH: 61
```

```
<212> TYPE: DNA
<213> ORGANISM: Homo Sapiens

<400> SEQUENCE: 645
aaatattttg cttaggtttg tatcatttaa wtacagatgg gagagtggat ttctaatctt    60
c                                                                   61

<210> SEQ ID NO 646
<211> LENGTH: 61
<212> TYPE: DNA
<213> ORGANISM: Homo Sapiens

<400> SEQUENCE: 646
cttcagtttt ctaaattatg tttgacatca rgacagtcaa gtcagtccag gatgagaaaa    60
g                                                                   61

<210> SEQ ID NO 647
<211> LENGTH: 61
<212> TYPE: DNA
<213> ORGANISM: Homo Sapiens

<400> SEQUENCE: 647
tcaccaatat cggtatcaca cagtctcgca ytttacataa ctgaaaaatc tgcgatcccc    60
t                                                                   61

<210> SEQ ID NO 648
<211> LENGTH: 61
<212> TYPE: DNA
<213> ORGANISM: Homo Sapiens

<400> SEQUENCE: 648
gatcagaact gcatgttgtt aatgacaatt rtgccaaaaa ataccccttg agtacattag    60
t                                                                   61

<210> SEQ ID NO 649
<211> LENGTH: 61
<212> TYPE: DNA
<213> ORGANISM: Homo Sapiens

<400> SEQUENCE: 649
ctaattttta acaaagttac tgacttttaa ytcacagaga aaaaaatgat ggtatgggag    60
t                                                                   61

<210> SEQ ID NO 650
<211> LENGTH: 61
<212> TYPE: DNA
<213> ORGANISM: Homo Sapiens

<400> SEQUENCE: 650
cctgaaagaa ttgacaaaaa gctccaggaa mtaataagca attatagcag ggttgcagga    60
t                                                                   61

<210> SEQ ID NO 651
<211> LENGTH: 61
<212> TYPE: DNA
<213> ORGANISM: Homo Sapiens

<400> SEQUENCE: 651
tagggcattg taatgaccat gagaattcat sggtagatct gtgagagaat ggagcatcaa    60
g                                                                   61
```

<210> SEQ ID NO 652
<211> LENGTH: 61
<212> TYPE: DNA
<213> ORGANISM: Homo Sapiens

<400> SEQUENCE: 652
gtgcaataat tagcagttag gtcagtatcc rgcacatagt gagcattcaa taattagtga    60
c                                                                    61

<210> SEQ ID NO 653
<211> LENGTH: 61
<212> TYPE: DNA
<213> ORGANISM: Homo Sapiens

<400> SEQUENCE: 653
agaaaaacca tagtgtgttg gccttgtaag ygggcttaga gattgtaggc atgcattggt    60
g                                                                    61

<210> SEQ ID NO 654
<211> LENGTH: 61
<212> TYPE: DNA
<213> ORGANISM: Homo Sapiens

<400> SEQUENCE: 654
aagaacaact agtaaattct tgactaaaat mctactgatg aagtaaaatt ctaactcaaa    60
a                                                                    61

<210> SEQ ID NO 655
<211> LENGTH: 61
<212> TYPE: DNA
<213> ORGANISM: Homo Sapiens

<400> SEQUENCE: 655
aggagaaaaa gaatattaca gttgaaatag scttcatttt cttcctagtc tctttacccg    60
c                                                                    61

<210> SEQ ID NO 656
<211> LENGTH: 61
<212> TYPE: DNA
<213> ORGANISM: Homo Sapiens

<400> SEQUENCE: 656
gaaggaagga taaaagttag gaagctctac wgcatttgat tggttgttgt acctcgtcac    60
c                                                                    61

<210> SEQ ID NO 657
<211> LENGTH: 61
<212> TYPE: DNA
<213> ORGANISM: Homo Sapiens

<400> SEQUENCE: 657
ttgtcttagc tacttttcga tctattttgc rcatagcctt ggatattctt gattttagta    60
t                                                                    61

<210> SEQ ID NO 658
<211> LENGTH: 61
<212> TYPE: DNA
<213> ORGANISM: Homo Sapiens

<400> SEQUENCE: 658

```
aggggggagaa gagaacaagt aaaggaaaca yggtgagtgc tgtggcagga tggagatgac    60
t                                                                     61

<210> SEQ ID NO 659
<211> LENGTH: 61
<212> TYPE: DNA
<213> ORGANISM: Homo Sapiens

<400> SEQUENCE: 659
actcaggaaa tatacctaga aatcagagtt wtggataccc tgtgatcaag acaatcaatt    60
t                                                                     61

<210> SEQ ID NO 660
<211> LENGTH: 61
<212> TYPE: DNA
<213> ORGANISM: Homo Sapiens

<400> SEQUENCE: 660
gagagtaggg gaggtgtcaa aatggataac rtaggcaata acagccaaat atgcccgtgt    60
t                                                                     61

<210> SEQ ID NO 661
<211> LENGTH: 61
<212> TYPE: DNA
<213> ORGANISM: Homo Sapiens

<400> SEQUENCE: 661
tattaaacgt tacaaactgg aattctgtca rttaattcct atgtactttc atatctgtat    60
t                                                                     61

<210> SEQ ID NO 662
<211> LENGTH: 61
<212> TYPE: DNA
<213> ORGANISM: Homo Sapiens

<400> SEQUENCE: 662
tctgattggg aatggacact atcagaatat wccgtcctgc tcacagaata tattataagg    60
a                                                                     61

<210> SEQ ID NO 663
<211> LENGTH: 61
<212> TYPE: DNA
<213> ORGANISM: Homo Sapiens

<400> SEQUENCE: 663
gaaaaggaat tctgaggaga gagtgatcaa rgtagcttaa atgttatatc agttattcat    60
t                                                                     61

<210> SEQ ID NO 664
<211> LENGTH: 61
<212> TYPE: DNA
<213> ORGANISM: Homo Sapiens

<400> SEQUENCE: 664
aagtaatata tttagccaat actggttatc ragagagaga gagagagaaa gagagagaga    60
g                                                                     61

<210> SEQ ID NO 665
<211> LENGTH: 61
```

```
<212> TYPE: DNA
<213> ORGANISM: Homo Sapiens

<400> SEQUENCE: 665
atatgtttat gaaaaagatg cccagtttca ractcttctc cttactctct agctatagcc    60
c                                                                    61

<210> SEQ ID NO 666
<211> LENGTH: 61
<212> TYPE: DNA
<213> ORGANISM: Homo Sapiens

<400> SEQUENCE: 666
agttagagtt caggcactta tcagctaaat raccttgaat ctgtgactag ttatctacaa    60
a                                                                    61

<210> SEQ ID NO 667
<211> LENGTH: 61
<212> TYPE: DNA
<213> ORGANISM: Homo Sapiens

<400> SEQUENCE: 667
acttgaaaaa gcataatctc ttgttgacaa ygccacagtt tacttctact aggaaagttt    60
a                                                                    61

<210> SEQ ID NO 668
<211> LENGTH: 61
<212> TYPE: DNA
<213> ORGANISM: Homo Sapiens

<400> SEQUENCE: 668
agttcctaaa catggtcctg ggaagagata yggtgaacta gcaatattat tcattctaac    60
a                                                                    61

<210> SEQ ID NO 669
<211> LENGTH: 61
<212> TYPE: DNA
<213> ORGANISM: Homo Sapiens

<400> SEQUENCE: 669
tttcttttaa tctaatctta attcttctgt scaagctaat tttcctgtac acatttattt    60
t                                                                    61

<210> SEQ ID NO 670
<211> LENGTH: 61
<212> TYPE: DNA
<213> ORGANISM: Homo Sapiens

<400> SEQUENCE: 670
tgttcatctt ctcgttatct tcagaatctc rtactttgca tatatttaat ttattcttgt    60
c                                                                    61

<210> SEQ ID NO 671
<211> LENGTH: 61
<212> TYPE: DNA
<213> ORGANISM: Homo Sapiens

<400> SEQUENCE: 671
aggcatatat tgctatcaat catcaatttt rggcattacc tacttatctt ttttatggta    60
a                                                                    61
```

<210> SEQ ID NO 672
<211> LENGTH: 61
<212> TYPE: DNA
<213> ORGANISM: Homo Sapiens

<400> SEQUENCE: 672
atgtgtgtaa gttggagact gttgagtgac yaaaagtttg cttctctcat tgaaatagga    60
a                                                                     61

<210> SEQ ID NO 673
<211> LENGTH: 61
<212> TYPE: DNA
<213> ORGANISM: Homo Sapiens

<400> SEQUENCE: 673
actgacttaa atgggagcta caaagaaaca yagacagtgc caagaagtca tcttaatagg    60
t                                                                     61

<210> SEQ ID NO 674
<211> LENGTH: 61
<212> TYPE: DNA
<213> ORGANISM: Homo Sapiens

<400> SEQUENCE: 674
aaaaccctat cctctacctt acttatgcta ycttacttct ctatcctttg tgtaatttct    60
g                                                                     61

<210> SEQ ID NO 675
<211> LENGTH: 61
<212> TYPE: DNA
<213> ORGANISM: Homo Sapiens

<400> SEQUENCE: 675
tgttatgggc tcatttatta gtggaaactc raacaaaatt catatcctgg tggtacacat    60
t                                                                     61

<210> SEQ ID NO 676
<211> LENGTH: 61
<212> TYPE: DNA
<213> ORGANISM: Homo Sapiens

<400> SEQUENCE: 676
tgagaatctt gcattttctc tgccagttac rtttgtattc atcttagcac tgatggaata    60
a                                                                     61

<210> SEQ ID NO 677
<211> LENGTH: 61
<212> TYPE: DNA
<213> ORGANISM: Homo Sapiens

<400> SEQUENCE: 677
ggctagagaa ggccagccct gatggccaac rtcctagcag aatataaggt gcttatccaa    60
t                                                                     61

<210> SEQ ID NO 678
<211> LENGTH: 61
<212> TYPE: DNA
<213> ORGANISM: Homo Sapiens

<400> SEQUENCE: 678

```
agccttagac atcttcagta tctcctgaga magttacctc ttagaaggca gctgccatac    60
t                                                                   61
```

<210> SEQ ID NO 679
<211> LENGTH: 61
<212> TYPE: DNA
<213> ORGANISM: Homo Sapiens

<400> SEQUENCE: 679

```
ttatatagat gtgaaccagg aactccctga ygaggtgatt ttgaatagag agttgaagga    60
g                                                                   61
```

<210> SEQ ID NO 680
<211> LENGTH: 61
<212> TYPE: DNA
<213> ORGANISM: Homo Sapiens

<400> SEQUENCE: 680

```
ggcctttaa gtgttttga aatatagcct maactaagaa tggtaaaaat tccatcaagg     60
t                                                                   61
```

<210> SEQ ID NO 681
<211> LENGTH: 61
<212> TYPE: DNA
<213> ORGANISM: Homo Sapiens

<400> SEQUENCE: 681

```
ttattgtcaa ggggagaaga taggtgtcct ycatgtaatc ataccaataa acacagcatt    60
a                                                                   61
```

<210> SEQ ID NO 682
<211> LENGTH: 61
<212> TYPE: DNA
<213> ORGANISM: Homo Sapiens

<400> SEQUENCE: 682

```
atttgatgtc atttggaaga aggattccag yggaaacaaa accatatatg agaggaggac    60
t                                                                   61
```

<210> SEQ ID NO 683
<211> LENGTH: 61
<212> TYPE: DNA
<213> ORGANISM: Homo Sapiens

<400> SEQUENCE: 683

```
ttgcctatat tcccaaagga ttaaaataaa kctaagtaca tttccccaaa gtttgaaacg    60
g                                                                   61
```

<210> SEQ ID NO 684
<211> LENGTH: 61
<212> TYPE: DNA
<213> ORGANISM: Homo Sapiens

<400> SEQUENCE: 684

```
ctgctagaac acacgacatg aaattaggaa ygacagtaag gctagaatct gtatcacgaa    60
g                                                                   61
```

<210> SEQ ID NO 685
<211> LENGTH: 61

<212> TYPE: DNA
<213> ORGANISM: Homo Sapiens

<400> SEQUENCE: 685
taattagcac atgaaaagtg aacatgaaga rataaacaga ggtgatttgg agaggtgaaa    60
c                                                                   61

<210> SEQ ID NO 686
<211> LENGTH: 61
<212> TYPE: DNA
<213> ORGANISM: Homo Sapiens

<400> SEQUENCE: 686
cacaaaatat gtgtcaattc cacaatccac maagagtttt ttctcttcac caaactcctc    60
c                                                                   61

<210> SEQ ID NO 687
<211> LENGTH: 61
<212> TYPE: DNA
<213> ORGANISM: Homo Sapiens

<400> SEQUENCE: 687
gaacaactct catgtataca actgaaaaat yacaaggtg tattcactta acacaaagtg     60
a                                                                   61

<210> SEQ ID NO 688
<211> LENGTH: 61
<212> TYPE: DNA
<213> ORGANISM: Homo Sapiens

<400> SEQUENCE: 688
ggacaatcaa ttgctcaatg gcagcaggta wttttgactt cactctctga tattcagcta    60
g                                                                   61

<210> SEQ ID NO 689
<211> LENGTH: 61
<212> TYPE: DNA
<213> ORGANISM: Homo Sapiens

<400> SEQUENCE: 689
actggcaact tccctcttcc agaaacgaga yagatacaaa aggaacttca gtaacatgaa    60
g                                                                   61

<210> SEQ ID NO 690
<211> LENGTH: 61
<212> TYPE: DNA
<213> ORGANISM: Homo Sapiens

<400> SEQUENCE: 690
tagaacgagt tgcggaagtt catggatgtt rcatttgcaa agattcaaaa cacaaatcaa    60
g                                                                   61

<210> SEQ ID NO 691
<211> LENGTH: 61
<212> TYPE: DNA
<213> ORGANISM: Homo Sapiens

<400> SEQUENCE: 691
caacaatcaa tgtaaatggc ttaaacttgc rattaaagga aagagagtct cagctgtttt    60
t                                                                   61

<210> SEQ ID NO 692
<211> LENGTH: 61
<212> TYPE: DNA
<213> ORGANISM: Homo Sapiens

<400> SEQUENCE: 692
aatcaggatg acttcagtgt tggccacatg bttatgggtg gatggccttg ggtacatcta    60
a                                                                   61

<210> SEQ ID NO 693
<211> LENGTH: 61
<212> TYPE: DNA
<213> ORGANISM: Homo Sapiens

<400> SEQUENCE: 693
tagacattag acttcagagg actattgtga rcattaaatg agattatgca tgggatgtgc    60
t                                                                   61

<210> SEQ ID NO 694
<211> LENGTH: 61
<212> TYPE: DNA
<213> ORGANISM: Homo Sapiens

<400> SEQUENCE: 694
atgtgatctt ggagacaata ttttatgttc ytagtctcta gttttcctat ttttgaaata    60
a                                                                   61

<210> SEQ ID NO 695
<211> LENGTH: 61
<212> TYPE: DNA
<213> ORGANISM: Homo Sapiens

<400> SEQUENCE: 695
cataactggt taccttaga tagtgtccaa yaaggcacct caaaatattc taagtgctct     60
a                                                                   61

<210> SEQ ID NO 696
<211> LENGTH: 61
<212> TYPE: DNA
<213> ORGANISM: Homo Sapiens

<400> SEQUENCE: 696
ctcagcctcc cgagtggctg cgactacggg matgtgttac caagccaggc taatttttg     60
t                                                                   61

<210> SEQ ID NO 697
<211> LENGTH: 61
<212> TYPE: DNA
<213> ORGANISM: Homo Sapiens

<400> SEQUENCE: 697
aggaaggaga ataactggca acccatttta rtctctaagg ctgagatatt acatttcatt    60
t                                                                   61

<210> SEQ ID NO 698
<211> LENGTH: 61
<212> TYPE: DNA
<213> ORGANISM: Homo Sapiens

<400> SEQUENCE: 698

```
tagtcatagt tataagcttg aactctgcag yagggccggc tgggattgaa ttctgactct    60
a                                                                   61
```

<210> SEQ ID NO 699
<211> LENGTH: 61
<212> TYPE: DNA
<213> ORGANISM: Homo Sapiens

<400> SEQUENCE: 699

```
cacaaggcaa aattgctggt ccatttccat rctgatgcta gttgcagaca ttgtatttca    60
t                                                                   61
```

<210> SEQ ID NO 700
<211> LENGTH: 61
<212> TYPE: DNA
<213> ORGANISM: Homo Sapiens

<400> SEQUENCE: 700

```
tagtatggta ctcacaatcc tagagattcc ygtctcctgg ttcttcaacc aaacactaat    60
c                                                                   61
```

<210> SEQ ID NO 701
<211> LENGTH: 61
<212> TYPE: DNA
<213> ORGANISM: Homo Sapiens

<400> SEQUENCE: 701

```
tacctaccac ccccacaagg caaaaggagg raatagtgag acaagaattc ttctactcca    60
g                                                                   61
```

<210> SEQ ID NO 702
<211> LENGTH: 61
<212> TYPE: DNA
<213> ORGANISM: Homo Sapiens

<400> SEQUENCE: 702

```
tcccacaccc actttatttt tttctcatcc rtgaaaacta gatatctaga aactactgct    60
a                                                                   61
```

<210> SEQ ID NO 703
<211> LENGTH: 61
<212> TYPE: DNA
<213> ORGANISM: Homo Sapiens

<400> SEQUENCE: 703

```
aatgtgagta gctgtttata cacagatcca ygaggaagct gcctctttta tggacactgc    60
a                                                                   61
```

<210> SEQ ID NO 704
<211> LENGTH: 61
<212> TYPE: DNA
<213> ORGANISM: Homo Sapiens

<400> SEQUENCE: 704

```
aagcatattg actgcccta actcaagccc ytaactctct aatttcactg atttctataa    60
t                                                                   61
```

<210> SEQ ID NO 705
<211> LENGTH: 61

```
<212> TYPE: DNA
<213> ORGANISM: Homo Sapiens

<400> SEQUENCE: 705
caattctcca acttttttgtt gaatgacttt rcagcaactt ccataaagtt atggagtcta      60
t                                                                      61

<210> SEQ ID NO 706
<211> LENGTH: 61
<212> TYPE: DNA
<213> ORGANISM: Homo Sapiens

<400> SEQUENCE: 706
atgccagagc attgtcagga ggcagggaaa yagactccat aactttatgg aagttgctgt      60
a                                                                      61

<210> SEQ ID NO 707
<211> LENGTH: 61
<212> TYPE: DNA
<213> ORGANISM: Homo Sapiens

<400> SEQUENCE: 707
gtttctccaa gggagactga cattctaagc mtatcagctc tgtctatctc tgctcctttg      60
a                                                                      61

<210> SEQ ID NO 708
<211> LENGTH: 61
<212> TYPE: DNA
<213> ORGANISM: Homo Sapiens

<400> SEQUENCE: 708
aaggattgac aaatgatgat ctttctgtcc rcaaggttct tatttcctgt gcaaaatgga      60
c                                                                      61

<210> SEQ ID NO 709
<211> LENGTH: 61
<212> TYPE: DNA
<213> ORGANISM: Homo Sapiens

<400> SEQUENCE: 709
gctgcttcca aagctactct aatcaccata ktctattatt cctacaaaag cctagtttac      60
c                                                                      61

<210> SEQ ID NO 710
<211> LENGTH: 61
<212> TYPE: DNA
<213> ORGANISM: Homo Sapiens

<400> SEQUENCE: 710
tgccaactag gaacaatttt acttcaagac rtttgactct cttctgtact ctatgcagaa      60
c                                                                      61

<210> SEQ ID NO 711
<211> LENGTH: 61
<212> TYPE: DNA
<213> ORGANISM: Homo Sapiens

<400> SEQUENCE: 711
ccccagaagc atctgggacc tttcggaccc rgaagttatg gccaagcgac ctaggctaac      60
a                                                                      61
```

<210> SEQ ID NO 712
<211> LENGTH: 61
<212> TYPE: DNA
<213> ORGANISM: Homo Sapiens

<400> SEQUENCE: 712
ggggtgtgct ggaacccacc cacaagacag rtatttgtgc ctcttcccag ccccatgttc    60
g                                                                   61

<210> SEQ ID NO 713
<211> LENGTH: 61
<212> TYPE: DNA
<213> ORGANISM: Homo Sapiens

<400> SEQUENCE: 713
gtataccagc aagcagcctc gacacttccc raacttcctc cttgctgaac tgcatcacgt    60
c                                                                   61

<210> SEQ ID NO 714
<211> LENGTH: 61
<212> TYPE: DNA
<213> ORGANISM: Homo Sapiens

<400> SEQUENCE: 714
gtcacgattc cacaaagaca taatgtcgta rtgtcaaggg tactgtgggc tcctagggga    60
g                                                                   61

<210> SEQ ID NO 715
<211> LENGTH: 61
<212> TYPE: DNA
<213> ORGANISM: Homo Sapiens

<400> SEQUENCE: 715
gcaaacattt gtttactacg aagcatcgga sttgaaatgg aggggacagc ctggccttgg    60
t                                                                   61

<210> SEQ ID NO 716
<211> LENGTH: 61
<212> TYPE: DNA
<213> ORGANISM: Homo Sapiens

<400> SEQUENCE: 716
ttcacatatg gaagcttccc aacccgagat yggtctaaat gcagaaactg gaactcacag    60
c                                                                   61

<210> SEQ ID NO 717
<211> LENGTH: 61
<212> TYPE: DNA
<213> ORGANISM: Homo Sapiens

<400> SEQUENCE: 717
aggtaggtgg gggcataaag gttagccaaa sttgaaaata aatatttggt tcactatcat    60
c                                                                   61

<210> SEQ ID NO 718
<211> LENGTH: 61
<212> TYPE: DNA
<213> ORGANISM: Homo Sapiens

<400> SEQUENCE: 718

```
gtgtgagcgg caaccgctgc tcggaacgag ycattccaac aagacacaga ggcgaactgg    60
c                                                                     61

<210> SEQ ID NO 719
<211> LENGTH: 61
<212> TYPE: DNA
<213> ORGANISM: Homo Sapiens

<400> SEQUENCE: 719
aaatgaggca gcagcatcat ctgcacccct ragctaagca atcatttcgc tggtgccccc    60
c                                                                     61

<210> SEQ ID NO 720
<211> LENGTH: 61
<212> TYPE: DNA
<213> ORGANISM: Homo Sapiens

<400> SEQUENCE: 720
gcagtccttc aaggtagcac ccgcccggtc ygattgggtg caggccgagc caggccctcc    60
a                                                                     61

<210> SEQ ID NO 721
<211> LENGTH: 61
<212> TYPE: DNA
<213> ORGANISM: Homo Sapiens

<400> SEQUENCE: 721
tagaatctgt gaaaggaaaa tagaaactca kgaccacagt tcattatgct tgaaagaaaa    60
a                                                                     61

<210> SEQ ID NO 722
<211> LENGTH: 61
<212> TYPE: DNA
<213> ORGANISM: Homo Sapiens

<400> SEQUENCE: 722
aagagacaaa tgtatgggag cagcagaata yttaatcact tttctgatgt gtgcagatac    60
g                                                                     61

<210> SEQ ID NO 723
<211> LENGTH: 61
<212> TYPE: DNA
<213> ORGANISM: Homo Sapiens

<400> SEQUENCE: 723
gtaatcgttt acccaatctc ctataaaaga yacattgttg tttctcttgt ttccatttgc    60
t                                                                     61

<210> SEQ ID NO 724
<211> LENGTH: 61
<212> TYPE: DNA
<213> ORGANISM: Homo Sapiens

<400> SEQUENCE: 724
agatttgaca ccactctgcc ttcgtcttct ytgcaaatac atctgcaaac ttcttcttca    60
t                                                                     61

<210> SEQ ID NO 725
<211> LENGTH: 61
```

```
<212> TYPE: DNA
<213> ORGANISM: Homo Sapiens

<400> SEQUENCE: 725
ctcaatgctg ttgaggagcc tcccagccta ygaacctggt attccagggt gccaagagtc    60
t                                                                   61

<210> SEQ ID NO 726
<211> LENGTH: 61
<212> TYPE: DNA
<213> ORGANISM: Homo Sapiens

<400> SEQUENCE: 726
tcctgaggga agctaggagc cataatctgg raagctttaa gacaacctct gttcacagta    60
a                                                                   61

<210> SEQ ID NO 727
<211> LENGTH: 61
<212> TYPE: DNA
<213> ORGANISM: Homo Sapiens

<400> SEQUENCE: 727
ttttaaaaag aatcagagtg tgttcagaaa rgggacattg cctatagata ttagatattg    60
c                                                                   61

<210> SEQ ID NO 728
<211> LENGTH: 61
<212> TYPE: DNA
<213> ORGANISM: Homo Sapiens

<400> SEQUENCE: 728
catgattatc tttgtataca gcctgttctg maactcacac atagtaaata ctccataaat    60
g                                                                   61

<210> SEQ ID NO 729
<211> LENGTH: 61
<212> TYPE: DNA
<213> ORGANISM: Homo Sapiens

<400> SEQUENCE: 729
taattcagga tcatttctcc acctggagat ycttcattac acctgcaatg acacttttc     60
a                                                                   61

<210> SEQ ID NO 730
<211> LENGTH: 61
<212> TYPE: DNA
<213> ORGANISM: Homo Sapiens

<400> SEQUENCE: 730
agaatgagtt atatcctcaa ttggtgacaa wctttctctt ttttttttct acttctattg    60
t                                                                   61

<210> SEQ ID NO 731
<211> LENGTH: 61
<212> TYPE: DNA
<213> ORGANISM: Homo Sapiens

<400> SEQUENCE: 731
tacatatacc ttcaaggatt tcagtgaagg rcttctttct aactttcctc cttaagataa    60
c                                                                   61
```

<210> SEQ ID NO 732
<211> LENGTH: 61
<212> TYPE: DNA
<213> ORGANISM: Homo Sapiens

<400> SEQUENCE: 732
tcatataatt acagtagaaa ctctcttgtc sagtccaatt tggatttgtt agttgattgt    60
a                                                                  61

<210> SEQ ID NO 733
<211> LENGTH: 61
<212> TYPE: DNA
<213> ORGANISM: Homo Sapiens

<400> SEQUENCE: 733
agcactctga agcctgtgcc ggctcaaggc kgtttatgga tttagggtgc cctgccataa    60
a                                                                  61

<210> SEQ ID NO 734
<211> LENGTH: 61
<212> TYPE: DNA
<213> ORGANISM: Homo Sapiens

<400> SEQUENCE: 734
caattccaag gcatattaaa aagtcatgat yaaaggggct taccacatga agtacaagaa    60
t                                                                  61

<210> SEQ ID NO 735
<211> LENGTH: 61
<212> TYPE: DNA
<213> ORGANISM: Homo Sapiens

<400> SEQUENCE: 735
actcacacgc ctcatgctat gttccgtaaa yacgttctca gagtaacact gaataaaatg    60
a                                                                  61

<210> SEQ ID NO 736
<211> LENGTH: 61
<212> TYPE: DNA
<213> ORGANISM: Homo Sapiens

<400> SEQUENCE: 736
attgctgttg taattagaaa agcagtgtga ygtagcaaag atgcacggaa gtgcctccct    60
c                                                                  61

<210> SEQ ID NO 737
<211> LENGTH: 61
<212> TYPE: DNA
<213> ORGANISM: Homo Sapiens

<400> SEQUENCE: 737
aataagatgg acttattgga cataatcatc rccatttaaa atgatttgga taggtgccat    60
g                                                                  61

<210> SEQ ID NO 738
<211> LENGTH: 61
<212> TYPE: DNA
<213> ORGANISM: Homo Sapiens

<400> SEQUENCE: 738

```
tttttttaagc tctgcaagtg aataccacat ktcaattgct gccaatgaga cagtccctga    60
a                                                                    61
```

<210> SEQ ID NO 739
<211> LENGTH: 61
<212> TYPE: DNA
<213> ORGANISM: Homo Sapiens

<400> SEQUENCE: 739

```
aatttcaggt ttgaaaactc aaaccaacag raagatatca cacctttgta tgtgcttctt    60
t                                                                    61
```

<210> SEQ ID NO 740
<211> LENGTH: 61
<212> TYPE: DNA
<213> ORGANISM: Homo Sapiens

<400> SEQUENCE: 740

```
gagcaaccca aatatttctg atgtaaatgg rtggtacaga gagatcttac ttcaagaaat    60
g                                                                    61
```

<210> SEQ ID NO 741
<211> LENGTH: 61
<212> TYPE: DNA
<213> ORGANISM: Homo Sapiens

<400> SEQUENCE: 741

```
agtatttctc aagcactttt aagcaaaggt ragtattcat acaagaaatt taggggaaa     60
a                                                                    61
```

<210> SEQ ID NO 742
<211> LENGTH: 61
<212> TYPE: DNA
<213> ORGANISM: Homo Sapiens

<400> SEQUENCE: 742

```
catggataat aattgacata taccttggag rccatttgga atctccataa acgaagaag     60
a                                                                    61
```

<210> SEQ ID NO 743
<211> LENGTH: 61
<212> TYPE: DNA
<213> ORGANISM: Homo Sapiens

<400> SEQUENCE: 743

```
ttaatcatta atattttcca tggatcaata ycctgtagaa gcatgagatg cagcagtgat    60
c                                                                    61
```

<210> SEQ ID NO 744
<211> LENGTH: 61
<212> TYPE: DNA
<213> ORGANISM: Homo Sapiens

<400> SEQUENCE: 744

```
cagaaagtaa taatttatat ttggcaggta kttcctgaaa ctgacacata agtaactcaa    60
g                                                                    61
```

<210> SEQ ID NO 745
<211> LENGTH: 61

```
-continued

<212> TYPE: DNA
<213> ORGANISM: Homo Sapiens

<400> SEQUENCE: 745
gttcacgatc aaggtgccag caagataagg yctcattctg aagtctcttc tcttggcttg      60
c                                                                     61

<210> SEQ ID NO 746
<211> LENGTH: 61
<212> TYPE: DNA
<213> ORGANISM: Homo Sapiens

<400> SEQUENCE: 746
gagtaataat tataattact gcctagttca yttccgtctt tgtgtggcca agattactga      60
a                                                                     61

<210> SEQ ID NO 747
<211> LENGTH: 61
<212> TYPE: DNA
<213> ORGANISM: Homo Sapiens

<400> SEQUENCE: 747
aatttgccta gaaattattt gcagataggc rctttctttt atgcacattt gaaaaccccta    60
t                                                                     61

<210> SEQ ID NO 748
<211> LENGTH: 61
<212> TYPE: DNA
<213> ORGANISM: Homo Sapiens

<400> SEQUENCE: 748
aagataagac aatgaaagag aagtcgaagt saggcccggc acggtggctc acgcctgtaa    60
a                                                                     61

<210> SEQ ID NO 749
<211> LENGTH: 61
<212> TYPE: DNA
<213> ORGANISM: Homo Sapiens

<400> SEQUENCE: 749
ataggaagac ctaactgtcc aatctgcata yaaaatggaa ttccagtttg ttaggggaag    60
g                                                                     61

<210> SEQ ID NO 750
<211> LENGTH: 61
<212> TYPE: DNA
<213> ORGANISM: Homo Sapiens

<400> SEQUENCE: 750
tcttcccctc atccccaaga tgcaacattt ytagtgatac caatttgcag gtatttcatc    60
g                                                                     61

<210> SEQ ID NO 751
<211> LENGTH: 61
<212> TYPE: DNA
<213> ORGANISM: Homo Sapiens

<400> SEQUENCE: 751
tctgtatgta ctgaggaaga atgaggcata ygatacacag aaagaaagca gcagagtaca    60
t                                                                     61
```

```
<210> SEQ ID NO 752
<211> LENGTH: 61
<212> TYPE: DNA
<213> ORGANISM: Homo Sapiens

<400> SEQUENCE: 752
cctatgcatc caaataactc acatcacaca rtggcttctt tggatgaatt aaaagtatct      60
a                                                                     61

<210> SEQ ID NO 753
<211> LENGTH: 61
<212> TYPE: DNA
<213> ORGANISM: Homo Sapiens

<400> SEQUENCE: 753
caatattaag tttcctgatg tgtaataagg mgagtaggtc ttatgtttaa aaatagacat      60
t                                                                     61

<210> SEQ ID NO 754
<211> LENGTH: 61
<212> TYPE: DNA
<213> ORGANISM: Homo Sapiens

<400> SEQUENCE: 754
agaaagatat gtgctattta agtgtcagag staggattgt ttaggccagt gatttttttt      60
t                                                                     61

<210> SEQ ID NO 755
<211> LENGTH: 61
<212> TYPE: DNA
<213> ORGANISM: Homo Sapiens

<400> SEQUENCE: 755
tctggagcgt gcagatgaag caggcagtca sggtaatgaa gtcggaaatg caagtccaga      60
g                                                                     61

<210> SEQ ID NO 756
<211> LENGTH: 61
<212> TYPE: DNA
<213> ORGANISM: Homo Sapiens

<400> SEQUENCE: 756
ctccagctcc ttctgatatt ctttctaata ygactttgta cctcttaagg aagacattca      60
t                                                                     61

<210> SEQ ID NO 757
<211> LENGTH: 61
<212> TYPE: DNA
<213> ORGANISM: Homo Sapiens

<400> SEQUENCE: 757
gaaacccaaa gtgtttgctg taatgaccag mgagtgtcag tgaaactcct tagcctaagg      60
a                                                                     61

<210> SEQ ID NO 758
<211> LENGTH: 61
<212> TYPE: DNA
<213> ORGANISM: Homo Sapiens

<400> SEQUENCE: 758
```

```
tattaacgca gatcgagttg ggaacgcacg stccatttcg acactcatca atgtcagtgc    60
a                                                                    61

<210> SEQ ID NO 759
<211> LENGTH: 61
<212> TYPE: DNA
<213> ORGANISM: Homo Sapiens

<400> SEQUENCE: 759
gtacctcctt tacagtattt acaacaataa ytttgatagc caacaacatt gagtaatttc    60
t                                                                    61

<210> SEQ ID NO 760
<211> LENGTH: 61
<212> TYPE: DNA
<213> ORGANISM: Homo Sapiens

<400> SEQUENCE: 760
ccctgctcca taaagacaga ggcaggacta ygtgggagag tggtcagccc ttcctgaacc    60
c                                                                    61

<210> SEQ ID NO 761
<211> LENGTH: 61
<212> TYPE: DNA
<213> ORGANISM: Homo Sapiens

<400> SEQUENCE: 761
taatcattag ctttggaaag tgagatcttc mtggtaaatg taaggactac actattcact    60
t                                                                    61

<210> SEQ ID NO 762
<211> LENGTH: 61
<212> TYPE: DNA
<213> ORGANISM: Homo Sapiens

<400> SEQUENCE: 762
accaataata ccttattttt ccaagcagtg yttaactata ctgagcacag acaaatgctc    60
c                                                                    61

<210> SEQ ID NO 763
<211> LENGTH: 61
<212> TYPE: DNA
<213> ORGANISM: Homo Sapiens

<400> SEQUENCE: 763
tttactcatc attttaaaag tttcgtatgt sttcatatgt attatgtatg tttccatttc    60
a                                                                    61

<210> SEQ ID NO 764
<211> LENGTH: 61
<212> TYPE: DNA
<213> ORGANISM: Homo Sapiens

<400> SEQUENCE: 764
agtgggagac agtatctgaa acagcctttg rcatgagtat gtttcatttc ttatgagaac    60
a                                                                    61

<210> SEQ ID NO 765
<211> LENGTH: 61
```

```
<212> TYPE: DNA
<213> ORGANISM: Homo Sapiens

<400> SEQUENCE: 765
tttcttatgg gggatgggaa gcaactatca rtggcatagc tgggtttgac tttatacttt    60
a                                                                    61

<210> SEQ ID NO 766
<211> LENGTH: 61
<212> TYPE: DNA
<213> ORGANISM: Homo Sapiens

<400> SEQUENCE: 766
cacattccac atagtctgca gtttcctcaa ycactttgca aaactgactg tcagacaacc    60
a                                                                    61

<210> SEQ ID NO 767
<211> LENGTH: 61
<212> TYPE: DNA
<213> ORGANISM: Homo Sapiens

<400> SEQUENCE: 767
ggctctgtca agcctgtaac tgtgcctttc mttgtactat aggtaatgta gaccatgaaa    60
t                                                                    61

<210> SEQ ID NO 768
<211> LENGTH: 61
<212> TYPE: DNA
<213> ORGANISM: Homo Sapiens

<400> SEQUENCE: 768
tctgatcttg cctcttcaca tcagcacatt ratgacatga cacatggacg ttgaggactc    60
c                                                                    61

<210> SEQ ID NO 769
<211> LENGTH: 61
<212> TYPE: DNA
<213> ORGANISM: Homo Sapiens

<400> SEQUENCE: 769
cccctgagaa caaccatgaa ccaccttgta yggttattga tgtaaagccc cagccagctc    60
t                                                                    61

<210> SEQ ID NO 770
<211> LENGTH: 61
<212> TYPE: DNA
<213> ORGANISM: Homo Sapiens

<400> SEQUENCE: 770
agtccccttt aatcagcatc cttacctgtc rtgggtgtta tcttttttct ctctctcttt    60
t                                                                    61

<210> SEQ ID NO 771
<211> LENGTH: 61
<212> TYPE: DNA
<213> ORGANISM: Homo Sapiens

<400> SEQUENCE: 771
taaaagtgca gtgtggagtg agaacacagt rcagcaaatt tttaatgtca gaaagtagca    60
a                                                                    61
```

```
<210> SEQ ID NO 772
<211> LENGTH: 61
<212> TYPE: DNA
<213> ORGANISM: Homo Sapiens

<400> SEQUENCE: 772
gaaaatctta ctgaccacat ggatgataaa stgcaaacac ctgtactcca gagataatct    60
c                                                                   61

<210> SEQ ID NO 773
<211> LENGTH: 61
<212> TYPE: DNA
<213> ORGANISM: Homo Sapiens

<400> SEQUENCE: 773
actgagaaaa ttctgatttt cgtcatttag kttattgccc taaattcaag aacattcatt    60
c                                                                   61

<210> SEQ ID NO 774
<211> LENGTH: 61
<212> TYPE: DNA
<213> ORGANISM: Homo Sapiens

<400> SEQUENCE: 774
tacatatctt tgatatacct agcaaggaga yataaattgc tccctgaata gtaaagcaga    60
a                                                                   61

<210> SEQ ID NO 775
<211> LENGTH: 61
<212> TYPE: DNA
<213> ORGANISM: Homo Sapiens

<400> SEQUENCE: 775
ccaagcactg tttttattact tgtgagatta ygttagtgtc ttttagaaaa acacataatt    60
a                                                                   61

<210> SEQ ID NO 776
<211> LENGTH: 61
<212> TYPE: DNA
<213> ORGANISM: Homo Sapiens

<400> SEQUENCE: 776
ttgtctgtcc tctttctact ttctggatac mttgtatgga cctagatgtg gttccaggga    60
c                                                                   61

<210> SEQ ID NO 777
<211> LENGTH: 61
<212> TYPE: DNA
<213> ORGANISM: Homo Sapiens

<400> SEQUENCE: 777
ggcacagtaa aacaaggtac gcacaaattt waaaagagag ctgaagtaat ttttgtaaaa    60
g                                                                   61

<210> SEQ ID NO 778
<211> LENGTH: 61
<212> TYPE: DNA
<213> ORGANISM: Homo Sapiens

<400> SEQUENCE: 778
```

```
tttatcttta agctgcattt accttttta mttgaaaccg caccaatctc ctctttggct    60
c                                                                   61
```

<210> SEQ ID NO 779
<211> LENGTH: 61
<212> TYPE: DNA
<213> ORGANISM: Homo Sapiens

<400> SEQUENCE: 779

```
tttgttcaac atacttgctt ttacttgttt ktcacttgga actgttaatg acaagaaata    60
a                                                                   61
```

<210> SEQ ID NO 780
<211> LENGTH: 61
<212> TYPE: DNA
<213> ORGANISM: Homo Sapiens

<400> SEQUENCE: 780

```
ctaacaattc agtcaagctc aataacttaa kgtatgtctt tcacaaatat aggttctcct    60
c                                                                   61
```

<210> SEQ ID NO 781
<211> LENGTH: 61
<212> TYPE: DNA
<213> ORGANISM: Homo Sapiens

<400> SEQUENCE: 781

```
gtgggaggtg gtctcacagc aggtctttac ragcctcccg tctttctgtg ttctgggaga    60
a                                                                   61
```

<210> SEQ ID NO 782
<211> LENGTH: 61
<212> TYPE: DNA
<213> ORGANISM: Homo Sapiens

<400> SEQUENCE: 782

```
ggaaatacac taacacagag tgcacatacc scatctttta agccgagttc cattacggca    60
t                                                                   61
```

<210> SEQ ID NO 783
<211> LENGTH: 61
<212> TYPE: DNA
<213> ORGANISM: Homo Sapiens

<400> SEQUENCE: 783

```
ctcacttcta ttttgttact gtccacctta yagctctaaa ggtaggcttc cttctatgct    60
c                                                                   61
```

<210> SEQ ID NO 784
<211> LENGTH: 61
<212> TYPE: DNA
<213> ORGANISM: Homo Sapiens

<400> SEQUENCE: 784

```
gtaatttcta tacttctgcc ttgattttg ygtgaggcct tgtatttacc ctattatagt    60
g                                                                   61
```

<210> SEQ ID NO 785
<211> LENGTH: 61

```
<212> TYPE: DNA
<213> ORGANISM: Homo Sapiens

<400> SEQUENCE: 785
agatataaat atacatgaac catgtgaaag ygataaaatg tcttcctgaa agtgaccaag      60
g                                                                     61

<210> SEQ ID NO 786
<211> LENGTH: 61
<212> TYPE: DNA
<213> ORGANISM: Homo Sapiens

<400> SEQUENCE: 786
tacacatgat atatacattg ctaaaaacca yatttgaatc tttcaactta taaatagtaa      60
g                                                                     61

<210> SEQ ID NO 787
<211> LENGTH: 61
<212> TYPE: DNA
<213> ORGANISM: Homo Sapiens

<400> SEQUENCE: 787
ccctcacatc cttttctcta ttactcatct yaggtacagg tagaaatata acaccaatga      60
a                                                                     61

<210> SEQ ID NO 788
<211> LENGTH: 61
<212> TYPE: DNA
<213> ORGANISM: Homo Sapiens

<400> SEQUENCE: 788
tttcactctg tgtcccataa cctgggaaca ytgatatgag gggtggggtc ccaaggaatt      60
g                                                                     61

<210> SEQ ID NO 789
<211> LENGTH: 61
<212> TYPE: DNA
<213> ORGANISM: Homo Sapiens

<400> SEQUENCE: 789
acagttgtca ctgatatatg actttgagaa yatgaactgc tgtataaatg ttaaatgttc      60
c                                                                     61

<210> SEQ ID NO 790
<211> LENGTH: 61
<212> TYPE: DNA
<213> ORGANISM: Homo Sapiens

<400> SEQUENCE: 790
cccttacatt ttacaccaga ggtaagtgtc ytgctccttt catactaatc cttgccctat      60
t                                                                     61

<210> SEQ ID NO 791
<211> LENGTH: 61
<212> TYPE: DNA
<213> ORGANISM: Homo Sapiens

<400> SEQUENCE: 791
atggtgagcc agatttggtt catggactgt ygtttgccaa atctgatcta gagaaatagg      60
a                                                                     61
```

<210> SEQ ID NO 792
<211> LENGTH: 61
<212> TYPE: DNA
<213> ORGANISM: Homo Sapiens

<400> SEQUENCE: 792
aaaaagctga catgagcaag gagttgagaa rtattcaagc aggatcaaag acagattgaa    60
c                                                                   61

<210> SEQ ID NO 793
<211> LENGTH: 61
<212> TYPE: DNA
<213> ORGANISM: Homo Sapiens

<400> SEQUENCE: 793
atgtaagatt gtgctataga aactacatgg ycacctccat ttctaaattg ttagaatgct    60
g                                                                   61

<210> SEQ ID NO 794
<211> LENGTH: 61
<212> TYPE: DNA
<213> ORGANISM: Homo Sapiens

<400> SEQUENCE: 794
aagatttatt tagtttatta atgaaggaat sacagtaatg gtaaagctgg ctcaaaagag    60
g                                                                   61

<210> SEQ ID NO 795
<211> LENGTH: 61
<212> TYPE: DNA
<213> ORGANISM: Homo Sapiens

<400> SEQUENCE: 795
atatttcttt caagctatga gaatgcaaga ytgtggaatt ttagtaagta gtctatatag    60
g                                                                   61

<210> SEQ ID NO 796
<211> LENGTH: 61
<212> TYPE: DNA
<213> ORGANISM: Homo Sapiens

<400> SEQUENCE: 796
agataatgaa atccatttgg gagctctgga maccttaact ggcatagatt tgagaagcca    60
t                                                                   61

<210> SEQ ID NO 797
<211> LENGTH: 61
<212> TYPE: DNA
<213> ORGANISM: Homo Sapiens

<400> SEQUENCE: 797
cactgtctta tttaatcctc acaacaagca rgtgaggaac ccatggcaca aagatattaa    60
g                                                                   61

<210> SEQ ID NO 798
<211> LENGTH: 61
<212> TYPE: DNA
<213> ORGANISM: Homo Sapiens

<400> SEQUENCE: 798

-continued aaccaatcac agtacattct tccctagac rcagagattt gtaaaaggga aaagatctat    60
t    61

<210> SEQ ID NO 799
<211> LENGTH: 61
<212> TYPE: DNA
<213> ORGANISM: Homo Sapiens

<400> SEQUENCE: 799
taaacattac aactgaactc atgctccatc wctttaattg gtgtaatcct tagggcctta    60
a    61

<210> SEQ ID NO 800
<211> LENGTH: 61
<212> TYPE: DNA
<213> ORGANISM: Homo Sapiens

<400> SEQUENCE: 800
gattgaagag acactgattt gcccaaataa yaggaagagg gggaagcaag taatattatg    60
t    61

<210> SEQ ID NO 801
<211> LENGTH: 61
<212> TYPE: DNA
<213> ORGANISM: Homo Sapiens

<400> SEQUENCE: 801
atctactgtt ccctctgctg ctgctgctcc yaactcgact ctagagtgcc ttactcgtgt    60
g    61

<210> SEQ ID NO 802
<211> LENGTH: 61
<212> TYPE: DNA
<213> ORGANISM: Homo Sapiens

<400> SEQUENCE: 802
aatgtaaagg tgttaaatta agacagctag raagtggttt aaacaataag aataaagagc    60
a    61

<210> SEQ ID NO 803
<211> LENGTH: 61
<212> TYPE: DNA
<213> ORGANISM: Homo Sapiens

<400> SEQUENCE: 803
agcagcctac tgagcagttg tttctacaag yatcataatg agctaacagc aaacctctgg    60
c    61

<210> SEQ ID NO 804
<211> LENGTH: 61
<212> TYPE: DNA
<213> ORGANISM: Homo Sapiens

<400> SEQUENCE: 804
ctctgtggca ttctggctcc agaagtcaga ygttcaacgc tgcatgaata acctatgcct    60
t    61

<210> SEQ ID NO 805
<211> LENGTH: 61

```
<212> TYPE: DNA
<213> ORGANISM: Homo Sapiens

<400> SEQUENCE: 805
aggagcaagg agagccagtc cgattcccca ractgaagca cttggagtcc agtgtttgag       60
g                                                                      61

<210> SEQ ID NO 806
<211> LENGTH: 61
<212> TYPE: DNA
<213> ORGANISM: Homo Sapiens

<400> SEQUENCE: 806
aagcccagtt tcagaattac tgttaactcc raattgccaa ttacagcttg actttgcagt       60
t                                                                      61

<210> SEQ ID NO 807
<211> LENGTH: 61
<212> TYPE: DNA
<213> ORGANISM: Homo Sapiens

<400> SEQUENCE: 807
acttcaagtt gttgcagaag ggatgatgag rttaatggag aacagaaaga aggtgaacta       60
g                                                                      61

<210> SEQ ID NO 808
<211> LENGTH: 61
<212> TYPE: DNA
<213> ORGANISM: Homo Sapiens

<400> SEQUENCE: 808
aatgcattgt ctacatcgga cagaaaagga mccagaagca tcacagactc ttgcaacacc       60
a                                                                      61

<210> SEQ ID NO 809
<211> LENGTH: 61
<212> TYPE: DNA
<213> ORGANISM: Homo Sapiens

<400> SEQUENCE: 809
ttggaaatca tgtatttgca atggtgttct yaaaaattag aatgttaaag agagccaaaa       60
t                                                                      61

<210> SEQ ID NO 810
<211> LENGTH: 61
<212> TYPE: DNA
<213> ORGANISM: Homo Sapiens

<400> SEQUENCE: 810
caaagtgtac tgtagataag gcaacttgta yagacatcag aattgaatcc atttgaagtc       60
a                                                                      61

<210> SEQ ID NO 811
<211> LENGTH: 61
<212> TYPE: DNA
<213> ORGANISM: Homo Sapiens

<400> SEQUENCE: 811
aagaagaata taattcctct agttaaagag mgtgttctga caataaactc taatatgaaa       60
g                                                                      61
```

-continued

<210> SEQ ID NO 812
<211> LENGTH: 61
<212> TYPE: DNA
<213> ORGANISM: Homo Sapiens

<400> SEQUENCE: 812
cagctcctct tggataagat ggtctactga yaggcctatg gtgataaaaa tgagcaaaat    60
g                                                                    61

<210> SEQ ID NO 813
<211> LENGTH: 61
<212> TYPE: DNA
<213> ORGANISM: Homo Sapiens

<400> SEQUENCE: 813
agtgccatgt tctagaggta caggctccaa raagtccaca ttcaaacatg gttttccagg    60
a                                                                    61

<210> SEQ ID NO 814
<211> LENGTH: 61
<212> TYPE: DNA
<213> ORGANISM: Homo Sapiens

<400> SEQUENCE: 814
atgaccttgg tttagcggtc agcaggtagc raggaaagtg atctcaaggg ccagaaagat    60
a                                                                    61

<210> SEQ ID NO 815
<211> LENGTH: 61
<212> TYPE: DNA
<213> ORGANISM: Homo Sapiens

<400> SEQUENCE: 815
aacagttgac ttttctcttt tatgggtgaa waaaggcttt gggtagcata gaagtggaga    60
t                                                                    61

<210> SEQ ID NO 816
<211> LENGTH: 61
<212> TYPE: DNA
<213> ORGANISM: Homo Sapiens

<400> SEQUENCE: 816
ctaagaattt ttaaaaagtg aaatttattg scagtagagt gtgtgatgca gaaagtactg    60
c                                                                    61

<210> SEQ ID NO 817
<211> LENGTH: 61
<212> TYPE: DNA
<213> ORGANISM: Homo Sapiens

<400> SEQUENCE: 817
tgaaatcaaa tgtgcgttga ggtgaaacac rttctgctag aaagctcata aagccatttt    60
g                                                                    61

<210> SEQ ID NO 818
<211> LENGTH: 61
<212> TYPE: DNA
<213> ORGANISM: Homo Sapiens

<400> SEQUENCE: 818

-continued

```
aataggccaa actgaacagg aaacaaactc rtaattgacc gctcttctgt aattataagg    60
a                                                                   61

<210> SEQ ID NO 819
<211> LENGTH: 61
<212> TYPE: DNA
<213> ORGANISM: Homo Sapiens

<400> SEQUENCE: 819
ggttaggttt aggtgaattt tcattcttcc rttttcctaa ttgctaccat aatcacatct    60
t                                                                   61

<210> SEQ ID NO 820
<211> LENGTH: 61
<212> TYPE: DNA
<213> ORGANISM: Homo Sapiens

<400> SEQUENCE: 820
aacgcccttc tctctgtgga ccgggagtct rctgttcacc actctcaccc cagagcctgt    60
c                                                                   61

<210> SEQ ID NO 821
<211> LENGTH: 61
<212> TYPE: DNA
<213> ORGANISM: Homo Sapiens

<400> SEQUENCE: 821
agagagtgtc gatactaggc aacaagcctc ygaacagata gtgttacccg gaacatcacc    60
c                                                                   61

<210> SEQ ID NO 822
<211> LENGTH: 61
<212> TYPE: DNA
<213> ORGANISM: Homo Sapiens

<400> SEQUENCE: 822
acatctcatc accctggaat ccaaacagga rgaaaagcgt gaggcccaaa gcctcttgtt    60
c                                                                   61

<210> SEQ ID NO 823
<211> LENGTH: 61
<212> TYPE: DNA
<213> ORGANISM: Homo Sapiens

<400> SEQUENCE: 823
tctccttact ttcctgttttt actgttctat rtccaggtaa tggtagttac agcagaagtt    60
t                                                                   61

<210> SEQ ID NO 824
<211> LENGTH: 61
<212> TYPE: DNA
<213> ORGANISM: Homo Sapiens

<400> SEQUENCE: 824
actctgttgc tgcaggctca ggtttagacc ytgcctttgc tctgcgcaca tgtccttccc    60
g                                                                   61

<210> SEQ ID NO 825
<211> LENGTH: 61
```

```
<212> TYPE: DNA
<213> ORGANISM: Homo Sapiens

<400> SEQUENCE: 825
aaaaactctt ttttttccta ttagaacatc raatacttct acagaatatt tctattctat      60
g                                                                      61

<210> SEQ ID NO 826
<211> LENGTH: 61
<212> TYPE: DNA
<213> ORGANISM: Homo Sapiens

<400> SEQUENCE: 826 agacccttc tttgggtaag tgtgtataag kttcaacaag ggaaatccat gtatgcatgc       60
a                                                                      61

<210> SEQ ID NO 827
<211> LENGTH: 61
<212> TYPE: DNA
<213> ORGANISM: Homo Sapiens

<400> SEQUENCE: 827
ctcaattgaa agagaggctt gagattacaa sgtgaaaact gtttcttgcc attattctgt      60
t                                                                      61

<210> SEQ ID NO 828
<211> LENGTH: 61
<212> TYPE: DNA
<213> ORGANISM: Homo Sapiens

<400> SEQUENCE: 828
gttctccaca tcagcaatga gactgtctca mattcatatt atttatgtgt tcactggagt      60
a                                                                      61

<210> SEQ ID NO 829
<211> LENGTH: 61
<212> TYPE: DNA
<213> ORGANISM: Homo Sapiens

<400> SEQUENCE: 829
tagcacagtg gaatccctac agacaagcag rgaagatggc tcgaaggaga tgcagcaaga      60
a                                                                      61

<210> SEQ ID NO 830
<211> LENGTH: 61
<212> TYPE: DNA
<213> ORGANISM: Homo Sapiens

<400> SEQUENCE: 830
gagaaggagg agctgaagta aacacccca wccttgtcag tctttggtta aagactctcc       60
t                                                                      61

<210> SEQ ID NO 831
<211> LENGTH: 61
<212> TYPE: DNA
<213> ORGANISM: Homo Sapiens

<400> SEQUENCE: 831
taaatatact ctttagatgg ctgctcctta ygacaaaggt tttatttggt gatttgatga      60
t                                                                      61
```

<210> SEQ ID NO 832
<211> LENGTH: 61
<212> TYPE: DNA
<213> ORGANISM: Homo Sapiens

<400> SEQUENCE: 832
ttaaaatgta gaaacctcaa tatcacttgg rttactagca aaagcatata tgacccattt    60
a                                                                    61

<210> SEQ ID NO 833
<211> LENGTH: 61
<212> TYPE: DNA
<213> ORGANISM: Homo Sapiens

<400> SEQUENCE: 833
attataaacc tagggatta tcagtctgca rtaaaactct ttttggactg aggcttattt    60
a                                                                    61

<210> SEQ ID NO 834
<211> LENGTH: 61
<212> TYPE: DNA
<213> ORGANISM: Homo Sapiens

<400> SEQUENCE: 834
atcctttcat gattacttta gagcaggaat rcccaatctt ttggcttccc tgggccacat    60
t                                                                    61

<210> SEQ ID NO 835
<211> LENGTH: 61
<212> TYPE: DNA
<213> ORGANISM: Homo Sapiens

<400> SEQUENCE: 835
gcccactgct tcccaccaat gagttaagta rttttttcttg cccatttctg caaatttgtg    60
t                                                                    61

<210> SEQ ID NO 836
<211> LENGTH: 61
<212> TYPE: DNA
<213> ORGANISM: Homo Sapiens

<400> SEQUENCE: 836
tgaaatatct ttttatctca tactaaaaat rcacgttttg ttcaggtaca ggattgctat    60
g                                                                    61

<210> SEQ ID NO 837
<211> LENGTH: 61
<212> TYPE: DNA
<213> ORGANISM: Homo Sapiens

<400> SEQUENCE: 837
aatctattca aatcttttgc tgttttgtat rtttgagtat tcatcctctt agtattgagt    60
t                                                                    61

<210> SEQ ID NO 838
<211> LENGTH: 61
<212> TYPE: DNA
<213> ORGANISM: Homo Sapiens

<400> SEQUENCE: 838

```
tttactgaat tcgtgtatca gttcaaatag yttgtttgct aaagtctttta tgtttttga    60
a                                                                   61
```

<210> SEQ ID NO 839
<211> LENGTH: 61
<212> TYPE: DNA
<213> ORGANISM: Homo Sapiens

<400> SEQUENCE: 839

```
ggaacttgta ttagcagctt tgaggatgac ragaaacaga atttaagtgc tacactagaa    60
t                                                                   61
```

<210> SEQ ID NO 840
<211> LENGTH: 61
<212> TYPE: DNA
<213> ORGANISM: Homo Sapiens

<400> SEQUENCE: 840

```
catgagggtt gcattccctc ttcagttgcc magcttttttc aggatgtgag gtcagcatat    60
t                                                                   61
```

<210> SEQ ID NO 841
<211> LENGTH: 61
<212> TYPE: DNA
<213> ORGANISM: Homo Sapiens

<400> SEQUENCE: 841

```
gtgggacctt tggagattta tggagtttag rgttacaagt atgatgtggc caccatactc    60
a                                                                   61
```

<210> SEQ ID NO 842
<211> LENGTH: 61
<212> TYPE: DNA
<213> ORGANISM: Homo Sapiens

<400> SEQUENCE: 842

```
cctgagttgc aaagcatata caggctgaag yacaatgtca agaaaacatg ttaaagggtg    60
g                                                                   61
```

<210> SEQ ID NO 843
<211> LENGTH: 61
<212> TYPE: DNA
<213> ORGANISM: Homo Sapiens

<400> SEQUENCE: 843

```
tgaaaataca gtacatttta gtatttactc wccatgctct tgaggttatt tatgtcaata    60
c                                                                   61
```

<210> SEQ ID NO 844
<211> LENGTH: 61
<212> TYPE: DNA
<213> ORGANISM: Homo Sapiens

<400> SEQUENCE: 844

```
tggccgagca gatgtgcagg actgggctaa ragcagaca ttcacccacc tctgagcaaa    60
c                                                                   61
```

<210> SEQ ID NO 845
<211> LENGTH: 61

```
<212> TYPE: DNA
<213> ORGANISM: Homo Sapiens

<400> SEQUENCE: 845
tactcaacat gtaaaggcag agtaggaatg rgaaagacta gggaaataag aagatcagaa    60
a                                                                    61

<210> SEQ ID NO 846
<211> LENGTH: 61
<212> TYPE: DNA
<213> ORGANISM: Homo Sapiens

<400> SEQUENCE: 846
gaatctttag attgctttgg atcgtacaga yattttaaca acattaattc ttcctatcca    60
t                                                                    61

<210> SEQ ID NO 847
<211> LENGTH: 61
<212> TYPE: DNA
<213> ORGANISM: Homo Sapiens

<400> SEQUENCE: 847
aattcacact aaaaatgact agatgaaaga ygtggtacta gaggctttgt atatgcctag    60
a                                                                    61

<210> SEQ ID NO 848
<211> LENGTH: 61
<212> TYPE: DNA
<213> ORGANISM: Homo Sapiens

<400> SEQUENCE: 848
gaggcatctc tgttttaaca agtccagtag kaagctcttg accaccctac cttacaaacc    60
t                                                                    61

<210> SEQ ID NO 849
<211> LENGTH: 61
<212> TYPE: DNA
<213> ORGANISM: Homo Sapiens

<400> SEQUENCE: 849
tctgcctggg aagccttccc ctgataccccc yagttggcag gagtcttcat ttgttctttt    60
c                                                                    61

<210> SEQ ID NO 850
<211> LENGTH: 61
<212> TYPE: DNA
<213> ORGANISM: Homo Sapiens

<400> SEQUENCE: 850
agccttctca tgctctcttt tacctaccac wtctgactga tagccaggcc ctgctattta    60
t                                                                    61

<210> SEQ ID NO 851
<211> LENGTH: 61
<212> TYPE: DNA
<213> ORGANISM: Homo Sapiens

<400> SEQUENCE: 851
tgaagtccat cccgatctga aggttcaccc rtcactaaga gacaaatggt gcttctgtta    60
a                                                                    61
```

<210> SEQ ID NO 852
<211> LENGTH: 61
<212> TYPE: DNA
<213> ORGANISM: Homo Sapiens

<400> SEQUENCE: 852
ttagcaactt gcacaaccat tgcactatgc kcattgattc tgtgagtcgg aatctggaat        60
a                                                                       61

<210> SEQ ID NO 853
<211> LENGTH: 61
<212> TYPE: DNA
<213> ORGANISM: Homo Sapiens

<400> SEQUENCE: 853
tccaggcttg gctggaatga tccaatactt sctatgattt tatcctcatt agccactcaa        60
c                                                                       61

<210> SEQ ID NO 854
<211> LENGTH: 61
<212> TYPE: DNA
<213> ORGANISM: Homo Sapiens

<400> SEQUENCE: 854
tatctctccc caggactgga ctctgagccc rtcattgaaa tgagagacca cgaggacggg        60
g                                                                       61

<210> SEQ ID NO 855
<211> LENGTH: 61
<212> TYPE: DNA
<213> ORGANISM: Homo Sapiens

<400> SEQUENCE: 855
atcttccttg gattatcaaa tgtgagtctg ycattgattc ccattgagac cctccctgat        60
a                                                                       61

<210> SEQ ID NO 856
<211> LENGTH: 61
<212> TYPE: DNA
<213> ORGANISM: Homo Sapiens

<400> SEQUENCE: 856
ttaaatgaaa gtggacacac catgactgga ratactatag gacttaattt taagaacaag        60
c                                                                       61

<210> SEQ ID NO 857
<211> LENGTH: 61
<212> TYPE: DNA
<213> ORGANISM: Homo Sapiens

<400> SEQUENCE: 857
ctgagtatct tactacatat tttacaaaag rctcattgtt tcacagtgtg ttattagaat        60
t                                                                       61

<210> SEQ ID NO 858
<211> LENGTH: 61
<212> TYPE: DNA
<213> ORGANISM: Homo Sapiens

<400> SEQUENCE: 858

```
caggaggcca gtttggatct gaaggtggta rgtaagaatt ctagatagat attttgtatt    60
c                                                                   61
```

<210> SEQ ID NO 859
<211> LENGTH: 61
<212> TYPE: DNA
<213> ORGANISM: Homo Sapiens

<400> SEQUENCE: 859

```
tccagcataa gtgaaaaaac agtgtttcgg rtacgctagt gtttctgaga caaatatgt     60
a                                                                   61
```

<210> SEQ ID NO 860
<211> LENGTH: 61
<212> TYPE: DNA
<213> ORGANISM: Homo Sapiens

<400> SEQUENCE: 860

```
ttttgtgatc atgcattttt ctgtaaagag ygcccacagc tttcattaga atttatgtgg    60
t                                                                   61
```

<210> SEQ ID NO 861
<211> LENGTH: 61
<212> TYPE: DNA
<213> ORGANISM: Homo Sapiens

<400> SEQUENCE: 861

```
aattgcaagc caatatttat aaccactgta maacgctgcc ctcattcttg acagggacaa    60
a                                                                   61
```

<210> SEQ ID NO 862
<211> LENGTH: 61
<212> TYPE: DNA
<213> ORGANISM: Homo Sapiens

<400> SEQUENCE: 862

```
caatgtagtg ggtcatgccc agcattgaaa mataatgaaa gagtagagag cagaatgaaa    60
t                                                                   61
```

<210> SEQ ID NO 863
<211> LENGTH: 61
<212> TYPE: DNA
<213> ORGANISM: Homo Sapiens

<400> SEQUENCE: 863

```
ccagaggaac aacagactat gtgtcactgg rccaaatgag ataacacctg tgaaggtcct    60
t                                                                   61
```

<210> SEQ ID NO 864
<211> LENGTH: 61
<212> TYPE: DNA
<213> ORGANISM: Homo Sapiens

<400> SEQUENCE: 864

```
gagtgctgag tcagagcctt aaaaggatgg ragttaagag caaaaatggg tattcctggt    60
g                                                                   61
```

<210> SEQ ID NO 865
<211> LENGTH: 61

```
<212> TYPE: DNA
<213> ORGANISM: Homo Sapiens

<400> SEQUENCE: 865
gtacaattag ggaaagcata acccagttga rcatgaccct cctaaaattt gctttcaaaa      60
t                                                                      61

<210> SEQ ID NO 866
<211> LENGTH: 61
<212> TYPE: DNA
<213> ORGANISM: Homo Sapiens

<400> SEQUENCE: 866
aggtgatgtg ataccgcacc ctgtagatat ytatgcctgt caagtattca taagcactct      60
t                                                                      61

<210> SEQ ID NO 867
<211> LENGTH: 61
<212> TYPE: DNA
<213> ORGANISM: Homo Sapiens

<400> SEQUENCE: 867
tggaactttg ctcatgtctg cgtcagtgga rcctagacct ggaatctcaa ttgtgtgatt      60
t                                                                      61

<210> SEQ ID NO 868
<211> LENGTH: 61
<212> TYPE: DNA
<213> ORGANISM: Homo Sapiens

<400> SEQUENCE: 868
tctacatcta ggctctattc tgtcctattg ratgtactgt ttatccctttt gccaataata     60
t                                                                      61

<210> SEQ ID NO 869
<211> LENGTH: 61
<212> TYPE: DNA
<213> ORGANISM: Homo Sapiens

<400> SEQUENCE: 869
attcaagttg ccatggcaaa ttacgataga rtggttggct actaaactac agaaatttat      60
t                                                                      61

<210> SEQ ID NO 870
<211> LENGTH: 61
<212> TYPE: DNA
<213> ORGANISM: Homo Sapiens

<400> SEQUENCE: 870
gttgaaatat caatagcttg attttagaca mgataaatct gaggtgccta ttagacatca      60
t                                                                      61

<210> SEQ ID NO 871
<211> LENGTH: 61
<212> TYPE: DNA
<213> ORGANISM: Homo Sapiens

<400> SEQUENCE: 871
cagcaaatat gggtgtgtat tggctgctac raaggaagtg tatgcctgaa ctatttgcta      60
a                                                                      61
```

<210> SEQ ID NO 872
<211> LENGTH: 61
<212> TYPE: DNA
<213> ORGANISM: Homo Sapiens

<400> SEQUENCE: 872
tgactctgag ttttgatgat tattccaact rctttcagaa acaataaatt ctaatgggct    60
c                                                                   61

<210> SEQ ID NO 873
<211> LENGTH: 61
<212> TYPE: DNA
<213> ORGANISM: Homo Sapiens

<400> SEQUENCE: 873
acttgatggg aaatgttctt agcttcaaat rtaaatgggt cctcccttta gctaaattcc    60
t                                                                   61

<210> SEQ ID NO 874
<211> LENGTH: 61
<212> TYPE: DNA
<213> ORGANISM: Homo Sapiens

<400> SEQUENCE: 874
gtttatagca gatggaaagg cgaatatagc stgcttttcc acataagagc ttgtcaggta    60
g                                                                   61

<210> SEQ ID NO 875
<211> LENGTH: 61
<212> TYPE: DNA
<213> ORGANISM: Homo Sapiens

<400> SEQUENCE: 875
agctctctga gctccatttc ttagcatttg sctgttcttt gtaactttaa taattgatct    60
t                                                                   61

<210> SEQ ID NO 876
<211> LENGTH: 61
<212> TYPE: DNA
<213> ORGANISM: Homo Sapiens

<400> SEQUENCE: 876
tgtcctgcta ttgtttctta agtgccaata sattaataca atatagcagg gctcacacag    60
c                                                                   61

<210> SEQ ID NO 877
<211> LENGTH: 61
<212> TYPE: DNA
<213> ORGANISM: Homo Sapiens

<400> SEQUENCE: 877
ttctactttg ttttagaaaa tgaaatggcc raatgaggat agagagaaaa ttaggaacat    60
c                                                                   61

<210> SEQ ID NO 878
<211> LENGTH: 61
<212> TYPE: DNA
<213> ORGANISM: Homo Sapiens

<400> SEQUENCE: 878

```
gatttttact tttagctatg agtttacttt ygtagaagta ggcataatat taaatcagag    60
a                                                                   61

<210> SEQ ID NO 879
<211> LENGTH: 61
<212> TYPE: DNA
<213> ORGANISM: Homo Sapiens

<400> SEQUENCE: 879
gcccagcgaa tccggatctc ctgtgtatgt saaccaagtc aaagtgcgag tctccgacgc    60
c                                                                   61

<210> SEQ ID NO 880
<211> LENGTH: 61
<212> TYPE: DNA
<213> ORGANISM: Homo Sapiens

<400> SEQUENCE: 880
tctattgtaa attgaccaga acaggaatac rtttgtgaat tcgtaacgta agaaggtagc    60
a                                                                   61

<210> SEQ ID NO 881
<211> LENGTH: 61
<212> TYPE: DNA
<213> ORGANISM: Homo Sapiens

<400> SEQUENCE: 881
taggacttcc agtactaagt tgaataaaag yggtctctcg tcttctcttg ccatcttcct    60
t                                                                   61

<210> SEQ ID NO 882
<211> LENGTH: 61
<212> TYPE: DNA
<213> ORGANISM: Homo Sapiens

<400> SEQUENCE: 882
ctgtgtatta catatagaag tactgtatat rgtgaggaat gccatcctgt gtgtgttgtt    60
a                                                                   61

<210> SEQ ID NO 883
<211> LENGTH: 61
<212> TYPE: DNA
<213> ORGANISM: Homo Sapiens

<400> SEQUENCE: 883
tcctccctgt cctcacactt gaacttcatg rtccaatcac ttcaataatt atcttgtcct    60
c                                                                   61

<210> SEQ ID NO 884
<211> LENGTH: 61
<212> TYPE: DNA
<213> ORGANISM: Homo Sapiens

<400> SEQUENCE: 884
aagacagccg cataagccat cggcaggaat yaaggtacag gaagggcttc ctggggtact    60
c                                                                   61

<210> SEQ ID NO 885
<211> LENGTH: 61
```

<212> TYPE: DNA
<213> ORGANISM: Homo Sapiens

<400> SEQUENCE: 885
cctcctatag tcaccttgca agtccaggac rgaaccagaa ttgacatctg agcctcctac    60
c                                                                    61

<210> SEQ ID NO 886
<211> LENGTH: 61
<212> TYPE: DNA
<213> ORGANISM: Homo Sapiens

<400> SEQUENCE: 886
ggggccttgt cggctattgc tgaggctttg kttttttactc tgagtcaact gggaggcatt    60
g                                                                    61

<210> SEQ ID NO 887
<211> LENGTH: 61
<212> TYPE: DNA
<213> ORGANISM: Homo Sapiens

<400> SEQUENCE: 887
actgtttaag tgtttattaa aaagtagagg raaagttgag aaattagaaa taaataataa    60
a                                                                    61

<210> SEQ ID NO 888
<211> LENGTH: 61
<212> TYPE: DNA
<213> ORGANISM: Homo Sapiens

<400> SEQUENCE: 888
gaagacagga gaagctcctc aacacaggga wagaattagt gagtaagagt cctcagggga    60
t                                                                    61

<210> SEQ ID NO 889
<211> LENGTH: 61
<212> TYPE: DNA
<213> ORGANISM: Homo Sapiens

<400> SEQUENCE: 889
ttatctgcta ctcttgtctt atttcatagc mattgccata gctggagact tcattatctc    60
a                                                                    61

<210> SEQ ID NO 890
<211> LENGTH: 61
<212> TYPE: DNA
<213> ORGANISM: Homo Sapiens

<400> SEQUENCE: 890
gtttcagcag attctgggta ttaaaaaact rgaacaccag ctcctttata atgcatgtca    60
g                                                                    61

<210> SEQ ID NO 891
<211> LENGTH: 61
<212> TYPE: DNA
<213> ORGANISM: Homo Sapiens

<400> SEQUENCE: 891
ctactgagct tccctgagtt ccaccttgag rtacaacttt tgcagaaatt agggtacaga    60
t                                                                    61

```
<210> SEQ ID NO 892
<211> LENGTH: 61
<212> TYPE: DNA
<213> ORGANISM: Homo Sapiens

<400> SEQUENCE: 892
agccacctaa gtggcagaaa ggatttgagc kctggcaata taggtacaac ttctgcacca    60
c                                                                   61

<210> SEQ ID NO 893
<211> LENGTH: 61
<212> TYPE: DNA
<213> ORGANISM: Homo Sapiens

<400> SEQUENCE: 893
tgctacctag gcagacacca ttagttgtac ytcataccaa ttcaccactt cttacatggt    60
a                                                                   61

<210> SEQ ID NO 894
<211> LENGTH: 61
<212> TYPE: DNA
<213> ORGANISM: Homo Sapiens

<400> SEQUENCE: 894
tttttcaatc ttcttacctg ttaccactct ycttattttc catagagctc tgattgtcat    60
c                                                                   61

<210> SEQ ID NO 895
<211> LENGTH: 61
<212> TYPE: DNA
<213> ORGANISM: Homo Sapiens

<400> SEQUENCE: 895
agaatttata ggggaaacag taccatttct rcatgacttt catttgcatt tgtttgttat    60
t                                                                   61

<210> SEQ ID NO 896
<211> LENGTH: 61
<212> TYPE: DNA
<213> ORGANISM: Homo Sapiens

<400> SEQUENCE: 896
ccttcttagg tcctgaatag tccttaggtc rttagcagtc tgactgagtc ttctcttact    60
g                                                                   61

<210> SEQ ID NO 897
<211> LENGTH: 61
<212> TYPE: DNA
<213> ORGANISM: Homo Sapiens

<400> SEQUENCE: 897
gtttaccaga attttgctta agtcatacta yggacctttc tgacttgaaa tcattttcga    60
g                                                                   61

<210> SEQ ID NO 898
<211> LENGTH: 61
<212> TYPE: DNA
<213> ORGANISM: Homo Sapiens

<400> SEQUENCE: 898
```

```
tagtaggtga tacagacaac aaattgacag ragctaatga aagcggtaca ctggaaatag      60
t                                                                     61

<210> SEQ ID NO 899
<211> LENGTH: 61
<212> TYPE: DNA
<213> ORGANISM: Homo Sapiens

<400> SEQUENCE: 899
cagccttggc tcttgcctag tagcgggcct ktgtagaaaa tcaaagggga aatgggaca      60 g                                                                     61

<210> SEQ ID NO 900
<211> LENGTH: 61
<212> TYPE: DNA
<213> ORGANISM: Homo Sapiens

<400> SEQUENCE: 900
gacaaactta aaaatcaagc gagatgcatt ycctagtaa atccctgttt tcctagtcct      60
t                                                                     61

<210> SEQ ID NO 901
<211> LENGTH: 61
<212> TYPE: DNA
<213> ORGANISM: Homo Sapiens

<400> SEQUENCE: 901
atatatgatt cataagatgt cttacgtttg ycggttctaa acatccttta tattttatca     60
t                                                                     61

<210> SEQ ID NO 902
<211> LENGTH: 61
<212> TYPE: DNA
<213> ORGANISM: Homo Sapiens

<400> SEQUENCE: 902
aaaaaatgac ataaatagat tctgatgttg yttcatttct gcagaagggt gttttatat      60 t                                                                     61

<210> SEQ ID NO 903
<211> LENGTH: 61
<212> TYPE: DNA
<213> ORGANISM: Homo Sapiens

<400> SEQUENCE: 903
acaaaaatac tagaagaaaa tctagggaaa wctcttcagg acaaaactct tctagacaat     60
g                                                                     61

<210> SEQ ID NO 904
<211> LENGTH: 61
<212> TYPE: DNA
<213> ORGANISM: Homo Sapiens

<400> SEQUENCE: 904
taatttcatg actttaaaaa atgaagctct maccttgaga tagatatctt tccaaaactg     60
t                                                                     61

<210> SEQ ID NO 905
<211> LENGTH: 61
```

```
<212> TYPE: DNA
<213> ORGANISM: Homo Sapiens

<400> SEQUENCE: 905
cactctcttc cagtttctgc taatgctact rctattgctt actacattat ccaagttgga    60
a                                                                    61

<210> SEQ ID NO 906
<211> LENGTH: 61
<212> TYPE: DNA
<213> ORGANISM: Homo Sapiens

<400> SEQUENCE: 906
ttgtaattga ttggtcaggt attttatagc raacttctat gtagaatata ggattagata    60
a                                                                    61

<210> SEQ ID NO 907
<211> LENGTH: 61
<212> TYPE: DNA
<213> ORGANISM: Homo Sapiens

<400> SEQUENCE: 907
gtattaaaga gagtgttctt tttactaaag ktatcgtctc ttggttaatt acttctgttt    60
t                                                                    61

<210> SEQ ID NO 908
<211> LENGTH: 61
<212> TYPE: DNA
<213> ORGANISM: Homo Sapiens

<400> SEQUENCE: 908
gaatatattg aatttatagc tttctaagtg raaatttgcc ttcttatttt gagattttat    60
t                                                                    61

<210> SEQ ID NO 909
<211> LENGTH: 61
<212> TYPE: DNA
<213> ORGANISM: Homo Sapiens

<400> SEQUENCE: 909
taatgacatt tcagtagtcc ttatggggtc wcaattgctc tattttttt tttatttaa    60
a                                                                    61

<210> SEQ ID NO 910
<211> LENGTH: 61
<212> TYPE: DNA
<213> ORGANISM: Homo Sapiens

<400> SEQUENCE: 910
catgcagata cctaaataca atcatttctc rctcaaagat ggggtatct tttgagaaat    60
g                                                                    61

<210> SEQ ID NO 911
<211> LENGTH: 61
<212> TYPE: DNA
<213> ORGANISM: Homo Sapiens

<400> SEQUENCE: 911
catgtcattg aaaaaatgtc caacagcata rgactaagtt gagaattggg gagctatacc    60
t                                                                    61
```

<210> SEQ ID NO 912
<211> LENGTH: 61
<212> TYPE: DNA
<213> ORGANISM: Homo Sapiens

<400> SEQUENCE: 912
tgtttaatgt ctctgctctg aacagatttc rattcttcaa gaggaaatca tatggcaatt    60
t                                                                    61

<210> SEQ ID NO 913
<211> LENGTH: 61
<212> TYPE: DNA
<213> ORGANISM: Homo Sapiens

<400> SEQUENCE: 913
tctcttaaat ttaatagtga taaaaagcta rccctgattt tcctaggggc cagagtaaat    60
t                                                                    61

<210> SEQ ID NO 914
<211> LENGTH: 61
<212> TYPE: DNA
<213> ORGANISM: Homo Sapiens

<400> SEQUENCE: 914
ttgtttcctg gaaaatggaa ataatatcag yaatgctgcc ctggccaggc acgtggctc     60
a                                                                    61

<210> SEQ ID NO 915
<211> LENGTH: 61
<212> TYPE: DNA
<213> ORGANISM: Homo Sapiens

<400> SEQUENCE: 915
taagggccca tataaatcat agaatttaaa mcacgttgga gtaagtactg aaggaaaacc    60
c                                                                    61

<210> SEQ ID NO 916
<211> LENGTH: 61
<212> TYPE: DNA
<213> ORGANISM: Homo Sapiens

<400> SEQUENCE: 916
aagtgagggg atcctcaagg cttttaattg rgctagcaca gcaataattt gacaatatga    60
a                                                                    61

<210> SEQ ID NO 917
<211> LENGTH: 61
<212> TYPE: DNA
<213> ORGANISM: Homo Sapiens

<400> SEQUENCE: 917
agatgcacag ctgatgaaag gtgaaactga yattctagcc catgttcagc cagttccaaa    60
t                                                                    61

<210> SEQ ID NO 918
<211> LENGTH: 61
<212> TYPE: DNA
<213> ORGANISM: Homo Sapiens

<400> SEQUENCE: 918

```
cttctatccc cgagtctaga ctctaccccc rcaatcttgg atgggagtgc tggaggccca    60
g                                                                    61

<210> SEQ ID NO 919
<211> LENGTH: 61
<212> TYPE: DNA
<213> ORGANISM: Homo Sapiens

<400> SEQUENCE: 919
attattttct gttacctata aagccaatgg yatcagaaag tacacaaggt ttgaatgcaa    60
t                                                                    61

<210> SEQ ID NO 920
<211> LENGTH: 61
<212> TYPE: DNA
<213> ORGANISM: Homo Sapiens

<400> SEQUENCE: 920
gtgggtgtca cccatacaga attggagaaa rggttatatt ctgcttttgc taatgattta    60
t                                                                    61

<210> SEQ ID NO 921
<211> LENGTH: 61
<212> TYPE: DNA
<213> ORGANISM: Homo Sapiens

<400> SEQUENCE: 921
gatggttgtc ctcaaagcag ccagcatttt katcaggctg gcgtctggtc ctgtattttt    60
c                                                                    61

<210> SEQ ID NO 922
<211> LENGTH: 61
<212> TYPE: DNA
<213> ORGANISM: Homo Sapiens

<400> SEQUENCE: 922
ctaggcacag tacactttga tcgttttccc raaaccgcgt tggacaccat ttttccatga    60
t                                                                    61

<210> SEQ ID NO 923
<211> LENGTH: 61
<212> TYPE: DNA
<213> ORGANISM: Homo Sapiens

<400> SEQUENCE: 923
tggcagactg acataactgg atgtgactat kgttatagct ggtgggacag actcctatcg    60
c                                                                    61

<210> SEQ ID NO 924
<211> LENGTH: 61
<212> TYPE: DNA
<213> ORGANISM: Homo Sapiens

<400> SEQUENCE: 924
taaagggctg ttcttgactg caggcagagc ygatttctga acatggactg tggggttctt    60
t                                                                    61

<210> SEQ ID NO 925
<211> LENGTH: 61
```

```
<212> TYPE: DNA
<213> ORGANISM: Homo Sapiens

<400> SEQUENCE: 925
agagagagag agagagagag attagatgga yaggtatgta gtttcaccta taagcaaagg    60
c                                                                   61

<210> SEQ ID NO 926
<211> LENGTH: 61
<212> TYPE: DNA
<213> ORGANISM: Homo Sapiens

<400> SEQUENCE: 926
ttggagaata ttatcactta ctgtactgtc rcaaatttca gataagttaa cattcctgaa    60
t                                                                   61

<210> SEQ ID NO 927
<211> LENGTH: 61
<212> TYPE: DNA
<213> ORGANISM: Homo Sapiens

<400> SEQUENCE: 927
tagagggagt tacattttgt tgaatttaga ragcaattta tgtggatgtt accatattca    60
a                                                                   61

<210> SEQ ID NO 928
<211> LENGTH: 61
<212> TYPE: DNA
<213> ORGANISM: Homo Sapiens

<400> SEQUENCE: 928
cttttagaac ggtgctgcca tgagttatga ytaaccgaga aaatgtatt ctatagccaa     60
a                                                                   61

<210> SEQ ID NO 929
<211> LENGTH: 61
<212> TYPE: DNA
<213> ORGANISM: Homo Sapiens

<400> SEQUENCE: 929
cagtagattg caattagagt ttacttgatt wggcaattat taaaaaatga acatttttttt  60
c                                                                   61

<210> SEQ ID NO 930
<211> LENGTH: 61
<212> TYPE: DNA
<213> ORGANISM: Homo Sapiens

<400> SEQUENCE: 930
gtgagtctgt attcaatttt gctcagagaa yatttgaagc actcaatatt taatttctta   60
t                                                                   61

<210> SEQ ID NO 931
<211> LENGTH: 61
<212> TYPE: DNA
<213> ORGANISM: Homo Sapiens

<400> SEQUENCE: 931
tatatattca gtatatcatt ttatatttga scaaaatcac aaatctatta atattgctaa   60
g                                                                   61
```

<210> SEQ ID NO 932
<211> LENGTH: 61
<212> TYPE: DNA
<213> ORGANISM: Homo Sapiens

<400> SEQUENCE: 932
gcaagctctt gatgcataga ctcacaagca raagtctact tattgagata ctgtgttgat    60
a                                                                   61

<210> SEQ ID NO 933
<211> LENGTH: 61
<212> TYPE: DNA
<213> ORGANISM: Homo Sapiens

<400> SEQUENCE: 933
aaatcatccc tgccattttt cctattcaaa yatgttctgg tatctactaa cacaactgta    60
t                                                                   61

<210> SEQ ID NO 934
<211> LENGTH: 61
<212> TYPE: DNA
<213> ORGANISM: Homo Sapiens

<400> SEQUENCE: 934
caaaggcagc ctcacacttt tctgctcagt rttcagttga cacctgccct tgttttgctt    60
c                                                                   61

<210> SEQ ID NO 935
<211> LENGTH: 61
<212> TYPE: DNA
<213> ORGANISM: Homo Sapiens

<400> SEQUENCE: 935
acaactcttt cttcaggaaa cctttgactc rtggtttata catacttttg tattaagttg    60
t                                                                   61

<210> SEQ ID NO 936
<211> LENGTH: 61
<212> TYPE: DNA
<213> ORGANISM: Homo Sapiens

<400> SEQUENCE: 936
agtggttgtg tgtatatctg agaagagaac rtaccaagca gagaaaacaa caaaaatcaa    60
a                                                                   61

<210> SEQ ID NO 937
<211> LENGTH: 61
<212> TYPE: DNA
<213> ORGANISM: Homo Sapiens

<400> SEQUENCE: 937
tttggtagtg caattgaaga ccacataaaa mtgctgctag aatgcatctc ctttgttagc    60
a                                                                   61

<210> SEQ ID NO 938
<211> LENGTH: 61
<212> TYPE: DNA
<213> ORGANISM: Homo Sapiens

<400> SEQUENCE: 938

```
gtgcactttg gaagttcact gcatttaatc rattcagagg atttctttt tttttaattt    60
t                                                                  61
```

<210> SEQ ID NO 939
<211> LENGTH: 61
<212> TYPE: DNA
<213> ORGANISM: Homo Sapiens

<400> SEQUENCE: 939

```
ggtaaatctc ttcttaaatt aaaacacaga ytatgttaca gcaagtcatt aagagtcata    60
a                                                                  61
```

<210> SEQ ID NO 940
<211> LENGTH: 61
<212> TYPE: DNA
<213> ORGANISM: Homo Sapiens

<400> SEQUENCE: 940

```
ctatcatttc ttttccaaaa ttacttctct ytatctggaa tttaattaat cgaaatgaat    60
t                                                                  61
```

<210> SEQ ID NO 941
<211> LENGTH: 61
<212> TYPE: DNA
<213> ORGANISM: Homo Sapiens

<400> SEQUENCE: 941

```
gctgcttcca aaaccaaaca ttctcttact rtgtgatcca gtgattacac tccttggtac    60
t                                                                  61
```

<210> SEQ ID NO 942
<211> LENGTH: 61
<212> TYPE: DNA
<213> ORGANISM: Homo Sapiens

<400> SEQUENCE: 942

```
acaggttata acagcttgca ttgcattccc sctaatttga gaatttctat gtcctcatca    60
a                                                                  61
```

<210> SEQ ID NO 943
<211> LENGTH: 61
<212> TYPE: DNA
<213> ORGANISM: Homo Sapiens

<400> SEQUENCE: 943

```
aaaaaaaaaa tcaaatatca tctgtttcta yaaatcaagg cctgaatatg tgtatttaca    60
t                                                                  61
```

<210> SEQ ID NO 944
<211> LENGTH: 61
<212> TYPE: DNA
<213> ORGANISM: Homo Sapiens

<400> SEQUENCE: 944

```
ccattactat taaagtgtaa cttttctca yaccagcttt ctaatttatt gatcttcttc    60
t                                                                  61
```

<210> SEQ ID NO 945
<211> LENGTH: 61

```
<212> TYPE: DNA
<213> ORGANISM: Homo Sapiens

<400> SEQUENCE: 945
caaagaaggt gtccacatgg catgtaagca ygtgaaagat gctctgaaca ccatttgtca    60
t                                                                    61

<210> SEQ ID NO 946
<211> LENGTH: 61
<212> TYPE: DNA
<213> ORGANISM: Homo Sapiens

<400> SEQUENCE: 946
ttggattttg ctagtgatac ttaactaatg rttcatactg tatttgaagt gtctgctgcc    60
a                                                                    61

<210> SEQ ID NO 947
<211> LENGTH: 61
<212> TYPE: DNA
<213> ORGANISM: Homo Sapiens

<400> SEQUENCE: 947
cttaaacaga aaataatttg ttcaaagtca sagtgtcaaa ccaggattaa acccaggtat    60
a                                                                    61

<210> SEQ ID NO 948
<211> LENGTH: 61
<212> TYPE: DNA
<213> ORGANISM: Homo Sapiens

<400> SEQUENCE: 948
ggtatatagg atacaataat ctgtgcattt racgacaaca gtactattta ctcatgacat    60
g                                                                    61

<210> SEQ ID NO 949
<211> LENGTH: 61
<212> TYPE: DNA
<213> ORGANISM: Homo Sapiens

<400> SEQUENCE: 949
atttgtaact tggcctatca gtttgagacc yttgttctag acactttgta tactgtctca    60
a                                                                    61

<210> SEQ ID NO 950
<211> LENGTH: 61
<212> TYPE: DNA
<213> ORGANISM: Homo Sapiens

<400> SEQUENCE: 950
taattaagcc acaaagcaca atgcaagttc rataatcact ggaaataata tgccttttaa    60
g                                                                    61

<210> SEQ ID NO 951
<211> LENGTH: 61
<212> TYPE: DNA
<213> ORGANISM: Homo Sapiens

<400> SEQUENCE: 951
attgaacttg gctctgaagt aaaacaatac rggttttga gtgatccagc agctgttcta     60
c                                                                    61
```

<210> SEQ ID NO 952
<211> LENGTH: 61
<212> TYPE: DNA
<213> ORGANISM: Homo Sapiens

<400> SEQUENCE: 952
gggaaagaag aaaagattcc gtattttta ytctggcttc cttgagcaca gctttcttct    60
c                                                                   61

<210> SEQ ID NO 953
<211> LENGTH: 61
<212> TYPE: DNA
<213> ORGANISM: Homo Sapiens

<400> SEQUENCE: 953
tcttgccatt ttgcttaatt gtatgattat stgaaagtag aatagaatc ctttgaactc    60
t                                                                   61

<210> SEQ ID NO 954
<211> LENGTH: 61
<212> TYPE: DNA
<213> ORGANISM: Homo Sapiens

<400> SEQUENCE: 954
ccagtgagcc aaattttaag taaacagaaa yggaaggtgc taagcaaaca aactccagcc    60
a                                                                   61

<210> SEQ ID NO 955
<211> LENGTH: 61
<212> TYPE: DNA
<213> ORGANISM: Homo Sapiens

<400> SEQUENCE: 955
ctcgcaagga ctgtttacat ctaacattgc htagatctga aataaataac actaggagga    60
a                                                                   61

<210> SEQ ID NO 956
<211> LENGTH: 61
<212> TYPE: DNA
<213> ORGANISM: Homo Sapiens

<400> SEQUENCE: 956
cctttgtgaa ttaatattaa cagataaagt rgagatccga ggcacttaca tgagtaaata    60
a                                                                   61

<210> SEQ ID NO 957
<211> LENGTH: 61
<212> TYPE: DNA
<213> ORGANISM: Homo Sapiens

<400> SEQUENCE: 957
ctcaccttcg tggttgacct tgtagtgcag sgtgacgggg ccgctgcacc tctggatggt    60
c                                                                   61

<210> SEQ ID NO 958
<211> LENGTH: 61
<212> TYPE: DNA
<213> ORGANISM: Homo Sapiens

<400> SEQUENCE: 958

```
actatattag acattacgga gcatataaaa kaaggcaagg agctgtcctt gaggagctga      60
g                                                                     61

<210> SEQ ID NO 959
<211> LENGTH: 61
<212> TYPE: DNA
<213> ORGANISM: Homo Sapiens

<400> SEQUENCE: 959
gtcttctcat aattgaagtg gttgtcgttg ygtgtgaggg cagcccttcg aaccagggag      60
g                                                                     61

<210> SEQ ID NO 960
<211> LENGTH: 61
<212> TYPE: DNA
<213> ORGANISM: Homo Sapiens

<400> SEQUENCE: 960
gaaaaaaata agaggtgttg agtgatgctt ycagaaagtt tccttaaact taaaggcata      60
a                                                                     61

<210> SEQ ID NO 961
<211> LENGTH: 61
<212> TYPE: DNA
<213> ORGANISM: Homo Sapiens

<400> SEQUENCE: 961
aactaacaga gcaggtatat gcctgttaga ycttagctgt ggggttcctt tactattggg      60
t                                                                     61

<210> SEQ ID NO 962
<211> LENGTH: 61
<212> TYPE: DNA
<213> ORGANISM: Homo Sapiens

<400> SEQUENCE: 962
agctctgcag tccaccacac ataagcacag ygcatggaaa atgggaagac agcttcttca      60
g                                                                     61

<210> SEQ ID NO 963
<211> LENGTH: 61
<212> TYPE: DNA
<213> ORGANISM: Homo Sapiens

<400> SEQUENCE: 963
cagattcagt agtatgtgat gtgccaaaga yagttttgga actgagaccc ggagtcacag      60
c                                                                     61

<210> SEQ ID NO 964
<211> LENGTH: 61
<212> TYPE: DNA
<213> ORGANISM: Homo Sapiens

<400> SEQUENCE: 964
agaatgtaga tatgagacag ctgatctcta sgaactgaat ttttagtgag taaagcaagc      60
a                                                                     61

<210> SEQ ID NO 965
<211> LENGTH: 61
```

<212> TYPE: DNA
<213> ORGANISM: Homo Sapiens

<400> SEQUENCE: 965
gcattctaca tggccactgg cattggcaca mataggtttg gcacataccc tctttgtgtg    60
g                                                                   61

<210> SEQ ID NO 966
<211> LENGTH: 61
<212> TYPE: DNA
<213> ORGANISM: Homo Sapiens

<400> SEQUENCE: 966
cagaacaatg tgtcactacc agaaaccatt ygctatctct gttccttgtt tgtatttctg    60
c                                                                   61

<210> SEQ ID NO 967
<211> LENGTH: 61
<212> TYPE: DNA
<213> ORGANISM: Homo Sapiens

<400> SEQUENCE: 967
tcagtcctga ctgcctctct gtgctcttca sattgacctg cttcagttgt ctctatcatc    60
g                                                                   61

<210> SEQ ID NO 968
<211> LENGTH: 61
<212> TYPE: DNA
<213> ORGANISM: Homo Sapiens

<400> SEQUENCE: 968
aatgcattgg cttttacttt ggatactccc rcatctagga gatatgggag cctttggagg    60
t                                                                   61

<210> SEQ ID NO 969
<211> LENGTH: 61
<212> TYPE: DNA
<213> ORGANISM: Homo Sapiens

<400> SEQUENCE: 969
aaagtcccag atggaaaccg agaccaagta ytttgccacc atctgaggat tagaggctgt    60
t                                                                   61

<210> SEQ ID NO 970
<211> LENGTH: 61
<212> TYPE: DNA
<213> ORGANISM: Homo Sapiens

<400> SEQUENCE: 970
tcccatttag gtaatatagg ataatttcct ygtctaaaga tccttcactt attcttattt    60
g                                                                   61

<210> SEQ ID NO 971
<211> LENGTH: 61
<212> TYPE: DNA
<213> ORGANISM: Homo Sapiens

<400> SEQUENCE: 971
ggttaaatgt gtcttgattt gaatggatat rgatggcgtg attttggtgt ttctgcccca    60
a                                                                   61

<210> SEQ ID NO 972
<211> LENGTH: 61
<212> TYPE: DNA
<213> ORGANISM: Homo Sapiens

<400> SEQUENCE: 972
gtcctcccct ccaaataccg tgggaataga rctgcttcat catgtccctg tgggcaccgt    60
t                                                                   61

<210> SEQ ID NO 973
<211> LENGTH: 61
<212> TYPE: DNA
<213> ORGANISM: Homo Sapiens

<400> SEQUENCE: 973
agggtgatat tgcaaaagta ttatcaaaga ragcatatga caggggagt ggagatttgg    60
a                                                                   61

<210> SEQ ID NO 974
<211> LENGTH: 61
<212> TYPE: DNA
<213> ORGANISM: Homo Sapiens

<400> SEQUENCE: 974
gataaaaaca aaatgcacag caaggctcgt rtagttaact acaggttctc atgagtacag    60
a                                                                   61

<210> SEQ ID NO 975
<211> LENGTH: 61
<212> TYPE: DNA
<213> ORGANISM: Homo Sapiens

<400> SEQUENCE: 975
ctcaaaccag tccagcaagc agggactata ragtgaggta gcaggaaata aggctggcaa    60
g                                                                   61

<210> SEQ ID NO 976
<211> LENGTH: 61
<212> TYPE: DNA
<213> ORGANISM: Homo Sapiens

<400> SEQUENCE: 976
cacgagggca gggaaataac agggctgata yggaaacagc tgtgggcaag gcaaggccca    60
a                                                                   61

<210> SEQ ID NO 977
<211> LENGTH: 61
<212> TYPE: DNA
<213> ORGANISM: Homo Sapiens

<400> SEQUENCE: 977
agaaaacccg aagtcagagc ttagtttggc rtacattttg ttcagcaaaa aacattattc    60
t                                                                   61

<210> SEQ ID NO 978
<211> LENGTH: 61
<212> TYPE: DNA
<213> ORGANISM: Homo Sapiens

<400> SEQUENCE: 978

```
caacagaaga gcttttcctg gtattttcgc rtgttctcta ttggtttggg ggaagaatcc      60
a                                                                     61
```

<210> SEQ ID NO 979
<211> LENGTH: 61
<212> TYPE: DNA
<213> ORGANISM: Homo Sapiens

<400> SEQUENCE: 979

```
ttaacaatca tcatgctaaa tcatgcctag ycatgaaaga gttttttggtt gtatgcttta    60
a                                                                     61
```

<210> SEQ ID NO 980
<211> LENGTH: 61
<212> TYPE: DNA
<213> ORGANISM: Homo Sapiens

<400> SEQUENCE: 980

```
tggaatacat ttaaacttct caggctggca rtaaatctca ggccaattta tttagacaac    60
t                                                                     61
```

<210> SEQ ID NO 981
<211> LENGTH: 61
<212> TYPE: DNA
<213> ORGANISM: Homo Sapiens

<400> SEQUENCE: 981

```
ttgataaata aaaacttctg gtttaagtag rgaagaagat gtttttaaggt cggttcttgg   60
a                                                                     61
```

<210> SEQ ID NO 982
<211> LENGTH: 61
<212> TYPE: DNA
<213> ORGANISM: Homo Sapiens

<400> SEQUENCE: 982

```
ccttcagttc ttgggaactg tgaccgactt yctgtcatgc tggtccatgt agccacccat    60
t                                                                     61
```

<210> SEQ ID NO 983
<211> LENGTH: 61
<212> TYPE: DNA
<213> ORGANISM: Homo Sapiens

<400> SEQUENCE: 983

```
atcagtaatt cactttctcc tcacaggcaa rattaagtct atcaatacag tactcagaag    60
t                                                                     61
```

<210> SEQ ID NO 984
<211> LENGTH: 61
<212> TYPE: DNA
<213> ORGANISM: Homo Sapiens

<400> SEQUENCE: 984

```
aagtaatttt aactttgtgg aacatgactc kgaattgggt agtagactgg ggcttagttg    60
t                                                                     61
```

<210> SEQ ID NO 985
<211> LENGTH: 61

```
<212> TYPE: DNA
<213> ORGANISM: Homo Sapiens

<400> SEQUENCE: 985
cctaaggtcg gtttcttcct ctgtagaatg sggatgaaaa tagaaatcac atcacccggt    60
t                                                                   61

<210> SEQ ID NO 986
<211> LENGTH: 61
<212> TYPE: DNA
<213> ORGANISM: Homo Sapiens

<400> SEQUENCE: 986
cctgttttca ctcatctctt cctttaaccc rgattccaag aaagcttgac aactgtctac    60
a                                                                   61

<210> SEQ ID NO 987
<211> LENGTH: 61
<212> TYPE: DNA
<213> ORGANISM: Homo Sapiens

<400> SEQUENCE: 987
gtagaagttg aaaggaaaaa ttggtctgaa stgtacttaa tccaaaactt aacttgaagt    60
a                                                                   61

<210> SEQ ID NO 988
<211> LENGTH: 61
<212> TYPE: DNA
<213> ORGANISM: Homo Sapiens

<400> SEQUENCE: 988
gaaagtcctc taagaattgg aatgcttgga ytgttaaaag tatccactga aaataaatta    60
a                                                                   61

<210> SEQ ID NO 989
<211> LENGTH: 61
<212> TYPE: DNA
<213> ORGANISM: Homo Sapiens

<400> SEQUENCE: 989
tgaaagttac ctattaggta cagtgtccaa ygtttgggtg atgggtaccc cagaagccta    60
a                                                                   61

<210> SEQ ID NO 990
<211> LENGTH: 61
<212> TYPE: DNA
<213> ORGANISM: Homo Sapiens

<400> SEQUENCE: 990
ctgaccctca atcggaatga ataatgagac kttcagctat ctccctgagg aggtgtgttt    60
t                                                                   61

<210> SEQ ID NO 991
<211> LENGTH: 61
<212> TYPE: DNA
<213> ORGANISM: Homo Sapiens

<400> SEQUENCE: 991
ttgaagaaag agtttcacat cactaaaaaa ragtttggag gcctgtgttg aacggcagca    60
g                                                                   61
```

<210> SEQ ID NO 992
<211> LENGTH: 61
<212> TYPE: DNA
<213> ORGANISM: Homo Sapiens

<400> SEQUENCE: 992
ccacaggtca cctaaaccca actcttcata ygtcttccaa ggaaccacgt cgctaaacaa    60
g                                                                   61

<210> SEQ ID NO 993
<211> LENGTH: 61
<212> TYPE: DNA
<213> ORGANISM: Homo Sapiens

<400> SEQUENCE: 993
actccgcggg acacgaggac acgggacggc rtctccagaa ttgcttgtta cgtaggaagc    60
g                                                                   61

<210> SEQ ID NO 994
<211> LENGTH: 61
<212> TYPE: DNA
<213> ORGANISM: Homo Sapiens

<400> SEQUENCE: 994
atctatcaat ctatcatcta tctagtctat mtacctactt atctctaatc acccaccaaa    60
a                                                                   61

<210> SEQ ID NO 995
<211> LENGTH: 61
<212> TYPE: DNA
<213> ORGANISM: Homo Sapiens

<400> SEQUENCE: 995
ataccagtcc tctgaacact tacagaaccg rcttgctgct catcacatac aacacgtgat    60
a                                                                   61

<210> SEQ ID NO 996
<211> LENGTH: 61
<212> TYPE: DNA
<213> ORGANISM: Homo Sapiens

<400> SEQUENCE: 996
tgggctgctt aataaccttc ctaacattcg rcattatttc tactttctag ccagaacatt    60
c                                                                   61

<210> SEQ ID NO 997
<211> LENGTH: 61
<212> TYPE: DNA
<213> ORGANISM: Homo Sapiens

<400> SEQUENCE: 997 tttttctag attgtcaggt ttttagcagc rccatattat ttctagtatc cttttcttat    60
c                                                                   61

<210> SEQ ID NO 998
<211> LENGTH: 61
<212> TYPE: DNA
<213> ORGANISM: Homo Sapiens

<400> SEQUENCE: 998

-continued

```
gagtcaccct ggtgtctgtg accaaggaat wtgagggcca caaggctgtg gtccaagacc    60
t                                                                    61

<210> SEQ ID NO 999
<211> LENGTH: 61
<212> TYPE: DNA
<213> ORGANISM: Homo Sapiens

<400> SEQUENCE: 999
taaatgcctg gaacaagtct gtcaaaaatg rtaatggctt ttctcactta cagtgggatt    60
g                                                                    61

<210> SEQ ID NO 1000
<211> LENGTH: 61
<212> TYPE: DNA
<213> ORGANISM: Homo Sapiens

<400> SEQUENCE: 1000
cataagctca ctggactctc agggcaggga rgaagatgct gtaggaatat ggaccaagca    60
c                                                                    61

<210> SEQ ID NO 1001
<211> LENGTH: 61
<212> TYPE: DNA
<213> ORGANISM: Homo Sapiens

<400> SEQUENCE: 1001
aattctgggg cttaaacaag cacattccaa rttaagaacc aatgacctaa gggaatgtct    60
g                                                                    61

<210> SEQ ID NO 1002
<211> LENGTH: 61
<212> TYPE: DNA
<213> ORGANISM: Homo Sapiens

<400> SEQUENCE: 1002
ctttatttaa actctcaacg attcagttct yttatctgga atgtcaggac agtaagggtt    60
g                                                                    61

<210> SEQ ID NO 1003
<211> LENGTH: 61
<212> TYPE: DNA
<213> ORGANISM: Homo Sapiens

<400> SEQUENCE: 1003
ggatatcaca caaagacaaa aaatccccac saaagaggct cacaatagaa gggacagtga    60
c                                                                    61

<210> SEQ ID NO 1004
<211> LENGTH: 61
<212> TYPE: DNA
<213> ORGANISM: Homo Sapiens

<400> SEQUENCE: 1004
gcacagcagg aagacagggc gctagggacc rgtttctacc tttgcttgcc tagagtaacc    60
a                                                                    61

<210> SEQ ID NO 1005
<211> LENGTH: 61
```

```
<212> TYPE: DNA
<213> ORGANISM: Homo Sapiens

<400> SEQUENCE: 1005
attgggcata caggtaggga tcccagtgtc rgaggcattt aacaagagga actccatctt    60
g                                                                   61

<210> SEQ ID NO 1006
<211> LENGTH: 61
<212> TYPE: DNA
<213> ORGANISM: Homo Sapiens

<400> SEQUENCE: 1006
agaaaagggc aagggtaat gggagcaaag saaagttcca tgaaagtcta gatcccagat     60
g                                                                   61

<210> SEQ ID NO 1007
<211> LENGTH: 61
<212> TYPE: DNA
<213> ORGANISM: Homo Sapiens

<400> SEQUENCE: 1007
cacaaggaag gtataagcca gaggattact rccatgctgt cattccccgg gaaaattggg    60
t                                                                   61

<210> SEQ ID NO 1008
<211> LENGTH: 61
<212> TYPE: DNA
<213> ORGANISM: Homo Sapiens

<400> SEQUENCE: 1008
agaacacatc accatccaaa gaaagaacag ytcctctggc agcttccttg caaggaagag    60
a                                                                   61

<210> SEQ ID NO 1009
<211> LENGTH: 61
<212> TYPE: DNA
<213> ORGANISM: Homo Sapiens

<400> SEQUENCE: 1009
gatgttgatg tatatttttg acatgaaatt wtgcttatgg tacactatta ggttaaaaaa    60
a                                                                   61

<210> SEQ ID NO 1010
<211> LENGTH: 61
<212> TYPE: DNA
<213> ORGANISM: Homo Sapiens

<400> SEQUENCE: 1010
acagagtctt taagaggtat gaaggaattg ytgtaggcca acagcatgtg gctcttaata    60
a                                                                   61

<210> SEQ ID NO 1011
<211> LENGTH: 61
<212> TYPE: DNA
<213> ORGANISM: Homo Sapiens

<400> SEQUENCE: 1011
ttgcctattg tctctatact gaactactga rctgtccttt atagcaatct cccccctcatc   60
c                                                                   61
```

<210> SEQ ID NO 1012
<211> LENGTH: 61
<212> TYPE: DNA
<213> ORGANISM: Homo Sapiens

<400> SEQUENCE: 1012
cttttgtgag ctgatttatc agcaaacctt sagaaggtga agcagaagtt ttttccttgg      60
t                                                                     61

<210> SEQ ID NO 1013
<211> LENGTH: 61
<212> TYPE: DNA
<213> ORGANISM: Homo Sapiens

<400> SEQUENCE: 1013
tgaaaaacct ctccatatgt ttctgatttg ycaggcaggg agaaccagaa aaccttccta      60
t                                                                     61

<210> SEQ ID NO 1014
<211> LENGTH: 61
<212> TYPE: DNA
<213> ORGANISM: Homo Sapiens

<400> SEQUENCE: 1014
acggcagggg cacacatggg ggctccctca kctggggatc tctcaggctt ttttcactct      60
c                                                                     61

<210> SEQ ID NO 1015
<211> LENGTH: 61
<212> TYPE: DNA
<213> ORGANISM: Homo Sapiens

<400> SEQUENCE: 1015
ttcactgact gtctttgctt cacagattcc rcttttgcta gatcaacaat acatcttgtt      60
t                                                                     61

<210> SEQ ID NO 1016
<211> LENGTH: 61
<212> TYPE: DNA
<213> ORGANISM: Homo Sapiens

<400> SEQUENCE: 1016
gtttaatggg gaccgtttca gttttacaaa katgaacggc cgtgatggtt gcacaaatta      60
t                                                                     61

<210> SEQ ID NO 1017
<211> LENGTH: 61
<212> TYPE: DNA
<213> ORGANISM: Homo Sapiens

<400> SEQUENCE: 1017
tggaatgctt aaaaaaagca ctgatagagc ragaaaatac ataccttact cacctgctac      60
a                                                                     61

<210> SEQ ID NO 1018
<211> LENGTH: 61
<212> TYPE: DNA
<213> ORGANISM: Homo Sapiens

<400> SEQUENCE: 1018

```
tgggggaagc acctatttac ttcccgttcc rtttcctagc tgtaagctct ctttccagca    60
g                                                                     61
```

<210> SEQ ID NO 1019
<211> LENGTH: 61
<212> TYPE: DNA
<213> ORGANISM: Homo Sapiens

<400> SEQUENCE: 1019

```
tgccctagaa aaaattacgg aaaggtaaag kctgtccttc cctgctgtgt gacagatgct    60
t                                                                     61
```

<210> SEQ ID NO 1020
<211> LENGTH: 61
<212> TYPE: DNA
<213> ORGANISM: Homo Sapiens

<400> SEQUENCE: 1020

```
gagatgttag ctaaaggata aaaccatcac mggaagaata agttcaagag atctattgtg    60
c                                                                     61
```

<210> SEQ ID NO 1021
<211> LENGTH: 61
<212> TYPE: DNA
<213> ORGANISM: Homo Sapiens

<400> SEQUENCE: 1021

```
ggactatgaa catgagttaa aaatgtgaca rtataatagg ccaaatgtct tttactttg     60
a                                                                     61
```

<210> SEQ ID NO 1022
<211> LENGTH: 61
<212> TYPE: DNA
<213> ORGANISM: Homo Sapiens

<400> SEQUENCE: 1022

```
tcaaataaac atttagtgag atcagtaaac rgtcagtgtt cctaaaaagt acacccaaat    60
g                                                                     61
```

<210> SEQ ID NO 1023
<211> LENGTH: 61
<212> TYPE: DNA
<213> ORGANISM: Homo Sapiens

<400> SEQUENCE: 1023

```
gttatttatt tttggagttc tgttaggtta ygaaaatggg ctaggcatgg tggctcacac    60
t                                                                     61
```

<210> SEQ ID NO 1024
<211> LENGTH: 61
<212> TYPE: DNA
<213> ORGANISM: Homo Sapiens

<400> SEQUENCE: 1024

```
ttggaaagca tctaattcct cttagcacaa ygtaagtaac aaaaaaaatg catgtcttac    60
t                                                                     61
```

<210> SEQ ID NO 1025
<211> LENGTH: 61

```
<212> TYPE: DNA
<213> ORGANISM: Homo Sapiens

<400> SEQUENCE: 1025
taagatgaga atttatttct ttcagtttga yctcttggta tttattgatt ttggaacatt      60
a                                                                     61

<210> SEQ ID NO 1026
<211> LENGTH: 61
<212> TYPE: DNA
<213> ORGANISM: Homo Sapiens

<400> SEQUENCE: 1026
agctcatctg atcctcacaa ccaaacatca mtgagttgga tagtatcccc atttaacaga      60
a                                                                     61

<210> SEQ ID NO 1027
<211> LENGTH: 61
<212> TYPE: DNA
<213> ORGANISM: Homo Sapiens

<400> SEQUENCE: 1027
aacctttata atgcccttca atggaaattt wtgtcaagta aattcaattc aagctatgat      60
a                                                                     61

<210> SEQ ID NO 1028
<211> LENGTH: 61
<212> TYPE: DNA
<213> ORGANISM: Homo Sapiens

<400> SEQUENCE: 1028
tgacggtaga attaagtttg aggaagattc raggatatgg attaaacagt cattcttctt      60
a                                                                     61

<210> SEQ ID NO 1029
<211> LENGTH: 61
<212> TYPE: DNA
<213> ORGANISM: Homo Sapiens

<400> SEQUENCE: 1029
cctaaaccaa ttactttcat accaggaaaa kcctttctag caccagcaaa atcccaccca      60
t                                                                     61

<210> SEQ ID NO 1030
<211> LENGTH: 61
<212> TYPE: DNA
<213> ORGANISM: Homo Sapiens

<400> SEQUENCE: 1030
ttttccgggt tgataggttt ttttggcaat ygaaatccct atttaacaga tttaaataaa      60
g                                                                     61

<210> SEQ ID NO 1031
<211> LENGTH: 61
<212> TYPE: DNA
<213> ORGANISM: Homo Sapiens

<400> SEQUENCE: 1031
ctgaataaag caagttgctc tccttaatgt sgtgggcctc attcaattag tagaaagcct      60
a                                                                     61
```

<210> SEQ ID NO 1032
<211> LENGTH: 61
<212> TYPE: DNA
<213> ORGANISM: Homo Sapiens

<400> SEQUENCE: 1032
ttagcaggag gatgcataac agagcggtat sttcaataac tgccaggttt ctgacatggg    60
c                                                                   61

<210> SEQ ID NO 1033
<211> LENGTH: 61
<212> TYPE: DNA
<213> ORGANISM: Homo Sapiens

<400> SEQUENCE: 1033
tgctgtccaa aagaaatata acatgagcct matatggaac tttaaatttt ctaataacta    60
c                                                                   61

<210> SEQ ID NO 1034
<211> LENGTH: 61
<212> TYPE: DNA
<213> ORGANISM: Homo Sapiens

<400> SEQUENCE: 1034
cacgtctact gattaaacac attaaacttt ygttacaaat ttcaatcaat ttataaaaat    60
t                                                                   61

<210> SEQ ID NO 1035
<211> LENGTH: 61
<212> TYPE: DNA
<213> ORGANISM: Homo Sapiens

<400> SEQUENCE: 1035
agtctccttc cagaaagcag tcaagcttaa ygaaacaagg ttgtttcctg agttccgaag    60
g                                                                   61

<210> SEQ ID NO 1036
<211> LENGTH: 61
<212> TYPE: DNA
<213> ORGANISM: Homo Sapiens

<400> SEQUENCE: 1036
ctgaggcata gagcggttaa gttacttacc raaggacaca aaattagtaa gtggcagagc    60
a                                                                   61

<210> SEQ ID NO 1037
<211> LENGTH: 61
<212> TYPE: DNA
<213> ORGANISM: Homo Sapiens

<400> SEQUENCE: 1037
gatcatatca gggaaatagt ggcctcatac kcatttgtat caccgttgga catcttgtaa    60
g                                                                   61

<210> SEQ ID NO 1038
<211> LENGTH: 61
<212> TYPE: DNA
<213> ORGANISM: Homo Sapiens

<400> SEQUENCE: 1038

```
ttgcaaatga gaatttatgg tggccacaat yagtactaga agatcaatta aataaatgga    60
a                                                                    61

<210> SEQ ID NO 1039
<211> LENGTH: 61
<212> TYPE: DNA
<213> ORGANISM: Homo Sapiens

<400> SEQUENCE: 1039
tagagctaat ccattattca aattttgtca rgaaaatctg gatgaattgt gtaaaactgc    60
c                                                                    61

<210> SEQ ID NO 1040
<211> LENGTH: 61
<212> TYPE: DNA
<213> ORGANISM: Homo Sapiens

<400> SEQUENCE: 1040
aaaattacag attgtctgat gcaactccat rtctactgac tgacgaattt caaagcatag    60
a                                                                    61

<210> SEQ ID NO 1041
<211> LENGTH: 61
<212> TYPE: DNA
<213> ORGANISM: Homo Sapiens

<400> SEQUENCE: 1041
ttacaattac agggtgattg gcgcaatgat rgaggcactg acaggagcaa gagaaaactt    60
c                                                                    61

<210> SEQ ID NO 1042
<211> LENGTH: 61
<212> TYPE: DNA
<213> ORGANISM: Homo Sapiens

<400> SEQUENCE: 1042
tttaaaagtt acacttgaaa taataggcaa maaacactga tccacattcc aactggtagg    60
c                                                                    61

<210> SEQ ID NO 1043
<211> LENGTH: 61
<212> TYPE: DNA
<213> ORGANISM: Homo Sapiens

<400> SEQUENCE: 1043
gataccacct tggagtgtta tcgaggtgag mtgtgctaga taaatcaatc aatacctgaa    60
a                                                                    61

<210> SEQ ID NO 1044
<211> LENGTH: 61
<212> TYPE: DNA
<213> ORGANISM: Homo Sapiens

<400> SEQUENCE: 1044
ttttgaaatg aaacataaag tcaggcataa yactaatcta gagtactcct gcctaggatc    60
a                                                                    61

<210> SEQ ID NO 1045
<211> LENGTH: 61
```

```
<212> TYPE: DNA
<213> ORGANISM: Homo Sapiens

<400> SEQUENCE: 1045
gatttgttgc aaagtctttt gcttaatagg mtactaaaca ctgaaaaaga caataattag    60
g                                                                    61

<210> SEQ ID NO 1046
<211> LENGTH: 61
<212> TYPE: DNA
<213> ORGANISM: Homo Sapiens

<400> SEQUENCE: 1046
atgattaatt acaaatagta gtgtataaac ygcacatatc gttttatttg cttcacacaa    60
t                                                                    61

<210> SEQ ID NO 1047
<211> LENGTH: 61
<212> TYPE: DNA
<213> ORGANISM: Homo Sapiens

<400> SEQUENCE: 1047
taggatactt attaagatgt cactcctcgc rggattgtgt gaagcaaata aaacgatatg    60
t                                                                    61

<210> SEQ ID NO 1048
<211> LENGTH: 61
<212> TYPE: DNA
<213> ORGANISM: Homo Sapiens

<400> SEQUENCE: 1048
gaggagaata tttgtatttg gaagaaacag ytatactttc aacttatttc agaagaaaat    60
a                                                                    61

<210> SEQ ID NO 1049
<211> LENGTH: 61
<212> TYPE: DNA
<213> ORGANISM: Homo Sapiens

<400> SEQUENCE: 1049
gtcctagtat gttgttaaaa ttgtctgtta ytctaagttt ataagaagga tcaatgatgt    60
a                                                                    61

<210> SEQ ID NO 1050
<211> LENGTH: 61
<212> TYPE: DNA
<213> ORGANISM: Homo Sapiens

<400> SEQUENCE: 1050
tgtgtttttt gaggaatcgt ttttttctac yttgccgaat atatgcatgt atagttgttt    60
g                                                                    61

<210> SEQ ID NO 1051
<211> LENGTH: 61
<212> TYPE: DNA
<213> ORGANISM: Homo Sapiens

<400> SEQUENCE: 1051
atttatatcc atctatctaa acctatctat ycaaaaactg tgtcaacaat gttgctcaat    60
t                                                                    61
```

<210> SEQ ID NO 1052
<211> LENGTH: 61
<212> TYPE: DNA
<213> ORGANISM: Homo Sapiens

<400> SEQUENCE: 1052
gtgtgtagtg tgaggcaaag ctgtgtctgc ygctaaagtt accctatgga gcattatcct    60
c                                                                    61

<210> SEQ ID NO 1053
<211> LENGTH: 61
<212> TYPE: DNA
<213> ORGANISM: Homo Sapiens

<400> SEQUENCE: 1053
accctatgga gcattatcct cagctgaaaa ratgtcagga ttctggaaaa ccaaaacaat    60
a                                                                    61

<210> SEQ ID NO 1054
<211> LENGTH: 61
<212> TYPE: DNA
<213> ORGANISM: Homo Sapiens

<400> SEQUENCE: 1054
tgtctttccc cactcaactt actgctcacg wagaaagatc agtgtcagct gttggcaaga    60
t                                                                    61

<210> SEQ ID NO 1055
<211> LENGTH: 61
<212> TYPE: DNA
<213> ORGANISM: Homo Sapiens

<400> SEQUENCE: 1055
aggaactatt caagatagcc tcgattcatg wcctgaatgt gtgtagataa atttataata    60
t                                                                    61

<210> SEQ ID NO 1056
<211> LENGTH: 61
<212> TYPE: DNA
<213> ORGANISM: Homo Sapiens

<400> SEQUENCE: 1056
taaaatagca agtaaatatt ttgactgtaa rgctaatagt tttgcatttt aattgcgttt    60
t                                                                    61

<210> SEQ ID NO 1057
<211> LENGTH: 61
<212> TYPE: DNA
<213> ORGANISM: Homo Sapiens

<400> SEQUENCE: 1057
aaatgaggat acaagacaaa gacgatacat wccgagcaaa taaggtgttg tatcatttta    60
t                                                                    61

<210> SEQ ID NO 1058
<211> LENGTH: 61
<212> TYPE: DNA
<213> ORGANISM: Homo Sapiens

<400> SEQUENCE: 1058

-continued

```
aatggaattc attctgaaaa tatacctgaa raagtctgtt tctaattatg gaattagtaa    60
a                                                                   61

<210> SEQ ID NO 1059
<211> LENGTH: 61
<212> TYPE: DNA
<213> ORGANISM: Homo Sapiens

<400> SEQUENCE: 1059
ctgctttagg cacagagtag agtatgcttt sgttgactaa actgagcaaa agcaagaaca    60
t                                                                   61

<210> SEQ ID NO 1060
<211> LENGTH: 61
<212> TYPE: DNA
<213> ORGANISM: Homo Sapiens

<400> SEQUENCE: 1060
aacatgtact gtgtaactgg aagttggctt sttttgatgg catttggata actataatta    60
c                                                                   61

<210> SEQ ID NO 1061
<211> LENGTH: 61
<212> TYPE: DNA
<213> ORGANISM: Homo Sapiens

<400> SEQUENCE: 1061
cagaaggcaa aactctctta gtcctttttt ygctgctata atagcaaacc acagactggt    60
t                                                                   61

<210> SEQ ID NO 1062
<211> LENGTH: 61
<212> TYPE: DNA
<213> ORGANISM: Homo Sapiens

<400> SEQUENCE: 1062
cagaatgaag tagggtatgc ctcacttact rgagtaaaaa cttatataca aaattgtaaa    60
a                                                                   61

<210> SEQ ID NO 1063
<211> LENGTH: 61
<212> TYPE: DNA
<213> ORGANISM: Homo Sapiens

<400> SEQUENCE: 1063
aggttgtatt tttatataag tctacacact wcactaaatt ctgaattcta ggcagagtac    60
c                                                                   61

<210> SEQ ID NO 1064
<211> LENGTH: 61
<212> TYPE: DNA
<213> ORGANISM: Homo Sapiens

<400> SEQUENCE: 1064
tgtcatacct aattcagaat atcgaagttt kcagacaaag aatttctatt ctattttaag    60
c                                                                   61

<210> SEQ ID NO 1065
<211> LENGTH: 61
```

```
<212> TYPE: DNA
<213> ORGANISM: Homo Sapiens

<400> SEQUENCE: 1065
taaaataaaa atggaaagta gtcaatggat rtggtttgat ttctgataat ttgaaataat    60
a                                                                    61

<210> SEQ ID NO 1066
<211> LENGTH: 61
<212> TYPE: DNA
<213> ORGANISM: Homo Sapiens

<400> SEQUENCE: 1066
ctactttcaa gaaggttctt gataatgcaa rttgtaatgg atttaacttg aaattcaaag    60
t                                                                    61

<210> SEQ ID NO 1067
<211> LENGTH: 61
<212> TYPE: DNA
<213> ORGANISM: Homo Sapiens

<400> SEQUENCE: 1067
ctgaagaaac atagatatga atgttaagcc yccattattt tctagtactc tctcagatat    60
a                                                                    61

<210> SEQ ID NO 1068
<211> LENGTH: 61
<212> TYPE: DNA
<213> ORGANISM: Homo Sapiens

<400> SEQUENCE: 1068
tggttaatat taactgtata cgatgtagtc yttatctgca ttgatttctg gtgaatcaag    60
a                                                                    61

<210> SEQ ID NO 1069
<211> LENGTH: 61
<212> TYPE: DNA
<213> ORGANISM: Homo Sapiens

<400> SEQUENCE: 1069
gaaagaagta actcaactag aatgggttag rttagaagta taaattagtt gacagagcat    60
t                                                                    61

<210> SEQ ID NO 1070
<211> LENGTH: 61
<212> TYPE: DNA
<213> ORGANISM: Homo Sapiens

<400> SEQUENCE: 1070
atgcctgaag agtaaaagag gtctattttc rtaactagaa gacgaaactg aaggttattt    60
t                                                                    61

<210> SEQ ID NO 1071
<211> LENGTH: 61
<212> TYPE: DNA
<213> ORGANISM: Homo Sapiens

<400> SEQUENCE: 1071
gcacaaggaa gatatgtata agaaggaaac rtagcaaagg caaaatattc tagttcactt    60
c                                                                    61
```

<210> SEQ ID NO 1072
<211> LENGTH: 61
<212> TYPE: DNA
<213> ORGANISM: Homo Sapiens

<400> SEQUENCE: 1072
ggaaccgata tgtgctttca gagttagctc rgtagggcaa tttcattttc tcttgatgtt    60
g                                                                    61

<210> SEQ ID NO 1073
<211> LENGTH: 61
<212> TYPE: DNA
<213> ORGANISM: Homo Sapiens

<400> SEQUENCE: 1073
agacataatt ggtttagtgg aaacatggtt rgtccgaatg ttaatcttcc ctcttaatat    60
g                                                                    61

<210> SEQ ID NO 1074
<211> LENGTH: 61
<212> TYPE: DNA
<213> ORGANISM: Homo Sapiens

<400> SEQUENCE: 1074
taggtttggt attccaaatg tagaaacgaa sgctcagaag agttacttgt cagaaagcaa    60
g                                                                    61

<210> SEQ ID NO 1075
<211> LENGTH: 61
<212> TYPE: DNA
<213> ORGANISM: Homo Sapiens

<400> SEQUENCE: 1075
aaatttaatt tccttttaga atttcagcaa rtaaacatta ctccatcaaa atttattttg    60
a                                                                    61

<210> SEQ ID NO 1076
<211> LENGTH: 61
<212> TYPE: DNA
<213> ORGANISM: Homo Sapiens

<400> SEQUENCE: 1076
tcctgaatat tggaagacca cagaaaatgc raagaaacca ggctcacatt tattttagtg    60
a                                                                    61

<210> SEQ ID NO 1077
<211> LENGTH: 61
<212> TYPE: DNA
<213> ORGANISM: Homo Sapiens

<400> SEQUENCE: 1077
tcaggaatga actggcttgt tactggttac ytgcacctgg tggaaaagta cactcaaggc    60
c                                                                    61

<210> SEQ ID NO 1078
<211> LENGTH: 61
<212> TYPE: DNA
<213> ORGANISM: Homo Sapiens

<400> SEQUENCE: 1078

```
cagtggagac ctgtaaccat tttcctgtaa yttggtacct gttagtctat cagctcagtg    60
a                                                                    61

<210> SEQ ID NO 1079
<211> LENGTH: 61
<212> TYPE: DNA
<213> ORGANISM: Homo Sapiens

<400> SEQUENCE: 1079
agtcacataa atttgtatgt accattcaat yctcaagaca acctgtaaat acaactatta    60
t                                                                    61

<210> SEQ ID NO 1080
<211> LENGTH: 61
<212> TYPE: DNA
<213> ORGANISM: Homo Sapiens

<400> SEQUENCE: 1080
atctatttat agaagttgtc acttaagctc ytaattttat caccaaattt caaatccaag    60
t                                                                    61

<210> SEQ ID NO 1081
<211> LENGTH: 61
<212> TYPE: DNA
<213> ORGANISM: Homo Sapiens

<400> SEQUENCE: 1081
agtaatgtct tacaaactgc atctgtttat stttaaattc caaatagaat gtcatccaaa    60
t                                                                    61

<210> SEQ ID NO 1082
<211> LENGTH: 61
<212> TYPE: DNA
<213> ORGANISM: Homo Sapiens

<400> SEQUENCE: 1082
gcaaaataaa ggtaagaaca atccacaaat kttcaactgt tcatatattt taaaagcttc    60
c                                                                    61

<210> SEQ ID NO 1083
<211> LENGTH: 61
<212> TYPE: DNA
<213> ORGANISM: Homo Sapiens

<400> SEQUENCE: 1083
ggtgtatctc ttgcattagc tgctgaggaa rcaagggagt actttgagac atgataatac    60
c                                                                    61

<210> SEQ ID NO 1084
<211> LENGTH: 61
<212> TYPE: DNA
<213> ORGANISM: Homo Sapiens

<400> SEQUENCE: 1084
ctcagcccac tgcaaaacat caggtctccc yctcttcatca gacttttatt tcattttgct   60
t                                                                    61

<210> SEQ ID NO 1085
<211> LENGTH: 61
```

```
<212> TYPE: DNA
<213> ORGANISM: Homo Sapiens

<400> SEQUENCE: 1085
cagacatgct aggtcttgaa gtaagaaaat yctagtgacc caaggaatcc tctggcattt    60
g                                                                     61

<210> SEQ ID NO 1086
<211> LENGTH: 61
<212> TYPE: DNA
<213> ORGANISM: Homo Sapiens

<400> SEQUENCE: 1086
ttttgaggac ttagtcataa attatttcct raggcccatg tctagaatgg tgtttctgag    60
g                                                                     61

<210> SEQ ID NO 1087
<211> LENGTH: 61
<212> TYPE: DNA
<213> ORGANISM: Homo Sapiens

<400> SEQUENCE: 1087
gttctggcag tttctgaact cttaatgata ytttgatgac atccagttag atgctgaata    60
c                                                                     61

<210> SEQ ID NO 1088
<211> LENGTH: 61
<212> TYPE: DNA
<213> ORGANISM: Homo Sapiens

<400> SEQUENCE: 1088
acatctgaga gactgtcatg aggggcctca ytcagagaaa attaccttaa agcaacatca    60
a                                                                     61

<210> SEQ ID NO 1089
<211> LENGTH: 61
<212> TYPE: DNA
<213> ORGANISM: Homo Sapiens

<400> SEQUENCE: 1089
aacaagaatg ctcagaaata gaatgctatg rcttttttttt tttcctttct gattaggatt    60
c                                                                     61

<210> SEQ ID NO 1090
<211> LENGTH: 61
<212> TYPE: DNA
<213> ORGANISM: Homo Sapiens

<400> SEQUENCE: 1090
atatatgagt ctatttttct gctttaatgg rtacaatagg gaacacataa gtgagtcatt    60
c                                                                     61

<210> SEQ ID NO 1091
<211> LENGTH: 61
<212> TYPE: DNA
<213> ORGANISM: Homo Sapiens

<400> SEQUENCE: 1091
tagttgagtt aaaatgggga tacatttag ktgatcaaga atatgaattt ttactactaa     60
t                                                                     61
```

<210> SEQ ID NO 1092
<211> LENGTH: 61
<212> TYPE: DNA
<213> ORGANISM: Homo Sapiens

<400> SEQUENCE: 1092
cagagaaaac tcagctctct ataaattttc sccttaaggc ctcagcaacc ttccattcac    60
c                                                                   61

<210> SEQ ID NO 1093
<211> LENGTH: 61
<212> TYPE: DNA
<213> ORGANISM: Homo Sapiens

<400> SEQUENCE: 1093
aatgatttgt tcactgtgt cttgccactc stttgataag cagtctctct caagaattgg    60
g                                                                   61

<210> SEQ ID NO 1094
<211> LENGTH: 61
<212> TYPE: DNA
<213> ORGANISM: Homo Sapiens

<400> SEQUENCE: 1094
tccatcttcg catgcctcta ttacgcctat stgaatgtgt tacaaatagt aggtaaccag    60
a                                                                   61

<210> SEQ ID NO 1095
<211> LENGTH: 61
<212> TYPE: DNA
<213> ORGANISM: Homo Sapiens

<400> SEQUENCE: 1095
cctaaaatca gactcaccgt tatctctatg ygcagaagct gtgcagttct caccaagtta    60
a                                                                   61

<210> SEQ ID NO 1096
<211> LENGTH: 61
<212> TYPE: DNA
<213> ORGANISM: Homo Sapiens

<400> SEQUENCE: 1096
aataccagtt ggactgagag cctttcaat ygtaggtaag agacagtcac agagactccc    60
a                                                                   61

<210> SEQ ID NO 1097
<211> LENGTH: 61
<212> TYPE: DNA
<213> ORGANISM: Homo Sapiens

<400> SEQUENCE: 1097
actaataaca actgtaattt caaagtatga ygaatgaatg tcatcagcat tttggaacat    60
c                                                                   61

<210> SEQ ID NO 1098
<211> LENGTH: 61
<212> TYPE: DNA
<213> ORGANISM: Homo Sapiens

<400> SEQUENCE: 1098

```
caatactctg cagactcgaa aaaacatyac rtacattctt ggaacttccc agtggtttaa    60
t                                                                  61
```

<210> SEQ ID NO 1099
<211> LENGTH: 61
<212> TYPE: DNA
<213> ORGANISM: Homo Sapiens

<400> SEQUENCE: 1099

```
gtcgattggt acatttgtgc aaagacagat wtgacttcca acaagacag acattcatta   60 t                                                                  61
```

<210> SEQ ID NO 1100
<211> LENGTH: 61
<212> TYPE: DNA
<213> ORGANISM: Homo Sapiens

<400> SEQUENCE: 1100

```
aagagcaggg atttccatga cctggggtct rtggatcagc ttctaaatac ccaaacctct   60
g                                                                  61
```

<210> SEQ ID NO 1101
<211> LENGTH: 61
<212> TYPE: DNA
<213> ORGANISM: Homo Sapiens

<400> SEQUENCE: 1101

```
gagcagggtg ggtgtgccct cctaagctct sgaatagcaa atgccaaact cacatgtctg   60
t                                                                  61
```

<210> SEQ ID NO 1102
<211> LENGTH: 61
<212> TYPE: DNA
<213> ORGANISM: Homo Sapiens

<400> SEQUENCE: 1102

```
cagaaatata ggtggtctgg aaagcaacct ygggagtttg tagttatgtc actactggca   60
g                                                                  61
```

<210> SEQ ID NO 1103
<211> LENGTH: 61
<212> TYPE: DNA
<213> ORGANISM: Homo Sapiens

<400> SEQUENCE: 1103

```
cagagtgata ctccatttag tctgtgaaaa wgtaatcaaa aggtcactca cctaagtggt   60
a                                                                  61
```

<210> SEQ ID NO 1104
<211> LENGTH: 61
<212> TYPE: DNA
<213> ORGANISM: Homo Sapiens

<400> SEQUENCE: 1104

```
ggagagtaga gtatggttta aactacagaa ygaagtgtac agattttaga ttctggcatg   60
t                                                                  61
```

<210> SEQ ID NO 1105
<211> LENGTH: 61

```
<212> TYPE: DNA
<213> ORGANISM: Homo Sapiens

<400> SEQUENCE: 1105
tagacatcca ataagatgct tactgagtaa yagaccccat tccataaggt tcaagtgaat      60
t                                                                     61

<210> SEQ ID NO 1106
<211> LENGTH: 61
<212> TYPE: DNA
<213> ORGANISM: Homo Sapiens

<400> SEQUENCE: 1106
aacaccaggt taccatccca gtttgtctta yaagattaac acaaaagaga accctatata      60
c                                                                     61

<210> SEQ ID NO 1107
<211> LENGTH: 61
<212> TYPE: DNA
<213> ORGANISM: Homo Sapiens

<400> SEQUENCE: 1107
ttcatgtcca agtgtattca gggtttagct ycaaattgta agtaagaaca tgcaatattt      60
c                                                                     61

<210> SEQ ID NO 1108
<211> LENGTH: 61
<212> TYPE: DNA
<213> ORGANISM: Homo Sapiens

<400> SEQUENCE: 1108
ttatttttca aaaatagag tgaaaaccaa yagtgaccta aatacagtgt gaatgcaaaa       60
a                                                                     61

<210> SEQ ID NO 1109
<211> LENGTH: 61
<212> TYPE: DNA
<213> ORGANISM: Homo Sapiens

<400> SEQUENCE: 1109
ataatgaatg cagtctcgcc attcaaatgc raccataagt acacagaaga taagaattta      60
a                                                                     61

<210> SEQ ID NO 1110
<211> LENGTH: 61
<212> TYPE: DNA
<213> ORGANISM: Homo Sapiens

<400> SEQUENCE: 1110
agagctttac caatgtgcct ggagcataat kaaagaggaa aaatcacatg tagggggcaag     60
t                                                                     61

<210> SEQ ID NO 1111
<211> LENGTH: 61
<212> TYPE: DNA
<213> ORGANISM: Homo Sapiens

<400> SEQUENCE: 1111
gacacgctgc agggaaggtc ccacattctg racctactgg aggttatagt cttacttctg      60
t                                                                     61
```

<210> SEQ ID NO 1112
<211> LENGTH: 61
<212> TYPE: DNA
<213> ORGANISM: Homo Sapiens

<400> SEQUENCE: 1112
tattcgctta agaatacca gttaccatcc rtatgctttc ggtactaaat ctccatttat    60
c                                                                  61

<210> SEQ ID NO 1113
<211> LENGTH: 61
<212> TYPE: DNA
<213> ORGANISM: Homo Sapiens

<400> SEQUENCE: 1113
aagaatattt catttgtacg gtggtcagta ytctctagtt taatgattta catttgaaag    60
t                                                                  61

<210> SEQ ID NO 1114
<211> LENGTH: 61
<212> TYPE: DNA
<213> ORGANISM: Homo Sapiens

<400> SEQUENCE: 1114
aaaaataatt tgtttttacg aacaatgaac yctctggctt attacacata ctttaaatac    60
t                                                                  61

<210> SEQ ID NO 1115
<211> LENGTH: 61
<212> TYPE: DNA
<213> ORGANISM: Homo Sapiens

<400> SEQUENCE: 1115
gtatcaggca ggagagttgc aaagcctctg yggatcaagt cttcagcttc agcaaaagcc    60
c                                                                  61

<210> SEQ ID NO 1116
<211> LENGTH: 61
<212> TYPE: DNA
<213> ORGANISM: Homo Sapiens

<400> SEQUENCE: 1116
aggtgagtgc tgtgataaag aactaaaagc yattgcctgg tacttaggaa gcacactaat    60
g                                                                  61

<210> SEQ ID NO 1117
<211> LENGTH: 61
<212> TYPE: DNA
<213> ORGANISM: Homo Sapiens

<400> SEQUENCE: 1117
aaaaggtaca aggtgatgtt tacacacaca ytgaggagag ggttttatta caaagtttac    60
a                                                                  61

<210> SEQ ID NO 1118
<211> LENGTH: 61
<212> TYPE: DNA
<213> ORGANISM: Homo Sapiens

<400> SEQUENCE: 1118

```
ccaaatagct tgttggcaag tacaagtata rtctagcatt tttataactg ggtactaaaa    60
a                                                                    61

<210> SEQ ID NO 1119
<211> LENGTH: 61
<212> TYPE: DNA
<213> ORGANISM: Homo Sapiens

<400> SEQUENCE: 1119
caactaccaa cttactgtga taagtcttac matagagcct tatcctagga actagagatg    60
a                                                                    61

<210> SEQ ID NO 1120
<211> LENGTH: 61
<212> TYPE: DNA
<213> ORGANISM: Homo Sapiens

<400> SEQUENCE: 1120
tttaaatagt gcctcccaca tataatgttt mccgaaagtg tatcttaata tctcctgaat    60
a                                                                    61

<210> SEQ ID NO 1121
<211> LENGTH: 61
<212> TYPE: DNA
<213> ORGANISM: Homo Sapiens

<400> SEQUENCE: 1121
aggtggtgat gggccaggtt tctgagatat rtttccaaga ggcttggcat gcatttgcac    60
t                                                                    61

<210> SEQ ID NO 1122
<211> LENGTH: 61
<212> TYPE: DNA
<213> ORGANISM: Homo Sapiens

<400> SEQUENCE: 1122
tactctctcc tggggtagtt tcaagtccca ytggctttaa atattgtcaa taaatcaaat    60
g                                                                    61

<210> SEQ ID NO 1123
<211> LENGTH: 61
<212> TYPE: DNA
<213> ORGANISM: Homo Sapiens

<400> SEQUENCE: 1123
aggtaccctc tttaccaatt gacagagatg raaacctgga ctccctactt ggccttctat    60
g                                                                    61

<210> SEQ ID NO 1124
<211> LENGTH: 61
<212> TYPE: DNA
<213> ORGANISM: Homo Sapiens

<400> SEQUENCE: 1124
gtatggatta atgaacatgt cttatgctta kgaagtggaa ctcattattc ttgattaaag    60
a                                                                    61

<210> SEQ ID NO 1125
<211> LENGTH: 61
```

```
<212> TYPE: DNA
<213> ORGANISM: Homo Sapiens

<400> SEQUENCE: 1125
catctttccc cctttccagg tcacccaaag stcagctctt aaagatacac tgttcctcaa    60
c                                                                   61

<210> SEQ ID NO 1126
<211> LENGTH: 61
<212> TYPE: DNA
<213> ORGANISM: Homo Sapiens

<400> SEQUENCE: 1126
tctatactaa atcctgattc tgtcccttgt ytgaactcac agtgtaccca tgtaattcta    60
c                                                                   61

<210> SEQ ID NO 1127
<211> LENGTH: 61
<212> TYPE: DNA
<213> ORGANISM: Homo Sapiens

<400> SEQUENCE: 1127
ctttctgttg ccctccaatt ctactactct mcgctgactc tgtcatttat atcctgattg    60
g                                                                   61

<210> SEQ ID NO 1128
<211> LENGTH: 61
<212> TYPE: DNA
<213> ORGANISM: Homo Sapiens

<400> SEQUENCE: 1128
ttggcctgat tttgttttg tctgtaaact yctgaagggt agaatttata ctcttttcat     60
c                                                                   61

<210> SEQ ID NO 1129
<211> LENGTH: 61
<212> TYPE: DNA
<213> ORGANISM: Homo Sapiens

<400> SEQUENCE: 1129
ctgaaagatg ctcctcttcc tcagaaaaag waaccctcgg acacaccagg tgtgggtcag    60
g                                                                   61

<210> SEQ ID NO 1130
<211> LENGTH: 61
<212> TYPE: DNA
<213> ORGANISM: Homo Sapiens

<400> SEQUENCE: 1130
atccaaaagt atcacatttt ctaaaaatac raacaaagct ttaatataat agataattac    60
t                                                                   61

<210> SEQ ID NO 1131
<211> LENGTH: 61
<212> TYPE: DNA
<213> ORGANISM: Homo Sapiens

<400> SEQUENCE: 1131
tcattggtca gtgatgggac aaaggctcgg yggttttga gctcccctgg tgattctaat     60
g                                                                   61
```

<210> SEQ ID NO 1132
<211> LENGTH: 61
<212> TYPE: DNA
<213> ORGANISM: Homo Sapiens

<400> SEQUENCE: 1132
ttcaccttgg ttctctgaca cccatggaaa rtttaggtta gggagagaga gtggaaagag    60
a                                                                   61

<210> SEQ ID NO 1133
<211> LENGTH: 61
<212> TYPE: DNA
<213> ORGANISM: Homo Sapiens

<400> SEQUENCE: 1133
cactatcacg agaacaaaat aagggtaaac rcctccatga ttaaattacc tcccactggg    60
t                                                                   61

<210> SEQ ID NO 1134
<211> LENGTH: 61
<212> TYPE: DNA
<213> ORGANISM: Homo Sapiens

<400> SEQUENCE: 1134
gaaactgcac ttaatttgct tgatggcata ratgtttcag tgcctagatg gtgtcagtca    60
c                                                                   61

<210> SEQ ID NO 1135
<211> LENGTH: 61
<212> TYPE: DNA
<213> ORGANISM: Homo Sapiens

<400> SEQUENCE: 1135
aggacattgc tgtaattttg tccccctcat rtccagcgag ttgtctgagg ctctccgtgt    60
t                                                                   61

<210> SEQ ID NO 1136
<211> LENGTH: 61
<212> TYPE: DNA
<213> ORGANISM: Homo Sapiens

<400> SEQUENCE: 1136
tccctaaaga actatccaat tttctgcctg ygctagtctt tgtgatgttt atgatgattt    60
a                                                                   61

<210> SEQ ID NO 1137
<211> LENGTH: 61
<212> TYPE: DNA
<213> ORGANISM: Homo Sapiens

<400> SEQUENCE: 1137
gccaagttgg gaccacgggc cgggctagaa ygatccatgg aaaagttctg tgctcagggg    60
a                                                                   61

<210> SEQ ID NO 1138
<211> LENGTH: 61
<212> TYPE: DNA
<213> ORGANISM: Homo Sapiens

<400> SEQUENCE: 1138

```
actcacctaa ggtcacagaa agaatggtac mgaggcaggg ttgagccaca ctgcctaatt    60
c                                                                  61
```

<210> SEQ ID NO 1139
<211> LENGTH: 61
<212> TYPE: DNA
<213> ORGANISM: Homo Sapiens

<400> SEQUENCE: 1139

```
aacagacatg gctgtcagca gttttggaga ygcaggtaat tagtcctgct ccagctcctg    60
c                                                                  61
```

<210> SEQ ID NO 1140
<211> LENGTH: 61
<212> TYPE: DNA
<213> ORGANISM: Homo Sapiens

<400> SEQUENCE: 1140

```
taaatagagg ctatgctttc ctctttgtat rtcccaaaac gccttcctca gcacaatagc    60
t                                                                  61
```

<210> SEQ ID NO 1141
<211> LENGTH: 61
<212> TYPE: DNA
<213> ORGANISM: Homo Sapiens

<400> SEQUENCE: 1141

```
ctcctggaca aggcagatgt ggtagtcttt rgatttagct atagtagttg tgactgaggt    60
c                                                                  61
```

<210> SEQ ID NO 1142
<211> LENGTH: 61
<212> TYPE: DNA
<213> ORGANISM: Homo Sapiens

<400> SEQUENCE: 1142

```
gcaaataaat atttcaagca ttcctataca rtttaaccac atcaatcaac tatagaataa    60
a                                                                  61
```

<210> SEQ ID NO 1143
<211> LENGTH: 61
<212> TYPE: DNA
<213> ORGANISM: Homo Sapiens

<400> SEQUENCE: 1143

```
cctgtgtgta gaaggcatag gtcattacac rctcctgatg ttgcctgcaa aggctatatt    60
t                                                                  61
```

<210> SEQ ID NO 1144
<211> LENGTH: 61
<212> TYPE: DNA
<213> ORGANISM: Homo Sapiens

<400> SEQUENCE: 1144

```
tgatggacta gttagaattt caccccgggt rtataagcct gaacccattg gtccatttct    60
a                                                                  61
```

<210> SEQ ID NO 1145
<211> LENGTH: 61

```
<212> TYPE: DNA
<213> ORGANISM: Homo Sapiens

<400> SEQUENCE: 1145
ttcctctctc caacatagtg ccagactctc rtattaggaa atgatgaaac catcaaccaa    60
a                                                                   61

<210> SEQ ID NO 1146
<211> LENGTH: 61
<212> TYPE: DNA
<213> ORGANISM: Homo Sapiens

<400> SEQUENCE: 1146
taaattgagt cactttcttg tcaaagagga sagtggttct tcagctctgg ggtcaatttt    60
a                                                                   61

<210> SEQ ID NO 1147
<211> LENGTH: 61
<212> TYPE: DNA
<213> ORGANISM: Homo Sapiens

<400> SEQUENCE: 1147
gttgtcatga caattaaatg acatcatgtg ygtgcaacca aaatagcatt tggctcatcc    60
t                                                                   61

<210> SEQ ID NO 1148
<211> LENGTH: 61
<212> TYPE: DNA
<213> ORGANISM: Homo Sapiens

<400> SEQUENCE: 1148
tcatcagaac tgccgcatcc tctctggccc rctttctgtc tggcatttgc ctgacatatt    60
c                                                                   61

<210> SEQ ID NO 1149
<211> LENGTH: 61
<212> TYPE: DNA
<213> ORGANISM: Homo Sapiens

<400> SEQUENCE: 1149
ctgccaagac ggaggagagg aggcagtgtc rttttttattt gtcacggtac tttctgtgca    60
c                                                                   61

<210> SEQ ID NO 1150
<211> LENGTH: 61
<212> TYPE: DNA
<213> ORGANISM: Homo Sapiens

<400> SEQUENCE: 1150
tgggtcatgg tcagaaaatg ttaaaagtca ytggatgaga gtatttctga ggtccctgag    60
a                                                                   61

<210> SEQ ID NO 1151
<211> LENGTH: 61
<212> TYPE: DNA
<213> ORGANISM: Homo Sapiens

<400> SEQUENCE: 1151
gaggaacaga tagagaggga caatacagcc yggtacagga gatgaagggc cccggggcca    60
t                                                                   61
```

<210> SEQ ID NO 1152
<211> LENGTH: 61
<212> TYPE: DNA
<213> ORGANISM: Homo Sapiens

<400> SEQUENCE: 1152
agctaaaaaa aaataaaagc ttagacacat rattttgagt aaagaaaaca aaaaagcca    60
g                                                                  61

<210> SEQ ID NO 1153
<211> LENGTH: 61
<212> TYPE: DNA
<213> ORGANISM: Homo Sapiens

<400> SEQUENCE: 1153
gactattcat atgtctatgt cttcagtgtt mtgtgagaga aaataaactt tatataattt    60
g                                                                  61

<210> SEQ ID NO 1154
<211> LENGTH: 61
<212> TYPE: DNA
<213> ORGANISM: Homo Sapiens

<400> SEQUENCE: 1154
gggaccaact gaacataacc tgcttaaaag wtccacctaa attattggaa tccttttata    60
t                                                                  61

<210> SEQ ID NO 1155
<211> LENGTH: 61
<212> TYPE: DNA
<213> ORGANISM: Homo Sapiens

<400> SEQUENCE: 1155
atgaggcaca catcctttg tgaactatag yccatgatac tacaatgaac aaagtacttg     60
g                                                                  61

<210> SEQ ID NO 1156
<211> LENGTH: 61
<212> TYPE: DNA
<213> ORGANISM: Homo Sapiens

<400> SEQUENCE: 1156
actaatctat ataaaaatgc agcattctga wccgcatgaa accatttaca aaattattga    60
a                                                                  61

<210> SEQ ID NO 1157
<211> LENGTH: 61
<212> TYPE: DNA
<213> ORGANISM: Homo Sapiens

<400> SEQUENCE: 1157
ttgttctgtc aagctcattt ctagggctca rttgccagtc atttatggcc agcgaaataa    60
a                                                                  61

<210> SEQ ID NO 1158
<211> LENGTH: 61
<212> TYPE: DNA
<213> ORGANISM: Homo Sapiens

<400> SEQUENCE: 1158

```
cctacccaag tgccatgggg ctcagtctct wcggagggac attttctttg tttttggttt    60
t                                                                    61
```

<210> SEQ ID NO 1159
<211> LENGTH: 61
<212> TYPE: DNA
<213> ORGANISM: Homo Sapiens

<400> SEQUENCE: 1159

```
atggaagtca atttctgagc ctctaagact sgcaagttgg gtataaacaa aggaatggct    60
g                                                                    61
```

<210> SEQ ID NO 1160
<211> LENGTH: 61
<212> TYPE: DNA
<213> ORGANISM: Homo Sapiens

<400> SEQUENCE: 1160

```
gtgtcctggt ttagacagta aatggttatt stgcttaatg caagccaagt taaagaacta    60
t                                                                    61
```

<210> SEQ ID NO 1161
<211> LENGTH: 61
<212> TYPE: DNA
<213> ORGANISM: Homo Sapiens

<400> SEQUENCE: 1161

```
accaaaccac agtcaatatc aatggcagaa yagcaggcat taactggaac tgacccaggc    60
a                                                                    61
```

<210> SEQ ID NO 1162
<211> LENGTH: 61
<212> TYPE: DNA
<213> ORGANISM: Homo Sapiens

<400> SEQUENCE: 1162

```
ctttggttat ccaatcaatc actttcattt sttggctttt gggcaaactt ttttaaaaaa    60
t                                                                    61
```

<210> SEQ ID NO 1163
<211> LENGTH: 61
<212> TYPE: DNA
<213> ORGANISM: Homo Sapiens

<400> SEQUENCE: 1163

```
atggtaaagg ctctggcttt gactctgaga yaagtcaaca aattgagaaa agactaaagc    60
a                                                                    61
```

<210> SEQ ID NO 1164
<211> LENGTH: 61
<212> TYPE: DNA
<213> ORGANISM: Homo Sapiens

<400> SEQUENCE: 1164

```
gcaagatagg atgtgggctg cagaaacaat yggggagaca tgagcctggt taaatattca    60
g                                                                    61
```

<210> SEQ ID NO 1165
<211> LENGTH: 61

```
<212> TYPE: DNA
<213> ORGANISM: Homo Sapiens

<400> SEQUENCE: 1165
aggcaacctg catgtatgaa agaactcaga yacaatggcc agtttcacaa aaggaaacaa    60
g                                                                   61

<210> SEQ ID NO 1166
<211> LENGTH: 61
<212> TYPE: DNA
<213> ORGANISM: Homo Sapiens

<400> SEQUENCE: 1166
aaaaactgtc tttcccaact gcatactaga rtattataga tttggaatat tttcttcttt    60
g                                                                   61

<210> SEQ ID NO 1167
<211> LENGTH: 61
<212> TYPE: DNA
<213> ORGANISM: Homo Sapiens

<400> SEQUENCE: 1167
tacccagaag aaatgccaag gttggaagta csagctatat agggtgtgtc aaaagagtcc    60
a                                                                   61

<210> SEQ ID NO 1168
<211> LENGTH: 61
<212> TYPE: DNA
<213> ORGANISM: Homo Sapiens

<400> SEQUENCE: 1168
tcagcctttc tcttacagct aaaagtgatc rtggcacgac acaggggcaa tgagctctaa    60
c                                                                   61

<210> SEQ ID NO 1169
<211> LENGTH: 61
<212> TYPE: DNA
<213> ORGANISM: Homo Sapiens

<400> SEQUENCE: 1169
tctcttagct caggcgtgaa gaaattcaga scacaggtag attaattaac tccaggaagg    60
a                                                                   61

<210> SEQ ID NO 1170
<211> LENGTH: 61
<212> TYPE: DNA
<213> ORGANISM: Homo Sapiens

<400> SEQUENCE: 1170
agagaaaaac accaggtagc cccctccagg yctcctgatg ctcagacctt gctcaagaag    60
g                                                                   61

<210> SEQ ID NO 1171
<211> LENGTH: 61
<212> TYPE: DNA
<213> ORGANISM: Homo Sapiens

<400> SEQUENCE: 1171
ctgaacaatc ccacgaagta gcatatttca yaatgaggac acagaagctc agaaaggctg    60
g                                                                   61
```

<210> SEQ ID NO 1172
<211> LENGTH: 61
<212> TYPE: DNA
<213> ORGANISM: Homo Sapiens

<400> SEQUENCE: 1172
agatgccaca agcaagactt caacccccta ygtggcaagt ccctgcccgt ctctcctctc    60
t                                                                    61

<210> SEQ ID NO 1173
<211> LENGTH: 61
<212> TYPE: DNA
<213> ORGANISM: Homo Sapiens

<400> SEQUENCE: 1173
aaaatgtctg cttctgcact tcccaaggac scttctaagc atcactcata attcaatatg    60
a                                                                    61

<210> SEQ ID NO 1174
<211> LENGTH: 61
<212> TYPE: DNA
<213> ORGANISM: Homo Sapiens

<400> SEQUENCE: 1174
atttgtgaat ggctcttgca aaccttaaca ygcaaagcta atgacagatt gtatcagagg    60
c                                                                    61

<210> SEQ ID NO 1175
<211> LENGTH: 61
<212> TYPE: DNA
<213> ORGANISM: Homo Sapiens

<400> SEQUENCE: 1175
tcctcagtcc tagaaatgcc acgtgaactt ygaacatgga aagttttta tttttgagag    60
a                                                                    61

<210> SEQ ID NO 1176
<211> LENGTH: 61
<212> TYPE: DNA
<213> ORGANISM: Homo Sapiens

<400> SEQUENCE: 1176
cagtttaaac aaaaactgcc caatgtctcc macaggcaat tgtgtagcaa caacagtcac    60
a                                                                    61

<210> SEQ ID NO 1177
<211> LENGTH: 61
<212> TYPE: DNA
<213> ORGANISM: Homo Sapiens

<400> SEQUENCE: 1177
gtagtgtggt attaaaatct aggacttcgg ratgcaatag cagtgctcag tttatttgtt    60
t                                                                    61

<210> SEQ ID NO 1178
<211> LENGTH: 61
<212> TYPE: DNA
<213> ORGANISM: Homo Sapiens

<400> SEQUENCE: 1178

-continued

```
acatattttg atccgattct agagctagca stcgctgtgt tgaaagtgat ggcggtgatg    60
t                                                                    61

<210> SEQ ID NO 1179
<211> LENGTH: 61
<212> TYPE: DNA
<213> ORGANISM: Homo Sapiens

<400> SEQUENCE: 1179
gtttatacaa tatcctctga aagcaactta saaggacaga aagcctgaaa caacaccatg    60
a                                                                    61

<210> SEQ ID NO 1180
<211> LENGTH: 61
<212> TYPE: DNA
<213> ORGANISM: Homo Sapiens

<400> SEQUENCE: 1180
aaaagcatat gaataccatt tatgataaac macaaagtct ctggatgggt aaatgcctca    60
t                                                                    61

<210> SEQ ID NO 1181
<211> LENGTH: 61
<212> TYPE: DNA
<213> ORGANISM: Homo Sapiens

<400> SEQUENCE: 1181
ggatgcctcc caataaagga actttcctca sagatcttgt agagttggtg aagagaatcg    60
a                                                                    61

<210> SEQ ID NO 1182
<211> LENGTH: 61
<212> TYPE: DNA
<213> ORGANISM: Homo Sapiens

<400> SEQUENCE: 1182
aagaattaga taatctatga aagatgtgac wagcctcatc gtgctcacta accatccatc    60
t                                                                    61

<210> SEQ ID NO 1183
<211> LENGTH: 61
<212> TYPE: DNA
<213> ORGANISM: Homo Sapiens

<400> SEQUENCE: 1183
gggtatataa ttactgctca gtgaaagtga ytatgcatac ctgtatcatc taaaggaatt    60
t                                                                    61

<210> SEQ ID NO 1184
<211> LENGTH: 61
<212> TYPE: DNA
<213> ORGANISM: Homo Sapiens

<400> SEQUENCE: 1184
gaagatgaga tattagaatt cccagtatag ktgtgtgtat attcatatgt ttgtatgtat    60
a                                                                    61

<210> SEQ ID NO 1185
<211> LENGTH: 61
```

```
<212> TYPE: DNA
<213> ORGANISM: Homo Sapiens

<400> SEQUENCE: 1185
aataaaagaa gaaaaaaaaa gatggcttag rttttaccca aagataaacc actttaggag    60
g                                                                   61

<210> SEQ ID NO 1186
<211> LENGTH: 61
<212> TYPE: DNA
<213> ORGANISM: Homo Sapiens

<400> SEQUENCE: 1186
gcagaagatc accttagaga aaatccgaac ygactctcct atcttagaag tcatccaggc    60
t                                                                   61

<210> SEQ ID NO 1187
<211> LENGTH: 61
<212> TYPE: DNA
<213> ORGANISM: Homo Sapiens

<400> SEQUENCE: 1187
aggccatgtt ccagcctctc catgccacca yttggttccc tttctgccca cctcctgtgg    60
g                                                                   61

<210> SEQ ID NO 1188
<211> LENGTH: 61
<212> TYPE: DNA
<213> ORGANISM: Homo Sapiens

<400> SEQUENCE: 1188
gtgacctgcc agaacatgtg ctaagtattt yccgtgcatt tcctcagtta attctaacaa    60
c                                                                   61

<210> SEQ ID NO 1189
<211> LENGTH: 61
<212> TYPE: DNA
<213> ORGANISM: Homo Sapiens

<400> SEQUENCE: 1189
aagaaggcct gaacctgcac acagcctgcc rctggggtat actagacaca gaggaggacc    60
g                                                                   61

<210> SEQ ID NO 1190
<211> LENGTH: 61
<212> TYPE: DNA
<213> ORGANISM: Homo Sapiens

<400> SEQUENCE: 1190
gggccctctg caaaattctc aagtgaggcc yaacaaatca caggccctgc atgtacacaa    60
a                                                                   61

<210> SEQ ID NO 1191
<211> LENGTH: 61
<212> TYPE: DNA
<213> ORGANISM: Homo Sapiens

<400> SEQUENCE: 1191
aaaaccagag aactaagccc cactccaggc kgaagaagtg cagccccagc ttactatcag    60
a                                                                   61
```

<210> SEQ ID NO 1192
<211> LENGTH: 61
<212> TYPE: DNA
<213> ORGANISM: Homo Sapiens

<400> SEQUENCE: 1192
ccatacctga acaaagcct tgcgctttaa rtaacagggg agcttccctc tcctctagga    60
g                                                                  61

<210> SEQ ID NO 1193
<211> LENGTH: 61
<212> TYPE: DNA
<213> ORGANISM: Homo Sapiens

<400> SEQUENCE: 1193
ttcttgatca ccatcacaga aaaactttct ytgaccatgt ctgtatcaaa tattgcatca    60
t                                                                  61

<210> SEQ ID NO 1194
<211> LENGTH: 61
<212> TYPE: DNA
<213> ORGANISM: Homo Sapiens

<400> SEQUENCE: 1194
atgaagtcaa agcccctcct cctcttgtcc rtagatagag tagaccaact cacagaactt    60
c                                                                  61

<210> SEQ ID NO 1195
<211> LENGTH: 61
<212> TYPE: DNA
<213> ORGANISM: Homo Sapiens

<400> SEQUENCE: 1195
ggcaggtcat gagtgattcc tgaatgataa ragattccat aggatttcag agaagagtca    60
c                                                                  61

<210> SEQ ID NO 1196
<211> LENGTH: 61
<212> TYPE: DNA
<213> ORGANISM: Homo Sapiens

<400> SEQUENCE: 1196
tgtctgtttt ctggcaatgg ccatcctagt rgacataaag tgatagctca atgtggtttt    60
g                                                                  61

<210> SEQ ID NO 1197
<211> LENGTH: 61
<212> TYPE: DNA
<213> ORGANISM: Homo Sapiens

<400> SEQUENCE: 1197
aaagagtgta gccttgggga cgtggaagcc yagagcattt ggaagacgca aacaagggag    60
a                                                                  61

<210> SEQ ID NO 1198
<211> LENGTH: 61
<212> TYPE: DNA
<213> ORGANISM: Homo Sapiens

<400> SEQUENCE: 1198

```
taaaaaactc tctatcgtat acatctttac mcacgctgca gcgccaagac tccaatggaa    60
t                                                                   61
```

<210> SEQ ID NO 1199
<211> LENGTH: 61
<212> TYPE: DNA
<213> ORGANISM: Homo Sapiens

<400> SEQUENCE: 1199

```
ttaaggtaga ttaagccatc gattgtatca wagagaaagt gtgaaaaact acttttagaa    60
a                                                                   61
```

<210> SEQ ID NO 1200
<211> LENGTH: 61
<212> TYPE: DNA
<213> ORGANISM: Homo Sapiens

<400> SEQUENCE: 1200

```
tgtctccaag aaattccaac gaacatgcac yctttagctg ctcttcctcc aacacacccc    60
a                                                                   61
```

<210> SEQ ID NO 1201
<211> LENGTH: 61
<212> TYPE: DNA
<213> ORGANISM: Homo Sapiens

<400> SEQUENCE: 1201

```
gagatggctc caaatgaga ttctacaact kagccactta caaaaagcta tcctgttgat     60
a                                                                   61
```

<210> SEQ ID NO 1202
<211> LENGTH: 61
<212> TYPE: DNA
<213> ORGANISM: Homo Sapiens

<400> SEQUENCE: 1202

```
caaaataagt atgctctatt tgttccttca matctctcca ggcctccagg cttaggaaag    60
c                                                                   61
```

<210> SEQ ID NO 1203
<211> LENGTH: 61
<212> TYPE: DNA
<213> ORGANISM: Homo Sapiens

<400> SEQUENCE: 1203

```
acaagcaact atcagcatat gcaagctatt rtttgttttg caccctattt gagaaacttt    60
c                                                                   61
```

<210> SEQ ID NO 1204
<211> LENGTH: 61
<212> TYPE: DNA
<213> ORGANISM: Homo Sapiens

<400> SEQUENCE: 1204

```
ggaagtcgct ggggagcccc aatgttagat mttattttca catcatcctt tctcctctcc    60
a                                                                   61
```

<210> SEQ ID NO 1205
<211> LENGTH: 61

```
<212> TYPE: DNA
<213> ORGANISM: Homo Sapiens

<400> SEQUENCE: 1205
tgtttctaga tgctgtatct agaactttt ygggttgact ctgttttgca caccataact    60
a                                                                   61

<210> SEQ ID NO 1206
<211> LENGTH: 61
<212> TYPE: DNA
<213> ORGANISM: Homo Sapiens

<400> SEQUENCE: 1206
ccctggaaat gagtaaatct gaaccacagg mcatgacaat cattcaaggt gctgtgctgg    60
a                                                                   61

<210> SEQ ID NO 1207
<211> LENGTH: 61
<212> TYPE: DNA
<213> ORGANISM: Homo Sapiens

<400> SEQUENCE: 1207
gcatgaagat agtggactgt gacacttgtt ragcagggaa gaattggtct gaagaatgct    60
t                                                                   61

<210> SEQ ID NO 1208
<211> LENGTH: 61
<212> TYPE: DNA
<213> ORGANISM: Homo Sapiens

<400> SEQUENCE: 1208
tgtctgactt gggcattaat gagatgaaga ygagactgta ggtcagatga tgactgtttt    60
t                                                                   61

<210> SEQ ID NO 1209
<211> LENGTH: 61
<212> TYPE: DNA
<213> ORGANISM: Homo Sapiens

<400> SEQUENCE: 1209
ctgcagtatt ttggccttc aggaaaagat stgctcaaag accaattgaa cattcttttc     60
t                                                                   61

<210> SEQ ID NO 1210
<211> LENGTH: 61
<212> TYPE: DNA
<213> ORGANISM: Homo Sapiens

<400> SEQUENCE: 1210
agaagaaatt cagcaaaatg tatcagaagc stttaacatc tcctgttaaa gaaagagcag    60
a                                                                   61

<210> SEQ ID NO 1211
<211> LENGTH: 61
<212> TYPE: DNA
<213> ORGANISM: Homo Sapiens

<400> SEQUENCE: 1211
tccgtagcaa ggctatagga acattgcatc raaaagtaca gcttctgggg ggtctctgtt    60
g                                                                   61
```

-continued

<210> SEQ ID NO 1212
<211> LENGTH: 61
<212> TYPE: DNA
<213> ORGANISM: Homo Sapiens

<400> SEQUENCE: 1212 agaattttt ccaatcttat tttctcctga rtaaaaggtt cctccaaatg agcccaacaa    60
t                                                                  61

<210> SEQ ID NO 1213
<211> LENGTH: 61
<212> TYPE: DNA
<213> ORGANISM: Homo Sapiens

<400> SEQUENCE: 1213
taactcacat tgagaacttg tgatctgaaa rcactaagga atttctgcca ttgcaggtag    60
g                                                                  61

<210> SEQ ID NO 1214
<211> LENGTH: 61
<212> TYPE: DNA
<213> ORGANISM: Homo Sapiens

<400> SEQUENCE: 1214
agcccctagt caccttctg aacaccataa rgtaagttgc gatctccatc agacactggg    60
g                                                                  61

<210> SEQ ID NO 1215
<211> LENGTH: 61
<212> TYPE: DNA
<213> ORGANISM: Homo Sapiens

<400> SEQUENCE: 1215
gccaggatcc aagaaaaaat ggaaagtaga ycaatgtaag cgttaaaaga acacatttta    60
t                                                                  61

<210> SEQ ID NO 1216
<211> LENGTH: 61
<212> TYPE: DNA
<213> ORGANISM: Homo Sapiens

<400> SEQUENCE: 1216
catttttctc tgttatgacc gtgttttttt kgtcatatat aagaaatctg tattcaggtc    60
t                                                                  61

<210> SEQ ID NO 1217
<211> LENGTH: 61
<212> TYPE: DNA
<213> ORGANISM: Homo Sapiens

<400> SEQUENCE: 1217
tctgataata aagatgattt tacttcttct yttccattgt ggataactta ttttttttct    60
t                                                                  61

<210> SEQ ID NO 1218
<211> LENGTH: 61
<212> TYPE: DNA
<213> ORGANISM: Homo Sapiens

<400> SEQUENCE: 1218

```
tggggaattg aataatagaa attttgaaga wggataggat cttggtgatc aattaatgta    60
c                                                                   61
```

<210> SEQ ID NO 1219
<211> LENGTH: 61
<212> TYPE: DNA
<213> ORGANISM: Homo Sapiens

<400> SEQUENCE: 1219

```
tggtttagat tttgtgatga ttctaaaata ytgacagtga attaatttgt tacttcaaaa    60
t                                                                   61
```

<210> SEQ ID NO 1220
<211> LENGTH: 61
<212> TYPE: DNA
<213> ORGANISM: Homo Sapiens

<400> SEQUENCE: 1220

```
ggcagatggt tcttcctttc tgtcaagagc ygtgtcttct gttttcccat caccgttgat    60
a                                                                   61
```

<210> SEQ ID NO 1221
<211> LENGTH: 61
<212> TYPE: DNA
<213> ORGANISM: Homo Sapiens

<400> SEQUENCE: 1221

```
cctttgatgg ttattaaaaa cagatgttca rtgttcttgg taaatcttaa aaattatgcc    60
t                                                                   61
```

<210> SEQ ID NO 1222
<211> LENGTH: 61
<212> TYPE: DNA
<213> ORGANISM: Homo Sapiens

<400> SEQUENCE: 1222

```
tgtatctctt ctctgtggct gctaaaagct ragaaagcct ccatctgtta ctaattcttg    60
t                                                                   61
```

<210> SEQ ID NO 1223
<211> LENGTH: 61
<212> TYPE: DNA
<213> ORGANISM: Homo Sapiens

<400> SEQUENCE: 1223

```
gcaatagtac caaggaccac agaagaagtg wtgttttgag aactatgcct agacctcaat    60
g                                                                   61
```

<210> SEQ ID NO 1224
<211> LENGTH: 61
<212> TYPE: DNA
<213> ORGANISM: Homo Sapiens

<400> SEQUENCE: 1224

```
atattcatca agtcagaggc ttcttagact ygctgccctt gactcactat gttgctctca    60
t                                                                   61
```

<210> SEQ ID NO 1225
<211> LENGTH: 61

```
<212> TYPE: DNA
<213> ORGANISM: Homo Sapiens

<400> SEQUENCE: 1225
tgcccttaaa ttaaaaacac cacctcaaac rgcaattaaa tgcgcataca catgtgtaat      60
g                                                                     61

<210> SEQ ID NO 1226
<211> LENGTH: 61
<212> TYPE: DNA
<213> ORGANISM: Homo Sapiens

<400> SEQUENCE: 1226
tgtcaccagc tatcatgctg ctcctgttaa ytgattcatt aatccagtac acccacatct      60
g                                                                     61

<210> SEQ ID NO 1227
<211> LENGTH: 61
<212> TYPE: DNA
<213> ORGANISM: Homo Sapiens

<400> SEQUENCE: 1227
cttattcata cacagactca cataaggcaa rtatcaactt tgttcctttc atgtttatta      60
a                                                                     61

<210> SEQ ID NO 1228
<211> LENGTH: 61
<212> TYPE: DNA
<213> ORGANISM: Homo Sapiens

<400> SEQUENCE: 1228
tgggaccacc atcatctatg tggttcatca wggactgaag ctctgttatg caccacatga      60
c                                                                     61

<210> SEQ ID NO 1229
<211> LENGTH: 61
<212> TYPE: DNA
<213> ORGANISM: Homo Sapiens

<400> SEQUENCE: 1229
caggaccatg aaggatttca agtaggtaca ygacaatcac atgggtattt tacaaagatc      60
a                                                                     61

<210> SEQ ID NO 1230
<211> LENGTH: 61
<212> TYPE: DNA
<213> ORGANISM: Homo Sapiens

<400> SEQUENCE: 1230
atgctagagg atggtgttat gaatagataa ytttgtcatt aaatgacgtc cactgctatg      60
a                                                                     61

<210> SEQ ID NO 1231
<211> LENGTH: 61
<212> TYPE: DNA
<213> ORGANISM: Homo Sapiens

<400> SEQUENCE: 1231
tttttcagtg cctgccattt tttattagtg rctccttaac aatctggcag gatatatagc      60
c                                                                     61
```

<210> SEQ ID NO 1232
<211> LENGTH: 61
<212> TYPE: DNA
<213> ORGANISM: Homo Sapiens

<400> SEQUENCE: 1232
tcctccttct cagctctctc cagtgtttgc rtctatcctt cagagccagc cccggctatg    60
t                                                                    61

<210> SEQ ID NO 1233
<211> LENGTH: 61
<212> TYPE: DNA
<213> ORGANISM: Homo Sapiens

<400> SEQUENCE: 1233
ccagggtttt ggagatgaaa cggacaaaaa mtttactcag ctgtcaaggc aggaacatat    60
t                                                                    61

<210> SEQ ID NO 1234
<211> LENGTH: 61
<212> TYPE: DNA
<213> ORGANISM: Homo Sapiens

<400> SEQUENCE: 1234
taaccaaaag gcattctaat tttcatgcta ygttgagtat aaatataaat tcaaggcagc    60
c                                                                    61

<210> SEQ ID NO 1235
<211> LENGTH: 61
<212> TYPE: DNA
<213> ORGANISM: Homo Sapiens

<400> SEQUENCE: 1235
agatccctca aatttttgtg aaatgattat mggtacaagt aagtggacaa gtattttaga    60
t                                                                    61

<210> SEQ ID NO 1236
<211> LENGTH: 61
<212> TYPE: DNA
<213> ORGANISM: Homo Sapiens

<400> SEQUENCE: 1236
ttagcatgtg tctaataaga atcaatcttt kcagttaaac aggcaaatgg gctaatgttc    60
t                                                                    61

<210> SEQ ID NO 1237
<211> LENGTH: 61
<212> TYPE: DNA
<213> ORGANISM: Homo Sapiens

<400> SEQUENCE: 1237
tcttcaaagc cagcttcata tcccatggta ytttctcact aacctcttac tcctaaccca    60
c                                                                    61

<210> SEQ ID NO 1238
<211> LENGTH: 61
<212> TYPE: DNA
<213> ORGANISM: Homo Sapiens

<400> SEQUENCE: 1238

```
ctaatgtact gaattcgccc atatgccccc mggcaagaag agagaaaaaa agttatttct    60
g                                                                    61

<210> SEQ ID NO 1239
<211> LENGTH: 61
<212> TYPE: DNA
<213> ORGANISM: Homo Sapiens

<400> SEQUENCE: 1239
ctctggaaac tttaagacct aggagcttat sagaaatgcg gaatctctgg ctgtgtcaag    60
a                                                                    61

<210> SEQ ID NO 1240
<211> LENGTH: 61
<212> TYPE: DNA
<213> ORGANISM: Homo Sapiens

<400> SEQUENCE: 1240
aagttcaaaa cttcatcaat cttagaacct waccaaactg aattggttta tcgtaactca    60
c                                                                    61

<210> SEQ ID NO 1241
<211> LENGTH: 61
<212> TYPE: DNA
<213> ORGANISM: Homo Sapiens

<400> SEQUENCE: 1241
ggaaggaaga aaagagaag aaaataacaa rctactctgg ctccataaac atgacttgcg    60
a                                                                    61

<210> SEQ ID NO 1242
<211> LENGTH: 61
<212> TYPE: DNA
<213> ORGANISM: Homo Sapiens

<400> SEQUENCE: 1242
tgtaagcacc ttgagagtaa gttatgagtc yttcatgtgt cccctgcacc gaacacaggt    60
t                                                                    61

<210> SEQ ID NO 1243
<211> LENGTH: 61
<212> TYPE: DNA
<213> ORGANISM: Homo Sapiens

<400> SEQUENCE: 1243 taggatctttt gcatgttcga gagggctctg ytgtgttcca ctgtagctgg ggattttgat    60
c                                                                    61

<210> SEQ ID NO 1244
<211> LENGTH: 61
<212> TYPE: DNA
<213> ORGANISM: Homo Sapiens

<400> SEQUENCE: 1244 tgatttatt ctcatagtca catttttgtg yttgttggaa tcataatgaa agcatacgca    60
t                                                                    61

<210> SEQ ID NO 1245
<211> LENGTH: 61
```

<212> TYPE: DNA
<213> ORGANISM: Homo Sapiens

<400> SEQUENCE: 1245
ctgctggcat tcactttctc tgtttagtaa rttcacccct ctggcatgtc ttccctagaa    60
t                                                                   61

<210> SEQ ID NO 1246
<211> LENGTH: 61
<212> TYPE: DNA
<213> ORGANISM: Homo Sapiens

<400> SEQUENCE: 1246
acctggccac cccaccctaa tcttttatta ygcagaaggt ttctacgtgg ccagcgcagc    60
c                                                                   61

<210> SEQ ID NO 1247
<211> LENGTH: 61
<212> TYPE: DNA
<213> ORGANISM: Homo Sapiens

<400> SEQUENCE: 1247
aagctcatga ttcttcagtt gacaggcgct wttcgtatgt taatccactg tgcaaatggc    60
c                                                                   61

<210> SEQ ID NO 1248
<211> LENGTH: 61
<212> TYPE: DNA
<213> ORGANISM: Homo Sapiens
<220> FEATURE:
<221> NAME/KEY: misc_feature
<222> LOCATION: (31)..(31)
<223> OTHER INFORMATION: n is a, c, g, or t

<400> SEQUENCE: 1248
gccatattcc atagtccatg acaatctttc nccctgcca gctgcccaag cgggtccaca    60
t                                                                   61

<210> SEQ ID NO 1249
<211> LENGTH: 61
<212> TYPE: DNA
<213> ORGANISM: Homo Sapiens

<400> SEQUENCE: 1249
ggggtttaag caggttagta caccgattct ytttctgaca gaagctggga caagagaata    60
g                                                                   61

<210> SEQ ID NO 1250
<211> LENGTH: 61
<212> TYPE: DNA
<213> ORGANISM: Homo Sapiens

<400> SEQUENCE: 1250
atttaataac ttagtaaagt tcaaaattgt sagttactta ttaaacataa acatgtgaca    60
a                                                                   61

<210> SEQ ID NO 1251
<211> LENGTH: 61
<212> TYPE: DNA
<213> ORGANISM: Homo Sapiens

<400> SEQUENCE: 1251

```
attaaaccag tctgcatcag ctacagtgta mgtctcagaa acagatctga aacccagct    60
g                                                                   61
```

<210> SEQ ID NO 1252
<211> LENGTH: 61
<212> TYPE: DNA
<213> ORGANISM: Homo Sapiens

<400> SEQUENCE: 1252

```
atgaaccctt ttccagggcc tggatagggc yattccctag gtccatgtgg gctgggagtt    60
c                                                                   61
```

<210> SEQ ID NO 1253
<211> LENGTH: 61
<212> TYPE: DNA
<213> ORGANISM: Homo Sapiens

<400> SEQUENCE: 1253

```
tatatgacat tgacttgggg atgaactctc mtttcccatg ctagcaaaca tcttggctgc    60
a                                                                   61
```

<210> SEQ ID NO 1254
<211> LENGTH: 61
<212> TYPE: DNA
<213> ORGANISM: Homo Sapiens

<400> SEQUENCE: 1254

```
gtcattgtaa aataccatct gcctgtcaag yattgtttta aaacattaaa tttgctaaat    60
a                                                                   61
```

<210> SEQ ID NO 1255
<211> LENGTH: 61
<212> TYPE: DNA
<213> ORGANISM: Homo Sapiens

<400> SEQUENCE: 1255

```
tgtgggatta ccagtccggg tatcagctct ytgttaatct tccagttctt gcatttctta    60
t                                                                   61
```

<210> SEQ ID NO 1256
<211> LENGTH: 61
<212> TYPE: DNA
<213> ORGANISM: Homo Sapiens

<400> SEQUENCE: 1256

```
attggcagac ttaattgctg ctattccaca sgctaaataa gagctggaaa ttaattttcg    60
c                                                                   61
```

<210> SEQ ID NO 1257
<211> LENGTH: 61
<212> TYPE: DNA
<213> ORGANISM: Homo Sapiens

<400> SEQUENCE: 1257

```
ttaatcataa aactttcatt ttccagatca magctaagaa aagattgcag agcaccaaat    60
a                                                                   61
```

<210> SEQ ID NO 1258
<211> LENGTH: 61

```
<212> TYPE: DNA
<213> ORGANISM: Homo Sapiens

<400> SEQUENCE: 1258
aagcaaagta cacctaactc tggctatccg yttcaatggc tcacaagaac ctgggcctcc    60
a                                                                   61

<210> SEQ ID NO 1259
<211> LENGTH: 61
<212> TYPE: DNA
<213> ORGANISM: Homo Sapiens

<400> SEQUENCE: 1259
tggtacttgc tgtcttttgt gatttactga ytttgctcca gggaaagctc taaaccatta   60
a                                                                   61

<210> SEQ ID NO 1260
<211> LENGTH: 61
<212> TYPE: DNA
<213> ORGANISM: Homo Sapiens

<400> SEQUENCE: 1260
ttgtaaattg atgagagcag tcctgcctgg rtggggcaag acagaaaggc tggaagttta   60
g                                                                   61

<210> SEQ ID NO 1261
<211> LENGTH: 61
<212> TYPE: DNA
<213> ORGANISM: Homo Sapiens

<400> SEQUENCE: 1261
ttctcatagt tctccactga aactctgtcc ytatcaaaca ataactctcg actccccac    60
a                                                                   61

<210> SEQ ID NO 1262
<211> LENGTH: 61
<212> TYPE: DNA
<213> ORGANISM: Homo Sapiens

<400> SEQUENCE: 1262
gtgatccttt tcattttttt cttagactgc yagtacatgt ttaacccatt tcttaagtta   60
t                                                                   61

<210> SEQ ID NO 1263
<211> LENGTH: 61
<212> TYPE: DNA
<213> ORGANISM: Homo Sapiens

<400> SEQUENCE: 1263
gtcattgctc tgccatcatt ggcttcttcc rtgtttactt tgtgccaggc catactgagc   60
c                                                                   61

<210> SEQ ID NO 1264
<211> LENGTH: 61
<212> TYPE: DNA
<213> ORGANISM: Homo Sapiens

<400> SEQUENCE: 1264
tgactaggag cttgctttgt acaggcaccg ygctaagttc ttacatgccc actgtaaggt   60
a                                                                   61
```

<210> SEQ ID NO 1265
<211> LENGTH: 61
<212> TYPE: DNA
<213> ORGANISM: Homo Sapiens

<400> SEQUENCE: 1265 gtagggctg tcgggggaat tacacgtgcc rtagaagtac atagaaggag catccagctt    60
t                                                                   61

<210> SEQ ID NO 1266
<211> LENGTH: 61
<212> TYPE: DNA
<213> ORGANISM: Homo Sapiens

<400> SEQUENCE: 1266
gagactgtgg tgctgtcctg caggcacatc rtggaagaac ttatcagacc catgactaca    60
a                                                                   61

<210> SEQ ID NO 1267
<211> LENGTH: 61
<212> TYPE: DNA
<213> ORGANISM: Homo Sapiens

<400> SEQUENCE: 1267
acctctttaa atattttaca gaattcgatt mttttcattg acaccatcag cctctattgt    60
c                                                                   61

<210> SEQ ID NO 1268
<211> LENGTH: 61
<212> TYPE: DNA
<213> ORGANISM: Homo Sapiens

<400> SEQUENCE: 1268
aagtatcaac atcttgtaac accctcttta ygagttaaca acaagcgttt tagtgcatta    60
a                                                                   61

<210> SEQ ID NO 1269
<211> LENGTH: 61
<212> TYPE: DNA
<213> ORGANISM: Homo Sapiens

<400> SEQUENCE: 1269
agtggctgga tgacaaagga ggaatcagca rgtgttttc tctgtcccct gtgtgcaggg     60
t                                                                   61

<210> SEQ ID NO 1270
<211> LENGTH: 61
<212> TYPE: DNA
<213> ORGANISM: Homo Sapiens

<400> SEQUENCE: 1270 cccctccct tctgaaacca tattttacat stctggtcct cattaaattt tctgtaactt     60
c                                                                   61

<210> SEQ ID NO 1271
<211> LENGTH: 61
<212> TYPE: DNA
<213> ORGANISM: Homo Sapiens

<400> SEQUENCE: 1271

```
aaatctagaa agctttgaca gtgggaatgc rtagtgaatg gctctaagtt ctccctccat    60
c                                                                    61

<210> SEQ ID NO 1272
<211> LENGTH: 61
<212> TYPE: DNA
<213> ORGANISM: Homo Sapiens

<400> SEQUENCE: 1272
cattaaagaa agggaggcat aaagagatct ygcccgatgt caacctagtg agtcactgat    60
g                                                                    61

<210> SEQ ID NO 1273
<211> LENGTH: 61
<212> TYPE: DNA
<213> ORGANISM: Homo Sapiens

<400> SEQUENCE: 1273
aacagtttat tattagacat gtaaaaacac ytttgtcact ctgactggta aagaatggca    60
t                                                                    61

<210> SEQ ID NO 1274
<211> LENGTH: 61
<212> TYPE: DNA
<213> ORGANISM: Homo Sapiens

<400> SEQUENCE: 1274
tccccttaga aatccaaaaa ggattgcatc raagttctgc tatgtgagca gcattttca    60
g                                                                    61

<210> SEQ ID NO 1275
<211> LENGTH: 61
<212> TYPE: DNA
<213> ORGANISM: Homo Sapiens

<400> SEQUENCE: 1275
agcaccgtgg gtgccttcag aattctgaaa rggccctgga tggtatcggg tagagccgct    60
g                                                                    61

<210> SEQ ID NO 1276
<211> LENGTH: 61
<212> TYPE: DNA
<213> ORGANISM: Homo Sapiens

<400> SEQUENCE: 1276
ctgtttctac actgtctgga agaagaatgg rcattgttac ctcaatatgg gaccaccagg    60
g                                                                    61

<210> SEQ ID NO 1277
<211> LENGTH: 61
<212> TYPE: DNA
<213> ORGANISM: Homo Sapiens

<400> SEQUENCE: 1277
gagtggttat gccaggcctg gttttctacc kccacctgcc tcacgggatt aatcatgtgc    60
c                                                                    61

<210> SEQ ID NO 1278
<211> LENGTH: 61
```

```
<212> TYPE: DNA
<213> ORGANISM: Homo Sapiens

<400> SEQUENCE: 1278
aaacggggat gcatctagga gtgcctgccc mgctgcctca gttctctgga gtgtaaggtt    60
a                                                                    61

<210> SEQ ID NO 1279
<211> LENGTH: 61
<212> TYPE: DNA
<213> ORGANISM: Homo Sapiens

<400> SEQUENCE: 1279
tatcagcaag acagtcaatg agatttagga rgaaggagaa tttatacctg ggggcggggc    60
a                                                                    61

<210> SEQ ID NO 1280
<211> LENGTH: 61
<212> TYPE: DNA
<213> ORGANISM: Homo Sapiens

<400> SEQUENCE: 1280
tcttttaacg ggagatttag gagagactca yagaaagagg atcaaaggtc aggagactgg    60
g                                                                    61

<210> SEQ ID NO 1281
<211> LENGTH: 61
<212> TYPE: DNA
<213> ORGANISM: Homo Sapiens

<400> SEQUENCE: 1281
accaaggacg tagtctcacc cagacagata sggtccctgc agctcttccc agctctcctc    60
a                                                                    61

<210> SEQ ID NO 1282
<211> LENGTH: 61
<212> TYPE: DNA
<213> ORGANISM: Homo Sapiens

<400> SEQUENCE: 1282
aggtctgggc tgcttcaatt tgtcttctgt ygtcagggct ccctgtgagg cctggcgaga    60
c                                                                    61

<210> SEQ ID NO 1283
<211> LENGTH: 61
<212> TYPE: DNA
<213> ORGANISM: Homo Sapiens

<400> SEQUENCE: 1283
ccagtcgcag tgaagactgc gcacaggagc rtgttcatag gagcatggag aaaggcccag    60
t                                                                    61

<210> SEQ ID NO 1284
<211> LENGTH: 61
<212> TYPE: DNA
<213> ORGANISM: Homo Sapiens

<400> SEQUENCE: 1284
cattcttgtg ggtaagttcc atgagggaag rtctttgttc agcttacagc tgtatctctg    60
t                                                                    61
```

<210> SEQ ID NO 1285
<211> LENGTH: 61
<212> TYPE: DNA
<213> ORGANISM: Homo Sapiens

<400> SEQUENCE: 1285
taatttgtct taactctttc atcttgcgta waatttccat tctgtcatcc acaaccggaa    60
t                                                                   61

<210> SEQ ID NO 1286
<211> LENGTH: 61
<212> TYPE: DNA
<213> ORGANISM: Homo Sapiens

<400> SEQUENCE: 1286
gggtaaataa tgaaagttct cttccacacc rtgttagcca ttttgagctt taatctggag    60
g                                                                   61

<210> SEQ ID NO 1287
<211> LENGTH: 61
<212> TYPE: DNA
<213> ORGANISM: Homo Sapiens

<400> SEQUENCE: 1287
ccacctgggt gtgcttaaaa agagacaaac rtggtaacga tcaaataccc tagataaaat    60
g                                                                   61

<210> SEQ ID NO 1288
<211> LENGTH: 61
<212> TYPE: DNA
<213> ORGANISM: Homo Sapiens

<400> SEQUENCE: 1288
tagttaatga catgaccata tttttatttt ygatgatcat tccggtgttt tagtgaattt    60
g                                                                   61

<210> SEQ ID NO 1289
<211> LENGTH: 61
<212> TYPE: DNA
<213> ORGANISM: Homo Sapiens

<400> SEQUENCE: 1289
ggtgccatta tttgaatgca tgaaacttct racctataag acatgaaata cattagccag    60
t                                                                   61

<210> SEQ ID NO 1290
<211> LENGTH: 61
<212> TYPE: DNA
<213> ORGANISM: Homo Sapiens

<400> SEQUENCE: 1290
atagtgggat cttgtttggg ttttcggaat ycactgtatg tctttgattg agcagtttaa    60
t                                                                   61

<210> SEQ ID NO 1291
<211> LENGTH: 61
<212> TYPE: DNA
<213> ORGANISM: Homo Sapiens

<400> SEQUENCE: 1291

| | |
|---|---|
| tttacaagct gccaggtgat ttaaatccac rtagtctacc agccaaactt agagcaaaca | 60 |
| g | 61 |

<210> SEQ ID NO 1292
<211> LENGTH: 61
<212> TYPE: DNA
<213> ORGANISM: Homo Sapiens

<400> SEQUENCE: 1292

| | |
|---|---|
| cctaacgttc ctgtgtttga tagcatcctc yttctactta gggcctgtgt gttagtaatg | 60 |
| c | 61 |

<210> SEQ ID NO 1293
<211> LENGTH: 61
<212> TYPE: DNA
<213> ORGANISM: Homo Sapiens

<400> SEQUENCE: 1293

| | |
|---|---|
| ctattttgcc caggtgaagc tggaccgctt rtactcttct ttgagaggag cagggtatga | 60 |
| c | 61 |

<210> SEQ ID NO 1294
<211> LENGTH: 61
<212> TYPE: DNA
<213> ORGANISM: Homo Sapiens

<400> SEQUENCE: 1294

| | |
|---|---|
| ttgcaataga gatgaccagc agctagctac rataattggt acgtaaatat acacattgtg | 60 |
| t | 61 |

<210> SEQ ID NO 1295
<211> LENGTH: 61
<212> TYPE: DNA
<213> ORGANISM: Homo Sapiens

<400> SEQUENCE: 1295

| | |
|---|---|
| gaaaatctta atctcccatt tggcccttc maaagtataa gcacagatta cttttcctat | 60 |
| c | 61 |

<210> SEQ ID NO 1296
<211> LENGTH: 61
<212> TYPE: DNA
<213> ORGANISM: Homo Sapiens

<400> SEQUENCE: 1296

| | |
|---|---|
| tgaacatgtc atggctcagg aatcagcttc rttaccgtga tattctttca ttgatgggtt | 60 |
| t | 61 |

<210> SEQ ID NO 1297
<211> LENGTH: 61
<212> TYPE: DNA
<213> ORGANISM: Homo Sapiens

<400> SEQUENCE: 1297

| | |
|---|---|
| acaaaatgtt attgaaatat tcggtcttaa satagaaaac ctatcaacct ttagtgtctg | 60 |
| t | 61 |

<210> SEQ ID NO 1298
<211> LENGTH: 61

```
<212> TYPE: DNA
<213> ORGANISM: Homo Sapiens

<400> SEQUENCE: 1298
tttcaaatga agcatgaagt tacatgcaat raactgaaat aaatttgatg ttgcctttgg      60
t                                                                     61

<210> SEQ ID NO 1299
<211> LENGTH: 61
<212> TYPE: DNA
<213> ORGANISM: Homo Sapiens

<400> SEQUENCE: 1299
tcaacatcct ttcacaatac ggctcttgac raggtaaaat ctagaggagt agtttatagc      60
t                                                                     61

<210> SEQ ID NO 1300
<211> LENGTH: 61
<212> TYPE: DNA
<213> ORGANISM: Homo Sapiens

<400> SEQUENCE: 1300
agatcaattt tttaaataag tacaaatctc yttcttaatc ggggtgacta ctggactaaa      60
g                                                                     61

<210> SEQ ID NO 1301
<211> LENGTH: 61
<212> TYPE: DNA
<213> ORGANISM: Homo Sapiens

<400> SEQUENCE: 1301
tgcttcttta tatgtaagag caggcattcc rtctacctaa attctgacaa gcccagtggg      60
c                                                                     61

<210> SEQ ID NO 1302
<211> LENGTH: 61
<212> TYPE: DNA
<213> ORGANISM: Homo Sapiens

<400> SEQUENCE: 1302
gtgtacactg gctgtgctgt ttctagcacc rtaaggcagt catcattatt gagccagggg      60
c                                                                     61

<210> SEQ ID NO 1303
<211> LENGTH: 61
<212> TYPE: DNA
<213> ORGANISM: Homo Sapiens

<400> SEQUENCE: 1303
aaaatgacat ttataatact aggtgctaat sagtaaggta aaatgtgata catctcaaga      60
g                                                                     61

<210> SEQ ID NO 1304
<211> LENGTH: 61
<212> TYPE: DNA
<213> ORGANISM: Homo Sapiens

<400> SEQUENCE: 1304
gaatggagtt tccattcttg ccctcaacat rcataagcga ctctttccca acatcatttt      60
c                                                                     61
```

<210> SEQ ID NO 1305
<211> LENGTH: 61
<212> TYPE: DNA
<213> ORGANISM: Homo Sapiens

<400> SEQUENCE: 1305
gcaacagatg acattatcaa aaatatgtct yttgaaaacc aagtcaagta cctagagatg    60
a                                                                   61

<210> SEQ ID NO 1306
<211> LENGTH: 61
<212> TYPE: DNA
<213> ORGANISM: Homo Sapiens

<400> SEQUENCE: 1306
agagagagtg tgtgtatgta tagtacagca rgagtaacaa cagggttgat attccacagt    60
t                                                                   61

<210> SEQ ID NO 1307
<211> LENGTH: 61
<212> TYPE: DNA
<213> ORGANISM: Homo Sapiens

<400> SEQUENCE: 1307
acttcctaag tgtttgagag gctgtcaagt rgggagtact ggaaaaatcc agggttctga    60
a                                                                   61

<210> SEQ ID NO 1308
<211> LENGTH: 61
<212> TYPE: DNA
<213> ORGANISM: Homo Sapiens

<400> SEQUENCE: 1308
cagcttctcg tagagttctg cacaagtcat yccgcagtag ggtgtgcctc ctggaagaca    60
a                                                                   61

<210> SEQ ID NO 1309
<211> LENGTH: 61
<212> TYPE: DNA
<213> ORGANISM: Homo Sapiens

<400> SEQUENCE: 1309
tgaaaaatgc gatagacaac aacaacagaa ytgatgcagc aaaagaattt gaattcaaat    60
a                                                                   61

<210> SEQ ID NO 1310
<211> LENGTH: 61
<212> TYPE: DNA
<213> ORGANISM: Homo Sapiens

<400> SEQUENCE: 1310
tacattctgg tacagccaca tgacagatta ytgagccatt aaaattatcc tcagggtgag    60
t                                                                   61

<210> SEQ ID NO 1311
<211> LENGTH: 61
<212> TYPE: DNA
<213> ORGANISM: Homo Sapiens

<400> SEQUENCE: 1311

```
ccagaaatat agcattttag tgcatttcac rtagtaacaa gagctaacag ctaatagatc    60
c                                                                   61
```

<210> SEQ ID NO 1312
<211> LENGTH: 61
<212> TYPE: DNA
<213> ORGANISM: Homo Sapiens

<400> SEQUENCE: 1312

```
gttggagata gaatcaggaa gaaataccag ktctcatact acatggtcat tcattccatt    60
a                                                                   61
```

<210> SEQ ID NO 1313
<211> LENGTH: 61
<212> TYPE: DNA
<213> ORGANISM: Homo Sapiens

<400> SEQUENCE: 1313

```
tcattattta cactaataat aatggcttgc rtttgaaata tgcttcagag ttaacacagc    60
a                                                                   61
```

<210> SEQ ID NO 1314
<211> LENGTH: 61
<212> TYPE: DNA
<213> ORGANISM: Homo Sapiens

<400> SEQUENCE: 1314

```
taagtaacac aggcacacca gatggattta yagtaaacag aagaaactta tgttagtctt    60
g                                                                   61
```

<210> SEQ ID NO 1315
<211> LENGTH: 61
<212> TYPE: DNA
<213> ORGANISM: Homo Sapiens

<400> SEQUENCE: 1315

```
ggagcagatg ttcaggtctg aatccagttt yttctagaca cctctttccg gatcaccccc    60
t                                                                   61
```

<210> SEQ ID NO 1316
<211> LENGTH: 61
<212> TYPE: DNA
<213> ORGANISM: Homo Sapiens

<400> SEQUENCE: 1316

```
catcttcccc ttgtccttct acggtggttt yctaacccaa cagagtggtc ctctgctcca    60
g                                                                   61
```

<210> SEQ ID NO 1317
<211> LENGTH: 61
<212> TYPE: DNA
<213> ORGANISM: Homo Sapiens

<400> SEQUENCE: 1317

```
cctgatctgg tccctgctac attctccaga kgcgttcttc agcttctgtc tccagccttc    60
t                                                                   61
```

<210> SEQ ID NO 1318
<211> LENGTH: 61

```
<212> TYPE: DNA
<213> ORGANISM: Homo Sapiens

<400> SEQUENCE: 1318
tcaattcaat acaacacatg acaagaaca kcatacccaa gttgccttca taaggacttt     60
c                                                                    61

<210> SEQ ID NO 1319
<211> LENGTH: 61
<212> TYPE: DNA
<213> ORGANISM: Homo Sapiens

<400> SEQUENCE: 1319
aaaggaacca gtctagttat gaaacaaaca yaggtaacct tgactctagg acttttatt     60
t                                                                    61

<210> SEQ ID NO 1320
<211> LENGTH: 61
<212> TYPE: DNA
<213> ORGANISM: Homo Sapiens

<400> SEQUENCE: 1320
gccaacacac attaaaggtc actattctgc rttaacttga aaagagcaaa agcactgttt     60
a                                                                    61

<210> SEQ ID NO 1321
<211> LENGTH: 61
<212> TYPE: DNA
<213> ORGANISM: Homo Sapiens

<400> SEQUENCE: 1321
tagcctagag gaagggctca gacactgtgc rctaaactaa ctaaacacat gaaacacacc     60
a                                                                    61

<210> SEQ ID NO 1322
<211> LENGTH: 61
<212> TYPE: DNA
<213> ORGANISM: Homo Sapiens

<400> SEQUENCE: 1322
gtttggatgc tgtttgagta agacctacac ygagaattct cttaaatacc tagaatttgt     60
g                                                                    61

<210> SEQ ID NO 1323
<211> LENGTH: 61
<212> TYPE: DNA
<213> ORGANISM: Homo Sapiens

<400> SEQUENCE: 1323
aatcatttta cctgagcact gattctgggt rctggcaaaa gcagtccccg gagcagctcc     60
t                                                                    61

<210> SEQ ID NO 1324
<211> LENGTH: 61
<212> TYPE: DNA
<213> ORGANISM: Homo Sapiens

<400> SEQUENCE: 1324
aggtatcaga tgctcaatgt cttacactta yggaaccgtc aaagacagct gttaaatgtc     60
c                                                                    61
```

-continued

<210> SEQ ID NO 1325
<211> LENGTH: 61
<212> TYPE: DNA
<213> ORGANISM: Homo Sapiens

<400> SEQUENCE: 1325
tacttctgaa aactatttct ttaccgaaga rcatagagaa ataagggagt aatttatcaa    60
c                                                                   61

<210> SEQ ID NO 1326
<211> LENGTH: 61
<212> TYPE: DNA
<213> ORGANISM: Homo Sapiens

<400> SEQUENCE: 1326
atttgagaac ctttcagtcc ccaacaaaca yggatggttg gtcaccttgg ttttaagtcc    60
t                                                                   61

<210> SEQ ID NO 1327
<211> LENGTH: 61
<212> TYPE: DNA
<213> ORGANISM: Homo Sapiens

<400> SEQUENCE: 1327
ctgataaaca cctttatcat gaattgaaag kttaagagtt acagaagatg tctggttttt    60
t                                                                   61

<210> SEQ ID NO 1328
<211> LENGTH: 61
<212> TYPE: DNA
<213> ORGANISM: Homo Sapiens

<400> SEQUENCE: 1328
tctattccag tagcactcat ggaagatacc mctaagaagg agcaatggca ttgctgaggg    60
g                                                                   61

<210> SEQ ID NO 1329
<211> LENGTH: 61
<212> TYPE: DNA
<213> ORGANISM: Homo Sapiens

<400> SEQUENCE: 1329
atgaattcta gtgttaaatt tgcaaaagaa ygttcagttt tcctggcatt taggatttta    60
a                                                                   61

<210> SEQ ID NO 1330
<211> LENGTH: 50
<212> TYPE: DNA
<213> ORGANISM: Homo Sapiens

<400> SEQUENCE: 1330
tgtttaaaga tagttcaaar tcaaatgagc aatacaggaa ctctaaatga               50

<210> SEQ ID NO 1331
<211> LENGTH: 61
<212> TYPE: DNA
<213> ORGANISM: Homo Sapiens

<400> SEQUENCE: 1331
gtaggagaaa ctatagcata ctctgaatag rcaatagcct agatgggagg gacagaatgg    60
c                                                                                                                          61

<210> SEQ ID NO 1332
<211> LENGTH: 61
<212> TYPE: DNA
<213> ORGANISM: Homo Sapiens

<400> SEQUENCE: 1332
cactttcccc actctagagc aatcctgctg ygtaaaatta gactgagaaa ttaaagccca    60
c                                                                    61

<210> SEQ ID NO 1333
<211> LENGTH: 61
<212> TYPE: DNA
<213> ORGANISM: Homo Sapiens

<400> SEQUENCE: 1333
tggaaagcat ttgctctcca ttaaacttac ygaaccttga caaaccagaa gggccaagaa    60
t                                                                    61

<210> SEQ ID NO 1334
<211> LENGTH: 61
<212> TYPE: DNA
<213> ORGANISM: Homo Sapiens

<400> SEQUENCE: 1334
gtgatgtggg aaagtggaag acccagacca rgaatcagaa gagctggatt ctagcaagtt    60
a                                                                    61

<210> SEQ ID NO 1335
<211> LENGTH: 61
<212> TYPE: DNA
<213> ORGANISM: Homo Sapiens

<400> SEQUENCE: 1335
caatagatgt tttacgttcc cttcgtaata wttaacgctt ggcctagatc cgagcattca    60
c                                                                    61

<210> SEQ ID NO 1336
<211> LENGTH: 61
<212> TYPE: DNA
<213> ORGANISM: Homo Sapiens
<220> FEATURE:
<221> NAME/KEY: misc_feature
<222> LOCATION: (31)..(31)
<223> OTHER INFORMATION: n is a, c, g, or t

<400> SEQUENCE: 1336
ttcctcttag cacaacctaa atagaatttg nagcttctcc tatgacagac tctatgtgca    60
a                                                                    61

<210> SEQ ID NO 1337
<211> LENGTH: 61
<212> TYPE: DNA
<213> ORGANISM: Homo Sapiens

<400> SEQUENCE: 1337
ttaacatcat ggcatagcca aaaaaccccca rtgtaatgca atactcttta tacttagata    60
t                                                                    61

```
<210> SEQ ID NO 1338
<211> LENGTH: 61
<212> TYPE: DNA
<213> ORGANISM: Homo Sapiens

<400> SEQUENCE: 1338 gcggggtgg tctgtgctta tgtttgcatc raggtggagg gtagtgttag aggtatgggg    60
c                                                                   61

<210> SEQ ID NO 1339
<211> LENGTH: 61
<212> TYPE: DNA
<213> ORGANISM: Homo Sapiens

<400> SEQUENCE: 1339
gtcagccact tcaaagaaga agagaatagg rgagatccgc ttaaaagcac aaggttgagt    60
c                                                                   61

<210> SEQ ID NO 1340
<211> LENGTH: 61
<212> TYPE: DNA
<213> ORGANISM: Homo Sapiens

<400> SEQUENCE: 1340
tccctgacct cgtggcaaag tacaacacca rtaacggggc tcccaaggat ttcctcccca    60
g                                                                   61

<210> SEQ ID NO 1341
<211> LENGTH: 61
<212> TYPE: DNA
<213> ORGANISM: Homo Sapiens

<400> SEQUENCE: 1341
atgtgagttt ataaaatgga acaattaggg rgtgatgtaa gtgctgaaca aaagaaggaa    60
c                                                                   61

<210> SEQ ID NO 1342
<211> LENGTH: 61
<212> TYPE: DNA
<213> ORGANISM: Homo Sapiens

<400> SEQUENCE: 1342
aggattaaaa taaatgctac cagttacagg satgcattaa attaataact ttttcccct     60 t                                                                   61

<210> SEQ ID NO 1343
<211> LENGTH: 61
<212> TYPE: DNA
<213> ORGANISM: Homo Sapiens

<400> SEQUENCE: 1343
ccaactggac cagcactcca ctggctgata ytgcccatca cagcacacca agaggccatg    60
a                                                                   61

<210> SEQ ID NO 1344
<211> LENGTH: 61
<212> TYPE: DNA
<213> ORGANISM: Homo Sapiens

<400> SEQUENCE: 1344
aaatgagggg tttgtgtctg atactcctga ytaagtattt ttgagaatct atttgcatgc    60
```

-continued

| | |
|---|---|
| t | 61 |

<210> SEQ ID NO 1345
<211> LENGTH: 61
<212> TYPE: DNA
<213> ORGANISM: Homo Sapiens

<400> SEQUENCE: 1345

| | |
|---|---|
| agaggagata gagctaaaga aaggaatctc rgtggaaacc cagacatccc cagaggagat | 60 |
| a | 61 |

<210> SEQ ID NO 1346
<211> LENGTH: 61
<212> TYPE: DNA
<213> ORGANISM: Homo Sapiens

<400> SEQUENCE: 1346

| | |
|---|---|
| tgttttttc ccctagttac tattactcca yacttcaagg tcaaatgcca ataaagtagc | 60 |
| a | 61 |

<210> SEQ ID NO 1347
<211> LENGTH: 61
<212> TYPE: DNA
<213> ORGANISM: Homo Sapiens

<400> SEQUENCE: 1347

| | |
|---|---|
| tcctagggga aatacaaggt taagtatcta ygtgtctctg gtcacaatat ttttataaaa | 60 |
| g | 61 |

<210> SEQ ID NO 1348
<211> LENGTH: 61
<212> TYPE: DNA
<213> ORGANISM: Homo Sapiens

<400> SEQUENCE: 1348

| | |
|---|---|
| agttcattca aattcaaaat attataggaa raaaacttgt acttcaaagg ctattctttc | 60 |
| a | 61 |

<210> SEQ ID NO 1349
<211> LENGTH: 61
<212> TYPE: DNA
<213> ORGANISM: Homo Sapiens

<400> SEQUENCE: 1349

| | |
|---|---|
| catgaagctt ataatttata gccttggttc racatggaat tgtttaacat tgcctataac | 60 |
| t | 61 |

<210> SEQ ID NO 1350
<211> LENGTH: 61
<212> TYPE: DNA
<213> ORGANISM: Homo Sapiens

<400> SEQUENCE: 1350

| | |
|---|---|
| aaagcagata cttataatga caacatcctg matcaaagaa agattccctt aactctttt | 60 |
| c | 61 |

<210> SEQ ID NO 1351
<211> LENGTH: 61
<212> TYPE: DNA
<213> ORGANISM: Homo Sapiens

<400> SEQUENCE: 1351
ttctatgctt acccatctgt ttttttccca stttgctcgt ctctgtactt tgttccatag    60
g                                                                    61

<210> SEQ ID NO 1352
<211> LENGTH: 61
<212> TYPE: DNA
<213> ORGANISM: Homo Sapiens

<400> SEQUENCE: 1352
tgttaggtac cttcacttat ataagccctt waatcacacc agcctacgga ctgattattc    60
a                                                                    61

<210> SEQ ID NO 1353
<211> LENGTH: 61
<212> TYPE: DNA
<213> ORGANISM: Homo Sapiens

<400> SEQUENCE: 1353
aaaggaggtt taaatgaata ctttgttttg ycatgttcaa aaaagagta ttaatatttt    60
g                                                                    61

<210> SEQ ID NO 1354
<211> LENGTH: 61
<212> TYPE: DNA
<213> ORGANISM: Homo Sapiens

<400> SEQUENCE: 1354
cagagacttt tctgatgatt tcaagtcctc rtaaacctag cagagaatgg accatgtgta    60
c                                                                    61

<210> SEQ ID NO 1355
<211> LENGTH: 61
<212> TYPE: DNA
<213> ORGANISM: Homo Sapiens

<400> SEQUENCE: 1355
cattcttgaa tatgaccttc tgaattggat wgcttttgta ttctagcaca ttttgttttg    60
t                                                                    61

<210> SEQ ID NO 1356
<211> LENGTH: 61
<212> TYPE: DNA
<213> ORGANISM: Homo Sapiens

<400> SEQUENCE: 1356
acaaggttcc caaaggccag tttgtgaatc rgaaccagtt ttcactagtg gtaaaatgag    60
a                                                                    61

<210> SEQ ID NO 1357
<211> LENGTH: 61
<212> TYPE: DNA
<213> ORGANISM: Homo Sapiens

<400> SEQUENCE: 1357
ttgtttatac atgggcatat ttatataaac rgggttacag gtctgtgtaa agaagttaca    60
t                                                                    61

```
<210> SEQ ID NO 1358
<211> LENGTH: 61
<212> TYPE: DNA
<213> ORGANISM: Homo Sapiens

<400> SEQUENCE: 1358
caccagctat tctaagtaag aactgaagaa mttttggatg gcatggaata tttcaaatat    60
t                                                                    61

<210> SEQ ID NO 1359
<211> LENGTH: 61
<212> TYPE: DNA
<213> ORGANISM: Homo Sapiens

<400> SEQUENCE: 1359
catatgatgg aagccctgcc ctctaggtac ygttagctta gttggagagg tgaaatctgg    60
t                                                                    61

<210> SEQ ID NO 1360
<211> LENGTH: 61
<212> TYPE: DNA
<213> ORGANISM: Homo Sapiens

<400> SEQUENCE: 1360
aagacatcca agacccaatg ctgcaagagg ragtgctggt tgcagccaca aaggctggca    60
c                                                                    61

<210> SEQ ID NO 1361
<211> LENGTH: 61
<212> TYPE: DNA
<213> ORGANISM: Homo Sapiens

<400> SEQUENCE: 1361
catcgcacat gaagcagacc caatgagtga stcagcaata aatcaacagt cttaatggag    60
a                                                                    61

<210> SEQ ID NO 1362
<211> LENGTH: 61
<212> TYPE: DNA
<213> ORGANISM: Homo Sapiens

<400> SEQUENCE: 1362
tttaataaga taatatgaga tgccatctaa rtaataatag gtacacttgt taagactttt    60
g                                                                    61

<210> SEQ ID NO 1363
<211> LENGTH: 61
<212> TYPE: DNA
<213> ORGANISM: Homo Sapiens

<400> SEQUENCE: 1363
tgattaggca ggttcagtag ggtgatattt staaagagct tggaacatgc caggtgcata    60
a                                                                    61

<210> SEQ ID NO 1364
<211> LENGTH: 61
<212> TYPE: DNA
<213> ORGANISM: Homo Sapiens

<400> SEQUENCE: 1364
ggtccgaagg tacttaagtg aacaagcaag yggatggagt ccatttgcca tgactcctgg    60
```

-continued a                                                              61

<210> SEQ ID NO 1365
<211> LENGTH: 61
<212> TYPE: DNA
<213> ORGANISM: Homo Sapiens

<400> SEQUENCE: 1365
cagtcgaggg catgcaaata atcatagccc rcagtctaca gccacaatgg acacacacag    60
g                                                              61

<210> SEQ ID NO 1366
<211> LENGTH: 61
<212> TYPE: DNA
<213> ORGANISM: Homo Sapiens

<400> SEQUENCE: 1366
aaatgttcct agggatatag ataattcaca raatgaaaga gtctaatcac atacataaga    60
g                                                              61

<210> SEQ ID NO 1367
<211> LENGTH: 61
<212> TYPE: DNA
<213> ORGANISM: Homo Sapiens

<400> SEQUENCE: 1367
caaaaagtct tttaaaaaaa aaggagtttc yctcaaacag cagttaactt agtaaataca    60
a                                                              61

<210> SEQ ID NO 1368
<211> LENGTH: 61
<212> TYPE: DNA
<213> ORGANISM: Homo Sapiens

<400> SEQUENCE: 1368
gtagtcgctg tcatcatagt agtagcagta yatgactgta ttaatgaccc ttcccttcc    60 c                                                              61

<210> SEQ ID NO 1369
<211> LENGTH: 61
<212> TYPE: DNA
<213> ORGANISM: Homo Sapiens

<400> SEQUENCE: 1369
tgggggcaaa tacatgcttc aaaatgttaa ygcacttttc acattttcta tcaaaaaaa    60 a                                                              61

<210> SEQ ID NO 1370
<211> LENGTH: 61
<212> TYPE: DNA
<213> ORGANISM: Homo Sapiens

<400> SEQUENCE: 1370
gtggcatgga gagttaaccc aagtcatagg yagaaagggc cctgccattt accctcctca    60
g                                                              61

<210> SEQ ID NO 1371
<211> LENGTH: 61
<212> TYPE: DNA
<213> ORGANISM: Homo Sapiens

<400> SEQUENCE: 1371
ttgacaagac catcaacatc agacaataaa rggcagtgac cactgagaga cgggaaacaa    60
g                                                                    61

<210> SEQ ID NO 1372
<211> LENGTH: 61
<212> TYPE: DNA
<213> ORGANISM: Homo Sapiens

<400> SEQUENCE: 1372
catacacaca cacacacacc ctcacgccca yagcaggtca gcttcctgac actttgaaca    60
g                                                                    61

<210> SEQ ID NO 1373
<211> LENGTH: 61
<212> TYPE: DNA
<213> ORGANISM: Homo Sapiens

<400> SEQUENCE: 1373
gagctccctc tcagcctttt gaactgatta ygctgttatt aaactttggt ggggaaagtt    60
a                                                                    61

<210> SEQ ID NO 1374
<211> LENGTH: 61
<212> TYPE: DNA
<213> ORGANISM: Homo Sapiens

<400> SEQUENCE: 1374
ggggaggggc aaaaaaggta atggaaggat kgttctgtag tttaatgaaa cgtacgttaa    60
t                                                                    61

<210> SEQ ID NO 1375
<211> LENGTH: 61
<212> TYPE: DNA
<213> ORGANISM: Homo Sapiens

<400> SEQUENCE: 1375
tggaagataa atcagatgtt ggttatggac raagtatttc ttcttcatct tccttaagaa    60
g                                                                    61

<210> SEQ ID NO 1376
<211> LENGTH: 61
<212> TYPE: DNA
<213> ORGANISM: Homo Sapiens

<400> SEQUENCE: 1376
caaacagaat taccctcaca tctcaactga rtcatgcaat taattaccca gaaatctccc    60
a                                                                    61

<210> SEQ ID NO 1377
<211> LENGTH: 61
<212> TYPE: DNA
<213> ORGANISM: Homo Sapiens

<400> SEQUENCE: 1377
gagcataagg catcagggga agcttaggga rgaaagtgag gcttgatctg aatttggact    60
t                                                                    61

```
<210> SEQ ID NO 1378
<211> LENGTH: 61
<212> TYPE: DNA
<213> ORGANISM: Homo Sapiens

<400> SEQUENCE: 1378
tagagggaag ggtagaagaa aggacctgac rggagttcaa tctaggaaga acaaaaagaa      60
g                                                                     61

<210> SEQ ID NO 1379
<211> LENGTH: 61
<212> TYPE: DNA
<213> ORGANISM: Homo Sapiens

<400> SEQUENCE: 1379
tgttaaatga cgtgaaagga aaaaagtggt yatcatgtgt gagacattat tatgtccaag      60
g                                                                     61

<210> SEQ ID NO 1380
<211> LENGTH: 61
<212> TYPE: DNA
<213> ORGANISM: Homo Sapiens

<400> SEQUENCE: 1380
ctcaatcgac tgattagtcc atcgcaaggc ytatctaatt aacttctaga ttcctctaaa      60
a                                                                     61

<210> SEQ ID NO 1381
<211> LENGTH: 61
<212> TYPE: DNA
<213> ORGANISM: Homo Sapiens

<400> SEQUENCE: 1381
gatcttctta aagaatccac aacggttatc mgattaaagc tgtgacccat ccccagctca      60
g                                                                     61

<210> SEQ ID NO 1382
<211> LENGTH: 61
<212> TYPE: DNA
<213> ORGANISM: Homo Sapiens

<400> SEQUENCE: 1382
tcactttgta ctggcaggct cgttttacct sattctagaa tatttaagaa tctaaaata      60
a                                                                     61

<210> SEQ ID NO 1383
<211> LENGTH: 61
<212> TYPE: DNA
<213> ORGANISM: Homo Sapiens

<400> SEQUENCE: 1383
agatatcaaa cccatcctga ggaagctccc rcgtatcaag aaacacttgt taaatggtga      60
t                                                                     61

<210> SEQ ID NO 1384
<211> LENGTH: 61
<212> TYPE: DNA
<213> ORGANISM: Homo Sapiens

<400> SEQUENCE: 1384
cttactccgg taagaggaag ctaacgctga yggttgtttg tttagaggga tctgtagcaa      60
```

-continued a                                                                61

<210> SEQ ID NO 1385
<211> LENGTH: 61
<212> TYPE: DNA
<213> ORGANISM: Homo Sapiens

<400> SEQUENCE: 1385
tcaccagcct ggccaacatg gcggaactcc ractttatta aaaataaaa aaaattagcc     60 a                                                                61

<210> SEQ ID NO 1386
<211> LENGTH: 61
<212> TYPE: DNA
<213> ORGANISM: Homo Sapiens

<400> SEQUENCE: 1386
tataaaagtg agccactgcc tggtcgagat mtttttaaat aatccattca gacaaaaata     60
g                                                                61

<210> SEQ ID NO 1387
<211> LENGTH: 61
<212> TYPE: DNA
<213> ORGANISM: Homo Sapiens

<400> SEQUENCE: 1387
tgtagtgtat gcgtagcctc tatctcgtat yttttttctat ttctcctccc cacaccatca     60
a                                                                61

<210> SEQ ID NO 1388
<211> LENGTH: 61
<212> TYPE: DNA
<213> ORGANISM: Homo Sapiens

<400> SEQUENCE: 1388
tacgtttcag gctcttttgt gtgtgtcact ktggggtttt tatgaagtag gctgtcttgt     60
t                                                                61

<210> SEQ ID NO 1389
<211> LENGTH: 61
<212> TYPE: DNA
<213> ORGANISM: Homo Sapiens

<400> SEQUENCE: 1389
acatttgaat aagactccaa aacgttgaat rtatgcatgg atcataaatc taaataacat     60
a                                                                61

<210> SEQ ID NO 1390
<211> LENGTH: 61
<212> TYPE: DNA
<213> ORGANISM: Homo Sapiens

<400> SEQUENCE: 1390
acaaattaat tacatttcat ttcatgagac rcataacaca agtgatctta tctctagttc     60
t                                                                61

<210> SEQ ID NO 1391
<211> LENGTH: 61
<212> TYPE: DNA
<213> ORGANISM: Homo Sapiens

```
<400> SEQUENCE: 1391
aaaagaacgt tgaggataag gagatctttg ktgaccctat gcatttaaac attttaaatg    60
g                                                                    61

<210> SEQ ID NO 1392
<211> LENGTH: 61
<212> TYPE: DNA
<213> ORGANISM: Homo Sapiens

<400> SEQUENCE: 1392
agtcaggatc ctgtaataga ccaggtatga raaggttggc ttggactaaa gtgatattgg    60
t                                                                    61

<210> SEQ ID NO 1393
<211> LENGTH: 61
<212> TYPE: DNA
<213> ORGANISM: Homo Sapiens

<400> SEQUENCE: 1393
tggctagaca tctccaggtc tcaagaacat ygcagcatgc cctttgtgcc agctgtttgg    60
g                                                                    61

<210> SEQ ID NO 1394
<211> LENGTH: 61
<212> TYPE: DNA
<213> ORGANISM: Homo Sapiens

<400> SEQUENCE: 1394
acaatgatgc aggcaccttt ggggaagtca rctacttctt cagtgatgac cctgacaggt    60
g                                                                    61

<210> SEQ ID NO 1395
<211> LENGTH: 61
<212> TYPE: DNA
<213> ORGANISM: Homo Sapiens

<400> SEQUENCE: 1395
acacaccagc tgacagccag tcagtgaaca rtgtggaaag gaagataggc atgacggcca    60
a                                                                    61

<210> SEQ ID NO 1396
<211> LENGTH: 61
<212> TYPE: DNA
<213> ORGANISM: Homo Sapiens

<400> SEQUENCE: 1396
acaccaaaac aagctttgat gaaaagaccc rtttccctgc tgtcccttga ttttcaggca    60
a                                                                    61

<210> SEQ ID NO 1397
<211> LENGTH: 61
<212> TYPE: DNA
<213> ORGANISM: Homo Sapiens

<400> SEQUENCE: 1397
aggagccagg ggtctgcagg ctgaataact rggattcgca gttctgatca gttcacagcc    60
a                                                                    61
```

```
<210> SEQ ID NO 1398
<211> LENGTH: 61
<212> TYPE: DNA
<213> ORGANISM: Homo Sapiens

<400> SEQUENCE: 1398
agtaaatgat aggtataaag agccactagc yatgaaaatt cccttttcaaa aaaagcctag    60 t                                                                    61

<210> SEQ ID NO 1399
<211> LENGTH: 61
<212> TYPE: DNA
<213> ORGANISM: Homo Sapiens

<400> SEQUENCE: 1399
ccctgggcct ggtagttaaa gactgacccg sacttaatcg gttatgttat ctatagatta    60
c                                                                    61

<210> SEQ ID NO 1400
<211> LENGTH: 61
<212> TYPE: DNA
<213> ORGANISM: Homo Sapiens

<400> SEQUENCE: 1400
ccatggccat gatcaacaaa gtgctatggg kacatggcta agaatcagg agcccatctg    60 g                                                                    61

<210> SEQ ID NO 1401
<211> LENGTH: 61
<212> TYPE: DNA
<213> ORGANISM: Homo Sapiens

<400> SEQUENCE: 1401
ctttgtttca ttctgactgc ttagtgccta stcttgggct aagggatgct gacaagctag    60
t                                                                    61

<210> SEQ ID NO 1402
<211> LENGTH: 61
<212> TYPE: DNA
<213> ORGANISM: Homo Sapiens

<400> SEQUENCE: 1402
cttaagaaga atttttccat gatgtgatga yagaatttgc agccagcaaa ggggatcata    60
g                                                                    61

<210> SEQ ID NO 1403
<211> LENGTH: 61
<212> TYPE: DNA
<213> ORGANISM: Homo Sapiens

<400> SEQUENCE: 1403
gtctgtgcga tcttaggtaa gccacttaaa wgctctctca gtttcctcta ctataaagtg    60
g                                                                    61

<210> SEQ ID NO 1404
<211> LENGTH: 61
<212> TYPE: DNA
<213> ORGANISM: Homo Sapiens

<400> SEQUENCE: 1404
gttttctatg tcttttttctg tggctccttg raaatgttaa aggcatgtct cagctacagc    60
```

```
a                                                                   61

<210> SEQ ID NO 1405
<211> LENGTH: 61
<212> TYPE: DNA
<213> ORGANISM: Homo Sapiens

<400> SEQUENCE: 1405
tgatgaaagt tcaccattgc tagacttgat mtcttctaat ccttaaacac tagagccaga    60
t                                                                   61

<210> SEQ ID NO 1406
<211> LENGTH: 61
<212> TYPE: DNA
<213> ORGANISM: Homo Sapiens

<400> SEQUENCE: 1406
acagcaagtg cttgctaagg ggtgttactg kcagcttttc tctgagtcca actcccatca    60
c                                                                   61

<210> SEQ ID NO 1407
<211> LENGTH: 61
<212> TYPE: DNA
<213> ORGANISM: Homo Sapiens

<400> SEQUENCE: 1407
tcagtgaatg gtgatgatga tgcagatgac ygaaaatgat aatggtaatg atgacaaatt    60
c                                                                   61

<210> SEQ ID NO 1408
<211> LENGTH: 61
<212> TYPE: DNA
<213> ORGANISM: Homo Sapiens

<400> SEQUENCE: 1408
gctggctgct gtggggagtc cccttggtta yatcttccca tctgtacaga cagcagcagg    60
t                                                                   61

<210> SEQ ID NO 1409
<211> LENGTH: 61
<212> TYPE: DNA
<213> ORGANISM: Homo Sapiens

<400> SEQUENCE: 1409
tcaagagatc taaatctggg tcagaactca ytgaatactt agctgggtga aattgaccaa    60
g                                                                   61

<210> SEQ ID NO 1410
<211> LENGTH: 61
<212> TYPE: DNA
<213> ORGANISM: Homo Sapiens

<400> SEQUENCE: 1410
tcatatttag tggcaaggca ctgtagcttc kgaagtcggg cttgtccatc gttaaagcct    60
g                                                                   61

<210> SEQ ID NO 1411
<211> LENGTH: 61
<212> TYPE: DNA
<213> ORGANISM: Homo Sapiens
```

<400> SEQUENCE: 1411
aatgtttcta aaaagtagat gcattcattt mtttccctgg catttcttga ctgcttactc    60
t                                                                   61

<210> SEQ ID NO 1412
<211> LENGTH: 61
<212> TYPE: DNA
<213> ORGANISM: Homo Sapiens

<400> SEQUENCE: 1412
cctggatctc taattcacta cttgaataaa rctagtcatt tgctacctta aacaggaaat    60
a                                                                   61

<210> SEQ ID NO 1413
<211> LENGTH: 61
<212> TYPE: DNA
<213> ORGANISM: Homo Sapiens

<400> SEQUENCE: 1413
ggcaaaggga ggaaagaaac aatgaatgac sagaacaaac atatgccacg caattctgaa    60
t                                                                   61

<210> SEQ ID NO 1414
<211> LENGTH: 61
<212> TYPE: DNA
<213> ORGANISM: Homo Sapiens

<400> SEQUENCE: 1414
gcattcctaa gacagaaatt tgccaaaaga ytgttgtaag tttaatgagg gaagagtcca    60
g                                                                   61

<210> SEQ ID NO 1415
<211> LENGTH: 61
<212> TYPE: DNA
<213> ORGANISM: Homo Sapiens

<400> SEQUENCE: 1415
agcattcaaa ttggtttaca ttgtgaaatt ytgacttgct cttacatata gaaatcatgt    60
c                                                                   61

<210> SEQ ID NO 1416
<211> LENGTH: 61
<212> TYPE: DNA
<213> ORGANISM: Homo Sapiens

<400> SEQUENCE: 1416
tttacaaaga actattagtt atgagcaaat kacctggtga gcacaccaaa catttagcca    60
t                                                                   61

<210> SEQ ID NO 1417
<211> LENGTH: 61
<212> TYPE: DNA
<213> ORGANISM: Homo Sapiens

<400> SEQUENCE: 1417
aagcagctct tcttgtactt tacttacaac rcagttaaca tccccttttgc agcttgtaga    60
a                                                                   61

```
<210> SEQ ID NO 1418
<211> LENGTH: 61
<212> TYPE: DNA
<213> ORGANISM: Homo Sapiens

<400> SEQUENCE: 1418
agctgtgtct gctgtcacat tggctccaca ytggggctct tacaaatatg tgtcacatct    60
a                                                                   61

<210> SEQ ID NO 1419
<211> LENGTH: 61
<212> TYPE: DNA
<213> ORGANISM: Homo Sapiens

<400> SEQUENCE: 1419
gaaatgcaaa tcttgggtgc tggtgcggga rgatgttgta gatctgggat tctcaaactt    60
t                                                                   61

<210> SEQ ID NO 1420
<211> LENGTH: 61
<212> TYPE: DNA
<213> ORGANISM: Homo Sapiens

<400> SEQUENCE: 1420
ggaagatttc agagctgttt cggaggcatc rctgccataa tatactgagg gcaagaaggg    60
g                                                                   61

<210> SEQ ID NO 1421
<211> LENGTH: 61
<212> TYPE: DNA
<213> ORGANISM: Homo Sapiens

<400> SEQUENCE: 1421
tccttgatgg aaccaaaccc agatcttctc yggcaatgga gatgccacac ataaagaaga    60
a                                                                   61

<210> SEQ ID NO 1422
<211> LENGTH: 61
<212> TYPE: DNA
<213> ORGANISM: Homo Sapiens

<400> SEQUENCE: 1422
aggaggaaga taaacaccat tctctgcttt yagtattata aaaccgtccc acaattccaa    60
c                                                                   61

<210> SEQ ID NO 1423
<211> LENGTH: 61
<212> TYPE: DNA
<213> ORGANISM: Homo Sapiens

<400> SEQUENCE: 1423
tgatgcttga aagggctgcc aatcacagta rccagttcct ctggctttgg ccataataaa    60
t                                                                   61

<210> SEQ ID NO 1424
<211> LENGTH: 61
<212> TYPE: DNA
<213> ORGANISM: Homo Sapiens

<400> SEQUENCE: 1424
tttccttatt taagcatctg tccaagtttg yatccgagca ttccttccct gcagggtggg    60
```

-continued g                                                              61

<210> SEQ ID NO 1425
<211> LENGTH: 61
<212> TYPE: DNA
<213> ORGANISM: Homo Sapiens

<400> SEQUENCE: 1425 tttattttc ttttctgtag tacatatttg rtgtctgagg tttgtctcca actccttttg      60
t                                                              61

<210> SEQ ID NO 1426
<211> LENGTH: 61
<212> TYPE: DNA
<213> ORGANISM: Homo Sapiens

<400> SEQUENCE: 1426
gttaaatggg gagatgccat gagacccaac ygctacccag agaggtacaa gccctgagga      60
t                                                              61

<210> SEQ ID NO 1427
<211> LENGTH: 61
<212> TYPE: DNA
<213> ORGANISM: Homo Sapiens

<400> SEQUENCE: 1427
cttctatttc tgttctgtgc agaataaact rctctctaaa ggcctgtctc atactcatcc      60
t                                                              61

<210> SEQ ID NO 1428
<211> LENGTH: 61
<212> TYPE: DNA
<213> ORGANISM: Homo Sapiens

<400> SEQUENCE: 1428
acgaggttgc tgccacttct cacatgcacc wcaacactgc tgttttacaa aaacttcaga      60
t                                                              61

<210> SEQ ID NO 1429
<211> LENGTH: 61
<212> TYPE: DNA
<213> ORGANISM: Homo Sapiens

<400> SEQUENCE: 1429
caaagacagt ctatacagac cggaagagat rtgtacttct tgtacaggca acaaggattg      60
c                                                              61

<210> SEQ ID NO 1430
<211> LENGTH: 61
<212> TYPE: DNA
<213> ORGANISM: Homo Sapiens

<400> SEQUENCE: 1430
agaactggtt ttgaattcca gtcctgaaac stactagctg ggtgatcttg gacaatttac      60
t                                                              61

<210> SEQ ID NO 1431
<211> LENGTH: 61
<212> TYPE: DNA
<213> ORGANISM: Homo Sapiens

<400> SEQUENCE: 1431
aagaaaaggg aaaggtcgca gaaatgtaga ygtaaagaca gaggtagctg catatttctg    60
a                                                                    61

<210> SEQ ID NO 1432
<211> LENGTH: 61
<212> TYPE: DNA
<213> ORGANISM: Homo Sapiens

<400> SEQUENCE: 1432
aaatgagctt caataaatga agaggcatac yacattctgg gaaaggaaga gtgaatgata    60
t                                                                    61

<210> SEQ ID NO 1433
<211> LENGTH: 61
<212> TYPE: DNA
<213> ORGANISM: Homo Sapiens

<400> SEQUENCE: 1433
actctgagat tgtcttgaaa atcctctcac rcttcctatg acaactctca atcaaccttc    60
t                                                                    61

<210> SEQ ID NO 1434
<211> LENGTH: 61
<212> TYPE: DNA
<213> ORGANISM: Homo Sapiens

<400> SEQUENCE: 1434
ctctcatcac aacccaaatg gcaaagtcca ygttctctgg cagggctcag ctggggaaag    60
a                                                                    61

<210> SEQ ID NO 1435
<211> LENGTH: 61
<212> TYPE: DNA
<213> ORGANISM: Homo Sapiens

<400> SEQUENCE: 1435
tacaaaggca tcaagaatag agagtagttt ygttagaacg gtgggagcag gagccagcag    60
a                                                                    61

<210> SEQ ID NO 1436
<211> LENGTH: 61
<212> TYPE: DNA
<213> ORGANISM: Homo Sapiens

<400> SEQUENCE: 1436
cttatggtag gtaggttgca gatttgagat ygagtcttaa aaagaacaag aaagaaaagg    60
g                                                                    61

<210> SEQ ID NO 1437
<211> LENGTH: 61
<212> TYPE: DNA
<213> ORGANISM: Homo Sapiens

<400> SEQUENCE: 1437
caggctgggg taagttcatg ttgccacgga ytctaggagg gatctctgaa gtgtcaagta    60
c                                                                    61

```
<210> SEQ ID NO 1438
<211> LENGTH: 61
<212> TYPE: DNA
<213> ORGANISM: Homo Sapiens

<400> SEQUENCE: 1438
gttcagagac atgcaaatca aaactacaac raggcaccac ctaacagcag tcagaatggc      60
t                                                                     61

<210> SEQ ID NO 1439
<211> LENGTH: 61
<212> TYPE: DNA
<213> ORGANISM: Homo Sapiens

<400> SEQUENCE: 1439
gaagcagcca acactagaaa tataaacgaa kgaatcatct atacagaggt agtaattaaa      60
g                                                                     61

<210> SEQ ID NO 1440
<211> LENGTH: 61
<212> TYPE: DNA
<213> ORGANISM: Homo Sapiens

<400> SEQUENCE: 1440
tgacaaataa tgttatgatg aatatcctga wacttgccta ttgagcaaat ttccaagttt      60
t                                                                     61

<210> SEQ ID NO 1441
<211> LENGTH: 61
<212> TYPE: DNA
<213> ORGANISM: Homo Sapiens

<400> SEQUENCE: 1441
ccagtggcct ctttacttct ccttcaaaga wtacccctgt acaagtccca ggttgcccca      60
a                                                                     61

<210> SEQ ID NO 1442
<211> LENGTH: 61
<212> TYPE: DNA
<213> ORGANISM: Homo Sapiens

<400> SEQUENCE: 1442
tttactgttg gtatgtggca gtgaaaaata yatcagcgac taacatggtt tggggtcatt      60
a                                                                     61

<210> SEQ ID NO 1443
<211> LENGTH: 61
<212> TYPE: DNA
<213> ORGANISM: Homo Sapiens

<400> SEQUENCE: 1443
ctcgttattc ccatttattg tacctctatg yttttttccta atagttttac ctaatattcc    60
t                                                                     61

<210> SEQ ID NO 1444
<211> LENGTH: 61
<212> TYPE: DNA
<213> ORGANISM: Homo Sapiens

<400> SEQUENCE: 1444
tgggcacaat tggttttaaa gatgcttaca rccccgttat cacctcataa aatggctcat     60
```

-continued t                                                              61

<210> SEQ ID NO 1445
<211> LENGTH: 61
<212> TYPE: DNA
<213> ORGANISM: Homo Sapiens

<400> SEQUENCE: 1445
tctgtaagca ctctgtctct cctctgatct mtactggtct caattgttta acaacttttta    60 a                                                              61

<210> SEQ ID NO 1446
<211> LENGTH: 61
<212> TYPE: DNA
<213> ORGANISM: Homo Sapiens

<400> SEQUENCE: 1446
tatccagctc ttctgttaag tgtgtcaaaa ytgaagtccg agagggtaga ttgtcacatt    60
t                                                              61

<210> SEQ ID NO 1447
<211> LENGTH: 61
<212> TYPE: DNA
<213> ORGANISM: Homo Sapiens

<400> SEQUENCE: 1447
ttccttatat ctttcttact catatattgg rttctatttc aacacatgct taatgaaaaa    60
a                                                              61

<210> SEQ ID NO 1448
<211> LENGTH: 61
<212> TYPE: DNA
<213> ORGANISM: Homo Sapiens

<400> SEQUENCE: 1448
gtccttgcac gttttgacaa ggggagagac mtgacctgag ttttgcttta gcaaggttaa    60
t                                                              61

<210> SEQ ID NO 1449
<211> LENGTH: 61
<212> TYPE: DNA
<213> ORGANISM: Homo Sapiens

<400> SEQUENCE: 1449
agtcttttca aagttgcagg agatgcagtt ktctaggctt ggtgctgaaa atatagataa    60
g                                                              61

<210> SEQ ID NO 1450
<211> LENGTH: 61
<212> TYPE: DNA
<213> ORGANISM: Homo Sapiens

<400> SEQUENCE: 1450
tgacattgat aaaatccacc aatcttgttc rgatttccca gttttacttg tactcatcta    60
t                                                              61

<210> SEQ ID NO 1451
<211> LENGTH: 61
<212> TYPE: DNA
<213> ORGANISM: Homo Sapiens

<400> SEQUENCE: 1451
gactgacagg aatattaaag aagagagtgg wtacaaagcg cccatcatac tttatagcaa    60
g                                                                   61

<210> SEQ ID NO 1452
<211> LENGTH: 61
<212> TYPE: DNA
<213> ORGANISM: Homo Sapiens

<400> SEQUENCE: 1452
atctagtggg gttcactcac ctttacaggg ractcaacgc tggtagccag ctccctattt    60
c                                                                   61

<210> SEQ ID NO 1453
<211> LENGTH: 61
<212> TYPE: DNA
<213> ORGANISM: Homo Sapiens

<400> SEQUENCE: 1453
cggcctgaga acacatcttt agtccagcag wtacatggca ctcatctcct caagagtcct    60
t                                                                   61

<210> SEQ ID NO 1454
<211> LENGTH: 61
<212> TYPE: DNA
<213> ORGANISM: Homo Sapiens

<400> SEQUENCE: 1454
ctaatggtgt gctatgtttt aatcactatg wtaaacctgg atacattgta taaccaatgc    60
a                                                                   61

<210> SEQ ID NO 1455
<211> LENGTH: 61
<212> TYPE: DNA
<213> ORGANISM: Homo Sapiens

<400> SEQUENCE: 1455
ttccggatct cctaggatag ttacatacgc rctatctgtt ggaacttgta gaattttctc    60
c                                                                   61

<210> SEQ ID NO 1456
<211> LENGTH: 61
<212> TYPE: DNA
<213> ORGANISM: Homo Sapiens

<400> SEQUENCE: 1456
agggcaaaga gaagggaaaa cctagaaaac ygagtcaaga gtcctgttgg atacagtttc    60
a                                                                   61

<210> SEQ ID NO 1457
<211> LENGTH: 61
<212> TYPE: DNA
<213> ORGANISM: Homo Sapiens

<400> SEQUENCE: 1457
gaggctttca aggcctttgt gatctgaatc rtattagctt ctcgtgtatc tgttgctgct    60
c                                                                   61

```
<210> SEQ ID NO 1458
<211> LENGTH: 61
<212> TYPE: DNA
<213> ORGANISM: Homo Sapiens

<400> SEQUENCE: 1458
gatatggtca aatctttgga gctccagggt rtataagaca atgatacctc ctccccagtt    60
t                                                                    61

<210> SEQ ID NO 1459
<211> LENGTH: 61
<212> TYPE: DNA
<213> ORGANISM: Homo Sapiens

<400> SEQUENCE: 1459
acacctcatt gtctcaccct gcccaacatt yggtgtggaa gattgagaat aatgtgaatt    60
t                                                                    61

<210> SEQ ID NO 1460
<211> LENGTH: 61
<212> TYPE: DNA
<213> ORGANISM: Homo Sapiens

<400> SEQUENCE: 1460
ccgtttataa agagatagct tgtgtagctt stctataggt gccctagat acagccatac     60 t                                                                    61

<210> SEQ ID NO 1461
<211> LENGTH: 61
<212> TYPE: DNA
<213> ORGANISM: Homo Sapiens

<400> SEQUENCE: 1461
ttagatttgc ttagccttga cagaaatact rggaaagaga caattatggc ttgccaaata    60
c                                                                    61

<210> SEQ ID NO 1462
<211> LENGTH: 61
<212> TYPE: DNA
<213> ORGANISM: Homo Sapiens

<400> SEQUENCE: 1462
aaaattgaat atgttttttcc tcctgcctaa racaaaacta cttaagggca aaaatttaaa   60
t                                                                    61

<210> SEQ ID NO 1463
<211> LENGTH: 61
<212> TYPE: DNA
<213> ORGANISM: Homo Sapiens

<400> SEQUENCE: 1463
ccatgctctt ttctactttg gggcttttgc rcctgttggt atttctgcat gaagtgttct    60
c                                                                    61

<210> SEQ ID NO 1464
<211> LENGTH: 61
<212> TYPE: DNA
<213> ORGANISM: Homo Sapiens

<400> SEQUENCE: 1464
ataattcaat ccagttagct cagttggcta satttttgat gcttactata ttgtacccat    60
``` g                                                               61

<210> SEQ ID NO 1465
<211> LENGTH: 61
<212> TYPE: DNA
<213> ORGANISM: Homo Sapiens

<400> SEQUENCE: 1465
tgagctaagg gagataacac atgtaaagta ytggtcacaa agtctgcctg tattaatcag    60
a                                                               61

<210> SEQ ID NO 1466
<211> LENGTH: 61
<212> TYPE: DNA
<213> ORGANISM: Homo Sapiens

<400> SEQUENCE: 1466
gttaatctca ggcccttttgg attcccctg ytgttggttt cctctacgtg tttagcacta    60
t                                                               61

<210> SEQ ID NO 1467
<211> LENGTH: 61
<212> TYPE: DNA
<213> ORGANISM: Homo Sapiens

<400> SEQUENCE: 1467
tagattcact aagttgaaaa gctcgtaaag rttacttttc tacaaaatac acaagcaatt    60
a                                                               61

<210> SEQ ID NO 1468
<211> LENGTH: 61
<212> TYPE: DNA
<213> ORGANISM: Homo Sapiens

<400> SEQUENCE: 1468
ttctagtcaa tattttgacg cacctaacaa ygatagttaa catttacata gtgctcattt    60
t                                                               61

<210> SEQ ID NO 1469
<211> LENGTH: 61
<212> TYPE: DNA
<213> ORGANISM: Homo Sapiens

<400> SEQUENCE: 1469
tcttctttta ttaccctgta aatgctgttt ygttaccctt tctcatacag gatctaatcc    60
a                                                               61

<210> SEQ ID NO 1470
<211> LENGTH: 61
<212> TYPE: DNA
<213> ORGANISM: Homo Sapiens

<400> SEQUENCE: 1470
agtataatct taaaaagaga tattagttcc rtcctgcttc tctcccacca actctgcttg    60
c                                                               61

<210> SEQ ID NO 1471
<211> LENGTH: 61
<212> TYPE: DNA
<213> ORGANISM: Homo Sapiens

<400> SEQUENCE: 1471
ctgaccaatg aaatagctgt acgtatttaa wgtagatcct tttatcacaa tttaaagctg      60
a                                                                       61

<210> SEQ ID NO 1472
<211> LENGTH: 61
<212> TYPE: DNA
<213> ORGANISM: Homo Sapiens

<400> SEQUENCE: 1472
aatcctacct gattagcatt tttagaaata yggaattgtt acatctattt cacatggtag      60
a                                                                       61

<210> SEQ ID NO 1473
<211> LENGTH: 61
<212> TYPE: DNA
<213> ORGANISM: Homo Sapiens

<400> SEQUENCE: 1473
tcgcaatgcc tgcatcactc acctcacttc wtcttatcat acaggcattt tgtcatctca      60
t                                                                       61

<210> SEQ ID NO 1474
<211> LENGTH: 61
<212> TYPE: DNA
<213> ORGANISM: Homo Sapiens

<400> SEQUENCE: 1474
ttgtttgagt aaatatgaag ttctaaggca rggaattctt tgaagagtaa gtagccacat      60
t                                                                       61

<210> SEQ ID NO 1475
<211> LENGTH: 61
<212> TYPE: DNA
<213> ORGANISM: Homo Sapiens

<400> SEQUENCE: 1475
tactgggata gagatggaag gctgactact yaagttacat gctcagagat gctaagacca      60
a                                                                       61

<210> SEQ ID NO 1476
<211> LENGTH: 61
<212> TYPE: DNA
<213> ORGANISM: Homo Sapiens

<400> SEQUENCE: 1476
tattcattca ttcatttatt caaagagtat rttatgccta ctctgtgtac agcacaatat      60
c                                                                       61

<210> SEQ ID NO 1477
<211> LENGTH: 61
<212> TYPE: DNA
<213> ORGANISM: Homo Sapiens

<400> SEQUENCE: 1477
tctaagtgtg agaagctctg gtgtacaagt grtgattgca aacaggggtc tggaagcccc      60
t                                                                       61

<210> SEQ ID NO 1478
<211> LENGTH: 61
<212> TYPE: DNA
<213> ORGANISM: Homo Sapiens

<400> SEQUENCE: 1478
gaagccggat gccactctgt cagtataaat yccagtgagg ctaatttagt ggagctgtag    60
c                                                                   61

<210> SEQ ID NO 1479
<211> LENGTH: 61
<212> TYPE: DNA
<213> ORGANISM: Homo Sapiens

<400> SEQUENCE: 1479
ttcatgtatt tacagagttg tgcaatcatc rctgtaacct aattttagaa tatatttatc    60
a                                                                   61

<210> SEQ ID NO 1480
<211> LENGTH: 61
<212> TYPE: DNA
<213> ORGANISM: Homo Sapiens

<400> SEQUENCE: 1480
tgaagtaaag agactggcgg gtagaaaggc rtaggataga gtcatagagt cactcagcag    60
a                                                                   61

<210> SEQ ID NO 1481
<211> LENGTH: 61
<212> TYPE: DNA
<213> ORGANISM: Homo Sapiens

<400> SEQUENCE: 1481
acaagacaga ggaccaggca ctgctcctag rtttaggcct gaaggatgct aagtgggtga    60
t                                                                   61

<210> SEQ ID NO 1482
<211> LENGTH: 61
<212> TYPE: DNA
<213> ORGANISM: Homo Sapiens

<400> SEQUENCE: 1482
tatttcaaag acagggtctt tgtcctttta wgactactca cttagcctaa tatcctcaac    60
g                                                                   61

<210> SEQ ID NO 1483
<211> LENGTH: 61
<212> TYPE: DNA
<213> ORGANISM: Homo Sapiens

<400> SEQUENCE: 1483
gagataattg gggtttctca tcagttgact kgagttgatc agagcccaga ttatactggg    60
t                                                                   61

<210> SEQ ID NO 1484
<211> LENGTH: 61
<212> TYPE: DNA
<213> ORGANISM: Homo Sapiens

<400> SEQUENCE: 1484
ggcccgaatt ctgtttagca cagagaagct matttatggt tgggtttttg gcttaaatcc    60

-continued t                                                              61

<210> SEQ ID NO 1485
<211> LENGTH: 61
<212> TYPE: DNA
<213> ORGANISM: Homo Sapiens

<400> SEQUENCE: 1485
agtatacacg caggtggata aaataaagaa rgtcagttta agtaagcacg cagtagccat    60
g                                                              61

<210> SEQ ID NO 1486
<211> LENGTH: 61
<212> TYPE: DNA
<213> ORGANISM: Homo Sapiens

<400> SEQUENCE: 1486
taaagtacac atggcaagta ttggttgata mgtagtttgt tgtcaattat agaaacaatt    60
t                                                              61

<210> SEQ ID NO 1487
<211> LENGTH: 61
<212> TYPE: DNA
<213> ORGANISM: Homo Sapiens

<400> SEQUENCE: 1487
catcggttca agaggctaac ctgtcttcac ygaattactt ttacaacttt gtacaaaatc    60
a                                                              61

<210> SEQ ID NO 1488
<211> LENGTH: 61
<212> TYPE: DNA
<213> ORGANISM: Homo Sapiens

<400> SEQUENCE: 1488
gggtttgtct ttattttaac gaactcaaat mtctaccagt gctgaggtga ctacccaggg    60
a                                                              61

<210> SEQ ID NO 1489
<211> LENGTH: 61
<212> TYPE: DNA
<213> ORGANISM: Homo Sapiens

<400> SEQUENCE: 1489
tggatgaaac catcttagga gtgtagaaaa rtaataggag agttccagaa actggatcca    60
g                                                              61

<210> SEQ ID NO 1490
<211> LENGTH: 61
<212> TYPE: DNA
<213> ORGANISM: Homo Sapiens

<400> SEQUENCE: 1490
tatattgaga ttaatacatg aaaatgctta raagtgatag gaattattga gaaacttatg    60
a                                                              61

<210> SEQ ID NO 1491
<211> LENGTH: 61
<212> TYPE: DNA
<213> ORGANISM: Homo Sapiens

```
<400> SEQUENCE: 1491
ctgacagatg caaagtttgg gttgttgtga yagttaccag tgtgggttca agtcttcact    60
c                                                                   61

<210> SEQ ID NO 1492
<211> LENGTH: 61
<212> TYPE: DNA
<213> ORGANISM: Homo Sapiens

<400> SEQUENCE: 1492
cctctgcaat ggggtccagg actgcatgga yggctcagat gaggggcccc actgccgagg    60
t                                                                   61

<210> SEQ ID NO 1493
<211> LENGTH: 61
<212> TYPE: DNA
<213> ORGANISM: Homo Sapiens

<400> SEQUENCE: 1493
ttctttataa attacccggt ctcagatatt yctgtatggc aatgcaaaac taattcatac    60
a                                                                   61

<210> SEQ ID NO 1494
<211> LENGTH: 61
<212> TYPE: DNA
<213> ORGANISM: Homo Sapiens

<400> SEQUENCE: 1494
agtgagtggt tagtaaacaa aaggaagaat saccttggcc ttagggttat aaccagacac    60
a                                                                   61

<210> SEQ ID NO 1495
<211> LENGTH: 61
<212> TYPE: DNA
<213> ORGANISM: Homo Sapiens

<400> SEQUENCE: 1495
ataaaagagt ggtaccatgc atcagaagta rgtcctagaa tgtgacaggt gaggtatggg    60
g                                                                   61

<210> SEQ ID NO 1496
<211> LENGTH: 61
<212> TYPE: DNA
<213> ORGANISM: Homo Sapiens

<400> SEQUENCE: 1496
tgttagaaaa gggctctcat ttggagaaat sagacgcatt caaataatat gaactggcca    60
g                                                                   61

<210> SEQ ID NO 1497
<211> LENGTH: 61
<212> TYPE: DNA
<213> ORGANISM: Homo Sapiens

<400> SEQUENCE: 1497
gagagatttc attacagtca ttctgttttc yttacttaac caaagcattg tacaaggaat    60
t                                                                   61
```

```
<210> SEQ ID NO 1498
<211> LENGTH: 61
<212> TYPE: DNA
<213> ORGANISM: Homo Sapiens

<400> SEQUENCE: 1498
gcagtttaaa ggatcaaatg agataatgag ygttaaggtg ttttgaaaaa catacaactg    60
c                                                                   61

<210> SEQ ID NO 1499
<211> LENGTH: 61
<212> TYPE: DNA
<213> ORGANISM: Homo Sapiens

<400> SEQUENCE: 1499
cttgcgaggc cctccaccca cctgttgaca rtctgggcat cggtgccttc acacatgctc    60
c                                                                   61

<210> SEQ ID NO 1500
<211> LENGTH: 61
<212> TYPE: DNA
<213> ORGANISM: Homo Sapiens

<400> SEQUENCE: 1500
ttctaggatg gtagagagta gtcttcagcc ygagagccat ccctagggaa gtagctgaat    60
t                                                                   61

<210> SEQ ID NO 1501
<211> LENGTH: 61
<212> TYPE: DNA
<213> ORGANISM: Homo Sapiens

<400> SEQUENCE: 1501
tttatctgtt tataagtacc aatacatcca rttccagtaa tgtgccacat atttgccaac    60
t                                                                   61

<210> SEQ ID NO 1502
<211> LENGTH: 61
<212> TYPE: DNA
<213> ORGANISM: Homo Sapiens

<400> SEQUENCE: 1502
ttgaattgta tttgtttttt ctgcagttgt rgcacaatac tggcacatag tgagcaagta    60
g                                                                   61

<210> SEQ ID NO 1503
<211> LENGTH: 61
<212> TYPE: DNA
<213> ORGANISM: Homo Sapiens

<400> SEQUENCE: 1503
cttcatgaga ttttgaagaa ttaattggga rtgtcaagga ttaaagttga gctgtcattt    60
a                                                                   61

<210> SEQ ID NO 1504
<211> LENGTH: 61
<212> TYPE: DNA
<213> ORGANISM: Homo Sapiens

<400> SEQUENCE: 1504
attgtggcaa agacacactt gattccagca sttacaatct agcatgtgag acaaacagtt    60
```

```
a                                                               61

<210> SEQ ID NO 1505
<211> LENGTH: 61
<212> TYPE: DNA
<213> ORGANISM: Homo Sapiens

<400> SEQUENCE: 1505
acgaggtata tcaggttgag ctatactggc yattacactt tggatactac tctaaatctc    60
t                                                                   61

<210> SEQ ID NO 1506
<211> LENGTH: 61
<212> TYPE: DNA
<213> ORGANISM: Homo Sapiens

<400> SEQUENCE: 1506
aaagctaaag atctgagggt ttttaaacct rcaaatcaca ccaacttcag tcaggctgtc    60
g                                                                   61

<210> SEQ ID NO 1507
<211> LENGTH: 61
<212> TYPE: DNA
<213> ORGANISM: Homo Sapiens

<400> SEQUENCE: 1507 caatttttc agtgtctcca agtcatagct sttctttcta taaagtgaag aaataaata     60 t                                                                   61

<210> SEQ ID NO 1508
<211> LENGTH: 61
<212> TYPE: DNA
<213> ORGANISM: Homo Sapiens

<400> SEQUENCE: 1508
aatgagtaag aagtgaggag gtgctctttt sagaagtgtg gtaagagaag acctttttga    60
a                                                                   61

<210> SEQ ID NO 1509
<211> LENGTH: 61
<212> TYPE: DNA
<213> ORGANISM: Homo Sapiens

<400> SEQUENCE: 1509
agtacagtat tataatctta tggtaccaca rtcatatatg cggcatatct ttgatggaaa    60
t                                                                   61

<210> SEQ ID NO 1510
<211> LENGTH: 61
<212> TYPE: DNA
<213> ORGANISM: Homo Sapiens

<400> SEQUENCE: 1510
aataaatatt ttacctatat gaaatacagt kgccaacttc tgtcattact taatagttac    60
a                                                                   61

<210> SEQ ID NO 1511
<211> LENGTH: 61
<212> TYPE: DNA
<213> ORGANISM: Homo Sapiens
```

```
<400> SEQUENCE: 1511
atttcattta tcctccaaag gaccttatga katgggcatt gttatattac acgtgaaaca    60
a                                                                    61

<210> SEQ ID NO 1512
<211> LENGTH: 61
<212> TYPE: DNA
<213> ORGANISM: Homo Sapiens

<400> SEQUENCE: 1512
aggctcataa ataaaacatt tccttttgta ygagctgaga gtataaatct tgagacagaa    60
a                                                                    61

<210> SEQ ID NO 1513
<211> LENGTH: 61
<212> TYPE: DNA
<213> ORGANISM: Homo Sapiens

<400> SEQUENCE: 1513
tcgtattgga agctttagcc agaacattca kgattaaaat cttcaatgac cctttacaa    60 a                                                                    61

<210> SEQ ID NO 1514
<211> LENGTH: 61
<212> TYPE: DNA
<213> ORGANISM: Homo Sapiens

<400> SEQUENCE: 1514 tatttttca gtatattcta accaatactc wtttctgacc ttcagaaaca catgtctaat    60
a                                                                    61

<210> SEQ ID NO 1515
<211> LENGTH: 61
<212> TYPE: DNA
<213> ORGANISM: Homo Sapiens

<400> SEQUENCE: 1515
gataggcatt gattacctgt atgtgaacat mttctgtaga gtgaataacg tgttaaaaag    60
t                                                                    61

<210> SEQ ID NO 1516
<211> LENGTH: 61
<212> TYPE: DNA
<213> ORGANISM: Homo Sapiens

<400> SEQUENCE: 1516
agtagatata attcaaagaa acataagaat wagtatggcc ctgttgccat tgtaaagact    60
t                                                                    61

<210> SEQ ID NO 1517
<211> LENGTH: 61
<212> TYPE: DNA
<213> ORGANISM: Homo Sapiens

<400> SEQUENCE: 1517
attactgttc cattgatgaa tcatattatg magtgtttga ccacaaagac tgcgtctgat    60
g                                                                    61
```

```
<210> SEQ ID NO 1518
<211> LENGTH: 61
<212> TYPE: DNA
<213> ORGANISM: Homo Sapiens

<400> SEQUENCE: 1518
aagcaaattg ctatttgggg accatagaca wgaggtaagg ctgtaagcag agatagccca      60
t                                                                     61

<210> SEQ ID NO 1519
<211> LENGTH: 61
<212> TYPE: DNA
<213> ORGANISM: Homo Sapiens

<400> SEQUENCE: 1519
tcatttcctg atcctattat tttgactcat rttagcccaa gaagagtatt cagtacttca      60
t                                                                     61

<210> SEQ ID NO 1520
<211> LENGTH: 61
<212> TYPE: DNA
<213> ORGANISM: Homo Sapiens

<400> SEQUENCE: 1520
aacattaaag aaaataacat gtatatactg yactcatgtc ccagtaacaa tctaacaaaa      60
t                                                                     61

<210> SEQ ID NO 1521
<211> LENGTH: 61
<212> TYPE: DNA
<213> ORGANISM: Homo Sapiens

<400> SEQUENCE: 1521
acagaaaatg ttgactattt gcaatggaac ygaaagtgaa aatacacaag gaggaaaaca      60
g                                                                     61

<210> SEQ ID NO 1522
<211> LENGTH: 61
<212> TYPE: DNA
<213> ORGANISM: Homo Sapiens

<400> SEQUENCE: 1522
ctcttgaaac tctttcacct tttgatcttg rtgacaaaca cattctaggc tttcctctta      60
c                                                                     61

<210> SEQ ID NO 1523
<211> LENGTH: 61
<212> TYPE: DNA
<213> ORGANISM: Homo Sapiens

<400> SEQUENCE: 1523 ccagggggc actttccgaa cactacttat ygaagattgt gagacaatga cagagagcca       60
a                                                                     61

<210> SEQ ID NO 1524
<211> LENGTH: 61
<212> TYPE: DNA
<213> ORGANISM: Homo Sapiens

<400> SEQUENCE: 1524
acttttacct ttgtgttttg actgttctaa rttatgcaac taatttgctt tgcattattt      60
``` a 61

<210> SEQ ID NO 1525
<211> LENGTH: 61
<212> TYPE: DNA
<213> ORGANISM: Homo Sapiens

<400> SEQUENCE: 1525
tggatttggt atctgggctt gcaggtccct rgtatagagc aatttgggca gtacctaaga      60
t                                                                      61

<210> SEQ ID NO 1526
<211> LENGTH: 61
<212> TYPE: DNA
<213> ORGANISM: Homo Sapiens

<400> SEQUENCE: 1526
cctatacatt tcttatattt ttgcaaagat sagttttaaa tttcagtgtg gtctaatttg      60
t                                                                      61

<210> SEQ ID NO 1527
<211> LENGTH: 61
<212> TYPE: DNA
<213> ORGANISM: Homo Sapiens

<400> SEQUENCE: 1527
gatagctaag cttcaggata taactcaaca matgaggaga gatttacatc cacggatgct      60
g                                                                      61

<210> SEQ ID NO 1528
<211> LENGTH: 61
<212> TYPE: DNA
<213> ORGANISM: Homo Sapiens

<400> SEQUENCE: 1528
tggatgaact cctttgccca cgtttctcag rtatttcatg ttaatgtcat gtatattctt      60
t                                                                      61

<210> SEQ ID NO 1529
<211> LENGTH: 61
<212> TYPE: DNA
<213> ORGANISM: Homo Sapiens

<400> SEQUENCE: 1529
taaaaagcta aagacaaaca ggctaaggat kacttcttgg tatcgaaatt tgacccattt      60
g                                                                      61

<210> SEQ ID NO 1530
<211> LENGTH: 61
<212> TYPE: DNA
<213> ORGANISM: Homo Sapiens

<400> SEQUENCE: 1530
ctgatatttc atctagactc aagcctcaca raggacttac atgtgtatcc aaatagtttt      60
c                                                                      61

<210> SEQ ID NO 1531
<211> LENGTH: 61
<212> TYPE: DNA
<213> ORGANISM: Homo Sapiens

```
<400> SEQUENCE: 1531
aagaattcac aagacatcat ctgctctaat kcaggtaaga agtataccct gtgaaaattg    60
t                                                                    61

<210> SEQ ID NO 1532
<211> LENGTH: 61
<212> TYPE: DNA
<213> ORGANISM: Homo Sapiens

<400> SEQUENCE: 1532
aagatgaaag gatatgataa gttcaggtaa ytgtttcatc cagcttatgt atatccaagg    60
t                                                                    61

<210> SEQ ID NO 1533
<211> LENGTH: 61
<212> TYPE: DNA
<213> ORGANISM: Homo Sapiens

<400> SEQUENCE: 1533
tgcaatttgg gatgcatgtc tttgtctaac rtagataagt agattcacat tttgcagggt    60
t                                                                    61

<210> SEQ ID NO 1534
<211> LENGTH: 61
<212> TYPE: DNA
<213> ORGANISM: Homo Sapiens

<400> SEQUENCE: 1534
ccacctttcc tctccaaaag aataagaagc raatcaattg tgaagatgga gcaggtgctg    60
t                                                                    61

<210> SEQ ID NO 1535
<211> LENGTH: 61
<212> TYPE: DNA
<213> ORGANISM: Homo Sapiens

<400> SEQUENCE: 1535
aagtaaggtt ttacatgtca ttatacacaa ytgcagagtt ttttgagagg ctctaatgaa    60
a                                                                    61

<210> SEQ ID NO 1536
<211> LENGTH: 61
<212> TYPE: DNA
<213> ORGANISM: Homo Sapiens

<400> SEQUENCE: 1536
agttgagggg aaaagccctt ttaacctgtt watgactgag gttagacttt tttgaattttt   60 t                                                                    61

<210> SEQ ID NO 1537
<211> LENGTH: 61
<212> TYPE: DNA
<213> ORGANISM: Homo Sapiens

<400> SEQUENCE: 1537
gaactgtaaa tagttcatca ctgagataca mgctttgtgg gacagaagtg gagaatgttg    60
t                                                                    61
```

```
<210> SEQ ID NO 1538
<211> LENGTH: 61
<212> TYPE: DNA
<213> ORGANISM: Homo Sapiens

<400> SEQUENCE: 1538
ctcaaagaag tctgaattat cgtaggcctt yacatatcac atatctttt gttctaaatt    60 t                                                                  61

<210> SEQ ID NO 1539
<211> LENGTH: 61
<212> TYPE: DNA
<213> ORGANISM: Homo Sapiens

<400> SEQUENCE: 1539
ttatctccta tatcctagga ttttgcgctg ygccaagcat acagtagaca ctccattagt    60
a                                                                  61

<210> SEQ ID NO 1540
<211> LENGTH: 61
<212> TYPE: DNA
<213> ORGANISM: Homo Sapiens

<400> SEQUENCE: 1540
gtgtattctc ttattgttgc tgacaattaa rccacatagc atttatatag gctggtggaa    60
g                                                                  61

<210> SEQ ID NO 1541
<211> LENGTH: 61
<212> TYPE: DNA
<213> ORGANISM: Homo Sapiens

<400> SEQUENCE: 1541
ttcaggggaa gttgtatgct gagataccag ycagatttct gttagaggcc ctgcttggaa    60
g                                                                  61

<210> SEQ ID NO 1542
<211> LENGTH: 61
<212> TYPE: DNA
<213> ORGANISM: Homo Sapiens

<400> SEQUENCE: 1542
gccaaggctg agtgatttag gagtcatgat rctggagaga ctcaagcccc actcccttcc    60
t                                                                  61

<210> SEQ ID NO 1543
<211> LENGTH: 61
<212> TYPE: DNA
<213> ORGANISM: Homo Sapiens

<400> SEQUENCE: 1543
ttgggtaccg gagggccgct tacgcaattc rcaagtgaac gaatttgggc gcccatggcg    60
a                                                                  61

<210> SEQ ID NO 1544
<211> LENGTH: 61
<212> TYPE: DNA
<213> ORGANISM: Homo Sapiens

<400> SEQUENCE: 1544
ccttaagtat ttattttatat gtgttgggaa wgtttcaaga cctgtcttct agctattcgg    60
```

-continued

| a | 61 |

<210> SEQ ID NO 1545
<211> LENGTH: 61
<212> TYPE: DNA
<213> ORGANISM: Homo Sapiens

<400> SEQUENCE: 1545

| gtcttgagta tctgtaagtg aatactggta rtcagcttgg ggtggagaga aagtgatttg | 60 |
| a | 61 |

<210> SEQ ID NO 1546
<211> LENGTH: 61
<212> TYPE: DNA
<213> ORGANISM: Homo Sapiens

<400> SEQUENCE: 1546

| ttatccccctt atccaggaaa gttaacagaa ragacacgtt aagagaagaa aatattctct | 60 |
| a | 61 |

<210> SEQ ID NO 1547
<211> LENGTH: 61
<212> TYPE: DNA
<213> ORGANISM: Homo Sapiens

<400> SEQUENCE: 1547

| aaaaaattat ctttgccact tttacaactg wcattcacaa attattaaac atgctttaaa | 60 |
| a | 61 |

<210> SEQ ID NO 1548
<211> LENGTH: 61
<212> TYPE: DNA
<213> ORGANISM: Homo Sapiens

<400> SEQUENCE: 1548

| ctgcagaaaa gtttctgtaa gcctgcctcc rgttgaccat gtggtacccc actgagcaga | 60 |
| c | 61 |

<210> SEQ ID NO 1549
<211> LENGTH: 61
<212> TYPE: DNA
<213> ORGANISM: Homo Sapiens

<400> SEQUENCE: 1549

| tctctgagga tatctggcat ctcttcctat stctgtgacc tttcttttct ttgccccctt | 60 |
| g | 61 |

<210> SEQ ID NO 1550
<211> LENGTH: 61
<212> TYPE: DNA
<213> ORGANISM: Homo Sapiens

<400> SEQUENCE: 1550

| atcctttagg ccttaacctg tgttgctaaa yggaccttca gaactccacc taacatgtca | 60 |
| g | 61 |

<210> SEQ ID NO 1551
<211> LENGTH: 61
<212> TYPE: DNA
<213> ORGANISM: Homo Sapiens

<400> SEQUENCE: 1551
tcttcctgaa ccaaaacacc tactcaagaa ytcctataaa cttccttacg ctttgtttta    60
a                                                                    61

<210> SEQ ID NO 1552
<211> LENGTH: 61
<212> TYPE: DNA
<213> ORGANISM: Homo Sapiens

<400> SEQUENCE: 1552
ctcacaaaag gcttagtgtc atcctaggag yaattagtga gttctcacac tatcagttct    60
c                                                                    61

<210> SEQ ID NO 1553
<211> LENGTH: 61
<212> TYPE: DNA
<213> ORGANISM: Homo Sapiens

<400> SEQUENCE: 1553
attagtttag aaatataatt caggaagcaa ratggaagac ataagaaaca aggcagagac    60
c                                                                    61

<210> SEQ ID NO 1554
<211> LENGTH: 61
<212> TYPE: DNA
<213> ORGANISM: Homo Sapiens

<400> SEQUENCE: 1554
agtgggaagg aaatgggaca gatatataga rgaatagcct atgagagctg tgtgaccatc    60
a                                                                    61

<210> SEQ ID NO 1555
<211> LENGTH: 61
<212> TYPE: DNA
<213> ORGANISM: Homo Sapiens

<400> SEQUENCE: 1555
ccatgaagct gtgtgctgtt agcaaagccc rttatgagaa taactgagag agctgacaat    60
a                                                                    61

<210> SEQ ID NO 1556
<211> LENGTH: 61
<212> TYPE: DNA
<213> ORGANISM: Homo Sapiens

<400> SEQUENCE: 1556
ttcaatattt cctcatgtgt tttccaggta staaagtccg tttatgtatc tctttcattc    60
t                                                                    61

<210> SEQ ID NO 1557
<211> LENGTH: 61
<212> TYPE: DNA
<213> ORGANISM: Homo Sapiens

<400> SEQUENCE: 1557
ctgacttatt gcctcaaacc tctacactaa yttagaagag aagaggcatg tacactttca    60
g                                                                    61

```
<210> SEQ ID NO 1558
<211> LENGTH: 61
<212> TYPE: DNA
<213> ORGANISM: Homo Sapiens

<400> SEQUENCE: 1558
aatatttgta ttctcatttc tatagcagta ygatcaccat agctgaaata tggaagtaac    60
c                                                                    61

<210> SEQ ID NO 1559
<211> LENGTH: 61
<212> TYPE: DNA
<213> ORGANISM: Homo Sapiens

<400> SEQUENCE: 1559
tacatattca ttcattgtct tttctgaaaa yggatggcca agattctaaa acactcaatt    60
c                                                                    61

<210> SEQ ID NO 1560
<211> LENGTH: 61
<212> TYPE: DNA
<213> ORGANISM: Homo Sapiens
<220> FEATURE:
<221> NAME/KEY: misc_feature
<222> LOCATION: (31)..(31)
<223> OTHER INFORMATION: n is a, c, g, or t

<400> SEQUENCE: 1560
catgttaatt tttgactgga ctaagtcaca naacagttca gtcatatgca atatttttta    60
t                                                                    61

<210> SEQ ID NO 1561
<211> LENGTH: 61
<212> TYPE: DNA
<213> ORGANISM: Homo Sapiens

<400> SEQUENCE: 1561
tatatttggg ctgataatgg tgtcaaacca ragagactag ctgacagcat cacactacag    60
g                                                                    61

<210> SEQ ID NO 1562
<211> LENGTH: 61
<212> TYPE: DNA
<213> ORGANISM: Homo Sapiens

<400> SEQUENCE: 1562
gcgtctgctg ggatacaatc agagaccagc mgctaacctc agggctttca gaaaataacg    60
g                                                                    61

<210> SEQ ID NO 1563
<211> LENGTH: 61
<212> TYPE: DNA
<213> ORGANISM: Homo Sapiens

<400> SEQUENCE: 1563
ggcacagcac agcttcccag gtgtaacaac ktggttggga taggagaaaa cggttgctcc    60
t                                                                    61

<210> SEQ ID NO 1564
<211> LENGTH: 61
<212> TYPE: DNA
<213> ORGANISM: Homo Sapiens
```

```
<400> SEQUENCE: 1564
gagcaggtga ttaaacctag caatggttta yatagagatc aaggctataa aggctgtgaa    60
a                                                                    61

<210> SEQ ID NO 1565
<211> LENGTH: 61
<212> TYPE: DNA
<213> ORGANISM: Homo Sapiens

<400> SEQUENCE: 1565
aatatttcta aaatatatt ctaaaaacta yactttcgcg ttgaacattt tattccaaaa    60
t                                                                    61

<210> SEQ ID NO 1566
<211> LENGTH: 61
<212> TYPE: DNA
<213> ORGANISM: Homo Sapiens

<400> SEQUENCE: 1566
gaggagctca agccctgctt caggtggaag sgcagttgcc tggccctagc caggatcaat    60
g                                                                    61

<210> SEQ ID NO 1567
<211> LENGTH: 61
<212> TYPE: DNA
<213> ORGANISM: Homo Sapiens

<400> SEQUENCE: 1567
actaaaaata tatgctactt tgcaagtacc rttatatgcc acgctagaga tttcacattt    60
t                                                                    61

<210> SEQ ID NO 1568
<211> LENGTH: 61
<212> TYPE: DNA
<213> ORGANISM: Homo Sapiens

<400> SEQUENCE: 1568
ctacgtcaaa cagataatag tcagtattaa rgaaacctaa aagaacatac atatagaaac    60
t                                                                    61

<210> SEQ ID NO 1569
<211> LENGTH: 61
<212> TYPE: DNA
<213> ORGANISM: Homo Sapiens

<400> SEQUENCE: 1569
agacagtcaa ttcaaagtct gccatagcat mcctaattac atccctattg cccctttct    60 a                                                                    61

<210> SEQ ID NO 1570
<211> LENGTH: 61
<212> TYPE: DNA
<213> ORGANISM: Homo Sapiens

<400> SEQUENCE: 1570
caacccacct acaaagcact tttaaacttc rtcagacctg cattaaccta ttgtcaacct    60
a                                                                    61
```

```
<210> SEQ ID NO 1571
<211> LENGTH: 61
<212> TYPE: DNA
<213> ORGANISM: Homo Sapiens

<400> SEQUENCE: 1571
ggtcatatga tagatttatg tttgacgtaa raaatggcca ggttgttttc cagggtaggt      60
g                                                                     61

<210> SEQ ID NO 1572
<211> LENGTH: 61
<212> TYPE: DNA
<213> ORGANISM: Homo Sapiens

<400> SEQUENCE: 1572
gcgaaacatc tctttgcata caaaggtact rtgattcgat ctccccaacg atttttaata     60
a                                                                     61

<210> SEQ ID NO 1573
<211> LENGTH: 61
<212> TYPE: DNA
<213> ORGANISM: Homo Sapiens

<400> SEQUENCE: 1573
tgcctctcag gcaaatctcc ctctgctctc rtcccacgaa aaggggggtgc ccaattccag     60 t                                                                     61

<210> SEQ ID NO 1574
<211> LENGTH: 61
<212> TYPE: DNA
<213> ORGANISM: Homo Sapiens

<400> SEQUENCE: 1574
gcttgtctct taacctctgg gcatctgttt satcctctgg gaacactgtt tctattccat     60
g                                                                     61

<210> SEQ ID NO 1575
<211> LENGTH: 61
<212> TYPE: DNA
<213> ORGANISM: Homo Sapiens

<400> SEQUENCE: 1575
catactgtgt tccaagtctt atattaggta ytgaaatgac tgtagtgaga agaatgaaaa     60
g                                                                     61

<210> SEQ ID NO 1576
<211> LENGTH: 61
<212> TYPE: DNA
<213> ORGANISM: Homo Sapiens

<400> SEQUENCE: 1576
ctgcttacat actaactacc caagcctttg mtgcctagta ctggcaacat ggttaaacat     60
g                                                                     61

<210> SEQ ID NO 1577
<211> LENGTH: 61
<212> TYPE: DNA
<213> ORGANISM: Homo Sapiens

<400> SEQUENCE: 1577
agctgtctta tgtttagagt agaatccaaa ycacttatca taacatataa gggccaatgt     60
```

-continued c                                                                              61

<210> SEQ ID NO 1578
<211> LENGTH: 61
<212> TYPE: DNA
<213> ORGANISM: Homo Sapiens

<400> SEQUENCE: 1578 acctaattttt tggtattcat ccattttttcc kgagaacaac acttttctca ttcttgctgt    60
c                                                                              61

<210> SEQ ID NO 1579
<211> LENGTH: 61
<212> TYPE: DNA
<213> ORGANISM: Homo Sapiens

<400> SEQUENCE: 1579
atcagatctg aaggtagtcc tgagtacccc yaacatacat agtatagtca gaaaaagttg    60
g                                                                              61

<210> SEQ ID NO 1580
<211> LENGTH: 61
<212> TYPE: DNA
<213> ORGANISM: Homo Sapiens

<400> SEQUENCE: 1580
attctgattt caacttattg ctcttttggg ktgaagtgga agatcctgaa tgactgctca    60
c                                                                              61

<210> SEQ ID NO 1581
<211> LENGTH: 61
<212> TYPE: DNA
<213> ORGANISM: Homo Sapiens

<400> SEQUENCE: 1581
tttctgactt ctgtgatcaa gaacagatta ytgagtctgc agctcccagc atgagcgatg    60
c                                                                              61

<210> SEQ ID NO 1582
<211> LENGTH: 61
<212> TYPE: DNA
<213> ORGANISM: Homo Sapiens

<400> SEQUENCE: 1582
aatacggtca gagagacaag aagagaacaa ycaaacagta tatttggcac tgtaaggagt    60
a                                                                              61

<210> SEQ ID NO 1583
<211> LENGTH: 61
<212> TYPE: DNA
<213> ORGANISM: Homo Sapiens

<400> SEQUENCE: 1583
aatctcagaa aaagatcacc cgtaagcata rtagtacagg ggtagtctga agtttgacta    60
a                                                                              61

<210> SEQ ID NO 1584
<211> LENGTH: 61
<212> TYPE: DNA
<213> ORGANISM: Homo Sapiens

<400> SEQUENCE: 1584
tcatttgata tacatactat attaaggctg yagttgatac cctgacaagt atgtaattca  60
t                                                                 61

<210> SEQ ID NO 1585
<211> LENGTH: 61
<212> TYPE: DNA
<213> ORGANISM: Homo Sapiens

<400> SEQUENCE: 1585
actctggttt gaccattacg ttgtagcgtg kttagcaact gtggttgtgt tggggtttgg  60
g                                                                 61

<210> SEQ ID NO 1586
<211> LENGTH: 61
<212> TYPE: DNA
<213> ORGANISM: Homo Sapiens

<400> SEQUENCE: 1586
aagaacccag gttaagctgg tagttgtaca rgcgaatcag gtataaagag cagatgaact  60
c                                                                 61

<210> SEQ ID NO 1587
<211> LENGTH: 61
<212> TYPE: DNA
<213> ORGANISM: Homo Sapiens

<400> SEQUENCE: 1587
ctgcattcat tcagagaaga tcctttgaca rctagtgaga tcccaggcac taatttgtca  60
t                                                                 61

<210> SEQ ID NO 1588
<211> LENGTH: 61
<212> TYPE: DNA
<213> ORGANISM: Homo Sapiens

<400> SEQUENCE: 1588
ttaggaattc agatggtagc aatgggtagc ktatactcag taagagagga acacaggtga  60
t                                                                 61

<210> SEQ ID NO 1589
<211> LENGTH: 61
<212> TYPE: DNA
<213> ORGANISM: Homo Sapiens

<400> SEQUENCE: 1589
gtaggagttt taagttgctc ttaggtggtt yttattcgct gcaggttatg ttagcttatt  60
t                                                                 61

<210> SEQ ID NO 1590
<211> LENGTH: 61
<212> TYPE: DNA
<213> ORGANISM: Homo Sapiens

<400> SEQUENCE: 1590
tgatcaatct ttgccaggtt agtcatgaaa ytgattcttc tgaaaagcta gatacacttc  60
c                                                                 61

```
<210> SEQ ID NO 1591
<211> LENGTH: 61
<212> TYPE: DNA
<213> ORGANISM: Homo Sapiens

<400> SEQUENCE: 1591
aagcaaaaga atattggagg caaaacaaca ycatattcaa gactcttctg atcttagaca      60
a                                                                     61

<210> SEQ ID NO 1592
<211> LENGTH: 61
<212> TYPE: DNA
<213> ORGANISM: Homo Sapiens

<400> SEQUENCE: 1592
agcaatatgc atcttgatgt aaagatttgt yatggaacac aaccaaactc atttaaccag      60
t                                                                     61

<210> SEQ ID NO 1593
<211> LENGTH: 61
<212> TYPE: DNA
<213> ORGANISM: Homo Sapiens

<400> SEQUENCE: 1593
ttattccaaa atgttaaaga atgctatttt yccctacact tagaatcaga gtaccagtaa      60
g                                                                     61

<210> SEQ ID NO 1594
<211> LENGTH: 61
<212> TYPE: DNA
<213> ORGANISM: Homo Sapiens

<400> SEQUENCE: 1594
attagtgctg ttttcctgat tttactatcc yttaacatta tccaagaata ccaatacatt      60
t                                                                     61

<210> SEQ ID NO 1595
<211> LENGTH: 61
<212> TYPE: DNA
<213> ORGANISM: Homo Sapiens

<400> SEQUENCE: 1595
tcagttaaca ttcttgagaa ggagataaac mgtaagcaag tgaacaggca cgtaaataat      60
a                                                                     61

<210> SEQ ID NO 1596
<211> LENGTH: 61
<212> TYPE: DNA
<213> ORGANISM: Homo Sapiens

<400> SEQUENCE: 1596
acttcagcta aattgttcta agttgttgat ragttgaaaa tgctctgcta acattttctt      60
t                                                                     61

<210> SEQ ID NO 1597
<211> LENGTH: 61
<212> TYPE: DNA
<213> ORGANISM: Homo Sapiens

<400> SEQUENCE: 1597
ccctcaaaga ggtgaaaact aaaagttata ygtgaaatgg ttatttagaa taccaattta      60
```

```
g                                                               61

<210> SEQ ID NO 1598
<211> LENGTH: 61
<212> TYPE: DNA
<213> ORGANISM: Homo Sapiens

<400> SEQUENCE: 1598
tttgagacct accaagcttt gtgttaagag ygaaacctgt aggcaattaa acatttgagc    60
c                                                                   61

<210> SEQ ID NO 1599
<211> LENGTH: 61
<212> TYPE: DNA
<213> ORGANISM: Homo Sapiens

<400> SEQUENCE: 1599
ttattcctcc attattagac catttgcctt sgtaaaagaa ctaattacta aattcactac    60
c                                                                   61

<210> SEQ ID NO 1600
<211> LENGTH: 61
<212> TYPE: DNA
<213> ORGANISM: Homo Sapiens

<400> SEQUENCE: 1600
cactaaataa aaatacaaat tgtcaccaaa rtatctgttt ttcctccttc catttctcct    60
g                                                                   61

<210> SEQ ID NO 1601
<211> LENGTH: 61
<212> TYPE: DNA
<213> ORGANISM: Homo Sapiens

<400> SEQUENCE: 1601
ctaaggaaat gctatgaaaa tcagtgcaca wctattcaca ttcccctttt tccttctaaa    60
a                                                                   61

<210> SEQ ID NO 1602
<211> LENGTH: 61
<212> TYPE: DNA
<213> ORGANISM: Homo Sapiens

<400> SEQUENCE: 1602
gttttctcca taaaaatgct gaacatctgg statttgcgc ccatacaggt gattggctga    60
g                                                                   61

<210> SEQ ID NO 1603
<211> LENGTH: 61
<212> TYPE: DNA
<213> ORGANISM: Homo Sapiens

<400> SEQUENCE: 1603
acaggtgatt ggctgagttt gaccccttc rtctggtagt ttggcatgag gaaaacactg    60
c                                                                   61

<210> SEQ ID NO 1604
<211> LENGTH: 61
<212> TYPE: DNA
<213> ORGANISM: Homo Sapiens
```

```
<400> SEQUENCE: 1604
aactaaaaca ggcccgttat tgtgtagaaa yagatgtgcc taaaggtgtg gtccccaaat    60
g                                                                   61

<210> SEQ ID NO 1605
<211> LENGTH: 61
<212> TYPE: DNA
<213> ORGANISM: Homo Sapiens

<400> SEQUENCE: 1605
taaataaaaa ctagcccaac tttttctcta yatacctttg gctctttttt tttttttttt    60
t                                                                   61

<210> SEQ ID NO 1606
<211> LENGTH: 61
<212> TYPE: DNA
<213> ORGANISM: Homo Sapiens

<400> SEQUENCE: 1606
gaatgagcca tttcttttga cccatttttt yctacttgcc agttctattt acattctcta    60
t                                                                   61

<210> SEQ ID NO 1607
<211> LENGTH: 61
<212> TYPE: DNA
<213> ORGANISM: Homo Sapiens

<400> SEQUENCE: 1607
ttttaaagac cccctcatgg tgacacggag raggagagcc agttgtttca aacacagctg    60
c                                                                   61

<210> SEQ ID NO 1608
<211> LENGTH: 61
<212> TYPE: DNA
<213> ORGANISM: Homo Sapiens

<400> SEQUENCE: 1608
ggcacacctt aggggaggat gtagctctca rtcatgaaac taacacattt ccacatttct    60
t                                                                   61

<210> SEQ ID NO 1609
<211> LENGTH: 61
<212> TYPE: DNA
<213> ORGANISM: Homo Sapiens

<400> SEQUENCE: 1609
agcattaatt tacttattca tcaaatactt wttgagcata ctgagtacca gccattgtgc    60
a                                                                   61

<210> SEQ ID NO 1610
<211> LENGTH: 61
<212> TYPE: DNA
<213> ORGANISM: Homo Sapiens

<400> SEQUENCE: 1610
ttttttcttt ctttgttctt gttttctctct rttctctcag tagtctacat ctccttggaa    60
a                                                                    61
```

```
<210> SEQ ID NO 1611
<211> LENGTH: 61
<212> TYPE: DNA
<213> ORGANISM: Homo Sapiens

<400> SEQUENCE: 1611
tattctcttt agctcacagg gcttcaaaaa ygtctatgct atccttcttt cagagattat    60
t                                                                   61

<210> SEQ ID NO 1612
<211> LENGTH: 61
<212> TYPE: DNA
<213> ORGANISM: Homo Sapiens

<400> SEQUENCE: 1612
ctgttttcca tagcagctgc actattttac mttcccacca gcaatgaaca aggattccaa    60
c                                                                   61

<210> SEQ ID NO 1613
<211> LENGTH: 61
<212> TYPE: DNA
<213> ORGANISM: Homo Sapiens

<400> SEQUENCE: 1613
aagcaaagga gcttcctaag agaagataac rcgctgagcc atgcccatgg cctttgcctc    60
c                                                                   61

<210> SEQ ID NO 1614
<211> LENGTH: 61
<212> TYPE: DNA
<213> ORGANISM: Homo Sapiens

<400> SEQUENCE: 1614
tctatttttt taaacaactc attttttaacc rtcttggtga aagagacaag gacgtaaatt    60
g                                                                   61

<210> SEQ ID NO 1615
<211> LENGTH: 61
<212> TYPE: DNA
<213> ORGANISM: Homo Sapiens

<400> SEQUENCE: 1615
gcagtagcag cccctaattc ctagcatctt sgagaaagac tagttctcaa gaatttgaaa    60
c                                                                   61

<210> SEQ ID NO 1616
<211> LENGTH: 61
<212> TYPE: DNA
<213> ORGANISM: Homo Sapiens

<400> SEQUENCE: 1616
cctgcactga gtttgggttt gaagaaggcc rgagaatttc cccgagcttt ttgaatatgc    60
t                                                                   61

<210> SEQ ID NO 1617
<211> LENGTH: 61
<212> TYPE: DNA
<213> ORGANISM: Homo Sapiens

<400> SEQUENCE: 1617
tgaacctaat atcattttca ctcttcatgc raaccctctt gttcctgtgg ttaaagaatc    60
``` a 61

<210> SEQ ID NO 1618
<211> LENGTH: 61
<212> TYPE: DNA
<213> ORGANISM: Homo Sapiens

<400> SEQUENCE: 1618
cgtattggca cggttgtctt ccaaacccat ygatgccgga acatgggtca ggaagaacac    60
a                                                                   61

<210> SEQ ID NO 1619
<211> LENGTH: 61
<212> TYPE: DNA
<213> ORGANISM: Homo Sapiens

<400> SEQUENCE: 1619
tcagccagga tttgatgttt cagccttgag rtagaacttc tttcagaaac gtcagttctt    60
g                                                                   61

<210> SEQ ID NO 1620
<211> LENGTH: 61
<212> TYPE: DNA
<213> ORGANISM: Homo Sapiens

<400> SEQUENCE: 1620
aaatcttcat aaacactcaa tttcagttct saccaaatat ggagtcaaac caactaagcc    60
a                                                                   61

<210> SEQ ID NO 1621
<211> LENGTH: 61
<212> TYPE: DNA
<213> ORGANISM: Homo Sapiens

<400> SEQUENCE: 1621
ggaaggtcga tgacccagtt aacaagccaa ytggcaaatg aacagggta tttatgaaaa    60 a                                                                   61

<210> SEQ ID NO 1622
<211> LENGTH: 61
<212> TYPE: DNA
<213> ORGANISM: Homo Sapiens

<400> SEQUENCE: 1622
gaagggtaaa gttaactttc taagacatac ragaggagtt gaaattagat gtgaatctag    60
a                                                                   61

<210> SEQ ID NO 1623
<211> LENGTH: 61
<212> TYPE: DNA
<213> ORGANISM: Homo Sapiens

<400> SEQUENCE: 1623
agatcggcaa tggctagtga catgtttgtg rgccaattat aaggtaaatg taagtcagta    60
t                                                                   61

<210> SEQ ID NO 1624
<211> LENGTH: 61
<212> TYPE: DNA
<213> ORGANISM: Homo Sapiens

<400> SEQUENCE: 1624
aatatacaca ttcaatgtca ccagagggaa rtggtaaaga acaacaccct ttggtatcag    60
g                                                                   61

<210> SEQ ID NO 1625
<211> LENGTH: 61
<212> TYPE: DNA
<213> ORGANISM: Homo Sapiens

<400> SEQUENCE: 1625
aagtctaact atcagtgagc gagcaggggg wgagcatttt ctttctgaag ggagttatta    60
c                                                                   61

<210> SEQ ID NO 1626
<211> LENGTH: 61
<212> TYPE: DNA
<213> ORGANISM: Homo Sapiens

<400> SEQUENCE: 1626
tgctttctgc cttctgtgtt gtttcggttc yagtgaccaa gggcacagct tggtgactgg    60
c                                                                   61

<210> SEQ ID NO 1627
<211> LENGTH: 61
<212> TYPE: DNA
<213> ORGANISM: Homo Sapiens

<400> SEQUENCE: 1627
taatacaatc atctgagtct tgtatggttt stgaaatgga tgctagaaga gataacttga    60
a                                                                   61

<210> SEQ ID NO 1628
<211> LENGTH: 61
<212> TYPE: DNA
<213> ORGANISM: Homo Sapiens

<400> SEQUENCE: 1628
ttatcaggca aggtatatgg ctggtagaaa rctctgagtc caaggcaaag tgactatcca    60
c                                                                   61

<210> SEQ ID NO 1629
<211> LENGTH: 61
<212> TYPE: DNA
<213> ORGANISM: Homo Sapiens

<400> SEQUENCE: 1629 ctcccccat catgactatt gccctacttt ragtagacat agattgagaa tatgttttgg     60
c                                                                   61

<210> SEQ ID NO 1630
<211> LENGTH: 61
<212> TYPE: DNA
<213> ORGANISM: Homo Sapiens

<400> SEQUENCE: 1630
ccctgccagc ttccccaggt ttttgtaggc rtcaaacgag acatataggat aggctctttc   60 c                                                                   61

```
<210> SEQ ID NO 1631
<211> LENGTH: 61
<212> TYPE: DNA
<213> ORGANISM: Homo Sapiens

<400> SEQUENCE: 1631
catctcccca ggcctttgct acaggttttc yagccctgga cggttcagga attgccctac    60
c                                                                   61

<210> SEQ ID NO 1632
<211> LENGTH: 61
<212> TYPE: DNA
<213> ORGANISM: Homo Sapiens

<400> SEQUENCE: 1632
agatcctttg gaagtcatga gcatctaagt yggtgagcta acattagga tattaaccag     60
a                                                                   61

<210> SEQ ID NO 1633
<211> LENGTH: 61
<212> TYPE: DNA
<213> ORGANISM: Homo Sapiens

<400> SEQUENCE: 1633
ttatataaca gctcaggacc aagaagttag ygttgaatgg ttatgttcac atgtggtcca    60
a                                                                   61

<210> SEQ ID NO 1634
<211> LENGTH: 61
<212> TYPE: DNA
<213> ORGANISM: Homo Sapiens

<400> SEQUENCE: 1634
ataattcctg tattattttt tggaaattat scattctgac agaaaagagc ctgggtggag    60
a                                                                   61

<210> SEQ ID NO 1635
<211> LENGTH: 61
<212> TYPE: DNA
<213> ORGANISM: Homo Sapiens

<400> SEQUENCE: 1635
caccttaaaa tcctctgtat cttggaaatg yatgtcagat tggcaaaaat ttaaggtatt    60
t                                                                   61

<210> SEQ ID NO 1636
<211> LENGTH: 61
<212> TYPE: DNA
<213> ORGANISM: Homo Sapiens

<400> SEQUENCE: 1636
attatatgaa taaatataaa tatctacatg ygtatatgga tatggaaaat atctgcgtgt    60
a                                                                   61

<210> SEQ ID NO 1637
<211> LENGTH: 61
<212> TYPE: DNA
<213> ORGANISM: Homo Sapiens

<400> SEQUENCE: 1637
tgtctgtgca aggacaagga aaagaatttc yctactggct cctgcccct ctagttcagg     60
```

```
g                                                              61

<210> SEQ ID NO 1638
<211> LENGTH: 61
<212> TYPE: DNA
<213> ORGANISM: Homo Sapiens

<400> SEQUENCE: 1638
aacacaggaa gcttcttgat tctaactcag rgaccctcat gaagttgaag tcaaggtgtt    60
g                                                              61

<210> SEQ ID NO 1639
<211> LENGTH: 61
<212> TYPE: DNA
<213> ORGANISM: Homo Sapiens

<400> SEQUENCE: 1639
tccaagatac aaaactctcc aggttttcct yttctacctc tagctccacc ttcttattcc    60
a                                                              61

<210> SEQ ID NO 1640
<211> LENGTH: 61
<212> TYPE: DNA
<213> ORGANISM: Homo Sapiens

<400> SEQUENCE: 1640
cactgaattt gtcaacttgg gtaccactga ygacaatatc cagagcagtt ttggcaaggc    60
a                                                              61

<210> SEQ ID NO 1641
<211> LENGTH: 61
<212> TYPE: DNA
<213> ORGANISM: Homo Sapiens

<400> SEQUENCE: 1641
gaaaagtgga gtcctagtaa gagtgcttta sactttagga aaatcttcaa caaatatgag    60
t                                                              61

<210> SEQ ID NO 1642
<211> LENGTH: 61
<212> TYPE: DNA
<213> ORGANISM: Homo Sapiens

<400> SEQUENCE: 1642
ttgggttcca ggcacagatg actggtagtg kttacctaga gttctgtgtt gagaaggatt    60
c                                                              61

<210> SEQ ID NO 1643
<211> LENGTH: 61
<212> TYPE: DNA
<213> ORGANISM: Homo Sapiens

<400> SEQUENCE: 1643
ggaggcggca gcagcaaagt cccaagaaca magtgctggt gtaggagtca ggcccgcatc    60
t                                                              61

<210> SEQ ID NO 1644
<211> LENGTH: 61
<212> TYPE: DNA
<213> ORGANISM: Homo Sapiens
```

```
<400> SEQUENCE: 1644
ctgaaaggtt cttcaaagtc aggtccctaa saaagctgtt ccatctccag ctcagcgtgt      60
t                                                                     61

<210> SEQ ID NO 1645
<211> LENGTH: 61
<212> TYPE: DNA
<213> ORGANISM: Homo Sapiens

<400> SEQUENCE: 1645
gccccagaag agaagaggct tctttctcac ygtgaggcag aaacaaattt atctgtatgt      60
a                                                                     61

<210> SEQ ID NO 1646
<211> LENGTH: 61
<212> TYPE: DNA
<213> ORGANISM: Homo Sapiens

<400> SEQUENCE: 1646
aagcagcctc cctctgttac tactataaac rcccattctg caggcagtgt gagggcacag      60
c                                                                     61

<210> SEQ ID NO 1647
<211> LENGTH: 61
<212> TYPE: DNA
<213> ORGANISM: Homo Sapiens

<400> SEQUENCE: 1647
ggtggaagca ccccacttcc tttacctggt stcccatcac ctatcagaac cagagagcgc      60
a                                                                     61

<210> SEQ ID NO 1648
<211> LENGTH: 61
<212> TYPE: DNA
<213> ORGANISM: Homo Sapiens

<400> SEQUENCE: 1648
agaatcccag ctcagatcca gcagaagaca yggcatgcga gatcttgaaa gatcccttt       60 g                                                                     61

<210> SEQ ID NO 1649
<211> LENGTH: 61
<212> TYPE: DNA
<213> ORGANISM: Homo Sapiens

<400> SEQUENCE: 1649
tgtggtagta tcgcagtgct tgtgtcgaag ycactcttat tttacctaat aatggcccca      60
a                                                                     61

<210> SEQ ID NO 1650
<211> LENGTH: 61
<212> TYPE: DNA
<213> ORGANISM: Homo Sapiens

<400> SEQUENCE: 1650
gtctcttatg cttctgggga gaaatcacca wctggcgagg gtttcctggc ctttgggggt      60
c                                                                     61
```

```
<210> SEQ ID NO 1651
<211> LENGTH: 61
<212> TYPE: DNA
<213> ORGANISM: Homo Sapiens

<400> SEQUENCE: 1651
gagcccttct attccttcca ctttgaccag kttttgcctc tcttggtggt gggtccctta    60
g                                                                    61

<210> SEQ ID NO 1652
<211> LENGTH: 61
<212> TYPE: DNA
<213> ORGANISM: Homo Sapiens

<400> SEQUENCE: 1652
gttagaaaag gagggaagtt acaattgcac rggggtagca tggcagactt tctggggatg    60
a                                                                    61

<210> SEQ ID NO 1653
<211> LENGTH: 61
<212> TYPE: DNA
<213> ORGANISM: Homo Sapiens

<400> SEQUENCE: 1653
acacagatgg gtatgggact ctgggccaaa ytgatgcttc tccaaacgat ttctactctt    60
t                                                                    61

<210> SEQ ID NO 1654
<211> LENGTH: 61
<212> TYPE: DNA
<213> ORGANISM: Homo Sapiens

<400> SEQUENCE: 1654
gaaagtcagt tccttgtctc tgttcttaac rccaggcctt tccaccgtat cggcaatttt    60
g                                                                    61

<210> SEQ ID NO 1655
<211> LENGTH: 61
<212> TYPE: DNA
<213> ORGANISM: Homo Sapiens

<400> SEQUENCE: 1655
cttttactta ttttgcccat gtccactcat kgttttttac tcattttcaa agggagtaca    60
c                                                                    61

<210> SEQ ID NO 1656
<211> LENGTH: 61
<212> TYPE: DNA
<213> ORGANISM: Homo Sapiens

<400> SEQUENCE: 1656
ctttcgtatg tatttgtgaa taacagaaga yacaatgaca tggtgatggt aacacatgtt    60
g                                                                    61

<210> SEQ ID NO 1657
<211> LENGTH: 61
<212> TYPE: DNA
<213> ORGANISM: Homo Sapiens

<400> SEQUENCE: 1657
tcctcgtgga tatagctgct catggttcca satcttggga aggacaaggt ttactcacac    60
``` a                                                                61

<210> SEQ ID NO 1658
<211> LENGTH: 61
<212> TYPE: DNA
<213> ORGANISM: Homo Sapiens

<400> SEQUENCE: 1658
gcgtgagcca ccgcgcctgg ccgagaaatt rgaattttac atcaaacaaa aagtagagct    60
c                                                                61

<210> SEQ ID NO 1659
<211> LENGTH: 61
<212> TYPE: DNA
<213> ORGANISM: Homo Sapiens

<400> SEQUENCE: 1659
gtgagaattt catggcccag atcataaggc rgagggcttt aaagttctct tcaaatcgca    60
c                                                                61

<210> SEQ ID NO 1660
<211> LENGTH: 61
<212> TYPE: DNA
<213> ORGANISM: Homo Sapiens

<400> SEQUENCE: 1660
gtctccaatc ttaatgccat gcccttgggg stgtatctag gaagtggcag ctccctgcat    60
t                                                                61

<210> SEQ ID NO 1661
<211> LENGTH: 61
<212> TYPE: DNA
<213> ORGANISM: Homo Sapiens

<400> SEQUENCE: 1661
tggtaaatat tttactaaac ggaatcgatc rtgtcttgaa ctaaaaacat cagcaaggca    60
t                                                                61

<210> SEQ ID NO 1662
<211> LENGTH: 61
<212> TYPE: DNA
<213> ORGANISM: Homo Sapiens

<400> SEQUENCE: 1662
atttctccat gctgttactt gtattgttgc rgagtagtat tcctttatat ggatgtatca    60
c                                                                61

<210> SEQ ID NO 1663
<211> LENGTH: 61
<212> TYPE: DNA
<213> ORGANISM: Homo Sapiens

<400> SEQUENCE: 1663
tactcagcaa acatattatc cagtttcttc sttgagcagg ccatatgatc atgtgatcag    60
c                                                                61

<210> SEQ ID NO 1664
<211> LENGTH: 61
<212> TYPE: DNA
<213> ORGANISM: Homo Sapiens

<400> SEQUENCE: 1664
tttcttgaaa actcaagaga atcttgaaac ygctgcaaaa atatgttaac ctggtaggat    60
a                                                                  61

<210> SEQ ID NO 1665
<211> LENGTH: 61
<212> TYPE: DNA
<213> ORGANISM: Homo Sapiens

<400> SEQUENCE: 1665
aggccaaagt ggcaggatca cttaagcctt kgagttcaag tttacagtga actgtggtca    60
t                                                                  61

<210> SEQ ID NO 1666
<211> LENGTH: 61
<212> TYPE: DNA
<213> ORGANISM: Homo Sapiens

<400> SEQUENCE: 1666
aatttttttc tttgagaatt caactcgaag katagtgagg aaaatgcctg attttttctga   60 a                                                                  61

<210> SEQ ID NO 1667
<211> LENGTH: 61
<212> TYPE: DNA
<213> ORGANISM: Homo Sapiens

<400> SEQUENCE: 1667
atgtggttct tgagtatgtc cagaattata wggctgttaa tgtgtcttga gccctgacct    60
a                                                                  61

<210> SEQ ID NO 1668
<211> LENGTH: 61
<212> TYPE: DNA
<213> ORGANISM: Homo Sapiens

<400> SEQUENCE: 1668
tattgctctt tatattaaag gggttatcat rttcactctg cttcaaatgt accaaatggt    60
a                                                                  61

<210> SEQ ID NO 1669
<211> LENGTH: 61
<212> TYPE: DNA
<213> ORGANISM: Homo Sapiens

<400> SEQUENCE: 1669
gtttgacaca aggaagattc tgggaagttg ragaagaaca gaacctggga ttggcagcgg    60
c                                                                  61

<210> SEQ ID NO 1670
<211> LENGTH: 61
<212> TYPE: DNA
<213> ORGANISM: Homo Sapiens

<400> SEQUENCE: 1670
taaaaatcag aaagtatctg aagttgtttt kgaagggaac aatgtgagta caaatattg     60 c                                                                  61

```
<210> SEQ ID NO 1671
<211> LENGTH: 61
<212> TYPE: DNA
<213> ORGANISM: Homo Sapiens

<400> SEQUENCE: 1671
gcagaagagc caaaggccct cggcagccaa rcatgttcaa cggccagtgc ccaggtcacc      60
a                                                                      61

<210> SEQ ID NO 1672
<211> LENGTH: 61
<212> TYPE: DNA
<213> ORGANISM: Homo Sapiens

<400> SEQUENCE: 1672
agggtcacct gggtagacac tgcccaaggc rgccgctgag ccttccccac aagaattgct      60
g                                                                      61

<210> SEQ ID NO 1673
<211> LENGTH: 61
<212> TYPE: DNA
<213> ORGANISM: Homo Sapiens

<400> SEQUENCE: 1673
aaaggagaaa acctgttttc tgtctttaac kgtccttccc ctcaactggg accctgtgct      60
c                                                                      61

<210> SEQ ID NO 1674
<211> LENGTH: 61
<212> TYPE: DNA
<213> ORGANISM: Homo Sapiens

<400> SEQUENCE: 1674
gagcagcgca cggggcttca tgtgcccact ycaggcctcc ccagccgaac atagatggga      60
a                                                                      61

<210> SEQ ID NO 1675
<211> LENGTH: 61
<212> TYPE: DNA
<213> ORGANISM: Homo Sapiens

<400> SEQUENCE: 1675
ttctaattgc tgacggtgtg gtagaagtta rtaaaactta gtatctccgt gttacctgtg      60
a                                                                      61

<210> SEQ ID NO 1676
<211> LENGTH: 61
<212> TYPE: DNA
<213> ORGANISM: Homo Sapiens

<400> SEQUENCE: 1676
attgtgtgca gcatacctag agcttacact rtgaactgta tcctaattta agctaattta      60
a                                                                      61

<210> SEQ ID NO 1677
<211> LENGTH: 61
<212> TYPE: DNA
<213> ORGANISM: Homo Sapiens

<400> SEQUENCE: 1677
cttttgttct gcttgctgta gatggagcag ktgaggaatg agctacttca ggagagagct      60
```

| | |
|---|---|
| g | 61 |

<210> SEQ ID NO 1678
<211> LENGTH: 61
<212> TYPE: DNA
<213> ORGANISM: Homo Sapiens

<400> SEQUENCE: 1678

| | |
|---|---|
| acgtcatcaa acacatgagt ggctcagaaa rcttcatcgg gtcattattt cttttttcatg | 60 |
| a | 61 |

<210> SEQ ID NO 1679
<211> LENGTH: 61
<212> TYPE: DNA
<213> ORGANISM: Homo Sapiens

<400> SEQUENCE: 1679

| | |
|---|---|
| cagaagcatg ggggtgagaa ggaagaaata kctctggatc agtgtgggcc aaaagttaat | 60 |
| t | 61 |

<210> SEQ ID NO 1680
<211> LENGTH: 61
<212> TYPE: DNA
<213> ORGANISM: Homo Sapiens

<400> SEQUENCE: 1680

| | |
|---|---|
| aacatctagg catgtgtgca agaaattctt ytatcactgg cttctataat tgagcaaggt | 60 |
| t | 61 |

<210> SEQ ID NO 1681
<211> LENGTH: 61
<212> TYPE: DNA
<213> ORGANISM: Homo Sapiens

<400> SEQUENCE: 1681

| | |
|---|---|
| tcttctaggt cccaggaggt agtctttggc stggtgtgac tgtgactgtg tcctccagct | 60 |
| c | 61 |

<210> SEQ ID NO 1682
<211> LENGTH: 61
<212> TYPE: DNA
<213> ORGANISM: Homo Sapiens

<400> SEQUENCE: 1682

| | |
|---|---|
| aaacatgcag gaataaggtc tgggaagatg yttcaagttc tgttcaaaaa agtatatcag | 60 |
| g | 61 |

<210> SEQ ID NO 1683
<211> LENGTH: 61
<212> TYPE: DNA
<213> ORGANISM: Homo Sapiens

<400> SEQUENCE: 1683

| | |
|---|---|
| aggctggtgt gtgaggttcc taatctccca rtcacagaag aaattatgtt caagacagct | 60 |
| c | 61 |

<210> SEQ ID NO 1684
<211> LENGTH: 61
<212> TYPE: DNA
<213> ORGANISM: Homo Sapiens

<400> SEQUENCE: 1684
gacacagctt aggtatgaaa atctggcaaa ycaatagtcc cccaaatgtg ttcttatgat    60
g                                                                   61

<210> SEQ ID NO 1685
<211> LENGTH: 61
<212> TYPE: DNA
<213> ORGANISM: Homo Sapiens

<400> SEQUENCE: 1685
aacagcatag tgacagatat ggcagagtgc rcaaaaccta aatagtatg tggccctta     60
c                                                                   61

<210> SEQ ID NO 1686
<211> LENGTH: 61
<212> TYPE: DNA
<213> ORGANISM: Homo Sapiens

<400> SEQUENCE: 1686
taactatctc atgaccgtgt ctgtgagtcc rttttatac agtcaaggtt caaacccagg    60
c                                                                   61

<210> SEQ ID NO 1687
<211> LENGTH: 61
<212> TYPE: DNA
<213> ORGANISM: Homo Sapiens

<400> SEQUENCE: 1687
aaaggccata gtttttaggc ccttgctcta raatgtttac tgaatctgag tgacagaccc    60
t                                                                   61

<210> SEQ ID NO 1688
<211> LENGTH: 61
<212> TYPE: DNA
<213> ORGANISM: Homo Sapiens

<400> SEQUENCE: 1688
actaataata ctgagcatct tttcatatac sagatacatc cttttggaa agcagtttag    60
t                                                                   61

<210> SEQ ID NO 1689
<211> LENGTH: 61
<212> TYPE: DNA
<213> ORGANISM: Homo Sapiens

<400> SEQUENCE: 1689
cagacacaaa aggccacatc ttacaggttt yacttacata caatgttcag aacatgtaga    60
t                                                                   61

<210> SEQ ID NO 1690
<211> LENGTH: 61
<212> TYPE: DNA
<213> ORGANISM: Homo Sapiens

<400> SEQUENCE: 1690
taatctagca gggaaaattt tcacattgga rttgagggat ctcttagact tcaccgtctg    60
c                                                                   61

```
<210> SEQ ID NO 1691
<211> LENGTH: 61
<212> TYPE: DNA
<213> ORGANISM: Homo Sapiens

<400> SEQUENCE: 1691
agaggtccct gggtccacaa cttctgttcg ytactccaca ttcttctgga ctctacccat     60
g                                                                    61

<210> SEQ ID NO 1692
<211> LENGTH: 61
<212> TYPE: DNA
<213> ORGANISM: Homo Sapiens

<400> SEQUENCE: 1692
tgagtttctc ttctgtcata tcacataaat kggttctgtc tagtctaagc ccagaggtgc     60
t                                                                    61

<210> SEQ ID NO 1693
<211> LENGTH: 61
<212> TYPE: DNA
<213> ORGANISM: Homo Sapiens

<400> SEQUENCE: 1693
ggactagcaa gtccagcctc accgtgtatc rccaaattgc tctccaaacg ataccaatct     60
c                                                                    61

<210> SEQ ID NO 1694
<211> LENGTH: 61
<212> TYPE: DNA
<213> ORGANISM: Homo Sapiens

<400> SEQUENCE: 1694
tgaccagtta ggaaaagaat cttccatata scctatcccc ctgcttgggt gggtgaggcg     60
a                                                                    61

<210> SEQ ID NO 1695
<211> LENGTH: 61
<212> TYPE: DNA
<213> ORGANISM: Homo Sapiens

<400> SEQUENCE: 1695
gatgtaaatg ttgaggcatg gaaggatctc ratgatctag tgtaaaacac cgtgtgcagc     60
a                                                                    61

<210> SEQ ID NO 1696
<211> LENGTH: 61
<212> TYPE: DNA
<213> ORGANISM: Homo Sapiens

<400> SEQUENCE: 1696
ctctcgcgat cagcagcagt aaacacacta rgaacgcact attaaaatga agagtgccta     60
c                                                                    61

<210> SEQ ID NO 1697
<211> LENGTH: 61
<212> TYPE: DNA
<213> ORGANISM: Homo Sapiens

<400> SEQUENCE: 1697
agcatccacc tttaacgaga aatcaaaaga rcaagaaacg tcatgccaat ctcctgtggg     60
```

```
g                                                               61

<210> SEQ ID NO 1698
<211> LENGTH: 61
<212> TYPE: DNA
<213> ORGANISM: Homo Sapiens

<400> SEQUENCE: 1698
gtatagaacc ttcatctcac ccatgcctcc yacagcatcc aggccccacc cagtgataag    60
a                                                               61

<210> SEQ ID NO 1699
<211> LENGTH: 61
<212> TYPE: DNA
<213> ORGANISM: Homo Sapiens

<400> SEQUENCE: 1699
taataagctt ccaggtgttg ttcctgatgc yggttcgtgc accagaatat gaacagcaat    60
a                                                               61

<210> SEQ ID NO 1700
<211> LENGTH: 61
<212> TYPE: DNA
<213> ORGANISM: Homo Sapiens

<400> SEQUENCE: 1700
ctgtatccat tcagtagcca atgtaaaatg rtgccaaact tactatttta gattgaaggg    60
a                                                               61

<210> SEQ ID NO 1701
<211> LENGTH: 61
<212> TYPE: DNA
<213> ORGANISM: Homo Sapiens

<400> SEQUENCE: 1701
ttgtggagtc agtaagatga tggtaaacag sgagatgcat ctcacaaata cccgtaccca    60
g                                                               61

<210> SEQ ID NO 1702
<211> LENGTH: 61
<212> TYPE: DNA
<213> ORGANISM: Homo Sapiens

<400> SEQUENCE: 1702
aactccatct taaacataaa ataaaataat yctggatcct cctgtactac ctgtgtgacc    60
t                                                               61

<210> SEQ ID NO 1703
<211> LENGTH: 61
<212> TYPE: DNA
<213> ORGANISM: Homo Sapiens

<400> SEQUENCE: 1703
gctgccggga agagagctaa taaaggaaac rgatgaggtg gtctaagggg cccagcagag    60
g                                                               61

<210> SEQ ID NO 1704
<211> LENGTH: 61
<212> TYPE: DNA
<213> ORGANISM: Homo Sapiens
```

<400> SEQUENCE: 1704
agaaaagtga ctctcgcaat ttattgccaa ygagaaccac cacattgttc attgattgca     60
t                                                                     61

<210> SEQ ID NO 1705
<211> LENGTH: 61
<212> TYPE: DNA
<213> ORGANISM: Homo Sapiens

<400> SEQUENCE: 1705
cttatctgag ttcctttctt agaaaactga ygctcgggcc tcccagagag tataaaggaa     60
c                                                                     61

<210> SEQ ID NO 1706
<211> LENGTH: 61
<212> TYPE: DNA
<213> ORGANISM: Homo Sapiens

<400> SEQUENCE: 1706
agggctcgag ttagattcag tattcaacca rtgttgctgc ttaagcctgt aaatgtatgg     60
t                                                                     61

<210> SEQ ID NO 1707
<211> LENGTH: 61
<212> TYPE: DNA
<213> ORGANISM: Homo Sapiens

<400> SEQUENCE: 1707
atccccatct agatgaagag acaagtagaa rggagatgca ggcatttcta ttttcagagt     60
a                                                                     61

<210> SEQ ID NO 1708
<211> LENGTH: 61
<212> TYPE: DNA
<213> ORGANISM: Homo Sapiens

<400> SEQUENCE: 1708
ctgtccccat ccaggcccttt tcttttggag ygttctcagt ataacccaac aggtggacac     60
a                                                                     61

<210> SEQ ID NO 1709
<211> LENGTH: 61
<212> TYPE: DNA
<213> ORGANISM: Homo Sapiens

<400> SEQUENCE: 1709
aggaataaaa aactcgccaa aatttcctaa sttgtagaat agaaatagtc acctccaaag     60
a                                                                     61

<210> SEQ ID NO 1710
<211> LENGTH: 61
<212> TYPE: DNA
<213> ORGANISM: Homo Sapiens

<400> SEQUENCE: 1710
attcttgagc aagggcacaa ggaaggaatg kttttctgct cctggatata atcttctcac     60
c                                                                     61

```
<210> SEQ ID NO 1711
<211> LENGTH: 61
<212> TYPE: DNA
<213> ORGANISM: Homo Sapiens

<400> SEQUENCE: 1711
atattgattg tctcacacag tttctgaacc rcaggaattc aggatggctt agtaggatgg    60
t                                                                  61

<210> SEQ ID NO 1712
<211> LENGTH: 61
<212> TYPE: DNA
<213> ORGANISM: Homo Sapiens

<400> SEQUENCE: 1712
aatggctgtt cagatttgca ttttaagtag yttactctga tcaagttgcc aagtgagaca    60
a                                                                  61

<210> SEQ ID NO 1713
<211> LENGTH: 61
<212> TYPE: DNA
<213> ORGANISM: Homo Sapiens

<400> SEQUENCE: 1713
gtgcttgtgt gcaacgcagc aactttttgct staccctgga gtctcaccaa agatggcctg    60
g                                                                  61

<210> SEQ ID NO 1714
<211> LENGTH: 61
<212> TYPE: DNA
<213> ORGANISM: Homo Sapiens

<400> SEQUENCE: 1714
tcctacggct gagaggatga aatttctgaa ygggcacttt gccgagtgag tgaccacatc    60
g                                                                  61

<210> SEQ ID NO 1715
<211> LENGTH: 61
<212> TYPE: DNA
<213> ORGANISM: Homo Sapiens

<400> SEQUENCE: 1715
aactctcata tattgaggat gggagtctag kaggggcatac ttgctttgga aaagtttgtt    60
t                                                                  61

<210> SEQ ID NO 1716
<211> LENGTH: 61
<212> TYPE: DNA
<213> ORGANISM: Homo Sapiens

<400> SEQUENCE: 1716
attttattta taatagaagg aaactgggaa maaccaaatg accatcaaca gataaaggga    60
c                                                                  61

<210> SEQ ID NO 1717
<211> LENGTH: 61
<212> TYPE: DNA
<213> ORGANISM: Homo Sapiens

<400> SEQUENCE: 1717
atcggagcag ctgcttccac cttgctttat yttcctgcag ataatgtcct gttcccgtca    60
```

```
t                                                              61

<210> SEQ ID NO 1718
<211> LENGTH: 61
<212> TYPE: DNA
<213> ORGANISM: Homo Sapiens

<400> SEQUENCE: 1718
acagcccaaa ttaagagctt ggcacccaat ycccacttgg actacaaatc acttcctctt    60
g                                                              61

<210> SEQ ID NO 1719
<211> LENGTH: 61
<212> TYPE: DNA
<213> ORGANISM: Homo Sapiens

<400> SEQUENCE: 1719
ttgatcagcg gcctccctgc tcctgttctc yagatagaag tttccctagt tttgctggtc    60
t                                                              61

<210> SEQ ID NO 1720
<211> LENGTH: 61
<212> TYPE: DNA
<213> ORGANISM: Homo Sapiens

<400> SEQUENCE: 1720
tttgtttgac ttaagggaaa caggtattat wtggcattcg acatcactaa tttaattaca    60
a                                                              61

<210> SEQ ID NO 1721
<211> LENGTH: 61
<212> TYPE: DNA
<213> ORGANISM: Homo Sapiens

<400> SEQUENCE: 1721
gaggtgacag gggcttctgt tttcttgagt ytccctgttt gctgatgtca tcccctccta    60
c                                                              61

<210> SEQ ID NO 1722
<211> LENGTH: 61
<212> TYPE: DNA
<213> ORGANISM: Homo Sapiens

<400> SEQUENCE: 1722
ccttctaagg gttagagaga caggatttta yagaatgcca tcacctgagg ctgtgacaat    60
g                                                              61

<210> SEQ ID NO 1723
<211> LENGTH: 61
<212> TYPE: DNA
<213> ORGANISM: Homo Sapiens

<400> SEQUENCE: 1723
aatatacaca tgtatatttc atttatgtta ytgatatcca tctgtttcat cagctcattt    60
t                                                              61

<210> SEQ ID NO 1724
<211> LENGTH: 61
<212> TYPE: DNA
<213> ORGANISM: Homo Sapiens
```

```
<400> SEQUENCE: 1724
ctggcttcaa aacgcagagc actagcattt ycatatgttt cagtaagtct cccagccttc    60
g                                                                   61

<210> SEQ ID NO 1725
<211> LENGTH: 61
<212> TYPE: DNA
<213> ORGANISM: Homo Sapiens

<400> SEQUENCE: 1725
ttttcatggg tagtgcttcc tgtcattcag ktctcagatc aaacactacc tctttaagag    60
c                                                                   61

<210> SEQ ID NO 1726
<211> LENGTH: 61
<212> TYPE: DNA
<213> ORGANISM: Homo Sapiens

<400> SEQUENCE: 1726
agcccacata agtatggcgt cttaccagta ractccgctg aatccgagga agggccttag    60
g                                                                   61

<210> SEQ ID NO 1727
<211> LENGTH: 61
<212> TYPE: DNA
<213> ORGANISM: Homo Sapiens

<400> SEQUENCE: 1727
tgacttattt ctccttccct ctattttaaa stcttgattc tatcatctgc ttgcctgcgt    60
a                                                                   61

<210> SEQ ID NO 1728
<211> LENGTH: 61
<212> TYPE: DNA
<213> ORGANISM: Homo Sapiens

<400> SEQUENCE: 1728
gctgatggaa gcagctgatg gagtggatgt rtataaggag cattgggcac cctgttagca    60
g                                                                   61

<210> SEQ ID NO 1729
<211> LENGTH: 61
<212> TYPE: DNA
<213> ORGANISM: Homo Sapiens

<400> SEQUENCE: 1729
cttagtgcaa atggcttcct ggtttgggta maaatttagc aactgaatgt gatcttgtgt    60
a                                                                   61

<210> SEQ ID NO 1730
<211> LENGTH: 61
<212> TYPE: DNA
<213> ORGANISM: Homo Sapiens

<400> SEQUENCE: 1730
agtggctctg tctaaattca aatccttcct watctaaccc ttggggagaa aacagtgtgt    60
g                                                                   61
```

```
<210> SEQ ID NO 1731
<211> LENGTH: 61
<212> TYPE: DNA
<213> ORGANISM: Homo Sapiens

<400> SEQUENCE: 1731
gtcctggtct gtcgctgact cttgggaact yaggtcaact cttcacctcc tggtctgtta      60
c                                                                      61

<210> SEQ ID NO 1732
<211> LENGTH: 61
<212> TYPE: DNA
<213> ORGANISM: Homo Sapiens

<400> SEQUENCE: 1732
tgtacaagtg ttgtccgtct aacctactta mcctttgtaa ttctattgtg atttgcttgg      60
c                                                                      61

<210> SEQ ID NO 1733
<211> LENGTH: 61
<212> TYPE: DNA
<213> ORGANISM: Homo Sapiens

<400> SEQUENCE: 1733
tcctattggg tcaggacttc acctgttgac stcgtttaac cttaattagt ttcatcaagg      60
c                                                                      61

<210> SEQ ID NO 1734
<211> LENGTH: 61
<212> TYPE: DNA
<213> ORGANISM: Homo Sapiens

<400> SEQUENCE: 1734
tcggtctgtg gtgtctggtg tgggacctca yatgaagggg gccacacagc acactccctg      60
t                                                                      61

<210> SEQ ID NO 1735
<211> LENGTH: 61
<212> TYPE: DNA
<213> ORGANISM: Homo Sapiens

<400> SEQUENCE: 1735
tcactgtgtc aatgcacgtg aaatgcatag racaaagaca tgtaaagata tgacctgtga      60
c                                                                      61

<210> SEQ ID NO 1736
<211> LENGTH: 61
<212> TYPE: DNA
<213> ORGANISM: Homo Sapiens

<400> SEQUENCE: 1736
caatgagctt aattgtgttc gcttaccaaa stcgcccccg ctcacggcga ttttagagga      60
a                                                                      61

<210> SEQ ID NO 1737
<211> LENGTH: 61
<212> TYPE: DNA
<213> ORGANISM: Homo Sapiens

<400> SEQUENCE: 1737
tcttttctca tagggtcagg tggctggatc staagaaatg gcctacatga cttatctctc      60
``` a                                                                              61

<210> SEQ ID NO 1738
<211> LENGTH: 61
<212> TYPE: DNA
<213> ORGANISM: Homo Sapiens

<400> SEQUENCE: 1738
aataaggaaa ggacagggca tggccacacc yaggtgtctc tgcagggttc tcttgggagc      60
c                                                                              61

<210> SEQ ID NO 1739
<211> LENGTH: 61
<212> TYPE: DNA
<213> ORGANISM: Homo Sapiens

<400> SEQUENCE: 1739
gctcatgtgc agagaaaatg ggatttgcca sctgttctca actcaaggca ggctctgtgt      60
c                                                                              61

<210> SEQ ID NO 1740
<211> LENGTH: 61
<212> TYPE: DNA
<213> ORGANISM: Homo Sapiens

<400> SEQUENCE: 1740
tcacaaatga tgagctcttt ggcatcatca rtccagccac aggagaatgg aaggatggta      60
a                                                                              61

<210> SEQ ID NO 1741
<211> LENGTH: 61
<212> TYPE: DNA
<213> ORGANISM: Homo Sapiens

<400> SEQUENCE: 1741
agtactcttg cagcgccccc aaaactctac ractggttca catctctgta tctttacatg      60
t                                                                              61

<210> SEQ ID NO 1742
<211> LENGTH: 61
<212> TYPE: DNA
<213> ORGANISM: Homo Sapiens

<400> SEQUENCE: 1742
tggtgaggga gcagaataca atttagtcca yaagaaatca taaacacaa atatgtaaga      60 g                                                                              61

<210> SEQ ID NO 1743
<211> LENGTH: 61
<212> TYPE: DNA
<213> ORGANISM: Homo Sapiens

<400> SEQUENCE: 1743
aggaagaaca tggactctgg agtctgttac kgccagtttt ggttctagta cgttaaactc      60
c                                                                              61

<210> SEQ ID NO 1744
<211> LENGTH: 61
<212> TYPE: DNA
<213> ORGANISM: Homo Sapiens

<400> SEQUENCE: 1744
ttggaaagtg tcctacatct gggactgtta maaagataag tcaacacagg gataaaaaaa        60
a                                                                       61

<210> SEQ ID NO 1745
<211> LENGTH: 61
<212> TYPE: DNA
<213> ORGANISM: Homo Sapiens

<400> SEQUENCE: 1745
acagagaatg tagaggaggc aagatggata rttatggagt caaagaaaaa aagtccaatg        60
t                                                                       61

<210> SEQ ID NO 1746
<211> LENGTH: 61
<212> TYPE: DNA
<213> ORGANISM: Homo Sapiens

<400> SEQUENCE: 1746
aacatggttt tgaggtactg aacggcatac rtaaaacatt ttcatcagaa gggaagtgag        60
g                                                                       61

<210> SEQ ID NO 1747
<211> LENGTH: 61
<212> TYPE: DNA
<213> ORGANISM: Homo Sapiens

<400> SEQUENCE: 1747
atgcactcca aaatatcctt tacaatgact yaatcactct tcagtatgga agaccaagga       60
a                                                                       61

<210> SEQ ID NO 1748
<211> LENGTH: 61
<212> TYPE: DNA
<213> ORGANISM: Homo Sapiens

<400> SEQUENCE: 1748
tattataatt aattcaaaaa ttgtccttct wcctatcagg tcctggctcc agactacctg       60
t                                                                       61

<210> SEQ ID NO 1749
<211> LENGTH: 61
<212> TYPE: DNA
<213> ORGANISM: Homo Sapiens

<400> SEQUENCE: 1749
ggctgtcttc cagaaatgat tttactctac kttctgcttt catcctcacc tcttctcctc       60
t                                                                       61

<210> SEQ ID NO 1750
<211> LENGTH: 61
<212> TYPE: DNA
<213> ORGANISM: Homo Sapiens

<400> SEQUENCE: 1750
aatgtagaca tgcagattag tacataactt ytgttgaata tgtatagaat gtgtagagga       60
a                                                                       61

```
<210> SEQ ID NO 1751
<211> LENGTH: 61
<212> TYPE: DNA
<213> ORGANISM: Homo Sapiens

<400> SEQUENCE: 1751
atttaacata ctcaaagtga acacatttat stttcctctg caaacctgct gcttctgcat       60
c                                                                       61

<210> SEQ ID NO 1752
<211> LENGTH: 61
<212> TYPE: DNA
<213> ORGANISM: Homo Sapiens

<400> SEQUENCE: 1752
gtcattaggg caatgcctgt acggttcctc rcagctcagt aaaggcggtg gttgccacca       60
g                                                                       61

<210> SEQ ID NO 1753
<211> LENGTH: 61
<212> TYPE: DNA
<213> ORGANISM: Homo Sapiens

<400> SEQUENCE: 1753
ctgttttcca aagtgactgc aatattttgc rttaccacta gacattttc agagttctgg        60 t                                                                       61

<210> SEQ ID NO 1754
<211> LENGTH: 61
<212> TYPE: DNA
<213> ORGANISM: Homo Sapiens

<400> SEQUENCE: 1754
cttgttcaag ggcacacagc cagctactag magaatctgg gataagagac atgaactccc       60
c                                                                       61

<210> SEQ ID NO 1755
<211> LENGTH: 61
<212> TYPE: DNA
<213> ORGANISM: Homo Sapiens

<400> SEQUENCE: 1755
cggtgcacca agctacatga cgcatctttg ytgagctgtg acggtattcc agggctgggc       60
t                                                                       61

<210> SEQ ID NO 1756
<211> LENGTH: 61
<212> TYPE: DNA
<213> ORGANISM: Homo Sapiens

<400> SEQUENCE: 1756
agagtatggg gaaatttcag gtgacagata yaaaggacaa atgtttaccc aaaaaatata      60
a                                                                       61

<210> SEQ ID NO 1757
<211> LENGTH: 61
<212> TYPE: DNA
<213> ORGANISM: Homo Sapiens

<400> SEQUENCE: 1757
tacatagttc atctgggata cagctcacaa rtctattctt taaacaatgg ttgaaaacaa      60
``` a	61

<210> SEQ ID NO 1758
<211> LENGTH: 61
<212> TYPE: DNA
<213> ORGANISM: Homo Sapiens

<400> SEQUENCE: 1758
catcttattg ctgagcgtag agttctgtac mtgattgtgt atatattgta gatactagac    60 c	61

<210> SEQ ID NO 1759
<211> LENGTH: 61
<212> TYPE: DNA
<213> ORGANISM: Homo Sapiens

<400> SEQUENCE: 1759
tctaagaccc ttcacttctt tctattccag ytgctcacct tagttcaggc catatcacct    60 c	61

<210> SEQ ID NO 1760
<211> LENGTH: 61
<212> TYPE: DNA
<213> ORGANISM: Homo Sapiens

<400> SEQUENCE: 1760
tgtgacacta catctctagc tccaaaatct rcttaggttt taaagcctct tggaaatctc    60 t	61

<210> SEQ ID NO 1761
<211> LENGTH: 61
<212> TYPE: DNA
<213> ORGANISM: Homo Sapiens

<400> SEQUENCE: 1761
aggcaagggt gaagacacac ctgcaggcca ytaatcttgc tacacagcat ccctatttta    60 a	61

<210> SEQ ID NO 1762
<211> LENGTH: 61
<212> TYPE: DNA
<213> ORGANISM: Homo Sapiens

<400> SEQUENCE: 1762
aaacagggct cttcctgatc tagctgttga ycacctcgtt aattttatca ttcatacctg    60 t	61

<210> SEQ ID NO 1763
<211> LENGTH: 61
<212> TYPE: DNA
<213> ORGANISM: Homo Sapiens

<400> SEQUENCE: 1763
tgaaggtatt cagcttgtgc taatagtctg kacttgtttt aaagacccag gaggtctttt    60 t	61

<210> SEQ ID NO 1764
<211> LENGTH: 61
<212> TYPE: DNA
<213> ORGANISM: Homo Sapiens

<400> SEQUENCE: 1764 accttctat atctttctct ggccaataac rctgtgatgc cattaaggca tgaagattca    60
a                                                                   61

<210> SEQ ID NO 1765
<211> LENGTH: 61
<212> TYPE: DNA
<213> ORGANISM: Homo Sapiens

<400> SEQUENCE: 1765
ttcaaggagt ggtctaatcc ctggactgct ktctgagtat cagtaattag taagcaggcc    60
a                                                                   61

<210> SEQ ID NO 1766
<211> LENGTH: 61
<212> TYPE: DNA
<213> ORGANISM: Homo Sapiens

<400> SEQUENCE: 1766
cttgacatgc ttttcactgc ttacatggtt rgtttcctac ctagctgaat gcaggcatct    60
g                                                                   61

<210> SEQ ID NO 1767
<211> LENGTH: 61
<212> TYPE: DNA
<213> ORGANISM: Homo Sapiens

<400> SEQUENCE: 1767
aggctgttgg ttacctggcc gggagctggc rgagaccagg atttctcctc gccgccgttg    60
c                                                                   61

<210> SEQ ID NO 1768
<211> LENGTH: 61
<212> TYPE: DNA
<213> ORGANISM: Homo Sapiens

<400> SEQUENCE: 1768
tttttgcatg cttcaaaatc aaaaggcggc rcagtgaaaa cattttaatt atttatgtat    60
t                                                                   61

<210> SEQ ID NO 1769
<211> LENGTH: 61
<212> TYPE: DNA
<213> ORGANISM: Homo Sapiens

<400> SEQUENCE: 1769
acatacctga taaacgcttt aggctgatgt mcccagcttc ttacatgtca ctctgcttaa    60
t                                                                   61

<210> SEQ ID NO 1770
<211> LENGTH: 61
<212> TYPE: DNA
<213> ORGANISM: Homo Sapiens

<400> SEQUENCE: 1770
tgggaacctt tccatgtttt agtatgtcct rgaagagtaa aataacact caaattttct    60
a                                                                   61

```
<210> SEQ ID NO 1771
<211> LENGTH: 61
<212> TYPE: DNA
<213> ORGANISM: Homo Sapiens

<400> SEQUENCE: 1771
tacatttagt tttgctactg tatatgagct yatgaaatgg acttcccttc cctaataata      60
t                                                                     61

<210> SEQ ID NO 1772
<211> LENGTH: 61
<212> TYPE: DNA
<213> ORGANISM: Homo Sapiens

<400> SEQUENCE: 1772
aacatggaca agttggaaga ggagcgactc yaaagtttgg caatggagcc cggagttttg      60
a                                                                     61

<210> SEQ ID NO 1773
<211> LENGTH: 61
<212> TYPE: DNA
<213> ORGANISM: Homo Sapiens

<400> SEQUENCE: 1773
tttcaaacaa ataattttcc ccacgtttta wcatctctat aatctgcata cgggttttca      60
c                                                                     61

<210> SEQ ID NO 1774
<211> LENGTH: 61
<212> TYPE: DNA
<213> ORGANISM: Homo Sapiens

<400> SEQUENCE: 1774 agatggggttg gggcagatcc agcagattac rttactgtga gggggtggtg gggaacacag    60
c                                                                     61

<210> SEQ ID NO 1775
<211> LENGTH: 61
<212> TYPE: DNA
<213> ORGANISM: Homo Sapiens

<400> SEQUENCE: 1775
actactgggg aacacatgga cattgctcct yagggcccat gtgcacctac gtggctccag      60
g                                                                     61

<210> SEQ ID NO 1776
<211> LENGTH: 61
<212> TYPE: DNA
<213> ORGANISM: Homo Sapiens

<400> SEQUENCE: 1776
aagaaactca catgcgtgaa ttacttcctt ygtgtcacat agtaaataga gccaggattc      60
a                                                                     61

<210> SEQ ID NO 1777
<211> LENGTH: 61
<212> TYPE: DNA
<213> ORGANISM: Homo Sapiens

<400> SEQUENCE: 1777
gtaaattctc aagttcttaa ggctgaatgt yatcttgtat tgtttcttgt atttgtgata      60
```

```
t                                                               61

<210> SEQ ID NO 1778
<211> LENGTH: 61
<212> TYPE: DNA
<213> ORGANISM: Homo Sapiens

<400> SEQUENCE: 1778
tttagttcca actaacaaag tctcactcta wgcactcatt ttctacttct ggatgtcttg    60
t                                                               61

<210> SEQ ID NO 1779
<211> LENGTH: 61
<212> TYPE: DNA
<213> ORGANISM: Homo Sapiens

<400> SEQUENCE: 1779
caaaacaaat agaagagcag tgagaatgaa rccatggtgc tatcttcgta tttatagtga    60
t                                                               61

<210> SEQ ID NO 1780
<211> LENGTH: 61
<212> TYPE: DNA
<213> ORGANISM: Homo Sapiens

<400> SEQUENCE: 1780
acagctaaaa gttggacaga gtggaagact ytcagttata tgcctgatta tagccaaact    60
a                                                               61

<210> SEQ ID NO 1781
<211> LENGTH: 61
<212> TYPE: DNA
<213> ORGANISM: Homo Sapiens

<400> SEQUENCE: 1781
tttctagtta ggctagaatc tttgtctttt ktaagataaa tgcggaagag taatttctca    60
a                                                               61

<210> SEQ ID NO 1782
<211> LENGTH: 61
<212> TYPE: DNA
<213> ORGANISM: Homo Sapiens

<400> SEQUENCE: 1782
gacaagtatg gtctaaggaa aaaacaagga wgaactcaag caagagttat cacattggcc    60
a                                                               61

<210> SEQ ID NO 1783
<211> LENGTH: 61
<212> TYPE: DNA
<213> ORGANISM: Homo Sapiens

<400> SEQUENCE: 1783
agtataggat tggtaaacct cggcgatatg wtaggttgga gccaaacttc aatgaattcg    60
a                                                               61

<210> SEQ ID NO 1784
<211> LENGTH: 61
<212> TYPE: DNA
<213> ORGANISM: Homo Sapiens
```

```
<400> SEQUENCE: 1784
tgtggaactg aaatgaattt gtcaacctca sattctgaat ttagaacttt atgaagtata    60
g                                                                   61

<210> SEQ ID NO 1785
<211> LENGTH: 61
<212> TYPE: DNA
<213> ORGANISM: Homo Sapiens

<400> SEQUENCE: 1785
ggaactattg ccaggctttt aggagctgcc rttgctaaca aatcagtttg ggtaggcagg    60
t                                                                   61

<210> SEQ ID NO 1786
<211> LENGTH: 61
<212> TYPE: DNA
<213> ORGANISM: Homo Sapiens

<400> SEQUENCE: 1786
atatatccat ttgagtggat aaatttgctt ycgtttgga gagttttact tttcacctgt     60
a                                                                   61

<210> SEQ ID NO 1787
<211> LENGTH: 61
<212> TYPE: DNA
<213> ORGANISM: Homo Sapiens

<400> SEQUENCE: 1787
atttccctga acttcataac ctgacaaacg ygctactcaa tccgtcattt caacaatctt    60
t                                                                   61

<210> SEQ ID NO 1788
<211> LENGTH: 61
<212> TYPE: DNA
<213> ORGANISM: Homo Sapiens

<400> SEQUENCE: 1788
gtaaatcata gagaattatt catggggtta maaagttagg gaatattact ttttatcatg    60
t                                                                   61

<210> SEQ ID NO 1789
<211> LENGTH: 61
<212> TYPE: DNA
<213> ORGANISM: Homo Sapiens

<400> SEQUENCE: 1789
gcatttcttc acctgtcaag tttagattat ytttaatgcc tcagcttcag tgttatctcc    60
t                                                                   61

<210> SEQ ID NO 1790
<211> LENGTH: 61
<212> TYPE: DNA
<213> ORGANISM: Homo Sapiens

<400> SEQUENCE: 1790
gaaaagttag agaatgggca ggcatcatgg yttaggcatc tatcccagca ttttgggtgg    60
c                                                                   61
```

```
<210> SEQ ID NO 1791
<211> LENGTH: 61
<212> TYPE: DNA
<213> ORGANISM: Homo Sapiens

<400> SEQUENCE: 1791
aaccactgca cacaatttca tgacagtgta ytccaccctt accccagagg aggttggcgt    60
a                                                                    61

<210> SEQ ID NO 1792
<211> LENGTH: 61
<212> TYPE: DNA
<213> ORGANISM: Homo Sapiens

<400> SEQUENCE: 1792
aagttagaaa acagacaaat tcgtggcagc rctttacata aaacaggaaa atgaatgaac    60
t                                                                    61

<210> SEQ ID NO 1793
<211> LENGTH: 61
<212> TYPE: DNA
<213> ORGANISM: Homo Sapiens

<400> SEQUENCE: 1793
agagagattc aacgtgtatc ttatgcctac rccaaacctg atatttatg gtgaatgcac    60 a                                                                    61

<210> SEQ ID NO 1794
<211> LENGTH: 61
<212> TYPE: DNA
<213> ORGANISM: Homo Sapiens

<400> SEQUENCE: 1794
tgaaagagag tgctgtccat cattgccccc rgtgagcact gttttcattc agggtaaaag    60
t                                                                    61

<210> SEQ ID NO 1795
<211> LENGTH: 61
<212> TYPE: DNA
<213> ORGANISM: Homo Sapiens

<400> SEQUENCE: 1795
tgggggagct gatttattaa tctattggaa stgctccaag tcaactaatt cagccatacg    60
g                                                                    61

<210> SEQ ID NO 1796
<211> LENGTH: 61
<212> TYPE: DNA
<213> ORGANISM: Homo Sapiens

<400> SEQUENCE: 1796
aaggtacagt aaaaatatgg tgtaagagat waaaaatgat agagctgtct agggcattta    60
c                                                                    61

<210> SEQ ID NO 1797
<211> LENGTH: 61
<212> TYPE: DNA
<213> ORGANISM: Homo Sapiens

<400> SEQUENCE: 1797
tgttacattt ctggagggtg atttggcaaa rtatagaaaa gactaaaaac atgcatattc    60
```

```
t                                                                      61

<210> SEQ ID NO 1798
<211> LENGTH: 61
<212> TYPE: DNA
<213> ORGANISM: Homo Sapiens

<400> SEQUENCE: 1798
agaaacattg tacccattta tatccacacc yctgaaagat gcacctgaat catttgaatc      60
t                                                                      61

<210> SEQ ID NO 1799
<211> LENGTH: 61
<212> TYPE: DNA
<213> ORGANISM: Homo Sapiens

<400> SEQUENCE: 1799
tgtctctctg aaatttgggg tgacaatcct rgagacaaga cctaagccta gcatgactta     60
t                                                                      61

<210> SEQ ID NO 1800
<211> LENGTH: 61
<212> TYPE: DNA
<213> ORGANISM: Homo Sapiens

<400> SEQUENCE: 1800
ccgggcagtc agatcgctgt ggcagtagtc yagcgccgtg acacagggtt ttgttgcagc     60
c                                                                      61

<210> SEQ ID NO 1801
<211> LENGTH: 61
<212> TYPE: DNA
<213> ORGANISM: Homo Sapiens

<400> SEQUENCE: 1801
gccagacact actctaagca ctttgcacat mgaaacccgc tcactaacaa caccacgaaa     60
t                                                                      61

<210> SEQ ID NO 1802
<211> LENGTH: 61
<212> TYPE: DNA
<213> ORGANISM: Homo Sapiens

<400> SEQUENCE: 1802
actctctagt tcagatttaa gtgagcaaat rtccatcacc cagcatctca catgcataga     60
g                                                                      61

<210> SEQ ID NO 1803
<211> LENGTH: 61
<212> TYPE: DNA
<213> ORGANISM: Homo Sapiens

<400> SEQUENCE: 1803
gcggatggcc cagaccacga cagtgaccga rgctgtggct ttccagtggg ggagcactcc     60
c                                                                      61

<210> SEQ ID NO 1804
<211> LENGTH: 61
<212> TYPE: DNA
<213> ORGANISM: Homo Sapiens
```

```
<220> FEATURE:
<221> NAME/KEY: misc_feature
<222> LOCATION: (31)..(31)
<223> OTHER INFORMATION: n is a, c, g, or t

<400> SEQUENCE: 1804
ggctgcagtg agatgaggac acaggagcac nttgggttag tctgcatctt ggtggctggt    60
g                                                                    61

<210> SEQ ID NO 1805
<211> LENGTH: 61
<212> TYPE: DNA
<213> ORGANISM: Homo Sapiens

<400> SEQUENCE: 1805
cagatcagga aactgagtcc cagaaggatt wagtcagtta cccaagttgt tctagttaaa    60
t                                                                    61

<210> SEQ ID NO 1806
<211> LENGTH: 61
<212> TYPE: DNA
<213> ORGANISM: Homo Sapiens

<400> SEQUENCE: 1806
acacggctgg aggccaccta cttctcacct yctgggcctg gcagcctccc ccagcctgat    60
c                                                                    61

<210> SEQ ID NO 1807
<211> LENGTH: 61
<212> TYPE: DNA
<213> ORGANISM: Homo Sapiens

<400> SEQUENCE: 1807
tcaggcactt aataaatatt aagggtgacc rgtgactcag gctctgcctc tgggaagtgg    60
c                                                                    61

<210> SEQ ID NO 1808
<211> LENGTH: 61
<212> TYPE: DNA
<213> ORGANISM: Homo Sapiens

<400> SEQUENCE: 1808
tgggctccct agggacatct ccatcaggaa katcctttgt tcctgacccc acctcctcta    60
c                                                                    61

<210> SEQ ID NO 1809
<211> LENGTH: 61
<212> TYPE: DNA
<213> ORGANISM: Homo Sapiens

<400> SEQUENCE: 1809
gactctttat cagttactat ggtggtaagt rcaagcaagg aagacagagg aaattctcta    60
g                                                                    61

<210> SEQ ID NO 1810
<211> LENGTH: 61
<212> TYPE: DNA
<213> ORGANISM: Homo Sapiens

<400> SEQUENCE: 1810
ccatggcagt ggctctgata accaagacag stcctgaatg actaacaggg ctggtagcgt    60
```

-continued c                                                                          61

<210> SEQ ID NO 1811
<211> LENGTH: 61
<212> TYPE: DNA
<213> ORGANISM: Homo Sapiens

<400> SEQUENCE: 1811
gagaacggtc caactcaggt aggcggatga ygaaggaaga gtgggaacat ttacaaagaa    60
g                                                                          61

<210> SEQ ID NO 1812
<211> LENGTH: 61
<212> TYPE: DNA
<213> ORGANISM: Homo Sapiens

<400> SEQUENCE: 1812
tttaaaaagc tctctagatg attctgaagt rcaaccatgt ttgaaaatca ccatcttaaa    60
g                                                                          61

<210> SEQ ID NO 1813
<211> LENGTH: 61
<212> TYPE: DNA
<213> ORGANISM: Homo Sapiens

<400> SEQUENCE: 1813
tagacgagac agaaagacaa agcaagacaa ygacagagat agaaaataca ggagacagaa    60
a                                                                          61

<210> SEQ ID NO 1814
<211> LENGTH: 61
<212> TYPE: DNA
<213> ORGANISM: Homo Sapiens

<400> SEQUENCE: 1814
gagaacagag agaaggccct ataaaggctg ytctatgggt ttttggtagg ggaggaggaa    60
g                                                                          61

<210> SEQ ID NO 1815
<211> LENGTH: 61
<212> TYPE: DNA
<213> ORGANISM: Homo Sapiens

<400> SEQUENCE: 1815
catattctgg gtagtgattt ttgcctctta mcttacttga tattttaata aactcacata    60
c                                                                          61

<210> SEQ ID NO 1816
<211> LENGTH: 61
<212> TYPE: DNA
<213> ORGANISM: Homo Sapiens

<400> SEQUENCE: 1816
gctgtaatac cgcttatttc agtatactta yctcacaggg tagtttgaag gtaaatttaa    60
t                                                                          61

<210> SEQ ID NO 1817
<211> LENGTH: 61
<212> TYPE: DNA
<213> ORGANISM: Homo Sapiens

```
<400> SEQUENCE: 1817
ctcaacagat ggtgactcct ggcactgtga ytccgttctt aaaaaggcgt tatattattc    60
a                                                                    61

<210> SEQ ID NO 1818
<211> LENGTH: 61
<212> TYPE: DNA
<213> ORGANISM: Homo Sapiens

<400> SEQUENCE: 1818
aaggtgtgaa actttaaggg cagacattag raaagtcttg ggcaacctgg atggttggtc    60
a                                                                    61

<210> SEQ ID NO 1819
<211> LENGTH: 61
<212> TYPE: DNA
<213> ORGANISM: Homo Sapiens

<400> SEQUENCE: 1819
actacaacat ttatgttgca cttatccaaa katttgacca gaatagaaaa tgccccttcc    60
a                                                                    61

<210> SEQ ID NO 1820
<211> LENGTH: 61
<212> TYPE: DNA
<213> ORGANISM: Homo Sapiens

<400> SEQUENCE: 1820
tcagctgcat ccaacgtcca ctgagagcta ytgtgggcta agatggtttt ggctgagagt    60
g                                                                    61

<210> SEQ ID NO 1821
<211> LENGTH: 61
<212> TYPE: DNA
<213> ORGANISM: Homo Sapiens

<400> SEQUENCE: 1821
gcaagtttct gcctctgctc ttcaatctcc rtgcccaggg tggagtgcct ctgcagcgca    60
g                                                                    61

<210> SEQ ID NO 1822
<211> LENGTH: 61
<212> TYPE: DNA
<213> ORGANISM: Homo Sapiens

<400> SEQUENCE: 1822
ttttaatctc ttctctgtcc tgctttcaag staagctcag ttttacactt atagaatcca    60
a                                                                    61

<210> SEQ ID NO 1823
<211> LENGTH: 61
<212> TYPE: DNA
<213> ORGANISM: Homo Sapiens

<400> SEQUENCE: 1823
ctttcacata aaattggagt agggtgggag ragaaccacc agcagcggca aaatgaggtc    60
t                                                                    61
```

<210> SEQ ID NO 1824
<211> LENGTH: 61
<212> TYPE: DNA
<213> ORGANISM: Homo Sapiens

<400> SEQUENCE: 1824
tgcgcattac tggaacaatg actgactgat rtaaaacgct aacagcagaa atacgggaaa    60
g                                                                    61

<210> SEQ ID NO 1825
<211> LENGTH: 61
<212> TYPE: DNA
<213> ORGANISM: Homo Sapiens

<400> SEQUENCE: 1825
acttcaagta accaaacaac tgtgaaagaa rgtttctcct ttagagatat ccagctaaa     60
a                                                                    61

<210> SEQ ID NO 1826
<211> LENGTH: 61
<212> TYPE: DNA
<213> ORGANISM: Homo Sapiens

<400> SEQUENCE: 1826
ctctaccacg tcagagggag ctacaaggtt yggaggatgg attcagagtg cacatagaac    60
g                                                                    61

<210> SEQ ID NO 1827
<211> LENGTH: 61
<212> TYPE: DNA
<213> ORGANISM: Homo Sapiens

<400> SEQUENCE: 1827 ttttttaaa gcaaaggata aatttgtgga saagtgacag gacaaatggg tttaggcagt     60
a                                                                    61

<210> SEQ ID NO 1828
<211> LENGTH: 61
<212> TYPE: DNA
<213> ORGANISM: Homo Sapiens

<400> SEQUENCE: 1828
agttatacca gagctgaact ccttgaagga rgtgtgtagg tctctcaggg actgctcttg    60
g                                                                    61

<210> SEQ ID NO 1829
<211> LENGTH: 61
<212> TYPE: DNA
<213> ORGANISM: Homo Sapiens

<400> SEQUENCE: 1829
gcgaaagaac cctggtgtgg gcaacggaga ygacgaggca gctgagttga tgcagcaggt    60
g                                                                    61

<210> SEQ ID NO 1830
<211> LENGTH: 61
<212> TYPE: DNA
<213> ORGANISM: Homo Sapiens

<400> SEQUENCE: 1830
ctagcagtag cctcaggaag aagagaaaaa ygtggatctt ggtaaaatac agcagtgcct    60

-continued t 61

<210> SEQ ID NO 1831
<211> LENGTH: 61
<212> TYPE: DNA
<213> ORGANISM: Homo Sapiens

<400> SEQUENCE: 1831
gaaactcatt cctgtatccc taatagtaaa kagagtgcct gacacatagc agcctggtga     60
a                                                                    61

<210> SEQ ID NO 1832
<211> LENGTH: 61
<212> TYPE: DNA
<213> ORGANISM: Homo Sapiens

<400> SEQUENCE: 1832
gtagagactt agcaaatgtt ggttccctct yattgactca ctcacacttt ggacaagacc     60
c                                                                    61

<210> SEQ ID NO 1833
<211> LENGTH: 61
<212> TYPE: DNA
<213> ORGANISM: Homo Sapiens

<400> SEQUENCE: 1833
gtctgtgacc cacacgttaa tatggcctca ytttgactaa gaccactatt cgagtaggtt     60
t                                                                    61

<210> SEQ ID NO 1834
<211> LENGTH: 61
<212> TYPE: DNA
<213> ORGANISM: Homo Sapiens

<400> SEQUENCE: 1834
tgatatataa caaatgcaga ggtagcctca ygcattaaac gtcttttttct tgctgatgga    60
a                                                                    61

<210> SEQ ID NO 1835
<211> LENGTH: 61
<212> TYPE: DNA
<213> ORGANISM: Homo Sapiens

<400> SEQUENCE: 1835
cttgtgcagc cctggcctcc ttttaatgtc yagaccagca tttctcaacc tcgacactac     60
t                                                                    61

<210> SEQ ID NO 1836
<211> LENGTH: 61
<212> TYPE: DNA
<213> ORGANISM: Homo Sapiens

<400> SEQUENCE: 1836
catcgggaag ctggggtaca tgttctgcta maacagggaa cacagctttt ccaaacatat     60
c                                                                    61

<210> SEQ ID NO 1837
<211> LENGTH: 61
<212> TYPE: DNA
<213> ORGANISM: Homo Sapiens

<400> SEQUENCE: 1837
gacactgggt cttcacacac acagcaagga ytgttaattc aaatgttcca gcacgtgaag    60
c                                                                   61

<210> SEQ ID NO 1838
<211> LENGTH: 61
<212> TYPE: DNA
<213> ORGANISM: Homo Sapiens

<400> SEQUENCE: 1838
tgttgtcata cttcaaatca tattccaaat ragcatcaaa ataataaca tgcggccggg    60
c                                                                   61

<210> SEQ ID NO 1839
<211> LENGTH: 61
<212> TYPE: DNA
<213> ORGANISM: Homo Sapiens

<400> SEQUENCE: 1839
ttctcatctt tcttggaaag tgggatgaac ragcagaaat aacaggaagg caaattcaag    60
c                                                                   61

<210> SEQ ID NO 1840
<211> LENGTH: 61
<212> TYPE: DNA
<213> ORGANISM: Homo Sapiens

<400> SEQUENCE: 1840
gtctttgcag atgtaactaa attaagatga rgccaccctg aattaggatg tgtcctgaat    60
c                                                                   61

<210> SEQ ID NO 1841
<211> LENGTH: 61
<212> TYPE: DNA
<213> ORGANISM: Homo Sapiens

<400> SEQUENCE: 1841
tgccccttcc ctctacaaaa ccatcagctc ygtgcaaact gggattttttg cctgaattgt   60
t                                                                   61

<210> SEQ ID NO 1842
<211> LENGTH: 61
<212> TYPE: DNA
<213> ORGANISM: Homo Sapiens

<400> SEQUENCE: 1842
agataacacc gcccagcctc ccctgcagct rgatggaggt cacatgcttg gatctggtca    60
a                                                                   61

<210> SEQ ID NO 1843
<211> LENGTH: 61
<212> TYPE: DNA
<213> ORGANISM: Homo Sapiens

<400> SEQUENCE: 1843
ctgtgactca agggcagcca caactctgtg ycagccataa ttgccatgcc atgcaagaat    60
g                                                                   61

```
<210> SEQ ID NO 1844
<211> LENGTH: 61
<212> TYPE: DNA
<213> ORGANISM: Homo Sapiens

<400> SEQUENCE: 1844
ggtctccagc ttcccagccc tcagcatgca mggtgagatg gatcctccta gaatacaagt    60
t                                                                    61

<210> SEQ ID NO 1845
<211> LENGTH: 61
<212> TYPE: DNA
<213> ORGANISM: Homo Sapiens

<400> SEQUENCE: 1845
gctgagagct ctctcttctc tgttacaaaa ygagataagc aagtgttaga attgccttaa    60
g                                                                    61

<210> SEQ ID NO 1846
<211> LENGTH: 61
<212> TYPE: DNA
<213> ORGANISM: Homo Sapiens

<400> SEQUENCE: 1846
cccactattt ttaaggaaga aatcattttg sttgaaggca tcactcttgg ttgtgatcag    60
a                                                                    61

<210> SEQ ID NO 1847
<211> LENGTH: 61
<212> TYPE: DNA
<213> ORGANISM: Homo Sapiens

<400> SEQUENCE: 1847
agatcagaaa tattcggagg aagaattgtg sctgtactga acatggacag attttttctt    60
g                                                                    61

<210> SEQ ID NO 1848
<211> LENGTH: 61
<212> TYPE: DNA
<213> ORGANISM: Homo Sapiens

<400> SEQUENCE: 1848
tcagcatcga cagggaagac agttttttca ytgtcagccg ttctgactgg ccgggtagga    60
a                                                                    61

<210> SEQ ID NO 1849
<211> LENGTH: 61
<212> TYPE: DNA
<213> ORGANISM: Homo Sapiens

<400> SEQUENCE: 1849
atgatggtta tccgggtccc aagtccaaag waagctagaa aaggctgcta actgggggag    60
g                                                                    61

<210> SEQ ID NO 1850
<211> LENGTH: 61
<212> TYPE: DNA
<213> ORGANISM: Homo Sapiens

<400> SEQUENCE: 1850
tccctgacag cccctgaggc accgtctgaa rcagggtcgg agctggatgg atcctgggga    60
```

-continued g                                                             61

<210> SEQ ID NO 1851
<211> LENGTH: 61
<212> TYPE: DNA
<213> ORGANISM: Homo Sapiens

<400> SEQUENCE: 1851
tgctgcccaa ggaggcgcag atctgcgaga rgcccaacct gaacgccatc aacatcacgg    60
c                                                                   61

<210> SEQ ID NO 1852
<211> LENGTH: 61
<212> TYPE: DNA
<213> ORGANISM: Homo Sapiens

<400> SEQUENCE: 1852
gcacatagtg ggtatccagt acgactccgc scttcctcac tcctttgttg gggtaagtaa    60
a                                                                   61

<210> SEQ ID NO 1853
<211> LENGTH: 61
<212> TYPE: DNA
<213> ORGANISM: Homo Sapiens

<400> SEQUENCE: 1853
taaaaactgg ggaaagagga tgaccaacac raaatcacca tcctaaaaga gttgacagtc    60
t                                                                   61

<210> SEQ ID NO 1854
<211> LENGTH: 61
<212> TYPE: DNA
<213> ORGANISM: Homo Sapiens

<400> SEQUENCE: 1854
cgtcacactg agagtatctg gagaccttca ygttggagga gtgatgctca agttagtaga    60
a                                                                   61

<210> SEQ ID NO 1855
<211> LENGTH: 61
<212> TYPE: DNA
<213> ORGANISM: Homo Sapiens

<400> SEQUENCE: 1855
ttaaatttct attcaaatgt attttttaga rcttgattgt tgttgcccgt acatgtatac    60
g                                                                   61

<210> SEQ ID NO 1856
<211> LENGTH: 61
<212> TYPE: DNA
<213> ORGANISM: Homo Sapiens

<400> SEQUENCE: 1856
ctacattagg ctataacttt tctttggatc mgtgccatgt gaacactaga aaccaacaca    60
g                                                                   61

<210> SEQ ID NO 1857
<211> LENGTH: 61
<212> TYPE: DNA
<213> ORGANISM: Homo Sapiens

<400> SEQUENCE: 1857
tgggcaccac cagcagcaac cactctggtg rctttaattt ctggtaagtc agacttttaa    60
a                                                                   61

<210> SEQ ID NO 1858
<211> LENGTH: 61
<212> TYPE: DNA
<213> ORGANISM: Homo Sapiens

<400> SEQUENCE: 1858
ctaactgtat atttgtaccc accactaatc wttccatagc ttgcaagacc agctctatct    60
a                                                                   61

<210> SEQ ID NO 1859
<211> LENGTH: 61
<212> TYPE: DNA
<213> ORGANISM: Homo Sapiens

<400> SEQUENCE: 1859
gtaggctggg ctaagctatg gtgtttggca ygttaggtat gttaaatgta tttttgactt    60
a                                                                   61

<210> SEQ ID NO 1860
<211> LENGTH: 61
<212> TYPE: DNA
<213> ORGANISM: Homo Sapiens

<400> SEQUENCE: 1860
gtgatttgtt ttctgaactc ctgcagggaa saaaaaaaag gtaatattgg ccccatacaa    60
t                                                                   61

<210> SEQ ID NO 1861
<211> LENGTH: 61
<212> TYPE: DNA
<213> ORGANISM: Homo Sapiens

<400> SEQUENCE: 1861
accacctcga atttggaaat actttcttca yttaacagag aggttgagta aattgcctca    60
g                                                                   61

<210> SEQ ID NO 1862
<211> LENGTH: 61
<212> TYPE: DNA
<213> ORGANISM: Homo Sapiens

<400> SEQUENCE: 1862
tatttggatt gaagtacata tcttgaatca rattaaagtt gtacagcatg taaggctaaa    60
t                                                                   61

<210> SEQ ID NO 1863
<211> LENGTH: 61
<212> TYPE: DNA
<213> ORGANISM: Homo Sapiens

<400> SEQUENCE: 1863
tcaatggata caaaagtatg taatagaagg rggctgatga tcagggaggg atagaaaaat    60
t                                                                   61

<210> SEQ ID NO 1864
<211> LENGTH: 61
<212> TYPE: DNA
<213> ORGANISM: Homo Sapiens

<400> SEQUENCE: 1864
agagatcttt cacctacttg cttagatgta ytcctcagta ttttattatt tctgttacta    60
t                                                                   61

<210> SEQ ID NO 1865
<211> LENGTH: 61
<212> TYPE: DNA
<213> ORGANISM: Homo Sapiens

<400> SEQUENCE: 1865
ggctaaaatt agttcttgaa ggatgaaaaa mgtcttattc cttttctgta taaagcacag    60
a                                                                   61

<210> SEQ ID NO 1866
<211> LENGTH: 61
<212> TYPE: DNA
<213> ORGANISM: Homo Sapiens

<400> SEQUENCE: 1866
ccaccacaca gtctgtagct tctagcctcc sttcctttgc acgtgccttt cccaggatcc    60
g                                                                   61

<210> SEQ ID NO 1867
<211> LENGTH: 61
<212> TYPE: DNA
<213> ORGANISM: Homo Sapiens

<400> SEQUENCE: 1867 acagggaga ttttgttca ctggtaacca maggtagaga gtgctgtatt cccccatgcc     60
a                                                                   61

<210> SEQ ID NO 1868
<211> LENGTH: 61
<212> TYPE: DNA
<213> ORGANISM: Homo Sapiens

<400> SEQUENCE: 1868
attctggctg ttagactgtg atgaagatgc mgacactcca ggattcagca gcctggggct    60
t                                                                   61

<210> SEQ ID NO 1869
<211> LENGTH: 61
<212> TYPE: DNA
<213> ORGANISM: Homo Sapiens

<400> SEQUENCE: 1869
tgatgcatga tttgcttact cacaatctaa katcttttct gtaacttgtc tctgggcctc    60
t                                                                   61

<210> SEQ ID NO 1870
<211> LENGTH: 61
<212> TYPE: DNA
<213> ORGANISM: Homo Sapiens

<400> SEQUENCE: 1870
ggatttatca tctttagaag tcagtgatgg ygcagttcat gttgcttggg ggtgtggaga    60
t                                                               61

<210> SEQ ID NO 1871
<211> LENGTH: 61
<212> TYPE: DNA
<213> ORGANISM: Homo Sapiens

<400> SEQUENCE: 1871
tgatcagctt tcataatca taggcctctt ygggctagca cttttcatac atcacacttg    60
g                                                               61

<210> SEQ ID NO 1872
<211> LENGTH: 61
<212> TYPE: DNA
<213> ORGANISM: Homo Sapiens

<400> SEQUENCE: 1872
gacacctcat ccaggatgga agcgggaacc raaagcctgg ctgagagacc ccaggggcct    60
g                                                               61

<210> SEQ ID NO 1873
<211> LENGTH: 61
<212> TYPE: DNA
<213> ORGANISM: Homo Sapiens

<400> SEQUENCE: 1873
aaccaaggcc acacccctag caagaggacc kgctttcacc agtaactgaa gctgtgcaga    60
g                                                               61

<210> SEQ ID NO 1874
<211> LENGTH: 61
<212> TYPE: DNA
<213> ORGANISM: Homo Sapiens

<400> SEQUENCE: 1874
tattgggtga caactctgtt tcaggtacta ygctagtctc ttcccacaag gacctcacag    60
c                                                               61

<210> SEQ ID NO 1875
<211> LENGTH: 61
<212> TYPE: DNA
<213> ORGANISM: Homo Sapiens

<400> SEQUENCE: 1875
acttgtacag gggtaggtag cataaaagac mgccgttctc aagaggcaac catgcgcctc    60
a                                                               61

<210> SEQ ID NO 1876
<211> LENGTH: 61
<212> TYPE: DNA
<213> ORGANISM: Homo Sapiens

<400> SEQUENCE: 1876
aatacacagt gctaactagc agagtcacgc rtcggaagtg tgctgggccc ataaaataca    60
c                                                               61

<210> SEQ ID NO 1877
<211> LENGTH: 61
<212> TYPE: DNA
<213> ORGANISM: Homo Sapiens -continued

```
<400> SEQUENCE: 1877
aacatgggac ttacagcatg agtatcattc rgccactaaa cagtacactt cacgcatgaa    60
c                                                                     61

<210> SEQ ID NO 1878
<211> LENGTH: 61
<212> TYPE: DNA
<213> ORGANISM: Homo Sapiens

<400> SEQUENCE: 1878
ggacatgaga aaatgctcat gatcaaatgg yaggagaacg aaactatatt tacagtacga    60
t                                                                     61

<210> SEQ ID NO 1879
<211> LENGTH: 61
<212> TYPE: DNA
<213> ORGANISM: Homo Sapiens

<400> SEQUENCE: 1879
actggggctc gccatctgca aatgaggtga ygctatttac cttgcagggc ccaagagggt    60
t                                                                     61

<210> SEQ ID NO 1880
<211> LENGTH: 61
<212> TYPE: DNA
<213> ORGANISM: Homo Sapiens

<400> SEQUENCE: 1880
gtgcaaagtg acagacaaat gagtcatccc yggtctttcc aaggacaggg actcatctgg    60
c                                                                     61

<210> SEQ ID NO 1881
<211> LENGTH: 61
<212> TYPE: DNA
<213> ORGANISM: Homo Sapiens

<400> SEQUENCE: 1881
atttgagagc tatatattta aatgcagtgc yaagggtttc atttaacacg aggaaaaaac    60
c                                                                     61

<210> SEQ ID NO 1882
<211> LENGTH: 61
<212> TYPE: DNA
<213> ORGANISM: Homo Sapiens

<400> SEQUENCE: 1882
ggaaaagata atttgctttc tctctcaagt yccacttatg tgtttgtaga ttagatttgg    60
c                                                                     61

<210> SEQ ID NO 1883
<211> LENGTH: 61
<212> TYPE: DNA
<213> ORGANISM: Homo Sapiens

<400> SEQUENCE: 1883
ctgtctccta agaactagga cactcaaata ygcaactgtg attacatgga aataaaaaca    60
c                                                                     61
```

<210> SEQ ID NO 1884
<211> LENGTH: 61
<212> TYPE: DNA
<213> ORGANISM: Homo Sapiens

<400> SEQUENCE: 1884
aggcgtaact aatctacacc cttcgaagcc rggacaggga agagaaagag gaggcaggca    60
g                                                                   61

<210> SEQ ID NO 1885
<211> LENGTH: 61
<212> TYPE: DNA
<213> ORGANISM: Homo Sapiens

<400> SEQUENCE: 1885
cagtgaccac cgttaggtga gcaaggcagt waaattacag agcaaaatct aacaggccag    60
a                                                                   61

<210> SEQ ID NO 1886
<211> LENGTH: 61
<212> TYPE: DNA
<213> ORGANISM: Homo Sapiens

<400> SEQUENCE: 1886
aggcaatctg gttgcagagc tccttactaa yaacagctca ctgcaggcac ttgtagcccc    60
a                                                                   61

<210> SEQ ID NO 1887
<211> LENGTH: 61
<212> TYPE: DNA
<213> ORGANISM: Homo Sapiens

<400> SEQUENCE: 1887
gcagcgcctg gcagagccag tgcagtcaga sgagccctga agtgtgggca caaaaacctg    60
c                                                                   61

<210> SEQ ID NO 1888
<211> LENGTH: 61
<212> TYPE: DNA
<213> ORGANISM: Homo Sapiens

<400> SEQUENCE: 1888
attgaaacca agttagttac agacatagat sccgtcttaa gcaaaggaca cacataatct    60
c                                                                   61

<210> SEQ ID NO 1889
<211> LENGTH: 61
<212> TYPE: DNA
<213> ORGANISM: Homo Sapiens

<400> SEQUENCE: 1889
taggaaactt cagaatacac agttgatcct mtctaaagac caccctgcag gtccaggcag    60
a                                                                   61

<210> SEQ ID NO 1890
<211> LENGTH: 61
<212> TYPE: DNA
<213> ORGANISM: Homo Sapiens

```
<400> SEQUENCE: 1890
ctctgaagtc aggaaactca tttaaacagg rtctgtaccg aaattcagga aggtcaagga      60
g                                                                     61

<210> SEQ ID NO 1891
<211> LENGTH: 61
<212> TYPE: DNA
<213> ORGANISM: Homo Sapiens

<400> SEQUENCE: 1891
tgagcagcgc cctttctgca gaaagtaaag mgcaccttgc cgagagatca tttgtttctg      60
t                                                                     61

<210> SEQ ID NO 1892
<211> LENGTH: 61
<212> TYPE: DNA
<213> ORGANISM: Homo Sapiens

<400> SEQUENCE: 1892
ccagtgagac gcagaaacgg atcctttgtc ygacttcctc cagattgcct ggggttggac      60
c                                                                     61

<210> SEQ ID NO 1893
<211> LENGTH: 61
<212> TYPE: DNA
<213> ORGANISM: Homo Sapiens

<400> SEQUENCE: 1893
acgtcacact ttgccaggaa actcgccttc raccaagaag gtccccagca aagtaactca      60
t                                                                     61

<210> SEQ ID NO 1894
<211> LENGTH: 61
<212> TYPE: DNA
<213> ORGANISM: Homo Sapiens

<400> SEQUENCE: 1894
gatttatacc aatcttgcac atattttact ycgaatttca caaactcaat tctctgcttt      60
c                                                                     61
```